(12) United States Patent
Hewitt et al.

(10) Patent No.: US 9,169,494 B2
(45) Date of Patent: Oct. 27, 2015

(54) RESTRICTIVE INVERTED TERMINAL REPEATS FOR VIRAL VECTORS

(75) Inventors: Curtis Hewitt, Austin, TX (US);
Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 61 days.

(21) Appl. No.: 13/521,448

(22) PCT Filed: Jan. 12, 2011

(86) PCT No.: PCT/US2011/020939
§ 371 (c)(1),
(2), (4) Date: Nov. 29, 2012

(87) PCT Pub. No.: WO2011/088081
PCT Pub. Date: Jul. 21, 2011

(65) Prior Publication Data
US 2013/0109742 A1    May 2, 2013

Related U.S. Application Data

(60) Provisional application No. 61/294,181, filed on Jan. 12, 2010.

(51) Int. Cl.
| *A01N 63/00* | (2006.01) |
| --- | --- |
| *C12N 15/864* | (2006.01) |
| *C07K 14/005* | (2006.01) |
| *C12N 15/86* | (2006.01) |

(52) U.S. Cl.
CPC .......... *C12N 15/8645* (2013.01); *C07K 14/005* (2013.01); *C12N 15/86* (2013.01); *C12N 2750/14122* (2013.01); *C12N 2750/14143* (2013.01); *C12N 2750/14162* (2013.01); *C12N 2820/60* (2013.01)

(58) Field of Classification Search
CPC ........................ C12N 15/861; C12N 15/8613
USPC ........................................................ 424/93.2
See application file for complete search history.

(56) References Cited

U.S. PATENT DOCUMENTS

| 6,984,517 | B1 | 1/2006 | Chiorini et al. |
| --- | --- | --- | --- |
| 2003/0129203 | A1 | 7/2003 | Vega et al. |
| 2004/0197895 | A1* | 10/2004 | Kotin et al. ................. 435/235.1 |
| 2005/0002908 | A1 | 1/2005 | Horer et al. |

OTHER PUBLICATIONS

Brister et al. (2000, J. Virology, vol. 74(17), pp. 7762-7771).*
Hewitt et al. IDS on Sep. 10, 2012.*
Brister, J.R. et al., "Mechanism of Rep-Mediated Adeno-Associated Virus Origin Nicking", *Journal of Virology*, Sep. 2000, vol. 74, No. 17, p. 7762-7771.
Cathomen, T. et al., "A Chimeric Protein Containing the N Terminus of the Adeno-Associated Virus Rep Protein Recognizes Its Target Site in an In Vivo Assay", *Journal of Virology*, Mar. 2000, vol. 74, No. 5, p. 2372-2382.
Farkas, S.L. et al., "A parvovirus isolated from royal python (*Python regius*) is a member of the genus *Dependovirus*", *Journal of General Virology* (2004), vol. 85, p. 555-561.
Hewitt, F.C. et al., "Creating a Novel Origin of Replication through Modulating DNA-Protein Interfaces", *PLoS One*, Jan. 22, 2010, vol. 5, Issue 1, pp. 1-13.
Hewitt, F.C. et al., "Reducing the Risk of Adeno-Associated Virus (AAV) Vector Mobilization with AAV Type 5 Vectors", *Journal of Virology*, Apr. 2009, vol. 83, No. 8, p. 3919-3929, Published Feb. 11, 2009.
Hewitt, F.C. et al., "Replication Specificity of Adeno-Associated Virus Genomes", *2008 DNA Replication and Genome Integrity Meeting*, Salk Institute, Jul. 20, 2008, 1 page.
International Preliminary Report on Patentability Corresponding to International Application No. PCT/US2011/020939; Date of Mailing: Jul. 26, 2012; 8 Pages.
Rabinowitz, J.E. et al., "Cross-Packaging of a Single Adeno-Associated Virus (AAV) Type 2 Vector Genome into Multiple AAV Serotypes Enables Transduction with Broad Specificity", *Journal of Virology*, Jan. 2002, vol. 76, No. 2, p. 791-801.
International Preliminary Report on Patentability Corresponding to International Application No. PCT/US2011/036215; Date of Mailing: Nov. 29, 2012; 7 Pages.
Extended European Search Report for EP Application No. 11733293. 2; Date of Mailing Jan. 9, 2014; 10 Pages.
Yoon et al., "Amino-terminal domain exchange redirects origin-specific interactions of adeno-associated virus Rep78 in vitro," J. Virol. 75:3230-3239 (2001).

* cited by examiner

*Primary Examiner* — Anoop Singh
*Assistant Examiner* — David A Montanari
(74) *Attorney, Agent, or Firm* — Myers Bigel Sibley & Sajovec, P.A.

(57) ABSTRACT

This invention relates to modified parvovirus inverted terminal repeats (ITRs) that do not functionally interact with wild-type large Rep proteins, synthetic Rep proteins that functionally interact with the modified ITRs, and methods of using the same for delivery of nucleic acids to a cell or a subject. The modifications provide a novel Rep-ITR interaction that limits vector mobilization, increasing the safety of viral vectors.

21 Claims, 65 Drawing Sheets

```
            |                       |         +
REP5  MATFYEVIVRVPFDVEEHLPGISDSFVDWVTGQIWELPPESDLNLTLVEQ   50
REP2  MPGFYEIVIKVPSDLDGHLPGISDSFVNWVAEKEWELPPDSDMDLNLIEQ   50
      *. ***::::** *:: **********:**: : *****:**::*.*:**

+   +   ++                  |      |  |
REP5  PQLTVADRIRRVFLYEWNKFSKQ-ESKFFVQFEKGSEYFHLHTLVETSGI   99
REP2  APLTVAEKLQRDFLTEWRRVSKAPEALFFVQFEKGESYFHMHVLVETTGV  100
      , ****::::* ** **.:.**  *:  ********..***:*.****:*:

^^  ^^  ^^ .   +   + +              ^ ^^  ^   ^
REP5  SSMVLGRYVSQIRAQLVKVVFQGIEPQINDWVAITKVKK--GGANKVVDS  147
REP2  KSMVLGRFLSQIREKLIQRIYRGIEPTLPNWFAVTKTRNGAGGGNKVVDE  159
      .******::****  ;*::  :::****  : :*.*:**.::  **.*****.

|            |
REP5  GYIPAYLLPKVQPELQWAWTNLDEYKLAALNLEERKRLVAQFLAESSQRS  197
REP2  CYIPNYLLPKTQPELQWAWTNMEQYLSACLNLTERKRLVAQHLTHVSQTQ  200
      *** *****.**********:::* *.*** ********.*:.  **  ,

REP5  -QEAASQREFSADPVIKSKTSQKYM  222
REP2  EQNKENQNPNSDAPVIRSKTSARYM  225
      *:  .*. * ***:**** :**
```

*FIG. 5A*

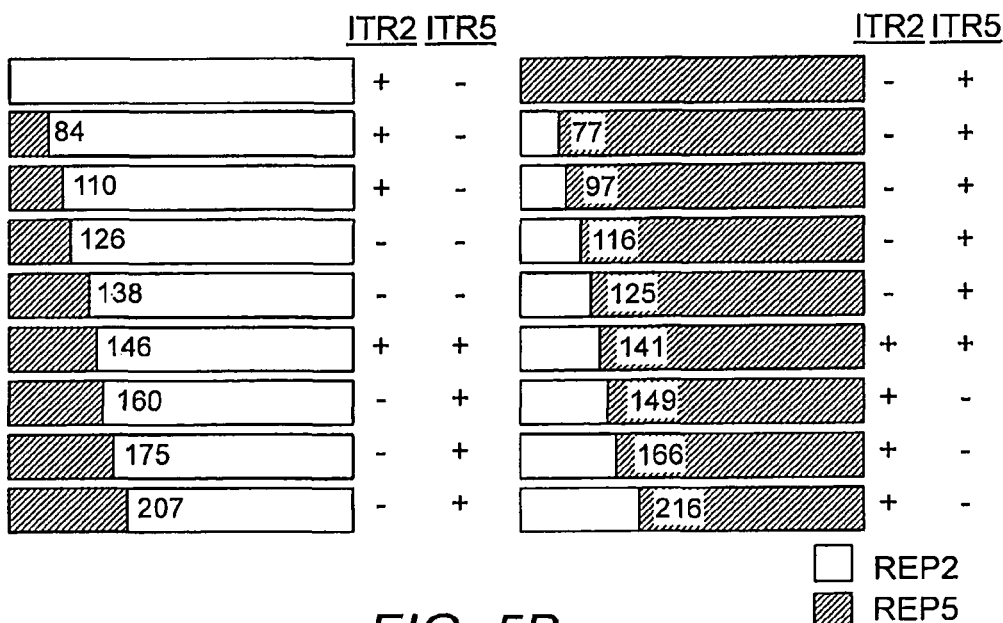

*FIG. 5B*

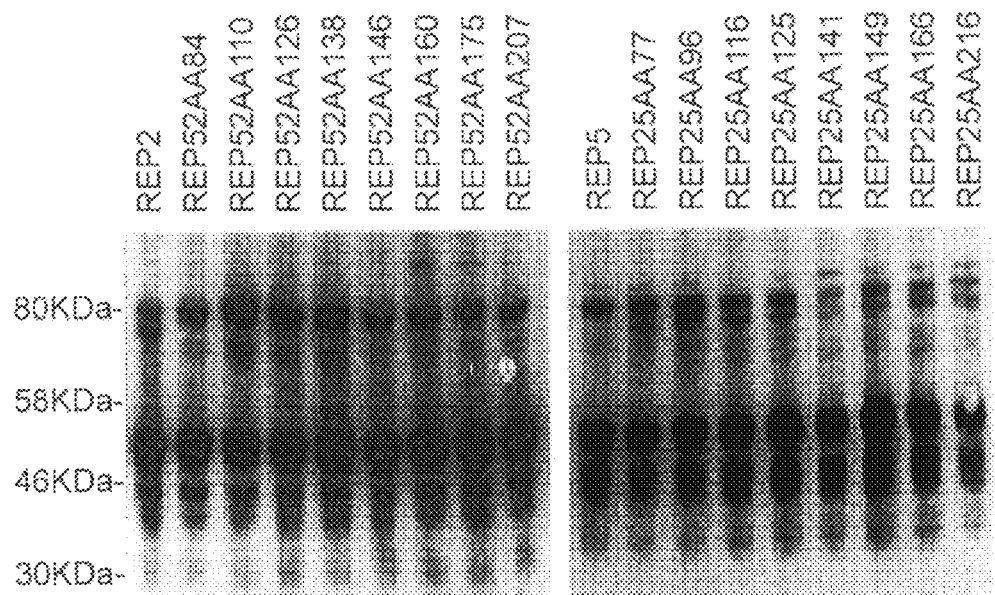
FIG. 5C
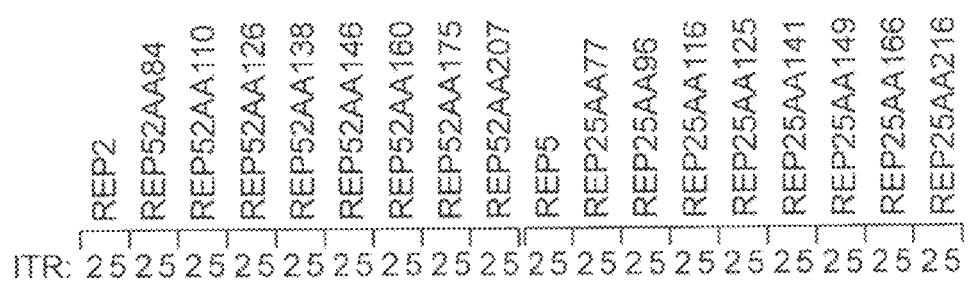
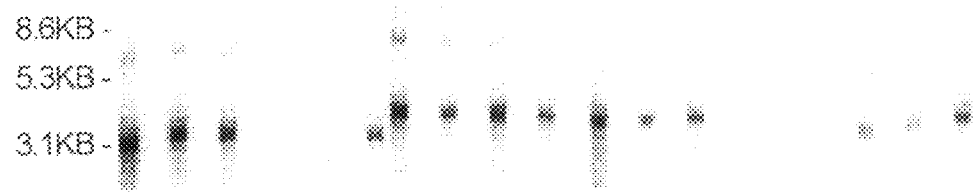
FIG. 5D

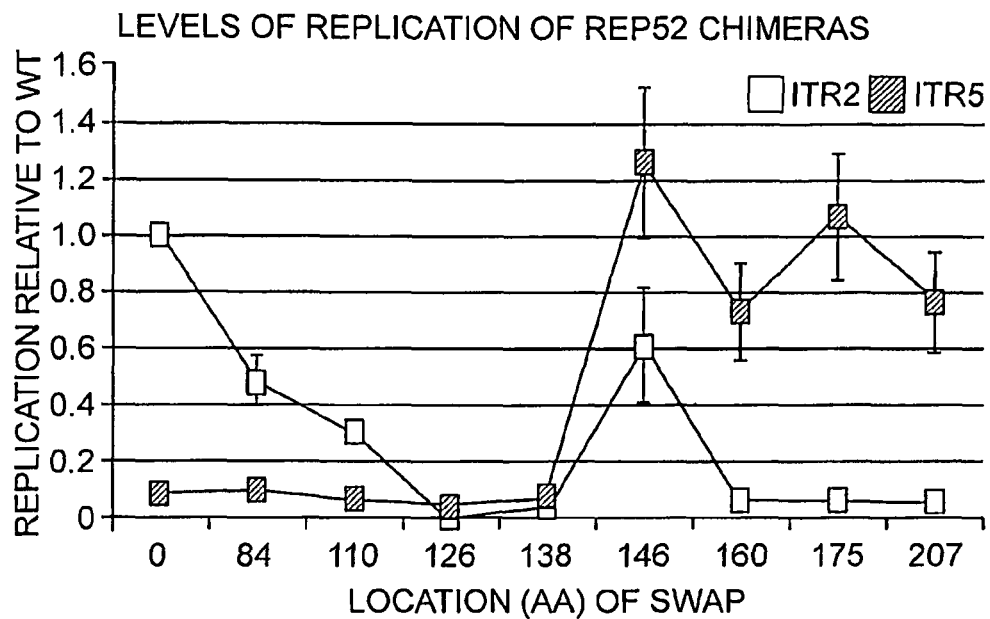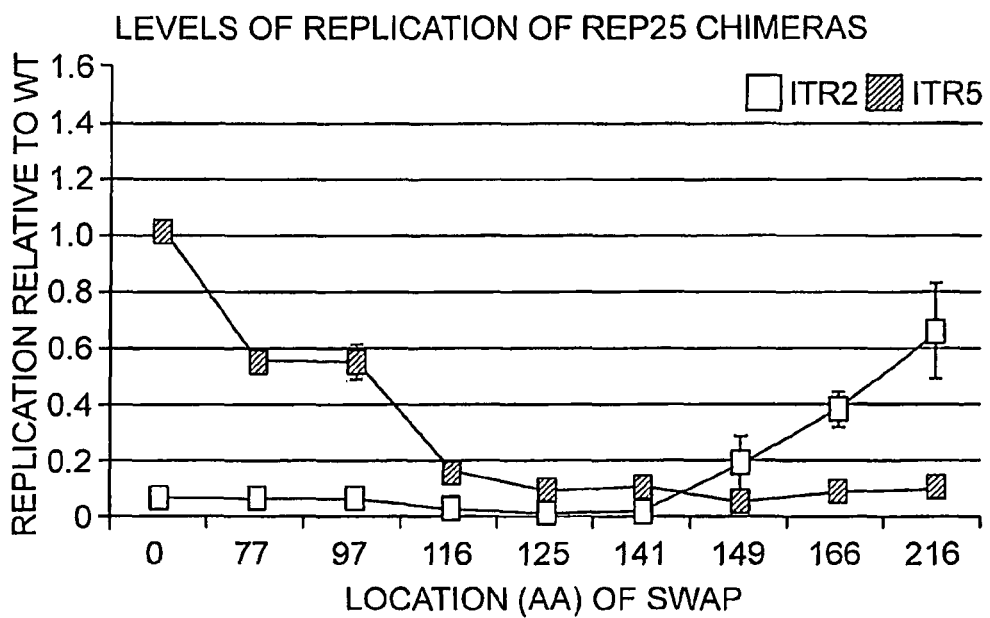
FIG. 5E

AAV-1, COMPLETE SEQUENCE, GENBANK ACCESSION NO. NC_002077 AND XIAO ET AL. (1999) J. VIROL. 73:3994
TTGCCCACTCCCTCTCTGCGCGCTCGCTCGCTCGGTGGGGCCTGCGGACCAAAGGTCCGCAGACGGCA
GAGCTCTGCTCTGCCGGCCCCACCGAGCGAGCGAGCGCGCAGAGAGGGAGTGGGCAACTCCATCACTA
GGGGTAATCGCGAAGCGCCTCCCACGCTGCCGCGTCAGCGCTGACGTAAATTACGTCATAGGGGAGTG
GTCCTGTATTAGCTGTCACGTGAGTGCTTTTGCGACATTTTGCGACACCACGTGGCCATTTAGGGTAT
ATATGGCCGAGTGAGCGAGCAGGATCTCCATTTTGACCGCGAAATTTGAACGAGCAGCAGCCATGCCG
GGCTTCTACGAGATCGTGATCAAGGTGCCGAGCGACCTGGACGAGCACCTGCCGGGCATTTCTGACTC
GTTTGTGAGCTGGGTGGCCGAGAAGGAATGGGAGCTGCCCCCGGATTCTGACATGGATCTGAATCTGA
TTGAGCAGGCACCCCTGACCGTGGCCGAGAAGCTGCAGCGCGACTTCCTGGTCCAATGGCGCCGCGTG
AGTAAGGCCCCGGAGGCCCTCTTCTTTGTTCAGTTCGAGAAGGGCGAGTCCTACTTCCACCTCCATAT
TCTGGTGGAGACCACGGGGGTCAAATCCATGGTGCTGGGCCGCTTCCTGAGTCAGATTAGGGACAAGC
TGGTGCAGACCATCTACCGCGGGATCGAGCCGACCCTGCCCAACTGGTTCGCGGTGACCAAGACGCGT
AATGGCGCCGGAGGGGGGAACAAGGTGGTGGACGAGTGCTACATCCCCAACTACCTCCTGCCCAAGAC
TCAGCCCGAGCTGCAGTGGGCGTGGACTAACATGGAGGAGTATATAAGCGCCTGTTTGAACCTGGCCG
AGCGCAAACGGCTCGTGGCGCAGCACCTGACCCACGTCAGCCAGACCCAGGAGCAGAACAAGGAGAAT
CTGAACCCCAATTCTGACGCGCCTGTCATCCGGTCAAAAACCTCCGCGCGCTACATGGAGCTGGTCGG
GTGGCTGGTGGACCGGGGCATCACCTCCGAGAAGCAGTGGATCCAGGAGGACCAGGCCTCGTACATCT
CCTTCAACGCCGCTTCCAACTCGCGGTCCCAGATCAAGGCCGCTCTGGACAATGCCGGCAAGATCATG
GCGCTGACCAAATCCGCGCCCGACTACCTGGTAGGCCCCGCTCCGCCCGCGGACATTAAAACCAACCG
CATCTACCGCATCCTGGAGCTGAACGGCTACGAACCTGCCTACGCCGGCTCCGTCTTTCTCGGCTGGG
CCCAGAAAAGGTTCGGGAAGCGCAACACCATCTGGCTGTTTGGGCCGGCCACCACGGGCAAGACCAAC
ATCGCGGAAGCCATCGCCCACGCCGTGCCCTTCTACGGCTGCGTCAACTGGACCAATGAGAACTTTCC
CTTCAATGATTGCGTCGACAAGATGGTGATCTGGTGGGAGGAGGGCAAGATGACGGCCAAGGTCGTGG
AGTCCGCCAAGGCCATTCTCGGCGGCAGCAAGGTGCGCGTGGACCAAAAGTGCAAGTCGTCCGCCCAG
ATCGACCCCACCCCCGTGATCGTCACCTCCAACACCAACATGTGCGCCGTGATTGACGGGAACAGCAC
CACCTTCGAGCACCAGCAGCCGTTGCAGGACCGGATGTTCAAATTTGAACTCACCCGCCGTCTGGAGC
ATGACTTTGGCAAGGTGACAAAGCAGGAAGTCAAAGAGTTCTTCCGCTGGGCGCAGGATCACGTGACC
GAGGTGGCCGATGAGTTCTACGTCAGAAAGGGTGGAGCCAACAAAAGACCCGCCCCGATGACGCGGA
TAAAAGCGAGCCCAAGCGGGCCTGCCCCTCAGTCGCGGATCCATCGACGTCAGACGCGGGAAGGAGCTC
CGGTGGACTTTGCCGACAGGTACCAAAACAAATGTTCTCGTCACGCGGGCATGCTTCAGATGCTGTTT
CCCTGCAAGACATGCGAGAGAATGAATCAGAATTTCAACATTTGCTTCACGCACGGGACGAGACTG
TTCAGAGTGCTTCCCCGGCGTGTCAGAATCTCAGCCGTCGTCAGAAAGAGGACGTATCGGAAACTCT
GTGCCATTCATCATCTGCTGGGCGGGCTCCCGAGATTGCTTGCTCGGCCTGCGATCTGGTCAACGTG
GACCTGGATGACTGTGTTTCTGAGCAATAAATGACTTAAACCAGGTATGGCTGCCGATGGTTATCTTC
CAGATTGGCTCGAGGACAACCTCTCTGAGGGCATTCGCGAGTGGTGGGACTTGAAACCTGGAGCCCGG
AAGCCCAAAGCCAACCCAACGCAGGACGACGGCCGGGGGTCTGGTGCTTCCTGGCTACAAGTACCT
CGGACCCTTCAACGGACTCGACAAGGGGGAGCCGTCAACGCGGCGGACGCAGCGGCCCTCGAGCACG
ACAAGGCCTACGACCAGCAGCTCAAAGCGGGTGACAATCCGTACCTGCGGTATAACCACGCCGACGCC
GAGTTTCAGGAGCGTCTGCAAGAAGATACGTCTTTTGGGGCCAACCCTCGGGCGAGCAGTCTTCCAGGC
CAAGAAGCGGGTTCTCGAACCTCTCGGTCTGGTTGAGGAAGGCGCTAAGACGGCTCCTGGAAAGAAAC
GTCCGGTAGAGCAGTCGCCCACAAGAGCCAGACTCCTCCTCGGGCATCGGCAAGACAGGCCAGCAGCCC
GCTAAAAAGAGACTCAATTTTGGTCAGACTGGCGACTCAGAGTCAGTCCCCGATCCACAACCTCTCGG
AGAACCTCCAGCAACCCCCGCTGCTGTGGGACCTACTACAATGGCTTCAGGCGGTGGCGCACCAATGG
CAGACAATAACGAAGGCGCCGACGGAGTGGGTAATGCCTCAGGAAATTGGCATTGGCGATTCCACATGG
CTGGGCGACAGAGTCATCACCACCAGCACCCGCACCTGGGCCTTGCCCACCTACAATAACCACCTCTA
CAAGCAAATCTCCAGTGCTTCAACGGGGGCCAGCAACGACAACCACTACTTCGGCTACAGCACCCCCT
GGGGGTATTTTGATTTCAACAGATTCCACTGCCACTTTTCACCACGTGACTGGCAGCGACTCATCAAC
AACAATTGGGGATTCCGGCCCAAGAGACTCAACTTCAAACTCTTCAACATCCAAGTCAAGGAGGTCAC
GACGAATGATGGCGTCACAACCATCGCTAATAACCTTACCAGCACGGTTCAAGTCTTCTCGGACTCGG
AGTACCAGCTTCCGTACGTCCTCGGCTCTGCGCACCAGGGCTGCCTCCCTCCGTTCCCGGCGGACGTG
TTCATGATTCCGCAATACGGCTACCTGACGCTCAACAATGGCAGCCAAGCCGTGGGACGTTCATCCTT
TTACTGCCTGGAATATTTCCCTTCTCAGATGCTGAGAACGGGCAACAACTTTACCTTCAGCTACACCT
TTGAGGAAGTGCCTTTCCACAGCAGCTACGCGCACAGCCAGAGCCTGGACCGGCTGATGAATCCTCTC
ATCGACCAATACCTGTATTACCTGAACAGAACTCAAAATCAGTCCGGAAGTGCCCAAAACAAGGACTT
GCTGTTTAGCCGTGGGTCTCCAGCTGGCATGTCTGTTCAGCCCAAAAACTGGCTACCTGGACCCTGTT
ATCGGCAGCAGCGCGTTTCTAAAACAAAAACAGACAACAACAACAGCAATTTTACCTGGACTGGTGCT
TCAAAATATAACCTCAATGGGCGTGAATCCATCATCAACCCTGGCACTGCTATGGCCTCACACAAAGA
CGACGAAGACAAGTTCTTTCCCATGAGCGGTGTCATGATTTTTGGAAAAGAGAGCGCCGGAGCTTCAA
ACACTGCATTGGACAATGTCATGATTACAGACGAAGAGGAAATTAAAGCCACTAACCCTGTGGCCACC
GAAAGATTTGGGACCGTGGCAGTCAATTTCCAGAGCAGCAGCACAGACCCTGCCGACCGGAGATGTGCA
TGCTATGGGAGCATTACCTGGCATGGTGTGGCAAGATAGAGACGTGTACCTGCAGGGTCCCATTTGGG
CCAAAATTCCTCACACAGATGGACACTTTCACCCGTCTCCTCTTATGGGCGGCTTTGGACTCAAGAAC
CCGCCTCCTCAGATCCTCATCAAAAACACGCCTGTTCCTGCGAATCCTCCGGCGGAGTTTTCAGCTAC
AAAGTTTGCTTCATTCATCACCCAATACTCCACAGGACAAGTGAGTGTGGAAATTGAATGGGAGCTGC
AGAAAGAAACAGCAAGCGCTGGAATCCCGAAGTGCAGTACACATCCAATTATGCAAAATCTGCCAAC
GTTGATTTTACTGTGGACAACAATGGACTTTATACTGAGCCTCGCCCCATTGGCACCCGTTACCTTAC
CCGTCCCCTGTAATTACGTGTTAATCAATAAACCGGTTGATTCGTTTCAGTTGAACTTTGGTCTCCTG
TCCTTCTTATCTTATCGGTTACCATGGTTATAGCTTACACATTAACTGCTTGGTTGCGCTTCGCGATA
AAAGACTTACGTCATCGGGTTACCCCTAGTGATGGAGTTGCCCACTCCCTCTCTGCGCGCTCGCTCGC
TCGGTGGGGCCTGCGGACCAAAGGTCCGCAGACGGCAGAGCTCTGCTCTGCCGGCCCCACCGAGCGAG
CGAGCGCGCAGAGAGGGAGTGGGCAA

FIG. 8

AAV-2, COMPLETE SEQUENCE, GENBANK ACCESSION NO. NC_001401 AND
CHIORINI ET AL. (1999) J. VIROL. 73:1309
TTGGCCACTCCCTCTCTGCGCGCTCGCTCGCTCACTGAGGCCGGGCGACCAAAGGTCGCCCGACGCCC
GGGCTTTGCCCGGGCGGCCTCAGTGAGCGAGCGAGCGCGCAGAGAGGGAGTGGCCAACTCCATCACTA
GGGGTTCCTGGAGGGGTGGAGTCGTGACGTGAATTACGTCATAGGGTTAGGGAGGTCCTGTATTAGAG
GTCACGTGAGTGTTTTGCGACATTTTGCGACACCATGTGGTCACGCTGGGTATTTAAGCCCGAGTGAG
CACGCAGGGTCTCCATTTTGAAGCGGGAGGTTTGAACGCGCAGCCGCCATGCCGGGGTTTTACGAGAT
TGTGATTAAGGTCCCCAGCGACCTTGACGGGCATCTGCCCGGCATTTCTGACAGCTTTGTGAACTGGG
TGGCCGAGAAGGAATGGGAGTTGCCGCCAGATTCTGACATGGATCTGAATCTGATTGAGCAGGCACCC
CTGACCGTGGCCGAGAAGCTGCAGCGCGACTTTCTGACGGAATGGCGCCGTGTGAGTAAGGCCCCGGA
GGCCCTTTTCTTTGTGCAATTTGAGAAGGGAGAGCTACTTCCACATGCACGTGCTCGTGGAAACCA
CCGGGGTGAAATCCATGGTTTTGGGACGTTTCCTGAGTCAGATTCGCGAAAAACTGATTCAGAGAATT
TACCGCGGGATCGAGCCGACTTTGCCAAACTGGTTCGCGGTCACAAAGACCAGAAATGGCGCCGGAGG
CGGGAACAAGGTGGTGGATGAGTGCTACATCCCCAATTACTTGCTCCCCAAAACCCAGCCTGAGCTCC
AGTGGGCGTGGACTAATATGGAACAGTATTTAAGCGCCTGTTTGAATCTCACGGAGCGTAAACGGTTG
GTGGCGCAGCATCTGACGCACGTGTCGCAGACGCAGGAGCAGAACAAAGAGAATCAGAATCCCAATTC
TGATGCGCCGGTGATCAGATCAAAAACTTCAGCCAGGTACATGGAGCTGGTCGGGTGGCTCGTGGACA
AGGGGATTACCTCGGAGAAGCAGTGGATCCAGGAGGACCAGGCCTCATACATCTCCTTCAATGCGGCC
TCCAACTCGCGGTCCCAAATCAAGGCTGCCTTGGACAATGCGGGAAAGATTATGAGCCTGACTAAAAC
CGCCCCCGACTACCTGGTGGGCCAGCAGCCCGTGGAGGACATTTCCAGCAATCGGATTTATAAAATTT
TGGAACTAAACGGGTACGATCCCCAATATGCGGCTTCCGTCTTTCTGGGATGGGCCACGAAAAGTTC
GGCAAGAGGAACACCATCTGGCTGTTTGGGCCTGCAACTACCGGGAAGACCAACATCGCGGAGGCCAT
AGCCCACACTGTGCCCTTCTACGGGTGCGTAAACTGGACCAATGAGAACTTTCCCTTCAACGACTGTG
TCGACAAGATGGTGATCTGGTGGGAGGAGGGGAAGATGACCGCCAAGGTCGTGGAGTCGGCCAAAGCC
ATTCTCGGAGGAAGCAAGGTGCGCGTGGACCAGAAATGCAAGTCCTCGGCCCAGATAGACCCGACTCC
CGTGATCGTCACCTCCAACACCAACATGTGCGCCGTGATTGACGGGAACTCAACGACCTTCGAACACC
AGCAGCCGTTGCAAGACCGGATGTTCAAATTTGAACTCACCCGCCGTCTGGATCATGACTTTGGGAAG
GTCACCAAGCAGGAAGTCAAAGACTTTTTTCCGGTGGGCAAAGGATCACGTGGTTGAGGTGGAGCATGA
ATTCTACGTCAAAAAGGGTGGAGCCAAGAAAAGACCCGCCCCCAGTGACGCAGATATAAGTGAGCCCA
AACGGGTGCGCGAGTCAGTTGCGCAGCCATCGACGTCAGACGCGGAAGCTTCGATCAACTACGCAGAC
AGGTACCAAAACAAATGTTCTCGTCACGTGGGCATGAATCTGATGCTGTTTCCCTGCAGACAATGCGA
GAGAATGAATCAGAATTCAAATATCTGCTTCACTCACGGACAGAAAGACTGTTTAGAGTGCTTTCCCG
TGTCAGAATCTCAACCCGTTTCTGTCGTCAAAAAGGCGTATCAGAAACTGTGCTACATTCATCATATC
ATGGGAAAGGTGCCAGACGCTTGCACTGCCTGCGATCTGGTCAATGTGGATTTGGATGACTGCATCTT
TGAACAATAAATGATTTAAATCAGGTATGGCTGCCGATGGTTATCTTCCAGATTGGCTCGAGGACACT
CTCTCTGAAGGAATAAGACAGTGGTGGAAGCTCAAACCTGGCCCACCACCACCAAAGCCCGCAGAGCG
GCATAAGGACGACAGCAGGGGTCTTGTGCTTCCTGGGTACAAGTACCTCGGACCCTTCAACGGACTCG
ACAAGGGAGAGCCGGTCAACGAGGCAGACGCTGCGGCCCTCGAGCACGACAAAGCCTACGACCGGCAG
CTCGACAGCGGAGACAACCCGTACCTCAAGTACAACCACGCCGACGCGGAGTTTCAGGAGCGCCTTAA
AGAAGATACGTCTTTTGGGGGCAACCTCGGACGAGCAGTCTTCCAGGCGAAAAAGAGGGTTCTTGAAC
CTCTGGGCCTGGTTGAGGAACCTGTTAAGACGGCTCCGGGAAAAAAGAGGCCGGTAGAGCACTCTCCT
GTGGAGCCAGACTCCTCCTCGGGAACCGGAAAGGCGGGCCAGCAGCCTGCAAGAAAAAGATTGAATTT
TGGTCAGACTGGAGACGCAGACTCAGTACCTGACCCCCAGCCTCTCGGACAGCCACCAGCAGCCCCCT
CTGGTCTGGGAACTAATACGATGGCTACAGGCAGTGGCGCACCAATGGCAGACAATAACGAGGGCGCC
GACGGAGTGGGTAATTCCTCCGGAAATTGGCATTGCGATTCCACATGGATGGGCGACAGAGTCATCAC
CACCAGCACCCGAACCTGGGCCCTGCCCACCTACAACAACCACCTCTACAAACAAATTTCCAGCCAAT
CAGGAGCCTCGAACGACAATCACTACTTTGGCTACAGCACCCCTTGGGGGTATTTTGACTTCAACAGA
TTCCACTGCCACTTTTCACCACGTGACTGGCAAAGACTCATCAACAACAACTGGGGATTCCGACCCAA
GAGACTCAACTTCAAGCTCTTTAACATTCAAGTCAAAGAGGTCACGCAGAATGACGGTACGACGACGA
TTGCCAATAACCTTACCAGCACGGTTCAGGTGTTTACTGACTCGGAGTACCAGCTCCCGTACGTCCTC
GGCTCGGCGCATCAAGGATGCCTCCCGCCGTTCCCAGCAGACGTCTTCATGGTGCCACAGTATGGATA
CCTCACCCTGAACAACGGGAGTCAGGCAGTAGGACGCTCTTCATTTTACTGCCTGGAGTACTTTCCTT
CTCAGATGCTGCGTACCGGAAACAACTTTACCTTCAGCTACACTTTTGAGGACGTTCCTTTCCACAGC
AGCTACGCTCACAGCCAGAGTCTGGACCGTCTCATGAATCCTCTCATCGACCAGTACCTGTATTACTT
GAGCAGAACAAACACTCCAAGTGGAACCACCACGCAGTCAAGGCTTCAGTTTTCTCAGGCCGGAGCGA
GTGACATTCGGGACCAGTCTAGGAACTGGCTTCCTGGACCCTGTTACCGCCAGCAGCGAGTATCAAAG
ACATCTGCGGATAACAACAACAGTGAATACTCGTGGACTGGAGCTACCAAGTACCACCTCAATGGCAG
AGACTCTCTGGTGAATCCGGGCCCGGCCATGGCAAGCCACAAGGACGATGAAGAAAAGTTTTTTCCTC
AGAGCGGGGTTCTCATCTTTGGGAAGCAAGGCTCAGAGAAAACAAATGTGAACATTGAAAAGGTCATG
ATTACAGACGAAGAGGAAATCGGAACAACCAATCCCGTGGCTACGGAGCAGTATGGTTCTGTATCTAC
CAACCTCCAGAGAGGCAACAGACAAGCAGCTACCGCAGATGTCAACACACAAGGCGTTCTTCCAGGCA
TGGTCTGGCAGGACAGAGATGTGTACCTTCAGGGGCCCATCTGGGCAAAGATTCCACACACGGACGGA
CATTTTCACCCCTCTCCCCTCATGGGTGGATTCGGACTTAAACACCCTCCTCCACAGATTCTCATCAA
GAACACCCCGGTACCTGCGAATCCTTCGACCACCTTCAGTGCGGCAAAGTTTGCTTCCTTCATCACAC
AGTACTCCACGGGACAGGTCAGCGTGGAGATCGAGTGGGAGCTGCAGAAGGAAAACAGCAAACGCTGG
AATCCCGAAATTCAGTACACTTCCAACTACAACAAGTCTGTTAATCGTGGACTTACCGTGGATACTAA
TGGCGTGTATTCAGAGCCTCGCCCCATTGGCACCAGATACCTGACTCGTAATCTGTAATTGCTTGTTA
ATCAATAAACCGTTTAATTCGTTTCAGTTGAACTTTGGTCTCTGCGTATTTCTTTCTTATCTAGTTTC
CATGGCTACGTAGATAAGTAGCATGGCGGGTTAATCATTAACTACAAGGAACCCCTAGTGATGGAGTT
GGCCACTCCCTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGAGAGGGAGTGGCCAA

*FIG. 9*

AAV-3A, COMPLETE SEQUENCE, GENBANK ACCESSION NO. NC_001729 AND
MURAMATSU ET AL. (1996) VIROLOGY 221:208
TTGGCCACTCCCTCTATGCGCACTCGCTCGCTCGGTGGGGCCTGGCGACCAAAGGTCGCCAGACGGACG
TGCTTTGCACGTCCGGCCCCACCGAGCGAGCGAGTGCGCATAGAGGGAGTGGCCAACTCCATCACTAGA
GGTATGGCAGTGACGTAACGCGAAGCGCGCGAAGCGAGACCACGCCTACCAGCTGCGTCAGCAGTCAGG
TGACCCTTTTGCGACAGTTTGCGACACCACGTGGCCGCTGAGGGTATATATTCTCGAGTGAGCGAACCA
GGAGCTCCATTTTGACCGCGAAATTTGAACGAGCAGCAGCCATGCCGGGGTTCTACGAGATTGTCCTGA
AGGTCCCGAGTGACCTGGACGAGCGCCTGCCGGGCATTTCTAACTCGTTTGTTAACTGGGTGGCCGAGA
AGGAATGGGACGTGCCGCCGGATTCTGACATGGATCCGAATCTGATTGAGCAGGCACCCCTGACCGTGG
CCGAAAAGCTTCAGCGCGAGTTCCTGGTGGAGTGGCGCCGCGTGAGTAAGGCCCCGGAGGCCCTCTTTT
TTGTCCAGTTCGAAAAGGGGGAGACCTACTTCCACCTGCACGTGCTGATTGAGACCATCGGGGTCAAAT
CCATGGTGGTCGGCCGCTACGTGAGCCAGATTAAAGAGAAGCTGGTGACCCGCATCTACCGCGGGGTCG
AGCCGCAGCTTCCGAACTGGTTCGCGGTGACCAAAACGCGAAATGGCGCCGGGGCGGGAACAAGGTGG
TGGACGACTGCTACATCCCCAACTACCTGCTCCCAAGACCCAGCCGAGCTCCAGTGGGCGTGGACTA
ACATGGACCAGTATTTAAGCGCCTGTTTGAATCTCGCGGAGCGTAAACGGCTGGTGGCGCAGCATCTGA
CGCACGTGTCGCAGACGCAGGAGCAGAACAAAGAGAATCAGAACCCCAATTCTGACGCGCCGGTCATCA
GGTCAAAAACCTCAGCCAGGTACATGGAGCTGGTCGGGTGGCTGGTGGACCGCGGGATCACGTCAGAAA
AGCAATGGATTCAGGAGGACCAGGCCTCGTACATCTCCTTCAACGCCGCCTCCAACTCGCGGTCCCAGA
TCAAGGCCGCGCTGGACAATGCCTCCAAGATCATGAGCCTGACAAAGACGGCTCCGGACTACCTGGTGG
GCAGCAACCCGCCGGAGGACATTACCAAAAATCGGATCTACCAAATCCTGGAGCTGAACCGGTACGATC
CGCAGTACGCGGCCTCCGTCTTCCTGGGCTGGGCGCAAAAGAAGTTCGGGAAGAGGAACACCATCTGGC
TCTTTGGGCCGGCCACGACGGGTAAAACCAACATCGCGGAAGCCATCGCCCACGCCGTGCCCTTCTACG
GCTGCGTAAACTGGACCAATGAGAACTTTCCCTTCAACGATTGCGTCGACAAGATGGTGATCTGGTGGG
AGGAGGGCAAGATGACGGCCAAGGTCGTGGAGAGCGCCAAGGCCATTCTGGGCGGAAGCAAGGTGCGCG
TGGACCAAAAGTGCAAGTCATCGGCCCAGATCGAACCCACTCCCGTGATCGTCACCTCCAACACCAACA
TGTGCGCCGTGATTGACGGGAACAGCACCACCTTCGAGCATCAGCAGCCGCTGCAGGACCGGATGTTTG
AATTTGAACTTACCCGCCGTTTGACACTTTGGGAAGGTCACCAAACAGGAAGTAAAGGACTTTT
TCCGGTGGGCTTCCGATCACGTGACTGACGTGGCTCATGAGTTCTACGTCAGAAAGGGTGGAGCTAAGA
AACGCCCCGCCTCCAATGACGCGGATGTAAGCGAGCCAAAACGGGAGTGCACGTCACTTGCGCAGCCGA
CAACGTCAGACGCGGAAGCACCGGCGGACTACGCGGACAGGTACCAAAACAAATGTTCTCGTCACGTGG
GCATGAATCTGATGCTTTTTCCCTGTAAAACATGCGAGAGAATGAATCAAATTTCCAATGTCTGTTTTA
CGCATGGTCAAAGAGACTGTGGGGAATGCTTCCCTGGAATGTCAGAATCTCAACCCGTTTCTGTCGTCA
AAAAGAAGACTTATCAGAAACTGTGTCCAATTCATCATATCCTGGGAAGGGCACCCGAGATTGCCTGTT
CGGCCTGCGATTTGGCCAATGTGGACTTGGATGACTGTGTTTCTGAGCAATAAATGACTTAAACCAGGT
ATGGCTGCTGACGGTTATCTTCCAGATTGGCTCGAGGACAACCTTTCTGAAGGCATTCGTGAGTGGTGG
GCTCTGAAACCTGGAGTCCCTCAACCCAAAGCGAACCAACAACACCAGGACAACCGTCGGGTCTTGTG
CTTCCGGGTTACAAATACCTCGGACCCGGTAACGGACTCGACAAAGGAGAGCCGGTCAACGAGGCGGAC
GCGGCAGCCCTCGAACACGACAAAGCTTACGACCAGCAGCTCAAGGCCGGTGACAACCCGTACCTCAAG
TACAACCACGCCGACGCCGAGTTTCAGGAGCGTCTTCAAGAAGATACGTCTTTTGGGGGCAACCTTGGC
AGAGCAGTCTTCCAGGCCAAAAAGAGGGATCCTTGAGCCTCTTGGTCTGGTTGAGGAAGCAGCTAAAACG
GCTCCTGGAAAGAAGGGGCTGTAGATCAGTCTCCTCAGGAACCGGACTCATCATCTGGTGTTGGCAAA
TCGGGCAAACAGCCTGCCAGAAAAAGACTAAATTTCGGTCAGACTGGAGACTCAGAGTCAGTCCCAGAC
CCTCAACCTCTCGGAGAACCCACCAGCAGCCCCCACAGATTTTGGGATTCAATACAATGGCTTCAGGCGGT
GGCGCACCAATGGCAGACAATAACGAGGGTGCCGATGGAGTGGGTAATTCCTCAGGAAATTGGCATTGC
GATTCCCAATGGCTGGGCGACAGAGTCATCACCACCAGCACCAGAACCTGGGCCCTGCCCACTTACAAC
AACCATCTCTACAAGCAAATCTCCAGCCAATCAGGAGCTTCAAACGACAACCACTACTTTGGCTACAGC
ACCCCTTGGGGGTATTTTGACTTTAACAGATTCCACTGCCACTTCTCACCACGTGACTGGCAGCGACTC
ATTAACAACAACTGGGGATTCCGGCCCAAGAAACTCAGCTTCAAGCTCTTCAACATCCAAGTTAGAGGG
GTCACGCAGAACGATGGCACGACGACTATTGCCAATAACCTTACCAGCACGGTTCAAGTGTTTACGGAC
TCGGAGTATCAGCTCCCGTACGTGCTCGGGTCGGCGCACCAAGGCTGTCTCCCGCGTTTCCAGCGGAC
GTCTTCATGGTCCCTCAGTATGGATACCTCACCCTGAACAACGGAAGTCAAGCGGTGGGACGCTCATCC
TTTTACTGCCTGGAGTACTTCCCTTCGCAGATGCTAAGGACTGGAAATAACTTCCAATTCAGCTATACC
TTCGAGGATGTACCTTTTCACAGCAGCTACGCTCACAGCCAGAGTTTGGATCGCTTGATGAATCCTCTT
ATTGATCAGTATCTGTACTACCTGAACAGAACAACCAACCTCTGGAACCAACCTCTGGAAAAACAATCACGG
CTGCTTTTTAGCCAGGCTGGGCCTCAGTCTATGTCTTTGCAGGCCAGAAATTGGCTACCTGGGCCCTGC
TACCGGCAACAGAGACTTTCAAAGACTGCTAACGACAACAACAACAGTAACTTTCCTTGGACAGCGGCC
AGCAAATATCATCTCAATGGCCGCGACTCGCTGGTGAATCCAGGACCAGCTATGGCCAGTCACAAGGAC
GATGAAGAAAAATTTTTCCCTATGCACGGCAACCTTATATTTGGCAAAGAAGGGACAACGGCAAGTAAC
GCAGAATTAGATAATGTAATGATTACGGATGAAGAAGAGATTCGTACCACCAATCCTGTGGCAACAGAG
CAGTATGGAACTGTGGCAAATAACTTGCAGAGCTCAAATACAGCTCCCACGACTGGAACTGTCAATCAT
CAGGGGGCCTTACCTGGCATGGTGTGGCAAGATCGTGACGTGTACCTTCAAGGACCTATCTGGGCAAAG
ATTCCTCACACGGATGGACACTTTCATCCTTCCTCTGATGGGAGGCTTTGGACTGAAAACATCCGCCT
CCTCAAATCATGATCAAAAATACTCCGGTACCGCAAATCCTCCGACACTTTCAGCCCGGCCAAGTTT
GCTTCATTTATCACTCAGTACTCCACTGGACAGGTCAGCGTGGAAATTGAGTGGGAGCTACAGAAAGAA
AACAGCAAACGTTGGAATCCAGAGATTCAGTACACTTCCAACTACAACAAGTCTGTTAATGTGGACTTT
ACTGTAGACACTAATGGTGTTTATAGTGAACCTCGCCCTATTGGAACCCGGTATCTCACACGAAACTTG
TGAATCCTGGTTAATCAATAAACCGTTTAATTCGTTTCAGTTGAACTTTGGCTCTTGTGCACTTCTTTA
TCTTTATCTTGTTTCCATGGCTACTGCGTAGATAAGCAGCGGCCTGCGGCGCTTGCGCTTCGCGGTTTA
CAACTGCTGGTTAATATTTAACTCTCGCCATACCTCTAGTGATGGAGTTGGCCACTCCCTCTATGCGCA
CTCGCTCGCTCGGTGGGGCCTGGCGACCAAAGGTCGCCAGACGGACGTGCTTTGCACGTCCGGCCCCAC
CGAGCGAGCGAGTGCGCATAGAGGGAGTGGCCAA

FIG. 10

AAV-3B, COMPLETE SEQUENCE, GENBANK ACCESSION NO. NC_001863
TGGCCACTCCCTCTATGCGCACTCGCTCGCTCGGTGGGGCCTGGCGACCAAAGGTCGCCAGACGGACGT
GCTTTGCACGTCCGGCCCCACCGAGCGAGCGAGTGCGCATAGAGGGAGTGGCCAACTCCATCACTAGAG
GTATGGCAGTGACGTAACGCGAAGCGCGCGAAGCGAGACCAGGCCTACCAGCTGCGTCAGCAGTCAGGT
GACCCTTTTGCGACAGTTTGCGACACCACGTGGCCGCTGAGGGTATATATTCTCGAGTGAGCGAACCAG
GAGCTCCATTTTGACCGCGAAATTTGAACGAGCAGCAGCCATGCCGGGGTTCTACGAGATTGTCCTGAA
GGTCCCGAGTGACCTGGACGAGCACCTGCCGGGCATTTCTAACTCGTTTGTTAACTGGGTGGCCGAGAA
GGAATGGGAGCTGCCGCCGGATTCTGACATGGATCCGAATCTGATTGAGCAGGCACCCCTGACCGTGGC
CGAAAAGCTTCAGCGCGAGTTCCTGGTGGAGTGGCGCCGCGTGAGTAAGGCCCCGGAGGCCCTCTTTTT
TGTCCAGTTCGAAAAGGGGGAGACCTACTTCCACCTGCACGTGCTGATTGAGACCATCGGGGTCAAATC
CATGGTGGTCGGCCGCTACGTGAGCCAGATTAAAGAGAAGCTGGTGACCCGCATCTACCGCGGGGTCGA
GCCGCAGCTTCCGAACTGTTCGCGGTGACCAAAACGCGAAATGGCGCCGGGGGCGGGAACAAGGTGGT
GGACGACTGCTACATCCCCAACTACCTGCTCCCCAAGACCCAGCCCGAGCTCCAGTGGGCGTGGACTAA
CATGGACCAGTATTTAAGCGCCTGTTTGAATCTCGCGGAGCGTAAACGGCTGGTGGCGCAGCATCTGAC
GCACGTGTCGCAGACGCAGGAGCAGAACAAAGAGAATCAGAACCCCAATTCTGACGCGCCGGTCATCAG
GTCAAAAACCTCAGCCAGGTACATGGAGCTGGTCGGGTGGCTGGTGGACGGCGGGATCACGTCAGAAAA
GCAATGGATTCAGGAGGACCAGGCCTCGTACATCTCCTTCAACGCCGCCTCCAACTCGCGGTCCCAGAT
CAAGGCCGCGCTGGACAATGCCTCCAAGATCATGAGCCTGACAAAGACGGCTCCGGACTACCTGGTGGG
CAGCAACCCGCCGGAGGACATTACCAAAAATCGGATCTACCAAATCCTGGAGCTGAACGGGTACGATCC
GCAGTACGCGGCCTCCGTCTTCCTGGGCTGGGCGCAAAAGAAGTTCGGGAAGAGGAACACCATCTGGCT
CTTTGGGCCGGCCACGACGGGTAAAACCAACATCGGAAGCCATCGCCCACGCCGTGCCCTTCTACGG
CTGCGTAAACTGGACCAATGAGAACTTTCCCTTCAACGATTGCGTCGACAAGATGGTGATCTGGTGGGA
GGAGGGCAAGATGACGGCCAAGGTCGTGGAGAGCGCCAAGGCCATTCTGGGCGGAAGCAAGGTGCGCGT
GGACCAAAAGTGCAAGTCATCGGCCCAGATCGAACCCACTCCCGTGATCGTCACCTCCAACACCAACAT
GTGCGCCGTGATTGACGGGAACAGCACCACCTTCGAGCATCAGCAGCCGCTGCAGGACCGGATGTTTAA
ATTTGAACTTACCCGCCGTTTGGACCATGACTTTGGGAAGGTCACCAAACAGGAAGTAAAGGACTTTTT
CCGGTGGGCTTCCGATCACGTGACTGACGTGGCTCATGAGTTCTACGTCAGAAAGGGTGGAGCTAAGAA
ACGCCCCGCCTCCAATGACGCGGATGTAAGCGAGCCAAAACGGCAGTGCACGTCACTTGCGCAGCCGAC
AACGTCAGACGCGGAAGCACCGGCGGACTACGCGGACAGGTACCAAAACAAATGTTCTCGTCACGTGGG
CATGAATCTGATGCTTTTTCCCTGTAAAACATGCGAGAGAATGAATCAAATTTCCAATGTCTGTTTTAC
GCATGGTCAAAGAGACTGTGGGGAATGCTTCCCTGGAATGTCAGAATCTCAACCCGTTTCTGTCGTCAA
AAAGAAGACTTATCAGAAACTGTGTCCAATTCATCATATCCTGGGAAGGGCACCCGAGATTGCCTGTTC
GGCCTGCGATTTGGCCAATGTGGACTTGGATGACTGTGTTTCTGAGCAATAAATGACTTAAACCAGGTA
TGGCTGCTGACGGTTATCTTCCAGATTGGCTCGAGGACAACCTTTCTGAAGGCATTCGTGAGTGGTGGG
CTCTGAAACCTGGAGTCCCTCAACCCAAAGCGAACCAACAACACCAGGACAACCGTCGGGGTCTTGTGC
TTCCGGGTTACAAATACCTCGGACCCCGGTAACGGACTCGACAAAGGAGAGCCGGTCAACGAGGCGGACG
CGGCAGCCCTCGAACACGACAAAGCTTACGACCAGCAGCTCAAGGCCGGTGACAACCCGTACCTCAAGT
ACAACCACGCCGACGCCGAGTTTCAGGAGCGTCTTCAAGAAGATACGTCTTTTGGGGGCAACCTTGGCA
GAGCAGTCTTCCAGGCCCAAAAAGGAGGATCCTTGAGGCCTCTTGGTCTGGTTGAGGAAGCAGCTAAAACGG
CTCCTGGAAAGAAGAGGCCTGTAGATCAGTCTCCTCAGGAACCGGACTCATCATCTGGTGTTGGCAAAT
CGGGCAAACAGCCTGCCAGAAAAAGACTAAATTTCGGTCAGACTGGCGACTCAGAGTCAGTCCCAGACC
CTCAACCTCTCGGAGAACCACCAGCAGCCCCCACAAGTTTGGGATCTAATACAATGGCTTCAGGCGGTG
GCGCACCAATGGCAGACAATAACGAGGGTGCCGATGGAGTGGGTAATTCCTCAGGAAATTGGCATTGCG
ATTCCCAATGGCTGGGCGACAGAGTCATCACCACCAGCACCAGAACCTGGGCCTGCCCACTTACAACA
ACCATCTCTACAAGCAAATCTCCAGCCAATCAGGAGCTTCAAACGACAACCACTACTTTGGCTACAGCA
CCCCTTGGGGGTATTTTGACTTTAACAGATTCCACTGCCACTTCTCACCACGTGACTGGCAGCGACTCA
TTAACAACAACTGGGGATTCCGGCCCAAGAAACTCAGCTTCAAGCTCTTCAACATCCAAGTTAAAGAGG
TCACGCAGAACGATGGCACGACGACTATTGCCAATAACCTTACCAGCACGGTTCAAGTGTTTACGGACT
CGGAGTATCAGCTCCCGTACGTGCTCGGGTCGGCGCACCAAGGCTGTCTCCCGCCGTTTCCAGCGGACG
TCTTCATGGTCCCTCAGTATGGATACCTCACCCTGAACAACGGAAGTCAAGCGGTGGGACGCTCATCCT
TTTACTGCCTGGAGTACTTCCCTTCGCAGATGCTAAGGACTGGAAATAACTTCCAATTCAGCTATACCT
TCGAGGATGTACCTTTTCACAGCAGCTACGCTCACAGCCAGAGTTTGGATCGCTTGATGAATCCTCTTA
TTGATCAGTATCTGTACTACCTGAACAGAACGCAAGGAACAACCTCTGGAACAACCAACCAATCACGGC
TGCTTTTTAGCCAGGCTGGGCCTCAGTCTATGTCTTTGCAGGCCAGAAATTGGCTACCTGGGCCCTGCT
ACCGGCAACAGAGACTTTCAAAGACTGCTAACGACAACAACAACAGTAACTTTCCTTGGACAGCGGCCA
GCAAATATCATCTCAATGGCCGCGACTCGCTGGTGAATCCAGGACCAGCTATGGCCAGTCACAAGGACG
ATGAAGAAAATTTTTCCCTATGCACGGCAATCTAATATTTGGAAAGAAGGGACAACGGCAAGTAACG
CAGAATTAGATAATGTAATGATTACGGATGAAGAAGAGATTCGTACCACCAATCCTGTGGCAACAGAGC
AGTATGGAACTGTGGCAAATAACTTGCAGAGCTCAAATACAGCTCCCACGACTAGAACTGTCAATGATC
AGGGGGCCTTACCTGGCATGGTGTGGCAAGATCGTGACGTGTACCTTCAAGGACCTATCTGGGCAAAGA
TTCCTCACACGGATGGACACTTTCATCCTTCTCCTCTGATGGGAGGCTTTGGACTGAAACATCCGCCTC
CTCAAATCATGATTCAAAAATACTCCGGTACCGGCAAATCTCCGACGACTTTCAGCCGCCGGCCAAGTTTG
CTTCATTTATCACTCAGTACTCCACTGGACAGGTCAGCGTGGAAATTGAGTGGGAGCTACAGAAAGAAA
ACAGCAAACGTTGGAATCCAGAGATTCAGTACACTTCCAACTACAACAAGTCTGTTAATGTGGACTTTA
CTGTAGACACTAATGGTGTTTATAGTGAACCTCGCCCTATTGGAACCGGTATCTCACACGAAACTTGT
AATCCTGGTTAATCAATAAACCGTTTAATTCGTTTCAGTTGAACTTTGGCTCTTGTGCACTTCTTATCT
TATCTTGTTTCCATGGCTACTGCGTAGATAAGCAGCGGCCTGCGGCGCTTGCGCTTCGCGGTTTACAAC
TGCTGGTTAATATTTAACTCTCGCCATACCTCTAGTGATGGAGTTGGCCACTCCCTCTATGCGCACTCG
CTCGCTCGGTGGGCCGGACGTGCAAAGCACGTCCGTCTGGCGACCTTTGGTCGCCAGGCCCCACCGAG
CGAGCGAGTGCGCATAGAGGGAGTGGCCAA

FIG. 11

AAV-4, COMPLETE SEQUENCE, GENBANK ACCESSION NO. NC_001829 AND
CHIORINI AT AL. (1997) J. VIROL. 71:6823
TTGGCCACTCCCTCTATGCGCGCTCGCTCACTCACTCGGCCCTCGGAGACCAAAGGTCTCCAGACTGCCG
GCCTCTGGCCGGCAGGGCCGAGTGAGTGAGCGAGCGCGCATAGAGGGAGTGGCCAACTCCATCATCTAG
GTTTGCCCACTGACGTCAATGTGACGTCCTAGGGTTAGGGAGGTCCCTGTATTAGCAGTCACGTGAGTG
TCGTATTTCGCGGAGCGTAGCGGAGCGCATACCAAGCTGCCACGTCACAGCCACGTGGTCCGTTTGCGA
CAGTTTGCGACACCATGTGGTCAGGAGGGTATATAACCGCGAGTGAGCCAGCGAGGAGCTCCATTTTGC
CCGCGAATTTTTGAACGAGCAGCAGCCATGCCGGGGTTCTACGAGATCGTGCTGAAGGTGCCCAGCGACC
TGGACGAGCACCTGCCCGGCATTTCTGACTCTTTTGTGAGCTGGGTGGCCGAGAAGGAATGGGAGCTGC
CGCCGGATTCTGACATGGACTTGAATCTGATTGAGCAGGCACCCCTGACCGTGGCCGAAAAGCTGCAAC
GCGAGTTCCTGGTCGAGTGGCGCCGCGTGAGTAAGGCCCCGGAGGCCCTCTTCTTTGTCCAGTTCGAGA
AGGGGACAGCTACTTCCACCGTGCACATCTGGTGGAGACACGTGGGCGTCAAATCCATGGTGGTGGGCC
GCTACGTGAGCCAGATTAAAGAGAAGCTGGTGACCCGCATCTACCGCGGGGTCGAGCCGCAGCTTCCGA
ACTGGTTCGCGGTGACCAAGACGCGTAATGGCGCCGGAGGCGGGAACAAGGTGGTGGACGACTGCTACA
TCCCCAACTACCTGCTCTCCCCAAGACCCAGCCCGAGCTCCAGTGGGCGTGGACTAACATGGACCAGTATA
TAAGCGCCTGTTTGAATCTCGCGGAGCGTAAACGGCTGGTGGCGCAGCATCTGACGCACGTGTCGCAGA
CGCAGGAGCAGAACAAGGAAAACCAGAACCCCAATTCTGACGCGCCGGTCATCAGGTCAAAAACCTCCG
CCAGGTACATGGAGCTGGTCGGGTGGCTGGTGGACCGCGGGATCACGTCAGAAAAGCAATGGATCCAGG
AGGACCAGGCGTCCTACATCTCCTTCAACGCCGCCTCCAACTCGCGGTCACAAATCAAGGCCGCGCTGG
ACAATGCCTCCAAAATCATGAGCCTGACAAAGACGCTCCGGACTACCTGGTGGGCCAGAACCCGCCGG
AGGACATTTCCAGCAACCGCATCTACCGAATCCTCGAGATGAACGGGTACGATCCGCAGTACGCGGCCT
CCGTCTTCCTGGGCTGGGCGCAAAAGAAGTTCGGGAAGAGGAACACCATCTGGCTCTTTGGGCCGGCCA
CGACGGGTAAAACCAACATCGCGGAAGCCATCGCCCACGCCGTGCCCTTCTACGGCTGCGTGAACTGGA
CCAATGAGAACTTTCCGTTCAACGATTGCGTCGACAAGATGGTGATCTGGTGGGAGGAGGGCAAGATGA
CGGCCAAGGTCGTAGAGAGCGCCAAGGCCATCCTGGGCGGAAGCAAGGTGCGCGTGGACCAAAAGTGCA
AGTCATCGGCCCAGATCGACCCAACTCCCGTGATCGTCACCTCCAACACCAACATGTGCGCGGTCATCG
ACGGAAACTCGACCACCTTCGAGCACCAACAACCACTCCAGGACCGGATGTTCAAGTTCGAGCTCACCA
AGCGCCTGGAGCACGACTTTGGCAAGGTCACCAAGCAGGAAGTCAAAGACTTTTTTCCGGTGGGCGTCAG
ATCACGTGACCGAGGTGACTCACGAGTTTTACGTCAGAAAGGGTGGAGCTAGAAAGAGGCCCGCCCCCA
ATGACGCAGATATAAGTGAGCCCAAGCGGGCCTGTCCGTCAGTTGCGCAGCCATCGACGTCAGACGCGG
AAGCTCCGGTCGACTACGCGGACAGGTACCAAAACAAATGTTCTCGTCACGTGGGTATGAATCTGATGC
TTTTTTCCCTGCCGGCAATGCGAGAGAATGAATCAGAATGTGGACATTTGCTTCACGCACGGGGTCATGG
ACTGTGCCGAGTGCTTCCCCGTGTCAGAATCTCAACCCGTGTCTGTCGTCAGAAAGCGGACGTATCAGA
AACTGTGTCCGATTCATCACATCATGGGGAGGGCGCCCGAGGTGGCCTGCTCGGCCTGCGAACTGGCCA
ATGTGGACTTGGATGACTGTGACATGGAACAATAAATGACTCAAACCAGATATGACTGACGGTTACCTT
CCAGATTGGCTAGAGGACAACCTCTCTGAAGGCGTTCGAGAGTGGTGGGCGCTGCAACCTGGAGCCCCT
AAACCCAAGGCAAATCAACAACATCAGGACAACGCTCGGGGTCTTGTGCTTCCGGGTTACAAATACCTC
GGACCCGGCAACGGACTCGACAAGGGGGAACCCGTCAACGCAGCGGACGCGGCCCTCGAGCACGAC
AAGGCCTACGACCAGCAGCTCAAGGCCGGTGACAACCCCTACCTCAAGTACAACCACGCCGACGCGGAG
TTCCAGCAGCGGCTTCAGGGCGACACATCGTTTGGGGGCAACCTCGGCAGAGCAGTCTTCCAGGCCAAA
AAGAGGGTTCTTGAACCTCTTGGTCTGGTTGAGCAAGCGGGTGAGACGGCTCCTGGAAAGAAGAGACCG
TTGATTGAATCCCCCCACGAGCCCGACTCCTCCACGGGTATCGGCAAAAAAGGCAAGCAGCCGGCTAAA
AAGAAGCTCGTTTTTCGAAGACGAAACTGGAGCAGGCGACGGACCCCCTGAGGGATCAACTTCCGGAGCC
ATGTCTGATGACAGTGAGATGCGTGCAGCAGCTGGCGGAGCTGCAGTCGAGGGCGGACAAGGTGCCGAT
GGAGTGGGTAATGCCTCGGGTGATTGGCATTGCGATTCCACCTGGTCTGAGGGCCACGTCACGACCACC
AGCACCAGAACCTGGTCTTGCCCAACTACAACCACCTCTACAAGCGACTCGGGAGAGAGCCTGCAG
TCCAACACCTACAACGGATTCTCCACCCCCTGGGGATACTTTGACTTCAACCGCTTCCACTGCCACTTC
TCACCACGTGACTGGCAGCGACTCATCAACAACAACTGGGGCATGCGACCCAAAGCCATGCGGGTCAAA
ATCTTCAACATCCAGGTCAAGGAGGTCACGACGTCGAACGGCGAGACAACGGTGGCTAATAACCTTACC
AGCACGGTTCAGATCTTTTGCGGACTCGTCGTACGAAACTGCCGTACGTGATGGATGCGGGTCAAGAGGGC
AGCCTGCCTCCTTTTCCCAACGACGTCTTTATGGTGCCCCAGTACGGCTACTGTGGACTGGTGACCGGC
AACACTTCGCAGCAACAGACTGACAGAAATGCCTTCTACTGCCTGGAGTACTTTCCTTCGCAGATGCTG
CGGACTGGCAACAACTTTGAAATTACGTACAGTTTTGAGAAGGTGCCTTTCCACTCGATGTACGCGCAC
AGCCAGAGCCTGGACCGCCTGATGAACCCTCTCATCGACCAGTACCTGTGGGGACTGCAATCGACCACC
ACCGGAACCACCCTGAATGCCGGGACTGCCACCACCAACTTTACCAAGCTGCGGCCTACCAACTTTTCC
AACTTTAAAAAGAACTGGCTGCCCGGGCCTTCAATCAAGCAGCAGGGCTTCTCAAAGACTGCCAATCAA
AACTACAAGATCCCTGCCACCGGGTCAGACAGTCTCATCAAATACGAGACGCACAGCACTCTGGACGGA
AGATGGAGTGCCCTGACCCCCGGACCTCCAATGGCCACGGCTGGACCTGCGGACAGCAAGTTCAGCAAC
AGCCAGCTCATCTTTGCGGACTGCTAAACAGAACGGCAACACGGCCACCGTACCCGGGACTCTGATCTTC
ACCTCTGAGGAGGAGCTGGCAGCCACCAACGCCACCGATACGGACATGTGGGGCAACCTACCTGGCGGT
GACCAGAGCAACAGCAACCTGCCGACCGTGGACAGACTGAACAGCCTTTGGAGCCGTGCCTGGAATGGTC
TGGCAAAACAGAGACATTTACTACCAGGGTCCCATTTGGGCCAAGATTCCTCATACCGATGGACACTTT
CACCCCTCACCGCTGATTGGTGGGTTTGGGCTGAAACACCCGCCTCCTCAAATTTTTATCAAGAACACC
CCGGTACCTGCGAATCCTGCAACGACCTTCAGCTCTACTCCGGTAAACTCCTTCATTACTCAGTACAGC
ACTGGCCAGGTGTCGGTGCAGATTGACTGGGAGATCCAGAAGGAGCGCTCCAAACGCTGGAACCCCGAG
GTCCAGTTTACCTCCAACTACGGACAGCAAAACTCTCTGTTGTGGGCTCCCGATGCGGCTGGGAAATAC
ACTGAGCCTAGGGCTATCGGTACCCGCTACCTCACCCACCACCTGTAATAACCTGTTAATCAATAAACC
GGTTTATTCGTTTCAGTTGAACTTTGGTCTCCGTGTCCTTCTTATCTTATCTCGTTTCCATGGCTACTG
CGTACATAAGCAGCGGCCTGCGCGCGCTTGCGCTTCGGCGTTTACAACTGCGGTTTAATCAGTAACTTCT
GGCAAACCAGATGATGGAGTTGGCCACATTAGCTATGCGGCGCTCGCTCACTCACTCGGCCCTGGAGACC
AAAGGTCTCCAGACTGCCGGCCTCTGGCCGGCAGGGCCGAGTGAGTGAGCGAGCGCGCATAGAGGGAGT
GGCCAA

*FIG. 12*

AAV-5, COMPLETE SEQUENCE, GENBANK ACCESSION NO. NC_006152 AND CIORINI
ET AL. (1999) J. VIROL. 73:1309
CTCTCCCCCCTGTCGCGTTCGCTCGCTCGCTGGCTCGTTTGGGGGGGTGGCAGCTCAAAGAGCTGCCAG
ACGACGGCCCTCTGGCCGTCGCCCCCCAAACGAGCCAGCGAGCGAGCGAACGCGACAGGGGGGAGAGT
GCCACACTCTCAAGCAAGGAGGTTTTGTAAGCAGTGATGTCATAATGATGTAATGCTTATTGTCACGCG
ATAGTTAATGATTAACAGTCATGTGATGTGTTTTATCCAATAGGAAGAAAGCGCGCGTATGAGTTCTCG
CGAGACTTCCGGGGTATAAAAGACCGAGTGAACGAGCCCGCCGCCATTCTTTGCTCTGGACTGCTAGAG
GACCCTCGCTGCCATGGCTACCTTCTATGAAGTCATTGTTCGCGTCCCATTTGACGTGGAGGAACATCT
GCCTGGAATTTCTGACAGCTTTGTGGACTGGGTAACTGGTCAAATTTGGGAGCTGCCTCCAGAGTCAGA
TTTAAATTTGACTCTGGTTGAACAGCCTCAGTTGACGGTGGCTGATAGAATTCGCCGCGTGTTCCTGTA
CGAGTGGAACAAATTTTCCAAGCAGGAGTCCAAATTCTTTGTGCAGTTTGAAAAGGGATCTGAATATTT
TCATCTGCACACGCTTGTGGAGACCTCCGGCATCTCTTCCATGGTCCTCGGCCGCTACGTGAGTCAGAT
TCGCGCCAGCTGGTGAAAGTGGTCTTCCAGGGAATTGAACCCCAGATCAACGACTGGGTCGCCATCAC
CAAGGTAAAGAAGGGCGGAGCCAATAAGGTGGTGGATTCTGGGTATATTCCCGCCTACCTGCTGCCGAA
GGTCCAACCGGAGCTTCAGTGGGCGTGGACAAACCTGGACGAGTATAAATTGGCCGCCCTGAATCTGGA
GGAGCGCAAACGGCTCGTCGCGCAGTTTCTGGCAGAATCCTCGCAGCGCTCGCAGGAGGCGGCTTCGCA
GCGTGAGTTCTCGGCTGACCCGGTCATCAAAAGCAAGACTTCCAGAAATACATGGCGCTCGTCAACTG
GCTCGTGGAGCACGGCATCACTTCCGAGAAGCAGTGGATCCAGGAAAATCAGGAGAGCTACCTCTCCTT
CAACTCCACCGGCAACTCTCGGAGCCAGATCAAGGCCGCGCTCGACAACGCGACCAAAATTATGAGTCT
GACAAAAAGCGCGGTGGACTACCTCGTGGGGAGCTCCGTTCCCGAGGACATTTCAAAAAACAGAATCTG
GCAAATTTTTGAGATGAATGGCTACGACCCGGCCTACGCGGGATCCATCCTCTACGGCTGGTGTCAGCG
CTCCTTCAACAAGAGGAACACCGTCTGGCTCTACGGACCCGCCACGACCGGCAAGACCAACATCGCGGA
GGCCATCGCCCACACTGTGCCCTTTTACGGCTGCGTGAACTGGACCAATGAAAACTTTCCCTTTAATGA
CTGTGTGGACAAAATGCTCATTTGGTGGGAGGAGGGAAAGATGACCAACAAGGTGGTTGAATCCGCCAA
GGCCATCCTGGGGGGCTCAAAGGTGCGGGTCGATCAGAAATGTAAATCCTCTGTTCAAATTGATTCTAC
CCCTGTCATTGTAACTTCCAATACAAACATGTGTGTGGTGGTGGATGGGAATTCCACGACCTTTGAACA
CCAGCAGCCGCTGGAGGACCGCATGTTCAAATTTGAACTGACTAAGCGGCTCCCCGCCAGATTTTGCAA
GATTACTAAGCAGGAAGTCAAGGACTTTTTTTGCTTGGGCAAAGGTCAATCAGGTGCCGGTGACTCACGA
GTTTAAAGTTCCCAGGGAATTGGCGGGAACTAAAGGGGCGGAGAAATCTCTAAAACGCCCACTGGGTGA
CGTCACCAATACTAGCTATAAAAGTCTGGAGAAGCGGGCCAGGCTCTCATTTGTTCCCGAGACGCCTCG
CAGTTCAGACGTGACTGTTGATCCCGCTCCTCTGCGACCGCTCAATTGGAATTCAAGGTATGATTGCAA
ATGTGACTATCATGCTCAATTTGACAACATTTCTAACAAATGTGATGAATGTGAATATTTGAATCGGGG
CAAAAATGGATGTATCTGTCACAATGTAACTCACTGTCAAATTTGTCATGGGATTCCCCCCTGGGAAAA
GGAAAAACTTGTCAGATTTTGGGGATTTTGACGATGCCAATAAAGAACAGTAAATAAAGCGAGTAGTCAT
GTCTTTTGTTGATCACCCTCCAGATTGGTTGGAAGAAGTTGGTGAAGGTCTTCGCGAGTTTTTTGGGCCT
TGAAGCGGGCCCACCGAAACCAAAACCCAATCAGCAGCATCAAGATCAAGCCCGTGGTCTTGTGCTGCC
TGGTTATAACTATCTCGGACCCGGAAACGGTCTCGATCGAGGAGAGCCTGTCAACAGGGCAGACGAGGT
CGCGCGAGAGCACGACATCTCGTACAACGAGCAGCTTGAGGCGGGAGACAACCCCTACCTCAAGTACAA
CCACGCGGACGCCGAGTTTCAGGAGAAGCTCGCGGACGACACATCCTTCGGGGGGAAACCTCGGAAAGGC
AGTCTTTCAGGCCAAGAAAAGGGTTCTCGAACCTTTTGGCCTGGTTGAAGAGGGTGCTAAGACGCCCC
TACCGGAAAGCGGATAGACGACCACTTTCCAAAAAGAAAGAAGGCTCGGACCGAAGAGGACTCCAAGCC
TTCCACCTCGTCAGCACGCCGAAGCTGGACCCAGCGGATCCCAGCCGCCTGCAAATCCCAACCAAACAGC
CTCAAGTTTGGGAGCTGATACAATGTCTGCCGGAGGTGGCGGCCCATTGGGCGACAATAACCAAGGTGC
CGATGGAGTGGGCAATGCCTCGGGAGATTGGCATTGCGATTCCACGTGGATGGGGGACAGAGTCGTCAC
CAAGTCCACCCGAACCCTGGGTGCTGCCCAGCTACAACAACCACCAGTACCGAGAGATCAAAAGCGGCTC
CGTCGACGGAAGCAACGCCAACGCCTACTTTGGATACAGCACCCCCTGGGGGTACTTTGACTTTAACCG
CTTCCACAGCCACTGGAGCCCCCGAGACTGGCAAAGACTCATCAACAACTACTGGGGCTTCAGACCCCG
GTCCCTCAGAGTCAAAATCTTCAACATTCAAGTCAAAGAGGTCACGGTGCAGGACTCCACCACCACCAT
CGCCAACAACCTCACCTCCACCGTCCAAGTGTTTACGGACGACGACTACCAGCTGCCCTACGTCGTCGG
CAACGGGACCGAGGGATGCCTGCCGGCCTTCCCTCCGCAGGTCTTTACGCTGCCGCAGTACGGTTACGC
GACGCTGAACCGCGACAACACAGAAATCCCACCGGAGGAGCAGCTTCTTCTGCCTAGAGTACTTTCC
CAGCAAGATGCTGAGAACGGGCAACAACTTTGAGTTTACCTACAACTTTGAGGAGGTGCCCTTCCACTC
CAGCTTCGCTCCCAGTCAGAACCTCTTCAAGCTGGCCAACCCGCTGGTGGACCAGTACTTGTACCGCTT
CGTGAGCACAAATAACACTGGCGGAGTCCAGTTCAACAAGAACCTGGCCGGGAGATACGCCAACACCTA
CAAAAACTGGTTCCCGGGGCCCATGGGCCGAACCCAGGGCTGGAACCTGGGCTCCGGGGTCAACCGCGC
CAGTGTCAGCGCCTTCGCCACGACCAATAGGATGGAGCTCGAGGGCGCGAGTTACCAGGTGCCCCCGCA
GCCGAACGGCATGACCAACAACCTCCAGGGCAGCAACACCTATGCCCTGGAGAACACTATGATCTTCAA
CAGCCAGCCGGCGAACCCGGGCACCACCGCGACCTACCTCGAGGGCAACATGCTCATCACCAGCGAGAG
CGAGACGCAGCCGGTGAACCGTGTGGCGTACAACGTCGGCGGGCAGATGGCCACCAACAACCAGAGCTC
CACCACTGCCCCCGCGACCGGCACGTACAACCTCCAGGAAATCGTGCCGGGCAGCGTGTGGATGGAGAG
GGACGTGTACCTCCAAGGACCCATCTGGGCCAAGATCCCAGAGACGGGGGCGCACTTTCACCCCTCTCC
GGCCATGGCGGATTTCGGACTCAAACACCCCACGCCCATGATGCTCATCAAGAACACGCCTGTCCCGGG
AAATATCACCAGCTTCTCGGACGTGCCCGTCAGCAGCTTCATCACCCAGTACAGCACCGGGCAGGTCAC
CGTGGAGATGGAGTGGGAGCTCAAGAAGGAAAACTCCAAGAGGTGGAACCCAGAGATCCAGTACACAAA
CAACTACAACGACCCCCAGTTTGTGGACTTTGCCCCGGACAGCACCGGGGAATACAGAACCACCAGACC
TATCGGAACCCGATACCTTACCCGACCCCCCTTTAACCCATTCATGTCGCATACCCTCAATAAACCGTGTA
TTCGTGTCAGTAAAATACTGCCTCTTGTGGTCATTCAATGAATAACAGCTTACAACATTTACAAAACCT
CCTTGCTTGAGAGTGTGGCACTCTCCCCCCTGTCGCGTTCGCTCGCTCGCTGGCTCGTTTGGGGGGCG
ACGGCCAGAGGGCCGTCGTCTGGCAGCTCTTTGAGCTGCCACCCCCCAAACGAGCCAGCGAGCGAGCG
AACGCGACAGGGGGGAGAG

FIG. 13

```
AAV-6, COMPLETE SEQUENCE, GENBANK ACCESSION NO. NC_001862
TTGGCCACTCCCTCTCTGCGCGCTCGCTCGCTCACTGAGGCCGGGCGACCAAAGGTCGCCCGACGCCCG
GGCTTTGCCCGGGCGGCCTCAGTGAGCGAGCGAGCGCGCAGAGAGGGAGTGGCCAACTCCATCACTAGG
GGTTCCTGGAGGGGTGGAGTCGTGACGTGAATTACGTCATAGGGTTAGGGAGGTCCTGTATTAGAGGTC
ACGTGAGTGTTTTGCGACATTTTGCGACACCATGTGGTCACGCTGGGTATTTAAGCCCGAGTGAGCACG
CAGGGTCTCCATTTTGAAGCGGGAGGTTTGAACGCGCAGCGCCATGCCGGGGTTTTACGAGATTGTGAT
TAAGGTCCCCAGCGACCTTGACGAGCATCTGCCCGGCATTTCTGACAGCTTTGTGAACTGGGTGGCCGA
GAAGGAATGGGAGTTGCCGCCAGATTCTGACATGGATCTGAATCTGATTGAGCAGGCACCCCTGACCGT
GGCCGAGAAGCTGCAGCGCGACTTCCTGGTCCAGTGGCGCCGCGTGAGTAAGGCCCCGGAGGCCCTCTT
CTTTGTTCAGTTCGAGAAGGGCGAGTCCTACTTCCACCTCCATATTCTGGTGGAGACCACGGGGGTCAA
ATCCATGGTGCTGGGCCGCTTCCTGAGTCAGATTAGGGACAAGCTGGTGCAGACCATCTACCGCGGGAT
CGAGCCGACCCTGCCCAACTGGTTCGCGGTGACCAAGACGCGTAATGGCGCCGGAGGGGGGAACAAGGT
GGTGGACGAGTGCTACATCCCCAACTACCTCCTGCCCAAGACTCAGCCCGAGCTGCAGTGGGCGTGGAC
TAACATGGAGGAGTATATAAGCGCGTGTTTAAACCTGGCCGAGCGCAAACGGCTCGTGGCGCACGACCT
GACCCACGTCAGCCAGACCCAGGAGCAGAACAAGGAGAATCTGAACCCCAATTCTGACGCGCCTGTCAT
CCGGTCAAAAACCTCCGCACGCTACATGGAGCTGGTCGGGTGGCTGGTGGACGGGGCATCACCTCCGA
GAAGCAGTGGATCCAGGAGGACCAGGCCTCGTACATCTCCTTCAACGCCGCCTCCAACTCGCGGTCCCA
GATCAAGGCCGCTCTGGACAATGCCGGCAAGATCATGGCGCTGACCAAATCCGCGCCCGACTACCTGGT
AGGCCCCGCTCCGCCCGCCGACATTAAAACCAACCGCATTTACCGCATCCTGGAGCTGAACGGCTACGA
CCCTGCCTACGCCGGCTCCGTCTTTCTCGGCTGGGCCCAGAAAAGGTTCGGAAAACGCAACACCATCTG
GCTGTTTGGGCCGGCCACCACGGGCAAGACCAACATCGCGGAAGCCATCGCCCACGCCGTGCCCTTCTA
CGGCTGCGTCAACTGGACCAATGAGAACTTTCCCTTCAACGATTGCGTCGACAAGATGGTGATCTGGTG
GGAGGAGGGCAAGATGACGGCCAAGGTCGTGGAGTCGGCCAAGGCCATTCTCGGCGGCAGCAAGGTGCG
CGTGGACCAAAAGTGCAAGTCGTCCGCCCAGATCGATCCCACCCCCGTGATCGTCACCTCCAACACCAA
CATGTGCGCCGTGATTGACGGGAACAGCACCACCTTCGAGCACCAGCAGCCGTTGCAGGACCGGATGTT
CAAATTTGAACTCACCCGCCGTCTGGAGCATGACTTTGGCAAGGTGACAAAGCAGGAAGTCAAAGAGTT
CTTCCGCTGGGCGCAGGATCACGTGACCGAAGTGGCGCATGAGTTCTACGTCAGAAAGGGTGGAGCCAA
CAAGAGACCCGCCCCCGATGACGCGGATAAAAGCGAGCCCAAGCGGGCCTGCCCCTCAGTCGCGGATCC
ATCGACGTCAGACGCGGAAGGAGCTCCGGTGGACTTTGCCGACAGGTACCAAAACAAATGTTCTCGTCA
CGCGGGCATGCTTCAGATGCTGTTTCCCTGCAAAACATGCGAGAGAATGAATCAGAATTTCAACATTTG
CTTCACGCACGGGACCAGAGACTGTTCAGAATGTTTCCCCGGCGTGTCAGAATCTCAACCGGTCGTCAG
AAAGAGGACGTATCGAAACTCTGTGCCATTCATCATCTGCTGGGGCGGGCTCCCGAGATTGCTTGCTC
GGCCTGCGATCTGGTCAACGTGGATCTGGATGACTGTGTTTCTGAGCAATAAATGACTTAAACCAGGTA
TGGCTGCCGATGGTTATCTTCCAGATTGGCTCGAGGACAACCTCTCTGAGGGCATTCGCGAGTGGTGGG
ACTTGAAACCTGGAGCCCCGAAACCCAAAGCCAACCAGCAAGGACCAGGACGACGGCCGGGGTCTGGTGC
TTCCTGGCTACAAGTACCTCGGACCCCTTCAACGACTCGACAAGGGGGAGCCCGTCAACGCGGCGGATG
CAGCGGCCCTCGAGCACGACAAGGCCTACGACCAGCAGCTCAAAGCGGGTGACAATCCGTACCTGCGGT
ATAACCACGCCGACGCCGAGTTTCAGGAGCGTCTGCAAGAAGATACGTCTTTTGGGGGCAACCTCGGGC
GAGCAGTCTTCCAGGCCAAGAAGAGGGTTCTCGAACCTTTTGGTCTGGTTGAGGAAGGTGCTAAGACGG
CTCCTGGAAAGAAACGTCCGGTAGAGCAGTCGCCACAAGAGCCAGACTCCTCCTCGGCATTGGCAAGA
CAGGCCAGCAGCCCGCTAAAAAGAGACTCAATTTTGGTCAGACTGGCGACTCAGAGTCAGTCCCCGACC
CACAACCTCTCGGAGAACCTCCAGCAACCCCCGCTGCTGTGGGACCTACTACAATGGCTTCAGGCGGTG
GCGCACCAATGGCAGACAATAACGAAGGCGCCGACGGAGTGGGTAATGCCTCAGGAAATTGGCATTGCG
ATTCCACATGGCTGGGCGACAGAGTCATCACCACCAGCACCCGAACATGGGCCTTGCCCACCTATAACA
ACCACCTCTACAAGCAAATCTCCAGTGCTTCAACGGGGGCCAGCAACGACAACCACTACTTCGGCTACA
GCACCCCCTGGGGGTATTTTGATTTCAACAGATTCCACTGCCATTTCTCACCACGTGACTGACTGGCAGCGAC
TCATCAACAACAATTGGGGATTCCGGCCCAAGAGACTCAACTTCAAGCTCTTCAACATCCAAGTCAAGG
AGGTCACGACGAATGATGGCGTCACGACCATCGCTAATAACCTTACCAGCACGGTTCAAGTCTTCTCGG
ACTCGGAGTACCAGTTGCCGTACGTCCTCGGCTCTGCGCACCAGGGCTGCCTCCCTCCGTTCCCGGCGG
ACGTGTTCATGATTCCAGCAGTACGGCTACCTAACGCTCAACAATGGCAGCCAGGCAGTGGGACGGTCAT
CCTTTTACTGCCTGGAATATTTCCCATCGCAGATGCTGAGAACGGGCAATAACTTTACCTTCAGCTACA
CCTTCGAGGACGTGCCTTTCCACAGCAGCTACGCGCACAGCCAGAGCCTGGACCGGCTGATGAATCCTC
TCATCGACCAGTACCTGTATTACCTGAACAGAACTCAGAATCAGTCCGGAAGTGCCCAAAACAAGGACT
TGCTGTTTAGCCGGGGGTCTCCAGCTGGCATGTCTGTTCAGCCCAAAAACTGGCTACCTGGACCCTGTT
ACCGGCAGCAGCGCGTTTCTAAAACAAAAACAGACAACAACAACAGCAACTTTACCTGGACTGGTGCTT
CAAAATATAACCTTAATGGGCGTGAATCTATAATCAACCCTGGCACTGCTATGGCCTCACACAAAGACG
ACAAAGACAAGTTCTTTCCCATGAGCGGTGTCATGATTTTTGGAAAGGAGAGCGCCGGAGCTTCAAACA
CTGCATTGGACAATGTCATGATCACAGACGAAGAGGAAATCAAAGCCACTAACCCCGTGGCCACCGAAA
GATTTGGGACTGTGGCAGTCAATCTCCAGAGCAGCAGCACAGACCCTGCCGACCGGAGATGTGCATGTTA
TGGGAGCCTTACCTGGAATGGTGTGGCAAGACAGAGACGTATACCTGCAGGGTCCTATTTGGGCCAAAA
TTCCTCACACGGATGGACACTTTCACCCGTCTCCTCTCATGGGCGGCTTTGGACTTAAGCACCCGCCTC
CTCAGATCCTCATCAAAAACACGCCTGTTCCTGCGAATCCTCCGGCAGATTTTTCGGCTACAAAGTTTG
CTTCATTCATCACCCAGTATTCCACAGGACAAGTGAGCGTGGAGATTGAATGGGAGCTGCAGAAAGAAA
ACAGCAAACGCTGGAATCCGGAAGTGCAGTATACATCTAACTATGCAAAATCTGCCAACGTTGATTTCA
CTGTGGACAACAATGGACTTTATACTGAGCCTCGCCCCATTGGCACCCGTTACCTCACCCGTCCCCTGT
AATTGTGTGTTAATCAATAAACCGGTTAATTCGTGTCAGTTGAACTTTGGTCTCATGTCGTTATTATCT
TATCTGGTCACCATAGCAACCGGTTACACATTAACTGCTTAGTTGCGCTTCGCGAATACCCCTAGTGAT
GGAGTTGCCCACTCCCTCTATGCGCGCTCGCTCGCTCGGTGGGGCCGGCAGAGCAGAGCTCTGCCGTCT
GCGGACCTTTGGTCCGCAGGCCCCACCGAGCGAGCGAGCGCGCATAGAGGGAGTGGGCAA
```

FIG. 14

AAV-7, COMPLETE SEQUENCE, GENBANK ACCESSION NO. AF513851 AND GAO ET
AL. (2002) PNAS 99:11854
TTGGCCACTCCCTCTATGCGCGCTCGCTCGCTCGGTGGGGCCTGCGGACCAAAGGTCCGCAGACGGCAG
AGCTCTGCTCTGCCGGCCCCACCGAGCGAGCGAGCGCGCATAGAGGGAGTGGCCAACTCCATCACTAGG
GGTACCGCGAAGCGCCTCCCACGCTGCCGCGTCAGCGCTGACGTAAATCACGTCATAGGGGAGTGGTCC
TGTATTAGCTGTCACGTGAGTGCTTTTGCGACATTTTGCGACACCACGTGGCCATTTGAGGTATATATG
GCCGAGTGAGCGAGCAGGATCTCCATTTTGACCGCGAAATTTGAACGAGCAGCAGCCATGCCGGGTTTC
TACGAGATCGTGATCAAGGTGCCGAGCGACCTGGACGAGCACCTGCCGGGCATTTCTGACTCGTTTGTG
AACTGGGTGGCCGAGAAGGAATGGGAGCTGCCCCCGGATTCTGACATGGATCTGAATCTGATCGAGCAG
GCACCCCTGACCGTGGCCGAGAAGCTGCAGCGCGACTTCCTGGTCCAATGGCGCCGCGTGAGTAAGGCC
CCGGAGGCCCTGTTCTTTGTTCAGTTCGAGAAGGGCGAGAGCTACTTCCACCTTCACGTTCTGGTGGAG
ACCACGGGGTCAAGTCCATGGTGCTAGGCCGCTTCCTGAGTCAGATTCGGGAGAAGCTGGTCCAGACC
ATCTACCGCGGGGTCGAGCCCACGCTGCCCAACTGGTTCGCGGTGACCAAGACGCGTAATGGCGCCGGC
GGGGGGAACAAGGTGGTGGACGAGTGCTACATCCCCAACTACCTCCTGCCCAAGACCCAGCCCGAGCTG
CAGTGGGCGTGGACTAACATGGAGGAGTATATAAGCGCGTGTTTGAACCTGGCCGAACGCAAACGGCTC
GTGGCGCAGCACCTGACCCACGTCAGCCAGACGCAGGAGCAGAACAAGGAGAATCTGAACCCCAATTCT
GACGCGCCCGTGATCAGGTCAAAAAACCTCCGCGCGCTACATGGAGCTGGTCGGGTGGCTGGTGGACCGG
GGCATCACCTCCGAGAAGCAGTGGATCCAGGAGGACCAGGCCTCGTACATCTCCTTCAACGCCGCTCC
AACTCGCGGTCCCAGATCAAGGCCGCGCTGGACAATGCCGGCAAGATCATGGCGCTGACCAAATCCGCG
CCCGACTACCTGGTGGGGCCCTCGCTGCCCGCGGACATTAAAACCAACCGCATCTACCGCATCCTGGAG
CTGAACGGGTACGATCCTGCCTACGCCGGCTCCGTCTTTCTGGCTGGGCCCAGAAAAAGTTCGGGAAG
CGCAACACCATCTGGCTGTTTGGGCCCGCCACCACCGGCAAGACCAACATTGCGGAAGCCATCGCCCAC
GCCGTGCCCTTCTACGGCTGCGTCAACTGGACCAATGAGAACTTTCCCTTCAACGATTGCGTCGACAAG
ATGGTGATCTGGTGGGAGGAGGGCAAGATGACGGCCAAGGTCGTGGAGTCCGCCAAGGCCATTCTCGGC
GGCAGCAAGGTGCGCGTGGACCAAAAGTGCAAGTCGCCCGATCAGCCCACCCCGTGATCGTC
ACCTCCAACACCAACATGTGCGCCGTGATTGACGGGAACAGCACCACCTTCGAGCACCAGCAGCCGTTG
CAGGACCGGATGTTCAAATTTGAACTCACCCGCCGTCTGGAGCACGACTTTGGCAAGGTGACGAAGCAG
GAAGTCAAAGAGTTCTTCCGCTGGGCCAGTGATCACGTGACCGAGGTGGCGCATGAGTTCTACGTCAGA
AAGGGCGGAGCCAGCAAAAGACCCGCCCCCCGATGAGCCCGATATAAGCGAGCCCAAGCGGGCCTGCCCC
TCAGTCGCGGATCCATCGACGTCAGACGCGGAAGGAGCTCCGGTGGACTTTGCCGACAGGTACCAAAAC
AAATGTTCTCGTCACGCGGGCATGATTCAGATGCTGTTTCCCTGCAAAACGTGCGAGAGAATGAATCAG
AATTTCAACATTTGCTTCACACACGGGGTCAGAGACTGTTTAGAGTGTTTCCCCGGCGTGTCAGAATCT
CAACCGGTCGTCAGAAAAAAGACGTATCGGAAACTCTGCGGATTCATCATCTGCTGGGGCGGGCGCCC
GAGATTGCTTGCTCGGCCTGCGACCTGGTCAACGTGGACCTGGACGACTGCGTTTCTGAGCAATAAATG
ACTTAAACCAGGTATGGCTGCCGATGGTTATCTTCCAGATTGGCTCGAGGACAACCTCTCTGAGGGCAT
TCGCGAGTGGTGGGACCTGAAACCTGGAGCCCCGAAACCCAAAGCCAACCAGCAAAAGCAGGACAACGG
CCGGGGTCTGGTGCTTCCTGGCTACAAGTACCTCGGACCCTTCAACGGACTCGACAAGGGGAGCCCGT
CAACGCGGCGGACGCAGCGGCCCTCGAGCACGACAAGGCCTACGACCAGCAGCTCAAAGCGGGTGACAA
TCCGTACCTGCGGTATAACCACGCGACGCCGAGTTTCAGGAGCGTCTGCAAGAAGATACGTCATTTGG
GGGCAACCTCGGGCGAGCAGTCTTCCAGGCCAAGAAGCGGGTTCTCGAACCTCTCGGTCTGGTTGAGGA
AGGCGCTAAGACGGCTCCTGCAAAGAAGAGACCCGGTAGAGCCGTCACCTCAGCGTTCCCCCGACTCCTC
CACGGGCATCGGCAAGAAAGGCCAGCAGCCCGCCAGAAAGAGACTCAATTTCGGTCAGACTGGCGACTC
AGAGTCAGTCCCCGACCCCTCAACCTCTCGGAGAACCTCCAGCAGCGCCCTCTAGTGTGGGATCTGGTAC
AGTGGCTGCAGGCGGTGGCGCACCAATGGCAGACAATAACGAAGGTGCCGACGGAGTGGGTAATGCCTC
AGGAAATTGCATTGCGATTCCACATGGCTGGGCGACAGAGTCATTACCACCAGCACCCGAACCTGGGC
CCTGCCCACCTACAACAACCACCTCTACAAGCAAATCTCCAGTGAAACTGCAGGTAGTACCAACGACAA
CACCTACTTCGGCTACAGCACCCCCTGGGGGTATTTTGACTTTAACAGATTCCACTGCCACTTCTCACC
ACGTGACTGGCAGCGACTCATCAACAACAACTGGGGATTCCGGCCCAAGAAGCTGCGGTTCAAGCTCTT
CAACATCCAGGTCAAGGAGGTCACGACGAATGACGGCGTTACGACCATCGCTAATAACCTTACCAGCAC
GATTCAGGTATTCTCGGACTCGGAATACCAGCTGCCGTACGTCCTCGGCTCTGCGCACCAGGGCTGCCT
GCCTCCGTTCCCGGCGGACGTCTTCATGATTCCTCAGTACGGCTACCTGACTCTCAACAATGGCAGTCA
GTCTGTGGACGTTCCTCCTTCTACTGCCTGGAGTATTTCCCCTCTCAGATGCTGAGAACGGGCAACAA
CTTTGAGTTCAGCTACAGCTTCGAGGACGTGCCTTTCCACAGCAGCTACGCACACAGCCAGAGCCTGGA
CCGGCTGATGAATCCCCTCATCGACCAGTACTTGTACTACCTGGCCAGAACACAGAGTAACCCAGGAGG
CACAGCTGGCAATCGGGAACTGCAGTTTTACCAGGGCGGGCCTTCAACTATGGCCGAACAAGCCAAGAA
TTGGTTACCTGGACCTTGCTTCCGGCAACAAAGAGTCTCCAAAACGCTCCAAAACGCCGAAAACCAACAGCAA
CTTTGCTTGGACTGGTGCCACCAAATATCACCTGAACGGCAGAAACTCGTTGGTTAATCCCGGCGTCGC
CATGGCAACTCACAAGGACGACGAGGACCGCTTTTTCCCATCCAGCGGAGTCCTGATTTTTGGAAAAAC
TGGAGCAACTAAACAAAACTACATTGGAAAATGTGTTAATGACAAATGAAGAAGAAATTCGTCCTACTAA
TCCTGTAGCCACGGAAGAATACGGGATAGTGCAGCAAAACTTACAAGCGGCTAATACTGCAGCCCAGAC
ACAAGTTGTCAACAACCAGGGAGCCTTACCTGGCATGGTCTGGCAGAACCGGGACGTGTACCTGCAGGG
TCCCATCTGGGCCAAGATTCCTCACACGGATGGCAACTTTCACCCGTCTCCTTTGATGGGCGGCTTTGG
ACTTAAACATCCGCCTCCTCAGATCCTGATCAAGAACACTCCCGTTCCCGCTAATCCTCCGGAGGTGTT
TACTCCTGCCAAGTTTGCTTCGTTCATCACACAGTACAGCACCGGACAAGTCAGCGTGGAAATCGAGTG
GGAGCTGCAGAAGGAAAACAGCAAGCGCTGGAACCCGGAGATTCAGTACACCTCCAACTTTGAAAAGCA
GACTGGTGTGGACTTTGCCGTTGACAGCCAGGGTGTTTACTCTGAGCCTCGCCCTATTGGCACTCGTTA
CCTCACCCGTAATCTGTAATTGCATGTTAATCAATAAACCGGTTGATTCGTTTCAGTTGAACTTTGGTC
TCCTGTGCTTCTTATCTTATCGGTTTCCATAGCAACTGGTTACACATTAACTGCTTGGGTGCGCTTCAC
GATAAGAACACTGACGTCACCGCGGTACCCCTAGTGATGAGTTGGCCACTCCCTCTATGCGCGCTCGC
TCGCTCGGTGGGCCTGCGGACCAAAGGTCCGCAGACGGCAGAGCTCTGCTCTGCCGGCCCCACCGAGC
GAGCGAGCGCGCATAGAGGGAGTGGCCAA

FIG. 15

AAV-8, COMPLETE SEQUENCE, GENBANK ACCESSION NO. AF513852 AND GAO ET
AL. (2002) PNAS 99:11854
CAGAGAGGGAGTGGCCAACTCCATCACTAGGGGTAGCGCGAAGCGCCTCCCACGCTGCCGCGTCAGC
GCTGACGTAAATTACGTCATAGGGGAGTGGTCCTGTATTAGCTGTCACGTGAGTGCTTTTGCGGCAT
TTTGCGACACCACGTGGCCATTTGAGGTATATATGGCCGAGTGAGCGAGCAGGATCTCCATTTTGAC
CGCGAAATTTGAACGAGCAGCAGCCATGCCGGGCTTCTACGAGATCGTGATCAAGGTGCCGAGCGAC
CTGGACGAGCACCTGCCGGGCATTTCTGACTCGTTTGTGAACTGGGTGGCCGAGAAGGAATGGGAGC
TGCCCCCGGATTCTGACATGGATCGGAATCTGATCGAGCAGGCACCCCTGACCGTGGCCGAGAAGCT
GCAGCGCGACTTCCTGGTCCAATGGCGCCGCGTGAGTAAGGCCCCGGAGGCCCTCTTCTTTGTTCAG
TTCGAGAAGGGCGAGAGCTACTTTCACCTGCACGTTCTGGTCGAGACCACGGGGGTCAAGTCCATGG
TGCTAGGCCGCTTCCTGAGTCAGATTCGGGAAAAGCTTGGTCCAGACCATCTACCCGCGGGGTCGAG
CCCCACCTTGCCCAACTGGTTCGCGGTGACCAAAGACGCGGTAATGGCGCCGGCGGGGGGGAACAAG
GTGGTGGACGAGTGCTACATCCCCAACTACCTCCTGCCCAAGACTCAGCCCGAGCTGCAGTGGGCGT
GGACTAACATGGAGGAGTATATAAGCGCGTGCTTGAACCTGGCCGAGCGCAAACGGCTCGTGGCGCA
GCACCTGACCCACGTCAGCCAGACGCAGGAGCAGAACAAGGAGAATCTGAACCCCAATTCTGACGCG
CCCGTGATCAGGTCAAAAACCTCCGCGCGCTATATGGAGCTGGTCGGGTGGCTGGTGGACCGGGGCA
TCACCTCCGAGAAGCAGTGGATCCAGGAGGACCAGGCCTCGTACATCTCCTTCAACGCCGCCTCCAA
CTCGCGGTCCCAGATCAAGGCCGCGCTGGACAATGCCGGCAAGATCATGGCGCTGACCAAATCCGCG
CCCGACTACCTGGTGGGGCCCTCGCTGCCCGCGGACATTACCCAGAACCGCATCTACCGCATCCTCG
CTCTCAACGGCTACGACCCTGCCTACGCCGGCTCCGTCTTTCTCGGCTGGGCTCAGAAAAAGTTCGG
GAAACGCAACACCATCTGGCTGTTTGGACCCGCCACCACCGGCAAGACCAACATTGCGGAAGCCATC
GCCCACGCCGTGCCCTTCTACGGCTGCGTCAACTGGACCAATGAGAACTTTCCCTTCAATGATTGCG
TCGACAAGATGGTGATCTGGTGGGAGGAGGGCAAGATGACGGCCAAGGTCGTGGAGTCCGCCAAGGC
CATTCTCGGCGGCAGCAAGGTGCGCGTGGACCAAAAGTGCAAGTCGTCCGCCCAGATCGACCCCACC
CCCGTGATCGTCACCTCCAACACCAACATGTGCGCCGTGATTGACGGGAACAGCACCACCTTCGAGC
ACCAGCAGCCTCTCCAGGACCGGATGTTTAAGTTCGAACTCACCCGCCGTCTGGAGCACGACTTTGG
CAAGGTGACAAAGCAGGAAGTCAAAGAGTTCTTCCGCTGGGCCAGTGATCACGTGACCGAGGTGGCG
CATGAGTTTTACGTCAGAAAGGGCGGAGCCAGCAAAAGACCCGCCCCCGATGACGCGGATAAAAGCG
AGCCCAAGCGGGCCTGCCCCTCAGTCGCCGGATCCATCGACGTCAGACGCGGAAGGAGCTCCGGTGA
CTTTGCCGACAGGTACCAAAACAAATGTTCTCGTCACGCGGGCATGCTTCAGATGCTGTTTCCCTGC
AAAACGTGCGAGAGAATGAATCAGAATTTCAACATTTGCTTCACACACGGGGTCAGAGACTGCTCAG
AGTGTTTCCCCGGCGTGTCAGAATCTCAACGGTCGTCAGAAAGAGGACGTATCGGAAACTCTGTGC
GATTCATCATCTGCTGGGGCGGGCTCCCGAGATTGCTTGCTCGGCCTGCGATCTGGTCAACGTGGAC
CTGGATGACTGTGTTTCTGAGCAATAAATGACTTAAACCAGGTATGGCTGCCGATGGTTATCTTCCA
GATTGGCTCGAGGACAACCTCTCTGAGGGCATTCGCGAGTGGTGGGCGCTGAAACCTGGAGCCCCGA
AGCCCAAAGCCAACCAGCAAAAGCAGGACGACGGCCGGGGTCTGGTGCTTCCTGGCTACAAGTACCT
CGGACCCTTCAACGGACTCGACAAGGGGGAGCCCGTCAACGCGGCGGACGCAGCGGCCCTCGAGCAC
GACAAGGCCTACGACCAGCAGCTGCAGGCGGGTGACAATCCGTACCTGCGGTATAACCACGCCGACG
CCGAGTTTCAGGAGCGTCTGCAAGAAGATACGTCTTTTGGGGGCAACCTCGGGCGAGCAGTCTTCCA
GGCCAAGAAGCGGGTTCTCGAACCTCTCGGTCTGGTTGAGGAAGGCGCTAAGACGGCTCCTGGAAAG
AAGAGACCGGTAGAGCCATCACCCCAGCGTTCTCCAGACTCCTCTACGGGCATCGGCAAGAAAGGCC
AACAGCCCGCCAGAAAAGACTCAATTTTGGTCAGACTGGCGACTCAGAGTCAGTTCCAGACCCTCA
ACCTCTCGGAGAACCTCCAGCAGCGCCCTCTGGTGTGGGACCTAATACAATGGCTGCAGGCGGTGGC
GCACCAATGGCAGACAATAACGAGGCGCCGACGGAGTGGGTAGTTCCTCGGGAAATTGGCATTGCG
ATTCCACATGGCTGGGCGACAGAGTCATCACCACCAGCACCCGAACCTGGGCCTGCCCACCTACAA
CAACCACCTCTACAAGCAAATCTCCAACGGGACATCGGGAGGAGCCACCAACGACAACACCTACTTC
GGCTACAGCACCCCCTGGGGGTATTTTGACTTTAACAGATTCCACTGCCACTTTTCACCACGTGACT
GGCAGCGACTCATCAACAACAACTGGGGATTCCGGCCCAAGAGACTCAGCTTCAAGCTCTTCAACAT
CCAGGTCAAGGAGGTCACGCAGAATGAAGGCACCAAGACCATCGCCAATAACCTCACCAGCACCATC
CAGGTGTTTACGGACTCGGAGTACCAGCTGCCGTACGTTCTCGGCTCTGCCCACCAGGGCTGCCTGC
CTCCGTTCCCGGCGGACGTGTTCATGATTCCCCAGTACGGCTACCTAACACTCAACAACGGTAGTCA
GGCCGTGGGACGCTCCTCCTTCTACTGCCTGGAATACTTTCCTTCGCAGATGCTGAGAACCGGCAAC
AACTTCCAGTTTACTTACACCTTCGAGGACGTGCCTTTCCACAGCAGCTACGCCCACAGCCAGAGCT
TGGACCGGCTGATGAATCCTCTGATTGACCAGTACCTGTACTACTTGTCTCGGACTCAAACAACAGG
AGGCACGGCAAATACGCAGACTCTGGGCTTCAGCCAAGGTGGGCCTAATACAATGGCCAATCAGGCA
AAGAACTGGCTGCCAGGACCCTGTTACCGCCAACAACGCGTCTCAACGACAACGGGCAAAACAACA
ATAGCAACTTTGCCTGGACTGCTGGGACCAAATACCATCTGAATGGAAGAATTCATTGGCTAATCC
TGGCATCGCTATGGCAACACACAAAGACGACGAGGAGCGTTTTTTTCCCAGTAACGGGATCCTGATT
TTTGGCAAACAAATGCTGCCAGAGACAATGCGGATTACAGCGATGTCATGCTCACCAGCGAGGAAG
AAATCAAAACCACTAACCCTGTGGCTACAGAGGAATACGGTATCGTGGCAGATAACTTCAGCAGCA
AAACACGGCTCCTCAAATTGGAACTGTCAACAGCCAGGGGCCTTACCCGGTATGGTCTGGCAGAAC
CGGGACGTGTACCTGCAGGGTCCCATCTGGGCCAAGATTCCTCACACGGACGGCAACTTCCACCCGT
CTCCGCTGATGGGCGGCTTTGGCCTGAAACATCCTCCGCCTCAGATCCTGATCAAGAACACGCCTGT
ACCTGCGGATCCTCCGACCACCTTCAACCAGTCAAAGCTGAACTCTTTCATCACGCAATACAGCACC
GGACAGGTCAGCGTGGAAATTGAATGGGAGCTGCAGAAGGAAAACAGCAAGCGCTGGAACCCCGAGA
TCCAGTACACCTCCAACTACTACAAATCTACAAGTGTGGACTTTGCTGTTAATACAGAAGGCGTGTA
CTCTGAACCCCGCCCCATTGGCACCCGTTACCTCACCCGTAATCTGTAATTGCCTGTTAATCAATAA
ACCGGTTGATTCGTTTCAGTTGAACTTTGGTCTCTGCG

AAV-9, GENBANK ACCESSION NO. AX753250 AND GAO ET AL. (MAY 14, 2003)
EP1310571
CAGAGAGGGAGTGGCCAACTCCATCACTAGGGGTAATCGCGAAGCGCCTCCCACGCTGCCGCGTC
AGCGCTGACGTAGATTACGTCATAGGGGAGTGGTCCTGTATTAGCTGTCACGTGAGTGCTTTTGC
GACATTTTGCGACACCACATGGCCATTTGAGGTATATATGGCCGAGTGAGCGAGCAGGATCTCCA
TTTTGACCGCGAAATTTGAACGAGCAGCAGCCATGCCGGGCTTCTACGAGATTGTGATCAAGGTG
CCGAGCGACCTGGACGAGCACCTGCCGGGCATTTCTGACTCTTTTGTGAACTGGGTGGCCGAGAA
GGAATGGGAGCTGCCCCCGGATTCTGACATGGATCGGAATCTGATCGAGCAGGCACCCCTGACCG
TGGCCGAGAAGCTGCAGCGCGACTTCCTGGTCCAATGGCGCCGCGTGAGTAAGGCCCCGGAGGCC
CTCTTCTTTGTTCAGTTCGAGAAGGGCGAGAGCTACTTTCACCTGCACGTTCTGGTCGAGACCAC
GGGGGTCAAGTCCATGGTGCTAGGCCGCTTCCTGAGTCAGATTCGGGAGAAGCTGGTCCAGACCA
TCTACCGCGGGATCGAGCCGACCCTGCCCAACTGGTTCGCGGTGACCAAGACGCGTAATGGCGCC
GGCGGGGGGAACAAGGTGGTGGACGAGTGCTACATCCCCAACTACCTCCTGCCCAAGACTCAGCC
CGAGCTGCAGTGGGCGTGGACTAACATGGAGGAGTATATAAGCGCGTGCTTGAACCTGGCCGAGC
GCAAACGGCTCGTGGCGCAGCACCTGACCCACGTCAGCCAGACGCAGGAGCAGAACAAGGAGAAT
CTGAACCCCAATTCTGACGCGCCCGTGATCAGGTCAAAAACCTCCGCGCGCTACATGGAGCTGGT
CGGGTGGCTGGTGGACCGGGGCATCACCTCCGAGAAGCAGTGGATCCAGGAGGACCAGGCCTCGT
ACATCTCCTTCAACGCCGCCTCCAACTCGCGGTCCCAGATCAAGGCCGCGCTGGACAATGCCGGC
AAGATCATGGCGCTGACCAAATCCGCGCCCGACTACCTGGTAGGCCCTTCACTTCCGGTGGACAT
TACGCAGAACCGCATCTACCGCATCCTGCAGCTCAACGGCTACGACCCTGCCTACGCCGGCTCCG
TCTTTCTGGCTGGGCACAAAAGAAGTTCGGGAAACGCAACACCATCTGGCTGTTTGGCCGGACC
ACCACGGGAAAGACCAACATCGCAGAAGCCATTGCCCACGCCGTGCCCTTCTACGGCTGCGTCAA
CTGGACCAATGAGAACTTTCCCTTCAACGATTGCGTCGACAAGATGGTGATCTGGTGGGAGGAGG
GCAAGATGACGGCCAAGGTCGTGGAGTCCGCCAAGGCCATTCTCGGCGGCAGCAAGGTGCGCGTG
GACCAAAAGTGCAAGTCGTCCGCCCAGATCGACCCCACTCCCGTGATCGTCACCTCCAACACCAA
CATGTGCGCCGTGATTGACGGGAACAGCACCACCTTCGAGCACCAGCAGCCTCTCCAGGACCGGA
TGTTTAAGTTCGAACTCACCCGCCGTCTGGAGCACGACTTTGGCAAGGTGACAAAGCAGGAAGTC
AAAGAGTTCTTCCGCTGGGCCAGTGATCACGTGACCGAGGTGGCGCATGAGTTTTACGTCAGAAA
GGGCGGAGCCAGCAAAAGACCCGCCCCGATGACGGGATAAAAGCGAGCCCAAGCGGGCCTGCC
CCTCAGTCGCGGATCCATCGACGTCAGACGCGGAAGGAGCTCCGGTGGACTTTGCCGACAGGTAC
CAAAACAAATGTTCTCGTCACGCGGGCATGCTTCAGATGCTGCTTCCCTGCAAAACGTGCGAGAG
AATGAATCAGAATTTCAACATTTGCTTCACACACGGGGTCAGAGACTGCTCAGAGTGTTTCCCCG
GCGTGTCAGAATCTCAACCGGTCGTCAGAAAGAGGACGTATCGGAAACTCTGTGCGATTCATCAT
CTGCTGGGGCGGGCTCCCGAGATTGCTTGCTCGGCCTGCGATCTGGTCAACGTGGACCTGGATGA
CTGTGTTTCTGAGCAATAAATGACTTAAACCAGGTATGGCTGCCGATGGTTATCTTCCAGATTGG
CTCGAGGACAACCTCTCTGAGGGCATTCGCGAGTGGTGGGCGCTGAAACCTGGAGCCCCGAAGCC
CAAAGCCAACCAGCAAAAGCAGGACGACGGCCGGGGTCTGGTGCTTCCTGGCTACAAGTACCTCG
GACCCTTCAACGGACTCGACAAGGGGGAGCCCGTCAACGCGGCGGACGCAGCGGCCCTCGAGCAC
GGCAAGGCCTACGACCAGCAGCTGCAGGCGGGTGACAATCCGTACCTGCGGTATAACCACGCCGA
CGCCGAGTTTCAGGAGCGTCTGCAAGAAGATACGTCTTTTGGGGGCAACCTCGGGCGAGCAGTCT
TCCAGGCCAAGAAGCGGGTTCTCGAACCTCTCGGTCTGGTTGAGGAAGGCGCTAAGACGGCTCCT
GGAAAGAAGAGACCGGTAGAGCCATCACCCCAGCGTTCTCCAGACTCCTCTACGGGCATCGGCAA
GAAAGGCCAACAGCCCGCCAGAAAAGACTCAATTTTGGTCAGACTGGCGACTCAGAGTCAGTTC
CAGACCCTCAACCTCTCGGAGAACCTCCAGCAGCGCCCTCTGGTGTGGGACCTAATACAATGGCT
GCAGGCGGTGGCGCACCAATGGCAGACAATAACGAAGGCGCCGACGGAGTGGGTAATTCCTCGGG
AAATTGGCATTGCCGATTCCACATGGCTGGGGGACAGAGTCATCACCACCAGCACCCGAACCTGGG
CATTGCCCACCTACAACAACCACCTCTACAAGCAAATCTCCAATGGAACATCGGGAGGAAGCACC
AACGACAACACCTACTTTGGCTACAGCACCCCCTGGGGGTATTTTGACTTCAACAGATTCCACTG
CCACTTCTCACCACGTGACTGGCAGCGACTCATCAACAACAACTGGGGATTCCGGCCAAAGAGAC
TCAACTTCAAGCTGTTCAACATCCAGGTCAAGGAGGTTACGACGAACGAAGGCACCAAGACCATC
GCCAATAACCTTACCAGCACCGTCCAGGTCTTTACGGACTCGGAGTACCAGCTACCGTACGTCCT
AGGCTCTGCCCACCAAGGATGCCTGCCACCGTTTCCTGCAGACGTCTTCATGGTTCCTCAGTACG
GCTACCTGACGCTCAACAATGGAAGTCAAGCGTTAGGACGTTCTTCTTTCTACTGTCTGGAATAC
TTCCCTTCTCAGATGCTGAGAACCGGCAACAACTTTCAGTTCAGCTACACTTTCGAGGACGTGCC
TTTCCACAGCAGCTACGCACACAGCCAGAGTCTAGATCGACTGATGAACCCCCTCATCGACCAGT
ACCTATACTACCTGGTCAGAACACAGACAACTGGAACTGGGGGAACTCAAACTTTGGCATTCAGC
CAAGCAGGCCCTAGCTCAATGGCCAATCAGGCTAGAAACTGGGTACCCGGGCCTTGCTACCGTCA
GCAGCGCGTCTCCACAACCACCAACCAAAATAACAACAGCAACTTTGCGTGGACGGGAGCTGCTA
AATTCAAGCTGAACGGGAGAGACTCGCTAATGAATCCTGGCGTGGCTATGGCATCGCACAAAGAC
GACGAGGACCGCTTCTTTCCATCAAGTGGCGTTCTCATATTTGGCAAGCAAGGAGCCGGGAACGA
TGGAGTCGACTACAGCCAGGTGCTGATTACAGATGAGGAAGAAATTAAAGCCACCAACCCTGTAG
CCACAGAGGAATACGGAGCAGTGGCCATCAACAACCAGGCCGCTAACACGCAGGCGCAAACTGGA
CTTGTGCATAACCAGGGAGTTATTCCTGGTATGGTCTGGCAGAACCGGGACGTGTACCTGCAGGG
CCCTATTTGGGCTAAAATACCTCACACAGATGGCAACTTTCACCCGTCTCCTCTGATGGGTGGAT
TTGGACTGAAACACCCACCTCCACAGATTCTAATTAAAAATACACCAGTGCCGGCAGATCCTCCT
CTTACCTTCAATCAAGCCAAGCTGAACTCTTTCATCACGCAGTACAGCACGGGACAAGTCAGCGT
GGAAATCGAGTGGGAGCTGCAGAAAGAAAACAGCAAGCGCTGGAATCCAGAGATCCAGTATACTT
CAAACTACTACAAATGTACAAATGTGGACTTTGCTGTCAATACCAAAGGTGTTTACTCTGAGCCT
CGCCCCATTGGTACTCGTTACCTCACCCGTAATTTGTAATTGCCTGTTAATCAATAAACCGGTTA
ATTCGTTTCAGTTGAACTTTGGTCTCTGCG

FIG. 17

AAV-11, NONSTRUCTURAL PROTEIN AND CAPSID PROTEIN GENES, COMPLETE CDS,
GENBANK ACCESSION NO. AY631966 AND MORI ET AL. (2004) VIROL. 330:375
ATGCCGGGCTTCTACGAGATCGTGATCAAGGTGCCGAGCGACCTGGACGAGCACCTGCCGGGC
ATTTCTGACTCGTTTGTGAACTGGGTGGCCGGAGAAGGAATGGGAGCTGCCCCCGGATTCTGAC
ATGGATCGGAATCTGATCGAGCAGGCCACCCCTGACCGTGGCCGAGAAGCTGCAGCGCGACTTC
CTGGTCCACTGGCGCCGCGTGAGTAAGGCCCCGGAGGCCCTCTTCTTTGTTCAGTTCGAGAAG
GGCGAGTCCTACTTCCACCTCCACGTTCTCGTCGAGACCACGGGGGTCAAGTCCATGGTCCTG
GGCCGCTTCCTGAGTCAGATCAGAGACAGGCTGGTGCAGACCATCTACCGCGGGGTCGAGCCC
ACGCTGCCCAACTGGTTCGCGGTGACCAAGACGCGAAATGGCGCCGGCGGGGGGAACAAGGTG
GTGGACGAGTGCTACATCCCCAACTACCTCCTGCCCAAGACCCAGCCCGAGCTGCAGTGGGCG
TGGACTAACATGGAGGAGTATATAAGCGCGTGTCTAAACCTCGCGGAGCGTAAACGGCTCGTG
GCGCAGCACCTGACCCACGTCAGCCAGCAGCAGGAGCAAGGAGAATCTGAACCCGAAT
TCTGACGCGCCCGTGATCAGGTCAAAAACCTCCGCGCGCTACATGGAGCTGGTCGGGTGGCTG
GTGGACCGGGGCATCACCTCCGAGAAGCAGTGGATCCAGGAGGACCAGGCCTCGTACATCTCC
TTCAACGCCGCCTCCAACTCGCGGTCCCAGATCAAGGCCGCGCTGGACAATGCCGGAAAGATC
ATGGCGCTGACCAAATCCGCGCCCGACTACCTGGTAGGCCCGTCCTTACCCGCGGACATTAAG
GCCAACCGCATCTACCGCATCCTGGAGCTCAACGGCTACGACCCCGCCTACGCCGGCTCCGTC
TTCCTGGGCTGGGCGCAGAAAAAGTTCGGTAAACGCAACACCATCTGGCTGTTTGGGCCCGCC
ACCACCGGCAAGACCAACATCGCGGAAGCCATAGCCCACGCCGTGCCCTTCTACGGCTGCGTG
AACTGGACCAATGAGAACTTTCCCTTCAACGATTGCGTCGACAAGATGGTGATCTGGTGGGAG
GAGGGCAAGATGACCGCCAAGGTCGTGGAGTCCGCCAAGGCCATTCTGGGCGGAAGCAAGGTG
CGCGTGGACCAAAAGTGCAAGTCCTCGGCCCAGATCGACCCCACGCCCGTGATCGTCACCTCC
AACACCAACATGTGCGCCGTGATCGACGGGAACAGCACCACCTTCGAGCACCAGCAGCCGCTG
CAGGACCGCATGTTCAAGTTCGAGCTCACCCGCCGTCTGGAGCACGACTTTGGCAAGGTGACC
AAGCAGGAAGTCAAAGAGTTCTTCCGCTGGGCTCAGGATCACGTGACTGAGGTGGCGCATGAG
TTCTACGTCAGAAAGGGCGGAGCCACCAAAAGACCCGCCCCAGTGACGCGGATATAAGCGAG
CCCAAGCGGGCCTGCCCCTCAGTTCCGGAGCCATCGAGCGTCAGACGCGGAAGCACCGGTGGAC
TTTGCGGACAGGTACCAAAACAAATGTTCTCGTCACGCGGGCATGCTTCAGATGCTGTTTCCC
TGCAAGACATGCGAGAGAATGAATCAGAATTTCAACGTCTGCTTCACGCACGGGTCAGAGAC
TGCTCAGAGTGCTTCCCCGGCGCGTCAGAATCTCAACCCGTCGTCAGAAAAAAGACGTATCAG
AAACTGTGCGCGATTCATCATCTGCTGGGGCGGGCACCCGAGATTGCGTGTTCGGCCTGCGAT
CTCGTCAACGTGGACTTGGATGACTGTGTTTCTGAGCAATAAATGACTTAAACCAGGTATGGC
TGCTGACGGTTATCTTCCAGATTGGCTCGAGGACAACCTCTCTGAGGGCATTCGCGAGTGGTG
GGACCTGAAACCTGGAGCCCCGAAGCCCAAGGCCAACCAGCAGAAGCAGGACGACGGCCGGGG
TCTGGTGCTTCCTGGCTACAAGTACCTCGGACCCTTCAACGGACTCGACAAGGGGGACCCCGT
CAACGCGGCGGACGCAGCGGCCCTCGAGCACGACCAAGGCCTACGACCAGCAGCTCAAAGCGGG
TGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTCCAGGCCAAGAAGAGGGTACTCGAACC
TCTGGGCCTGGTTGAAGAAGGTGCTAAAACGGCTCCTGGAAAGAAGAGACCGTTAGAGTCACC
ACAAGAGCCCGACTCCTCCTCGGGCATCGGCAAAAAAGGCAAACAACCAGCCAGAAAGAGGCT
CAACTTTGAAGAGGACACTGGAGCCGGAGACGGACCCCCTGAAGGATCAGATACCAGCGCCAT
GTCTTCAGACATTGAAATGCGTGCAGCACCGGGCGGAAATGCTGTCGATGCGGGACAAGGTTC
CGATGGAGTGGGTAATGCCTCGGGTGATTGGCATTGCGATTCCACCTGGTCTGAGGGCAAGGT
CACAACAACCTCGACCAGAACCTGGGTCTTGCCCACCTACAACAACCACTTGTACCTGCGTCT
CGGAACAACATCAAGCAGCAACACCTACAACGGATTCTCCACCCCCTGGGGATATTTTGACTT
CAACAGATTCCACTGTCACTTCTCACCACGTGACTGGCAAAGACTCATCAACAACAACTGGGG
ACTACGACCAAAAGCCATCGCGCGTTAAAAATCTTCAATATCCAAGTTAAGGAGGTCACAACGTC
GAACGGCGAGACTACGGTCGCTAATAACCTTACCAGCACGGTTCAGATATTTGCGGACTCGTC
GTATGAGCTCCCGTACGTGATGGACGCTGGACAAGAGGGGAGCCTGCCTCCTTTCCCCAATGA
CGTGTTCATGGTGCCTCAATATGGCTACTGTGGCATCGTGACTGGCGAGAATCAGAACCAAAC
GGACAGAAACGCTTTCTACTGCCTGGAGTATTTTCCTTCGCAAATGTTGAGAACTGGCAACAA
CTTTGAAATGGCTTACAACTTTGAGAAGGTGCCGTTCCACTCAATGTATGCTCACAGCCAGAG
CCTGGACAGACTGATGAATCCCCTCCTGGACCAGTACCTGTGGCACTTACAGTCGACTACCTC
TGGAGAGACTCTGAATCAAGGCAATGCAGCAACCACATTTGGAAAAATCAGGAGTGGAGACTT
TGCCTTTTACAGAAAGAACTGGCTGCCTGGGCCTTGTGTTAAACAGCAGAGATTCTCAAAAAC
TGCCAGTCAAAATTACAAGATTCCTGCCAGCGGGGGCAACGCTCTGTTAAAGTATGACACCCA
CTATACCCTTAAACAACCGCTGGAGCAACATCGCGCCCGGACCTCCAATGGCCACAGCCGGACC
TTCGGATGGGGACTTCAGTAACGCCCCAGCTTATATTCCCTGGACCCATCTGTTACCGGAAATAC
AACAACTTCAGCCAACAATCTGTTGTTTACATCAGAAGAAGAAATTGCTGCCACCAACCCAAG
AGACACGGACATGTTTGGCCAGATTGCTGACAATAATCAGAATGCTACAACTGCTCCCATAAC
CGGCAACGTGACTGCTATGGGAGTGCTGCCTGGCATGGTGTGGCAAAACAGAGACATTTACTA
CCAAGGGCCAATTTGGGCCAAGATCCCACACGCGGACGGACATTTTCATCCTTCACCGCTGAT
TGGTGGGTTTGGACTGAAACACCCGCCTCCCAGATATTCATCAAGAACACTCCCGTACCTGC
CAATCCTGCGACAACCTTCACTGCAGCCAGAGTGGACTCTTTCATCACACAATACAGCACCGG
CCAGGTCGCTGTTCAGATTGAATGGGAAATTGAAAAGGAACGCTCCAAACGCTGGAATCCTGA
AGTGCAGTTTACTTCAAACTATGGAACCAGTCTTCTATGTTGTGGGCTCCTGATACAACTGG
GAAGTATACAGAGCCGCGGGTTATTGGCTCTCGTTATTTGACTAATCATTTGTAA

FIG. 18

AAV-13, NONSTRUCTURAL PROTEIN AND CAPSID PROTEIN GENES, COMPLETE CDS,
GENBANK ACCESSION NO. EU285562 AND SCHMIDT ET AL. (2008) J. VIROL.
82:8911
CCGCGAGTGAGCGAACCAGGAGCTCCATTTTGCCCGCGAATTTTGAACGAGCAGCAGCCATGC
CGGGATTCTACGAGATTGTCCTGAAGGTGCCCAGCGACCTGGACGAGCACCTGCCTGGCATTT
CTGACTCTTTTGTAAACTGGGTGGCGGAGAAGGAATGGGAGCTGCCGCCGGATTCTGACATGG
ATCTGAATCTGATTGAGCAGGCACCCCTAACCGTGGCCGAAAAGCTGCAACGCGAATTCCTGG
TCGAGTGGCGCCGCGTGAGTAAGGCCCCGGAGGCCCTCTTCTTTGTTCAGTTCGAGAAGGGGG
ACAGCTACTTCCACCTACACATTCTGGTGGAGACCGTGGGCGTGAAATCCATGGTGGTGGGCC
GCTACGTGAGCCAGATTAAAGAGAAGCTGGTGACCCGCATCTACCGCGGGGTCGAGCCGCAGC
TTCCGAACTGGTTCGCGGTGACCAAGACGCGTAATGGCGCCGGAGGCGGGAACAAGGTGGTGG
ACGACTGCTACATCCCCAACTACCTGCTCCCCAAGACCCAGCCCGAGCTCCAGTGGGCGTGGA
CTAATATGGACCAGTATTTAAGCGCCTGTTTGAATCTCGCGGAGCGTAAACGGCTGGTGGCGC
AGCATCTGACGCACGTGTCGCAGACGCAGGAGCAGAACAAAGAGAACCAGAATCCCAATTCTG
ACGCGCCGGTGATCAGATCAAAAACCTCCGCGAGGTACATGGAGCTGGTCGGGTGGCTGGTGG
ACCGCGGGATCACGTCAGAAAAGCAATGGATCCAGGAGGACCAGGCCTCTTACATCTCCTTCA
ACGCCGCCTCCAACTCGCGGTCACAAATCAAGGCCGCACTGGACAATGCCTCCAAATTTATGA
GCCTGACAAAAACGGCTCCGGACTACCTGGTGGGAAACAACCCGCCGGAGGACATTACCAGCA
ACCGGATCTACAAAATCCTCGAGATGAACGGGTACGATCCGCAGTACGCGGCCTCCGTCTTCC
TGGGCTGGGCGCAAAAGAAGTTCGGGAAGAGGAACACCATCTGGCTCTTTGGGCCGGCCACGA
CGGGTAAAACCAACATCGCTGAAGCTATCGCCCACGCCGTGCCCTTTTACGGCTGCGTGAACT
GGACCAATGAGAACTTTCCGTTCAACGATTGCGTCGACAAGATGGTGATCTGGTGGGAGGAGG
GCAAGATGACGGCCAAGGTCGTGGAGTCCGCCAAGGCCATTCTGGGCGGAAGCAAGGTGCGCG
TGGACCAAAAGTGCAAGTCATCGGCCCAGATCGACCCAACTCCCGTCATCGTCACCTCCAACA
CCAACATGTGCGCGGTCATCGACGGAAATTCCACCACCTTCGAGCACCAACAACCACTCCAAG
ACCGGATGTTCAAGTTCGAGCTCACCAAGCGCCTGGAGCACGACTTTGGCAAGGTCACCAAGC
AGGAAGTCAAGGACTTTTTCCGGTGGGCGTCAGATCACGTGACTGAGGTGTCTCACGAGTTTT
ACGTCAGAAAGGGTGGAGCTAGAAAGAGGCCCGCCCCCAATGACGCAGATATAAGTGAGCCCA
AGCGGGCCTGTCCGTCAGTTGCGCAGCCATCGACGTCAGACGCGGAAGCTCCGGTGGACTACG
CGGACAGGTACCAAAACAAATGTTCTCGTCACGTGGGCATGAATCTGATGCTTTTTCCCTGCC
GGCAATGCGAGAGAATGAATCAGAATGTGACTTGCTTCACGCACGGGGTCATGGACTGTG
CCGAGTGCTTCCCCGTGTCAGAATCTCAACCCGTGTCTGTCGTCAGAAAGCGGACATATCAGA
AACTGTGTCCGATTCATCACATCATGGGGAGGGCGCCCGAGGTGGCTTGTTCGGCCTGCGATC
TGGCCAATGTGGACTTGGATGACTGTGACATGGAGCAATAAATGACTCAAACCAGATATGACT
GACGGTTACCTTCCAGATTGGCTAGAGGACAACCTCTCTGAAGGCGTTCGAGAGTGGTGGGCG
CTGCAACCTGGAGCCCCTAAACCCAAGCAAATCAACAACATCAGGACAACGCTCGGGGTCTT
GTGCTTCCGGGTTACAAATACCTCGGACCCGGCAACGGACTTGACAAGGGGGAACCCGTCAAC
GCAGCGGACGCGGCAGCCCTCGAACACGACAAGGCCTACGACCAGCAGCTCAAGGCCGGTGAC
AACCCCTACCTCAAGTACAACCGACGCCGACGCCGAGTTTCAGGAGCGTCTTCAAGAAGATACG
TCTTTTGGGGGCAACCTCGGACGAGCAGTCTTCCAGGCCAAAAAGAGGATCCTTGAGCCTCTG
GGTCTGGTTGAGGAAGCGGCTAAGACGGCTCCTGGAAAAAGAGACCTGTAGAGCAATCTCCA
GCAGAACCGGACTCCTCTTCGGGCATCGGCAAATCAGGCCAGCAGCCCGCTAGAAAAAGACTG
AATTTTGGTCAGACTGGCGACACAGAGTCAGCCCCCCTCAACCACTCGGACAACCTCCC
GCAGCCCCCTCTGGTGTGGGATCTACTACAATGGCTTCAGGCGGTGGCGCACCAATGGCAGAC
AATAACGAGGGTGCCGATGGAGTGGGTAATTCCTCAGGAAATTGGCATTGCGATTCCCAATGG
CTGGGCGACAGAGTCATCACCACCAGCACCCGCACCTGGGCCCTGCCCACCTACAACAATCAC
CTCTACAAGCAAATCTCCAGCCAATCAGGAGCCACCAACGACAACCACTACTTTGGCTACAGC
ACCCCCTGGGGGTATTTTGACTTCAACAGATTCCACTGCCACTTTTCACCACGTGACTGGCAA
AGACTCATCAACAACAACTGGGGATTCCGACCCAAGAGACTCAACTTCAAGCTCTTTAACATT
CAAGTCAAAGAGGTCACGCAGAATGACGGTACGACGACGATTGCCAATAACCTTACCAGCACG
GTTCAGGTGTTTACTGACTCCGAGTACCAGCTCCCGTACGTCCTCGGCTCGGCGCATCAGGGA
TGCCTCCCGCCGTTCCCAGCAGACGTCTTCATGGTCCCACAGTATGGATACCTCACCCTGAAC
AACGGGAGTCAGGCGGTAGGACGCTCTTCCTTTTACTGCCTGGAGTACTTCCTTCTCAGATG
CTGCCTACTGGAAACAACTTTCAGTTTAGCTACACTTTTGAAGACGTGCCTTTCCACAGCAGC
TACGCTCACAGCCAAAGTCTGGACCGTCTCATGAATCCTCTGATCGACCAGTACCTGTACTAT
CTGAACAGGACACAAACAGCCAGTGGAACTCAGCAGTCTCGGCTACTGTTTAGCCAAGCTGGA
CCCACCAGTATGTCTCTTCAAGCTAAAAACTGGCTGCCTGGACCTTGCTACAGACAGCAGCGT
CTGTCAAAGCAGGCAAACGACAACAACAGCAACTTTCCCTGGACTGGTGCCACCAAATAT
CATCTGAATGGCCGGGACTCATTGGTGAACCCGGGCCCTGCTATGGCCAGTCACAAGGATGAC
AAAGAAAAGTTTTTCCCCATGCATGGAACCCTGATATTTGGTAAAGAAGGAACAAATGCCAAC
AACGCGGATTTGGAAAATGTCATGATTACAGATGAAGAAGAAATCCGCACCACCAATCCCGTG
GCTACGGAGCAGTACGGGACTGTGTCAAATAATTTGCAAAACTCAAACGCTGGTCCAACTACT
GGAACTGTCAATCACCAAGGAGCGTTACCTGGTATGGTGTGGCAGGATCGAGACGTGTACCTG
CAGGGACCCATTTGGGCCAAGATTCCTCACACCGATGGACACTTTCATCCTTCTCCACTGATG
GGAGGTTTTGGGCTCAAACACCCGCCTCCTCAGATCATGATCAAAAACACTCCCGTTCCAGCC
AATCCTCCCACAAACTTTAGTGCGGCAAAGTTTGCTTCCTTCATCACACAGTACTCCACGGGG
CAGGTCAGCGTGGAGATCGAGTGGGAGCTGCAGAAGGAGAACAGCAAACGCTGGAATCCCGAA
ATTCAGTACACTTCCAACTACAACAAATCTGTTAATGTGGACTTTACTGTGGACACTAATGGT
GTGTATTCAGAGCCTCGCCCCATTGGCACCAGATACCTGACTCGTAATCTGTAATTGCTTGTT
AATCAATAAACCGGTTAATTCG

FIG. 19

B19 PARVOVIRUS, COMPLETE SEQUENCE, GENBANK ACCESSION NO. NC_000883 AND
SHADE ET AL. (1986) J. VIROL. 58:921
CCAAATCAGATGCCGCCGGTCGCCGCCGGTAGGCGGGACTTCCGGTACAAGATGGCGGACAATTACGTCATTT
CCTGTGACGTCATTTCCTGTGACGTCACTTCCGGTGGGCGGGACTTCCGGAATTAGGGTTGGCTCTGGGCCAG
CTTGCTTGGGGTTGCCTTGACACTAAGACAAGCGGCGCGCCGCTTGTCTTAGTGGCACGTCAACCCCAAGCGC
TGGCCCAGAGCCAACCCTAATTCCGGAAGTCCCGCCCACCGGAAGTGACGTCACAGGAAATGACGTCACAGGA
AATGACGTAATTGTCCGCCATCTTGTACCGGAAGTCCCGCCTACCGGCGGCGACCGGCGGCATCTGATTTGGT
GTCTTCTTTTAAATTTTAGCGGGCTTTTTTCCCGCCTTATGCAAATGGGCAGCCATTTTAAGTGTTTCACTAT
AATTTTATTGGTCAGTTTTGTAACGGTTAAAATGGGCGGAGCGTAGGCGGGGACTACAGTATATATAGCACGG
CACTGCCGCAGCTCTTTCTTTCTGGGCTGCTTTTTCCTGGACTTTCTTGCTGTTTTTTGTGAGCTAACTAACA
GGTATTTATACTACTTGTTAACATACTAACATGGAGCTATTTAGAGGGGTGCTTCAAGTTTCTTCTAATGTTC
TGGACTGTGCTAACGATAACTGGTGGTGCTCTTTACTGGATTTAGACACTTCTGACTGGGAACCACTAACTCA
TACTAACAGACTAATGGCAATATACTTAAGCAGTGTGGCTTCTAAGCTTGACTTTACCGGGGGGCCACTAGCG
GGGTGCTTGTACTTTTTTCAAGTAGAATGTAACAAATTTGAAGAAGGCTATCATATTCATGTGGTTATTGGGG
GGCCAGGGTTAAACCCCAGAAACCTCACAGTGTGTGTAGAGGGGTTATTTAATAATGTACTTTATCACCTTGT
AACTGAAAATGTAAAGCTAAAATTTTTGCCAGGAATGACTACAAAAGGCAAATACTTTAGAGATGGAGAGCAG
TTTATAGAAAACTATTTAATGAAAAAAATACCTTTAAATGTTGTATGGTGTGTTACTAATATTGATGGATATA
TAGATACCTGTATTTCTGCTACTTTTAGAAGGGGAGCTTGCCATGCCAAGAAACCCCGCATTACCACAGCCAT
AAATGACACTAGTAGTGATGCTGGGGAGTCTAGCGGCACAGGGGCAGAGGTTGTGCCAATTAATGGGAAGGGA
ACTAAGGCTAGCATAAAGTTTCAAACTATGGTAAACTGGTTGTGTGAAAACAGAGTGTTTACAGAGGATAAGT
GGAAACTAGTTGACTTTAACCAGTACACTTTACTAAGCAGTAGTCACAGTGGAAGTTTTCAAATTCAAAGTGC
ACTAAAACTAGCAATTTATAAAGCAACTAATTTAGTGCCTACAAGCACATTTCTATTGCATACAGACTTTGAG
CAGGTTATGTGTATTAAAGACAATAAAATTGTTAAATTGTTACTTTGTCAAAACTATGACCCCCTATTAGTGG
GGCAGCATGTGTTAAAGTGGATTGATAAAAAATGTGGCAAGAAAAATACACTGTGGTTTTATGGCCGCCAAG
TACAGGAAAAACAAACTTGGCAATGGCCATTGCTAAAAGTGTTCCAGTATATGGCATGGTTAACTGGAATAAT
GAAAACTTTCCATTTAATGATGTAGCAGGGAAAAGCTTGGTGGTCTGGGATGAAGGTATTATTAAGTCTACAA
TTGTAGAAGCTGCAAAAGCCATTTTAGGCGGGCAACCCACCACCAGGGTAGATCAAAAAATACGTGGAAGTAGC
TGTGCCTGGAGTACCTGTGGTTATAACCAGCAATGGTGACATTACTTTTGTTGTAAGCGGGAACACTACAACA
ACTGTACATGCTAAAGCCTTAAAAGAGCGAATGGTAAAGTTAAACTTTACTGTAAGATGCAGCCCTGACATGG
GGTTACTAACAGAGGCTGATGTACAACAGTGGCTTACATGGTGTAATGCACAAAGCTGGGACCACTATGAAAA
CTGGGCAATAAACTACACTTTTGATTTCCCTGGAATTAATGCAGATGCCCTCCACCCAGACCTCCAAACCACC
CCAATTGTCACAGACACCAGTATCAGCAGCAGTGGTGGTGAAAGCTCTGAAGAACTCAGTGAAAGCAGCTTTT
TTAACCTCATCACCCCAGGCGCCTGGAACACTGAAACCCCGCGCTCTAGTACGCCCATCCCCGGGACCAGTTC
AGGAGAATCATTTGTCGGAAGCTCAGTTTCCTCCGAAGTTGTAGCTGCATCGTGGGAAGAAGCCTTCTACACA
CCTTTGGCAGACCAGTTTCGTGAACTGTTAGTTGGGGTTGATTATGTGTGGGACGGTGTAAGGGGTTTACCTG
TGTGTTGTGTGCAACATATTAACAATAGTGGGGGAGGCTTGGGACTTTGTCCCCATTGCATTAATGTAGGGGC
TTGGTATAATGGATGGAAATTTCGAGAATTTACCCCAGATTTGGTGCGGTGTAGCTGCCATGTGGGAGCTTCT
AATCCCTTTTCTGTGCTAACCTGCAAAAATGTGCTTACCTGTCTGGATTGCAAAGCTTTTGTAGATTATGAGT
AAAGAAAGGTGGCAAATGGTGGGAAAGTGATGATAAATTTGCTAAAGCTGTGTATCAGCAATTTGTGGAATTTT
ATGAAAAGGTTACTGGAACAGACTTAGAGCTTATTCAAATATTAAAAGATCACTATAATATTTCTTTAGATAA
TCCCCTAGAAAACCCATCCTCTCTGTTTGACTTAGTTGCTCGTATTAAAAATAACCTTAAAAACTCTCCAGAC
TTATATAGTCATCATTTTCAAAGTCATGGACAGTTATCTGACCACCCCCATGCCTTATCATCCAGTAGCAGTC
ATGCAGAACCTAGAGGAGAAAATGCAGTATTATCTAGTGAAGACTTACACAAGCCTGGGCAAGTTAGCGTACA
ACTACCCGGTACTAACTATGTTGGGCCTGGCAATGAGCTACAAGCTGGGCCCCCGCAAAGTGCTGTTGACAGT
GCTGCAAGGATTCATGACTTTAGGTATAGCCAATTGGCTAAGTTGGGAATAAATCCATATACTCATTGGACTG
TAGCAGATGAAGAGCTTTTAAAAAATATAAAAAATGAAACTGGGTTTCAAGCACAAGTAGTAAAAGACTACTT
TACTTTAAAAGGTGCAGCTGCCCCTGTGGCCCATTTTCAAGGAAGTTTGCCGGAAGTTCCCGCCTTACAACGCC
TCAGAAAAATACCCAAGCATGACTTCAGTTAATTCTGCAGAAGCCAGCACTGGTGCAGGAGGGGGTGGCAGTA
ATCCTGTCAAAAGCATGTGGAGTGAGGGGGCCACTTTTAGTGCCAACTCTGTAACTTGTACATTTTCCAGACA
GTTTTTAATTCCTTATGACCCCAGAGCACCATTATAAGGTGTTTTCTCCCGCAGCAAGCAGCTGCCACAATGCC
AGTGGAAAGGAGGCAAAGGTTTGCACAATTAGTCCATAATGGGATACTCAACCCCATGGAGATATTTAGATT
TTAATGCTTTAAATTTATTTTTTTCACCTTTAGAGTTTCAGCACTTAATTGAAAATTATGGAAGTATAGCTCC
TGATGCTTTAACTGTAACATATCAGAAATTGCTGTTAAGGATGTTACAGACAAAACTGGAGGGGGGGTACAG
GTTACTGACAGCACTACAGGGCGCCTATCCATGTTAGTAGACCATGAATACAAGTACCCCATATGTGTTAGGAC
AAGGTCAGGATACTTTAGCCCCAGAACTTCCTATTTGGGTATACTTTCCCCCTCAATATGCTTACTTAACAGT
AGGAGATGTTAACACACAAGGAATCTCTGGAGACAGCAAAAATTAGCAAGTGAAGAATCAGCATTTTATGTT
TTGGAACACAGTTCTTTTCAGCTTTTAGGTACAGGAGGTACAGCAACTATGTCTTATAAGTTTCCTCCAGTGC
CCCCAGAAAATTTAGAGGGCTGCAGTCAACACTTTTATGAAATGTACAATCCCTTATACGGATCCCGCTTAGG
GGTTCCTGACACATTAGGAGGTGACCCAAAATTTAGATCTTTAACACATGAAGACCATGCAATTCAGCCCCAA
AACTTCATGCCAGGGCCACTAGTAAACTCAGTGTCTACAAAGGAGGGAGACAGCTCTAATACTGGAGCTGGAA
AAGCCTTAACAGGCCTTAGCACAGGCACCTCTCAAAACACTAGAATATCCTTACGCCCTGGGCCAGTGTCACA
GCCATACCACCACTGGGACACAGATAAATATGTTCCAGGAATAAATGCCATTTCTCATGGTCAGACCACTTAT
GGTAACGCTGAAGACAAAGAGTATCAGCAAGGAGTGGGTAGATTTCCAAATGAAAAAGAACAGCTAAAACAGT
TACAGGGTTTAAACATGCACACCTATTTCCCCAATAAAGGAACCCAGCAATATACAGATCAAATTGAGCGCCC
CCTAATGGTGGGTTCTGTATGGAACAGAAGAGCCCTTCACTATGAACGCCAACTTCACTGCATTGCAGAGCAT
TTAGATGACAGTTTTAAAACTCAGTTTGCAGCCTTAGGAGGATGGGGTTTGCATCAGCCACCTCCTCAAATAT
TTTTAAAAATATTACCACAAAGTGGGCCAATTGGAGGTATTAAATCAATGGGAATTACTACCTTAGTTCAGTA
TGCCGTGGGAATTATGACAGTAACTATGACATTTAAATTGGGGCCCCGTAAAGCTACGGGCAGGTGGAATCCT
CAACCTGGAGTATATCCCCCGCACGCAGCAGGTCATTTACCCATATGTACTATATGACCCCACAGCTACAGATG
CAAAACAACACCACAGGCATGGATACGAAAAGCCTGAAGAATTGTGGACAGCCAAAAGCCGTGTGCACCCATT
GTAAACACTCCCCACCGGTGCCTCAGCCAGGATGCGTAACTAAACGCCCACCAGTACACCCAGACTGTACCT
GCCCCCTCCTGTACCTATAAGACAGCCTAACACAAAAGATATAGACAATGTAGAATTTAAGTACTTAACCAGA
TATGAACAACATGTTATTAGAATGTTAAGATTGTGTAATATGTATCAAAATTTAGAAAAATAAACATTTGTTG
TGGTTAAAAAATTATGTTGTTTGTGCGCTTTAAAAATTTAAAAGAAGCACCAAATCAGATGCCGCCGGTCGCCC
CGGTAGGCGGGACTTCCGGTACAAGATGGCGGACAATTACGTCATTTCCTGTGACGTCATTTCCTGTGACGTC
ACTTCCGGTGGGCGGGACTTCCGGAATTAGGGTTGGCTCTGGGCCAGCGCTTGGGGTTGACGTGCCACTAAGA
CAAGCGGCGCGCCGCTTGTCTTAGTGTCAAGGCAACCAAGCCAAGCTGGCCCAGAGCCAACCCTAATTCCGG
AAGTCCCGCCCACCGGAAGTGACGTCACAGGAAATGACGTCACAGGAAATGACGTAATTGTCCGCCATCTTGT
ACCGGAAGTCCCGCCTACCGGCGGCGACCGGCGGCATCTGATTTGG

FIG. 20

MINUTE VIRUS FROM MOUSE (MVM), COMPLETE SEQUENCE, GENBANK ACCESSION
NO. NC 001510
ATTTTTAGAACTGACCAACCATGTTCACGTAAGTGACGTGATGACGCGCGCTGCGCGCGCCTTC
GGACGTCACACGTCACTTACGTTTCACATGGTTGGTCAGTTCTAAAAATGATAAGCGGTTCAGGGA
GTTTAAACCAAGGCGCGAAAAGGAAGTGGGCGTGGTTTAAAGTATATAAGCAACTACTGAAGTCAG
TTACTTATCTTTTCTTTCATTCTGTGAGTCGAGACGCACAGAAAGAGAGTAACCAACTAACCATGG
CTGGAAATGCTTACTCTGATGAAGTTTTGGGAGCAACCAACTGGTTAAAGGAAAAAAGTAACCAGG
AAGTGTTCTCATTTGTTTTTAAAAATGAAAATGTTCAACTGAATGGAAAAGATATCGGATGGAATA
GTTACAAAAAAGAGCTGCAGGAGGACGAGCTGAAATCTTTACAACGAGGAGCCGGAAACTACTTGGG
ACCAAAGCGAGGACATGGAATGGGAAACCACAGTGGATGAAATGACCAAAAAGCAAGTATTCATTT
TTGATTCTTTGGTTAAAAAATGTTTATTTGAAGTGCTTAACACAAAGAATATATTTCCTGGTGATG
TTAATTGGTTTGTGCAACATGAATGGGGAAAAGACCAAGGCTGGCACTGCCATGTACTAATTGGAG
GAAAGGACTTTAGTCAAGCTCAAGGGAAATGGTGGAAGGCAACTAAATGTTTACTGGAGCAGAT
GGTTGGTAACAGCCTGTAATGTGCAACTAACACCAGCTGAAAGAATTAAACTAAGAGAAATAGCAG
AAGACAATGAGTGGGTTACTCTACTTACTTATAAGCATAACATGCGGCCAAACAAAAAAGACTATACCAAGT
GTGTTCTTTTTGGAAACATGATTGCTTACTATTTTTTAACTAAAAAGAAAATAAGCACTAGTCCAC
CAAGAGACGGAGGCTATTTTCTTAGCAGTGACTCTGGCTGGAAAACTAACTTTTTAAAAGAAGGCG
AGCGCCATCTAGTGAGCAAACTATACACTGATGACATGCGGCCAGAAACGGTTGAAACCACAGTAA
CCACTGCGCAGGAAACTAAGCGCGGCAGAATTCAAACTAAAAAAGAAGTTTCTATTAAAACTACAC
TTAAAGAGCTGGTGCATAAAAGAGTAACCTCACCAGAGGACTGGATGATGATGCAGCCAGACAGTT
ACATTGAAATGATGGCTCAACCAGGTGGAGAAAACCTGCTGAAAAATACGCTAGAGATTTGTTAC
TAACTCTAGCCAGAACCAAAACAGCATTTGACTTAATTTTAGAAAAAGCTGAAACCAGCAAACTAA
CCAACTTTTCACTGCCTGACACAAGAACCTGCAGAATTTTTGCTTTTCATGGCTGGAACTATGTTA
AAGTTTGCCATGCTATTTGCTGTGTTTTAAACAGACAAGGAGGCAAAAGAAATACTGTTTTATTTC
ATGGACCAGCCAGCACAGGCAAATCTATTATTGCAAGCCATAGCACAAGCAGTTGGCAATGTTG
GTTGCTATAATGCAGCCAATGTAAACTTTCCATTTAATGACTGTACCAACAAGAACTTGATTTGGG
TAGAAGAAGCTGGTAACTTTGGACAGCAAGTAAACCAGTTTAAAGCCATTTGCTCTGGTCAAACTA
TTCGCATTGATCAAAAAGGAAAAGGCAGCAAACAGATTGAACCAACACCAGTCATCATGACCACAA
ATGAGAACATTACAGTGGTCAGAATAGGCTGCGAAGAAAGACCAGAACACACTCAACCAATCAGAG
ACAGAATGCTTAACATTCATCTAACACATACCTTGCCTGGTGACTTTGGTTTGGTTGACAAAAATG
AATGGCCCATGATTTGTGCTTGGTTGGTAAAGAATGGTTACCAATCTACCATGGCAAGCTACTGTG
CTAAATGGGGCAAAGTTCCTGATTGGTCAGAAAACTGGGCGGAGCCAAAGGTGCCAACTCCTATAA
ATTTACTAGGTTCGGCACGCTCACCATTCACGACACCGAAAAGTACGCCTCTCAGCCAGAACTATG
CACTAACTCCACTTGCATCGGATCTCGAGGACCTGGCTTTAGAGCCTTGGAGCACACCAAATACTC
CTGTTGCGGGCACTGCAGAAACCCAGAACACTGGGGAAGCTGGTTCCAAAGCCTGCCAAGATGGTC
AACTGAGCCCAACTTGGTCAGAGATCGAGGAGGATTTGAGAGCGTGCTTCGGTGCGGAACCGTTGA
AGAAAGACTTCAGCGAGCCGCTGAACTTGGACTAAGGTACGATGGCGCCTCCAGCTAAAAGAGCTA
AAAGAGGTAAGGGTTTAAGGGATGGTTGGTTGCGGTGGGGTATTAATGTTTAATTACCTGTTTTACAG
GCCTGAAATCACTTGGTTTAGGTTGGGTGCCTCCTGGCTACAAGTACCTGGGACCAGGGAACAGC
CTTGACCAAGGAGAACCAACCAATCCATCTGACGCCGCTGCCAAAGAGCACGACGAGGCCTATGAT
CAATACATCAAATCTGGAAAAAATCCTTACCTGTACTGCTGCGATCAACGCTTTATTGAC
CAAACCAAGGACGCCAAAGACTGGGGAGGCAAGGTTGGTCACTACTTTTTTAGAACCAAGCGCGCT
TTTGCACCTAAGCTTGCTACTGACTCTGAACCTGGAACTTCTGGTGTAAGCAGAGCTGGTAAACGC
ACTAGACCACCTGCTTACATTTTTATTAACCAAGCCAGAGCTAAAAAAAACTTACTTCTTCTGCT
GCACAGCAAAGCAGTCAAACCATGAGTGATGCGCACCAGCCAACCTGACAGCGGAAACGCTGTCCAC
TCAGCTGCAAGAGTTGAACGAGCAGCTGACGGCCCTGGAGGCTCTGGGGGTGGGGGCTCTGGCGGG
GGTGGGGTTGGTTTCTACTGGGTCTTATGATAATCAAACGCATTATAGATTCTTGGGTGACGGC
TGGGTAGAAATTACTGCACTAGCAACTAGACTAGTACATTTAAACATGCCTAAATCAGAAAACTAT
TGCAGAATCAGAGTTCACAATACAACAGACACATCAGTCAAAGGCAACATGGCAAAAGATGATGCT
CATGAGCAAATTTGGACACCATGGACGCTTGGTGGATGCTAATGCTTGGAGAGTTTGGCTCCAGCCA
AGTGACTGGCAATACATTTGCAACACCATGAGCCAGCTTAACTTGGTATCACTTGATCAAGAAATA
TTCAATGTAGTGCTGAAAACTGTTACAGAGCAAGACTTAGGAGGTCAAGCTATAAAAATATACAAC
AATGACCTTACAGCTTGCATGATGGTTGCAGTAGACTCAAACAACATTTTGCCATACACACCTGCA
GCAAACTCAATGGAAACACTTGGTTTCTACCCCTGGAAACCAACCATAGCCATCACCATACAGGTAC
TATTTTTGCGTTGACAGAGATCTTTCAGTGACCTACGAAAATCAAGAAGGCACAGTTGAACATAAT
GTGATGGGAACACCAAAAGGAAATGAATTCTCAATTTTTTACCATTGAGAACACACAACAAAATCACA
TTGCTCAGAACAGGGGACGAATTTGCCACAGGTACTTACTACTTTGACACAAATTCAGTTAAACTC
ACACACACGTGGCAAACCAACCGTCAACTTGGACAGCCTCCACTGCTGTCAACCTTTCCTGAAGCT
GACACTGATGCAGGTACACTTACTGCTCAAGGGAGCAGACATGGAACAACACAAATGGGGGTTAAC
TGGGTGAGTGAAGCAATCAGAACCAGACCTGCTCAAGTAGGATTTTGTCAACCACACAATGACTTT
GAAGCCAGCAGAGCTGGACCATTTGCTGCCCCAAAAGTTCCAGCAGATATTACTCAAGGAGTAGAC
AAAGAAGCCAGTCAGTGTTAGATACAGTTATGGCAAACAGCGTGTGAAAATTGGCTTCACAT
GGACCAGCACCAGAGCGCTACACATGGGATGAAACAAGCTTTGGTTCAGGTAGACACCAAAGAT
GGTTTTATTCAATCAGCACCACTAGTTGTTCCACCACCACTAAATGGCATTCTTACAAATGCAAAC
CCTATTGGGACTAAAAATGACATCATTTTTTCAAATGTTTTTAACAGCTATGGTCCACTAACTGCA
TTTTCACACCCAAGTCCTGTATACCCTCAAGGACAAATATGGGACAAAGAACTAGATCTTGAACAC
AAACCTAGACTTCACATAACTGCTCCATTTGTTTGTAAAAACAATGCACCTGGACAAATGTTGGTT
AGATTAGGACCAAACCTAATATGATCAAACGGAGCCACACTTTCTAGAATTGTTACA
TACGGTACATTTTTCTGGAAAGGAAAACTAACCATGAGAGCAAAACTTAGAGCTAACACCACTTGG
AACCCAGTGTACCAAGTAAGTGCTGAAGACAATGGCAACTCATACATGAGTGTAACTAAAATGGTTTA
CCAACTGCTACTGGAAACATGCAGTCTGTGCCGCTTATAACAAGACCTGTTGCTAGAAATACTTAC
TAACTAACCATGCTTTTTCTTTCTGTACTTCATATATTATTAAGACTAATAAAGATCAACATAGA
AATATAATATTACGTATAGATTTAAGAAATAGAATAATATGGTACTTAGTAACTGTTAAAAATAAT
AGAACCTTTGGAATAACAAGATAGTTAGTTGGTTAATGTTAGATAGAATAAGAAGATCATGTATAA
TGAATAAAAGGGTGGAAGGTGGTTGGTAGGTTAATGTTAGATAGAATAAGAAGATCATGTATAAT
GAATAAAAGGGTGGTTTGGTAGGTATTCCCTTAGACTTTGATGTTAAGGACCAAAAAAAAT
AATAAAACTTTTTTAAAACTCAACCAAGACTACTGTCTATTCAGTGACCAACTGAACCATTAGTA
TTACTATGTTTTTAGGGTGGGAGGGTGGGAGATACATGTGTTCGCTATGAGCGAACTGGTACTGGT
TGGTTGCTCTGCTCAACCAACCAGACCGGCAAAGCCGGTCTGGTTGGTTGAGCGCAACCAACCAGT
ACCAGTTCGCTCATAGCCGAACACATGTATCTCCCACCCTCCCACCCTAAAAACATAGTAATACTAA
T

FIG. 21

GOOSE PARVOVIRUS, COMPLETE SEQUENCE, GENBANK ACCESSION NO. NC 001701
CTCATTGGAGGGTTCGTTCGTTCGAACCAGCCAATCAGGGGAGGGGGAAGTGACGCAAGTTCCGG
TCACATGCTTCCGGTGACGCACATCCGGTGACGTAGTTCCGGTCACGTGCTTCCTGTCACGTGTT
TCCGGTCACGTGACTTCCGGTCATGTGACTTCCGGTGACGTGTTTCCGGCTGTTAGGTTGACCAC
GCGCATGCCGCGCGGTCAGCCCAATAGTTAAGCCGGAAACACGTCACCGGAAGTCACATGACCGG
AAGTCACGTGACCGGAAACACGTGACAGGAAGCACGTGACCGGAACTACGTCACCGGATGTGCGT
CACCGGAAGCATGTGACCGGAACTTGCGTCACTTCCCCCTCCCCTGATTGGCTGGTTCGAACGAA
CGAACCCTCCAATGAGACTCAAGGACAAGAGGATATTTTGCGCGCCAGGAAGTGACGTGCAATGC
CACCCTATATAAGCCAGGAAACTTCCGGTTTAGTTCATTCGTTACTCTGCTCTCAGAGAGAACGG
ACCTCAGGTCGGAGAGATGGCACTTTCTAGGCCTCTTCAGATTTCTTCTGATAAATTCTATGAAG
TTATTATTAGATTATCATCGGATATTGATCAAGATGTCCCCGGTCTGTCTCTTAACTTTGTAGAA
TGGCTTTCTACCGGAGTTTGGGAGCCCACGGGCATCTGGAACATGGAGCATGTGAATCTACCGAT
GGTGACCTTGGCAGAGAAGATCAAGAACATTTTCATACAAAGATGGAATCAGTTCAACCAGGACG
AAACGGACTTCTTCTTTCAACTGGAAGAAGGCAGTGAGTACATTCATCTTCATTGCTGTATTGCC
CAGGGCAATGTACGGTCTTTTGTTCTCGGGAGATATATGTCTCAGATAAAAGACTCTATCATAAG
AGATGTATATGAAGGGAAACAAATCAAGATCCCCGATTGGTTTGCTATTACTAAAACCAAGAGGG
GAGGACAGAATAAGACCGTGACTGCAGCATACATACTGCATTACCTTATTCCTAAAAAGCAACCT
GAACTGCAATGGGCCTTTACCAATATGCCTTTATTCACTGCTGCTGCTCTTTGTCTGCAAAAGCG
GCAAGAATTGCTGGATGCATTTCAAGAAAGTGATTTGGCTGCCCCTTTACCTGATCCTCAAGCAT
CAACTGTGGCACCGCTTATTTCCAACAGAGCGGCAAAGAACTATAGCAACCTTGTTGATTGGCTC
ATTGAAATGGGGATAACATCTGAGAAGCAATGGCTCACTGAGAACCGAGAGAGCTACAGAAGCTT
TCAAGCAACTTCTTCAAATAATAGACAAGTGAAAGCTGCACTGGAAAATGCCCGTGCTGAAATGT
TATTGACAAAGACTGCAACTGATTACCTGATAGGAAAAGACCCTGTCCTGGATATAACTAAGAAT
AGGGTCTATCAAATTCTGAAAATGAATAACTACAACCCTCAATACATAGGAAGTATCCTGTGCGG
CTGGGTGAAGAGAGAGTTCAACAAAAGAAACGCCATATGGCTCTACGGACCTGCCACCACCGGGA
AGACCAACATTGCAGAAGCTATTGCCCATGCTGTACCCTTCTATGGCTGTGTTAACTGGACTAAT
GAGAACTTTCCTTTTAATGATTGTGTTGATAAAATGCTGATTTGGTGGGAGGAGGGAAAAATGAC
TAATAAGGTTGTTGAATCTGCAAAAGCAATTTTGGGAGGGTCTGCTGTCCGGGTAGACCAGAAAT
GTAAAGGATCTGTTTGTATTGAACCTACTCCTGTAATTATTACTAGTAATACTGATATGTGTATG
ATTGTTGATGGCAACTCTACTACAATGGAACATAGAATACCATTAGAGGAGCGTATGTTTCAAAT
TGTCCTATCACATAAATTGGAGCCTTCTTTTGGAAAAATTTCTAAAAAAGAAGTCAGAGAATTTT
TCAAATGGGCCAATGACAATCTAGTTCCTGTTGTGTCTGAGTTCAAAGTCCGAACTAATGAACAA
ACCAACTTGCCAGAGCCCGTTCCTGAACGAGCGAACGAGCCGGAGGAGCCTCCTAAGATCTGGGC
TCCTCCTACTAGGGAGGAGTTAGAAGAGCTTTTAAGAGCCAGCCCAGAATTGTTCTCATCAGTCG
CTCCAATTCCTGTGACTCCTCAGAACTCCCCTGAGCCTAAGAGAAGCAGGAACAATTACCAGGTA
CGCTGCGCTTTGCATACTTATGACAATTCTATGGATGTATTTGAATGTATGGAATGTGAGAAAGC
AAACTTTCCTGAATTTCAACCTCTGGGAGAAAATTATTGTGATGAACATGGGTGGTATGATTGTG
CTATATGTAAAGAGTTGAAAAATGAACTTGCAGAAATTGAGCATGTGTTTGAGCTTGATGATGCT
GAAAATGAACAATAAAGATGACTCAAAGCAGATATGTCTACTTTTTTAGATTCTTTTGAAGAGTG
GTATGAGACTGCAGCCGCCTCGTGGCGGAATCTGAAAGCTGGAGCCCCTCAGCCAAAACCAAACC
AGCAGTCTCAGTCTGTGTCTCCAGACAGAGAACCCGAACGAAAAGATAATAATCGGGGCTTTGTA
CTTCCTGGCTATAAGTATCTTGGGCCTGGTAACGGCCTGGATAAAGGCCCACCTGTCAATAAGGC
GGACAGCGTCGCGCTTGAACACGACAAGGCCTATGACCAGCAGCTTAAAGCGGGAGACAACCCAT
ATATAAAATTCAATCACGCTGACCAGGACTTTATAGATAGCCTCCAAGACGACCAGTCATTCGGA
GGTAATCTTGGAAAGGCTGTATTTCAGGCCAAAAAACGTATCTTAGAGCCATTTGGCCTAGTAGA
AGATCCTGTCAACACGGCACCTGCAAAAAAAAATACAGGGAAGCTTACTGACCATTACCCGGTAG
TTAAGAAGCCTAAACTTACCGAGGAAGTCAGTGCGGGAGGTGGTAGCAGTGCCGTACAAGACGGA
GGAGCCACCGCGGAGGGCACCGAACCTGTGGCAGCATCTGAAATGGCAGAGGGAGGAGGCGGAGC
TATGGGCGACTCTTCAGGGGGTGCCGATGGAGTGGGTAATGCCTCGGGAAATTGGCATTGCGATT
CCCAATGGATGGGAAACACAGTCATCACAAAGACCACCAGAACCTGGGTCCTGCCAAGCTACAAC
AACCACATCTACAAAGCAATTACCAGCGGAACCTCTCAAGATGCAAATGTCCAGTATGCAGGATA
CAGTACCCCCTGGGGGTACTTTGATTTCAACCGCTTCCACTGCCACTTCTCCCCTAGAGACTGGC
AGAGACTTATCAACAACCATTGGGGAATCAGACCCAAGTCTCTTAAATTCAAGATCTTCAATGTC
CAAGTCAAAGAAGTCACAACGCAGGATCAGACAAAGACCATTGCAAACAATCTCACCTCAACAAT
TCAAGTCTTTACGGATGATGAGCATCAACTCCCGTATGTCCTGGGCTCGGCTACGGAAGGCACCA
TGCCGCCGTTCCCGTCGGATGTCTATGCCCTGCCGCAGTACGGGTACTGCACAATGCACACCAAC
CAGAATGGAGCACGGTTCAATGACCGTAGTGCATTCTACTGCTTAGAGTACTTCCCTAGTCAGAT
GCTAAGAACAGGCAACAACTTTGAGTTCACATTTGACTTTGAAGAAGTTCCTTTCCATAGCATGT
TCGCTCATTCACAGGACTTAGACAGGCTGATGAACCCCCTAGTGGATCAATACCTCTGGAATTTC
AATGAGGTAGACAGCAGCAGAAATGCTCAATTTAAAAAGGCTGTGAAAGGGGCTTATGGCACCAT
GGGCCGCAATTGGCTGCCAGGACCTAAATTCCTGGATCAAAGAGTTAGGGCCTACACAGGAGGAA
CAGACAACTATGCAAACTGGAACATCTGGAGTAATGGGAACAAGGTGAATTTGAAAGACAGACAG
TATCTCCTACAACCCGGACCTGTGTCAGCTACTTACACAGAAGGGGAGGCTTCCAGCCTTCCAGC
TCAAAATATTTTAGGATAGCTAAAGATCCATACAGATCAGGCAGCACTACAGCAGGAATAAGTG
ACATTATGGTCACGGAAGAACAAGAAGTAGCACCTACAAATGGAGTAGGGTGGAAACCATATGGT
AGGACTGTAACGAATGAACAAAACACTACTACAGCTCCTACAAGTTCAGATCTGGATGTTCTTGG
AGCTTTACCAGGAATGGTTTGGCAGAACAGGGATATATATCTGCAGGGACCTATTGGGGCAAAAA
TACCGAAGACTGATGGTAAATTCCATCCTTCTCCGAATCTCGGAGGATTTGGCCTGCACAATCCA
CCACCGCAGGTGTTCATCAAGAATACACCAGTGCCTGCAGACCCTCCAGTAGAATACGTGCACCA
GAAGTGGAATTCCTACATAACCCAGTACTCTACGGGCCAGTGTACAGTAGAGATGGTGTGGGAGC
TGAGAAAAGAGAATTCAAAGAGATGGAACCCAGAAATCCAGTTCACCAGTAATTTCAGTAACAGA
ACAAGCATAATGTTTGCACCTAATGAAACTGGTGGATATGTAGAAGATAGATTGATTGGAACCAG
ATATCTAACTCAAAATCTGTAAATTCTGTGTAAAAATTCAAATAAAGCACTTCCTGGCGCGCAAA
ATATCCTCTTGTCCTTGAGTCTCATTGGAGGGTTCGTTCGTTCGAACCAGCCAATCAGGGGAGGG
GGAAGTGACGCAAGTTCCGGTCACATGCTTCCGGTGACGCACATCCGGTGACGTAGTTCCGGTCA
CGTGCTTCCTGTCACGTGTTTCCGGTCACGTGACTTCCGGTCATGTGACTTCCGGTGACGTGTTT
CCGGCTTAACTATTGGGCTGACCGCGCGCATGCGCGTGGTCAACCTAACAGCCGGAAACACGTCA
CCGGAAGTCACATGACCGGAAGTCACGTGACCGGAAACACGTGACAGGAAGCACGTGACCGGAAC
TACGTCACCGGATGTGCGTCACCGGAAGCATGTGACCGGAACTTGCGTCACTTCCCCCTCCCCTG
ATTGGCTGGTTCGAACGAACGAACCCTCCAATGAGA

FIG. 22

SNAKE PARVOVIRUS 1, COMPLETE GENOME, GENBANK ACCESSION NO.
NC_006148 AND FARKAS ET AL. (2004) J. GEN. VIROL. 85:555
CGCCCCACCCCTAGTGATCGCGCGCGCTCTCTCTTGGGGCCTGACGGCCGAAGGCCGTCAGCT
GCCGAGCTTCGCTCGGCAGGCCCCAAGAGAGAGCGCGCCGCGATCACTAGGGGTGGGGCGAGTG
CCCTGCTCAACGGGTTTTTTGGTGGGCGGAGCAATGACGTCAGCGGACATGTCTGGACATGTC
TTTGAGCAAGTCCATATAAGGAGTTCCGCCGGATATGCAAATGAGCAATCGCGCAAAGCATTT
TGGGTAGTCACCATGAATAAAAAGGACAGCAAGAAAGATGACGCCCCATAATTTTAATAGGAA
TTTTAACCATGGCGTTTTACGAGGTTGTGTTTCGTTTGCCAAGAGACAATAACAACTTGTTGG
ATGAAGATAGATATCAGCCAGAGTTGAAAGAAGAAGATGACTGGCCTGAGGAATATTTAACCA
GTGAAGATGCCAGCTTTATCGGACTAGCGTATGCTGTGCTAAGTGAAATTCGGAGATTCTTTG
GAAAGGAACTACAATGGTTTGCCCAGGTTGAATGGTGTCCTACTGCTGGTTACCACATGCATG
TTTTGTTGAACCATCCTAAGCTGAGTAACCAGACTTATGGAAGAAAAGGTCAATGAACTGGCTT
GCCGTATAGTCGATACCTTTGGCCTAATTAATCCAGAAGAAGTCATCAGTACCCATTATGTTA
AAAGCAACTATGGACATAAAAAGGTGAGAGTCATTCACCTAGAGTCTTATTTGAAGAACTACT
TTTTCAGAAAGACTTTAGCTCCTCCCAATTATTACCGAGGAAGGAGACTATAAAAGAGAGGAAG
AAGTCGTGCTGTGGGCATTTACGAATATCGTCGCTTGGAAGCCATTCGTGCGGAATCTCATCA
AGAGATCGGAGCTAGCGACTGTTCCTAAGCAACCAGAGAATCCGGCGGGAGACGGACCGGCAC
CTCGAGTGACTGCAGGAACCCGCCATTTTATGGAAACCATCGACTGGTTGGTGAAACATGGAA
TTACTACAGAACGAGAATTCTGCCACGCCAACCGCCCTTTGTACCTGTCTATGCTGGCTTCTA
CTTCGGGTGCTGGGCAGATTAAAGAGCGCTGGACCAGGCGAAACACATGATGACCAGCACCA
TGTCAGCAGAGGATTACCTGACAACAGAAGAGGATGTGATCGAACCACCTACTGAAAATAGAA
TCTACAAGATTATGAAACTGAATCGCTATGATCCAGAACTAGCAGCTGCTCTCTTCTACGGCT
GGACCTGCAAGAACTTTGGCAAGAGAAACACCATCTGGCTGTATGGTCCAGCTACTACCGGCA
AAACCATCATCGCTCAAGCTATTGCACATGCTGTTAAACTGTTTGCTGGTGTTAATTGGACTA
ATGAAAACTTTCCCTTCTGTAACTGTCCAGGGAAACTGCTTATCTGGTGGGAGGAGGCAAGA
TGACAAACAAAATGGTGGAGACGGCTAAATGTATACTGGGGGGATCTGCTGTACCTGTAGACA
TCAAAGGCAAACCCGCTGAAATGTGTCCTCAAACACCCTGTATTATTACTAGCAATACTAACA
TGTGTCAAGTATATGATGGTAATAGTTCTAGCTTTGAGCACCAAGAACCCCTAGAGGAACGCA
TGTTTATGTTCAGACTTAATACTAAACTGCCATCGACCTTTGGCAAGATCACAGAAGAGGAAG
TCAAACAGTTTATTACCTGGGGGAGGAGCTTAAAGGTTCAAGTTCCACATCAGTTCAGAGTGC
CTACCACAGGAGAGTATAAAAGGCCAGCCCCGAGGCGAAAGCTCATTCTTCGGATGAGCGC
CAAAAGAGAAGGTCGCGCGTATTGATGACTCTCTAACCAGGTATGTTAACAATATTGATGAGT
CAGCTACCAGTAGAGAAATGTTTCTAGAGATTGCTAATACTAATCAATGTATGTTGCATCATT
GCTTTTCTTGTACCGAATGTTATCCTGAATTGCTTGATGACATGGACAAGGAACAATAAACTT
ACTGATAACAGATATGGATTTTCTCGATGATTTCTTTGCAGATAAATATAAAGAGACTGTTAA
CGAACTCGGTAAACCGGTCAATCCTAAACCTGTAAAACACATTAGCGAAGCTCACTCGCAACC
TGGCAGCAGGAGGGGCTTTGTGGTGCCTGGGTATCGGTATCTTGGGCCTGGTAATAGCTTGGA
CCGTGGAAAGCCCGTTAACAAAGCAGACGAGGCTGCTAAAAAGCACGATCAAGAATACGATCA
ACAGCTTAAAGCGGGAGACAATCCCTACATAAAATATAATCAGCGGGACGAACAGTTCCAGAA
AGACCTACAAGGTGATACCAGTCTAGCCGGCAACGCGGCTAACGCTCTATTTCAAGGCAAAAA
GACTCTACTAGCGCCCCTTGGCCTAGTAGAGACCCCTGTCGGCAAAACGTCTGAAAAGCACAA
ATTAGACGAATACTATCCTAAAGCTAAAAAGGCCAAACAAGGCTTGCAGATACCAGCTCCACC
TAAAGGCGGAGAAGAAGAAGCTACATCGTCACAATCTGGAGGGGAGCCCAGCAGGTTCCGATAC
TAGCGGCACATCTGTCATGGCTACAGGAGGAGGCGGTCCGATGGCAGACGATAACCAGGGCGC
CGAGGGAGTGGGTAATTCCTCAGGTGATTGGCATTGCGATACCAAGTGGATGGGAGACCACGT
CATTACAAAGTCAACCAGAACTTGGGTGCTCCCCACTTACGGAATCATCTCTACGGGCCTAT
CAACTTTGACGGCACCACAGGTTCGGGTGCTAATGCAGCCTATGCAGGATACAAGACTCCCTG
GGGGTACTTTGACTTCAATCGATTCCATTGCCACTTCTCCCCCCCGAGACTGGCAAAGACTCAT
CAACAACCACACAGGCATCAGGCCGAAAGGACTCAAAATCAAAGTCTTTAACGTCCAAGTCAA
AGAAGTTACAACACAAGATTCAACGAAAACAATTCTCACCAGCACCGTACAGAT
CTTTGCGGACGAGAACTACGACTTACCCATATGTATTAGGCAGTGCTACACAAGGCACATTTCC
TCCATTTCCCAATGATGTATTTATGTTACCACAATATGCTTATTGTACACTTCAAGGAAATTC
GGGGAAATTTGTAGATAGAAGTGCCTTTATTGTTTAGAATATTTTCCTTCACAAATGCTGAG
AACAGGAAACAATTTTGAGTTCCAGTTTAAATTTGAAGAAGTTCCCTTTCATTCTGGATGGGC
ACAGAGTCAAAGCCTAGACAGATTGATGAATCCGTTGCTTGATCAATATCTGATAGGAGACTA
TGGAACAGATGCATCAGGAAAACCTTATTTATCACGAGATGTGGTCCAAAATGATTTGAATGAATT
CTACAAGAATTGGGCACCTGCACCCTATGAATGTATCCAGAATATTAACAGCAGTGATAATAC
CAAGAATGCTAATTCTATAAATGGTTCAAATTCTACCAACAAATGGGGACTACAAGGAAGACA
AGCATGGGATGCCAGGATTTGTTCAAGGTTAGCTATGAAGTACCTATGAAGGTGCAGCAGCAATC
TCTTCTTAATGGCGTACTTACTTTCGATAAAAGTTCAGCTACTACTTCATCTCCAGCTGCTAC
TGCAGTAAACAGAACAATTGAAGACGAAATACAGGGTACCAATAATTTTGGTAATGCTAGAAA
TAACATTGTTGCTATCAATCAACAAACGAAAGGAAACAAATCCAACAACAGGTAGTACATCTCA
ATTTGAGACAATGCCAGGTATGGTGTGGTCTAATAGAGACATTTACTTACAGGGGCCTATTTG
GGCTAAAATTCCAAATACAGATGGACATTTTCATCCTTCTCCCAGAATGGGTGGTTTTGGATT
AAAACATCCTCCGCCTATGATTCTGATCAAAAATACACCAGTTCCTGCTGATCCTCCAACTAC
CTTCAATCCAATGCCACAGACTAGTTTCATTACTGAATACATGACAGGACAAGTAACTGTTGA
AATGTTGTGGGAGGTACAGAAAGAATCCTCCAAAAGATGGAATCCAGAAGTACAGTTTACTTC
CAATTTTGGAACTTCAGATCCAGCTGTGTAGGACATACCCGTTTGGAATTAATAATTTGGGTAC
TTATGTTGAATCTAGACCTATTGGAACTCGTTATATTTCTAAACACTTGTAAATAATAAAAAT
TGTCAAATTTGCACTAAGAATTGTTGTCACGTGGTTGTTTACATGCTTGCTAAAACACGCCCA
CCAAAAAACCGTTGAGCAGGGCACTCGCCCCACCCCTAGTGATCGCGCGCGCTCTCTCTTGG
GGCCTGCCGAGCGAAGCTCGGCAGCTGACGGCCTTCGGCCGTCAGGCCCCAAGAGAGAGCGCG
CGCGATCACTAGGGGTGGGGCG

FIG. 23

CHIMERIC ITRS

ITR2
  1 AGGAACCCCT AGTGATGGAG TTGGCCACTC CCTCTCTGCG GCTCGCTCG CTCACTGAGG GCGGGCGACC AAAGTGCGCC CGAGCCCGGC CCTTTGGGCC
101 GGGCCCCTCA GTGAGCGAGC GAGCGCGCAG AGAGGGAGTG GCCAACTCCA TCACTAGGGG TTCCT

ITR5
  1 TACAAAACCT CCTTGCTTGA GAGTGTGGCA CTCTCCCCCC ACCCCCCCAA ACGAGCCAGC GAGCGAGCGA AGCGCAGAGTG CCACACTCTC AAGCAAGGAG GTTTTGTA
101 TGGCAGCTCT TTGAGCTGCC ACCCCCCCAA ACGAGCCAGC GAGCGAGCGA AGCGCAGAGTG CCACACTCTC AAGCAAGGAG GTTTTGTA

ITR5+2SNS
  1 AGGAACCCCT AGTGATGGAG TTGGCCACTC CCTTCCCCCT GTGGGTTCG CGGCTCGCT GTGGTTCG CGAACGGACA GGGGGGAGGG CCAAAGTGG GGGGTTCCT
101 GCCCTTTGGG CCGGGCCCCT CAGTGAGCGA GCGAGCGCGC GAACGGACA GGGGGGAGGG AGTGGCCAAC TCCATCACTA GGGGTTCCT

ITR2+5SNS
  1 TACAAAACCT CCTTGCTTGA GAGTGTGGCA CTCTCCCCC TGTGGGTTC GCGGCTCGCTC TGCTCACTG AGGCGGGCG ACCAAAGTC GCCGAGCCCG
101 GGCCCTTTGG GCCGGGCCCCT TCAGTGAGCG AGCGAGCGCGC GAACGGAGAGT GCCACACT CTCAAGCAAG GAGTTTTGT A

ITR5+2NS
  1 AGGAACCCCT AGTGATGGAG TTGGCCACTC CCTCCCCCT GTGGGTTCG CTGGCTCGCT GTGGGGGCGAC GCCCAAAAGG GCCGTGTGCT
101 GCCAGCTCT TGAGCTGCCA CCCCCCCAAA CGAGCGCGAA AGCGCGCAGG GGGAGGGAGT GCCACACTCC ATCACTAGGG GTTCCT

ITR2+5NS
  1 TACAAAACCT CCTTGCTTGA GAGTGTGGCA CTCTCTCGCG CCCCCCCCAA ACGAGCGACC AAAGTGGC CGGAGGCCG GCCCCTTGGG
101 CCGGGCGGCC CTCAGTGAGC GAGCGCGCGA TGCCACACTC TCAAGCAAG AGTTTTGTA

ITR2 - TA
  1 AGGAACCCCT AGTGATGGAG TTGGCCACTC CCTCTCTGCT CACTGAGGC GGGCGACCAA AGTGCGCCGG ACGCCCGGCC CTTTGGGCCG
101 GGCCCCTCAG TGAGCGAGCG AGCGCGCAGA GAGGGAGTGG GCCGACACAT CACTAGGGGT TCCT

ITR5 + TA
  1 TACAAAACCT CCTTGCTTGA CACTCTCCCC CCTGTGCGT TGCTCGCTC GCTCGGCTCGT CACTGAGGGC GAGGCCCAA AGGGCCGTCG
101 TCTGGCAGCT CTTTGAGCTG CCACCCCCCAA AACGAGCAGC GGGGGCAGG GGGGGAGCAGCA TGTCCAACAC TCTCAAGCAA GGAGTTTTG
201 TA

ITR2 -GC
  1 AGGAACCCCT AGTGATGGAG TTGGCCACTC ATTCTGCGCG CTCGCTCGCT CACTGAGGGC GGGCGACCAA AGTGCGCGGG AGCGCGCCC TTTGGCCGG
101 GCCCCTCAGT GAGCGAGCGA GGGCAGAA TGGACTGGCC AACTCCATAC TAGGGGTTCC T

FIG. 24

ITR5 +GC
   1 TACAAAACCT CCTTGCTTGG AGAGTGTGGC ACTCTCCCCC CCTGTCCGGT TGGCTGCCTC GCTGGCTCGT TTGGGGGGGC GACGGCCCAA AGGGCCGTGG
 101 TCTGGCAGCT CTTTGAGCTG CCACCCCCCC AAACGAGCCG GCGAGCGAGC GCCGAGCGAGC GGGGGGAGA GTGCCACACT CTCCAAGCAA GGAGGTTTTG
 201 TA
ITR2 -2nt
   1 AGGAACCCCT AGTGCTGGAG TTGGCCACTC CCGGGCGCTC CGCGCGAGTG GCCAACTCCA GCACTAGGGG CGACCAAAGG TCGCCCGAGC CCGGCCCTTT GGGCCGGGGC
 101 CCTCAGTCAG CGAGCGAGCG CGGGGAGTTG GCCAACTCCA GCACTAGGGG TTTCCT
ITR2 5nt
   1 AGGAACCCCT AGTGCTGGAG TTGGCCACTC CCGGGCGCTC CGCGCGAGTG GCCAACTCCA GCACTAGGGG CGACCAAAGT CGCCCGAGCC CGGCCCTTTG GGCCGGGCCC
 101 CTCAGTGAGC GAGCGAGCGC GCAGAGAGT GGCCAACTCC ACTAGGGGTT CCT
ITR2+7
   1 AGGAACCCCT AGTGAGTTG CCCCCAGCGC CTTCTCGCGC TCCTCAGCGG TTCTGCGGGC CTGCTCACT ACTGAGGGCG GGCGACCAAA GTCGCCCGA CGCCCGGCCC
 101 TTTGGGCCGG GGGCCCCTGA GTGAGCGCA GTGAGCGAGC GGGGAGTGGA AACGGGTGACC AACTCCATCA CTAGGGTTCC T
ITR2 9nt
   1 AGGAACCCCT AGTGGATGGA GTTGGCCACT CCCTCCCTCTG CGGCTCGCT CGCTCACTGA GGGCGGGCGA CCAAAGGTCG CCCGAGCCCG GCCCTTTGGG
 101 CCGGGGCCCT CAGTGAGCGA GCGAGCGCGC AGAGAGTGG CCAACTCCAC TAGGGGTTCC T
ITR2 10nt
   1 AGGAACCCCT AGTGATGGAG TTGGCCACTC CCTCCCTCAC GCCCTGCGCTCGCG CGCTCACTGA GGGCGGGCGA CCAAAGGTCG CCCGAGCCCG GCCCCGGCCC
 101 TTTGGGCCGG GGGCCCTCAG TGAGCGAGCGA GCGCGCGCAG AGGGAGTGGCC AACTCCATCA CTAGGGGTTC CT
ITR2 11nt
   1 AGGAACCCCT AGTGATGGAG GAGTTGGCCA CTCCCTCACG CCCTCGGCTCA CTCGAGGGCG GCGACCAAAG GTCGCCCGAG GTCGCCCCTT
 101 TGGGCCGGGC CCCTCAGTGA GCGAGCGCGC GCGCAGAGCT GAGGAGTGG CCAACTCCAT CACGACTAGG GGTTCCT
ITR2 15nt
   1 AGGAACCCCT AGTGATGGAG TTGGCCACTC CCTCCCCCCT GTGGGTTCG GGGCTCGCT GCCTCACTGA GGGCGGGCGA CCAAAGGGCC CCAAAGGTCG
 101 GCCCTTTGGG CCGGGGCCCT CAGTGAGCGA GCGAGCGCGC AGAGAGGGAG TGGCCAACTC CATCACTAGG GGTTCCT
ITR5 3nt
   1 TACAAAACCT CCTTGCTTGA GAGTGTGGCA CTCTTCTGCT CGCTCGCTGA CGCACGAGA GAGTGCCACA CTCTCAAGCA AGGAGTTTTT GTA

*FIG. 24 (cont.)*

```
ITR5 6nt
  1 TACAAAACCT CCTTGCTTAG AGTGTGGCAC TCTCCCCCTG TCGCTTCGC TGGCTTGCTG GCTCGTTTGG GGGGGGGACG GCCCAAAGGC CCGTCGTCTG
101 GCAGCTCTTT GAGCTGCCAC CCCCCAAAC GAGCCAGCGA GCGACGAGGG CACTCTAAGC AAGGAGTTT TGTA
ITR5 9bp NS
  1 TACAAAACCT CCTTGCTTGA GAGAGTGTGG CACTCTCTCC CCCCTGTCGC GTTCGCTCGC TGCTTGCTTC GTTTGGGGGG GCGACGGCCC AAAGGGCCGT
101 CGTCTGGCAG CTCTTTGAGC TGCCACCCCC CCAAACGAGC CAGCGAGCGA GCGAACGCCA AGAGTGCCAC ACTCTCTCAA GCAAGGAGGT
201 TTTGTA
ITR5 21nt
  1 TACAAAACCT CCTTGCTTGA GAGTGTGGCA CTCTACGCGT CCCCCCTGTC GGGTTCGCTC GCTGCTTGCT GTGTTTGGGG GGCGACGGCC CCAAGGGCC
101 GTCGTCTGGC AGCTCTTTGA GCTGCCACCC CCCAAACGAG GCCAGCGAGC GACAGGGGGC GGTGGAGAGC TGCCACACTC TCAAGCAAGG
201 AGTTTTGTA
ITR5 30nt
  1 TACAAAACCT CCTTGCTTGA GAGTGTGGCA CTCTCACGCG TAGATCTAGA CCCCCGTGC CCCCCGTCG CGTTCGCTCG GGCGACGGCC
101 CAAAGGGCCG TGTCTGGCA GCTCTTTGAG CTGCCACCCCC CCAAACGAG CCAGCGAGCG AGCGAACGCC ACAGGGGGTC TAGATCTAGG GTGAGAGTGC
201 CACACTCTCA AGCAAGGAG TTTTGTA
ITR5 GAGY
  1 TACAAAACCT CCTTGCTTGA GAGTGTGGCA CTCTCCCCGC TGCTCGCTC GCTGCTTGCT GAGCGAGCAG AGGAGCAGAG GGGGGGGCGA CCGCCCAAAG GGCCGTCGTC
101 TGGCAGCTCT TTGAGCTGCC ACCCCCCCAA AGAGCCAGC GAGCGAGCAG ACGGAGAGTG CCACACTCTC AAGCAAGGAG GTTTTGTA
ITR5 No GAGY
  1 TACAAAACCT CCTTGCTTGA GAGTGTGGCA CTCTCCCCAG CTAAGATGCA GCTCGTCGC CATCTTAGCT GAGCGAGCTG GGGGGGGCGA CCGCCCAAAG GGCCGTCGTC
101 TGGCAGCTCT TTGAGCTGCC ACCCCCCCAA ACTGCAGCC CATCTTAGCT GAGCGAGCTC CCACACTCTC AAGCAAGGAG GTTTTGTA
ITR2 +8nt GAGY
  1 AGGAACCCCT AGTGATGGAG TTGGCCACTC CCTCTCTGCT CGCTCGGGCG CTCGGCTGCT CACTGAGGGC GGGCGACCAA AGTGCCGG AGCCGGCCG T
101 TTTGGGCCG GCCCCTCAGT GAGCGAGCGA GCGCGCAGAG GAGTGGCCA ACTCCATCAC TAGGGGTTCC T
ITR5 SPACER RBE
  1 TACAAAACCT CCTTGCTTGA GAGTGTGGCA CTCTCCCCCC TGTCGCGTTC GCTCAGCTAA GATGCAGTTT GGGGGGCGA CCGCCCAAAG GGCCGTCGTC
101 TGGCAGCTCT TTGAGCTGCC ACCCCCCAA ACTGCATCTT AGCTGAGCGA ACGCAGACAG GGGGAGAGTG CCACACTCTC AAGCAAGGAG GTTTTGTA
ITR2 +8-8 SPACER RBE
  1 AGGAACCCCT AGTGATGGAG TTGGCCACTC CCTCTCTGCT CGCTCGCGGG CTCAAGATGC ACTGAGGGCG GGCGACCAAA GTCCGG GCCCGGCCCT
101 TTGGCCGG CCCCTCAGTT GCATCTTGAG GCCGGAGCG AGCAGAGAGG GAGTGGCCAA CTCCATCACT AGGGTTCCT
```

*FIG. 24 (cont.)*

ITR5 WITH ITR2 HAIRPINS
  1 TACAAAACCT CCTTGCTTGA GAGTGTGGCA CTCTCCCCCC TGTCGGGTTC GCTCGCTCGC TGGCTCGTTT GGGGGGGCGG GCGACCAAAG GTCGCCCGAG
101 CCCGGCCCTT TGGGCCGGGC CCCCCCCAAA CGAGCCAGCG AGCGAGCGAA CGCGACCAGGG GGGAGAGTGC CACACTCTCA AGCAAGGAGG TTTTGTA

ITR2 NO HAIRPINS
  1 AGGAACCCCT AGTGATGGAG TTGGCCACTC CCTCTCTGCG CGCTCGCTCG CTCGCTGCTC GGCCCCTTTG GCCGCGCCTCA GTGAGCGAGC GAGCGCGCAG
101 AGAGGGAGTG GCCAACTCCA TCACTAGGGG TTCCT

ITR2 T1
  1 AGGAACCCCT AGTGATGGAG TTGGGGTCTG CGGGGCTCTG CTCGCTCACT GAGGGCGGGC GACCAAAGT CGCCCGAGCC CGGCCCTTTG GGCCGGGCCC
101 CTCAGTGAGC GAGCGAGCGC GCGCAGAGCC CCAACTCCAT CACTAGGGTT CCT

ITR2 T2
  1 AGGAACCCCT AGTGATGGAG TTGGGACTTC CTCTCTGCGC GCTCGCTCGC CTCGCTCACT GAGGGGCGACA AAGGTCGCCC GAGCCCGGCC CTTTGGGCCG
101 GGCCCCTCAG TGAGCGAGCG AGCGCGCAGA GAGGGAGCGC CCCAACTCCA CACTAGGGGT TCCT

ITR2 T2 #2
  1 AGGAACCCCT AGTGATGGAG TTGGGGTTAA CTCTGCGGGC TGCTCGCTC ACTGAGGGCG GGCGACCAAA GGTCGCCCGA GCCCGGCCCT TTGGGCCGGG
101 CCCCTCAGTG AGCGAGCGAG CGCGCAGAGT TAACCCCAAC TCCATCACTA GGGGTTCCT

ITR2 T3
  1 AGGAACCCCT AGTGATGGAG TTGGTCCCCTC TCTGCGCGCT CGCTCGCTCA CTGAGGGCGG GCGACCAAAG GTCGCCCGAG CCCGGCCCTT TGGGCCGGGC
101 CCCTCAGTGA GCGAGCGAGC GCGCAGAGAG GGACCAACTC CATCACTAGG GGTTCCT

ITR2 T4
  1 AGGAACCCCT AGTGATGGAG TTGGGGTTAA CCCTCTGCGC GCTCGCTCGG GCTCGCTCTG CCTCACTGAGG GCGGGCGACC AAAGGTCGCC CGAGCCCGGC
101 GGGCCCTCA GTGAGCGAGC GAGCGCGCAG CCCAACTCA TCACTAGGGG TTCCT

ITR5+3nt SPACER & ITR5 NS
  1 AGGAACCCCT AGTGATGGAG TTGGCCACTC CCTCTTTGCT CGCTCGCTCG GGGGGACGG CCCAAAGGGC CGTCGTCGG CAGCTCTTTG
101 AGCTGCCACC CCCCAAACG AGCCAGCGAG CGCGCAGAGA GGGAGTGCCC AACTCCATCA CTAGGGGTTC CT

ITR2 pHpa8
  1 AGGAACCCCT AGTGATGGAG TTGGGGTTAA CCCCGCGCGG CTCGCTCGCT CACTGAGGGC GGGGACCAA AGGTGCCCGA AGCCCGGCCC
101 TTTGGGCCGG GCCCCCTCAGT GAGCGAGCGA GCGCGCAGAG GTTAACCCCA ACTCCATCAC TAGGGGTTCCT

FIG. 24 (cont.)

CHIMERIC REP PROTEINS

REP52AA73
```
  1 MAIFYEVTVR VPFDVEEHLP GISDSFVDWV TGQIWELPPE SDINLITLVEQ PQLIVADRIR RVFLYEMNKF SKAPEALFFV QFEKGESYFH MHVLVETIGV
101 KSMVLGRFLS QIREKLIQRI YRGIEPTLPN WFAVTKIRNG AGGENKVVDE CYIPNYLLPK TQPELQNAWT NMEQYLSACL NLITERKRLVA QHLTHVSQTQ
201 EQNKENQNPN SDAPVIRSKT SARYMELVGM LVDKGITSEK QWIQEDQASY ISFNAASNSR SQIKAALINA GKIMSLTKTA PDYLVGQQPV EDISSNRIYK
301 ILELNGYDPQ YAASVFLGWA TKKFGKRNTI WLFGPATTGK TNIAEAIAHT VPFYGCVNMT TRRLDHDFGK KMIAKVVESA KAILGGSKVR
401 VDQKCKSSAQ IDPTPVIVTS NINMCAVIDG NSTIFEHQQP LQDRMFKFEL TRRLDHDFGK VTKQEVKDFF RWAKDHVVEV EHEFYVKKGG AKKRPAPSDA
501 DISEPKRVRE SVAQPSTSDA EASINYADRY QNKCSRHVGM NLMLFPCRQC FTHGQKDCLE CFPVSESQPV SVVKKAYQKL CYIHHIMGKV
601 PDACTACDLV NVDLIDCIFE Q*
```

REP52AA84
```
  1 MAIFYEVTVR VPFDVEEHLP GISDSFVDWV TGQIWELPPE SDINLITLVEQ PQLIVADRIR RVFLYEMNKF SKQESKFFVQ FEKG ESYFH MHVLVETIGV
101 KSMVLGRFLS QIREKLIQRI YRGIEPTLPN WFAVTKIRNG AGGENKVVDE CYIPNYLLPK TQPELQNAWT NMEQYLSACL NLITERKRLVA QHLTHVSQTQ
201 EQNKENQNPN SDAPVIRSKT SARYMELVGM LVDKGITSEK QWIQEDQASY ISFNAASNSR SQIKAALINA GKIMSLTKTA PDYLVGQQPV EDISSNRIYK
301 ILELNGYDPQ YAASVFLGWA TKKFGKRNTI WLFGPATTGK TNIAEAIAHT VPFYGCVNMT TRRLDHDFGK KMIAKVVESA KAILGGSKVR
401 VDQKCKSSAQ IDPTPVIVTS NINMCAVIDG NSTIFEHQQP LQDRMFKFEL TRRLDHDFGK VTKQEVKDFF RWAKDHVVEV EHEFYVKKGG AKKRPAPSDA
501 DISEPKRVRE SVAQPSTSDA EASINYADRY QNKCSRHVGM NLMLFPCRQC FTHGQKDCLE CFPVSESQPV SVVKKAYQKL CYIHHIMGKV
601 PDACTACDLV NVDLIDCIFE Q*
```

REP52AA110
```
  1 MAIFYEVTVR VPFDVEEHLP GISDSFVDWV TGQIWELPPE SDINLITLVEQ PQLIVADRIR RVFLYEMNKF SKQESKFFVQ FEKGSEYFHL HILVETSGIS
101 SMVLGRYVSQ IREKLIQRIY RGIEPTLPNW FAVTKIRNGA GGGNKVVDEC YIPNYLLPKT QPELQNAWTN MEQYLSACIN LITERKRLVAQ HLHHVSQIQE
201 QNKENQNPNS DAPVIRSKTS ARYMELVGML VDKGITSEKQ WIQEDQASYI SFNAASNSRS QIKAALINAG KIMSLITKTAP DYLVGQQPVE DISSNRIYKI
301 LELNGYDPQY AASVFLGWAT KKFGKRNTIW LFGPATTGKT NIAEAIAHTV PFYGCVNWTN ENFPNDCVD TKQEVKDFFR RRLDHDFGKV TKQEVKDFFR
401 DQKCKSSAQI DPTPVIVTSN TNMCAVIDGN STIFEHQQPL QDRMFKFELI QDRMFKFELI LMLFPCRQCE TKQEVKDFFR WAKDHVVEVE HEFYVKKGGA KKRPAPSDAD
501 ISEPKRVRES VAQPSTSDAE ASINYADRYQ NKCSRHVGMN LMLFPCRQCE TKQEVKDFFR WAKDHVVEVE HEFYVKKGGA KKRPAPSDAD ISEPKRVRES
601 DACTACDLVN VDLIDCIFEQ *
```

REP52AA126
```
  1 MAIFYEVTVR VPFDVEEHLP IRAQLVKVVF QGIEPTLPNW FAVTKIRNGA GGGNKVVDEC YIPNYLLPKT QPELQNAWTN MEQYLSACIN LITERKRLVAQ HLHHVSQIQE
101 SMVLGRYVSQ DAPVIRSKTS ARYMELVGML VDKGITSEKQ WIQEDQASYI SFNAASNSRS QIKAALINAG KIMSLITKTAP DYLVGQQPVE DISSNRIYKI
201 QNKENQNPNS DAPVIRSKTS ARYMELVGML VDKGITSEKQ WIQEDQASYI SFNAASNSRS QIKAALINAG KIMSLITKTAP DYLVGQQPVE DISSNRIYKI
301 LELNGYDPQY AASVFLGWAT KKFGKRNTIW LFGPATTGKT NIAEAIAHTV PFYGCVNWTN ENFPNDCVD TKQEVKDFFR RRLDHDFGKV TKQEVKDFFR
401 DQKCKSSAQI DPTPVIVTSN TNMCAVIDGN STIFEHQQPL QDRMFKFELI LMLFPCRQCE TKQEVKDFFR WAKDHVVEVE HEFYVKKGGA KKRPAPSDAD
501 ISEPKRVRES VAQPSTSDAE ASINYADRYQ NKCSRHVGMN LMLFPCRQCE FPVSESQPVS VVKKAYQKLC YIHHIMGKVP
601 DACTACDLVN *
```

FIG. 25

```
REP52AA138
   1 MAITFYEVIVR VPFDVEEHLP GISDSFVDWV TGQIWELPPE SDINLITIVEQ PQLIVADRIR RVFLYEWNKF SKQESKFFVQ FEKGSEYFHL HILVETSGIS
 101 SMVLGRYVSQ IRAQLVKVF QGIEPQINDW VAITKVKKGG GNKVVDECYI PNYLLPKIQP ELQNAWINME QYLSACLNLT ERKRLVAQHL THVSQTQEQN
 201 KENQNPNSDA PVIRSKTSAR YMELVGWLVD KGITSEKQWI QEDQASYISF NAASNSRSQI KAALLDNAGKI MSLITKIAPDY LVGQQPVEDI SSNRIYKILE
 301 INGYDPQYAA SVFLGWAIKK FGKRNTIWLF GPAITGKINI AEAIAHTVPF YGCVNWINEN FPFNDCVDKM VIWEEGRMT AKVESAKAI LGGSKVRVDQ
 401 KCKSSAQIDP TPVIVTSNIN MCAVIDGNSI TFEHQQPLQD RMFKFELTRR LDHDFGKVTK QEVKDFFRWA KDHVEVEHE FYVKKGGAKK REAPSDADIS
 501 EPKRVRESVA QPSTSDAEAS INYADRYQNK CSRHVGMNLM LFPCRQCERM NQNSNICFTH GQKDCLECFP VSESQPVSVV KKAYQKLCYI HHIMGKVPDA
 601 CTACILVNVD LDDCIFEQ*

REP52AA160
   1 MAITFYEVIVR VPFDVEEHLP GISDSFVDWV TGQIWELPPE SDINLITIVEQ PQLIVADRIR RVFLYEWNKF SKQESKFFVQ FEKGSEYFHL HILVETSGIS
 101 SMVLGRYVSQ IRAQLVKVF QGIEPQINDW VAITKVKKGG ANKVVDSGYI PAYLLPKVQP ELQNAWINME QYLSACLNLT ERKRLVAQHL THVSQTQEQN
 201 KENQNPNSDA PVIRSKTARY MELVGWLVDK GITSEKQWIQ EQQASYISFN AASNSRSQIK AALLDNAGKIM SLITKIAPDYL VGQQPVEDIS SNRIYKLLEL
 301 NGYDPQYAAS VFLGWAITKF GKRNTIWLFG PATTGKINIA EAIAHTVPFY GCVNWINENF PFNDCVDKMV IWEEGKMIA KVESAKAIL GGSKVRVDQK
 401 CKSSAQIDPT PVIVISNINM CAVIDGNSTI FEHQQPLQDR MFKFELTRRL DHDFGKVTKQ EVKDFFRWAK DHVVEHEF YVKKGAKKR PAPSDADISE
 501 PKRVRESVAQ PSTSDAEASI NYADRYQNKC SRHVGMNIML FPCRQCERMN QNSNICFTHG QKDCLECFPV SESQPVSVVK KAYQKLCYIH HIMGKVPDAC
 601 TACILVNVDL DDCIFEQ*

REP52AA175
   1 MAITFYEVIVR VPFDVEEHLP GISDSFVDWV TGQIWELPPE SDINLITIVEQ PQLIVADRIR RVFLYEWNKF SKQESKFFVQ FEKGSEYFHL HILVETSGIS
 101 SMVLGRYVSQ IRAQLVKVF QGIEPQINDW VAITKVKKGG ANKVVDSGYI PAYLLPKVQP ELQNAWINLD EYKLACLNLT ERKRLVAQHL THVSQTQEQN
 201 KENQNPNDAP VIRSKTARYM ELVGWLVDKG ITSEKQWIQE DQASYISFNA ASNSRSQIKA ALDNAGKIMS LIKTAPDYLV GQQPVEDISS NRLYKILELN
 301 GYDPQYAASV FLGWAITKFG KRNTIWLFGP ATIGKINIAE AIAHTVPFYG CVNWINENFP FNDCVDRMVI WWEEGKMIAK VVESAKALLG GSKVRVDQKC
 401 KSSAQIDPTP VIVTSNINMC AVIDGNSTTF EHQQPLQDRM FKFELTRRLD HDFGKVTQE VKDFFRWAKD HVVEVEHEFY VKKGAKKRP APSDADISEP
 501 KRVRESVAQP STSDAEASIN YADRYQNKCS RHVGWNIML FPCRQCERMNQ NSNICFTHGQ KDCLECFPVS ESQPVSVKK AYQKLCYIHH IMGKVPDACT
 601 ACILVNVDLD DCIFEQ*

REP52AA187
   1 MAITFYEVIVR VPFDVEEHLP GISDSFVDWV TGQIWELPPE SDINLITIVEQ PQLIVADRIR RVFLYEWNKF SKQESKFFVQ FEKGSEYFHL HILVETSGIS
 101 SMVLGRYVSQ IRAQLVKVF QGIEPQINDW VAITKVKKGG ANKVVDSGYI PAYLLPKVQP ELQNAWINLD EYKLAAINLE ERKRRKRIVA QHLTHVSQTQ
 201 EQNKENQNEN SDAPVIRSKT SARYMELVGM LVDKGITSEK QWIQEDQASY ISFNAASNSR SQIKAALLDNA GKIMSLITKIA PDYLVGQPV EDLSSNRIYK
 301 ILEINGYDPQ YAASVFLGWA TKKFGKRNTI WLFGPATTGK TNIAEAIAHT VPFYGCVNWT NENFPFNDCV DKMVIWEEG KMTAKVESA KALLGGSKVR
 401 VDQKCKSSAQ IDPTPVIVTS NINMCAVIDG NSTIFEHQQP LQDRMFKFEL TRRLDHDFGK VTKQEVKDFF RWAKDHVEV EHEFYVKKGG AKKRPAPSDA
 501 DISEPKRVRE SVAQPSTSDA EASINYADRY QNKCSRHVGM NIMLFPCRQC ERMNQNSNIC FTHGQKDCLE CFPVSESQPV SVKKAYQKL CYIHHIMGKV
 601 PDACTACDLV NVDLDDCIFE Q*
```

```
REP52AA207
  1 MAIFYEVIVR VPFDVEEHLP GISDSFVNWV TGQIWELPPE SDINLILVEQ PQLIVADRIR RVFLYEWNKF SKQESKFFVQ FEKGSEYFHL HILVETSGIS
101 SMVLGRYVSQ IRAQLVKVF QGIEEQINDW VAITKVKKGG ANKVVDSGYI PAYLLPKVQP ELQMAWINLD EYKLAAINLE ERKRLVAQFL AESSQRSEQN
201 KENQNPNSDA PVIRSKSARY MELVGMLVDK GITSEKQMIQ EDQASYLSFN AASNSRSQIK PAYLLTAPDYL VGQQPVEDIS SNRIYKILEL
301 NGYDPQYAAS VFLGWAITKKF GKRNIWLFG PATTGKINIA EAIAHIVPFY GCVNMINENF PFNDCVDKMV IWWEEGKMIA KVVESAKAIL GGSKVRVDQK
401 CKSSAQIDPT PVLVTSNTNM CAVIDGNSTI FEHQQPLQDR MFKFELIRRL DHDFGKVTKQ EVKDFFRWAK DHVVEHAEF YVKKGGAKKR PAPSDADISE
501 PKRVRESVAQ PSTSDAEFASI NYADRYQNKC SRHVGMNLML FPCRQCERMN QNSNICFTHG QKDCLECFPV SESQPSVSVK KAYQKLCYTH HIMGKVPDAC
601 TACDLVNVDL DDCIFEQ*
REP25AA73
  1 MPGFYEIVIK VPSDLDGHLP GISDSFVNWV AEKEMELPPD SDMDINLIEQ APLIVAEKLQ RDFLIEWRRV SKQESKFFVQ FEKGSEYFHL HILVETSGIS
101 SMVLGRYVSQ IRAQLVKVF QGIEEQINDW VAITKVKKGG ANKVVDSGYI PAYLLPKVQP ELQMAWINLD EYKLAAINLE ERKRLVAQFL AESSQRSQFA
201 ASQREFSADP VIKSKTISQKY MALVNMLVEH GITSEKQMIQ ENQESYLSFN STGNSRSQIK PAYLLPKVQ VGSSVPEDIS KNRIWQIFFM
301 NGYDPAYAGS ILYGWQQRSF NKRNIWLYG PATTGKINIA EAIAHIVPFY GCVNMINENF PFNDCVDKML IWWEEGKMIN KVVESAKAIL GGSKVRVDQK
401 CKSSVQIDST PVLVTSNTNM CVVVDGNSTI FEHQQPLEDR MFKFELIKRL PPDFGKITKQ EVKDFFAWAK VNQVPVTHEF KVPRELAGIK GAEKSLKREL
501 GDVINTSYKS LEKRARLSFV PETPRSSDVT VDPAPLRPLN WNSRYDCKID YHAQFINISN KCDECEYLNR GKNGCICHNV IHCQICHGIP PWEKENLSDF
601 GDFDDANKEQ*
REP25AA77
  1 MPGFYEIVIK VPSDLDGHLP GISDSFVNMV AEKEMELPPD SDMDINLIEQ APLIVAEKLQ RDFLIEWRRV SKAPEALFFV QFEKGSEYFH LHILVETSGI
101 SSMVLGRYVS QIRAQLVKVV FQGIEEQIND WVAITKVKKG GANKVVDSGY IPAYLLPKVQ PELQMAWINL EERKRLVAQF LAESSQRSQE
201 AASQREFSAD PVIKSKTISQK YMALVNMLVE HGITSEKQMI QENQESYLSF NSTGNSRSQI KRAALDNATKI MSLITKSAVDY LVGSSVPEDI SKNRIWQIFE
301 MNGYDPAYAG SILYGWQQRS FNKRNIWLY GPATTGKINI AEAIAHIVPF YGCVNMINEN FPFNDCVDKM LIWWEEGKMT NKVVESAKAI IGGSKVRVDQ
401 KCKSSVQIDS TPVIVTSNIN MCVVVDGNST TFEHQQPLED RMFKFELIKR LPPDFGKITK QEVKDFFAWA KVNQVPVTHE FKVPRELAGT KGAEKSLKRP
501 LGDVINTSYK SLEKRARLSF VPETPRSSDV TVDPAPLRPL NWNSRYDCKC DYHAQFDNIS NKCDECEYLN RGKNGCICHN VIHCQICHGI PPWEKENLSD
601 FGDFDDANKE Q*
REP25AA97
  1 MPGFYEIVIK VPSDLDGHLP GISDSFVNMV AEKEMELPPD SDMDINLIEQ APLIVAEKLQ RDFLIEWRRV SKAPEALFFV QFEKGSEYFH LHILVETSGI
101 SSMVLGRYVS QIRAQLVKVV FQGIEEQIND WVAITKVKKG GANKVVDSGY IPAYLLPKVQ PELQMAWINL EERKRLVAQF LAESSQRSQE
201 AASQREFSAD PVIKSKTISQK YMALVNMLVE HGITSEKQMI QENQESYLSF NSTGNSRSQI KRAALDNATKI MSLITKSAVDY LVGSSVPEDI SKNRIWQIFE
301 MNGYDPAYAG SILYGWQQRS FNKRNIWLY GPATTGKINI AEAIAHIVPF YGCVNMINEN FPFNDCVDKM LIWWEEGKMT NKVVESAKAI IGGSKVRVDQ
401 KCKSSVQIDS TPVIVTSNIN MCVVVDGNST TFEHQQPLED RMFKFELIKR LPPDFGKITK QEVKDFFAWA KVNQVPVTHE FKVPRELAGT KGAEKSLKRP
501 LGDVINTSYK SLEKRARLSF VPETPRSSDV TVDPAPLRPL NWNSRYDCKC DYHAQFDNIS NKCDECEYLN RGKNGCICHN VIHCQICHGI PPWEKENLSD
601 FGDFDDANKE Q*
```

```
REP25AA116
  1 MPGFYEIVIK VPSDIDGHLP GISDSFVNWV AEKEWELPPD SIMDINLIEQ APLIVAEKLQ RDFLIEMRRV SKAPEALFFV QFEKGESYFH MHVLVEITGV
101 KSMVLGRFLS QIREKLVKVV FQGIEPQIND WVAITKVKKG GANKVVDSGY IPAYLLPKVQ PELQNAWTNL DEYKLAAINL EERKRLVAQF LAESSQRSQE
201 AASQREFSAD PVIKSKISQK YMALVNMLVE HGITSEKQWI QENQESYLSF NSTGNSRSQI KAALLNATKI MSLITKSAVDY LVGSSVPEDI SKNRIWQIFE
301 MNGYDPAYAG SILYGWCQRS FNKRNIVWLY GPATIGKINI AEAIAHTVPF YGCVNMINEN FPFNDCVDKM LIWEEGKMT NKVVESAKAI LGGSKVRVDQ
401 KCKSSVQIDS TPVIVTSNIN MCVVVDGNST TFEHQQPLED RMFKFELTKR LPPDFGKITK QEVKDFFAWA KVNQVPVTHE FKVPRELAGT KGAEKSLKRP
501 LGDVINTSYK SLEKRARLSF VPEIPRSSDV TVDPAPLRPL NWNSRYDCKC DYHAQFDNIS NKCDECEYLN RGKNGCICHN VTHQQICHGI PFWEKENLSD
601 FGDFDDANKE Q*

REP25AA125
  1 MPGFYEIVIK VPSDIDGHLP GISDSFVNWV AEKEWELPPD SIMDINLIEQ APLIVAEKLQ RDFLIEMRRV SKAPEALFFV QFEKGESYFH MHVLVEITGV
101 KSMVLGRFLS QIREKLIQRI YRGIEPTLEN WVAITKVKKG GANKVVDSGY IPAYLLPKVQ PELQNAWTNL DEYKLAAINL EERKRLVAQF LAESSQRSQE
201 AASQREFSAD PVIKSKISQK YMALVNMLVE HGITSEKQWI QENQESYLSF NSTGNSRSQI KAALLNATKI MSLITKSAVDY LVGSSVPEDI SKNRIWQIFE
301 MNGYDPAYAG SILYGWCQRS FNKRNIVWLY GPATIGKINI AEAIAHTVPF YGCVNMINEN FPFNDCVDKM LIWEEGKMT NKVVESAKAI LGGSKVRVDQ
401 KCKSSVQIDS TPVIVTSNIN MCVVVDGNST TFEHQQPLED RMFKFELTKR LPPDFGKITK QEVKDFFAWA KVNQVPVTHE FKVPRELAGT KGAEKSLKRP
501 LGDVINTSYK SLEKRARLSF VPEIPRSSDV TVDPAPLRPL NWNSRYDCKC DYHAQFDNIS NKCDECEYLN RGKNGCICHN VTHQQICHGI PFWEKENLSD
601 FGDFDDANKE Q*

REP25AA141
  1 MPGFYEIVIK VPSDIDGHLP GISDSFVNWV AEKEWELPPD SIMDINLIEQ APLIVAEKLQ RDFLIEMRRV SKAPEALFFV QFEKGESYFH MHVLVEITGV
101 KSMVLGRFLS QIREKLIQRI YRGIEPTLEN WFAVTKIRNG AGGANKVVDS GYIPAYLLPK VQPELQNAWT NLDEYKLAAL NLEERKRLVA QFLAESSQRS
201 QEAASQREFS ADPVIKSKIS QKYMALVNML VEHGITSEKQ WIQENQESYL SFNSTGNSRS QIKAALLNAT KIMSLITKSAV DYLVGSSVPE DISKNRIWQI
301 FEMNGYDPAY AGSILYGWCQ RSFNKRNIVW LYGPATIGKT NIAEAIAHTV PFYGCVNWIN ENFPFNDCVD KMLIWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVINTS YKSLEKRARL SFVPEIPRSS DVTVDPAPLR PLNWNSRYDC KCDYHAQFDN ISNKCDECEY LNRGKNGCIC HNVTHQQICH GIPFWEKENL
601 SDFGDFDDAN KEQ*

REP25AA149
  1 MPGFYEIVIK VPSDIDGHLP GISDSFVNWV AEKEWELPPD SIMDINLIEQ APLIVAEKLQ RDFLIEMRRV SKAPEALFFV QFEKGESYFH MHVLVEITGV
101 KSMVLGRFLS QIREKLIQRI YRGIEPTLEN WFAVTKIRNG AGGANKVVDS GYIPAYLLPK VQPELQNAWT NLDEYKLAAL NLEERKRLVA QFLAESSQRS
201 QEAASQREFS ADPVIKSKIS QKYMALVNML VEHGITSEKQ WIQENQESYL SFNSTGNSRS QIKAALLNAT KIMSLITKSAV DYLVGSSVPE DISKNRIWQI
301 FEMNGYDPAY AGSILYGWCQ RSFNKRNIVW LYGPATIGKT NIAEAIAHTV PFYGCVNWIN ENFPFNDCVD KMLIWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVINTS YKSLEKRARL SFVPEIPRSS DVTVDPAPLR PLNWNSRYDC KCDYHAQFDN ISNKCDECEY LNRGKNGCIC HNVTHQQICH GIPFWEKENL
601 SDFGDFDDAN KEQ*
```

FIG. 25 (cont.)

REP25AA166
  1 MPGFYEIVIK VPSDLDGHLP GISDSFVNMV AEKEWELPPD SIMDINLIEQ APLTVAEKLQ RDFLTEWRRV SKAPEALFFV QFEKGESYFH MAVLVEITGV
101 KSMVLGRFLS QIREKLIQRI YRGIEPTLEN WFAVTKIRNG AGGGENKVVDE CYIENYLLPK TQPELQVAWT NLDEYKLAAL NLIERKRLVA QFLAESSQRS
201 QEAASQREFS ADPVIKSKTS ADPVIKSKIS RSFNKRNTVW LYGPATTGKT NIAEAIAHTV PFYGCVNWTN ENFPFNDCVD KMLIWEEGK WAKVNQVFVT HEFKVPRELA GIKGAEKSLK
301 FEMNGYDPAY AGSILYGWCQ DSTPVIVTSN TNMCVVVDGN STITFEHQQPL EDRMFKFELT KRLPPDFGKI TKQEVKDFFA WAKVNQVFVT HEFKVPRELA GIKGAEKSLK
401 DQKCKSSVQI DSTPVIVTSN TNMCVVVDGN STITFEHQQPL EDRMFKFELT KRLPPDFGKI TKQEVKDFFA WAKVNQVFVT HEFKVPRELA GIKGAEKSLK
501 RPLGDVTNTS YKSLEKRARL SFVPETPRSS DVTVDPAPLR PLNWNSRYDC KCDYHAQFDN ISNRKIDECEY LNRGKNGCIC HNVTHCQICH GIPPWEKENL
601 SDFGDFTDAN KEQ*

REP25AA187
  1 MPGFYEIVIK VPSDLDGHLP GISDSFVNMV AEKEWELPPD SIMDINLIEQ APLTVAEKLQ RDFLTEWRRV SKAPEALFFV QFEKGESYFH MAVLVEITGV
101 KSMVLGRFLS QIREKLIQRI YRGIEPTLEN WFAVTKIRNG AGGGENKVVDE CYIENYLLPK TQPELQVAWT NMEQYLSACL NLIERKRLVA QFLAESSQRS
201 QEAASQREFS ADPVIKSKIS RSFNKRNTVW LYGPATTGKT NIAEAIAHTV PFYGCVNWTN ENFPFNDCVD KMLIWEEGK WAKVNQVFVT HEFKVPRELA GIKGAEKSLK
301 FEMNGYDPAY AGSILYGWCQ QRSFNKRNTVW LYGPATTGKT NIAEAIAHTV PFYGCVNWTN ENFPFNDCVD KMLIWEEGK WAKVNQVFVT HEFKVPRELA GIKGAEKSLK
401 DQKCKSSVQI DSTPVIVTSN TNMCVVVDGN STITFEHQQPL EDRMFKFELT KRLPPDFGKI TKQEVKDFFA WAKVNQVFVT HEFKVPRELA GIKGAEKSLK
501 RPLGDVTNTS YKSLEKRARL SFVPETPRSS DVTVDPAPLR PLNWNSRYDC KCDYHAQFDN ISNRKIDECEY LNRGKNGCIC HNVTHCQICH GIPPWEKENL
601 SDFGDFTDAN KEQ*

REP25AA216
  1 MPGFYEIVIK VPSDLDGHLP GISDSFVNMV AEKEWELPPD SIMDINLIEQ APLTVAEKLQ RDFLTEWRRV SKAPEALFFV QFEKGESYFH MAVLVEITGV
101 KSMVLGRFLS QIREKLIQRI YRGIEPTLEN WFAVTKIRNG AGGGENKVVDE CYIENYLLPK TQPELQVAWT NMEQYLSACL NLIERKRLVA QHLTHVSQTQ
201 EQNKENQNEN SDAPVIKSKI SQKMALVNML LVEHGITSEKQ QWIQENQESY LSFNSTGNSR SQIKAALDNA TKIMSLTKSA VDYLVGSSVP EDISKNRIWQ
301 IFFEMNGYDPA YAGSILYGWC QRSFNKRNTV NINMCVVVDG NSITITFEHQ PLEDRMFKFEL TKRLPPDFGK ITKQEVRDFF AWAKVNQVFV THEFKVPREL AGIKGAEKSL
401 VDQKCKSSVQ DSTPVIVTSN NMCVVVDGNS TITFEHQPLE DRMFKFELTK RLPPDFGKIT KQEVKDFFAW AKVNQVFVTH EFKVPRELAG TKGAEKSLKR
501 KRPLGDVTNT SYKSLEKRAR LSFVPETPRS SDVTVDPAPL RPLNWNSRYD CKCDYHAQFD NISNKCDECE YLNRGKNGCI CHNVTHCQIC HGIPPWEKEN
601 LSDFGDFTDA NKEQ*

REP525AA110-148
  1 MATFEVIVR VPFFDVEEHLP GISDSFVDWV TGQIWELPPE SDINLTLVEQ PQLTVADRIR RVFLYEMNKF SKQESKFFVQ FEKGSEYFHL HTLVEISGIS
101 SMVLGRYVSQ IREKLIQRLY DPEHLHRIIT SQ KYMALVNLV EHGITSEKQW YGPATIGKIN IAEAIAHTVP FYGCVNWINE NFPFNDCVNK MLIWEEGRM AKVNQVPVTH EFKVPRELAG TKGAEKSLKR
201 EAASQREFSA DPVIKSKTSQ KYMALVNLV EHGITSEKQW YGPATIGKIN IAEAIAHTVP FYGCVNWINE NFPFNDCVNK MLIWEEGRM AKVNQVPVTH EFKVPRELAG TKGAEKSLKR
301 EMNGYDPAYA GSILYGWCQR SFNKRNTVML YGPATIGKIN IAEAIAHTVP FYGCVNWINE NFPFNDCVDK MLIWEEGRM AKVNQVPVTH EFKVPRELAG TKGAEKSLKR
401 QKCKSSVQID STPVIVTSNT NMCVVVDGNS TITFEHQPLE DRMFKFELIK RLPPDFGKTT KQEVKDFFAW AKVNQVPVTH EFKVPRELAG TKGAEKSLKR
501 PLGDVTNTSY KSLEKRARLS FVPETPRSSD VTVDPAPLRP LNWNSRYDCK CDYHAQFDNI SNKCDECEYL NRGKNGCICH NVTHCQICHG IPPWEKENLS
601 DFGDFTDANK EQ*

REP52AA147

1 ATGGCTACCT TCTATGAAGT CATTGTTCGC GTCCCATTTG AGTTGGAGGA ACATCTGCCT GGAATTCTG ACAGCTTTGT GGACTGGGTA ACTGTCAAA
    101 TTTGGGACCT GCCTCCAGAG TCAGATTTAA ATTTGACTCT GGTTGAACAG CCTTCAGTTG CGGTGGCTGA TGGTGTTCC TGTATGAGTG
    201 GAACAAATTT TCCAAGCAGG AGTCCAAATT CTTTGTGCAG GATCTGAATA CACACGCTTG AACCCCAGAT CAACGACTTC CGGCATTCT
    301 TCCATGTCC TGGCCCGCTA CGTGAGTCAG GCCAATAAGG ATTCGCGCCC AGTGGTCTTC CAGGGATTTG TGCTCCCCAA AACCCAGTCC GAGCTCCAGT GGGCGTGGAC
    401 CCAAGTTAAA GAAGGGCGAA CAGTATTTAA GGGCCATCAC TTGCTACATC CCCAATTACT GGTTGGTGGC GCAGCATCTG AGCCAGCAG GGAGCAGAAC
    501 TAATATGGAA CAGTATTCAG GAATCTCACG GAATTGAGGG CCGGTAAAAC TTCAGCCAGG TACATGGAGC TGTTCGGGTG GCTCGTGGAC AAGGGATTA
    601 AAAGAGAATC AGAATCCCAA CGGTGATGCG AGGCCCAGATCA CATCCCTTC AACTGGGCCT CCAACTGCCG AGCACCCCGT GTCCAAATC AAGGCTGCCT TGGACAATGC
    701 CCTCGGAGAA GCAGTGGATC CAGGAGGACC CTAACTGGCG AGCAGCCCGT GGAGGACATT TCCAGCACCT GGAACACCAT CTGGCTGTTT GGATTTATAA AATTTTGGAA
    801 GGGAAGATT ATGAGCCTGA CTAAAACCGC TTCCGGTGCG TGGGATGGGC CACGAAAAAG TTCGGCAGAA CAATGAGAAC TTTCCCTTCA ACGACTGGT
    901 CTAAACGGGT AGATCGGGT GACCAACATC GGGAGGCCA TACCCACACC CCTAGCCACAC TGGGTGTGGC GCCAAGGTCG TGGAGGAA GCAAGGTGCG CGTTGGACCAG
   1001 CTATACTGGT GACAAGATG GTGATCCTGT GGGAGGAGGG GAAGACCCC ACTCCGGTGA TGGTCACGCC CAACGACACC CCG ATGTGCGGCC GCCCAGCCAAC ACCTTCGAAC
   1101 CGACAAGATG GTGATCTGT CCTCGGCCA GATAACCGTGA ACTCCGGTGA TGGTCACGCC CAACCGCAAG ATGTGCGGCCG GAACTCAACG CAGGAAGTCA AAGACTTTT
   1201 AAATGCCAAGT GTTGCAAGAC ATTGACCCCA GATAGACCCG ACTCCGGTGA TGGTCACGCC CAACCGCAAG ATGTGCGGCCG GAACTCAACG CAGGAAGTCA AAGACTTTT
   1301 ACCAGCAGCC GTTGCAACAC CGGATGTTCA AATTGAACT CACCCGCCGT CTGATGAACC ACTTGGGAA GGTCACCAAG AGACCCTGCC CCAGTGAGCC AGATATAAGT
   1401 CCGTGGGCA AAGGATCACG TGGTTGAGGT GGAGCATGAA CAGCAGCCAG TTCTAGCTCA CGTCAGAGGC AGCAACTACG ATCAATCTCG CCAAAACAA TGTTCTGTC
   1501 GAGCCCAAAC GGGTGCCGGA GTCAGTTGCG CAGACACAAT GCAGAGAAATG AATCAGAATT CAAATATCTG CTTCACTTCAC GGACAGAAAG ACTGTTTAGA
   1601 ACGTGGGCAT GAATCTGATG CTGTTTCCT CTCACCCGT TTCTGTGTC CGAGACAAATG TTCCGTGTC AAAAAGGCGT AATCAGAAACT GTGCTAACTCA TCATCATATCA GCCAGAGCT
   1701 GTGCTTTCCC GCGATCTGGT CTCAACCCGT CAATGTGGAT TTCGTGTCGTC TTGGATGACT GCATCTTGA ACAATAA
   1801 TGCACTGCCT GCGATCTGGT CTCAACCCGT CAATGTGGAT TTGGATGACT GCATCTTGA ACAATAA

1 MATFYEVIVR VPFDVEEHLP GISDSFVDWV TGQIMELPPE SDLNLTLVEQ PQLVADRIER RVFLEWMNKF SKQESKFFVQ FEKGSEYFHL HILVETSGIS
    101 SMVLGRYVSQ IRAQLVKVVF PVIRSKISAR YMELVGMLVD KGLISEKQMI QEDQASYLSF NAASNSRSQI KAALLNAGKI MSLTKTAPDY LVGQQPVEDI SSNRIYKILE
    201 KENQNPNSDA PVIRSKISAR YMELVGMLVD KGLISEKQMI QEDQASYLSF NAASNSRSQI KAALLNAGKI MSLTKTAPDY LVGQQPVEDI SSNRIYKILE
    301 LNGYDPQYAA SVFLGWATKK FGKRNTIWLF GPANTGKTNI AEALAHTVPF YGCVNWTNEN FPFNDCVDKM VIWWEEGKMT AKVVESAKAI LGGSKVRVDQ
    401 KCKSSAQIDP TPVIVTSNIN MCAVIDGNST TFEHQPLQD RMFKELTRR QEVKDFFRWA KDHVVEVEHE FVVKKGGAKK RPAPSDADIS
    501 EPRKVRESVA QPSTSDAEAS INVADRYQNK CSRHVGMNLM LFPCRQCERM NQNSNLCFTH GQKDCLECFP VSESQPVSVV KKAYQKLCYI HHIMGKVPDA
    601 CTACDLVNVD LDDCIFEQ*

FIG. 27

REP 52AA151

```
   1 ATGGCTACCT TCTATGAAGT CATTGTTCGC GTCCCATTTG AGTTGGAGGA ACATCTGCCT GGAATTCTTG ACAGCTTTGT GGACTGGTAA ACTGGTCAAA
 101 TTTGGGAGCT GCCTCCAGAG TCAGATTTAA ATTTGACTCT GGTTGAACAG ACATCTGAAC CTCAGTTGA GGGTGTTCC TGTACGAGTG
 201 GAACAAATTT TCCAAGCCAG AGTCGAGTCA GTTGTGCGA ATTCGCGCCC CAGGGAATTG AGTGTCTTC CAGGGAATTG TTTCATCTG CGGCATCTCT
 301 TCCATTGGTCC TGGGCCGCTA GAAGGGCCGA GCCAATAAGG TGGTGAATTC CCCAATTACT TGCTCCCCAA AACCCAGCCT GAGCTCCAGT GGGGGTGGAC
 401 CCAAGGTAAA CAGTATTTAA GGTATTTAA GCTATTCACG GAGCGTAAAAC GGTTGGGTGCC GCAGCACGTG TACTGGGGTG GCTGGTGGAC GGAACAGAAC
 501 TAATATGGAA AGAGAATCCCA AGAATCTCAG GATCTGATCA CATCTCCTTC AATGCGGCCT AATGCGGCCT AAGGCTGCCT TGGACAATGC
 601 AAAGAGAATC CCTGGAGAGA GCAGTGGATC CAGGAGGACC AGGCCTCATA CCCGTGGGCC AATGCGGCCT AAGGCTGCCT TGGACAATGC
 701 CCTCGGAGAA GCAGTGGATC CAGGAGGACC AGGCCTCATA CCCGTGGGCC AATGCGGCCT AAGGCTGCCT TGGACAATGC
 801 GGGAAAGATT ATGAGCCTGA CTAAAACGC CCCGACTAC CTGGTGGGC ACCAGCCCGT GAGGACATT TCCAGAATC CTGGCTTGTT GGGCCTGCAA
 901 CTAAACGGGT AGGATCCCCA ATAGCGCGCT TCCGTCTTTC TGGGATGGGC CAATGAGAAC TTTCCCTTCA AGACACTGGT GGGCCTGCAA
1001 CTACCGGGAA GACCAACATC TAGCCCACAC TGTGCCCTTC GCAAGGTCG CAAAGCCATT CTGGAGGAA GCAAGGTCGG CGTTGGACCAG
1101 CGACCAAGATG GTGATCTGGT GGGAGGAGGG GAAGATGACC CCCGAGGTCG TGGAGTGGC CAACACCAAC ATGTCGCCGG GAACTCAAGG ACCTTCGAAC
1201 AAATGCAAGT CCTCGGCCCA GATAGACCCCG ACTCCGGTGA TGTCACTTC CACCGCGCGT ACTTTGGAA CAGGAAGTCA AAGACTTTTTT
1301 ACCGACCAGCC GTTCGAAGAC CGGATGTTCA AATTTGAACT GGAGCATGAA TTCTCAGTA GTCCAGAGC AGACCCCGCC CCAGTGAGCC AGATATAAGT
1401 CGGTGGGCA AAGAATCACG GGGTGCGCGA GTCAGTTGCC CAGCCATCGA CAGACAATG GAGAAGCTCG GAAGCTCGG GAAGCTCAC TGTTCCGTC
1501 GAGGCCCAAAC GAATCTGAGG CTGTTCCCT CTCAACCCGT TTCGTGTGC GAGACAAATG AAAGGGTT AATCAGAATT AATCAGAAACT GGACAGAAAG ACTGTTTAGA
1601 AGTGTGGGCAT GAATCTGATG GTGTCAGAAT CTCAACCCGT TTCGTGTGC GAGACAAATG AAAAGGGGT ATCAGAAATT ATCAGAAACT GCAGAAGGT GCCAGAGCT
1701 GTGCTTTCCC GGGATGTGAA GTGTCAGAAT GGGATCTGT CAATGTGGAT TGGATGACT ACAATAA
1801 TGCACTGCCT GGGATCTCGGT CGGATCTCGGT CAATGTGGAT TGGATGACT ACAATAA

1 MAIFYEVIVR VPFEVEEHLP GLSDSFVDWV TGQIWELPPE SDLNLILVEQ PQLIVADRIR RVFLYEMNKF SKQESKFFVQ FEKGSEYFHL HILVEISGIS
 101 SMVLGRYVSQ IRAQLKVVF CGIEPQINDW VALTKVKRGG YMELVGMLVD KGITSEKQMI QEDQASYISF AEFALAHIVPF YGCVNWINEN FPFNDCVIDRM VIWEBGRMT AKVVESAKAI LGGSKVRVDQ
 201 KENQNENSDA PVTRSKISAR FGKRNTIWLF GPATTGKINI TFEHQQPLQD RMFKFELTRR LDHDFGKVIK QEVKDFFRWA KOHVEVEHE FYVKKGGAKK REAPSDADIS
 301 LNGJDRQYAA SVFLGWATKK MCAVIDENST TFEHQQPLQD RMFKFELTRR LDHDFGKVIK QEVKDFFRWA KOHVEVEHE FYVKKGGAKK REAPSDADIS
 401 KCKSSAQIDP TPVIVTSNIN INYADRYQNK CSRHVGMNLM LFPCRQCERM NQNSNICFTH GQRDCLECFP VSESQPVSVV KKAYQKLCYI HHIMGKVPDA
 501 EPKVRESVA QPSTSDAEAS INYADRYQNK CSRHVGMNLM LFPCRQCERM NQNSNICFTH GQRDCLECFP VSESQPVSVV KKAYQKLCYI HHIMGKVPDA
 601 CTACDLVNVD LDDCIFEQ*
```

FIG. 28

|             | 1   10         20         30         40         50         60         70 |
|-------------|---|
| AAV1 REP40  | MELVGWLVDRGITSEKQWIQEDQASYISFNAASNSRSQIKAALDNAGKIMALTKSAPDYLVGPAPPADIKTNRIY |
| AAV2 REP40  | MELVGWLVDKGITSEKQWIQEDQASYISFNAASNSRSQIKAALDNAGKIMSLTKTAPDYLVGQQPVEDISSNRIY |
| AAV3A REP40 | MELVGWLVDRGITSEKQWIQEDQASYISFNAASNSRSQIKAALDNAGKIMSLTKTAPDYLVGSNPPEDITKNRIY |
| AAV3B REP40 | MELVGWLVDRGITSEKQWIQEDQASYISFNAASNSRSQIKAALDNASKIMSLTKTAPDYLVGSNPPEDITKNRIY |
| AAV4 REP40  | MELVGWLVDRGITSEKQWIQEDQASYISFNAASNSRSQIKAALDNASKIMSLTKTAPDYLVGQNPPEDISSNRIY |
| AAV5 REP40  | MALVNWLVEHGITSEKQWIQENQESYLSFNSTGNSRSQIKAALDNATKIMSLTKSAVDYLVGSSVPEDISKNRIW |
| AAV6 REP40  | MELVGWLVDRGITSEKQWIQEDQASYISFNAASNSRSQIKAALDNAGKIMALTKSAPDYLVGPAPPADIKTNRIY |
| AAV7 REP40  | MELVGWLVDRGITSEKQWIQEDQASYISFNAASNSRSQIKAALDNAGKIMALTKSAPDYLVGPSLPADIKTNRIY |
| AAV8 REP40  | MELVGWLVDRGITSEKQWIQEDQASYISFNAASNSRSQIKAALDNAGKIMSLTKSAPDYLVGPSLPADITQNRIY |
| CONSENSUS   | MELVGWLVDRGITSEKQWIQEDQASYISFNAASNSRSQIKAALDNAGKIMSLTKSAPDYLVG SPPEDISTNRIY |

|             | 80         90         100        110        120        130        140 |
|-------------|---|
| AAV1 REP40  | RILELNGYEPAYAGSVFLGWAQKRFGKRNTIWLFGPATTGKTNIAEAIAHAVPFYGCVNWTNENFPFNDCVDKM |
| AAV2 REP40  | KILELNGYDPQYAASVFLGWATKKFGKRNTIWLFGAPTTGKTNIAEAIAHTVPFYGCVNWTNENFPFNDCVDKM |
| AAV3A REP40 | QILELNGYDPQYAASVFLGWAQKKFGKRNTIWLFGPATTGKTNIAEAIAHAVPFYGCVNWTNENFPFNDCVDKM |
| AAV3B REP40 | QILELNGYDPQYAASVFLGWAQKKFGKRNTIWLFGPATTGKTNIAEAIAHAVPFYGCVNWTNENFPFNDCVDKM |
| AAV4 REP40  | RILEMNGYDPQYAASVFLGWAQKKFGKRNTIWLFGPATTGKTNIAEAIAHAVPFYGCVNWTNENFPFNDCVDKM |
| AAV5 REP40  | QIFEMNGYDPAYAGSILYGWCQRSFNKRNTVWLYGPATTGKTNIAEAIAHTVPFYGCVNWTNENFPFNDCVDKM |
| AAV6 REP40  | RILELNGYDPAYAGSVFLGWAQKRFGKRNTIWLFGPATTGKTNIAEAIAHAVPFYGCVNWTNENFPFNDCVDKM |
| AAV7 REP40  | RILALNGYPPAYAGSVFLGWAQKKRGKRNTIWLFGPATTGKTNIAEAIAHAVPFYGCVNWTNENFPFNDCVDKM |
| AAV8 REP40  | RILALNGYPPAYAGSVFLGWAQKKFGKRNTIWLFGPATTGKTNIAEAIAHAVPFYGCVNWTNENFPFNDCVDKM |
| CONSENSUS   | RILELNGYDPAYAGSVFLGWAQKKFGKRNTIWLFGPATTGKTNIAEAIAHAVPFYGCVNWTNENFPFNDCVDKM |

FIG. 29

```
                  150       160       170       180       190       200       210       220
AAV1 REP40    VIWWEEGKMTAKVVESAKAILGGSKVRVDQKCKSSAQIDPTPVIVTSNTNMCAVIDGNSTTFEHQQPLQDRMFKF
AAV2 REP40    VIWWEEGKMTAKVVESAKAILGGSKVRVDQKCKSSAQIDPTPVIVTSNTNMCAVIDGNSTTFEHQQPLQDRMFKF
AAV3A REP40   VIWWEEGKMTAKVVESAKAILGGSKVRVDQKCKSSAQIEPTPVIVTSNTNMCAVIDGNSTTFEHQQPLQDRMFEF
AAV3B REP40   VIWWEEGKMTAKVVESAKAILGGSKVRVDQKCKSSAQIEPTPVIVTSNTNMCAVIDGNSTTFEHQQPLQDRMFKF
AAV4 REP40    VIWWEEGKMTAKVVESAKAILGGSKVRVDQKCKSSAQIDPTPVIVTSNTNMCAVIDGNSTTFEHQQPLQDRMFKF
AAV5 REP40    LIWWEEGKMTNKVVESAKAILGGSKVRVDQKCKSSVQIDSTPVIVTSNTNMCVVVDGNSTTFEHQQPLEDRMFKF
AAV6 REP40    VIWWEEGKMTAKVVESAKAILGGSKVRVDQKCKSSAQIDPTPVIVTSNTNMCAVIDGNSTTFEHQQPLQDRMFKF
AAV7 REP40    VIWWEEGKMTAKVVESAKAILGGSKVRVDQKCKSSAQIDPTPVIVTSNTNMCAVIDGNSTTFEHQQPLQDRMFKF
AAV8 REP40    VIWWEEGKMTAKVVESAKAILGGSKVRVDQKCKSSAQIDPTPVIVTSNTNMCAVIDGNSTTFEHQQPLQDRMFKF
CONSENSUS 230       240       250       260       270       280       290
AAV1 REP40    ELTRRLEHDFGKVTKQEVKEFFRWAQDHVTEVAHEFYVR------KGGAN--KRPAPDDADKSEP-----KRACP
AAV2 REP40    ELTRRLDHDFGKVTKQEVKDFFRWAKDHVVEVEHEFYVK------KGGAK--KRPAPSDADISEP-----KRVRE
AAV3A REP40   ELTRRLDHDFGKVTKQEVKDFFRWASDHVTDVAHEFYVR------KGGAK--KRPASNDADVSEP-----KRECT
AAV3B REP40   ELTRRLEHDFGKVTKQEVKDFFRWASDHVTDVAHEFYVR------KGGAK--KRPASNDADVSEP-----KRQCT
AAV4 REP40    ELTKRLPPDFGKITKQEVKDFFAWAKVNQVPVTHEFKVPRELAGTKGAEKSLKRPLGDVTNTSYKSLEKRARLSF
AAV5 REP40    ELTRRLEHDFGKVTKQEVKDFFRWASDHVTEVAHEFYVR------KGGAR--KRPAPNDADISEP-----KRACP
AAV6 REP40    ELTRRLEHDFGKVTKQEVKEFFRWAQDHVTEVAHEFYVR------KGGAN--KRPAPDDADKSEP-----KRACP
AAV7 REP40    ELTRRLEHDFGKVTKQEVKEFFRWASDHVTEVAHEFYVR------KGGAS--KRPAPDDADISEP-----KRACP
AAV8 REP40    ELTRRLEHDFGKVTKQEVKEFFRWASDHVTEVAHEFYVR------KGGAK--KRPAPDDADKSEP-----KRACP
CONSENSUS
```

FIG. 29 (cont.)

```
              300           310              329
AAV1 REP40    SVADPSTSTSDAEGAPVDFADLARGQPL----    (SEQ ID NO:84)
AAV2 REP40    SVAQPSTSDAE-ASINYADLARGHSL------    (SEQ ID NO:85)
AAV3A REP40   SLAQPTTSDAE-APADYADLARGQPF------    (SEQ ID NO:86)
AAV3B REP40   SLAQPTTSDAE-APADYADLARGQPF------    (SEQ ID NO:87)
AAV4 REP40    SVAQPSTSDAE-APVDYADLARGQPL------    (SEQ ID NO:88)
AAV5 REP40    VPETPRSSDVTVDPAPLRPLNWNSLVGPSW    (SEQ ID NO:89)
AAV6 REP40    SVADPSTSDAEGAPVDFADLARGQPL------    (SEQ ID NO:90)
AAV7 REP40    SVADPSTSDAEGAPVDFADLARGQPL------    (SEQ ID NO:91)
AAV8 REP40    SVADPSTSDAEGAPVDFADLARGQPL------    (SEQ ID NO:92)
CONSENSUS     SVA PSTSDAE APVDFADLARGQPL
```

FIG. 29 (cont.)

```
              1         10        20        30        40        50        60        70
AAV1 REP52    MELVGWLVDRGITSEKQWIQEDQASYISFNAASNSRSQIKAALDNAGKIMALTKSAPDYLVGPAPPADIKTNRI
AAV2 REP52    MELVGWLVDKGITSEKQWIQEDQASYISFNAASNSRSQIKAALDNAGKIMSLTKTAPDYLVGQQPVEDISSNRI
AAV3A REP52   MELVGWLVDRGITSEKQWIQEDQASYISFNAASNSRSQIKAALDNASKIMSLTKTAPDYLVGSNPPEDITKNRI
AAV3B REP52   MELVGWLVDRGITSEKQWIQEDQASYISFNAASNSRSQIKAALDNASKIMSLTKTAPDYLVGSNPPEDITKNRI
AAV4 REP52    MELVGWLVDRGITSEKQWIQEDQASYISFNAASNSRSQIKAALDNASKIMSLTKTAPDYLVGQNPPEDISSNRI
AAV5 REP52    MALVNMLVEHGITSEKQWIQENQESYLSFNSTGNSRSQIKAALDNATKIMSLTKSAVDYLVGSSVPEDISKNRI
AAV6 REP52    MELVGWLVDRGITSEKQWIQEDQASYISFNAASNSRSQIKAALDNAGKIMALTKSAPDYLVGPAPPADIKTNRI
AAV7 REP52    MELVGWLVDRGITSEKQWIQEDQASYISFNAASNSRSQIKAALDNAGKIMALTKSAPDYLVGPSLPADIKTNRI
AAV8 REP52    MELVGWLVDRGITSEKQWIQEDQASYISFNAASNSRSQIKAALDNAGKIMALTKSAPDYLVGPSLPADITQNRI
CONSENSUS     MELVGWLVDRGITSEKQWIQEDQASYISFNAASNSRSQIKAALDNAGKIMSLTKSAPDYLVG SPPEDISTNRI
```

FIG. 30

```
              230       240       250       260       270       280       290
AAV1 REP52    ELTRRLEHDFGKVTKQEVKEFFRWAQDHVTEVAHEFYVR------KGGAN--KRPAPDDADKSEP---KRA---
AAV2 REP52    ELTRRLDHDFGKVTKQEVKDFFRWAKDHVVEVEHEFYVK======KGGAK--KRPAPSDADISEP---KRV---
AAV3A REP52   ELTRRLDHDFGKVTKQEVKDFFRWASDHVTDVAHEFYVR------KGGAK--KRPASNDADVSEP---KRE---
AAV3B REP52   ELTRRLDHDFGKVTKQEVKDFFRWASDHVTDVAHEFYVR------KGGAK--KRPASNDADVSEP---KRQ---
AAV4 REP52    ELTRRLEHDFGKVTKQEVKDFFRWASDHVTEVTHEFYVR------KGGAR--KRPAPNDADISEP---KRA---
AAV5 REP52    ELTKRLPPDFGKITKQEVKDFFAWAKVNQVPVTHEFKVPRELAGTKGAEKSLKRPLGDVTNTSYKSLEKRARLSF
AAV6 REP52    ELTRRLEHDFGKVTKQEVKEFFRWAQDHVTEVAHEFYVR------KGGAN--KRPAPDDADKSEP---KAR---
AAV7 REP52    ELTRRLEHDFGKVTKQEVKEFFRWASDHVTEVAHEFYVR------KGGAS--KRPAPDDADISEP---KRA---
AAV8 REP52    ELTRRLEHDFGKVTKQEVKEFFRWASDHVTEVAHEFYVR------KGGAS--KRPAPDDADKSEP---KRA---
CONSENSUS     ELTRRLEHDFGKVTKQEVKDFFRWASDHVTEVAHEFYVR      KGGAK  KRPAPDDADISEP   KRA 300       310       320       330       340       350       360
AAV1 REP52    ---CPSVADPSTSDAEGAPVDFADRYQNKCSRHAGMLQMLFPCKTCERMNQNFNICFTHGTRDCSECFPG
AAV2 REP52    ---RESVAQPSTSDAE-ASINYADRYQNKCSRHVGMNLMLFPCRQCERMNQNSNICFTHGQKDCLECFPV
AAV3A REP52   ---CTSLAQPTTSDAE-APADYADRYQNKCSRHVGMNLMLFPCKTCERMNQISNVCFTHGQRDCGECFPG
AAV3B REP52   ---CTSLAQPTTSDAE-APADYADRYQNKCSRHVGMNLMLFPCKTCERMNQISNVCFTHGQRDCGECFPG
AAV4 REP52    ---CPSVAQPSTSDAE-APVDYADRYQNKCSRHVGMNLMLFPCRQCERMNQNVDICFTHGVMDCAECFPV
AAV5 REP52    VPETPRSSDVTVDPAPLRPLNWNSRYDCKCDYHAQFDNISNKCDECEYLNRGKNGCICHNVTHCQICHGI
AAV6 REP52    ---CPSVADPSTSDAEGAPVDFADRYQNKCSRHAGMLQMLFPCKTCERMNQNFNICFTHGTRDCSECFPG
AAV7 REP52    ---CPSVADPSTSDAEGAPVDFADRYQNKCSFHAGMIQMLFPCKTCERMNQNFNICFTHGVRDCLECFPG
AAV8 REP52    ---CPSVADPSTSDAEGAPVDFADRYQNKCSRHAGMLQMLFPCKTCERMNQNFNICFTHGVRDCSECFPG
CONSENSUS        CPSVADPSTSDAE APVDFADRYQNKCSRHAGM QMLFPCKTCERMNQN NICFTHG RDC ECFPG
```

```
            370       380       390       400       410       420
AAV1 REP52  VSESQ--PVVRKRTYRKLCAIHHLLGRAPEIACSACDLVNVDLDDCVSEQ-    (SEQ ID NO:94)
AAV2 REP52  S-ESQPVSVVKK-AYQKLCYIHHIMGKVPD-ACTACDLVNVDLDDCIFEQ-    (SEQ ID NO:96)
AAV3A REP52 MSESQPVSVVKKKTYQKLCPIHHILGRAPEIACSACDLANVDLDDCVSEQ-    (SEQ ID NO:97)
AAV3B REP52 MSESQPVSVVKKKTYQKLCPIHHILGRAPEIACSACDLANVDLDDCVSEQ-    (SEQ ID NO:98)
AAV4 REP52  S-ESQPVSVVRKRTYQKLCPIHHIMGRAPEVACSACELANVDLDDCDMEQ-    (SEQ ID NO:99)
AAV5 REP52  P------------PWEK--ENLS------DFG---DFDDANKEQ-          (SEQ ID NO:100)
AAV6 REP52  VSESQ--PVVRKRTYRKLCAIHHLLGRAPEIACSACDLVNVDLDDCVSEQ-    (SEQ ID NO:101)
AAV7 REP52  VSESQ--PVVRKKTYRKLCAIHHLLGRAPEIACSACDLVNVDLDDCVSEQ-    (SEQ ID NO:95)
AAV8 REP52  VSESQ--PVVRKRTYRKLCAIHHLLGRAPEIACSACDLVNVDLDDCVSEQ-    (SEQ ID NO:102)
CONSENSUS   VSESQ   VVRKRTY KLC IHHILGRAPEIACSACDLVNVDLDDCVSEQ
```

FIG. 31

```
            1         10        20        30        40        50        60        70
AAV1 REP68  MPGFYEIVIKVPSDLDEHLPGISDSFVSWVAEKEWELPPDSDMDLNLIEQAPLTVAEKLQRDFLVQWRRVSKAP
AAV2 REP68  MPGFYEIVIKVPSDLDEHLPGISDSFVNWVAEKEWELPPDSDMDLNLIEQAPLTVAEKLQRDFLTEWRRVSKAP
AAV3A REP68 MPGFYEIVLKVPSDLDERLPGISNSFVNWVAEKEWDVPPDSDMDPNLIEQAPLTVAEKLQREFLVEWRRVSKAP
AAV3B REP68 MPGFYEIVLKVPSDLDEHLPGISNSFVNWVAEKEWELPPDSDMDPNLIEQAPLTVAEKLQREFLVEWRRVSKAP
AAV4 REP68  MPGFYEIVIKVPSDLDEHLPGISDSFVSWVAEKEWELPPDSDMDLNLIEQAPLTVAEKLQREFLVEWRRVSKAP
AAV5 REP68  MATFYEVIVRVPFDVEEHLPGISDSFVDWVTGQIWELPPESDLNLTLVEQPQLTVADRIRRVFLYEWNKFSKQ-
AAV6 REP68  MPGFYEIVIKVPSDLDEHLPGISDSFVNWVAEKEWELPPDSDMDLNLIEQAPLTVAEKLQRDFLVQWRRVSKAP
AAV7 REP68  MPGFYEIVIKVPSDLDEHLPGISDSFVNWVAEKEWELPPDSDMDLNLIEQAPLTVAEKLQRDFLVQWRRVSKAP
AAV8 REP68  MPGFYEIVIKVPSDLDEHLPGISDSFVNWVAEKEWELPPDSDMDRNLIEQAPLTVAEKLQRDFLVQWRRVSKAP
```

```
AAV1 REP68  FALFFVQFEKGESYFHLHILVETTGVKSMVLGRFLSQIRDKLVQTIYRG-IEPTLPNWFAVTKTRNGAGGG-NKV
AAV2 REP68  EALFFVQFEKGESYFHLHVLVETTGVKSMVLGRFLSQIREKLIQRIYRG-IEPTLPNWFAVTKTRNGAGGG-NKV
AAV3A REP68 EALFFVQFEKGETYFHMHVLVETTGVKSMVLIETIGVKSMVVGRYVSQIKEKLVTRIYRG-VEPQLPNWFAVTKTRNGAGGG-NKV
AAV3B REP68 EALFFVQFEKGETYFHLHVLIETIGVKSMVVGRYVSQIKEKLVTRIYRG-VEPQLPNWFAVTKTRNGAGGG-NKV
AAV4 REP68  EALFFVQFEKGDSYFHLHILVETTGVKSMVVGRYVSQIKEKLVTRIYRG-VEPQLPNWFAVTKTRNGAGGG-NKV
AAV5 REP68  ESKFFVQFEKGSEYFHLHTLVETSGISSMVLGRYVSQIRAQLVKVFQG-IEPQINDWAITKVKK---GGANKV
AAV6 REP68  EALFFVQFEKGESYFHLHILVETTGVKSMVLGRFLSQIRDKLVQTIYRG-IEPTLPNWFAVTKTRNGAGGG-NKV
AAV7 REP68  EALFFVQFEKGESYFHLHVLVETTGVKSMVLGRFLSQIREKLVQTIYRG-VEPTLPNWFAVTKTRNGAGGG-NKV
AAV8 REP68  EALFFVQFELGESYFHLVLVETTGVKSMVLGRFLSQIREKLGPDHLPAGSSPTLPNWFAVTKDAVMAPAGGNKV

AAV1 REP68  VDECYIPNYLLPKTQPELQWAWTNMEEYISACLNLAERKRLVAQHLTHVSQTQEQNKENLNPNSDAPVIRSKTSA
AAV2 REP68  VDECYIPNYLLPKTQPELQWAWTNMEQYLSACLNLTERKRLVAQHLTHVSQTQEQNKENQNPNSDAPVIRSKTSA
AAV3A REP68 VDDCYIPNYLLPKTQPELQWAWTNMDQYLSACLNLAERKRLVAQHLTHVSQTQEQNKENQNPNSDAPVIRSKTSA
AAV3B REP68 VDDCYIPNYLLPKTQPELQWAWTNMDQYLSACLNLAERKRLVAQHLTHVSQTQEQNKENQNPNSDAPVIRSKTSA
AAV4 REP68  VDDCYIPNYLLPKVQPELQWAWTNMDQYISACLNLAERKRLVAQHLTHVSQTQEQNKENQNPNSDAPVIRSKTSA
AAV5 REP68  VDSGYIPAYLLPKVQPELQWAWTNLDEYKLAALNLEERKRLVAQFLAESSQRS-QEAASQREFSADPVIKSKTSQ
AAV6 REP68  VDECYIPNYLLPKTQPELQWAWTNMEEYISACLNLAERKRLVAQHLTHVSQTQEQNKENLNPNSDAPVIRSKTSA
AAV7 REP68  VDECYIPNYLLPKTQPELQWAWTNMEEYISACLNLAERKRLVAHDLTHVSQTQEQNKENLNPNSDAPVIRSKTSA
AAV8 REP68  VDECYIPNYLLPKTQPELQWAWTNMEEYISACLNLAERKRLVAQHLTHVSQTQEQNKENLNPNSDAPVIRSKTSA
```

FIG. 31 (cont.)

```
AAV1 REP68  RYMELVGWLVDRGITSEKQWIQEDQASYISFNAASNSRSQIKAALDNAGKIMALTKSAPDYLVGPAPPADIKTNR
AAV2 REP68  RYMELVGWLVDKGITSEKQWIQEDQASYISFNAASNSRSQIKAALDNAGKIMSLTKTAPDYLVGQQPVEDISSNR
AAV3A REP68 RYMELVGWLVDRGITSEKQWIQEDQASYISFNAASNSRSQIKAALDNASKIMSLTKTAPDYLVGSNPPEDITKNR
AAV3B REP68 RYMELVGWLVDRGITSEKQWIQEDQASYISFNAASNSRSQIKAALDNASKIMSLTKTAPDYLVGSNPPEDITKNR
AAV4 REP68  RYMELVGWLVDRGITSEKQWIQEDQASYISFNAASNSRSQIKAALDNASKIMSLTKTAPDYLVGQNPPEDISSNR
AAV5 REP68  KYMALVNWLVEHGITSEKQWIQENQESYLSFNSTGNSRSQIKAALDNATKIMSLTKSAVDYLVGSSVPEDISKNR
AAV6 REP68  RYMELVGWLVDRGITSEKQWIQEDQASYISFNAASNSRSQIKAALDNAGKIMALTKSAPDYLVGPAPPADIKTNR
AAV7 REP68  RYM LVGWLVDRGITSEKQWIQEDQASYISFNAASNSRSQIKAALDNAGKIMALTKSAPDYLVGPSLPADIKTNR
AAV8 REP68  RYMELVGWLVDRGITSEKQWIQEDQASYISFNAASNSRSQIKAALDNAGKIMALTKSAPDYLVGPSLPADITQNR

AAV1 REP68  IYRILELNGYEPAYAGSVFLGWAQKRFGKRNTIWLFGPATTGKTNIAEAIAHAVPFYGCVNWTNENFPFNDCVDK
AAV2 REP68  IYKILELNGYDPQYAASVFLGWATKKFGKRNTIWLFGPATTGKTNIAEAIAHTVPFYGCVNWTNENFPFNDCVDK
AAV3A REP68 IYQILELNGYDPQYAASVFLGWAQKFGKRNTIWLFGPATTGKTNIAEAIAHAVPFYGCVNWTNENFPFNDCVDK
AAV3B REP68 IYQILELNGYDPQYAASVFLGWAQKFGKRNTIWLFGPATTGKTNIAEAIAHAVPFYGCVNWTNENFPFNDCVDK
AAV4 REP68  IYRILEMNGYDPAYAGSILYGWCQRSFNKRNTVWLYGPATTGKTNIAEAIAHTVPFYGCVNWTNENFPFNDCVDK
AAV5 REP68  IWQIFEMNGYDPAYAGS ILYGWCQRSFNKRNTVWLYGPATTGKTNIAEAIAHTVPFYGCVNWTNENFPFNDCVDK
AAV6 REP68  IYRILELNGYDPAYAGSVFLGWAQKRFGKRNTIWLFGPATTGKTNIAEAIAHAVPFYGCVNWTNENFPFNDCVDK
AAV7 REP68  IYRILELNGYDPAYAGSVFLGWAQKKFGKRNTIWLFGPATTGKTNIAEAIAHAVPFYGCVNWTNENFPFNDCVDK
AAV8 REP68  IYRILALNGYDPAYAGSVFLGWAQKKFGKRNTIWLFGPATTGKTNIAEAIAHAVPFYGCVNWTNENFPFNDCVDK
```

FIG. 31 (cont.)

```
              380        390        400        410        420        430        440
              |          |          |          |          |          |          |
AAV1 REP68    MVIWWEEGKMTAKVVESAKAILGGSKVRVDQKCKSSAQIDPTPVIVTSNTNMCAVIDGNSTTFEHQQPLQDRMFK
AAV2 REP68    MVIWWEEGKMTAKVVESAKAILGGSKVRVDQKCKSSAQIDPTPVIVTSNTNMCAVIDGNSTTFEHQQPLQDRMFK
AAV3A REP68   MVIWWEEGKMTAKVVESAKAILGGSKVRVDQKCKCKSSAQIDPTPVIVTSNTNMCAVIDGNSTTFEHQQPLQDRMFE
AAV3B REP68   MVIWWEEGKMTAKVVESAKAILGGSKVRVDQKCKCKSSAQIEPTPVIVTSNTNMCAVIDGNSTTFEHQQPLQDRMFE
AAV4 REP68    MVIWWEEGKMTAKVVESAKAILGGSKVRVDQKCKSSAQIEPTPVIVTSNTNMCAVIDGNSTTFEHQQPLQDRMFK
AAV5 REP68    MLIWWEEGKMTNKVVESAKAILGGSKVRVDQKCKSSVQIDSTPVIVTSNTNMCVVVDGNSTTFEHQQPLEDRMFK
AAV6 REP68    MVIWWEEGKMTAKVVESAKAILGGSKVRVDQKCKCKSSAQIDPTPVIVTSNTNMCAVIDGNSTTFEHQQPLQDRMFK
AAV7 REP68    MVIWWEEGKMTAKVVESAKAILGGSKVRVDQKCKSSAQIDPTPVIVTSNTNMCAVIDGNSTTFEHQQPLQDRMFK
AAV8 REP68    MVIWWEEGKMTAKVVESAKAILGGSKVRVDQKCKCKSSAQIDPTPVIVTSNTNMCAVIDGNSTTFEHQQPLQDRMFK 450        460        470        480        490        500        510
              |          |          |          |          |          |          |
AAV1 REP68    FELTRRLEHDFGKVTKQEVKEFFRWAQDHVTEVAHEFYVR------KGGAN--KRPAPDDADKSEP----
AAV2 REP68    FELTRRLDHDFGKVTKQEVKEFFRWAKDHVTEVAHEFYVK------KGGAK--KRPAPSDADISEP----
AAV3A REP68   FELTRRLDHDFGKVTKQEVKDFFRWASDHVTEVAHEFYVR------KGGAK--KRPAPSDADVSEP----
AAV3B REP68   FELTRRLDHDFGKVTKQEVKDFFRWASDHVTDVAHEFYVR------KGGAK--KRPASNDADVSEP----
AAV4 REP68    FELTKRLEHDFGKVTKQEVKDFFRWASDHVTEVTHEFYVR------KGGAR--KRPAPNDADISEP----
AAV5 REP68    FELTKRLPPDFGKITKQEVTKQEVKDFFAWAKVNQVPVTHEFKVPRELAGTKGAEKSLKRPLGDVTNTSYKSLEK
AAV6 REP68    FELTRRLEHDFGKVTKQEVKEFFRWAQDHVTEVAHEFYVR------KGGAN--KRPAPDDADKSEP----
AAV7 REP68    FELTRRLEHDFGKVTKQEVKEFFRWASDHVTEVAHEFYVR------KGGAS--KRPAPDDADISEP----
AAV8 REP68    FELTRRLEHDFGKVTKQEVKEFFRWASDHVTEVAHEFYVR------KGGAS--KRPAPDDADKSEP----
```

FIG. 31 (cont.)

|     | 520 | 530 | 540 | 555 |     |
| --- | --- | --- | --- | --- | --- |
| AAV1 REP68 | -KRACPSVADPSTSDAEGAPVDFADLARGQPL---- | | | | (SEQ ID NO:104) |
| AAV2 REP68 | -KRVRESVAQPSTSDAE-ASINYADLARGHSL---- | | | | (SEQ ID NO:105) |
| AAV3A REP68 | -KRECTSLAQPTTSDAE-APADYADLARGQPF---- | | | | (SEQ ID NO:106) |
| AAV3B REP68 | -KRQCTSLAQPTTSDAE-APADYADLARGQPF---- | | | | (SEQ ID NO:107) |
| AAV4 REP68 | -KRACPSVAQPSTSDAE-APVDYADLARGQPL---- | | | | (SEQ ID NO:108) |
| AAV5 REP68 | RARLSFVPETPRSSDVTVDPAPLRPLNWNSLVGRSW | | | | (SEQ ID NO:109) |
| AAV6 REP68 | -KRACPSVADPSTSDAEGAPVDFADLARGQPL---- | | | | (SEQ ID NO:110) |
| AAV7 REP68 | -KRACPSVADPSTSDAE-APVDFADLARGQPL---- | | | | (SEQ ID NO:111) |
| AAV8 REP68 | -KRACPSVADPSTSDAEGAPVDFADLARGQPL---- | | | | (SEQ ID NO:112) |

FIG. 31 (cont.)

|     | 1 | 10 | 20 | 30 | 40 | 50 | 60 | 70 |
| --- | --- | --- | --- | --- | --- | --- | --- | --- |
| AAV1 REP78 | MPGFYEIVIKVPSDLDEHLPGISDSFVSWVAEKEWELPPDSDMDLNLIEQAPLTVAEKLQRDFLVQWRRVSKAP | | | | | | | |
| AAV2 REP78 | MPGFYEIVIKVPSDLDEHLPGISDSFVNWVAEKEWELPPDSDMDLNLIEQAPLTVAEKLQRDFLTEWRRVSKAP | | | | | | | |
| AAV3A REP78 | MPGFYEIVLKVPSDLDERLPGISNSFVNWVAEKEWDVPPDSDMDPNLIEQAPLTVAEKLQREFLVEWRRVSKAP | | | | | | | |
| AAV3B REP78 | MPGFYEIVLKVPSDLDEHLPGISNSFVNWVAEKEWELPPDSDMDLNLIEQAPLTVAEKLQREFLVEWRRVSKAP | | | | | | | |
| AAV4 REP78 | MPGFYEIVLKVPSDLDEHLPGISDSFVSWVAEKEWELPPDSDMDLNLIEQAPLTVAEKLQRDFLVEWRRVSKAP | | | | | | | |
| AAV5 REP78 | MATFYEVIVRVPFDVEEHLPGISDSFVDWVTGQIWELPPESDLNLTLVEQPQLTVADRIRRVFLYEWNKFSKQ- | | | | | | | |
| AAV6 REP78 | MPGFYEIVIKVPSDLDEHLPGISDSFVNWVAEKEWELPPDSDMDLNLIEQAPLTVAEKLQRDFLVQWRRVSKAP | | | | | | | |
| AAV7 REP78 | MPGFYEIVIKVPSDLDEHLPGISDSFVNWVAEKEWELPPDSDMDLNLIEQAPLTVAEKLQRDFLVQWRRVSKAP | | | | | | | |
| AAV8 REP78 | MPGFYEIVIKVPSDLDEHLPGISDSFVNWVAEKEWELPPDSDMDRNLIEQAPLTVAEKLQRDFLVQWRRVSKAP | | | | | | | |
| CONSENSUS | | | | | | | | |

FIG. 32

```
                80         90        100        110        120        130        140
AAV1 REP78    EALFFVQFEKGESYFHLHILVETTGVKSMVLGRFLSQIRDKLVQTIYRG--IEPTLPNWFAVTKTRNGAGGG-NKV
AAV2 REP78    EALFFVQFEKGESYFHMHVLVETTGVKSMVLGRFLSQIREKLIQRIYRG--IEPTLPNWFAVTKTRNGAGGG-NKV
AAV3A REP78   EALFFVQFEKGETYFHLHVLIETTGVKSMVVGRYVSQIKEKLVTRIYRG--VEPQLPNWFAVTKTRNGAGGG-NKV
AAV3B REP78   EALFFVQFEKGETYFHLHVLIETTGVKSMVVGRYVSQIKEKLVTRIYRG--VEPQLPNWFAVTKTRNGAGGG-NKV
AAV4 REP78    EALFFVQFEKGDSYFHLHILVETTGVKSMVVGRYVSQIKEKLVTRIYRG--VEPQLPNWFAVTKTRNGAGGG-NKV
AAV5 REP78    ESKFFVQFEKGSEYFHLHILVETSGISSMVLGRYVSQIRAQLVKVFQG--IEPQINDWVAITKVKK---GGANKV
AAV6 REP78    EALFFVQFEKGESYFHLHILVETTGVKSMVLGRFLSQIRDKLVQTIYRG--IEPTLPNWFAVTKTRNGAGGG-NKV
AAV7 REP78    EALFFVQFEKGESYFHLHVLVETTGVKSMVLGRFLSQIREKLVQTIYRG--VEPTLPNWFAVTKTRNGAGGG-NKV
AAV8 REP78    EALFFVQFEKGLSYFHLHVLVETTGVKSMVLGRFLSQIREKLGPDHLPAGSSPTLPNWFAVTKDAVMAPAGGNKV
CONSENSUS     EALFFVQFEKGESYFHLHVLVETTGVKSMVLGRFLSQIREKLV       IYRG IEPTLPNWFAVTKTRNGAGGG NKV 150       160        170        180        190        200        210       220
AAV1 REP78    VDECYIPNYLLPKTQPELQWAWTNMEEYISACLNLAERKRLVAQHLTHVSQTQEQNKENLNPNSDAPVIRSKTSA
AAV2 REP78    VDECYIPNYLLPKTQPELQWAWTNMEQYISACLNLTERKRLVAQHLTHVSQTQEQNKENLNPNSDAPVIRSKTSA
AAV3A REP78   VDDCYIPNYLLPKTQPELQWAWTNMDQYISACLNLAERKRLVAQHLTHVSQTQEQNKENQNPNSDAPVIRSKTSA
AAV3B REP78   VDDCYIPNYLLPKTQPELQWAWTNMDQYISACLNLAERKRLVAQHLTHVSQTQEQNKENQNPNSDAPVIRSKTSA
AAV4 REP78    VDDCYIPNYLLPKTQPELQWAWTNMDQYISACLNLAERKRLVAQHLTHVSQTQEQNKENQNPNSDAPVIRSKTSA
AAV5 REP78    VDSCYIPAYLLPKVQPELQWAWTNLDEYKLAAINLEERKRLVAQFLAESSQRS-QEAASQREFSADPVIKSKTSQ
AAV6 REP78    VDECYIPNYLLPKTQPELQWAWTNMEEYISACLNLAERKRLVAQHLTHVSQTQEQNKENLNPNSDAPVIRSKTSA
AAV7 REP78    VDECYIPNYLLPKTQPELQWAWTNMEEYISACLNLAERKRLVAHDLTHVSQTQEQNKENLNPNSDAPVIRSKTSA
AAV8 REP78    VDECYIPNYLLPKTQPELQWAWTNMEEYISACLNLAERKRLVAQHLTHVSQTQEQNKENLNPNSDAPVIRSKTSA
CONSENSUS     VDECYIPNYLLPKTQPELQWAWTNMEEYISACLNLAERKRLVAQHLTHVSQTQEQNKENLNPNSDAPVIRSKTSA
```

FIG. 32 (cont.)

```
              230        240        250        260        270        280        290
              |          |          |          |          |          |          |
AAV1 REP78    RYMELVGWLVDRGITSEKQWIQEDQASYISFNAASNSRSQIKAALDNAGKIMALTKSAPDYLVGPAPPADIKTNR
AAV2 REP78    RYMELVGWLVDKGITSEKQWIQEDQASYISFNAASNSRSQIKAALDNAGKIMSLTKTAPDYLVGQQPVEDISSNR
AAV3A REP78   RYMELVGWLVDRGITSEKQWIQEDQASYISFNAASNSRSQIKAALDNASKIMSLTKTAPDYLVGSNPPEDITKNR
AAV3B REP78   RYMELVGWLVDRGITSEKQWIQEDQASYISFNAASNSRSQIKAALDNASKIMSLTKTAPDYLVGSNPPEDITKNR
AAV4 REP78    RYMELVGWLVDRGITSEKQWIQEDQASYISFNAASNSRSQIKAALDNASKIMSLTKTAPDYLVGSNPPEDISSNR
AAV5 REP78    KYMALVNWLVEHGITSEKQWIQENQESYLSFNSTGNSRSQIKAALDNATKIMSLTKSAVDYLVGSSVPEDISKNR
AAV6 REP78    RYMELVGWLVDRGITSEKQWIQEDQASYISFNAASNSRSQIKAALDNAGKIMALTKSAPDYLVGPAPPADIKTNR
AAV7 REP78    RYMELVGWLVDRGITSEKQWIQEDQASYISFNAASNSRSQIKAALDNAGKIMSLTKSAPDYLVGPSLPADIKTNR
AAV8 REP78    RYMELVGWLVDRGITSEKQWIQEDQASYISFNAASNSRSQIKAALDNAGKIMSLTKSAPDYLVGPSLPADITQNR
CONSENSUS     RYMELVGWLVDRGITSEKQWIQEDQASYISFNAASNSRSQIKAALDNAGKIMSLTKSAPDYLVG SPPEDISTNR 300        310        320        330        340        350        360        370
              |          |          |          |          |          |          |          |
AAV1 REP78    IYRILELNGYEPAYAGSVFLGWAQKRFGKRNTIWLFGPATTGKTNIAEAIAHAVPFYGCVNWTNENFPFNDCVDK
AAV2 REP78    IYKILELNGYDPQYAASVFLGWATKKFGKRNTIWLFGPATTGKTNIAEAIAHTVPFYGCVNWTNENFPFNDCVDK
AAV3A REP78   IYQILELNGYDPQYAASVFLGWAQKKFGKRNTIWLFGPATTGKTNIAEAIAHAVPFYGCVNWTNENFPFNDCVDK
AAV3B REP78   IYQILELNGYDPQYAASVFLGWAQKKFGKRNTIWLFGPATTGKTNIAEAIAHAVPFYGCVNWTNENFPFNDCVDK
AAV4 REP78    IYRILEMNGYDPQYAAGSVFLGWAQKKFGKRNTIWLYGPATTGKTNIAEAIAHTVPFYGCVNWTNENFPFNDCVDK
AAV5 REP78    IWQIFEMNGYDPAYAGSILYGWCQRSFNKRNTVWLYGPATTGKTNIAEAIAHAVPFYGCVNWTNENFPFNDCVDK
AAV6 REP78    IYRILELNGYDPAYAGSVFLGWAQKRFGKRNTIWLFGPATTGKTNIAEAIAHAVPFYGCVNWTNENFPFNDCVDK
AAV7 REP78    IYRILELNGYDPAYAGSVFLGWAQKKFGKRNTIWLFGPATTGKTNIAEAIAHAVPFYGCVNWTNENFPFNDCVDK
AAV8 REP78    IYRILALNGYDPAYAGSVFLGWAQKKFGKRNTIWLFGPATTGKTNIAEAIAHAVPFYGCVNWTNENFPFNDCVDK
CONSENSUS     IYRILELNGYDPAYAGSVFLGWAQKKFGKRNTIWLFGPATTGKTNIAEAIAHAVPFYGCVNWTNENFPFNDCVDK
```

SNAKE ITR EGFP VECTOR PLASMID (pSnTR-eGFP)

FIG. 34

SNAKE REPCAP2 PLASMID (PSNREPCAP2)
TCGCGCGTTTCGGTGATGACGGTGAAAACCTCTGACACATGCAGCTCCCGGAGACGGTCACAGCTTGTCTGTAAGCG
GATGCCGGGAGCAGACAAGCCCGTCAGGGCGCGTCAGCGGGTGTTGGCGGGTGTCGGGGCTGGCTTAACTATGCGGC
ATCAGAGCAGATTGTACTGAGAGTGCACCATATGCGGTGTGAAATACCGCACAGATGCGTAAGGAGAAAATACCGCA
TCAGGAAATTGTAAACGTTAATATTTTGTTAAAATTCGCGTTAAATTTTTGTTAAATCAGCTCATTTTTTAACCAAT
AGGCCGAAATCGGCAAAATCCCTTATAAATCAAAAGAATAGACCGAGATAGGGTTGAGTGTTGTTCCAGTTTGGAAC
AAGAGTCCACTATTAAAGAACGTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCGGAACCCTAAAGGGAGCCCCC
GATTTAGAGCTTGACGGGGAAAGCCGGCGAACGTGGCGAGGAAGGAAGGGAAGAAAGCGAAAGGAGCGGGCGCTAGG
GCGCTGGCAAGTGTAGCGGTCACGCTGCGCGTAACCACCACACCCGCCGCGCTTAATGCGCCGCTACAGGGCGCGTC
GCGCCATTCGCCATTCAGGCTGCGCAACTGTTGGGAAGGGCGATCGGTGCGGGCCTCTTCGCTATTACGCCAGCTGG
CGAAAGGGGGATGTGCTGCAAGGCGATTAAGTTGGGTAACGCCAGGGTTTTCCCAGTCACGACGTTGTAAAACGACG
GCCAGTGAATTGTAATACGACTCACTATAGGGCGAATTCGAGCTCGCAGCGGACATGTCTGGACATGTCTTGAGCA
AGTCCATATAAGGAGTTCCGCCGGATATGCAAATGAGCAATCGCGCAAAGCATTTTGGGTAGTCACCATGAATAAAA
AGGACAGCAAGAAAGATGACGCCCCATAATTTTAATAGGAATTTTAACCATGGCGTTTTACGAGGTTGTGTTTCGTT
TGCCAAGAGACAATAACAACTTGTTGGATGAAGATAGATATCAGCCAGAGTTGAAAGAAGAAGATGACTGGCCTGAG
GAATATTTAACCAGTGAAGATGCCAGCTTTATCGGACTAGCGTATGCTGTGCTAAGTGAAATTCGGAGATTCTTTGG
AAAGGAACTACAATGGTTTGCCCAGGTTGAATGGTGTCCTACTGCTGGTTACCACATGCATGTTTGTTGAACCATC
CTAAGCTGAGTAACCAGACTTATGGAAGAAAGGTCAATGAACTGGCTTGCCGTATAGTCGATACCTTTGGCCTAATT
AATCCAGAAGAAGTCATCAGTACCCATTATGTTAAAAGCAACTATGGACATAAAAAGGTGAGAGTCATTCACCTAGA
GTCTTATTTGAAGAACTACTTTTTCAGAAAGACTTTAGCTCCTCCCAATTATACCGAGGAAGGAGACTATAAAAGAG
AGGAAGAAGTCGTGCTGTGTGGGCATTTACGAATATCGTCGCTTGGAAGCCATTCGTGCGGAATCTCATCAAGAGATCG
GAGCTAGCGACTGTTCCTAAGCAACCAGAGAATCCGCGGGAGACGGACCGGCACCTCGAGTGACTGCAGGAACCCG
CCATTTATGGAAACCATCGACTGGTTGGTGAAACATGGAATTACTACAGAACGAGAATTCTGCCACGCCAACCGCC
CTTTGTACCTGTCTATGCTGGCTTCTACTTCGGGTGCTGGGCAGATTAAAAGAGCGCTGGACCAGGCGAAACACATG
ATGACCAGCACCATGTCAGCAGAGGATTACCTGACAACAGAAGAGGATGTGATCGAACCACCTACTGAAAATAGAAT
CTACAAGATTATGAAACTGAATCGCTATGATCCAGAACTAGCAGCTGCTCTCTTCTACGGCTGACCTGCAAGAACT
TTGGCAAGAGAAACACCATCTGGCTGTATGGTCCAGCTACTACGGCAAAACCATCATCGCTCAAGCTATTGCACAT
GCTGTTAAACTGTTTGCTGGTGTTAATTGGACTAATGAAAACTTTCCCTTCTGTAACTGTCCAGGGAAACTGCTTAT
CTGGTGGGAGGAGGGCAAGATGACAAACAAAATGGTGGAGACGGCTAAATGTATACTGGGGGGATCTGCTGTACCTG
TAGACATCAAAGGCAAACCCGCTGAAATGTGTCCTCAAACACCCTGTATTATTACTAGCAATACTAACATGTGTCAA
GTATATGATGGTAATAGTTCTAGCTTTGAGCACCAAGAACCCCTAGAGGAACGCATGTTTATGTTCAGACTTAATAC
TAAACTGCCATCGACCTTTGGCAAGATCACAGAAGAACTAGCAGCTCTGGGCTGGCAGAGGAGCTTAAAGG
TTCAAGTTCCACATCAGTTCAGAGTGCCTACCACAGGAGAGTATAAAAGGCCAGCCCCGAGGCGAAAGCTCATTCT
TCGGATGAGCCGCCAAAAGAGAAGGTCGCGCGTATTGATGACTCTCTAACCAGGTATGTTAACAATATTGATGAGTC
AGCTACCAGTAGAGAAATGTTTCTAGAGATTGCTAATACTAATCAATGTATGTTGCATCATTGCTTTTCTTGTACCG
AATGTTATCCTGAATTGCTTGATGACATGGACAAGGAACAATAAACTTACTGATAACAGATATGGCTGCCGATGGTT
ATCTTCCAGATTGGCTCGAGGACACTCTCTCTGAAGGAATAAGACAGTGGTGGAAGCTCAAACCTGGCCCACCACCA
CCAAAGCCCGCAGAGCCGGCATAAGGACGACAGCAGGGGTCTTGTGCTTCCTGGGTACAAGTACCTCGGACCCTTCAA
CGGACTCGACAAGGGAGAGCCGGTCAACGAGGCACCGCGGCCCTCGAGCACGACAAAGCCTACGACCGGCAGC
TCGACAGCGGAGACAACCCGTACCTCAAGTACAACCACGCCGACGCGGAGTTTCAGGAGCGCCTTAAAGAAGATACG
TCTTTTGGGGGCAACCTCGGACGAGCAGTCTTCCAGGCGAAAAAGAGGGTTCTTGAACCTCTGGGCCTGGTTGAGGA
ACCTGTTAAGACGGCTCCGGGAAAAAAGAGGCCGGTAGAGCACTCTCCTGTGGAGCCAGACTCCTCCTCGGGAACCG
GAAAGCGGGCCAGCAGCCTGCAAGAAAAAGATTGAATTTTTGGTCAGACTGGAGACGCAGACTCAGTACCTGACCCC
CAGCCTCTCGGACAGCCACCAGCAGCCCCCTCTGGTCTGGGAACTAATACGATGGCTACAGGCAGTGGCGCACCAAT
GGCAGACAATAACGAGGGCGCCGACGGAGTGGGTAATTCCTCGGGAAATTGGCATTGCGATTCCACATGGATGGGCG
ACAGAGTCATCACCACCAGCACCCGAACCTGGGCCCTGCCCACCTACAACAACCACCTCTACAAACAAATTTCCAGC
CAATCAGGAGCCTCGAACGACAATCACTACTTTGGCTACAGCACCCCTTGGGGGTATTTTGACTTCAACAGATTCCA
CTGCCACTTTTCACCACGTGACTGGCAAAGACTCATCAACAACAACTGGGGATTCCGACCCAAGAGACTCAACTTCA
AGCTCTTTAACATTCAAGTCAAAGAGGTTACGCAGAATGACGGTACGACGACGATTGCCAATAACCTTACCAGCACG
GTTCAGGTGTTTACTGACTCGGAGTACCAGCTCCCGTACGTCCTCGGCTCGGCGCATCAAGGATGCCTCCCGCCGTT
CCCAGCAGACGTCTTCATGGTGCCACAGTATGGATACCTCACCCTGAACAACGGGAGTCAGGCAGTAGGACGCTCTT
CATTTTACTGCCTGGAGTACTTTCCTTCTCAGATGCTGCGTACCGGAAACAACTTTACCTTCAGCTACACTTTTGAG
GACGTTCCTTTCCACAGCAGCTACGCTCACAGCCAGAGTCTGGACCGTCTCATGAATCCTCTCATCGACCAGTACCT
GTATTACTTGAGCAGAACAACACTCCAAGTGGAACCACCACGCAGTTCAAGCTTCAAGGCTTCAGTTTTCTCAGGCCGGAGCGA
GTGACATTCGGGACCAGTCTAGGAACTGGCTTCCTGACCCTGTTACCGCCAGCAGCGAGTATCAAAGACATCTGCG
GATAACAACAACAGTGAATACTCGTGGACTGGAGCTACCAAGTACCACCTCAATGGCAGAGACTCTCTGGTGAATCC
GGGCCCGGCCATGGCAAGCCACAAGGACGATGAAGAAAAGTTTTTTCCTCAGAGCGGGGTTCTCATCTTTGGGAAGC
AAGGCTCAGAGAAAACAAATGTGGACATTGAAAAGGTCATGATTACAGACGAAGAGGAAATCAGGACAACCAATCCC
GTGGCTACGGAGCAGTATGGTTCTGTATCTACCAACCTCCAGAGAGGCAACAGACAAGCAGCTACCGCAGATGTCAA
CACACAAGGCGTTCTTCCAGGCATGGTCTGGCAGGACAGAGATGTGTACCTTCAGGGGCCCATCTGGGCAAAGATTC
CACACACGGACGGACATTTTCACCCCCTCTCCCCTCATGGGTGGATTCGGACTTAAACACCCTCCTCCACAGATTCTC

```
ATCAAGAACACCCCGGTACCTGCGAATCCTTCGACCACCTTCAGTGCGGCAAAGTTTGCTTCCTTCATCACACAGTA
CTCCACGGGACAGGTCAGCGTGGAGATCGAGTGGGAGCTGCAGAAGGAAAACAGCAAACGCTGGAATCCCGAAATTC
AGTACACTTCCAACTACAACAAGTCTGTTAATGTGGACTTTACTGTGGACACTAATGGCGTGTATTCAGAGCCTCGC
CCCATTGGCACCAGATACCTGACTCGTAATCTGTAATTGCTTGTTAATCAATAAACCGTTTAATTCGTTTCAGTTGA
ACTTTGGTGTCGCGGCCGCTCGATAAGCTTTTGTTCCCTTTAGTGAGGGTTAATTCCGAGCTTGGCGTAATCATGGT
CATAGCTGTTTCCTGTGTGAAATTGTTATCCGCTCACAATTCCACACAACATACGAGCCGGAAGCATAAAGTGTAAA
GCCTGGGGTGCCTAATGAGTGAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTATTGGGCGCTCTTCCGCTTCCT
CGCTCACTGACTCGCTGCGCTCGGTCGTTCGGCTGCGGCGAGCGGTATCAGCTCACTCAAAGGCGGTAATACGGTTA
TCCACAGAATCAGGGGATAACGCAGGAAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAGCCACTGGTAACAGGATT
AGCAGAGCGAGGTATGTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAAAAAG
GATCTTCACCTAGATCCTTTTAAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCCATAGTTGCCTGACTC
CCCGTCGTGTAGATAACTACGATACGGGAGGGCTTACCATCTGGCCCCAGTGCTGCAATGATACCGCGAGACCCACG
CTCACCGGCTCCAGATTTATCAGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAGTTAATAGTTTGCGCAACGTT
GTTGCCATTGCTACAGGCATCGTGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTGCTCTTGCCCGGC
GTCAATACGGGATAATACCGCGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAAAAGTGCCACCTGACGTC
TAAGAAACCATTATTATCATGACATTAACCTATAAAAATAGGCGTATCACGAGGCCCTTTCGTC
```

FIG. 35 (cont.)

RESTRICTIVE INVERTED TERMINAL REPEATS FOR VIRAL VECTORS

RELATED APPLICATIONS

This application is a 35 U.S.C. §371 national phase application of PCT Application PCT/US2011/020939, filed Jan. 12, 2011 which claims priority to U.S. Provisional Application No. 61/294,181, filed Jan. 12, 2010. The entire content of each of these applications is incorporated herein by reference.

STATEMENT OF FEDERAL SUPPORT

This invention was made with government support under Grant Nos. GM0529299, HL066973, HL051818, AI072176 and AI007419 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. §1.821, entitled 5470-547_ST25.txt, 454,116 bytes in size, generated on Nov. 7, 2012 and filed via EFS-Web, is provided in lieu of a paper copy. This Sequence Listing is hereby incorporated by reference into the specification for its disclosures.

FIELD OF THE INVENTION

This invention relates to modified parvovirus inverted terminal repeats (ITRs) that do not functionally interact with wild-type large Rep proteins, synthetic Rep proteins that functionally interact with the modified ITRs, and methods of using the same for delivery of nucleic acids to a cell or a subject. The modifications provide a novel Rep-ITR interaction that may limit vector mobilization, increasing the safety of viral vectors.

BACKGROUND OF THE INVENTION

The adeno-associated viruses (AAV) are members of the family Parvoviridae and the genera Dependoviruses. Serotypes 1 through 4 were originally identified as contaminates of adenovirus preparations (Carter and Laughlin (1984) in, The Parvoviruses p. 67-152 New York, N.Y.) whereas type 5 was isolated from a patient wart that was HPV positive. To date, twelve molecular clones have been generated representing the serotypes of human/primate AAV (Bantel-Schaal et al. (1999) *J. Virol.* 73: 939; Chiorini at al. (1997) *J. Virol.* 71:6823; Chiorini et al. (1999) *J. Virol.* 73:1309; Gao et al. (2002) *Proc. Nat. Acad Sci. USA* 99:11854; Mori et al. (2004) *Virol.* 330:375; Muramatsu et al. (1996) *Virol.* 221:208; Ruffing et al. (1994) *J. Gen. Virol.* 75:3385; Rutledge et al. (1998) *J. Virol.* 72:309; Schmidt et al. (2008) *J. Virol.* 82:8911; Srivastava et al. (1983) *J. Virol.* 45:555; Xiao et al. (1999) *J. Virol.* 73:3994). These clones have provided valuable reagents for studying the molecular biology of serotype specific infection. Transduction of these viruses naturally results in latent infections, with completion of the life cycle generally requiring helper functions not associated with AAV viral gene products. As a result, all of these serotypes are classified as non-pathogenic and are believed to share a safety profile similar to the more extensively studied AAV type 2 (Carter and Laughlin (1984) in, The Parvoviruses p. 67-152 New York, N.Y.).

General understanding of the mechanisms required for function at origins of replication has grown immensely since the first prokaryotic origins were characterized. While the DNA-protein interactions necessary for replication in prokaryotes, lower eukaryotes, and bacteriophages are generally well understood, mechanisms employed in the majority of higher eukaryotes and vertebrate viruses, such as AAV, are still being determined. The inverted terminal repeats (ITRs) of AAV and other Parvoviruses act as the origin of replication. These elements flank the short, single stranded genome and typically possess a T-shaped secondary structure. The replication strategies of the genus *Dependovirus*, including those of AAV, have been well characterized. The viral non-structural or Replication proteins (Rep) are the only factors required to interact with the ITR in order to catalyze replication (Im and Muzyczka (1990) *Cell* 61:447). The majority of AAV serotypes possess highly conserved origins of replication with interchangeable DNA-protein interactions. However, the Rep proteins of several serotypes interact exclusively with their cognate ITR. Discovering the mechanisms which drive Rep-ITR specificity promises to advance our understanding of DNA-protein interactions at viral origins of replication. These findings also promise to shed light on how eukaryotic and prokaryotic proteins achieve selectivity to DNA substrates.

The AAV rep gene encodes four multifunctional proteins (Hermonat et al. (1984) *J. Virol.* 51:329; Tratschin et al. (1984) *J. Virol.* 51:611; Mendelson et al. (1986) *J. Virol.* 60:823; Trempe et al. (1987) *Virol.* 161:18) that are expressed from two promoters at map units 5 (p5) and 19 (p19). The larger Rep proteins transcribed from the p5 promoter (Rep78 and Rep68), are essentially identical except for unique carboxy termini generated from unspliced (Rep78) and spliced (Rep68) transcripts, respectively (Srivastava et al, (1983) *J. Virol.* 45:555). The two smaller Rep proteins, Rep52 and Rep40, are transcribed from the p19 promoter and represent amino terminal truncations of Rep78 and Rep68, respectively.

Several biochemical activities of Rep78 and Rep68 have been characterized as involved in AAV replication. These include specific binding to the AAV ITR (Ashktorah et al. (1989) *J. Virol.* 63:3034; Im et al. (1989) *J. Virol.* 63:3095; Snyder et al. (1993) *J. Virol.* 67:6096) and site-specific endonuclease cleavage at the terminal resolution site (trs) (Im et al. (1990) *J. Virol.* 63:447; Im et al. (1992) *J. Virol.* 66:1119; Snyder et al., (1990) *Cell* 60:105; Snyder et al. (1990) *J. Virol.* 64:6204). Rep78/68 also possess ATP dependent DNA-DNA helicase (Im et al., (1990) *J. Virol.* 63:447; Im et al. (1992) *J. Virol.* 66:1119) and DNA-RNA helicase as well as ATPase activities (Wonderling et al. (1995) *J. Virol.* 69:3542). In addition to these activities involved in replication, Rep78/68 also regulate transcription from the viral promoters (Beaton et al. (1989) *J. Virol,* 63:4450; Labow et al. (1986) *J. Virol.* 60:251; Tratschin et al. (1986) *Mol. Cell. Biol.* 6:2884; Kyostio et al. (1994) *J. Virol.* 68:2947; Pereira et al. (1997) *J. Virol.* 71:1079), and have been shown to mediate viral targeted integration (Xiao, W., (1996), "Characterization of cis and trans elements essential for the targeted integration of recombinant adeno-associated virus plasmid vectors", Ph.D. Dissertation, University of North Carolina-Chapel Hill; Balague et al. (1997) *J. Virol.* 71:3299; LaMartina et al. (1998) *J. Virol.* 72:7653; Pieroni et al. (1998) *Virol.* 249:249).

Like Rep proteins, the AAV ITRs are involved in nearly every aspect of the viral life-cycle. The secondary structure of the ITR is necessary to prime synthesis of the second strand to allow transcription of the viral genes (Hauswirth and Berns (1977) *J. Virol.* 78:488). The full length Rep proteins contain a unique N-terminal DNA binding region which specifically recognizes the ITR at the 16 nt Rep-binding element (RBE) and at the tip of one of the hairpin stems known as the RBE' (FIG. 1A) (Ryan et al. (1996) *J. Virol.* 70:1542; Brister and Muzyczka (2000) *J. Virol.* 74:7762). Rep molecules multimerize on the ITR allowing the C-terminus of Rep, acting as an ATP-dependent SF3 helicase, to unwind the ITR and form a putative internal hairpin (Im and Muzyczka (1990) *Cell* 61:447; Hermonat and Batchu (1997) *FEBS Lett.* 20:180). This hairpin, (here, termed 'nicking stem') contains the terminal resolution site (trs) where Rep nicks the ITR in a site-specific manner (Brister and Muzyczka (1999) *J. Virol.* 73:9325). This DNA cleavage is important for replication of the closed ITR and to initiate subsequent rounds of genomic replication. Replicated genomes can undergo replication again or be encapsidated in the presence of the smaller Rep proteins (King et al. (2001) *EMBO J.* 20:3282).

The ITR sequences of twelve human/primate AAV serotypes have been published. These sequences typically display 80% or greater nucleotide conservation and segregate into two groups (Hewitt et al. (2009) *J. Virol.* 83:3919). The AAV2 Rep proteins (Rep2) are able to function on the ITR of every known AAV serotype except those of AAV5 (ITR5; Hewitt et al. (2009) *J. Virol.* 83:3919; Grimm et al. (2006) *J. Virol.* 80:426). Consistently, the AAV5 Rep proteins (Rep5) are unable to catalyze replication of the ITR of AAV2 (ITR2). Replicative specificity between these serotypes does not exist at the level of binding, as Rep2 and Rep5 can bind interchangeably to ITR2 or ITR5 (Chiorini et al. (1999) *J. Virol.* 73:4293). Instead, specificity is created by the inability of Rep to cleave the ITR of the opposite serotype. This occurs despite high conservation between the ITR2 and ITR5 sequence, secondary structure, and location of elements required for Rep interaction (RBE, RBE', trs, nicking stem).

All current AAV vectors in clinical trials utilize ITR2s. However, using ITR2s for therapeutic purposes creates a safety risk due to the ubiquity of AAV2 in the human population as well as other AAVs whose Rep proteins can replicate ITR2s. In this manner, rAAV vectors have the potential to be "mobilized" out of the target tissue into different tissues of the body or into other individuals in the population (Hewitt et al. (2009) *J. Virol.* 83:3919).

The present invention provides a solution to vector mobilization through the creation of a novel Rep-ITR interaction. A vector utilizing this novel interaction cannot be mobilized by one or more of the wild-type AAV serotypes which infect humans, nor the non-human serotypes which can potentially infect human hosts.

SUMMARY OF THE INVENTION

The present invention relates to the discovery of unique mechanisms at the DNA and protein level to achieve Rep-ITR specificity and utilizes these factors to create novel AAV origins of replication. Thus, one aspect of the invention relates to a polynucleotide comprising at least one parvovirus inverted terminal repeat (ITR), wherein said ITR comprises: (a) a first structural element that functionally interacts with a large Rep protein from a first AAV but does not functionally interact with a large Rep protein from a second AAV; and (b) a second structural element that that functionally interacts with the large Rep protein from the second AAV but does not functionally interact with the large Rep protein from the first AAV; wherein the ITR functionally interacts with a synthetic AAV large Rep protein. The invention further relates to a viral vector and a recombinant parvovirus particle comprising the polynucleotide of the invention. Further provided are pharmaceutical formulations comprising a virus particle of the invention in a pharmaceutically acceptable carrier.

Another aspect of the invention relates to a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV and said second structural element functionally interacts with a large Rep protein from a second AAV that is different from the first AAV. The invention further relates to polynucleotides encoding the synthetic large Rep protein and vectors and cells comprising the polynucleotide.

An additional aspect of the invention relates to a method of producing a recombinant parvovirus particle, comprising providing to a cell permissive for parvovirus replication: (a) a recombinant parvovirus template comprising (i) a heterologous nucleotide sequence, and (ii) the parvovirus terminal repeat sequence of the invention; (b) a polynucleotide encoding a Rep protein of the invention; under conditions sufficient for the replication and packaging of the recombinant parvovirus template; whereby recombinant parvovirus particles comprising the parvovirus capsid encoded by the cap coding sequences and packaging the recombinant parvovirus template are produced in the cell.

A further aspect of the invention relates to a method of delivering a nucleic acid to a cell, comprising introducing into a cell the recombinant parvovirus particle of the invention.

Another aspect of the invention relates to a method of administering a nucleic acid to a mammalian subject comprising administering to the mammalian subject a cell that has been contacted with the recombinant parvovirus particle of the invention under conditions sufficient for the parvovirus particle vector genome to enter the cell.

A further aspect of the invention relates to a method of administering a nucleic acid to a mammalian subject comprising administering to the mammalian subject the recombinant parvovirus particle of the invention.

An additional aspect of the invention relates to a parvovirus template comprising (i) a heterologous nucleotide sequence, and (ii) at least one snake AAV ITR sequence and a parvovirus particle comprising the parvovirus template.

A further aspect of the invention relates to a method of producing a parvovirus particle, comprising providing to a cell permissive for parvovirus replication: (a) a recombinant parvovirus template comprising (i) a heterologous nucleotide sequence, and (ii) at least one snake AAV ITR sequence; (b) a polynucleotide encoding snake AAV Rep protein and mammalian AAV Cap protein; (c) a polynucleotide encoding mammalian Rep52 and/or Rep40 proteins; under conditions sufficient for the replication and packaging of the recombinant parvovirus template; whereby recombinant parvovirus particles comprising a parvovirus capsid encoded by the cap coding sequences and packaging the recombinant parvovirus template are produced in the cell.

Another aspect of the invention relates to use of the recombinant parvovirus particle of the invention for delivering a nucleic acid to a cell.

An additional aspect of the invention relates to use of a cell that has been contacted with the recombinant parvovirus particle of the invention for delivering a nucleic acid to a mammalian subject.

A further aspect of the invention relates to use of the recombinant parvovirus particle of the invention for delivering a nucleic acid to a mammalian subject.

Another aspect of the invention relates to use of the recombinant parvovirus particle of the invention for the manufacture of a medicament for delivering a nucleic acid to a cell.

An additional aspect of the invention relates to use of a cell that has been contacted with the recombinant parvovirus particle of the invention for the manufacture of a medicament for delivering a nucleic acid to a mammalian subject.

A further aspect of the invention relates to use of the recombinant parvovirus particle of the invention for the manufacture of a medicament for delivering a nucleic acid to a mammalian subject.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not C or V; etc. as if each such possible disclaimer is expressly set forth herein.

These and other aspects of the invention are set forth in more detail in the description of the invention below.

BRIEF DESCRIPTION OF THE DRAWINGS

FIGS. 5A-5E show the cloning and characterization of chimeric Reps. (A) An alignment of the N-termini of Rep2 (SEQ ID NO:114) and Rep5 (SEQ ID NO:118). (*) represents conserved amino acids. (:) and (.) indicate conservative substitutions. (^) indicates residues implicated in RBE binding interactions. (') indicates residues which participate in the endonucleolytic active site. (+) indicates residues implicated in RBE' binding. (B) Chimeric Reps created and their ability to replicate ITR2 or ITR5 flanked vectors. Numbers indicate the amino acid (aa) position of the switch from one Rep to the other. (+) indicates the presence of replication, (−) indicates the absence. (C) Western blot for expression of the chimeric Reps. (D) Southern blot demonstrating replication of an ITR2 or an ITR5 vector by the chimeric Reps. Note that the ITR5 vector is 500 bp larger than the ITR2 vector. (E) Level of replication of the chimeric Reps relative to wt Rep2 or Rep5.

FIG. 8 shows an illustrative genomic DNA sequence for AAV-1; GenBank Accession No. NC 002077; SEQ ID NO:1.

FIG. 9 shows an illustrative genomic DNA sequence for AAV-2; GenBank Accession No. NC 001401; SEQ ID NO:2.

FIG. 10 shows an illustrative genomic DNA sequence for AAV-3A; GenBank Accession No. NC 001729; SEQ ID NO:3.

FIG. 11 shows an illustrative genomic DNA sequence for AAV-3B; GenBank Accession No. NC 001863; SEQ ID NO:4.

FIG. 12 shows an illustrative genomic DNA sequence for AAV-4; GenBank Accession No. NC 001829; SEQ ID NO:5.

FIG. 13 shows an illustrative genomic DNA sequence for AAV-5; GenBank Accession No. NC 006152; SEQ ID NO:6.

FIG. 14 shows an illustrative genomic DNA sequence for AAV-6; GenBank Accession No. NC 001862; SEQ ID NO:7.

FIG. 15 shows an illustrative genomic DNA sequence for AAV-7; GenBank Accession No. AF513851; SEQ ID NO:8.

FIG. 16 shows an illustrative genomic DNA sequence for AAV-8; GenBank Accession No. AF513852; SEQ ID NO:9.

FIG. 17 shows an illustrative genomic DNA sequence for AAV-9; GenBank Accession No. AX753250; SEQ ID NO:10.

FIG. 18 shows an illustrative genomic DNA sequence for AAV-11; GenBank Accession No. AY631966; SEQ ID NO:11.

FIG. 19 shows an illustrative genomic DNA sequence for AAV-13; GenBank Accession No. EU285562; SEQ ID NO:12.

FIG. 20 shows an illustrative genomic DNA sequence for B19 parvovirus; GenBank Accession No. NC 000883; SEQ ID NO:13.

FIG. 21 shows an illustrative genomic DNA sequence for Minute Virus from Mouse (MVM); GenBank Accession No. NC 001510; SEQ ID NO:14.

FIG. 22 shows an illustrative genomic DNA sequence for goose parvovirus; GenBank Accession No. NC 001701; SEQ ID NO:15.

FIG. 23 shows an illustrative genomic DNA sequence for snake parvovirus 1; GenBank Accession No. NC 006148; SEQ ID NO:16.

FIG. 24 provides an exemplary listing of the chimeric ITRs that were synthesized as part of the Examples described below: ITR2 (SEQ ID NO:17), ITR5 (SEQ ID NO:18), ITR5+2SNS (SEQ ID NO:19), ITR2+5SNS (SEQ ID NO:20), ITR5+2NS (SEQ ID NO:21), ITR2+5NS (SEQ ID NO:22), ITR2-TA (SEQ ID NO:23), ITR5+TA (SEQ ID NO:24), ITR2-GC (SEQ ID NO:25), ITR5+GC (SEQ ID NO:26), ITR2-2nt (SEQ ID NO:27), ITR2 5nt (SEQ ID NO:28), ITR2+7 (SEQ ID NO:29), ITR2 9nt (SEQ ID NO:30), ITR2 10nt (SEQ ID NO:31), ITR2 11nt (SEQ ID NO:32), ITR2 15nt (SEQ ID NO:33), ITR5 3nt (SEQ ID NO:34), ITR5 Ent (SEQ ID NO:35), ITR5 9 bp NS (SEQ ID NO:36), ITR5 21nt (SEQ ID NO:37), ITR5 30nt (SEQ ID NO:38), ITR5 GAGY (SEQ ID NO:39), ITR5 no GAGY (SEQ ID NO:40), ITR2+8nt GAGY (SEQ ID NO:41), ITR5 Spacer RBE (SEQ ID NO:42), ITR2+8-8 Spacer RBE (SEQ ID NO:43), ITR5 with ITR2 hairpins (SEQ ID NO:44), ITR2 no hairpins (SEQ ID NO:45), ITR2 T1 (SEQ ID NO:46), ITR2 T2 (SEQ ID NO:47), ITR2 T2 #2 (SEQ ID NO:48), ITR2 T3 (SEQ ID NO:49), ITR2 T4 (SEQ ID NO:50), ITR5+ 3nt Spacer & ITR5 NS (SEQ ID NO:51), and ITR2 pHpa8 (SEQ ID NO:52).

Figure 25:
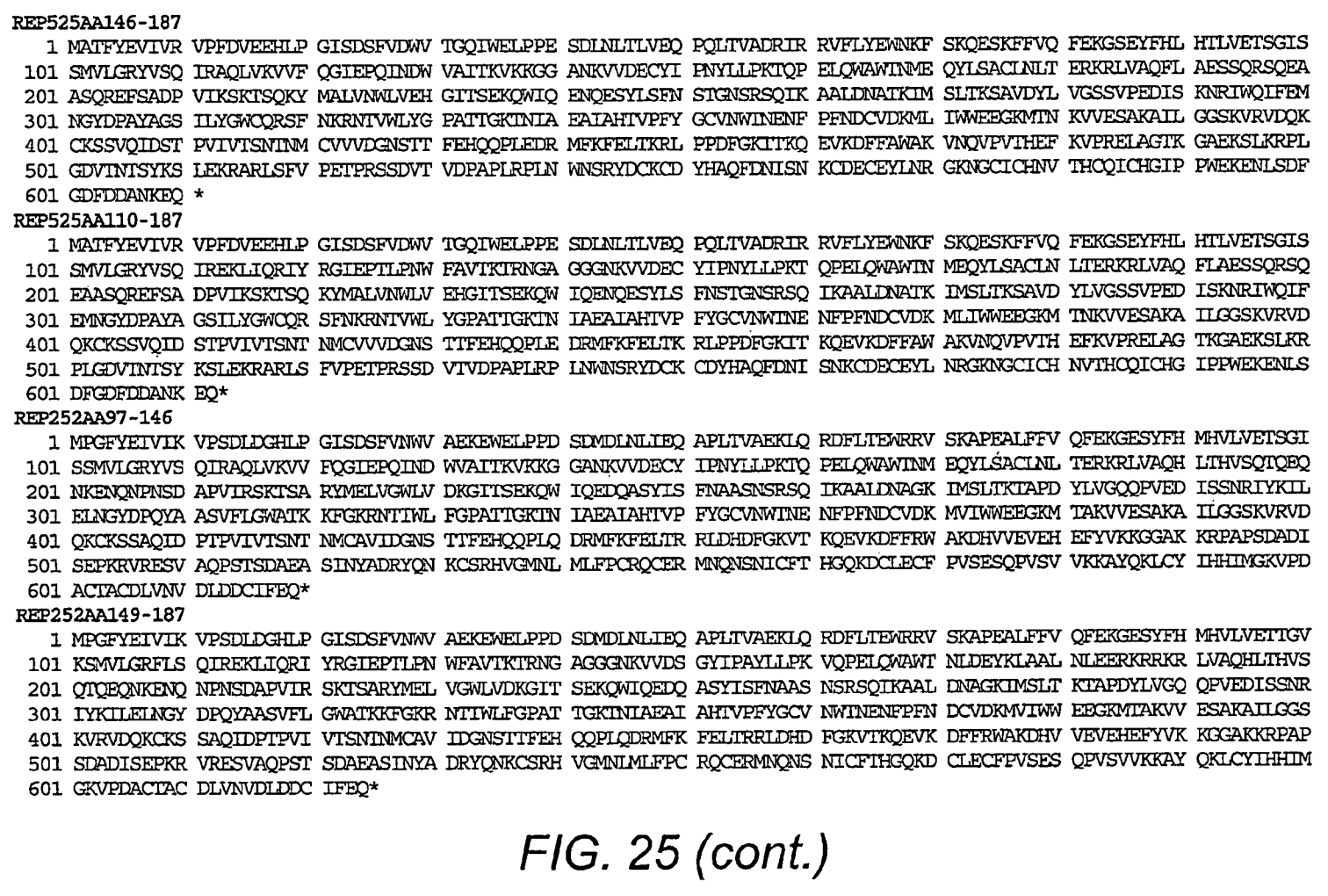
Figures 25, 26:
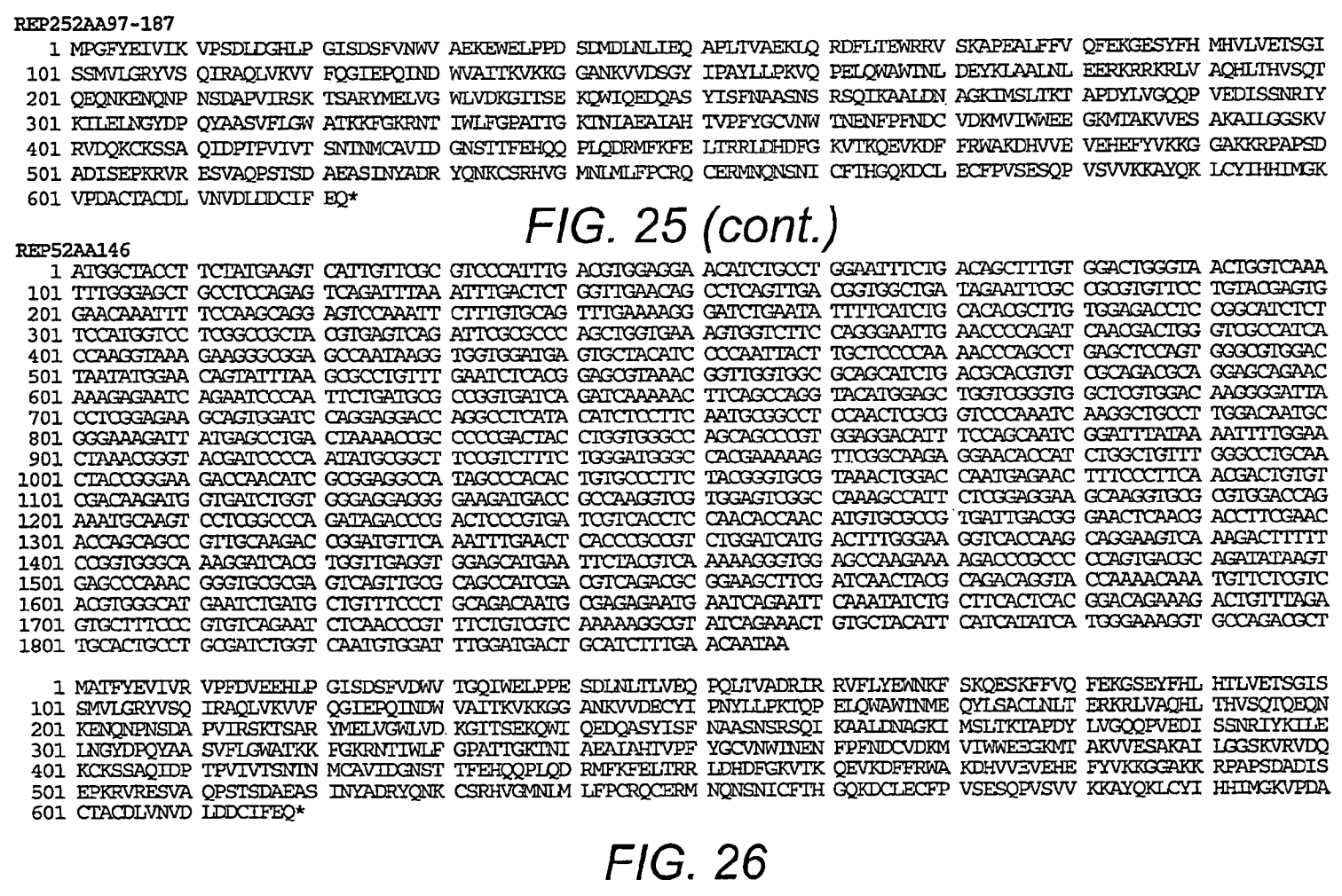

FIG. 25 provides an exemplary listing of the chimeric Rep proteins that were synthesized as part of the Examples described below: Rep52aa73 (SEQ ID NO:53), Rep52aa84 (SEQ ID NO:54), Rep52aa110 (SEQ ID NO:55), Rep52aa126 (SEQ ID NO:56), Rep52aa138 (SEQ ID NO:57), Rep52aa160 (SEQ ID NO:58), Rep52aa175 (SEQ ID NO:59), Rep52aa187 (SEQ ID NO:60), Rep52aa207 (SEQ ID NO:61), Rep25aa73 (SEQ ID NO:62), Rep25aa77 (SEQ ID NO:63), Rep25aa97 (SEQ ID NO:64), Rep25aa116 (SEQ ID NO:65), Rep25aa125 (SEQ ID NO:66), Rep25aa141 (SEQ ID NO:67), Rep25aa149 (SEQ ID NO:68), Rep25aa166 (SEQ ID NO:69), Rep25aa187 (SEQ ID NO:70), Rep25aa216 (SEQ ID NO:71), Rep525aa110-148 (SEQ ID NO:72), Rep525aa146-187 (SEQ ID NO:73), Rep525aa110-187 (SEQ ID NO:74), Rep252aa97-146 (SEQ ID NO:75), Rep252aa149-187 (SEQ ID NO:76), and Rep252aa97-187 (SEQ ID NO:77).

FIG. 26 shows both the nucleotide and amino acid sequences of a chimeric Rep protein of the invention: Rep52aa146 (SEQ ID NO:78 and SEQ ID NO:79, respectively).

FIG. 27 shows both the nucleotide and amino acid sequences of a chimeric Rep protein of the invention: Rep52aa147 (SEQ ID NO:80 and SEQ ID NO:81, respectively).

FIG. 28 shows both the nucleotide and amino acid sequences of a chimeric Rep protein of the invention: Rep52aa151 (SEQ ID NO:82 and SEQ ID NO:83, respectively).

FIG. 29 shows an alignment of the amino acid sequences of exemplary Rep40 proteins from AAV1 (SEQ ID NO:84), AAV2 (SEQ ID NO:85), AAV3A (SEQ ID NO:86), AAV3B (SEQ ID NO:87), AAV4 (SEQ ID NO:88), AAV5 (SEQ ID NO:89), AAV6 (SEQ ID NO:90), AAV7 (SEQ ID NO:91) and AAV8 (SEQ ID NO:92), as well as a consensus sequence (SEQ ID NO:93). Dashes indicate gaps in the sequence and shading indicates positions of sequence homology.

FIG. 31 shows an alignment of the amino acid sequences of exemplary Rep68 proteins from AAV1 (SEQ ID NO:104), AAV2 (SEQ ID NO:105), AAV3A (SEQ ID NO:106), AAV3B (SEQ ID NO:107), AAV4 (SEQ ID NO:108), AAV5 (SEQ ID NO:109), AAV6 (SEQ ID NO:110), AAV7 (SEQ ID NO:111) and AAV8 (SEQ ID NO:112). Dashes indicate gaps in the sequence and shading indicates positions of sequence homology.

FIG. 32 shows an alignment of the amino acid sequences of exemplary Rep78 proteins from AAV1 (SEQ ID NO:113), AAV2 (SEQ ID NO:114), AAV3A (SEQ ID NO:115), AAV3B (SEQ ID NO:116), AAV4 (SEQ ID NO:117), AAV5 (SEQ ID NO:118), AAV6 (SEQ ID NO:119), AAV7 (SEQ ID NO:120) and AAV8 (SEQ ID NO:121), as well as a consensus sequence (SEQ ID NO:122). Dashes indicate gaps in the sequence and shading indicates positions of sequence homology.

FIG. 33 shows the nucleotide sequence of the snake ITR utilized in Example 9 (SEQ ID NO:123).

FIG. 34 shows the nucleotide sequence of the snake ITR eGFP vector plasmid (SEQ ID NO:124) used to synthesize the snake vector described in Example 9.

FIG. 35 shows the nucleotide sequence of the pSnRepCap2 plasmid (SEQ ID NO:125) used to synthesize the snake vector described in Example 9.

DETAILED DESCRIPTION OF THE INVENTION

Figure 1A:
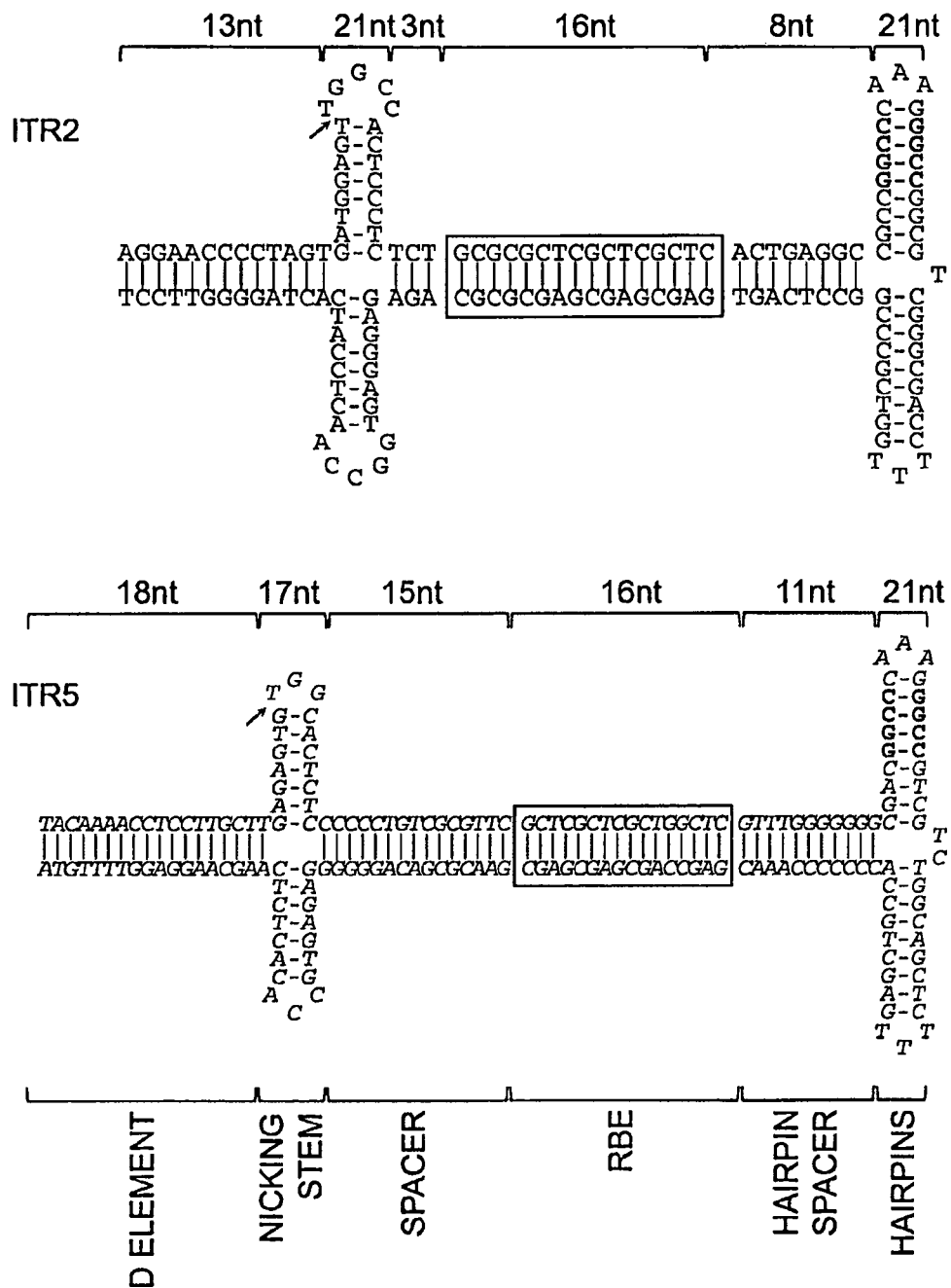
FIGS. 1A-1B show the cloning and characterization of chimeric ITRs. (A) Sequence and structure of ITR2 (SEQ ID NO:17) (black) and ITR5 (SEQ ID NO:18) (blue) shown with incorporation of SfiI sites for cloning (green). Length in nt of ITR elements indicated above brackets. RBE is boxed. RBE' is indicated by a hatched circle. Nicking stem is extruded with arrow indicating the nicking site and hatched box indicating the trs. The four initial chimeric ITRs generated (SEQ ID NOS:19-22) are shown (right). (B) Replication assay and quantitation of chimeric Reps. Replication products from the indicated ITR and either Rep2 or Rep5 were analyzed by Southern blot. Monomeric (m) and dimeric (d) replicating species are indicated. The level of replication of each sample was measured by densitometric analysis and compared to wt replication.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage. See, e.g., *Patent In User Manual*, 99-102 (November 1990) (U.S. Patent and Trademark Office).

Except as otherwise indicated, standard methods known to those skilled in the art may be used for the construction of recombinant parvovirus and rAAV constructs, packaging vectors expressing the parvovirus Rep and/or Cap sequences, and transiently and stably transfected packaging cells. Such techniques are known to those skilled in the art. See, e.g., SAMBROOK et al. MOLECULAR CLONING: A LABORATORY MANUAL 2nd Ed. (Cold Spring Harbor, N.Y., 1989); AUSUBEL et al. CURRENT PROTOCOLS IN MOLECULAR BIOLOGY (Green Publishing Associates, Inc. and John Wiley & Sons, Inc., New York).

DEFINITIONS

The following terms are used in the description herein and the appended claims:

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). See, in re Herz, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panlcukopenia virus, feline parvovirus, goose parvovirus, HI parvovirus, muscovy duck parvovirus, snake parvovirus, and B19 virus (See, e.g., FIGS. 20-23). Other autonomous parvoviruses are known to those skilled in the art. See, e.g., FIELDS et al. VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIGS. 8-19; FIELDS et al. VIROLOGY, volume 2, chapter 69 (4th ed., Lippincott-Raven Publishers); and Table 1.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al. VIROLOGY, volume 2, chapter 69 (4th ed., Lippincott-Raven Publishers). A number of relatively new AAV serotypes and clades have been identified (See, e.g., Gao et al. (2004) *J. Virol.* 78:6381; Moris et al. (2004) *Virol.* 33-:375; and Table 1).

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., FIGS. 8-23; GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, 302275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al. (1999) *J. Virol.* 73: 939; Chiorini et al. (1997) *J. Virol.* 71:6823; Chiorini et al. (1999) *J. Virol.* 73:1309; Gao et al. (2002) *Proc. Nat. Acad. Sci. USA* 99:11854; Moris et al. (2004) *Virol.* 33-:375-383; Mori et al. (2004) *Virol.* 330:375; Muramatsu et al. (1996) *Virol.* 221: 208; Ruffing et al. (1994) *J. Gen. Virol.* 75:3385; Rutledge et al. (1998) *J. Virol.* 72:309; Schmidt et al. (2008) *J. Virol.* 82:8911; Shade et al., (1986) *J. Virol.* 58:921; Srivastava et al. (1983) *J. Virol.* 45:555; Xiao et al. (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" or "infection" of a cell by a parvovirus or AAV means that the parvovirus/AAV enters the cell to establish an active (i.e., lytic) infection. As used herein, "transduction" of a cell by AAV means that the AAV enters the cell to establish a latent infection. See, e.g., FIELDS et al. VIROLOGY, volume 2, chapter 69 (3d ed., Lippincott-Raven Publishers).

TABLE 1

| Complete Genomes | GenBank Accession Number |
|---|---|
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |

TABLE 1-continued

| Complete Genomes | GenBank Accession Number |
|---|---|
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |

TABLE 1-continued

| Complete Genomes | GenBank Accession Number |
|---|---|
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, PASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease Or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) Curr. Topics Microbiol. Immunol. 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al. FIG. 24 provides examples of synthetic ITRs contemplated by the present invention.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al. VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) Mol. Therapy 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 2

| Amino Acid Residue | Abbreviation | |
| --- | --- | --- |
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

Further, the non-naturally occurring amino acid can be an "unnatural" amino acid as described by Wang et al. (2006) *Annu. Rev. Biophys. Biomol. Struct.* 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

TABLE 3

| Modified Amino Acid Residue | Abbreviation |
| --- | --- |
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |

TABLE 3-continued

| Modified Amino Acid Residue | Abbreviation |
| --- | --- |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al. VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the term "synthetic large Rep protein" refers to a large Rep protein having an amino acid sequence that differs from a wild-type large Rep protein sequence. The sequence of the synthetic large Rep protein may differ from a wild-type sequence due to one or more deletions, additions, substitutions, or any combination thereof. The difference between the synthetic and wild-type sequences may be as little as a single amino acid change, e.g., a change in 1, 2, 3, 4, 5, 6, 7, 8, 9, 10, 15, 20, 25, 30, 35, 40, 45, 60, 60, 70, 80, 90, 100, 125, 150, 175, 200, 225, 250, 275, 300, 325, 350, 375, 400. 425, 450, 475, 500, 525, 550, 575, or 600 or more amino acids or any range therein. In certain embodiments, the synthetic large Rep protein is a chimeric Rep protein comprising portions of the wild-type sequence of two or more different large Rep proteins. In other embodiments, the synthetic large Rep protein is a chimeric Rep protein comprising portions of the wild-type sequence of two or more different large Rep proteins, one or more portions of which have been modified from the wild-type sequence.

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

As used herein, the term "structural element," when used with respect to a parvovirus ITR, refers to a portion of the ITR that, based on nucleotide sequence, secondary structure, or both, plays a role in the functional interaction of a large Rep protein with the ITR, e.g., a portion that, when removed from the ITR, prevents functional interaction with a large Rep protein. In some embodiments, the structural element physically interacts with the large Rep protein.

As used herein, the term "functionally interacts" refers to an interaction between an ITR and a large Rep protein (e.g., binding) that ultimately results in nicking of the ITR and replication of a polynucleotide in which the ITR is present.

As used herein, the term "nicking stem" refers to a hairpin loop structure present in a parvovirus ITR that is nicked by a large Rep protein during replication of a polynucleotide in which the ITR is present.

As used herein, the term "extended RBE" refers to the nucleotide sequence of a parvovirus ITR between the nicking stem and the RBE (the spacer sequence as shown in FIG. 1A) which, in certain parvoviruses (e.g., AAV5), functions as an extension of the RBE (i.e., is recognized and bound by a large Rep protein). The term "extended RBE" is only applicable to the spacer sequence when the sequence functions as an extension of the RBE.

Modified Parvovirus ITRs

The present invention provides modified parvovirus ITRs and synthetic Rep proteins that functionally interact with the modified ITRs. The modified ITRs are unique in that they do not functionally interact with wild-type Rep proteins and may reduce or avoid vector mobilization.

One aspect of the invention relates to a polynucleotide comprising at least one parvovirus ITR, wherein the ITR comprises: (a) a first structural element that functionally interacts with a large Rep protein from a AAV but does not functionally interact with a large Rep protein from a second AAV; and (b) a second structural element that functionally interacts with the large Rep protein from the second AAV but does not functionally interact with the large Rep protein from the first AAV; wherein the ITR functionally interacts with a synthetic AAV large Rep protein. In one embodiment, the ITR does not functionally interact with any wild-type large Rep protein, e.g., AAV2 Rep, AAV5 Rep, or any other known Rep protein. In particular embodiments, the synthetic large Rep protein comprises an amino acid sequence selected from the group consisting of SEQ ID NOS:79, 81, and 83 or an amino acid sequence having at least 80% identity to one of SEQ ID NOS: 79, 81, and 83, e.g., at least 85%, 90%, 95%, 96%, 97%, 98%, or 99% identity. In one embodiment, the ITR further comprises a third structural element that functionally interacts with a large Rep protein from an AAV that is the same as or different from the first and/or second AAV.

In one embodiment of the invention, the parvovirus ITR is from an autonomous parvovirus. In another embodiment, the parvovirus ITR is from an AAV, e.g., an AAV selected from the group consisting of AAV1, AAV2, AAV3, AAV4, AAV5, AAV6, AAV7, AAV8, AAV9, AAV10, AAV11, AAV12, and AAV 13. In a further embodiment, the parvovirus ITR is from a non-human AAV such as snake AAV, avian AAV, bovine AAV, canine AAV, equine AAV, ovine AAV, goat AAV, or shrimp AAV.

The structural element of the ITR can be any structural element that is involved in the functional interaction of the ITR with a large Rep protein. In certain embodiments, the structural element provides selectivity to the interaction of an ITR with a large Rep protein, i.e., determines at least in part which Rep protein functionally interacts with the ITR. In other embodiments, the structural element physically interacts with a large Rep protein when the Rep protein is bound to the ITR. Each structural element can be, e.g., a secondary structure of the ITR, a nucleotide sequence of the ITR, a spacing between two or more elements, or a combination of any of the above. In one embodiment, the structural elements are selected from the group consisting of a nicking stem, a spacer, a RBE, an extended RBE, and any combination thereof. In a particular embodiment, the first structural element is a nicking stem. In another embodiment, the second structural element is a RBE. In a further embodiment, the second structural element is an extended RBE. In an additional embodiment, the second structural element is a spacer.

The ability of a structural element to functionally interact with a particular large Rep protein can be altered by modifying the structural element. For example, the nucleotide sequence of the structural element can be modified as compared to the wild-type sequence of the ITR. In one embodiment, the structural element (e.g., the nicking stem, spacer, RBE, and/or extended RBE) of an ITR can be removed and replaced with a wild-type structural element from a different parvovirus. For example, the replacement structure can be from AAV1, AAV2, AAV3, AAV4, AAV5, AAV6, AAV7, AAV8, AAV9, AAV10, AAV11, AAV12, AAV13, snake parvovirus (e.g., royal python parvovirus), bovine parvovirus, goat parvovirus, avian parvovirus, canine parvovirus, equine parvovirus, shrimp parvovirus, porcine parvovirus, or insect AAV. For example, the ITR can be an AAV2 ITR and the nicking stem or RBE can be replaced with a structural element from AAV5. In another example, the ITR can be an AAV5 ITR and the nicking stem, RBE, or extended RBE can be replaced with a structural element from AAV2. In one example, the ITR can be an AAV2 ITR with the nicking stem replaced with the AAV5 ITR nicking stem, e.g., the ITR of SEQ ID NO:22 or a modified sequence thereof. In another example, the AAV ITR can be an AAV5 ITR with the nicking stem replaced with the AAV2 ITR nicking stem, e.g., the ITR of SEQ ID NO:21 or a modified sequence thereof.

In one embodiment, the nucleotide sequence of the structural element can be modified (e.g., by modifying 1, 2, 3, 4, 5, 6, 7, 8, 9, 10, 11, 12, 13, 14, 15, 16, 17, 18, 19, or 20 or more nucleotides or any range therein) to produce a synthetic structural element. In certain embodiments, the specific ITRs exemplified herein (SEQ ID NOS:17-52) can be modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the ITR can have at least 80% identity with one of the ITRs of SEQ ID NOS:17-52, e.g., at least 85%, 90%, 95%, 96%, 97%, 98%, or 99% identity. In one embodiment, the structural element is a nicking stem and the modified sequence is a modified terminal resolution site (trs) sequence. For example, a nicking stem can be modified to comprise the ITR2 trs (GGT/TGG) or the ITR5 trs (AGTG/TGG). In another embodiment, the structural element is a RBE or an extended RBE and the sequence is a modified at the nucleotides responsible for binding specificity. For example, the sequence of a RBE or an extended RBE can be modified to make the sequence closer to or further from the consensus GAGY binding sites recognized by Rep. In one example, the spacer or extended RBE can be modified to comprise one or more exact GAGY repeats (e.g., the of SEQ ID NO:39 or a modified sequence thereof), e.g., 1, 2, 3, or 4 or more exact GAGY repeats.

In a different embodiment, the structure of the structural element can be modified. For example, the structural element can be a nicking stem and the modification can be a change in the height of the stem and/or the number of nucleotides in the loop. For example, the height of the stem can be about 2, 3, 4, 5, 6, 7, 8, or 9 nucleotides or more or any range therein. In one embodiment, the nicking stem height can be about 5 nucleotides to about 9 nucleotides and functionally interacts with Rep2. In another embodiment, the nicking stem height can be about 7 nucleotides and functionally interacts with Rep5. In another example, the loop can have 3, 4, 5, 6, 7, 8, 9, or 10 nucleotides or more or any range therein. In another example, the structural element can be a RBE or an extended RBE and the number of GAGY binding sites or GAGY-related binding sites within the RBE or extended RBE can be increased or decreased. In one example, the RBE or extended RBE can comprise 1, 2, 3, 4, 5, or 6 or more GAGY binding sites or any range therein. Each GAGY binding site can independently be an exact GAGY sequence or a sequence similar to GAGY as long as the sequence is sufficient to bind a Rep protein.

In another embodiment, the spacing between two elements (such as the nicking stem and the RBE or the RBE and a hairpin) can be altered (e.g., increased or decreased) to alter functional interaction with a large Rep protein. For example, the spacing can be about 1, 2, 3, 4, 5, 6, 7, 8, 9, 10, 11, 12, 13, 14, 15, 16, 17, 18, 19, 20, or 21 nucleotides or more or any range therein. In one embodiment, the spacer between the nicking stem and the RBE is about 3 nucleotides in length and functionally interacts with Rep2. In another embodiment, the spacer between the nicking stem and the RBE is about 3 nucleotides (e.g., the ITR of SEQ ID NO:34 or a modified sequence thereof) to about 21 nucleotides in length (e.g., the ITR of SEQ ID NO:37 or a modified sequence thereof) and functionally interacts with Rep5. In one embodiment, the spacer is the 15 nucleotide spacer of the AAV5 ITR or a sequence having at least 80% identity thereto, e.g., at least 85%, 90%, 95%, 96%, 97%, 98%, or 99% identity.

In a representative embodiment, the polynucleotide comprises at least one parvovirus ITR, wherein said ITR comprises: (a) a first structural element that functionally interacts with a large Rep protein from one or more of AAV1, AAV2, AAV3, AAV4, AAV6, AAV7, AAV8, AAV9, AAV10, AAV 11, AAV12, and AAV13 but does not functionally interact with a large Rep protein from AAV5; and (b) a second structural element that functionally interacts with the large Rep protein from AAV5 but does not functionally interact with the large Rep protein from one or more of AAV1, AAV2, AAV3, AAV4, AAV6, AAV7, AAV8, AAV9, AAV10, AAV 11, AAV12, and AAV13; wherein the ITR functionally interacts with a synthetic AAV large Rep protein comprising an amino acid sequence selected from SEQ ID NOS: 79, 81, and 83.

In one aspect of the invention the polynucleotide comprising the modified ITR of the invention further comprises a second ITR which may be the same as or different from the first ITR. In one embodiment, the polynucleotide further comprises a heterologous nucleic acid, e.g., a sequence encoding a protein or a functional RNA. In some embodiments, the second ITR cannot be resolved by the Rep protein, i.e., resulting in a double stranded viral DNA.

The invention also provides a viral vector comprising the polynucleotide comprising the modified ITR of the invention. The viral vector can be a parvovirus vector, e.g., an AAV vector. The invention further provides a recombinant parvovirus particle (e.g., a recombinant AAV particle) comprising the modified ITR of the invention. Viral vectors and viral particles are discussed further below.

Synthetic Rep Proteins

One aspect of the invention relates to synthetic large Rep proteins that functionally interact with the modified ITRs of the invention. Thus, in one aspect, the invention relates to a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV but does not functionally interact with a large Rep protein from a second AAV and said second structural element functionally interacts with a large Rep protein from a second AAV but does not functionally interact with a large Rep protein from the first AAV. In one embodiment, the protein comprises a third portion that functionally interacts with a third structural element that functionally interacts with a large Rep protein from an AAV that is the same as or different from the first and/or second AAV. In one embodiment, the first structural element is a nicking stem and the first portion of the synthetic large Rep protein functional interacts with the nicking stem. In another embodiment, the second structural element is a spacer, RBE, or extended RBE and the second portion of the synthetic large Rep protein functional interacts with the spacer, RBE, or extended RBE.

In one embodiment, one or more portions of the synthetic large Rep protein comprise a wild-type amino acid sequence from a parvovirus Rep protein. In another embodiment, one or more portions of the synthetic large Rep protein comprise an amino acid sequence that is modified as compared to the wild-type sequence of a parvovirus Rep protein. The modification can be an addition, deletion, substitution, or any combination thereof. The synthetic large Rep protein can comprise one or more modified amino acids, e.g., about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 150, 175, 200, 225, 250, 275, 300, 325, 350, 375, 400, 425, 450, 475, 500, 525, 550, 575, or 600 or more amino acids or any range therein.

In one embodiment of the invention, the first and second portions (and/or the third portion) are directly linked to each other. In another embodiment, the portions are connected by a linker, e.g., 1, 2, 3, 4, 5, or 6 or more amino acids. The synthetic large Rep protein can comprise further portions (e.g., from Rep or another protein or synthetic sequences) that are not involved in the functional interaction with an ITR. Examples of other sequences can include, without limitation, localization signals, tags for improved isolation, etc.

In one embodiment, the first portion of the synthetic large Rep protein comprises, consists essentially of, or consists of an amino acid sequence from about residue 97 to about residues 146-151 of a wild-type AAV5 Rep sequence, e.g., SEQ ID NO:118. For example the first portion can comprise, consist essentially of or consist of an amino acid sequence from about residue 1, 5, 10, 15, 20, 25, 30, 35, 40, 45, 50, 55, 60, 65, 70, 75, 80, 85, 90, or 95 to about residue 146, 147, 148, 149, 151, or 151 of a wild-type AAV5 Rep sequence or any range therein. In certain embodiments, the first portion comprises, consists essentially of, or consists of an amino acid sequence having at least 80% identity to a sequence from about residue 97 to about residues 146451 of a wild-type AAV5 Rep sequence, e.g., at least 85%, 90%, 95%, 96%, 97%, 98%, or 99% identity.

In one embodiment, the second portion of the synthetic large Rep protein comprises, consists essentially of or consists of an amino acid sequence from about residue 149 to about residue 187 of a wild-type AAV2 Rep sequence, e.g., SEQ ID NO:114. For example, the second portion can comprise, consist essentially of, or consist of an amino acid sequence from about residue 149 to about residue 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, or 620 of a wild-type AAV2 Rep sequence or any range therein. In certain embodiments, the second portion comprises, consists essentially of, or consists of an amino acid sequence having at least 80% identity to a sequence from about residue 149 to about residue 187 of a wild-type AAV5 Rep sequence, e.g., at least 85%, 90%, 95%, 96%, 97%, 98%, or 99% identity.

In a representative embodiment of the synthetic large Rep protein, the first portion comprises, consists essentially of, or consists of an amino acid sequence from about residue 97 to about residues 146-151 of a wild-type AAV5 Rep sequence and the second portion comprises, consists essentially of, or consists of an amino acid sequence from about residue 149 to about residue 187 of a wild-type AAV2 Rep sequence. In another representative embodiment, the first portion comprises, consists essentially of, or consists of an amino acid sequence from about residue 1 to about residues 146-151 of a wild-type AAV5 Rep sequence and the second portion comprises, consists essentially of, or consists of an amino acid sequence from about residue 149 to about residue 621 of a wild-type AAV2 Rep sequence. In certain embodiments, the synthetic large Rep protein comprises, consists essentially of, or consists of an amino acid sequence of SEQ ID NOS: 79, 81, and 83. In other embodiments, the synthetic large Rep protein comprises, consists essentially of, or consists of an amino acid sequence having at least 80% identity to an amino acid sequence of SEQ ID NOS: 79, 81, and 83, e.g., at least 85%, 90%, 95%, 96%, 97%, 98%, or 99% identity.

Figure 32:
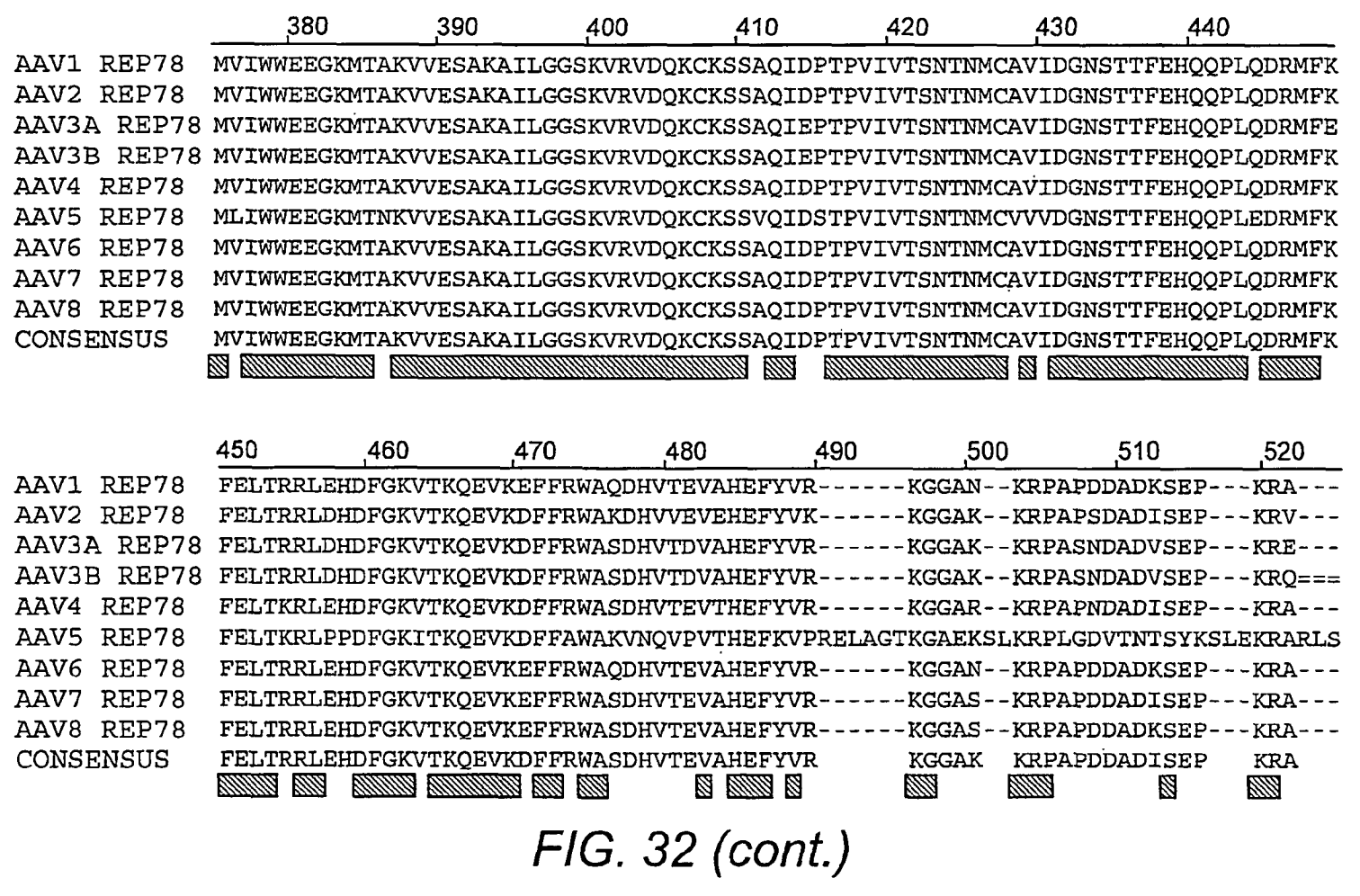

In certain embodiments, the portion of the synthetic large Rep protein from a wild-type AAV2 Rep sequence as described above can be replaced with the corresponding portion from another human AAV serotype Rep protein other than AAV5, e.g., AAV1, AAV3, AAV4, AAV6, AAV7, AAV8, AAV9, AAV10, AAV11, AAV12, or AAV13. The structural and functional similarity between the Rep proteins of AAV2 and other human serotypes (with the exception of AAV5) may allow substitution of Rep sequences between the serotypes (see FIGS. 31 and 32).

In certain embodiments, one or more of the portions the synthetic Rep proteins can be modified to differ from the wild-type sequence (e.g., by modifying 1, 2, 3, 4, 5, 6, 7, 8, 9, 10, 11, 12, 13, 14, 15, 16, 17, 18, 19, or 20 or more aa or any range therein). In other embodiments, the synthetic Rep proteins exemplified herein can be modified (e.g., by modifying 1, 2, 3, 4, 5, 6, 7, 8, 9, 10, 11, 12, 13, 14, 15, 16, 17, 18, 19, or 20 or more aa or any range therein). In some embodiments, the modified synthetic Rep proteins retain amino acid Y156 (numbering according to Rep2). In other embodiments, modified synthetic Rep proteins retain amino acids C151, N155, and/or T161 (numbering according to Rep2). In other embodiments, modified synthetic Rep proteins retain amino acids G148, A152, and/or V158 (numbering according to Rep5). These specific amino acids may be important for activity and/or specificity.

The invention also provides polynucleotides (optionally, isolated polynucleotides) encoding the synthetic Rep proteins of the invention. In some embodiments, the polynucleotides further encode one or more parvovirus Cap proteins. Further provided are vectors comprising the polynucleotides, and cells (in vivo or in culture) comprising the polynucleotides and/or vectors of the invention. Suitable vectors include, without limitation, viral vectors (e.g., adenovirus, AAV, herpesvirus, vaccinia, poxviruses, baculoviruses, Epstein-Barr virus, and the like), plasmids, phage, YACs, BACs, and the like. In some embodiments, the polynucleotide is stably integrated into the genome of a cell. Such polynucleotides, vectors and cells can be used, for example, as reagents (e.g., helper packaging constructs or packaging cells) for the production of virus vectors as described herein.

Snake AAV ITRs

One aspect of the invention relates to the discovery that a snake AAV ITR sequence can function as a part of a parvovirus vector yet is not recognized by the Rep proteins of mammalian (e.g., human or primate) parvoviruses. Vector mobilization may therefore be reduced or avoided. Thus, one aspect of the invention relates to a parvovirus template comprising (i) a heterologous nucleotide sequence, and (ii) at least one snake AAV ITR sequence. The snake AAV ITR sequence can be from a royal python AAV. In one embodiment, the snake AAV ITR sequence comprises the nucleotide sequence of SEQ ID NO:123. In a further embodiment, the snake AAV ITR sequence comprises the nucleotide sequence of SEQ ID NO:123 that has been modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the parvovirus template comprises at least a portion of a snake AAV ITR, e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, or 150 or more contiguous nucleotides of a snake AAV ITR or any range therein. In certain embodiments, the parvovirus template comprises two snake AAV ITR sequences.

The invention further relates to a parvovirus particle comprising the snake parvovirus template of the invention. In certain embodiments, the parvovirus particle comprises a mammalian capsid, e.g., a human or primate capsid.

In one aspect, the invention relates to the discovery of methods for producing parvovirus particles comprising a snake AAV ITR, including the requirement for a mammalian small Rep protein. Thus, one aspect of the invention relates to a method of producing a parvovirus particle, comprising providing to a cell (e.g., a mammalian cell such as a human or primate cell) permissive for parvovirus replication: (a) a recombinant parvovirus template comprising (i) a heterologous nucleotide sequence, and (ii) at least one snake AAV ITR sequence; (b) a polynucleotide encoding one or more snake AAV Rep proteins and mammalian AAV Cap protein(s); and (c) a polynucleotide encoding mammalian Rep52 and/or Rep40 proteins; under conditions sufficient for the replication and packaging of the recombinant parvovirus template; whereby recombinant parvovirus particles packaging the recombinant parvovirus template are produced in the cell. In one embodiment, the mammalian AAV Cap protein is a human or primate AAV Cap protein. In another embodiment, the mammalian AAV Rep 52 and/or Rep 40 proteins are human or primate Rep52 and/or Rep40 proteins (including modified forms thereof), e.g., from AAV2. In some embodiments, the polynucleotide encoding snake AAV Rep protein and mammalian AAV Cap protein also encodes the mammalian Rep52 and/or Rep40 proteins. In other embodiments, the polynucleotide encoding snake AAV Rep protein and mammalian AAV Cap protein is separate from the polynucleotide encoding the mammalian Rep52 and/or Rep40 proteins. In some embodiments, the polynucleotide encoding snake AAV Rep protein and mammalian AAV Cap protein is the plasmid pSnRepCap2 (SEQ ID NO:125).

In other embodiments, other non-human AAV ITR sequences not recognized by the Rep proteins of human or primate parvoviruses may be used. Examples include, without limitation, sequences from shrimp, insect, goat, bovine, equine, canine, and equine AAVs.

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) a heterologous nucleotide sequence, and (ii) the modified parvovirus ITR of the invention; (b) a polynucleotide encoding a synthetic large Rep protein of the invention; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

The cell can be a cell that is permissive for parvovirus viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into parvovirus virions, e.g., are not flanked by TRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one non-limiting illustration, the helper construct can be a hybrid adenovirus or hybrid herpesvirus comprising the parvovirus rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the parvovirus template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by TRs so that these sequences are not packaged into the parvovirus virions.

Zhang et al., ((2001) *Gene Ther.* 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and parvovirus template as described, for example, by Urabe et al., (2002) *Human Gene Ther.* 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses), immunogenic (e.g., for vaccines), or diagnostic polypeptides.

Therapeutic polypeptides include, but are not limited to, cystic fibrosis transmembrane regulator protein (CFTR), dystrophin (including mini- and micro-dystrophins (see, e.g., Vincent et al., (1993) *Nature Genetics* 5:130; U.S. Patent Publication No. 2003/017131; International publication WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor −3 and −4, brain-derived neurotrophic factor, bone morphogenic proteins [including RANKL and VEGF], glial derived growth factor, transforming growth factor −α and −β, and the like), lysosomal acid α-glucosidase, α-galactosidase A, receptors (e.g., the tumor necrosis growth factory soluble receptor), S100A1, parvalbumin, adenylyl cyclase type 6, a molecule that effects G-protein coupled receptor kinase type 2 knockdown such as a truncated constitutively active bARKet, anti-inflammatory factors such as TRAP, anti-myostatin proteins, aspartoacylase, and monoclonal antibodies (including single chain monoclonal antibodies; an exemplary Mab is the Herceptin® Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof.

Parvovirus vectors can also be used to deliver monoclonal antibodies and antibody fragments, for example, an antibody or antibody fragment directed against myostatin (see, e.g., Fang et al., *Nature Biotechnol.* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech* 17:246; U.S. Pat. No. 6,013,487; U.S. Pat. No. 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), RNAi to a sarcoglycan [e.g., α, β, γ], RNAi against myostatin, myostatin propeptide, follistatin, or activin type II soluble receptor, RNAi against anti-inflammatory polypeptides such as the Ikappa B dominant mutant, and RNAi directed against pathogenic organisms and viruses (e.g., hepatitis B virus, human immunodeficiency virus, CMV, herpes simplex virus, human papilloma virus, etc.).

Alternatively, in particular embodiments of this invention, the heterologous nucleic acid may encode protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, enos, inos, or bone morphogenic proteins (including BNP 2, 7, etc., RANKL and/or VEGF).

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Set USA* 91:8507; U.S. Pat. No. 5,916,563 to Young et al., U.S. Pat. No. 5,905,040 to Mazzara et al., U.S. Pat. No. 5,882,652, U.S. Pat. No. 5,863,541 to Samulski et al). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or Sly envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et at, (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178:489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins;

prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex viva, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), serca2a, zinc finger proteins that regulate the phospholamban gene, Barka, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

Virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid as described above.

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), blood vessel cells (e.g., endothelial cells, intimal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, kidney cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above), The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

Administration can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis earls, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent muscular dystrophy or heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes (e.g., insulin), hemophilia (e.g., Factor IX or Factor VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating and/or preventing metabolic disorders are described above. The use of muscle as a platform to express a nucleic acid of interest is described in U.S. Patent Publication No. 2002/0192189.

Thus, as one aspect, the invention further encompasses a method of treating and/or preventing a metabolic disorder in a subject in need thereof, the method comprising: administering a treatment or prevention effective amount of a virus vector of the invention to a subject (e.g., to skeletal muscle of a subject), wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mix-1, mir-133, mir-206 and/or mir-208.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 2004-0013645).

The virus vectors disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are as known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and periocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

Example 1

Materials and Methods

Rep Cloning— pXR2 (Rep2Cap2) and pRep5Cap2 AAV helper plasmids served as templates for Rep cloning. The primer sequences used are indicated in Table 4. Two cloning strategies were used. Existing restriction sites were incorporated into primers for PCR (PCR-RD in Table 4) utilizing either pXR out fw or pXR out rev primers. PfuTurbo DNA Polyrnerase (Stratagene, La Jolla, Calif.) was used at the manufacturer's recommendations for all PCR reactions. PCR-RD products were digested with the enzymes indicated in Table 4 (NEB, Ipswich, Mass.) prior to ligation with T4 DNA Ligase (Invitrogen, Carlsbad, Calif.) according to the manufacturer's instructions. Alternately, an overlap-extension mediated PCR (OE-PCR) approach was used to produce Rep chimeras (Higuchi et al. (1988) *Nucleic Acids Res.* 16:7351). The Rep2 and Rep5 junction was incorporated into forward and reverse primers which were used in separate PCR reactions with the pXR out fw and rev primers (Table 4, only fw oligos indicated, rev oligos complimentary to fw). These overlapping PCR products were combined into a single PCR reaction and cycled as follows: 1 cycle at 94° C. for 30 seconds, 18 cycles of 30 seconds at 94° C., 30 seconds at 65° C., and 4 minutes at 72° C., 1 cycle of 10 minutes at 72° C. 1 µl of this reaction was used as template for a nested PCR with the pXR in fw and rev primers. Chimeras with the N-terminus of Rep2 and C-terminus of Rep5 were cloned into the Rep25aa166 construct between the PpuMI and MfeI sites. Chimeras with the N-terminus of Rep5 and C-terminus of Rep2 were cloned into the 52aa160 construct between the PpuMI and BstBI sites. All constructs were verified by DNA sequencing at the UNC-CH Genome Analysis Facility.

TABLE 4

| Clone/Primer | Coning Method | Orientation | Sequence | SEQ ID NO |
|---|---|---|---|---|
| pXR out fw | | Forward | 5' CGAAAAGTGCCACCTGACGTCTAAGAAACC | 126 |
| pXR in fw | | Forward | 5' TCGAATTCGACGGCCAGTGAATTGTAATACGACTC | 127 |
| pXR out rev | | Reverse | 5' CCATGATTACGCCAAGCTCGGAATTAACCGCATGCGA | 128 |
| pXR in rev | | Reverse | 5' CCATGGCCGGGCCCGGATTCACC | 129 |
| Rep52aa84 | PCR-RD AleI | Reverse | 5' TTCACCCCGGTGGTTTCCACGAGCACGTGCATGTGGAAGTAGCTCTCT CCCTTTTCAAACTGCACAAAG | 130 |
| Rep52aa110 | PCR-RD EagI | Forward | 5' CCTCGGCCGCTACGTGAGTCAGATTCGCGAAAAACTGATTCAGAG | 131 |
| Rep52aa126 | OE PCR | Forward | 5' GTGGTCTTCCAGGGAATTGAACCCACTTTGCCAAACTGGTTCGCGGTC | 132 |
| Rep52aa138 | OE PCR | Forward | 5' CTGGGTCGCCATCACCAAGGTAAAGAAGGGAGGCGGGAACAAGGTGGT GGATGAG | 133 |
| Rep52aa146 | OE PCR | Forward | 5' GCGGAGCCAATAAGGTGGTGGATGAGTGCTACATCCCCAATTACTTGC TC | 134 |
| Rep52aa160 | PCR-RD Bpu101 | Reverse | 5' ACTGGAGCTCAGGTTGGACCTTCGGCAGCAGGTAG | 135 |
| Rep52aa175 | OE PCR | Forward | 5' CGTGGACAAACCTGGACGAGTATAAATTGGCCTGTTTGAATCTCACGG AGCGTAAAC | 136 |

TABLE 4-continued

| Clone/Primer | Coning Method | Orientation | Sequence | SEQ ID NO |
|---|---|---|---|---|
| Rep52aa187 | OE PCR | Forward | 5' CTGAATCTGGAGGAGCGCAAACGGTTGGTGGCGCAGCATCTGACGCAC | 137 |
| Rep52aa207 | PCR-RD SgrAI | Reverse | 5' GATCACCGGCGCATCCGAGAACTCACGCTGCGAAGC | 138 |
| Rep25aa77 | OE PCR | Forward | 5' TAAGGCCCCGGAGGCCCTTTTCTTTGTGCAGTTTGAAAAGGGATCTG | 139 |
| Rep25aa97 | OE PCR | Forward | 5' CCACATGCACGTGCTCGTGGAAACCTCCGGCATCTCTTCCATGGTCCTCG | 140 |
| Rep25aa116 | PCR-RD NruI | Forward | 5' TCAGATTCGCGAAAAACTGGTGAAAGTGGTCTTCCAGG | 141 |
| Rep25aa125 | OE PCR | Forward | 5' GAATTTACCGCGGGATCGAGCCG CAGATCAACGACTGGGTCGCCATC | 142 |
| Rep25aa141 | OE PCR | Forward | 5' GGTCACAAAGACCAGAAATGGCGCCGGCGGAGCCAATAAGGTGGTGGATTCTGG | 143 |
| Rep25aa149 | OE PCR | Forward | 5' GAGGCGGGAACAAGGTGGTGGATTCTGGGTATATTCCCGCCTACCTGC | 144 |
| Rep25aa166 | PCR-RD Bpu101 | Forward | 5' CCAGCCTGAGCTCCAGTGGGCGTGGACAAACCTG | 145 |
| Rep25aa187 | OE PCR | Forward | 5' GTTTGAATCTCACGGAGCGTAAACGGCTCGTCGCGCAGTTTCTGGCAG | 146 |
| Rep25aa216 | PCR-RD SgrAI | Forward | 5' ATGCGCCGGTGATCAAAAGCAAGACTTCCCAGAAATACATGG | 147 |
| ITR2 Half1 Kpn | | Forward | 5' ATTATAGGTACCAGGAACCCCTAGTGATG | 148 |
| ITR2 Half 1 Sfi | | Reverse | 5' TAATAGGGCCCAAAGGGCCGGG | 149 |
| ITR2 Half2 Sfi | | Forward | 5' TTAATAGGCCCTTTGGGCCGGG | 150 |
| ITR2 Half2 Hind | | Reverse | 5' TATAATAAGCTTAGGAACCCCTAGTGATGGAG | 151 |
| ITR5 Half1 Kpn | | Forward | 5' ATTATAGGTACCTACAAAACCTCCTTGCTTGAG | 152 |
| ITR5 Half1 Sfi | | Reverse | 5' TTAATAGGCCCTTTGGGCCGTCGC | 153 |
| ITR5 Half2 Sfi | | Forward | 5' TTAATAGGCCCAAAGGGCCGTCGTC | 154 |
| ITR5 Half2 Hind | | Reverse | 5' TATAATAAGCTTTACAAAACCTCCTTGCTTGAGAG | 155 |

ITR Cloning—

ITRs were cloned into a pUC-18 plasmid with a GFP cassette (CMV promoter, SV40 polyA) cloned between the KpnI and EcoRI restriction sites. The ITRs were synthesized in two halves as 4 nmol Ultramer DNA oligos (Integrated DNA Technologies, Coralville, Iowa). SfiI restriction sites were incorporated into one hairpin arm the ITR for cloning (FIG. 1A). Due to inconsistencies of the reported sequence at the tip of the ITR5 hairpins between Chiorini et al. (1999), the published GenBank sequence (accession number NC_006152), and restriction mapping, an ITR2 hairpin was utilized for the ITR5 construct (FIG. 1A). 200 pg of each oligo was amplified in a PCR reaction using the ITR primers listed in Table 4. 2.5 U of PfuTurbo DNA Polymerase (Stratagene, La Jolla, Calif.) was used to amplify each half of the ITR as follows: 1 cycle at 94° C. for 4 minutes, 35 cycles of 45 seconds at 94° C., 30 seconds at 50° C., and 30 seconds at 72° C., 1 cycle of 10 minutes at 72° C. PCR reactions were purified and subject to digestion by KpnI and SfiI or HindIII and SfiI (NEB, Ipswich, Mass.). A triple ligation with the pUC-18 GFP plasmid and each half of the ITR was performed with T4 DNA Ligase (Invitrogen, Carlsbad, Calif.) for 1.5 hours at room temperature. All constructs were verified by DNA sequencing at the UNC-CII Genome Analysis Facility after linearization of the plasmid and ablation of the ITR secondary structure by SfiI digestion.

Western Blot Analysis—

Samples for Western blot analysis were harvested 48-72 hours after transfection of Ad-helper plasmid and the appropriate AAV helper construct. Cells were washed and resuspended in 100 μl PBS prior to addition of 100 μl 2× Laemmli Sample Buffer (100 mM Tris pH 6.8, 4% SDS, 200 mM DTT, 20% glycerol, 0.1% Bromophenol Blue). Samples were briefly sonicated and boiled for 10 minutes. Samples were run on NUPAGE 4-12% Bis-Tris gels (Invitrogen, Carlsbad, Calif.) at 160 volts for 90 minutes. Protein was transferred to a Nitrocellulose membrane (Invitrogen, Carlsbad, Calif.) via a wet transfer for 60 minutes at 30 volts. Gels were blocked overnight in 10% nonfat dry milk in 1×PBS/Tween (0.05%). Detection of both Rep2 and Rep5 proteins (all four sizes) was achieved with a monoclonal Anti-Adeno-Associated Virus Rep Protein antibody (clone 259.5, American Research Products, Belmont, Mass.) at a 1:20 dilution in PBS/Tween for 60 minutes at room temperature. After washing, a secondary HRP anti-mouse antibody was added at a 1:5,000 dilution in PBS/Tween for one hour at room temperature. After washing, SuperSignal West Femto Maximum Sensitivity Substrate (Pierce, Rockford, Ill.) was added and blots were exposed to X-ray film.

Cell Culture and rAAV Production—

HEK 293 cells were obtained from ATCC and cultured in Dulbecco Modified Eagle Medium (DMEM) supplemented with 10% Fetal Bovine Serum (Sigma, St. Louis, Mo.) and 100 units/ml penicillin and 100 μg/ml streptomycin and grown at 37° C. with 5% $CO_2$ saturation. Transfections were performed in six-well cell culture plates. 0.75 μg each of Ad-helper plasmid, AAV helper plasmid (either Rep2Cap2, Rep5Cap2, or the Rep mutant described), and the GFP plasmid containing the ITR (mutant or wt ITR as specified in text) were triple-transfected with polyethyleneimine (PEI) (25,000 linear molecular weight) as described (Xiao et at (1998) *J. Virol.* 72:2224). Cells were harvested 48-72 hours post-transfection.

Hirt DNA Purification and Southern Blot Analysis—

Hirt DNA purification was performed as described (Hirt (1967) *J. Mol. Biol.* 26:365). Cells were harvested 48-72 hours post-transfection, washed in PBS, and resuspended in 370 µl Hirt Solution (0.01M Tris-HCl pH 7.5 and 0.1M EDTA) prior to addition of 25 µl 10% SDS and 165 µl 5M NaCl. Samples were incubated at 4° C. overnight prior to centrifugation. DNA was purified by phenol chloroform extraction and precipitated by an equal volume of isopropanol prior to resuspension in 50 µl sterile ddH$_2$O. 5 ul of each sample was digested with 4 U DpnI (NEB, Ipswich, Mass.) 2-4 hours at 37° C. prior to gel electrophoresis and Southern blot analysis to remove non-replicated transfected plasmid (Chomezynski (1992) *Anal. Biochem.* 201:134). The nylon membrane (Hybond-XL; GE Healthcare Life Sciences, Piscataway, N.J.) was hybridized to a probe corresponding to the GFP open reading frame labeled with the Random Primed DNA Labeling Kit (Roche, Indianapolis, Ind.) and d-CTP P$^{32}$. Blots were visualized after exposure to a phosphorimager screen (GE Healthcare Life Sciences, Piscataway, N.J.).

Densitometry—

Densitometry was performed using the public domain NIH Image program (developed at the U.S. National Institutes of Health available on the Internet at the NIH website). Densitometry analysis of a DpnI resistant band on the agarose gel prior to transfer was used as a loading control to normalize values obtained from the Southern blot. The lowest value (absence of any vector replication) was subtracted from all values to account for background. In order to gauge relative replication efficiency, values for ITR2 vectors were divided by the value obtained from the Rep2-ITR2 control. ITR5 vectors were compared to the Rep5-ITR5 control. All values were obtained in triplicate (n=3). Error bars represent standard error (standard deviation divided by the root of 3). All samples were compared to controls on the same blot.

Molecular Modeling—

Molecular models were generated using Swiss-Model (available at the expasy.org website). The published crystal structure of the N-terminus of Rep5 complexed with the RBE (PDB accession #1rz9) was used as a template for all models. Visualization of protein structure rendering of images were performed with PyMOL (available at pymol.org). DNA folding was performed using the DNA mfold server (available at mfold.bioinfo.rpi.edu).

Example 2

Construction and Characterization of Chimeric ITRs

Previously, AAV replicative specificity was postulated to be driven by the trs sequence (Chiorini et al. (1999) *J. Virol.* 73:4293; Chiorini et al. (1999) *J. Virol.* 73:1309). Rep2 can nick the ITR2 trs (AGT/TGG) and the AAVS1 trs of human chromosome 19 (GGT/TGG) (Wu et al. (2001) *Arch. Biochem. Biophys.* 389:271). Rep5 nicks only the ITR5 trs (AGTG/TGG). However, alignment of the ITR2 and ITR5 sequences revealed several significant sequence and structural differences outside the trs sequence (FIG. 1A). The spacing between the putative RBE and the nicking stem was significantly different; three nucleotides (nt) for ITR2 and 15 nt for ITR5. Additionally, while the trs sequence is not tightly conserved between ITR2 and ITR5, neither is the height or overall length of the putative nicking stem.

A novel method was used to generate mutant ITRs in order to determine which portions of the ITR were responsible for replicative specificity. Previous studies have investigated Rep-ITR interactions in vitro largely due to the difficulty of synthesizing full length ITRs for in vivo assays. PCR through the secondary structure of the ITR is inefficient and sequencing through these elements typically requires radiolabeled chain-terminator sequencing (Young et al. (2000) *J. Virol.* 74:3953). The AAV ITRs are highly recombinogenic and are frequently mutated even in a plasmid context (Samulski et al. (1983) *Cell* 33:135).

Figure 36A:
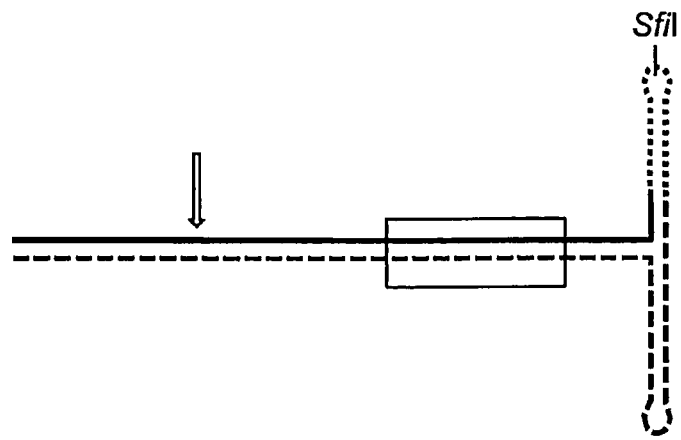
FIG. 36 shows a diagram of ITR synthesis. (A) The ITR was synthesized in two pieces (dark blue and light blue) overlapping across one hairpin stem holding the SfiI site (orange). (B) Each half was amplified via PCR prior to digestion and cloning. (C) Proper triple-ligation with pUC18-CMV GFP produced an ITR in DD format.
Figure 36B:
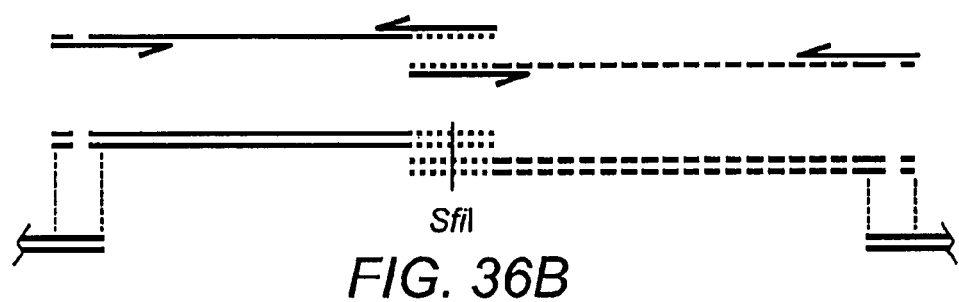
Figure 36C:
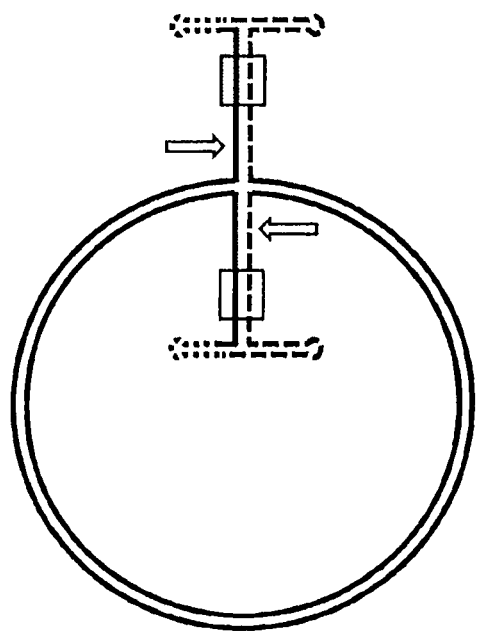

In order to address these concerns, the ITRs were synthesized and amplified in halves (FIG. 36). To assemble the halves, a SfiI site was included in one of the hairpin arms of the ITR. SfiI allowed the conservation of the RBE' sequence (Brister and Muzyczka (2000) *J. Virol.* 74:7762). Cloning the ITR in a double D element (DD) format required only one ITR per plasmid for replication (Xiao et al. (1997) *J. Virol.* 71:941). The three core Rep functions necessary for AAV replication (Rep binding, helicase, and nicking) were analyzed by the presence or absence of intracellular replication of the plasmid. This assay provided the ability to quantitate Rep-ITR function in a physiological setting, removing the concern that highly purified Rep protein might take on aberrant function in vitro. This system also avoided concerns that previous in vitro assays used only a fragment of the ITR or that oligos used to recapitulate the ITR might not fold correctly.

An alignment of ITR2 (SEQ ID NO:17) and ITR5 (SEQ ID NO:18) (FIG. 1A) revealed several divergent elements which might confer Rep specificity. The spacer and nicking stem elements appeared to be the most likely candidates for unique interactions with their cognate Rep protein. This hypothesis was supported by low homology of these elements between AAV2 and AAV5.

Figure 1A:
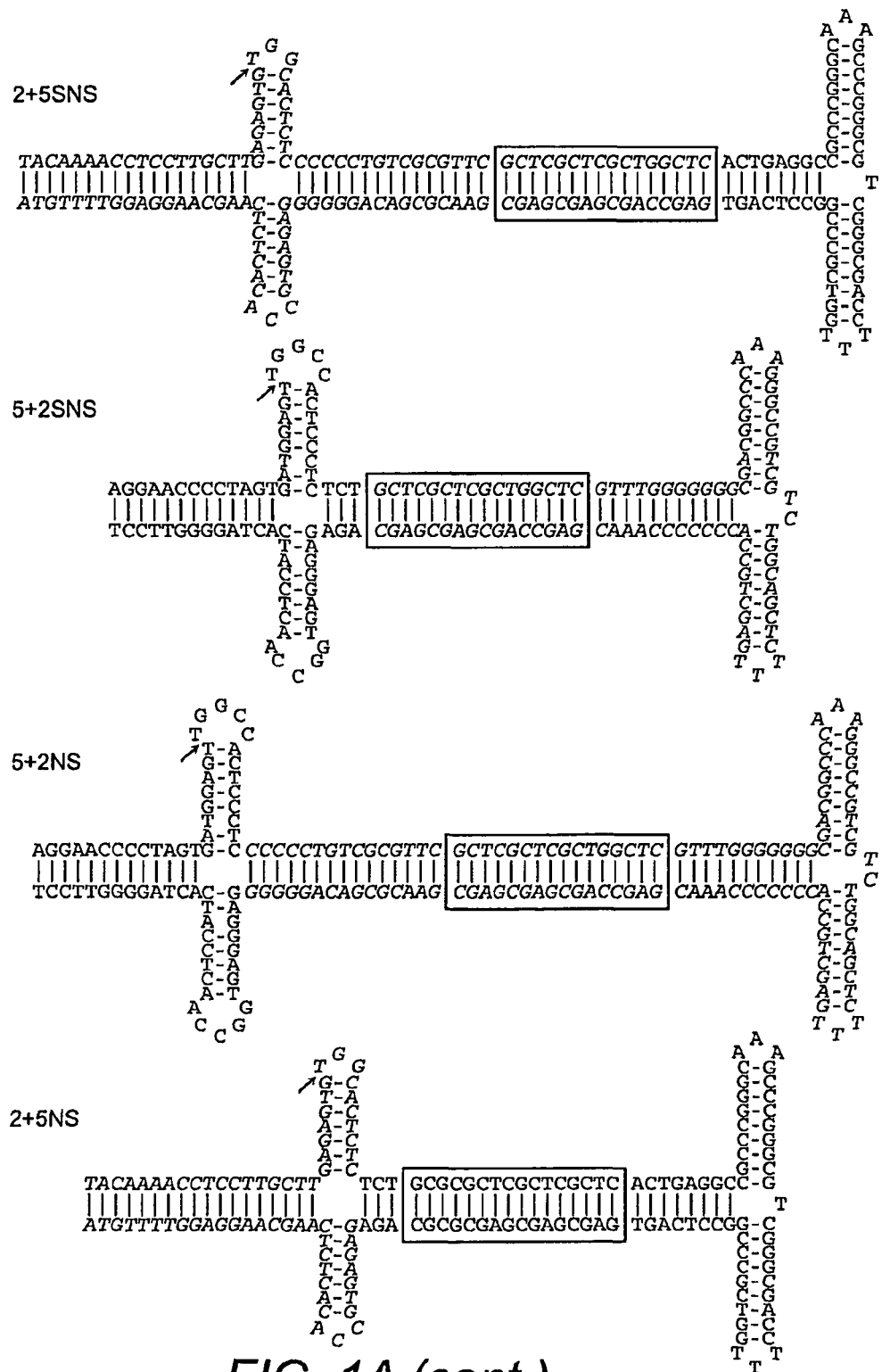
Figure 1B:
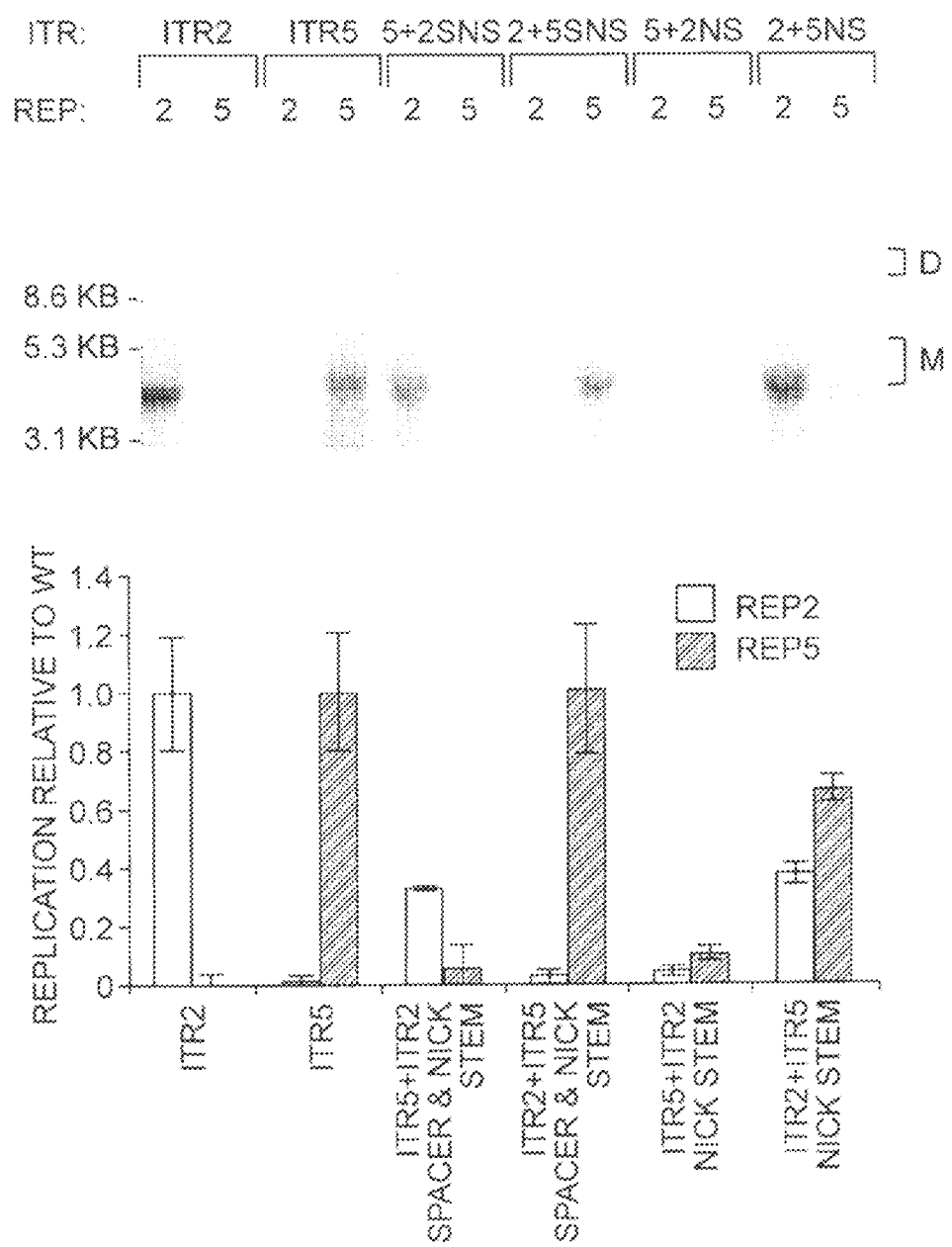

Wt ITRs containing the SfiI site functioned as expected with Rep2 specific to ITR2 and Rep5 specific to ITR5 (FIG. 1B). Rep2-ITR2 replicated approximately 2-fold better than Rep5-ITR5, potentially due to the lower folding energy of ITR5 resulting in reduced plasmid stability prior to replication. Due to this minor difference in replicative fidelity, all ITRs replicated with Rep2 were normalized to Rep2-ITR2, while ITRs replicated with Rep5 were normalized to Rep5-ITR5 (FIG. 1B).

In order to confirm that the RBE and hairpin arms played no role in Rep specificity, we generated a chimeric ITR with ITR5 binding elements and an ITR2 spacer and nicking stem (ITR5+2SNS, SEQ ID NO:19). Only Rep2 replicated this ITR, confirming the determinants of replicative specificity lie in the spacer/nicking stem elements (FIG. 1B). While ITR5+2SNS replication was not as efficient as ITR2-Rep2, it was replicated at ITR5-Rep5 levels. Conversely, Rep5 specifically replicated an ITR comprised of ITR2 hairpins and hairpin spacer and the ITR5 spacer and nicking stem (ITR2+5SNS, SEQ ID NO:20, FIG. 1B). Rep5 replicated this ITR at wt levels. These data demonstrated that Rep-ITR specificity lies outside of the ITR binding regions.

Next, chimeric ITRs were created to explore whether the nicking stem or the spacing between the RBE and nicking stem harbored unique interactions with the Rep protein. An ITR with the ITR5 binding elements and spacer and the ITR2 nicking stem could not be replicated by either Rep2 or Rep5 (ITR5+2NS, SEQ ID NO:21, FIG. 1B). The corresponding chimeric ITR (ITR2 binding elements and spacer with an ITR5 nicking stem) was replicated by both Rep2 and Rep5

(ITR2+5NS, SEQ ID NO:22, FIG. 1B). This disparity suggested that the spacer and nicking stem play different roles in Rep-ITR specificity between AAV2 and AAV5.

Example 3

The Nicking Stem is Important for ITR5 Specificity

Figure 2A:
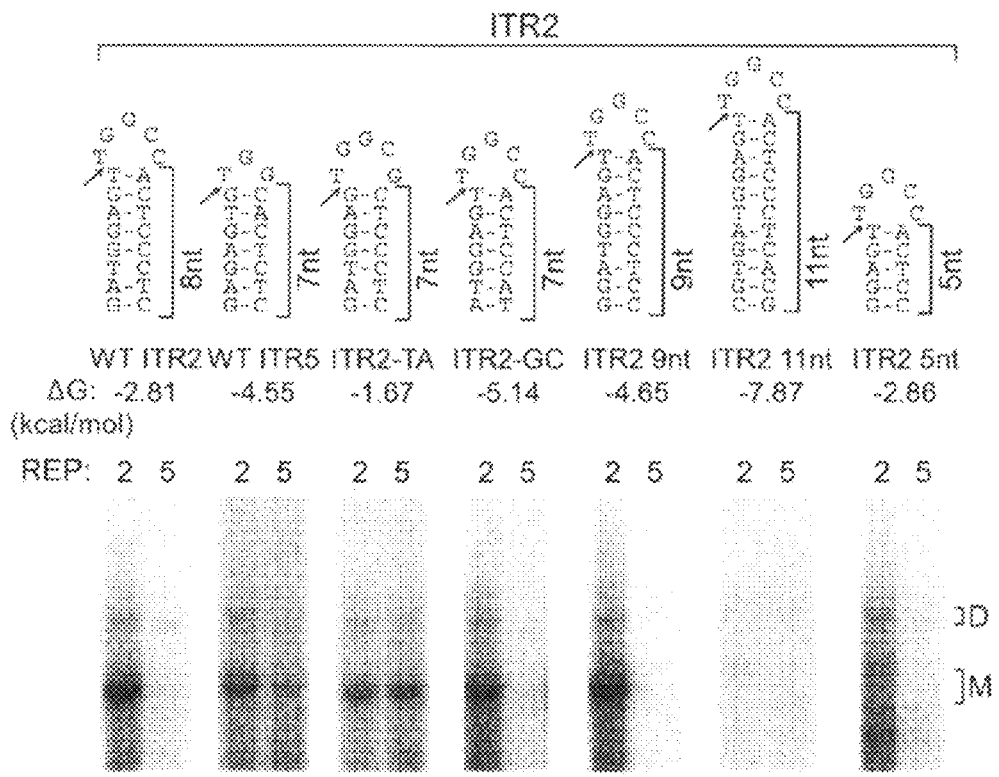
FIGS. 2A-2D show the relation of nicking stem height and sequence to Rep-ITR specificity. (A) Sequence of nicking stem in an otherwise ITR2 context (SEQ ID NOS:17, 18, 23, 25, 30, 32, 28). Arrow indicates trs site. Brackets indicate height of putative stems in nt from the base of the stem to the putative nicking site. Predicted ΔG values for the hairpins are below. Southern blot analysis of the ITRs replicated by Rep2 or Rep5 are shown below. (B) Quantitation of the Southern blots relative to wt replication from (A). (C) Same as (A), except nicking stems indicated were used in an ITR5 context (SEQ ID NOS:17, 18, 24, 26, 35). (D) Quantitation of the Southern blots relative to wt replication from (C).

ITR2+5NS (SEQ ID NO:22) established that Rep2 is capable of nicking an ITR with an ITR5 nicking stem and that Rep-ITR specificity is not driven exclusively by the trs sequence (FIG. 1B). In order to determine the flexibility of Rep2 toward mutant nicking stems, ITR2s containing altered forms of the hairpin were generated (FIG. 2A). Rep2 is able to replicate an ITR with an ITR5 nicking stem even though the ITR5 nicking stem contains a different trs sequence, is one bp shorter, and has two fewer unpaired nucleotides at its tip (FIG. 2A). The substitution of the ITR5 nicking stem into ITR2 also allowed replication by Rep5.

To determine which element of the ITR2 nicking stem prevented Rep5 activity, specific portions of the ITR2 stem were altered. First, one bp at the top of the putative ITR2 nicking stem was removed to lower the height to that of ITR5 (ITR2-TA, SEQ ID NO:23). Removing the T-A by also resulted in a trs resembling ITR5, nicking between G/T opposed to TTT. Rep2 continued to function on this ITR as did Rep5, demonstrating that Rep5 can tolerate five unpaired nucleotides at the tip of the stem as long as the stem height and nt sequence are correct. A similar deletion from the base of the ITR2 nicking stem reduced the height to that of ITR5 while retaining the ITR2 nicking site (ITR2-GC, SEQ ID NO:25). Rep2 continued to function efficiently on this ITR while Rep5 activity was ablated. This data suggested that the inability of Rep5 to function on ITR2 is primarily the sequence of the trs, specifically the requirement for a nick to be generated between G/T.

To determine the extent of Rep2 flexibility for different nicking stems, three additional ITR2 mutants were created. Extending the nicking stem by one bp at the base had no effect on replication by Rep2 (ITR2 9nt, SEQ ID NO:30). However, a three by extension was sufficient to ablate Rep2 function on the ITR (ITR2 11nt, SEQ ID NO:32). Surprisingly, Rep2 was able to tolerate a three by deletion from the base of the stem, underlining the flexibility of Rep2 with respect to nicking stem substrates (ITR2 5nt, SEQ ID NO:28).

Figure 2B:
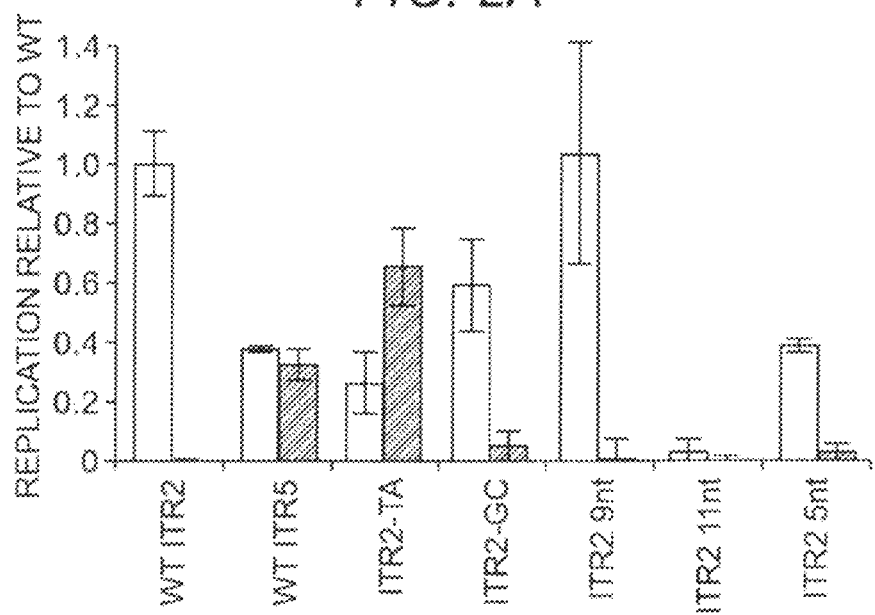
Figure 2C:
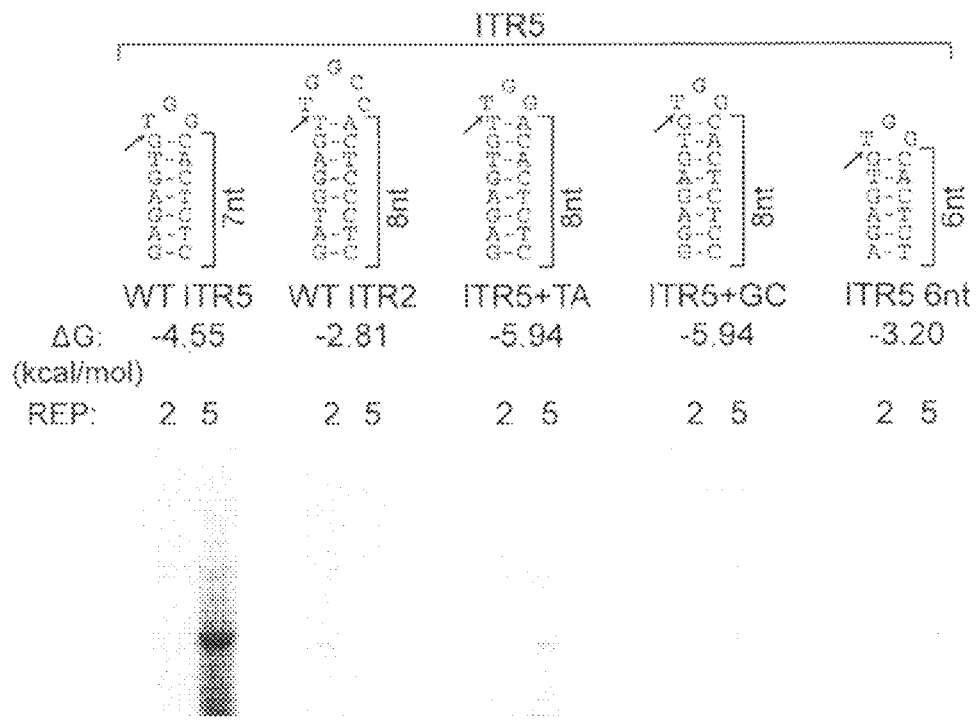
Figure 2D:
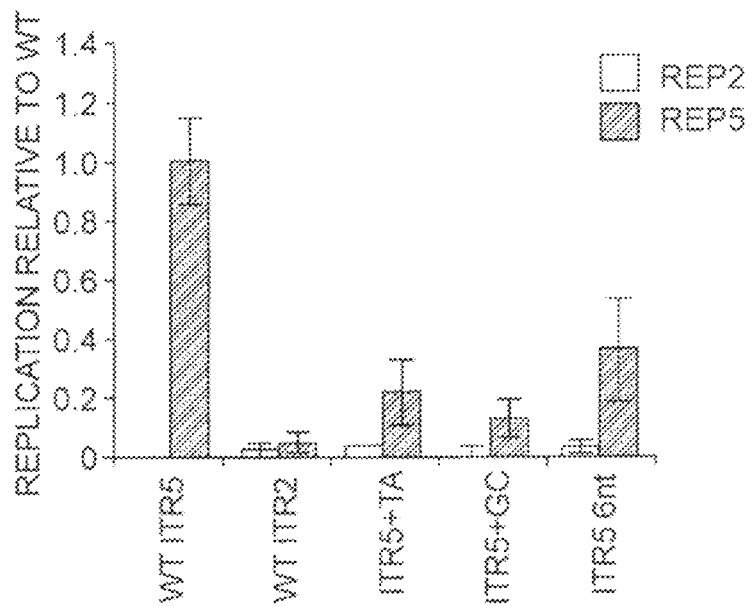

In order to explore the level of flexibility Rep5 possessed toward non-wt nicking stems, a panel of mutant ITR5s harboring altered nicking stems were created (FIG. 2C). Curiously, Rep2 replicated none of these ITRs, suggesting an element outside the ITR5 nicking stem is responsible for preventing Rep2 function. As in FIG. 1B, replacement of the ITR5 nicking stem with that of ITR2 resulted in the ablation of replication by Rep5, attributable to the incompatible trs sequence. The addition of one bp at the top of the ITR5 nicking stem severely decreased the ability of Rep5 to replicate the ITR (ITR5+TA, SEQ ID NO:24, FIG. 2D). This insertion disrupted the ITR5 trs sequence and increased the size of the stem one bp. However, the low level of replication by Rep5 on ITR5+TA suggests that the entire trs site of ITR2 is necessary to confer Rep2 specificity, not just the presence of a T/T nick site.

The addition of one bp to the base of the ITR5 nicking stem, preserving the ITR5 trs at the tip, nearly eliminated replication by Rep5 (ITR5+GC, SEQ ID NO:26). Likewise, the removal of one bp from the base of the ITR5 nicking stem strongly decreased replication by Rep5 (ITR5 6nt, SEQ ID NO:35, FIG. 2D). This data suggests that Rep5 is sensitive both to the height of the nicking stem as well as to the sequence of the trs. Thus, Rep5 is unable to replicate ITR2 because the ITR2 nicking stem is one bp too tall and has an incompatible trs sequence.

Example 4

Spacer Length is Important for ITR2, not ITR5

While Rep2 can replicate a vector with an ITR5 nicking stem, it can not replicate wt ITR5 (FIG. 1B). The only difference between ITR5+2SNS (which Rep2 can replicate) and ITR5+2NS (which Rep2 cannot replicate) is the ITR5 spacer (FIG. 1B). The wt Rep2 spacer is three nt long while the wt Rep5 spacer is 15 nt long. Thus, we hypothesized that Rep2 may be sensitive to spacer length.

Figure 3A:
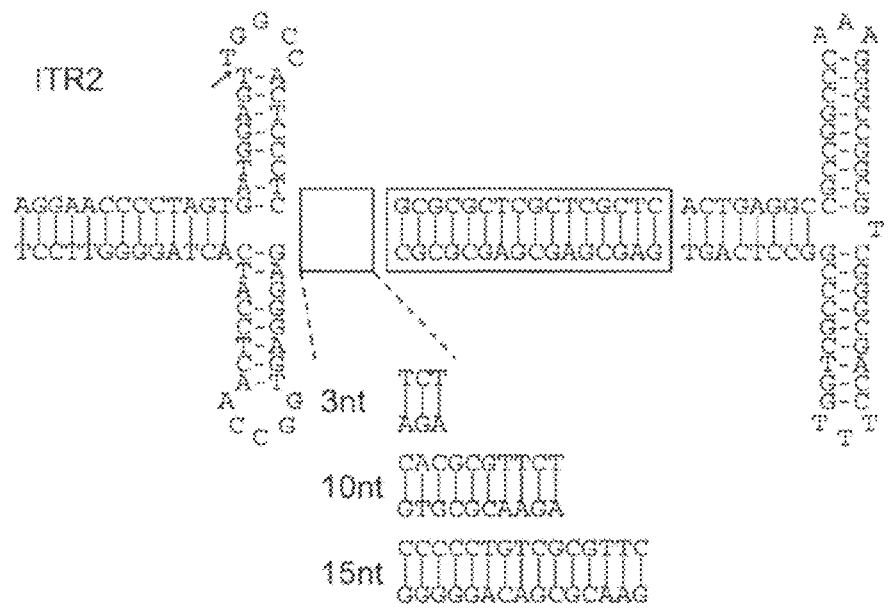
FIGS. 3A-3D show the effect of RBE-nicking stem spacing on Rep-ITR specificity. (A) ITR2 mutants were synthesized with the indicated spacing between the RBE and nicking stem (SEQ ID NOS:17, 31, 33). (B) Southern blot analysis of the ITRs depicted in (A) replicated by either Rep2 or Rep5 (Left). Quantitation of Southern blots relative to wt replication (Right). (C) ITR5 mutants synthesized as in (A) (SEQ ID NOS:34, 18, 37, 38). (D) Southern blot analysis and quantitation of (C).
Figure 3B:
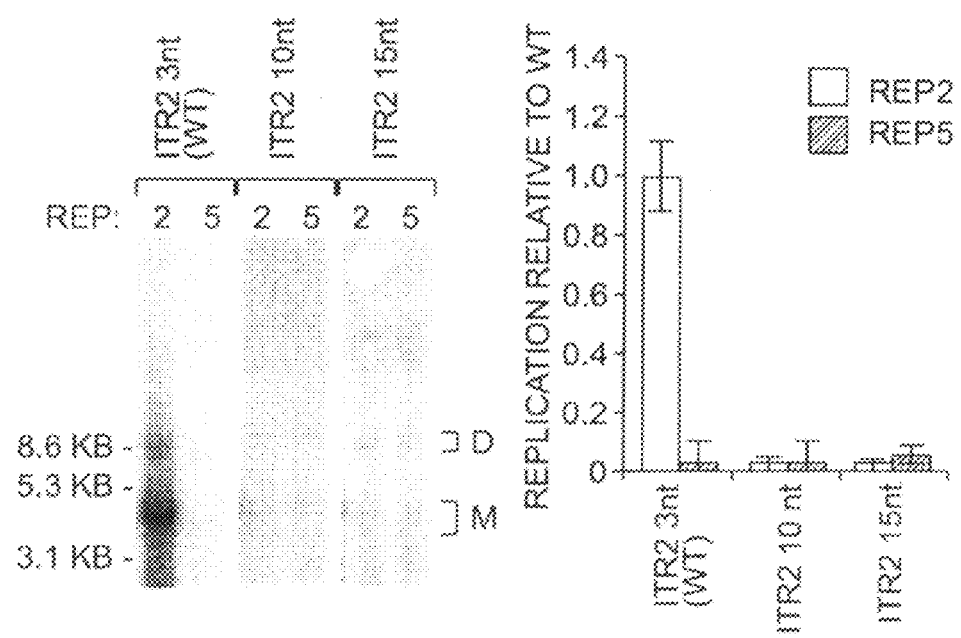
Figure 3C:
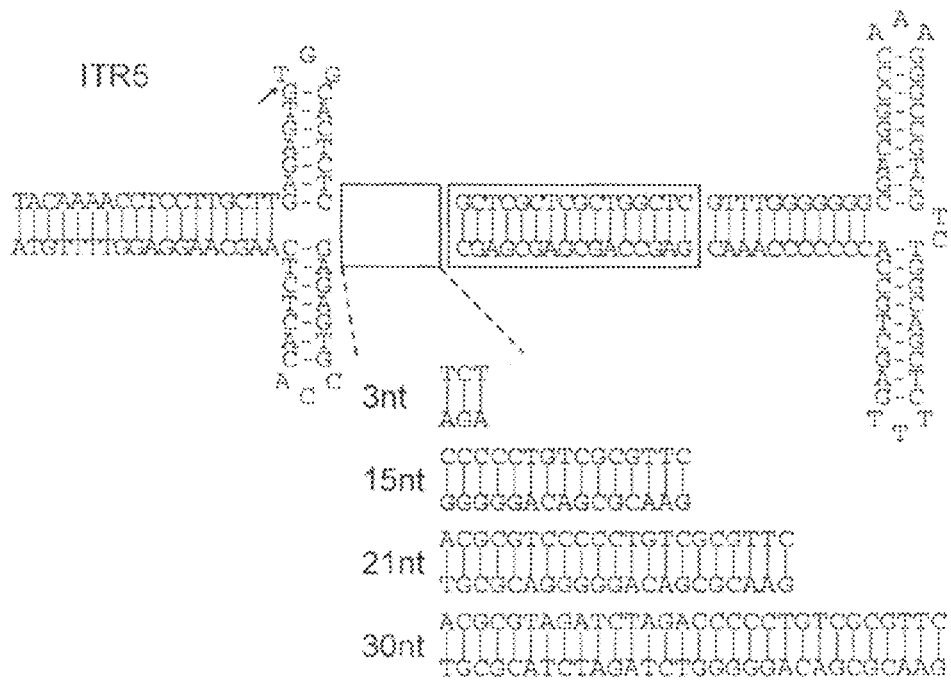

To explore the effect of spacer length on ITR2 and ITR5, a series of mutant ITR2s and ITR5s with differing spacer lengths were generated (FIGS. 3A and 3C). An insertion extending the ITR2 spacer to 10 nt ablated replication by Rep2 (ITR2 10nt, SEQ ID NO:31, FIG. 3B), Similarly, substitution of the ITR2 spacer with the 15 nt spacer of ITR5 also ablated replication by Rep2 (ITR2 15nt, SEQ ID NO:33, FIG. 3B). Rep5 was unable to replicate any of these vectors due to the presence of the ITR2 stem loop.

Figure 3D:
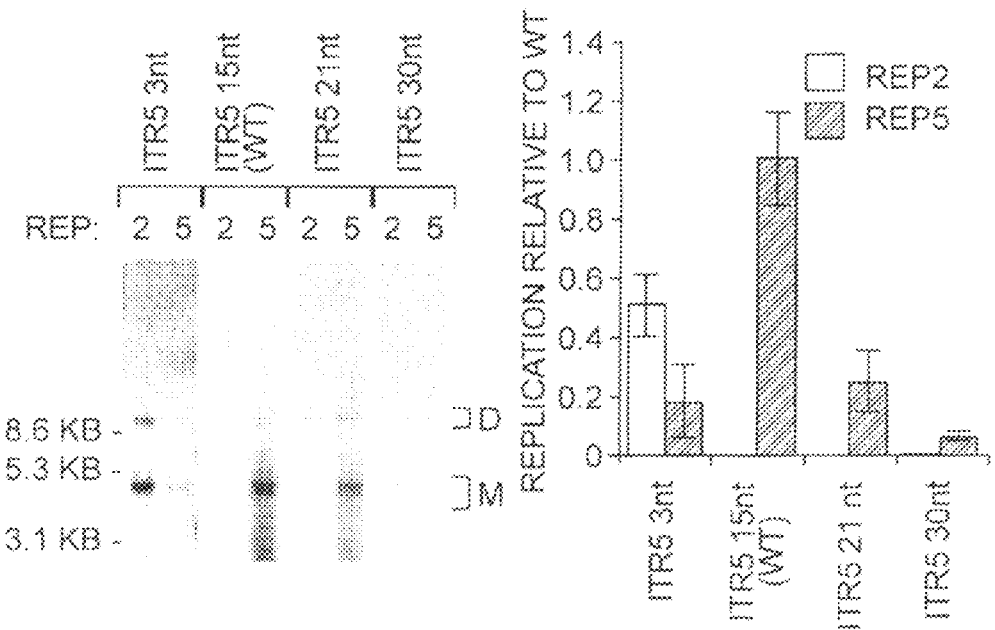

Rep5 displayed greater flexibility toward spacer elements of differing lengths. Replacing the 15 nt ITR5 spacer with that of ITR2 resulted in an ITR in which Rep5 retained the ability to replicate at a reduced level (ITR5 3nt, SEQ ID NO:34, FIG. 3D). Additionally, the presence of the three nt spacer allowed Rep2 to function on this ITR. The addition of six nt to the ITR5 spacer (for a total spacer length of 21nt) resulted in an ITR capable of being replicated by Rep5 at an efficient level (ITR5 21nt, SEQ ID NO:37, FIG. 3D). Replication by Rep5 was effectively abolished only after the insertion of 15 nt into the spacer (ITR5 30nt, SEQ ID NO:38, FIG. 3D). This panel of mutant ITR5s demonstrates the importance of a three nt spacer element for Rep2 function.

This data confirmed that the length of the ITR5 spacer was important to block Rep2 function. Even small insertions into the ITR2 spacer were not tolerated by Rep2. Meanwhile, Rep5 is flexible in regard to spacer length, demonstrating the ability to function on ITRs with spacers from 3-21 nt.

Example 5

The ITR5 Spacer Acts as a RBE for Rep5

Figure 4A:
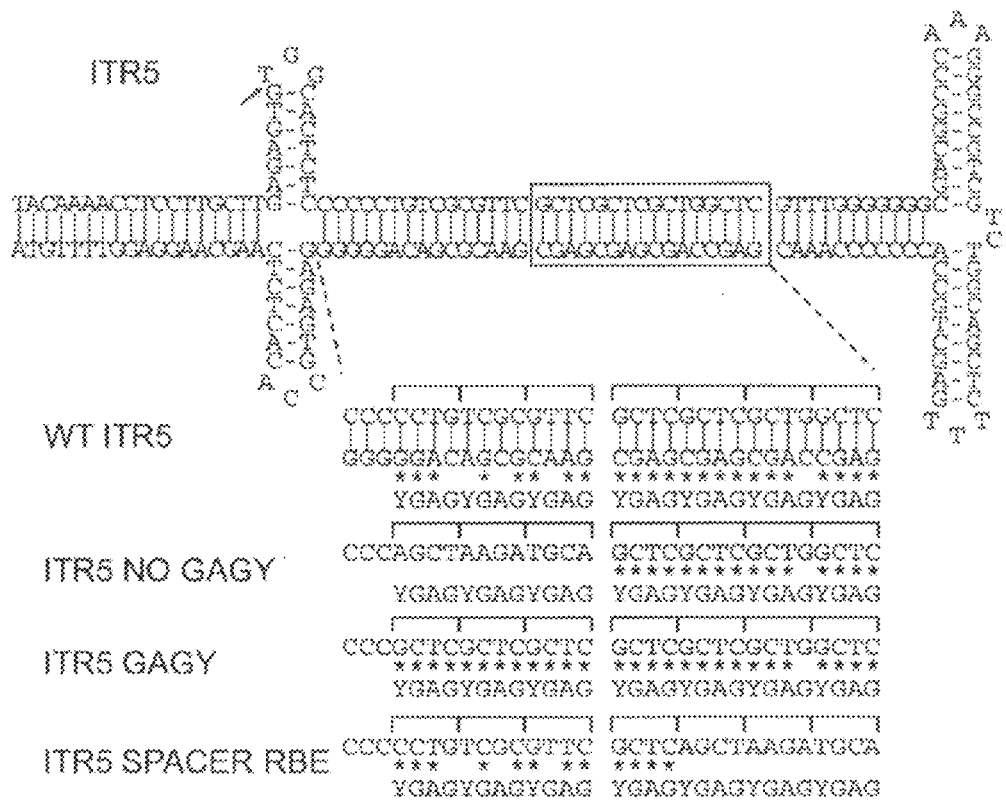
FIGS. 4A-4D demonstrate that the ITR5 spacer acts as a RBE for Rep5. (A) ITR5 mutants were synthesized with the indicated RBE and spacer sequence (SEQ ID NOS:18, 40, 39, 42). Brackets indicate individual tetranucleotide repeats bound by Rep monomers. Both strands of the wt ITR5 sequence are shown to illustrate conservation with the GAGY motif (indicated by *). Only one strand shown on others. (B) Southern blot analysis of the ITRs depicted in (A) replicated by either Rep2 or Rep5 (Left). Quantitation of Southern blots relative to wt replication (Right). (C) ITR2 mutants were generated with the RBE and spacer sequences indicated (SEQ ID NOS:17, 29, 41, 43). (D) Southern blot analysis and quantitation for (C).

The inability of Rep2 to function on ITRs with spacers longer than three nt led to the question of why Rep5 was so flexible in this regard. It was hypothesized that Rep5 might specifically bind the ITR5 spacer just as it binds the RBE. The inability of Rep2 to bind this sequence would preclude its function on ITR5. Supporting this hypothesis was a moderately conserved GAGY Rep binding motif extending throughout the ITR5 spacer (FIG. 4A). Additionally, as Rep monomers bind every four nt, the binding of three Rep5 monomers to the 15 nt spacer element would result in a three nt spacer, similar to that of ITR2 (Hickman et al. (2004) *Mol. Cell* 13:403).

Figure 4B:
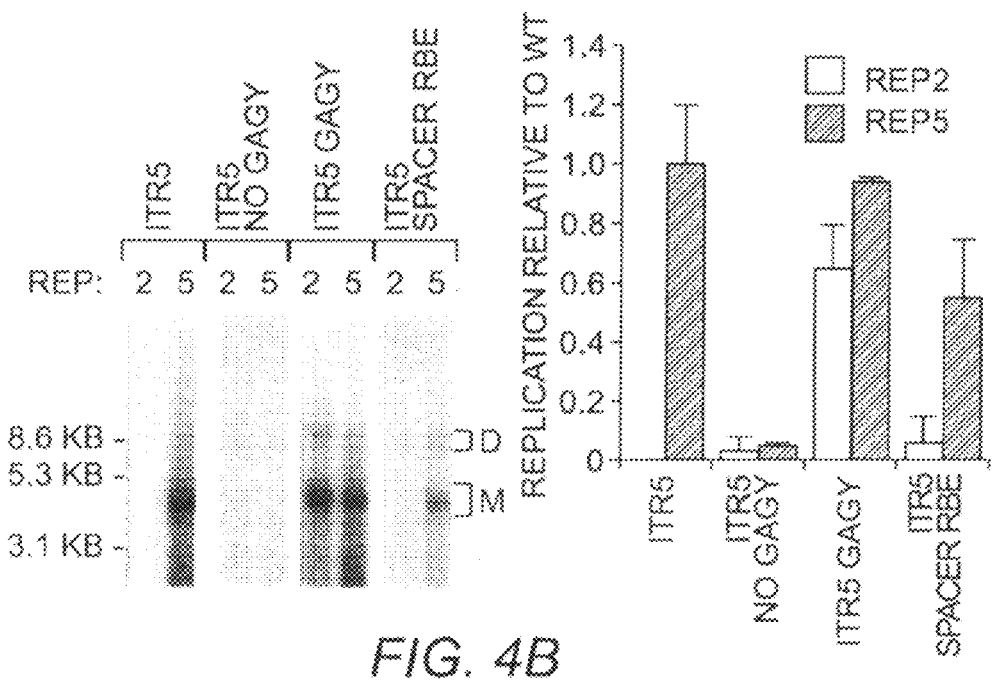

If Rep5 does bind the loosely conserved GAGY motif, the removal of that motif from the spacer should abolish Rep5 function. Indeed, the ITR5 No GAGY mutant (SEQ ID NO:40) could not be replicated by Rep2 or Rep5 (FIG. 4B). This suggested that the specific sequence of the ITR5 spacer plays an active role in the Rep5-ITR5 interaction. Conversely, a spacer with a pure GAGY repeat should not disrupt the ability of Rep5 to function on the ITR. Indeed, Rep5 was able to replicate this ITR at wt levels (ITR5 GAGY, SEQ ID NO:39, FIG. 4B). Rep2 was also able to replicate this ITR efficiently, suggesting the poorly conserved nature of the GAGY repeat within the ITR5 spacer prevents an important DNA-protein interaction with Rep2 necessary for replication.

To explore how the ITR5 spacer functioned as an RBE, we removed three GAGY repeats from the hairpin side of the RBE (ITR5 Spacer RBE, SEQ ID NO:42, FIG. 4A). This essentially shifted the 16 nt RBE 12 nt closer to the nicking stem. Rep5 replicated this ITR efficiently, confirming the ITR5 spacer acts as a RBE (FIG. 4B). The slight reduction in replication fidelity of this ITR, as compared with that of wt ITR5, may signal the inability of Rep to properly interact with the RBE' (Brister and Muzyczka (2000) *J. Virol.* 74:7762). Rep2 was again unable to replicate ITR5 Spacer RBE due to its inability to interact with the ITR5 spacer.

Figure 4C:
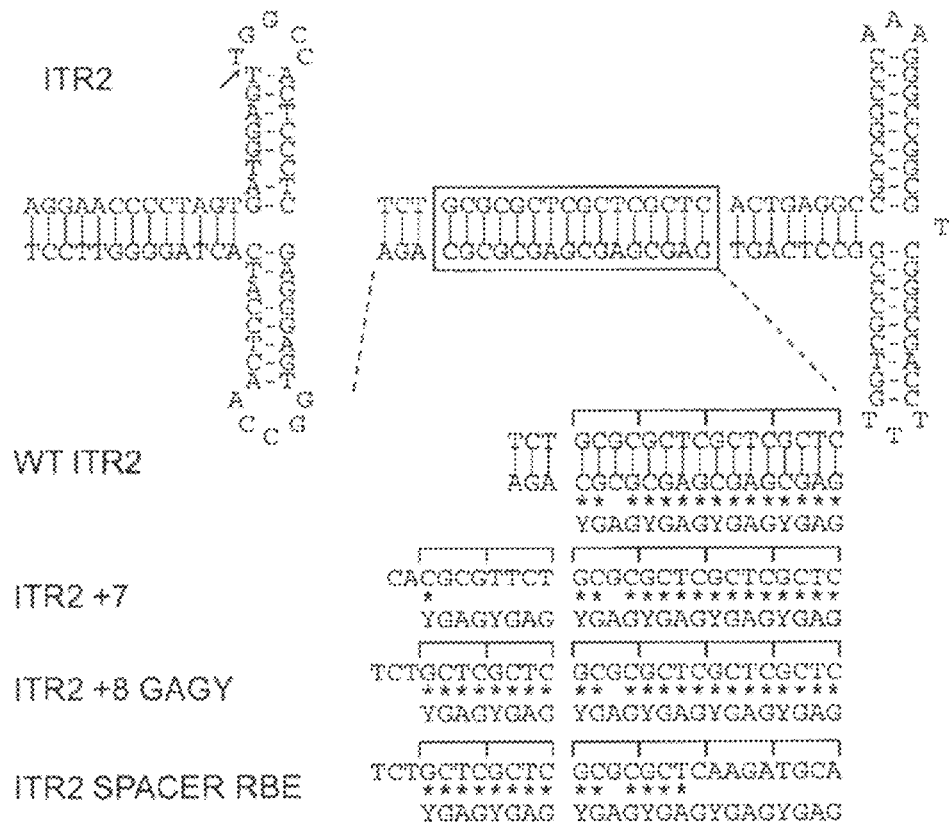
Figure 4D:
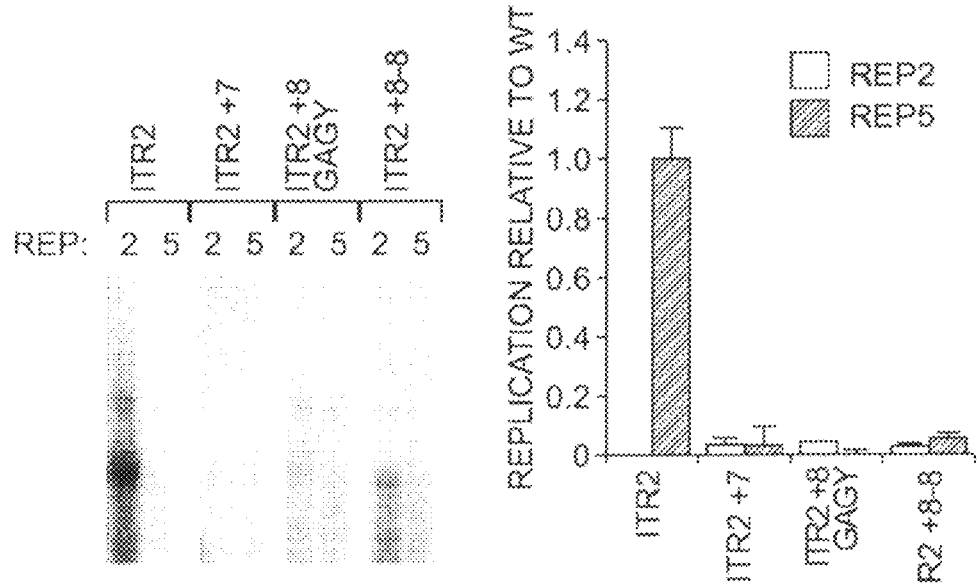

Next, we sought to extend the ITR2 spacer element to function as an extended RBE (FIG. 4C). The seven nt insertion attempted in FIG. 3A possessed essentially no GAGY homology (ITR2+7, SEQ ID NO:29, FIG. 4C). As a result, Rep2 could not replicate this ITR (FIG. 4D). Eight nt (two four nt GAGY repeats) inserted into the ITR2 spacer between the RBE and the existing spacer (ITR2+8 GAGY, SEQ ID NO:41) prevented replication by Rep2, demonstrating that the ITR2 RBE cannot be extended. This suggests that Rep2 may be dependent on RBE' binding or a specific spacer length for proper oligomerization to function on its cognate ITR. Curiously, this requirement does not apply to Rep2 function on ITR5 GAGY (FIG. 4A).

Similar to ITR5 Spacer RBE, we retained the eight nt GAGY insertion into ITR2 while removing eight nt of GAGY from the hairpin side of the RBE (ITR2+8-8 Spacer RBE, SEQ ID NO:43, FIG. 4C). This shifted the RBE eight nt closer to the nicking stem. Rep2 replicated this ITR very inefficiently at a level below the detection threshold of densitometric analysis (FIG. 4D, Southern).

Example 6

Identification of Regions in Rep Responsible for ITR Specificity

Identifying the two elements of the ITR responsible for Rep specificity allowed us to map the regions of Rep2 and Rep5 involved in ITR specificity. We focused exclusively on the N-terminal 208 aa of the large Rep proteins as this region encompasses the DNA binding and endonucleolytic activity of the protein (Yoon et al. (2001) *J. Virol.* 75:3230). This region displays approximately 60% sequence conservation evenly distributed across the protein sequence (FIG. 5A). Residues involved in the active site of the protein are 100% conserved between Rep2 and Rep5 (Hickman et al. (2002) *Mol. Cell* 10:327). Residues implicated in binding the RBE' are highly conserved (Hickman et al. (2004) *Mol. Cell* 13:403). Residues which bind the RBE display nearly perfect conservation except for two conservative substitutions near aa 140.

In order to map the regions of Rep involved in ITR specificity, a panel of chimeric Reps derived from Rep2 and Rep5 were generated (FIG. 5B). The ability of each chimeric Rep to replicate an ITR2- or ITR5-flanked vector in HEK 293 cells was determined by Southern blot (FIGS. 5B and 5D). Each Rep in the panel was verified by DNA sequencing and Western blot analysis (FIG. 5C). Every chimeric Rep showed similar protein expression profiles compared to wt. Densitometric analysis provided a comparison of the replication efficiency of each chimeric Rep with that of wt Rep2 or Rep5 (FIG. 5E). Chimeric Reps were named according to the aa location of the swap between serotypes; for instance, Rep25aa77 (SEQ ID NO:63) possesses the N-terminal 76 aa of Rep2 and the C-terminus of Rep5.

In the case of Rep5, replacement of the N-terminal 77 or 97 aa with Rep2 had no effect on ITR specificity nor a significant impact on replicative fidelity (FIGS. 5D and 5E). Larger pieces of Rep2 substituted onto the N-terminus of Rep5 were sufficient to prevent efficient replication of ITR5s (Rep25aa116, SEQ ID NO:65; Rep25aa125, SEQ ID NO:66; Rep25aa141, SEQ ID NO:67). This suggested that these chimeras possessed interruptions of a critical region of Rep5 for ITR5 specificity.

Rep2-based chimeras were unable to replicate ITR5s without the inclusion of the N-terminal 146 aa of Rep5 (Rep52aa146, SEQ ID NO:79, FIG. 5D). Rep52aa146 replicated ITR5 at wt levels, as did the three chimeras with larger portions of Rep5 on the N-terminus (Rep52aa160, SEQ ID NO:58; Rep52aa175, SEQ ID NO:59; Rep52aa207, SEQ ID NO:61). This mapping reveals that the critical region for ITR specificity in Rep5 lies between aa 97-146. Surprisingly, the Rep52aa146 clone also functioned efficiently on ITR2, constituting a Rep capable of replicating ITR2 and ITR5. This suggested that ITR specificity existed in two different regions of Rep.

For Rep2, the N-terminal 83 or 109 aa of Rep5 could be substituted with no effect on ITR specificity or major influence on replicative fidelity (Rep52aa84, SEQ ID NO:54; Rep52aa110, SEQ ID NO:55; FIGS. 5D and 5E). Chimeras including slightly larger portions of Rep5 were unable to replicate either ITR, again suggesting the interruption of a domain critical for ITR specificity (Rep52aa126, SEQ ID NO:56; Rep52aa138, SEQ ID NO:57).

Rep5-based chimeras were unable to replicate ITR2s without the inclusion of the N-terminal 149 aa of Rep2. However, ITR2 replication was inefficient (Rep25aa149, SEQ ID NO:68, FIGS. 5D and 5E). The inclusion of larger portions of Rep2 allowed replication of ITR2s to increase to wt levels (Rep25aa166, SEQ ID NO:69; Rep25aa216, SEQ ID NO:71). This data maps the Rep2 region involved in ITR specificity to aa 110-149. However, unlike Rep5, this was not the only region which played a role in ITR specificity. The ability of the Rep52aa146 chimera to replicate ITR2 and ITR5 vectors demonstrated a second region of Rep2 between aa 138-160 sufficient to allow replication of ITR2s even when the other critical region (aa 110-149) was Rep5. The isolation of two different Rep regions involved in ITR specificity was consistent with the discovery of two independent elements governing specificity within the ITR.

Example 7

Characterization of Rep Regions Involved in ITR Specificity

Figures 6A, 6B:
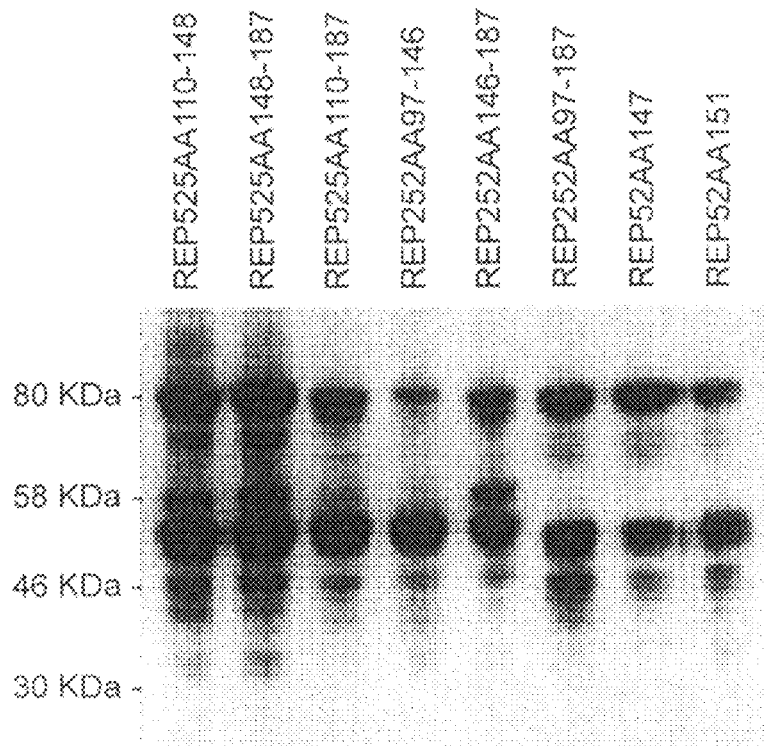
FIGS. 6A-6G show the characterization of Rep regions involved in ITR specificity. (A) Chimeric Reps and their ability to replicate ITR2 or ITR5 flanked vectors. Numbers indicate the aa position of the switch from one Rep to the other. (+) indicates the presence of replication, (−) indicates the absence. Region 1 and 2 involved in Rep-ITR specificity are indicated. (B) Western blot for expression of chimeric Reps. (C) Southern blot demonstrating replication of an ITR2 or ITR5 vector by the chimeric Reps. Note that the ITR5 vector is 500 bp larger than the ITR2 vector. (D) Structural model illustrating the two Rep regions. Rep2 structure is blue, Rep5 is purple. The nucleophilic tyrosine is indicated. Black hatched circle indicates the predicted structural difference of region 1 in the major groove of the ITR. (E) Structural model as in (D). The nucleophilic tyrosine is indicated. (F) Detailed structural view of region 1. The side-chains of non-conserved residues from Rep5 (purple) and Rep2 (blue) are shown. Three Rep5 residues implicated in RBE' binding are indicated. (G) Detailed structural view of region 2. Side chains of active site residues are shown in black. Side chains of non-conserved residues in this region are shown for Rep2 (blue) and Rep5 (purple). The nucleophilic tyrosine is indicated, as is the adjacent Rep2 Asn-155.

To characterize the Rep domains identified in FIG. 5, chimeric Rep proteins which specifically exchanged the regions implicated in ITR specificity were created (FIG. 6A). Region 1 existed in Rep2 from aa 110-149 and in Rep5 from aa97-146. Region 2 lay within Rep2 from aa 149-187 and Rep5 from aa 146-187. As in FIG. 5, all chimeras were verified by DNA sequencing and Western blot analysis (FIG. 6B). Chimeras were then assayed for the ability to replicate ITR2- or ITR5-flanked vectors (FIG. 6C).

Figure 6C:
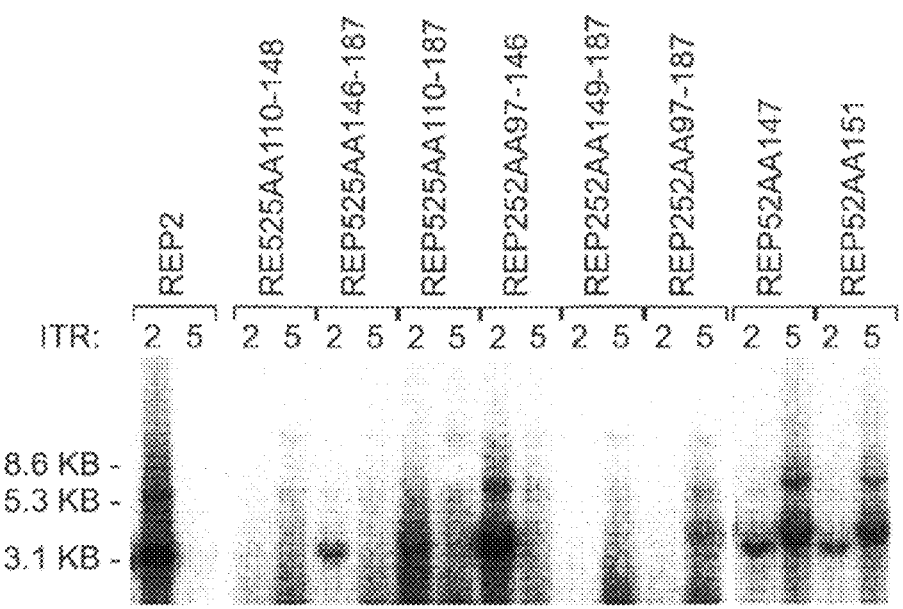

Replacing Rep5 region 1 with Rep2 yielded a clone unable to replicate either vector, suggesting the chimera lacked the ability to bind the ITR5 spacer or nick the ITR2 nicking stem (Rep525aa110-148, SEQ ID NO:72, FIG. 6C). Replacing Rep5 region 2 with that of Rep2 allowed this chimera to replicate an ITR2 vector, suggesting region 2 of Rep2 was critical to nick the ITR2 nicking stem (Rep525aa146-187, SEQ ID NO:73). The inability of this chimera to recognize ITR5 is harder to explain as Rep52aa146 could replicate ITR2 and ITR5 efficiently (FIG. 5B). This result suggests that Rep2 region 2 makes specific contacts within Rep2 aa 188-208 which are necessary in order to function on the ITR5 nicking stem. Replacing regions 1 and 2 of Rep5 with Rep2 resulted in a Rep chimera which replicated only ITR2s (Rep525aa110-187, SEQ ID NO:74).

Replacing Rep2 region 1 with Rep5 resulted in replication of only ITR2s, again demonstrating a connection between Rep2 region 2 and the ITR2 nicking stem (Rep252aa97-146, SEQ ID NO:75). The lack of ITR5 replication by Rep252aa97-146 is difficult to explain based on the Rep52aa146 chimera which replicates ITR2s and ITR5s efficiently (FIG. 5B). This result suggests that Rep5 region 1 makes specific contacts within the preceding 96 aa of Rep5 in order to replicate ITR5. Replacing Rep2 region 2 with Rep5 resulted in a chimera unable to replicate either ITR (Rep252aa149-187, SEQ ID NO:76). This chimeric Rep possesses neither Rep2 region 2 (required to nick the ITR2 nicking stem) nor Rep5 region 1 which appears to interact with the ITR5 spacer. Finally, replacing both Rep2 regions 1 and 2 with Rep5 resulted in a chimera capable of replicating only ITR5 vectors (Rep252aa97-187, SEQ ID NO:77).

Figure 6D:
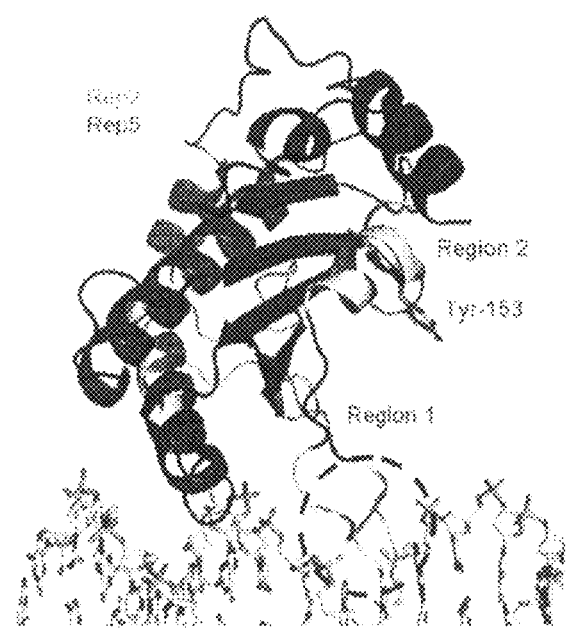

The crystal structure of the N-terminal 193 aa of Rep5 complexed to the RBE allowed the location of these two critical regions to be modeled (Hickman et al. (2004) *Mol. Cell* 13:403). The structure of the N-terminus of Rep2 was modeled with Swiss-Model software using Rep5 as a template. The location of region 1 supports its involvement with the spacer/RBE (FIG. 6D). This region interacts with the major groove of the ITR where one of the most apparent structural differences between Rep2 and Rep5 is predicted (FIG. 6D, hatched circle). Rep2 contains a two aa insertion in this loop with respect to Rep5. This insertion and other non-conservative substitutions are likely responsible for the inability of Rep2 to interact with the ITR5 spacer.

Figure 6E:
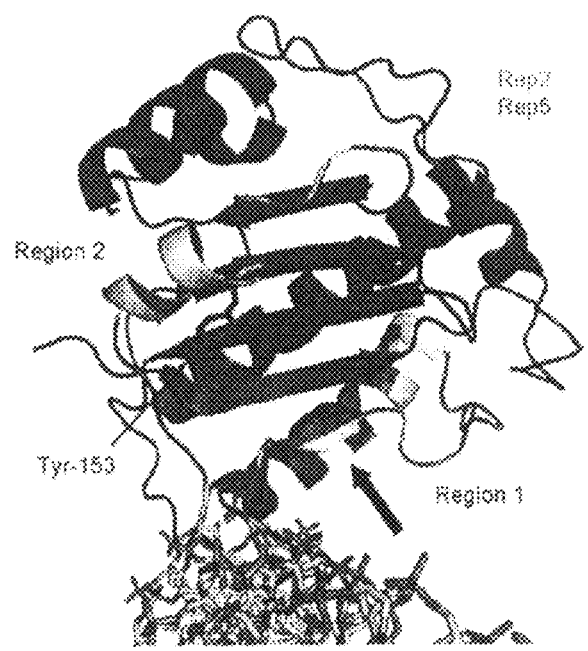
Figure 6F:
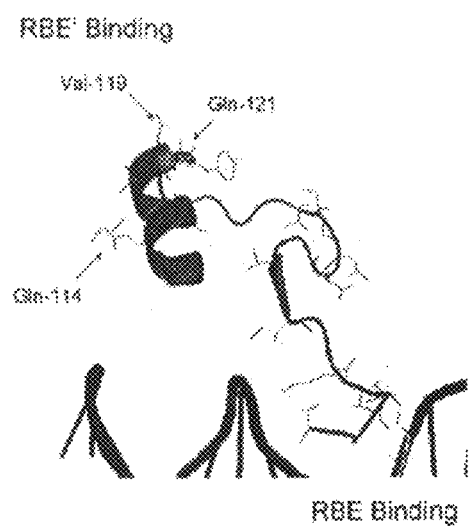

Viewing Rep along the length of the ITR illustrates that region 1 constitutes much of the base of the protein (FIG. 6E). Both Reps are predicted to participate in a β-sheet motif in the center of this region, while areas of reduced homology exist toward either side (the loop interacting with the major groove of the ITR on one side, RBE' interactions on the other). A more detailed look at region 1 reveals the greatest disparity between Rep2 and Rep5 occurs at the RBE binding interface in the major groove of the ITR (FIG. 6F).

Figure 6G:
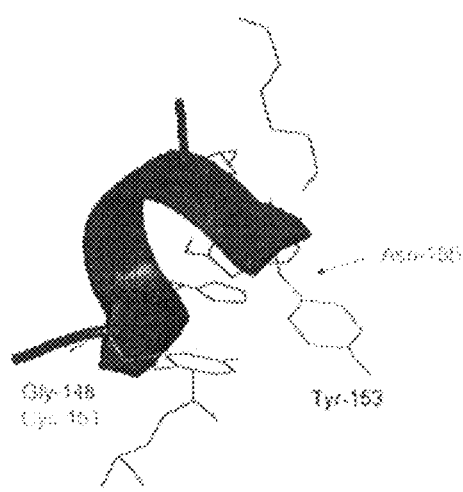

There is very little predicted structural difference between region 2 of Rep2 and Rep5 (FIGS. 6D and 6E). In an effort to dissect this region, we created two additional clones: Rep52aa147 (SEQ ID NO:81) and Rep52aa151 (SEQ ID NO:83) (FIG. 6A). Like Rep52aa146, both of these Reps were able to replicate ITR2 and ITR5 vectors (FIG. 6C). Rep52aa146 and Rep52 aa147 replicated ITR2 and ITR5 vectors with equivalent efficiency, suggesting E147 of Rep2 is not involved in ITR specificity. Rep52aa151 did display a modest reduction in ITR2 replication compared to Rep52aa146, suggesting that C151 of Rep2 plays a role in ITR2 specificity. Because Rep52aa160 can not replicate ITR2, this leaves only two other non-conserved residues between Rep2 and Rep5 in this region (N155 and T161). Both of these residues lie near the active site and are likely to interact with the nicking stem or active site. N155 lies directly adjacent to Y156, the nucleophilic tyrosine, and may play a major role in ITR2 specificity (FIG. 6G).

Example 8

Structure-Function Model of Rep-ITR Specificity

In order to unify the ITR and Rep elements involved in specificity into a single model, the chimeric Reps separating region 1 and region 2 along with the chimeric ITRs separating the nicking stem and spacer were utilized. Rep2, Rep5, Rep52aa146 (which divides region 1 and 2 of Rep and can replicate ITR2 and ITR5), and Rep25aa149 (essentially no ITR2 or ITR5 replication) were selected. These Reps were tested for their ability to replicate ITR2, ITR5, ITR2+5NS (which is replicated by both Rep2 and Rep5), and ITR5+2NS (which is replicated by neither Rep2 nor Rep5).

Figure 7A:
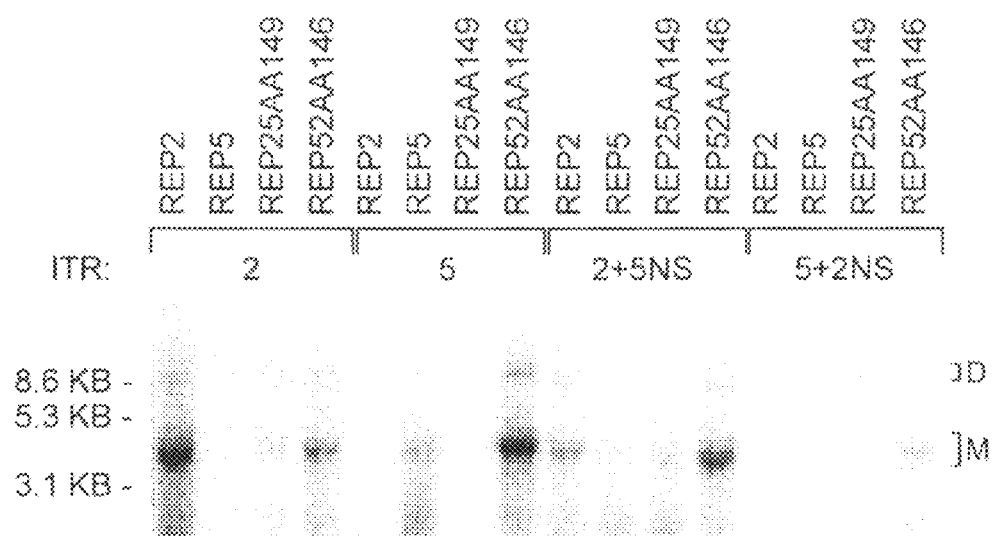
FIGS. 7A-7C show a model of Rep-ITR specificity. (A) Southern blot of Hirt DNA demonstrating replication of the indicated ITR vector by the indicated Rep. (B) Table indicating the presence (+) or absence (−) of replication of the gel from (A). (C) Model of a novel AAV origin of replication. The chimeric ITR can be replicated only by a chimeric Rep protein. Rep5 sequence in region 1 (blue) is required for the extended RBE of ITR5 (purple). Rep2 sequence in region 2 (yellow) is required to function on an ITR2 nicking stem (cyan).
Figure 7B:
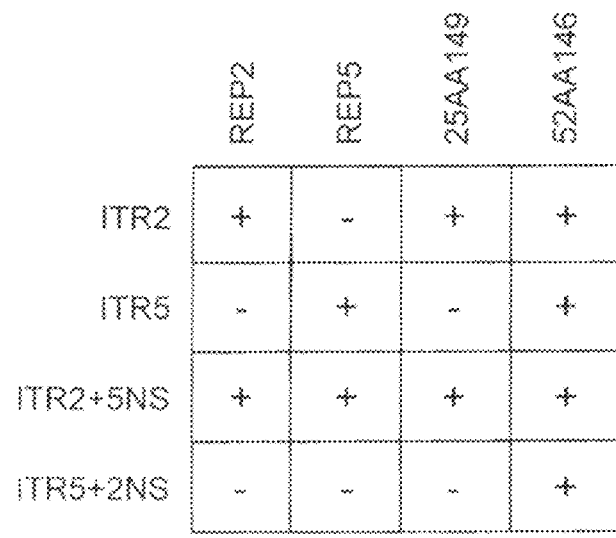

Only Rep2 and Rep52aa146 efficiently replicated ITR2 (FIGS. 7A and 7B). Only Rep5 and Rep52aa146 replicated ITR5. As in FIG. 1, Rep2 and Rep5 replicated ITR2+5NS. Additionally, Rep25aa149 (SEQ ID NO:68) and Rep52aa146 (SEQ ID NO:79) replicated ITR2+5NS. This ITR appears to be universally replicated by every Rep in this assay due to the exclusion of DNA elements involved in protein specificity. The three nt ITR2 spacer is amenable to the DNA binding region 1 of Rep2 and Rep5. The seven by tall ITR5 nicking stem functions with region 2 of Rep2 and Rep5. Thus, any combination of these regions constitutes a Rep protein capable of replicating ITR2+5NS.

Figure 7C:
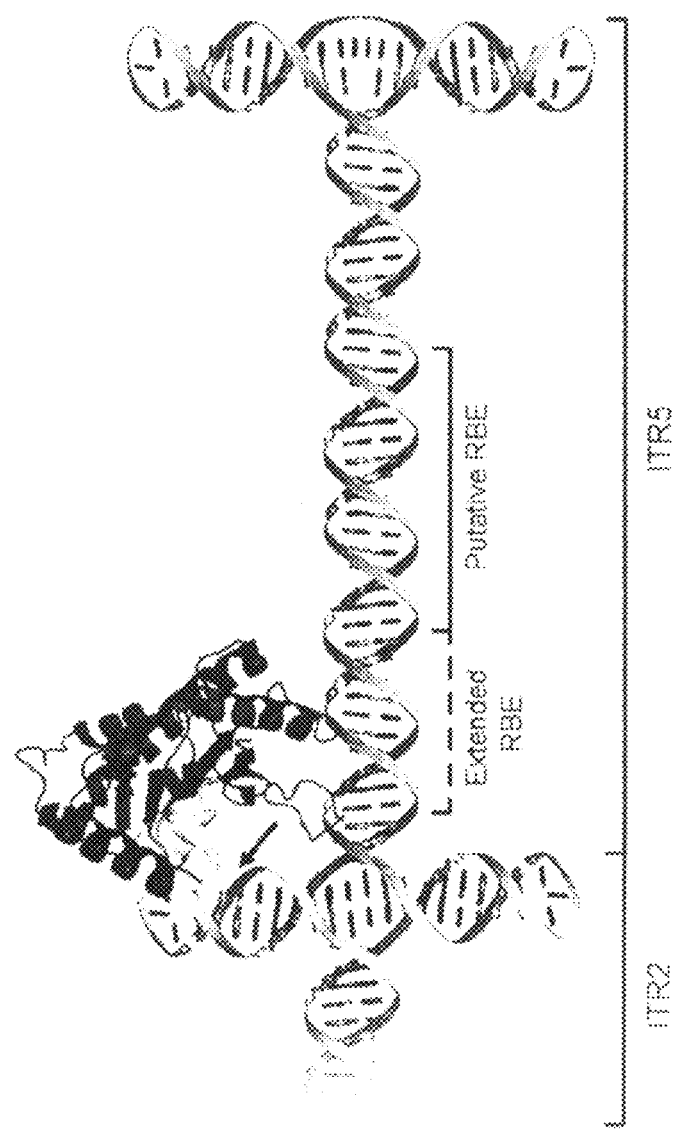
Figure 30:
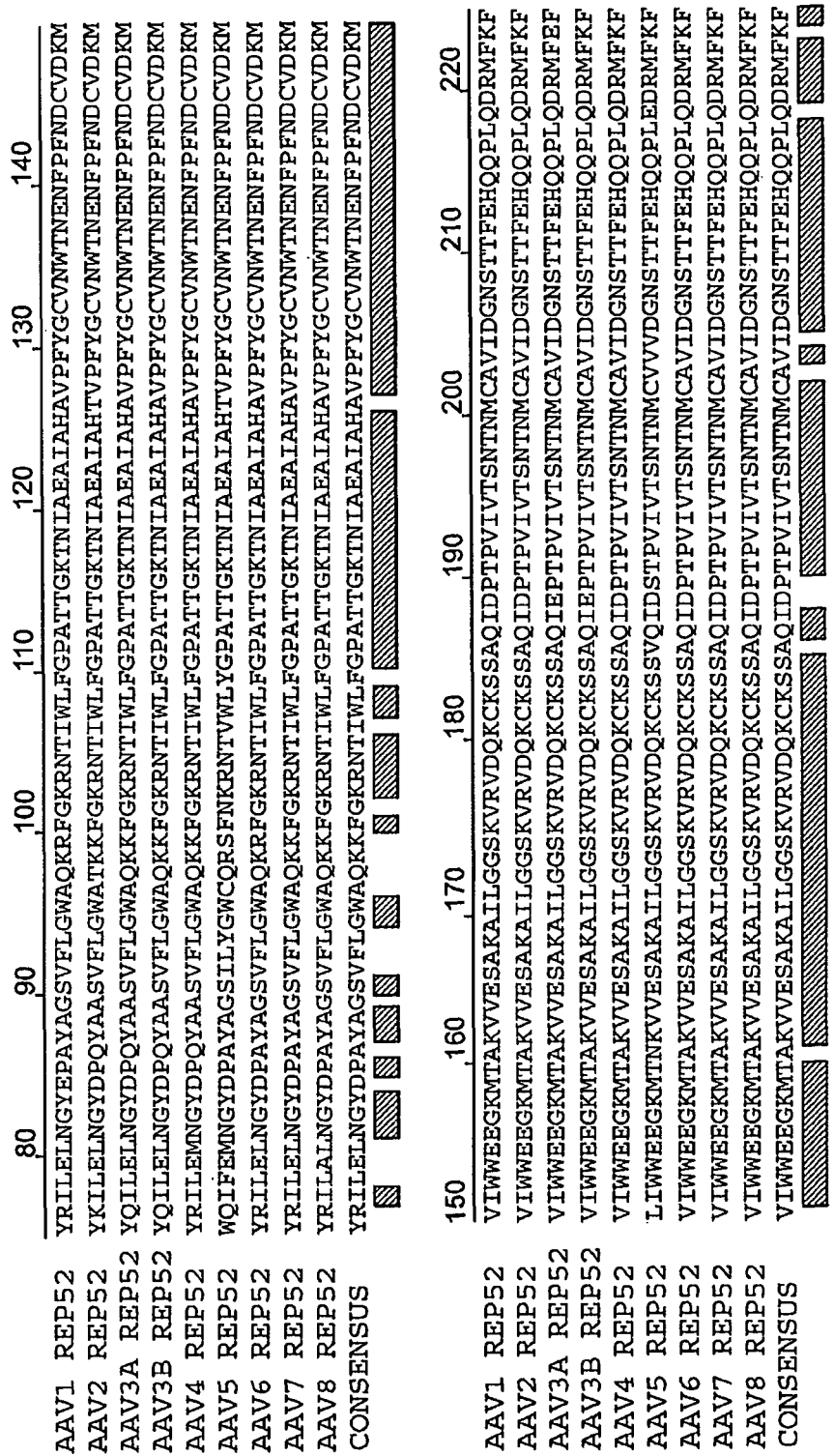
FIG. 30 shows an alignment of the amino acid sequences of exemplary Rep52 proteins from AAV1 (SEQ ID NO:94), AAV2 (SEQ ID NO:95), AAV3A (SEQ ID NO:96), AAV3B (SEQ ID NO:97), AAV4 (SEQ ID NO:98), AAV5 (SEQ ID NO:99), AAV6 (SEQ ID NO:100), AAV7 (SEQ ID NO:101) and AAV8 (SEQ ID NO:102), as well as a consensus sequence (SEQ ID NO:103). Dashes indicate gaps in the sequence and shading indicates positions of sequence homology.

Finally, neither Rep2 nor Rep5 replicated ITR5+2NS. Rep2 is unable to interact properly with the 15 nt ITR5 spacer. Rep5 is unable to function on the ITR2 nicking stem. For these reasons, Rep25aa149 was also unable to catalyze replication. However, Rep52aa146 was able to replicate this ITR due to the proper combination of Rep regions (FIG. 7C). Rep52aa146 possesses Rep5 region 1 which interacts with the 15 nt ITR5 spacer. This chimera also possesses Rep2 region 2, which functions on the ITR2 nicking stem. This recombinant DNA-protein interaction is unique from either AAV2 or AAV5 and constitutes a novel Parvovirus origin of replication.

Taken as a whole, this work illustrates two specific mechanisms of DNA-protein specificity at the Parvovirus origin of replication. Chimeric ITRs narrowed the DNA elements involved in specificity to the spacer and nicking stem sequences (FIG. 1B). These results contradicted previous assertions that Rep-ITR specificity were driven solely by the nicking sequence as Rep2 efficiently nicked an ITR harboring the ITR5 nicking stem (Chiorini et al. (1999) *J. Virol.* 73:4293). Rep2 is highly flexible in the sequence and height of its nicking stem while Rep5 is highly specific to its cognate stem (FIG. 2).

Three residues of Rep2 are important to cleave the ITR2 nicking stem (FIGS. 5 and 6). Residues C151, N155, and T161 all lie in the active site of the protein in a predicted alpha helix along with the nucleophilic tyrosine Y156. How these residues (termed Rep region 2) grant Rep2 flexibility toward mutant nicking stems remains unclear. The corresponding Rep5 residues (G148, A152, and V158) may participate in highly specific interactions which require specific height and sequence considerations for the ITR5 nicking stem.

AAV5 Rep-ITR specificity is mediated by the ITR5 spacer. Replacement of the three nt ITR2 spacer with the 15 nt ITR5 spacer ablated replication by Rep2 (FIG. 2B). A poorly conserved Rep binding element allows Rep5 to interact with the elongated ITR5 spacer (FIG. 4B). Mutating the spacer to include a strong Rep binding element allowed Rep2 and Rep5 to replicate the ITR. However, insertion of a Rep binding element into the ITR2 spacer still largely decreased Rep2 function. While this data might suggest that additional Rep5 molecules bind to ITR5, previous in vitro experiments have not come to this conclusion, although those studies were performed in the absence of hairpins on the ITRs (Chiorini et al. (1999) *J. Virol.* 73:4293).

A 49 aa region of Rep5 interacts with the ITR5 spacer (aa 97-146, FIGS. 5 and 6). The crystal structure of the N-terminus of Rep5 reveals that this region (region 1) possesses residues which specifically bind to the RBE and RBE' of the ITR. Major structural differences in the Rep5 loop which binds the major groove of the RBE likely account for the majority of ITR5 spacer specificity. While FIG. 1B predicts RBE' binding should not play a role in Rep-ITR specificity, it is possible that RBE' contacts alter the secondary structure of region 1 as it interacts with the RBE.

Because the regions of Rep conferring ITR specificity were separate (region 1 of Rep5 from aa97-146 and region 2 of Rep2 from aa151-161), a chimeric Rep possessing both regions was able to efficiently replicate ITR2 and ITR5. An ITR which could be replicated by any wt or chimeric Rep was constructed by excluding the DNA elements required for specificity; the ITR5 spacer and the ITR2 nicking stem. Most significantly, a novel origin of replication was generated. This ITR contained both of the elements for Rep specificity; the ITR5 spacer and the ITR2 nicking stem. As a result, only a chimeric Rep protein made up of Rep5 region 1 and Rep2 region 2 was able to replicate the ITR. The creation of a unique origin of replication highlights the power of studying the DNA-protein interactions of a viral origin of replication.

The creation of a unique DNA-protein interaction was possible because of the separation of the specific Rep-ITR interactions in AAV2 and AAV5. How and why these two different DNA-protein interactions evolved is unclear. It is likely due to evolutionary divergence in the ITR sequence which may have occurred in different hosts (AAV2 is related to other primate AAVs, AAV5 is related to non-primate AAVs such as goat and bovine). This model of replicative specificity can likely be extended to other parvoviruses such as snake AAV which has a highly conserved T-shaped ITR structure but different spacer and nicking stem lengths (Farkas et al. (2004) *J. Gen. Virol.* 85:555).

These results also stand to improve the safety of future AAV therapeutic vectors. The danger of AAV vector mobilization by wt AAV could be averted if therapeutic vectors harbored figs which no wt Rep could replicate (Hewitt et al. (2009) *J. Virol.* 83:3919).

Example 9

Snake ITR Vector Production

Figures 32, 33:
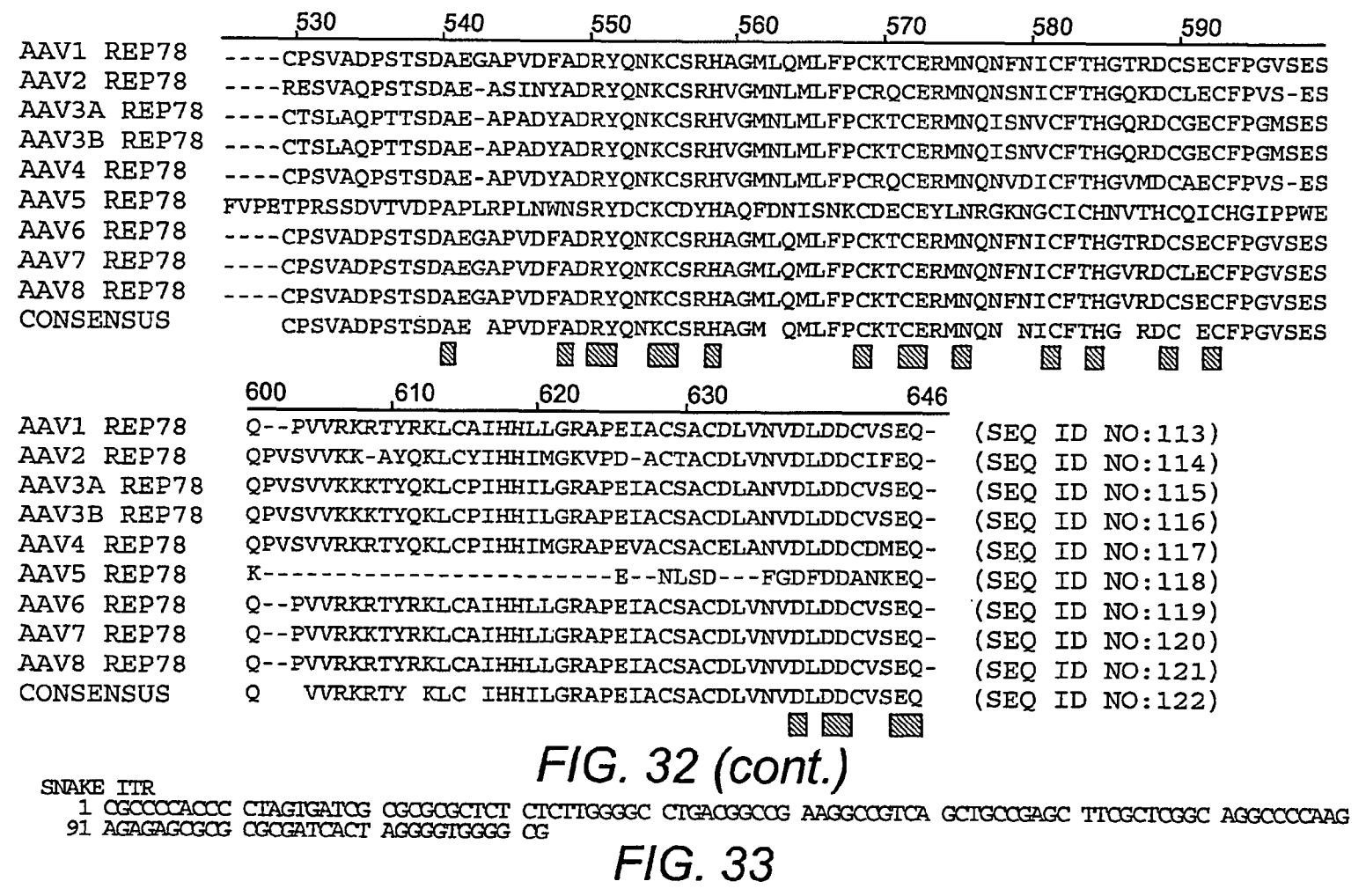
Figure 34:
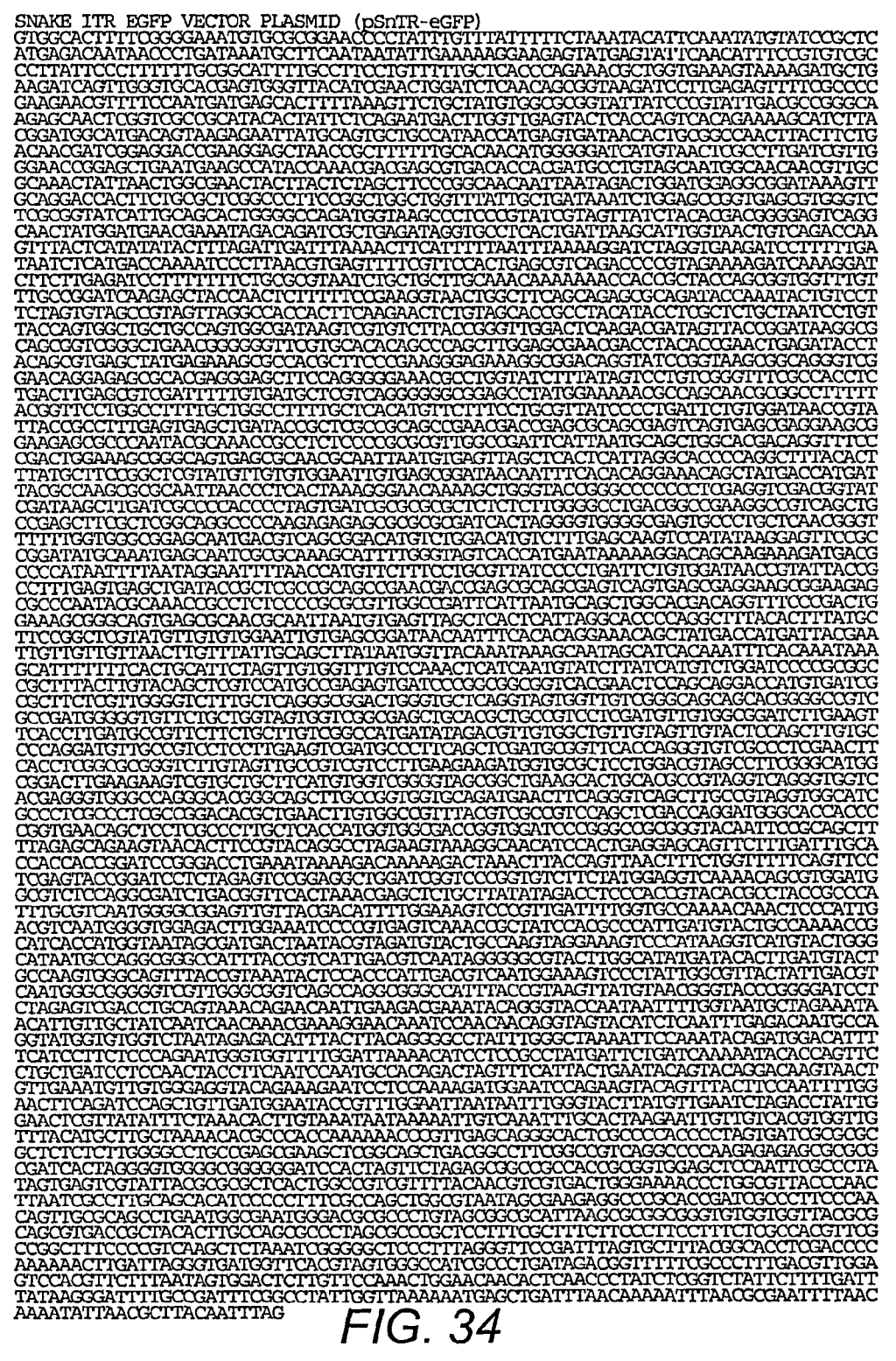

HEK 293 cells were cultured in Dulbecco Modified Eagle Medium (DMEM) supplemented with 10% Fetal Bovine Serum (Sigma, St. Louis, Mo.) and 100 units/nil penicillin and 100 µg/ml streptomycin and grown at 37° C. with 5% $CO_2$ saturation. To produce snake (royal python) ITR vectors, 10 µg of each of the following plasmids were transfected by PEI into HEK 293 cells in a 15 cm culture dish: pXX680 (Ad helper plasmid), pSnTR-eGFP (the ITR containing plasmid, SEQ ID NO:124), pSnRepCap2 (AAV helper plasmid containing the snake Rep genes and AAV2 Cap genes, SEQ ID NO:125), and pXR2 (AAV helper plasmid containing the AAV2 Rep and Cap genes). See FIGS. 33-35. Alternately, a plasmid expressing only the small AAV2 Rep proteins (Rep52 and Rep40) could be used in place of pXR2. 48 hours post-transfection, the cells were harvested and vector was purified by CsCl gradient centrifugation as previously described for other AAV vectors.

The foregoing is illustrative of the present invention, and is not to be construed as limiting thereof. The invention is defined by the following claims, with equivalents of the claims to be included therein.

What is claimed is:

1. A polynucleotide comprising at least one parvovirus inverted terminal repeat (ITR), wherein said ITR comprises:
   (a) a first structural element that functionally interacts with a large Rep protein from a first adeno-associated virus (AAV) but does not functionally interact with a large Rep protein from a second AAV; and
   (b) a second structural element that functionally interacts with the large Rep protein from the second AAV but does not functionally interact with the large Rep protein from the first AAV;
wherein the ITR functionally interacts with a synthetic AAV large Rep protein; and
wherein one of the structural elements is a nicking stem.

2. The polynucleotide of claim 1, wherein said ITR does not functionally interact with any wild-type large Rep protein.

3. The polynucleotide of claim 1, wherein said structural elements are selected from the group consisting of a nicking stem, a Rep binding element (RBE), and an extended RBE.

4. The polynucleotide of claim 1, wherein said first structural element is a nicking stem.

5. The polynucleotide of claim 1, wherein said second structural element is a spacer, a RBE or an extended RBE.

6. The polynucleotide of claim 1, wherein said ITR further comprises a third structural element that functionally interacts with a large Rep protein from an AAV that is the same as or different from the first and/or second AAV.

7. The polynucleotide of claim 1, further comprising a heterologous nucleic acid.

8. A viral vector comprising the polynucleotide of claim 1.

9. A recombinant parvovirus particle comprising the polynucleotide of claim 1.

10. The polynucleotide of claim 1, wherein said parvovirus is an adeno-associated virus (AAV).

11. The polynucleotide of claim 1, wherein said first and/or second structural element has a modified sequence as compared to the wild-type sequence of the ITR.

12. The polynucleotide of claim 11, wherein said modified sequence is a wild-type sequence from a different ITR.

13. The polynucleotide of claim 11, wherein said modified sequence is a synthetic sequence.

14. The polynucleotide of claim 11, wherein said first structural element is a nicking stem and said nicking stem comprises a wild-type AAV2 sequence.

15. The polynucleotide of claim 11, wherein said first structural element is a modified nicking stem comprising a change in height as compared to a wild-type sequence.

16. The polynucleotide of claim 11, wherein said first structural element is a modified nicking stem comprising a modified sequence as compared to a wild-type sequence.

17. The polynucleotide of claim 16, wherein said modified sequence is a modified terminal resolution site (trs) sequence.

18. The polynucleotide of claim 11, wherein said second structural element is a RBE and said RBE comprises a wild-type AAV5 sequence.

19. The polynucleotide of claim 11, wherein said second structural element is a RBE comprising a change in length or sequence relative to a wild-type sequence.

20. The viral vector of claim 8, which is an AAV vector.

21. The recombinant parvovirus particle of claim 9, which is an AAV particle.

* * * * *

UNITED STATES PATENT AND TRADEMARK OFFICE
CERTIFICATE OF CORRECTION

PATENT NO.        : 9,169,494 B2
APPLICATION NO.   : 13/521448
DATED             : October 27, 2015
INVENTOR(S)       : Hewitt et al.

It is certified that error appears in the above-identified patent and that said Letters Patent is hereby corrected as shown below:

In the Specification
Column 5, Line 25: Please correct "C or V;" to read -- G or V; --
Column 10, Line 49: Please correct "302275," to read -- J02275, --
Column 13, Line 54: Please correct "PASTA," to read -- FASTA, --
Column 23, Line 33: Please correct "14651" to read -- 146-151 --
Column 28, Line 54: Please correct "factory soluble" to read -- factorα soluble --
Column 30, Line 21: Please correct "HIV or Sly" to read -- HIV or SIV --
Column 45, Line 62: Please correct "UNC-CII" to read -- UNC-CH --
Column 46, Line 50: Please correct "RepS" to read -- Rep5 --
Column 49, Line 24: Please correct "T-A by also" to read -- T-A bp also --
Column 49, Line 26: Please correct "TTT." to read -- T/T. --
Column 49, Line 27: Please correct "RepS," to read -- Rep5, --
Column 49, Line 41: Please correct "three by" to read -- three bp --
Column 49, Line 43: Please correct "three by" to read -- three bp --
Column 54, Line 26: Please correct "seven by" to read -- seven bp --
Column 56, Line 19: Please correct "100 units/nil" to read -- 100 units/ml --

Signed and Sealed this
Twenty-eighth Day of June, 2016

Michelle K. Lee
*Director of the United States Patent and Trademark Office*

SEQUENCE LISTING

<160> NUMBER OF SEQ ID NOS: 155

<210> SEQ ID NO 1
<211> LENGTH: 4718
<212> TYPE: DNA
<213> ORGANISM: Adeno-associated virus 1

<400> SEQUENCE: 1

```
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga     180
cgtaaattac gtcataaggg agtggtcctg tattagctgt cacgtgagtg cttttgcgac     240
attttgcgac accacgtggc catttagggt atatatggcc gagtgagcga gcaggatctc     300
cattttgacc gcgaaatttg aacgagcagc agccatgccg ggcttctacg agatcgtgat     360
caaggtgccg agcgacctgg acgagcacct gccgggcatt tctgactcgt ttgtgagctg     420
ggtggccgag aaggaatggg agctgccccc ggattctgac atggatctga atctgattga     480
gcaggcaccc ctgaccgtgg ccgagaagct gcagcgcgac ttcctggtcc aatggcgccg     540
cgtgagtaag gccccggagg ccctcttctt tgttcagttc gagaagggcg agtcctactt     600
ccacctccat attctggtgg agaccacggg ggtcaaatcc atggtgctgg gccgcttcct     660
```

-continued

```
gagtcagatt agggacaagc tggtgcagac catctaccgc gggatcgagc cgaccctgcc    720
caactggttc gcggtgacca agacgcgtaa tggcgccgga gggggaaaca aggtggtgga    780
cgagtgctac atccccaact acctcctgcc caagactcag cccgagctgc agtgggcgtg    840
gactaacatg gaggagtata taagcgcctg tttgaacctg gccgagcgca aacgggctcgt   900 ggcgcagcac ctgacccacg tcagccagac ccaggagcag aacaaggaga atctgaaccc    960
caattctgac gcgcctgtca tccggtcaaa aacctccgcg cgctacatgg agctggtcgg   1020
gtggctggtg gaccggggca tcacctccga gaagcagtgg atccaggagg accaggcctc   1080
gtacatctcc ttcaacgccg cttccaactc gcggtcccag atcaaggccg ctctggacaa   1140
tgccggcaag atcatggcgc tgaccaaatc cgcgcccgac tacctggtag ccccgctcc    1200 gcccgcggac attaaaacca accgcatcta ccgcatcctg gagctgaacg gctacgaacc   1260
tgcctacgcc ggctccgtct ttctcggctg gcccagaaaa aggttcggga agcgcaacac   1320 catctgctg tttgggccgg ccaccacggg caagaccaac atcgcggaag ccatcgccca   1380
cgccgtgccc ttctacggct gcgtcaactg gaccaatgag aactttccct tcaatgattg   1440
cgtcgacaag atggtgatct ggtgggagga gggcaagatg acggccaagg tcgtggagtc   1500
cgccaaggcc attctcggcg gcagcaaggt gcgcgtggac caaaagtgca agtcgtccgc   1560
ccagatcgac cccacccccg tgatcgtcac ctccaacacc aacatgtgcg ccgtgattga   1620
cgggaacagc accaccttcg agcaccagca gccgttgcag gaccggatgt tcaaattga   1680 actcacccgc cgtctggagc atgactttgg caaggtgaca aagcaggaag tcaaagagtt   1740
cttccgctgg gcgcaggatc acgtgaccga ggtggcgcat gagttctacg tcagaaaggg   1800
tggagccaac aaaagaccccg ccccgatga cgcggataaa agcgagccca gcgggcctg   1860 cccctcagtc gcggatccat cgacgtcaga gcggaagga gctccggtgg actttgccga   1920
caggtaccaa aacaaatgtt ctcgtcacgc gggcatgctt cagatgctgt tccctgcaa   1980 gacatgcgag agaatgaatc agaatttcaa catttgcttc acgcacggga cgagagactg   2040
ttcagagtgc ttccccggcg tgtcagaatc tcaaccggtc gtcagaaaga ggacgtatcg   2100
gaaactctgt gccattcatc atctgctggg gcgggctccc gagattgctt gctcggcctg   2160
cgatctggtc aacgtggacc tggatgactg tgtttctgag caataaatga cttaaaccag   2220
gtatggctgc cgatggttat cttccagatt ggctcgagga caacctctct gagggcattc   2280
gcgagtggtg ggacttgaaa cctggagccc cgaagcccaa agccaaccag caaaagcagg   2340
acgacggccg gggtctggtg cttcctggct acaagtacct cggacccttc aacggactcg   2400
acaaggggga gcccgtcaac gcggcggacg cagcggccct cgagcacgac aaggcctacg   2460
accagcagct caaagcgggt gacaatccgt acctgcggta taccacgcc gacgccgagt   2520 tcaggagcg tctgcaagaa gatacgtctt ttgggggcaa cctcgggcga gcagtcttcc   2580
aggccaagaa gcgggttctc gaaccctctcg gtctggttga ggaaggcgct aagacggctc   2640
ctggaaagaa acgtccggta gagcagtcgc acaagagcc agactcctcc tcgggcatcg   2700
gcaagacagg ccagcagccc gctaaaaaga gactcaattt tggtcagact ggcgactcag   2760
agtcagtccc cgatccacaa cctctcggag aacctccagc acccccgct gctgtgggac   2820 ctactacaat ggcttcaggc ggtggcgcac caatggcaga caataacgaa ggcgccgacg   2880
gagtgggtaa tgcctcagga aattggcatt gcgattccac atggctgggc gacagagtca   2940
tcaccaccag caccccgcacc tgggccttgc ccacctacaa taaccactc tacaagcaaa   3000 tctccagtgc ttcaacgggg gccagcaacg acaaccacta cttcggctac agcacccct   3060
```

```
gggggtattt tgatttcaac agattccact gccacttttc accacgtgac tggcagcgac    3120
tcatcaacaa caattgggga ttccggccca agagactcaa cttcaaactc ttcaacatcc    3180
aagtcaagga ggtcacgacg aatgatggcg tcacaaccat cgctaataac cttaccagca    3240
cggttcaagt cttctcggac tcggagtacc agcttccgta cgtcctcggc tctgcgcacc    3300
agggctgcct ccctccgttc ccggcggacg tgttcatgat ccgcaatacg gctacctga    3360 cgctcaacaa tggcagccaa gccgtgggac gttcatcctt ttactgcctg aatatttcc    3420 cttctcagat gctgagaacg ggcaacaact ttaccttcag ctacaccttt gaggaagtgc    3480 cttttccacag cagctacgcg cacagccaga gcctggaccg gctgatgaat cctctcatcg    3540 accaataccct gtattacctg aacagaactc aaaatcagtc cggaagtgcc caaacaagg    3600 acttgctgtt tagccgtggg tctccagctg gcatgtctgt tcagcccaaa aactggctac    3660
ctggaccctg ttatcggcag cagcgcgttt ctaaaacaaa aacagacaac aacaacagca    3720
attttacctg gactggtgct tcaaaatata acctcaatgg cgtgaatcc atcatcaacc    3780 ctggcactgc tatggcctca cacaaagacg acgaagacaa gttcttcccc atgagcggtg    3840
tcatgatttt tggaaaagag agcgccggag cttcaaacac tgcattggac aatgtcatga    3900
ttacagacga agaggaaatt aaagccacta accctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg    4080
ccaaaattcc tcacacagat ggacacttc acccgtctcc tcttatgggc ggctttggac    4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttacttac ccgtccctg taattacgtg    4440 ttaatcaata aaccggttga ttcgtttcag ttgaactttg gtctcctgtc cttcttatct    4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                            4718
```

<210> SEQ ID NO 2
<211> LENGTH: 4679
<212> TYPE: DNA
<213> ORGANISM: Adeno-associated virus 2

<400> SEQUENCE: 2

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtggagtcg tgacgtgaat tacgtcatag    180
ggttagggag gtcctgtatt agaggtcacg tgagtgtttt cgacatttt gcgacaccat    240 gtggtcacgc tgggtattta agcccgagtg agcacgcagg gtctccattt tgaagcggga    300
ggtttgaacg cgcagccgcc atgccggggt tttacgagat tgtgattaag gtccccagcg    360
accttgacga gcatctgccc ggcatttctg acagctttgt gaactgggtg gccgagaagg    420
```

```
aatgggagtt gccgccagat tctgacatgg atctgaatct gattgagcag gcacccctga    480
ccgtggccga aagctgcag cgcgactttc tgacggaatg gcgccgtgtg agtaaggccc     540
cggaggccct tttctttgtg caatttgaga agggagagag ctacttccac atgcacgtgc    600
tcgtggaaac caccggggtg aaatccatgg ttttgggacg tttcctgagt cagattcgcg    660
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca    1020
aggggattac ctcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagcccgtg gaggacattt    1200
ccagcaatcg gatttataaa attttggaac taaacgggta cgatccccaa tatgcggctt    1260
ccgtcttttct gggatgggcc acgaaaaagt tcggcaagag gaacaccatc tggctgtttg    1320
ggcctgcaac taccgggaag accaacatcg cggaggccat agcccacact gtgcccttct    1380
acgggtgcgt aaactggacc aatgagaact ttcccttcaa cgactgtgtc gacaagatgg    1440
tgatctggtg ggaggagggg aagatgaccg ccaaggtcgt ggagtcggcc aaagccattc    1500
tcggaggaag caaggtgcgc gtggaccaga atgcaagtc ctcggcccag atagacccga    1560
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agacttttc cggtgggcaa    1740
aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaaggcgta tcagaaactg tgctacattc    2100
atcatatcat gggaaaggtg ccagacgctt gcactgcctg cgatctggtc aatgtggatt    2160
tggatgactg catctttgaa caataaatga tttaaatcag gtatggctgc cgatggttat    2220
cttccagatt ggctcgagga cactctctct gaaggaataa gacagtggtg gaagctcaaa    2280
cctggcccac caccaccaaa gcccgcagag cggcataagg acgacagcag ggtcttgtg     2340
cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt tcaggagcg ccttaaagaa     2520
gatacgtctt tggggggcaa cctcggacga gcagtcttcc aggcgaaaaa gagggttctt    2580
gaacctctgg gcctggttga ggaacctgtt aagacggctc cgggaaaaaa gaggccggta    2640
gagcactctc ctgtggagcc agactcctcc tcgggaaccg gaaaggcggg ccagcagcct    2700
gcaagaaaaa gattgaattt tggtcagact ggagacgcag actcagtacc tgaccccag    2760
cctctcggac agccaccagc agccccctct ggtctgggaa ctaatacgat ggctacaggc    2820
```

-continued

```
agtggcgcac caatggcaga caataacgag ggcgccgacg gagtgggtaa ttcctcggga    2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc acccccttggg ggtattttga cttcaacaga    3060
ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct tcattttta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg acccctgtta ccgccagcag    3660
cgagtatcaa agacatctgc ggataacaac aacagtgaat actcgtggac tggagctacc    3720
aagtaccacc tcaatggcag agactctctg gtgaatccgg gccgggccat ggcaagccac    3780
aaggacgatg aagaaaagtt ttttcctcag agcggggttc tcatctttgg aagcaaggc    3840 tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta acacccctcc tccacagatt    4140
ctcatcaaga cacccgggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa    4679
```

<210> SEQ ID NO 3
<211> LENGTH: 4726
<212> TYPE: DNA
<213> ORGANISM: Adeno-associated virus 3A

<400> SEQUENCE: 3

```
ttggccactc cctctatgcg cactcgctcg ctcggtgggg cctggcgacc aaaggtcgcc      60
agacggacgt gctttgcacg tccggcccca ccgagcgagc gagtgcgcat agagggagtg     120
gccaactcca tcactagagg tatggcagtg acgtaacgcg aagcgcgcga agcgagacca     180
cgcctaccag ctgcgtcagc agtcaggtga cccttttgcg acagtttgcg acaccacgtg     240
```

```
gccgctgagg gtatatattc tcgagtgagc gaaccaggag ctccattttg accgcgaaat    300
ttgaacgagc agcagccatg ccgggggttct acgagattgt cctgaaggtc ccgagtgacc    360
tggacgagcg cctgccgggc atttctaact cgtttgttaa ctgggtggcc gagaaggaat    420
gggacgtgcc gccggattct gacatggatc cgaatctgat tgagcaggca cccctgaccg    480
tggccgaaaa gcttcagcgc gagttcctgg tggagtggcg ccgcgtgagt aaggccccgg    540
aggccctctt ttttgtccag ttcgaaaagg gggagaccta cttccacctg cacgtgctga    600
ttgagaccat cggggtcaaa tccatggtgg tcggccgcta cgtgagccag attaaagaga    660
agctggtgac ccgcatctac cgcggggtcg agccgcagct tccgaactgg ttcgcggtga    720
ccaaaacgcg aaatggcgcc gggggcggga acaaggtggt ggacgactgc tacatcccca    780
actacctgct ccccaagacc cagcccgagc tccagtgggc gtggactaac atggaccagt    840
atttaagcgc ctgtttgaat ctcgcggagc gtaaacggct ggtggcgcag catctgacgc    900
acgtgtcgca gacgcaggag cagaacaaag agaatcagaa ccccaattct gacgcgccgg    960
tcatcaggtc aaaaacctca gccaggtaca tggagctggt cgggtggctg gtggaccgcg   1020
ggatcacgtc agaaaagcaa tggattcagg aggaccaggc ctcgtacatc tccttcaacg   1080
ccgcctccaa ctcgcggtcc cagatcaagg ccgcgctgga caatgcctcc aagatcatga   1140
gcctgacaaa gacggctccg gactacctgg tgggcagcaa cccgccggag gacattacca   1200
aaaatcggat ctaccaaatc ctggagctga acggtgtacga tccgcagtac gcggcctccg   1260
tcttcctggg ctgggcgcaa aagaagttcg ggaagaggaa caccatctgg ctctttgggc   1320
cggccacgac gggtaaaacc aacatcgcgg aagccatcgc ccacgccgtg cccttctacg   1380
gctgcgtaaa ctggaccaat gagaactttc ccttcaacga ttgcgtcgac aagatggtga   1440
tctggtggga ggagggcaag atgacggcca aggtcgtgga gagcgccaag gccattctgg   1500
gcggaagcaa ggtgcgcgtg gaccaaaagt gcaagtcatc ggcccagatc gaacccactc   1560
ccgtgatcgt cacctccaac accaacatgt gcgccgtgat tgacgggaac agcaccacct   1620
tcgagcatca gcagccgctg caggaccgga tgtttgaatt tgaacttacc cgccgtttgg   1680
accatgactt tgggaaggtc accaaacagg aagtaaagga cttttttccgg tgggcttccg   1740 atcacgtgac tgacgtggct catgagttct acgtcagaaa gggtggagct aagaaacgcc   1800
ccgcctccaa tgacgcggat gtaagcgagc caaaacggga gtgcacgtca cttgcgcagc   1860
cgacaacgtc agacgcggaa gcaccggcgg actacgcgga caggtaccaa aacaaatgtt   1920
ctcgtcacgt gggcatgaat ctgatgcttt ttccctgtaa aacatgcgag agaatgaatc   1980
aaatttccaa tgtctgtttt acgcatggtc aaagagactg tggggaatgc ttccctggaa   2040
tgtcagaatc tcaacccgtt tctgtcgtca aaaagaagac ttatcagaaa ctgtgtccaa   2100
ttcatcatat cctgggaagg gcacccgaga ttgcctgttc ggcctgcgat ttggccaatg   2160
tggacttgga tgactgtgtt tctgagcaat aaatgactta aaccaggtat ggctgctgac   2220
ggttatcttc cagattggct cgaggacaac ctttctgaag gcattcgtga gtggtgggct   2280
ctgaaacctg gagtccctca acccaaagcg aaccaacaac accaggacaa ccgtcgggt   2340 cttgtgcttc cgggttacaa atacctcgga cccgtaacg gactcgacaa aggagagccg    2400
gtcaacgagg cggacgcggc agccctcgaa cacgacaaag cttacgacca gcagctcaag   2460
gccggtgaca cccgtacct caagtacaac cacgccgacg ccgagtttca ggagcgtctt    2520
caagaagata cgtctttttgg gggcaacctt ggcagagcag tcttccaggc caaaaagagg    2580
atccttgagc ctcttggtct ggttgaggaa gcagctaaaa cggctcctgg aaagaagggg    2640
```

```
gctgtagatc agtctcctca ggaaccggac tcatcatctg gtgttggcaa atcgggcaaa    2700
cagcctgcca gaaaaagact aaatttcggt cagactggag actcagagtc agtcccagac    2760
cctcaacctc tcggagaacc accagcagcc cccacaagtt tgggatctaa tacaatggct    2820
tcaggcggtg gcgcaccaat ggcagacaat aacgagggtg ccgatggagt gggtaattcc    2880
tcaggaaatt ggcattgcga ttcccaatgg ctgggcgaca gagtcatcac caccagcacc    2940
agaacctggg ccctgcccac ttacaacaac catctctaca gcaaatctc cagccaatca    3000
ggagcttcaa cgacaaccca ctactttggc tacagcaccc cttgggggta ttttgacttt    3060
aacagattcc actgccactt ctccaccgt gactggcagc gactcattaa caacaactgg    3120
ggattccggc caagaaaact cagcttcaag ctcttcaaca tccaagttag aggggtcacg    3180
cagaacgatg gcacgacgac tattgccaat aaccttacca gcacggttca agtgtttacg    3240
gactcggagt atcagctccc gtacgtgctc gggtcggcgc accaaggctg tctcccgccg    3300
tttccagcgg acgtcttcat ggtccctcag tatggatacc tcaccctgaa caacggaagt    3360
caagcggtgg gacgctcatc ctttactgc ctggagtact ccccttcgca gatgctaagg    3420
actggaaata acttccaatt cagctatacc ttcgaggatg taccttttca cagcagctac    3480
gctcacagcc agagtttgga tcgcttgatg aatcctctta ttgatcagta tctgtactac    3540
ctgaacagaa cgcaaggaac aacctctgga acaaccaacc aatcacggct gcttttagc    3600
caggctgggc ctcagtctat gtctttgcag gccagaaatt ggctacctgg gccctgctac    3660
cggcaacaga gactttcaaa gactgctaac gacaacaaca acagtaactt ccttggaca    3720
gcggccagca aatatcatct caatggccgc gactcgctgg tgaatccagg accagctatg    3780
gccagtcaca aggacgatga agaaaaattt ttccctatgc acggcaatct aatattggc    3840
aaagaaggga caacggcaag taacgcagaa ttagataatg taatgattac ggatgaagaa    3900
gagattcgta ccaccaatcc tgtggcaaca gagcagtatg gaactgtggc aaataacttg    3960
cagagctcaa atacagctcc cacgactgga actgtcaatc atcagggggc cttacctggc    4020
atggtgtggc aagatcgtga cgtgtaccct caaggaccta tctgggcaaa gattcctcac    4080
acggatggac actttcatcc ttctcctctg atgggaggct ttggactgaa acatcgcct    4140
cctcaaatca tgatcaaaaa tactccggta ccggcaaatc ctccgacgac tttcagcccg    4200
gccaagtttg cttcattta cactcagtac tccactggac aggtcagcgt ggaaattgag    4260
tgggagctac agaaagaaaa cagcaaacgt tggaatccag agattcagta cacttccaac    4320
tacaacaagt ctgttaatgt ggactttact gtagacacta tggtgtttac ttgtgaacct    4380
cgccctattg aacccggta tctcacacga aacttgtgaa tcctggttaa tcaataaacc    4440
gtttaattcg tttcagttga actttggctc ttgtgcactt cttaatctt atcttgtttc    4500
catggctact gcgtagataa gcagcggcct gcggcgcttg cgcttcgcgg tttacaactg    4560
ctggttaata tttaactctc gccataccc tagtgatgga gttggccact ccctctatgc    4620
gcactcgctc gctcggtggg gcctggcgac caaaggtcgc cagacggacg tgctttgcac    4680
gtccggcccc accgagcgag cgagtgcgca tagagggagt ggccaa              4726
```

<210> SEQ ID NO 4
<211> LENGTH: 4722
<212> TYPE: DNA
<213> ORGANISM: Adeno-associated virus 3B

<400> SEQUENCE: 4

-continued

| | |
|---|---|
| tggccactcc ctctatgcgc actcgctcgc tcggtggggc ctggcgacca aaggtcgcca | 60 |
| gacggacgtg cttttgcacgt ccggccccac cgagcgagcg agtgcgcata gagggagtgg | 120 |
| ccaactccat cactagaggt atggcagtga cgtaacgcga agcgcgcgaa gcgagaccac | 180 |
| gcctaccagc tgcgtcagca gtcaggtgac ccttttgcga cagtttgcga caccacgtgg | 240 |
| ccgctgaggg tatatattct cgagtgagcg aaccaggagc tccattttga ccgcgaaatt | 300 |
| tgaacgagca gcagccatgc cggggttcta cgagattgtc ctgaaggtcc cgagtgacct | 360 |
| ggacgagcac ctgccgggca tttctaactc gtttgttaac tgggtggccg agaaggaatg | 420 |
| ggagctgccg ccggattctg acatggatcc gaatctgatt gagcaggcac ccctgaccgt | 480 |
| ggccgaaaag cttcagcgcg agttcctggt ggagtggcgc cgcgtgagta aggccccgga | 540 |
| ggccctcttt tttgtccagt tcgaaaaggg ggagacctac ttccacctgc acgtgctgat | 600 |
| tgagaccatc ggggtcaaat ccatggtggt cggccgctac gtgagccaga ttaaagagaa | 660 |
| gctggtgacc cgcatctacc gcggggtcga gccgcagctt ccgaactggt tcgcggtgac | 720 |
| caaaacgcga aatggcgccg ggggcgggaa caaggtggtg acgactgct acatccccaa | 780 |
| ctacctgctc cccaagaccc agcccgagct ccagtgggcg tggactaaca tggaccagta | 840 |
| tttaagcgcc tgtttgaatc tcgcggagcg taaacgctg gtggcgcagc atctgacgca | 900 |
| cgtgtcgcag acgcaggagc agaacaaaga gaatcagaac cccaattctg acgcgccggt | 960 |
| catcaggtca aaaacctcag ccaggtacat ggagctggtc gggtggctgg tggaccgcgg | 1020 |
| gatcacgtca gaaaagcaat ggattcagga ggaccaggcc tcgtacatct ccttcaacgc | 1080 |
| cgcctccaac tcgcggtccc agatcaaggc cgcgctggac aatgcctcca agatcatgag | 1140 |
| cctgacaaag acggctccgg actacctggt gggcagcaac ccgccggagg acattaccaa | 1200 |
| aaatcggatc taccaaatcc tggagctgaa cgggtacgat ccgcagtacg cggcctccgt | 1260 |
| cttcctgggc tgggcgcaaa agaagttcgg gaagaggaac accatctggc tctttgggcc | 1320 |
| ggccacgacg ggtaaaaacca acatcgcgga agccatcgcc cacgccgtgc ccttctacgg | 1380 |
| ctgcgtaaac tggaccaatg agaactttcc cttcaacgat tgcgtcgaca agatggtgat | 1440 |
| ctggtgggag gagggcaaga tgacggccaa ggtcgtggag agcgccaagg ccattctggg | 1500 |
| cggaagcaag gtgcgcgtgg accaaaagtg caagtcatcg gcccagatcg aacccactcc | 1560 |
| cgtgatcgtc acctccaaca ccaacatgtg cgccgtgatt gacgggaaca gcaccacctt | 1620 |
| cgagcatcag cagccgctgc aggaccggat gtttaaattt gaacttaccc gccgtttgga | 1680 |
| ccatgacttt gggaaggtca ccaaacagga agtaaaggac ttttttccggt gggcttccga | 1740 |
| tcacgtgact gacgtggctc atgagttcta cgtcagaaag ggtggagcta agaaacgccc | 1800 |
| cgcctccaat gacgcggatg taagcgagcc aaaacggcag tgcacgtcac ttgcgcagcc | 1860 |
| gacaacgtca gacgcggaag caccggcgga ctacgcggac aggtaccaaa acaaatgttc | 1920 |
| tcgtcacgtg ggcatgaatc tgatgctttt tccctgtaaa acatgcgaga gaatgaatca | 1980 |
| aatttccaat gtctgtttta cgcatggtca aagagactgt ggggaatgct tccctggaat | 2040 |
| gtcagaatct caacccgttt ctgtcgtcaa aaagaagact tatcagaaac tgtgtccaat | 2100 |
| tcatcatatc ctgggaaggg cacccgagat tgcctgttcg gcctgcgatt tggccaatgt | 2160 |
| ggacttggat gactgtgttt ctgagcaata aatgacttaa accaggtatg gctgctgacg | 2220 |
| gttatcttcc agattggctc gaggacaacc tttctgaagg cattcgtgag tggtgggctc | 2280 |
| tgaaacctgg agtccctcaa cccaaagcga accaacaaca ccaggacaac cgtcgggtc | 2340 |
| ttgtgcttcc gggttacaaa tacctcggac ccggtaacgg actcgacaaa ggagagccgg | 2400 |

```
tcaacgaggc ggacgcggca gccctcgaac acgacaaagc ttacgaccag cagctcaagg    2460
ccggtgacaa cccgtacctc aagtacaacc acgccgacgc cgagtttcag gagcgtcttc    2520
aagaagatac gtcttttggg ggcaaccttg gcagagcagt cttccaggcc aaaaagagga    2580
tccttgagcc tcttggtctg gttgaggaag cagctaaaac ggctcctgga agaagaggc     2640 ctgtagatca gtctcctcag gaaccggact catcatctgg tgttggcaaa tcggcaaac    2700 agcctgccag aaaaagacta aatttcggtc agactggcga ctcagagtca gtcccagacc    2760
ctcaacctct cggagaacca ccagcagccc ccacaagttt gggatctaat acaatggctt    2820
caggcggtgg cgcaccaatg gcagacaata acgagggtgc cgatggagtg ggtaattcct    2880
caggaaattg gcattgcgat tcccaatggc tgggcgacag agtcatcacc accagcacca    2940
gaacctgggc cctgcccact acaacaacc atctctacaa gcaaatctcc agccaatcag     3000
gagcttcaaa cgacaaccac tactttggct acagcacccc ttgggggtat tttgactta    3060 acagattcca ctgccacttc tcaccacgtg actggcagcg actcattaac aacaactggg    3120
gattccggcc caagaaactc agcttcaagc tcttcaacat ccaagttaaa gaggtcacgc    3180
agaacgatgg cacgacgact attgccaata accttaccag cacggttcaa gtgtttacgg    3240
actcggagta tcagctcccg tacgtgctcg gtcggcgca ccaaggctgt ctcccgccgt      3300
ttccagcgga cgtcttcatg gtccctcagt atggatacct caccctgaac aacgaagtc     3360 aagcggtggg acgctcatcc ttttactgcc tggagtactt cccttcgcag atgctaagga    3420
ctggaaataa cttccaattc agctatacct tcgaggatgt accttttcac agcagctacg    3480
ctcacagcca gagtttggat cgcttgatga atcctcttat tgatcagtat ctgtactacc    3540
tgaacagaac gcaaggaaca acctctggaa caaccaacca atcacggctg cttttagcc    3600 aggctgggcc tcagtctatg tctttgcagg ccagaaattg gctacctggg ccctgctacc    3660
ggcaacagag actttcaaag actgctaacg acaacaacaa cagtaacttt ccttggacag    3720
cggccagcaa atatcatctc aatggccgcg actcgctggt gaatccagga ccagctatgg    3780
ccagtcacaa ggacgatgaa gaaaaatttt tccctatgca cggcaatcta atatttggca    3840
aagaagggac aacggcaagt aacgcagaat tagataatgt aatgattacg gatgaagaag    3900
agattcgtac caccaatcct gtggcaacag agcagtatgg aactgtggca ataaacttgc    3960
agagctcaaa tacagctccc acgactagaa ctgtcaatga tcaggggcc ttacctggca     4020 tggtgtggca agatcgtgac gtgtaccttc aaggacctat ctgggcaaag attcctcaca    4080
cggatggaca ctttcatcct tctcctctga tgggaggctt tggactgaaa catccgcctc    4140
ctcaaatcat gatcaaaaat actccggtac cggcaaatcc tccgacgact ttcagcccgg    4200
ccaagtttgc ttcatttatc actcagtact ccactggaca ggtcagcgtg gaaattgagt    4260
gggagctaca gaaagaaaac agcaaacgtt ggaatccaga gattcagtac acttccaact    4320
acaacaagtc tgttaatgtg gactttactg tagacactaa tggtgtttat agtgaacctc    4380
gccctattgg aacccggtat ctcacacgaa acttgtaatc ctggttaatc aataaaccgt    4440
ttaattcgtt tcagttgaac tttggctctt gtgcacttct tatcttatct tgtttccatg    4500
gctactgcgt agataagcag cggcctgcgg cgcttgcgct tcgcggttta caactgctgg    4560
ttaatattta actctcgcca tacctctagt gatggagttg gccactccct ctatgcgcac    4620
tcgctcgctc ggtggggccg gacgtgcaaa gcacgtccgt ctggcgacct ttggtcgcca    4680
ggccccaccg agcgagcgag tgcgcataga gggagtggcc aa                      4722
```

<210> SEQ ID NO 5
<211> LENGTH: 4767
<212> TYPE: DNA
<213> ORGANISM: Adeno-associated virus 4

<400> SEQUENCE: 5

| | | | | | |
|---|---|---|---|---|---|
| ttggccactc | cctctatgcg | cgctcgctca | ctcactcggc | cctggagacc | aaaggtctcc | 60 |
| agactgccgg | cctctggccg | gcagggccga | gtgagtgagc | gagcgcgcat | agagggagtg | 120 |
| gccaactcca | tcatctaggt | tgcccactg | acgtcaatgt | gacgtcctag | ggttagggag | 180 |
| gtccctgtat | tagcagtcac | gtgagtgtcg | tatttcgcgg | agcgtagcgg | agcgcatacc | 240 |
| aagctgccac | gtcacagcca | cgtggtccgt | ttgcgacagt | ttgcgacacc | atgtggtcag | 300 |
| gagggtatat | aaccgcgagt | gagccagcga | ggagctccat | tttgcccgcg | aattttgaac | 360 |
| gagcagcagc | catgccgggg | ttctacgaga | tcgtgctgaa | ggtgcccagc | gacctggacg | 420 |
| agcacctgcc | cggcatttct | gactcttttg | tgagctgggt | ggccgagaag | gaatgggagc | 480 |
| tgccgccgga | ttctgacatg | gacttgaatc | tgattgagca | ggcaccctg | accgtggccg | 540 |
| aaaagctgca | acgcgagttc | ctggtcgagt | ggcgccgcgt | gagtaaggcc | ccggaggccc | 600 |
| tcttctttgt | ccagttcgag | aaggggggaca | gctacttcca | cctgcacatc | ctggtggaga | 660 |
| ccgtgggcgt | caaatccatg | gtggtgggcc | gctacgtgag | ccagattaaa | gagaagctgg | 720 |
| tgacccgcat | ctaccgcggg | gtcgagccgc | agcttccgaa | ctggttcgcg | gtgaccaaga | 780 |
| cgcgtaatgg | cgccggaggc | gggaacaagg | tggtggacga | ctgctacatc | cccaactacc | 840 |
| tgctccccaa | gacccagccc | gagctccagt | gggcgtggac | taacatggac | cagtatataa | 900 |
| gcgcctgttt | gaatctcgcg | gagcgtaaac | ggctggtggc | gcagcatctg | acgcacgtgt | 960 |
| cgcagacgca | ggagcagaac | aaggaaaacc | agaaccccaa | ttctgacgcg | ccggtcatca | 1020 |
| ggtcaaaaac | ctccgccagg | tacatggagc | tggtcgggtg | gctggtggac | cgcgggatca | 1080 |
| cgtcagaaaa | gcaatggatc | caggaggacc | aggcgtccta | catctccttc | aacgccgcct | 1140 |
| ccaactcgcg | gtcacaaatc | aaggccgcgc | tggacaatgc | ctccaaaatc | atgagcctga | 1200 |
| caaagacggc | tccggactac | ctggtgggcc | agaacccgcc | ggaggacatt | tccagcaacc | 1260 |
| gcatctaccg | aatcctcgag | atgaacgggt | acgatccgca | gtacgcggcc | tccgtcttcc | 1320 |
| tgggctgggc | gcaaaagaag | ttcgggaaga | ggaacaccat | ctggctcttt | gggccggcca | 1380 |
| cgacgggtaa | aaccaacatc | gcggaagcca | tcgcccacgc | cgtgcccttc | tacggctgcg | 1440 |
| tgaactggac | caatgagaac | tttccgttca | acgattgcgt | cgacaagatg | gtgatctggt | 1500 |
| gggaggaggg | caagatgacg | gccaaggtcg | tagagagcgc | caaggccatc | ctgggcggaa | 1560 |
| gcaaggtgcg | cgtggaccaa | aagtgcaagt | catcggccca | gatcgaccca | actcccgtga | 1620 |
| tcgtcacctc | caacaccaac | atgtgcgcgg | tcatcgacgg | aaactcgacc | accttcgagc | 1680 |
| accaacaacc | actccaggac | cggatgttca | agttcgagct | caccaagcgc | ctggagcacg | 1740 |
| actttggcaa | ggtcaccaag | caggaagtca | aagacttttt | ccgtgggcg | tcagatcacg | 1800 |
| tgaccgaggt | gactcacgag | ttttacgtca | aaagggtgg | agctagaaag | aggcccgccc | 1860 |
| ccaatgacgc | agatataagt | gagcccaagc | gggcctgtcc | gtcagttgcg | cagccatcga | 1920 |
| cgtcagacgc | ggaagctccg | gtggactacg | cggacaggta | ccaaaacaaa | tgttctcgtc | 1980 |
| acgtgggtat | gaatctgatg | cttttttccct | gccggcaatg | cgagagaatg | aatcagaatg | 2040 |
| tggacatttg | cttcacgcac | ggggtcatgg | actgtgccga | gtgcttcccc | gtgtcagaat | 2100 |
| ctcaacccgt | gtctgtcgtc | agaaagcgga | cgtatcagaa | actgtgtccg | attcatcaca | 2160 |

```
tcatggggag ggcgcccgag gtggcctgct cggcctgcga actggccaat gtggacttgg    2220
atgactgtga catggaacaa taaatgactc aaaccagata tgactgacgg ttaccttcca    2280
gattggctag aggacaacct ctctgaaggc gttcgagagt ggtgggcgct gcaacctgga    2340
gccctaaac ccaaggcaaa tcaacaacat caggacaacg ctcggggtct tgtgcttccg     2400
ggttacaaat acctcggacc cggcaacgga ctcgacaagg gggaacccgt caacgcagcg    2460
gacgcggcag ccctcgagca cgacaaggcc tacgaccagc agctcaaggc cggtgacaac    2520
ccctacctca gtacaaccca cgccgacgcg gagttccagc agcggcttca gggcgacaca    2580
tcgtttgggg gcaacctcgg cagagcagtc ttccaggcca aaagagggt tcttgaacct     2640
cttggtctgg ttgagcaagc gggtgagacg gctcctggaa agaagagacc gttgattgaa    2700
tcccccagc agcccgactc ctccacgggt atcggcaaaa aaggcaagca gccggctaaa     2760
aagaagctcg tttcgaaga cgaaactgga gcaggcgacg gaccccctga gggatcaact      2820
tccggagcca tgtctgatga cagtgagatg cgtgcagcag ctggcggagc tgcagtcgag    2880
ggcggacaag gtgccgatgg agtgggtaat gcctcgggtg attggcattg cgattccacc    2940
tggtctgagg gccacgtcac gaccaccagc accagaacct gggtcttgcc cacctacaac    3000
aaccacctct acaagcgact cggagagagc ctgcagtcca cacctacaa cggattctcc     3060
acccctggg gatactttga cttcaaccgc ttccactgcc acttctcacc acgtgactgg      3120
cagcgactca tcaacaacaa ctgggcatg cgacccaaag ccatgcgggt caaaatcttc      3180
aacatccagg tcaaggaggt cacgacgtcg aacggcgaga caacggtggc taataacctt    3240
accagcacgg ttcagatctt tgcggactcg tcgtacgaac tgccgtacgt gatggatgcg    3300
ggtcaagagg gcagcctgcc tccttttccc aacgacgtct ttatggtgcc ccagtacggc    3360
tactgtggac tggtgaccgg caacacttcg cagcaacaga ctgacagaaa tgccttctac    3420
tgcctggagt actttccttc gcagatgctg cggactggca caactttga aattacgtac     3480
agttttgaga aggtgccttt ccactcgatg tacgcgcaca gccagagcct ggaccggctg    3540
atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga ctggctgccc cgggccttca atcaagcagc agggcttctc aaagactgcc    3720
aatcaaaact caaagatccc tgccaccggg tcagacagtc tcatcaaata cgagacgcac    3780
agcactctgg acggaagatg gagtgccctg accccggac ctccaatggc cacggctgga    3840
cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccaccg atacggacat gtggggcaac ctacctggcg tgaccagag caacagcaac    4020
ctgccgaccg tggacagact gacagccttg ggagccgtgc ctggaatggt ctggcaaaac    4080
agagacattt actaccaggg tcccatttgg gccaagattc ctcataccga tggacacttt    4140
caccccctcac cgctgattgg tgggtttggg ctgaaacacc cgcctcctca aattttttatc   4200
aagaacaccc cggtacctgc gaatcctgca acgaccttca gctctactcc ggtaaactcc    4260
ttcattactc agtacagcac tggccaggtg tcggtgcaga ttgactggga gatccagaag    4320
gagcggtcca aacgctggaa ccccgaggtc cagtttacct ccaactacgg acagcaaaac    4380
tctctgttgt gggctcccga tgcggctggg aaatacactg agcctagggc tatcggtacc    4440
cgctacctca cccaccacct gtaataaacct gttaatcaat aaaccggttt attcgtttca    4500
```

-continued

```
gttgaacttt ggtctccgtg tccttcttat cttatctcgt ttccatggct actgcgtaca   4560
taagcagcgg cctgcggcgc ttgcgcttcg cggtttacaa ctgccggtta atcagtaact   4620
tctggcaaac cagatgatgg agttggccac attagctatg cgcgctcgct cactcactcg   4680
gccctggaga ccaaaggtct ccagactgcc ggcctctggc cggcagggcc gagtgagtga   4740
gcgagcgcgc atagagggag tggccaa                                      4767

<210> SEQ ID NO 6
<211> LENGTH: 4642
<212> TYPE: DNA
<213> ORGANISM: Adeno-associated virus 5

<400> SEQUENCE: 6
ctctcccccc tgtcgcgttc gctcgctcgc tggctcgttt ggggggggtgg cagctcaaag    60 agctgccaga cgacggccct ctggccgtcg cccccccaaa cgagccagcg agcgagcgaa   120
cgcgacaggg gggagagtgc cacactctca agcaagggg ttttgtaagc agtgatgtca   180
taatgatgta atgcttattg tcacgcgata gttaatgatt aacagtcatg tgatgtgttt   240
tatccaatag gaagaaagcg cgcgtatgag ttctcgcgag acttccgggg tataaaagac   300
cgagtgaacg agcccgccgc cattctttgc tctggactgc tagaggaccc tcgctgccat   360
ggctaccttc tatgaagtca ttgttcgcgt cccatttgac gtggaggaac atctgcctgg   420
aatttctgac agctttgtgg actgggtaac tggtcaaatt tgggagctgc tccagagtc   480 agatttaaat ttgactctgg ttgaacagcc tcagttgacg gtggctgata gaattcgccg   540
cgtgttcctg tacgagtgga acaaattttc caagcaggag tccaaattct ttgtgcagtt   600
tgaaaaggga tctgaatatt ttcatctgca cacgcttgtg gagacctccg gcatctcttc   660
catggtcctc ggccgctacg tgagtcagat tcgcgcccag ctggtgaaag tggtcttcca   720
gggaattgaa ccccagatca acgactgggt cgccatcacc aaggtaaaga agggcggagc   780
caataaggtg gtggattctg gtatattcc cgcctacctg ctgccgaagg tccaaccgga   840
gcttcagtgg gcgtggacaa acctggacga gtataaattg gccgccctga atctggagga   900
gcgcaaacgg ctcgtcgcgc agtttctggc agaatcctcg cagcgctcgc aggaggcggc   960
ttcgcagcgt gagttctcgg ctgacccggt catcaaaagc aagacttccc agaaatacat  1020
ggcgctcgtc aactggctcg tggagcacgg catcacttcc gagaagcagt ggatccagga  1080
aaatcaggag agctacctct ccttcaactc caccggcaac tctcggagcc agatcaaggc  1140
cgcgctcgac aacgcgacca aaattatgag tctgacaaaa agcgcggtgg actacctcgt  1200
ggggagctcc gttcccgagg acatttcaaa aaacagaatc tggcaaattt ttgagatgaa  1260
tggctacgac ccggcctacg cgggatccat cctctacggc tggtgtcagc gctccttcaa  1320 caaggaggaac accgtctggc tctacggacc cgccacgacc ggcaagacca acatcgcgga  1380
ggccatcgcc cacactgtgc cttttacgg ctgcgtgaac tggaccaatg aaaactttcc  1440
ctttaatgac tgtgtggaca aaatgctcat ttggtgggag gagggaaaga tgaccaacaa  1500
ggtggttgaa tccgccaagg ccatcctggg gggctcaaag gtgcgggtcg atcagaaatg  1560
taaatcctct gttcaaattg attctacccc tgtcattgta acttccaata caaacatgtg  1620
tgtggtggtg gatgggaatt ccacgacctt tgaacaccag cagccgctgg aggaccgcat  1680
gttcaaattt gaactgacta agcggctccc gccagatttt ggcaagatta ctaagcagga  1740
agtcaaggac ttttttgctt gggcaaaggt caatcaggtg ccggtgactc acgagtttaa  1800
agttcccagg gaattggcgg gaactaaagg ggcggagaaa tctctaaaac gcccactggg  1860
```

```
tgacgtcacc aatactagct ataaaagtct ggagaagcgg gccaggctct catttgttcc    1920
cgagacgcct cgcagttcag acgtgactgt tgatcccgct cctctgcgac cgctcaattg    1980
gaattcaagg tatgattgca aatgtgacta tcatgctcaa tttgacaaca tttctaacaa    2040
atgtgatgaa tgtgaatatt tgaatcgggg caaaaatgga tgtatctgtc acaatgtaac    2100
tcactgtcaa atttgtcatg ggattccccc ctgggaaaag gaaaacttgt cagattttgg    2160
ggattttgac gatgccaata agaacagta aataaagcga gtagtcatgt cttttgttga    2220
tcaccctcca gattggttgg aagaagttgg tgaaggtctt cgcgagtttt gggccttga    2280 agcgggccca ccgaaaccaa aacccaatca gcagcatcaa gatcaagccc gtggtcttgt    2340
gctgcctggt tataactatc tcggacccgg aaacggtctc gatcgaggag agcctgtcaa    2400
cagggcagac gaggtcgcgc gagagcacga catctcgtac aacgagcagc ttgaggcggg    2460
agacaacccc tacctcaagt acaaccacgc ggacgccgag tttcaggaga agctcgccga    2520
cgacacatcc ttcgggggaa acctcggaaa ggcagtcttt caggccaaga aaagggttct    2580
cgaacctttt ggcctggttg aagagggtgc taagacggcc cctaccggaa agcggataga    2640
cgaccacttt ccaaaaagaa agaaggctcg gaccgaagag gactccaagc cttccacctc    2700
gtcagacgcc gaagctggac ccagcggatc ccagcagctg caaatcccag cccaaccagc    2760
ctcaagtttg ggagctgata caatgtctgc gggaggtggc ggcccattgg gcgacaataa    2820
ccaaggtgcc gatggagtgg gcaatgcctc gggagattgg cattgcgatt ccacgtggat    2880
gggggacaga gtcgtcacca agtccacccg aacctgggtg ctgcccagct acaacaacca    2940
ccagtaccga gagatcaaaa gcggctccgt cgacggaagc aacgccaacg cctactttgg    3000
atacagcacc ccctgggggt actttgactt taaccgcttc cacagccact ggagcccccg    3060
agactggcaa agactcatca caactactg gggcttcaga ccccggtccc tcagagtcaa    3120
aatcttcaac attcaagtca aagaggtcac ggtgcaggac tccaccacca ccatcgccaa    3180
caacctcacc tccaccgtcc aagtgtttac ggacgacgac taccagctgc cctacgtcgt    3240
cggcaacggg accgagggat gcctgccggc cttccctccg caggtcttta cgctgccgca    3300
gtacggttac gcgacgctga accgcgacaa cacagaaaat cccaccgaga ggagcagctt    3360
cttctgccta gagtactttc ccagcaagat gctgagaacg ggcaacaact ttgagtttac    3420
ctacaacttt gaggaggtgc ccttccactc cagcttcgct cccagtcaga acctgttcaa    3480
gctggccaac ccgctggtgg accagtactt gtaccgcttc gtgagcacaa ataacactgg    3540
cggagtccag ttcaacaaga acctggccgg gagatacgcc aacacctaca aaactggtt    3600 cccggggccc atgggccgaa cccagggctg gaacctgggc tcggggtca accgcgccag    3660 tgtcagcgcc ttcgccacga ccaataggat ggagctcgag ggcgcgagtt accaggtgcc    3720
cccgcagccg aacggcatga ccaacaacct ccagggcagc aacacctatg ccctggagaa    3780
cactatgatc ttcaacagcc agccggcgaa cccgggcacc accgccacgt acctcgaggg    3840
caacatgctc atcaccagcg agagcgagac gcagccggtg aaccgcgtgg cgtacaacgt    3900
cggcgggcag atggccacca caaccagag ctccaccact gccccgcgca ccggcacgta    3960
caacctccag gaaatcgtgc ccggcagcgt gtggatggag agggacgtgt acctccaagg    4020
acccatctgg gccaagatcc cagagacggg ggcgcacttt caccccctc cggccatggg    4080 cggattcgga ctcaaacacc caccgccat gatgctcatc aagaacacgc ctgtgccgg    4140 aaatatcacc agcttctcgg acgtgcccgt cagcagcttc atcacccagt acagcaccgg    4200
```

-continued

```
gcaggtcacc gtggagatgg agtgggagct caagaaggaa aactccaaga ggtggaaccc      4260
agagatccag tacacaaaca actacaacga cccccagttt gtggactttg ccccggacag      4320
caccggggaa tacagaacca ccagacctat cggaacccga taccttaccc gaccccttta      4380
acccattcat gtcgcatacc ctcaataaac cgtgtattcg tgtcagtaaa atactgcctc      4440
ttgtggtcat tcaatgaata acagcttaca acatctacaa aacctccttg cttgagagtg      4500
tggcactctc cccctgtcg cgttcgctcg ctcgctggct cgtttggggg ggtggcagct       4560
caaagagctg ccagacgacg gccctctggc cgtcgccccc ccaaacgagc cagcgagcga      4620
gcgaacgcga cagggggggag ag                                              4642
```

<210> SEQ ID NO 7
<211> LENGTH: 4683
<212> TYPE: DNA
<213> ORGANISM: Adeno-associated virus 6

<400> SEQUENCE: 7

```
ttggccactc cctctctgcg cgctcgctcg ctcactgagg ccgggcgacc aaaggtcgcc       60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240 gtggtcacg tgggtattta agcccgagtg agcacgcagg gtctccattt tgaagcggga     300
ggtttgaacg cgcagcgcca tgccggggtt ttacgagatt gtgattaagg tccccagcga     360
ccttgacgag catctgcccg gcatttctga cagctttgtg aactgggtgg ccgagaagga     420
atgggagttg ccgccagatt ctgacatgga tctgaatctg attgagcagg caccc ctgac     480 cgtggccgag aagctgcagc gcgacttcct ggtccagtgg cgccgcgtga gtaaggcccc    540
ggaggccctc ttctttgttc agttcgagaa gggcgagtcc tacttccacc tccatattct    600
ggtggagacc acgggggtca aatccatggt gctgggccgc ttcctgagtc agattaggga    660
caagctggtg cagaccatct accgcgggat cgagccgacc ctgcccaact ggttcgcggt    720
gaccaagacg cgtaatggcg ccggaggggg gaacaaggtg gtggacgagt gctacatccc    780
caactacctc ctgcccaaga ctcagcccga gctgcagtgg gcgtggacta acatggagga    840
gtatataagc gcgtgtttaa acctggccga gcgcaaacgg ctcgtggcgc acgacctgac    900
ccacgtcagc cagacccagg agcagaacaa ggagaatctg aaccccaatt ctgacgcgcc    960
tgtcatccgg tcaaaaacct ccgcacgcta catggagctg gtcgggtggc tggtggaccg    1020
gggcatcacc tccgagaagc agtggatcca ggaggaccag gcctcgtaca tctccttcaa    1080
cgccgcctcc aactcgcggt cccagatcaa ggccgctctg gacaatgccg caagatcat    1140 ggcgctgacc aaatccgcgc cgactacct ggtaggcccc gctccgcccg ccgacattaa    1200
aaccaaccgc atttaccgca tcctggagct gaacggctac gaccctgcct acgccggctc    1260
cgtctttctc ggctgggccc agaaaaggtt cggaaaacgc aacaccatct ggctgtttgg    1320
gccggccacc acgggcaaga ccaacatcgc ggaagccatc gcccacgccg tgcccttcta    1380
cggctgcgtc aactgaccca atgagaactt tcccttcaac gattgcgtcg acaagatggt    1440
gatctggtgg gaggagggca aagatgacgg caaggtcgtg gagtccgcca aggccattct    1500
cggcggcagc aaggtgcgcg tggaccaaaa gtgcaagtcg tccgcccaga tcgatcccac    1560
ccccgtgatc gtcacctcca acaccaacat gtgcgccgtg attgacggga acagcaccac    1620
cttcgagcac cagcagccgt tgcaggaccg gatgttcaaa tttgaactca ccccgccgtct   1680
```

```
ggagcatgac tttggcaagg tgacaaagca ggaagtcaaa gagttcttcc gctgggcgca    1740
ggatcacgtg accgaggtgg cgcatgagtt ctacgtcaga aagggtggag ccaacaagag    1800
acccgccccc gatgacgcgg ataaaagcga gcccaagcgg gcctgcccct cagtcgcgga    1860
tccatcgacg tcagacgcgg aaggagctcc ggtggacttt gccgacaggt accaaaacaa    1920
atgttctcgt cacgcgggca tgcttcagat gctgtttccc tgcaaaacat gcgagagaat    1980
gaatcagaat ttcaacattt gcttcacgca cgggaccaga gactgttcag aatgtttccc    2040
cggcgtgtca gaatctcaac cggtcgtcag aaagaggacg tatcggaaac tctgtgccat    2100
tcatcatctg ctggggcggg ctcccgagat tgcttgctcg gcctgcgatc tggtcaacgt    2160
ggatctggat gactgtgttt ctgagcaata aatgacttaa accaggtatg ctgccgatg    2220
gttatcttcc agattggctc gaggacaacc tctctgaggg cattcgcgag tggtgggact    2280
tgaaacctgg agcccgaaa cccaaagcca accagcaaaa gcaggacgac ggccggggtc    2340
tggtgcttcc tggctacaag tacctcggac ccttcaacgg actcgacaag ggggagcccg    2400
tcaacgcggc ggatgcagcg gccctcgagc acgacaaggc ctacgaccag cagctcaaag    2460
cgggtgacaa tccgtacctg cggtataacc acgccgacgc cgagtttcag gagcgtctgc    2520
aagaagatac gtcttttggg ggcaaccctcg gcgagcagt cttccaggcc aagaagaggg    2580
ttctcgaacc ttttggtctg gttgaggaag gtgctaagac ggctcctgga agaaacgtc    2640
cggtagagca gtcgccacaa gagccagact cctcctcggg cattggcaag acaggccagc    2700
agcccgctaa aaagagactc aatttttggtc agactggcga ctcagagtca gtccccgacc    2760
cacaacctct cggagaacct ccagcaaccc ccgctgctgt gggacctact acaatggctt    2820
caggcggtgg cgcaccaatg gcagacaata cgaaggcgc cgacggagtg ggtaatgcct    2880
caggaaattg gcattgcgat tccacatggc tgggcgacag agtcatcacc accagcaccc    2940
gaacatgggc cttgcccacc tataacaacc acctctacaa gcaaatctcc agtgcttcaa    3000
cgggggccag caacgacaac cactacttcg gctacagcac cccctggggg tattttgatt    3060
tcaacagatt ccactgccat ttctcaccac gtgactggca gcgactcatc aacaacaatt    3120
ggggattccg gcccaagaga ctcaacttca agctcttcaa catccaagtc aaggaggtca    3180
cgacgaatga tggcgtcacg accatcgcta ataaccttac cagcacggtt caagtcttct    3240
cggactcgga gtaccagttg ccgtacgtcc tcggctctgc gcaccagggc tgcctccctc    3300
cgttcccggc ggacgtgttc atgattccgc agtacggcta cctaacgctc aacaatggca    3360
gccaggcagt gggacggtca tccttttact gcctggaata tttcccatcg cagatgctga    3420
gaacgggcaa taactttacc ttcagctaca ccttcgagga cgtgcctttc cacagcagct    3480
acgcgcacag ccagagcctg gaccggctga tgaatcctct catcgaccag tacctgtatt    3540
acctgaacag aactcagaat cagtccggaa gtgcccaaaa caaggacttg ctgtttagcc    3600
gggggtctcc agctggcatg tctgttcagc ccaaaaactg gctacctgga ccctgttacc    3660
ggcagcagcg cgtttctaaa acaaaaacag acaacaacaa cagcaacttt acctggactg    3720
gtgcttcaaa atataaacctt aatgggcgtg aatctataat caaccctggc actgctatgg    3780
cctcacacaa agacgacaaa gacaagttct ttcccatgag cggtgtcatg attttttggaa    3840
aggagagcgc cggagcttca aacactgcat tggacaatgt catgatcaca gacgaagagg    3900
aaatcaaagc cactaacccc gtggccaccg aaagatttgg gactgtggca gtcaatctcc    3960
agagcagcag cacagaccct gcgaccggag atgtgcatgt tatgggagcc ttacctggaa    4020
```

| | |
|---|---|
| tggtgtggca agacagagac gtataccctgc agggtcctat ttgggccaaa attcctcaca | 4080 |
| cggatggaca cttcaccccg tctcctctca tgggcggctt tggacttaag cacccgcctc | 4140 |
| ctcagatcct catcaaaaac acgcctgttc ctgcgaatcc tccggcagag ttttcggcta | 4200 |
| caaagtttgc ttcattcatc acccagtatt ccacaggaca agtgagcgtg agattgaat | 4260 |
| gggagctgca gaaagaaaac agcaaacgct ggaatcccga agtgcagtat acatctaact | 4320 |
| atgcaaaatc tgccaacgtt gatttcactg tggacaacaa tggactttat actgagcctc | 4380 |
| gccccattgg cacccgttac ctcacccgtc cctgtaatt gtgtgttaat caataaaccg | 4440 |
| gttaattcgt gtcagttgaa ctttggtctc atgtcgttat tatcttatct ggtcaccata | 4500 |
| gcaaccggtt acacattaac tgcttagttg cgcttcgcga atacccctag tgatggagtt | 4560 |
| gcccactccc tctatgcgcg ctcgctcgct cggtggggcc ggcagagcag agctctgccg | 4620 |
| tctgcggacc tttggtccgc aggccccacc gagcgagcga gcgcgcatag agggagtggg | 4680 |
| caa | 4683 |

<210> SEQ ID NO 8
<211> LENGTH: 4721
<212> TYPE: DNA
<213> ORGANISM: Adeno-associated virus 7

<400> SEQUENCE: 8

| | |
|---|---|
| ttggccactc cctctatgcg cgctcgctcg ctcggtgggg cctgcggacc aaaggtccgc | 60 |
| agacggcaga gctctgctct gccggcccca ccgagcgagc gagcgcgcat agagggagtg | 120 |
| gccaactcca tcactagggg taccgcgaag cgcctccccac gctgccgcgt cagcgctgac | 180 |
| gtaaatcacg tcataggga gtggtcctgt attagctgtc acgtgagtgc ttttgcgaca | 240 |
| ttttgcgaca ccacgtggcc atttgaggta tatatggccg agtgagcgag caggatctcc | 300 |
| attttgaccg cgaaatttga acgagcagca gccatgccgg gtttctacga gatcgtgatc | 360 |
| aaggtgccga cgaccctgga cgagcacctg ccgggcattt ctgactcgtt tgtgaactgg | 420 |
| gtggccgaga aggaatggga gctgccccg gattctgaca tggatctgaa tctgatcgag | 480 |
| caggcacccc tgaccgtggc cgagaagctg cagcgcgact ccctggtcca atggcgccgc | 540 |
| gtgagtaagg ccccggaggc cctgttcttt gttcagttcg agaagggcga gagctacttc | 600 |
| caccttcacg ttctggtgga gaccacgggg gtcaagtcca tggtgctagg ccgcttcctg | 660 |
| agtcagattc gggagaagct ggtccagacc atctaccgcg gggtcgagcc cacgctgccc | 720 |
| aactggttcg cggtgaccaa gacgcgtaat ggcgccggcg gggggaacaa ggtggtggac | 780 |
| gagtgctaca tccccaacta cctcctgccc aagacccagc ccgagctgca gtgggcgtgg | 840 |
| actaacatgg aggagtatat aagcgcgtgt ttgaacctgg ccgaacgcaa acggctcgtg | 900 |
| gcgcagcacc tgacccacgt cagccagacg caggagcaga acaaggagaa tctgaacccc | 960 |
| aattctgacg cgcccgtgat caggtcaaaa acctccgcgc gctacatgga gctggtcggg | 1020 |
| tggctggtgg accggggcat cacctccgag aagcagtgga tccaggagga ccaggcctcg | 1080 |
| tacatctcct tcaacgccgc ctccaactcg cggtcccaga tcaaggccgc gctggacaat | 1140 |
| gccggcaaga tcatgcgcct gaccaaatcc gcgcccgact acctggtggg gcctcgctg | 1200 |
| cccgcggaca ttaaaaccaa ccgcatctac cgcatcctgg agctgaacgg gtacgatcct | 1260 |
| gcctacgccg gctccgtctt tctcggctgg gcccagaaaa agttcgggaa gcgcaacacc | 1320 |
| atctggctgt tgggcccgc caccaccggc aagaccaaca ttgcggaagc catcgcccac | 1380 |
| gccgtgccct tctacggctg cgtcaactgg accaatgaga actttcccct caacgattgc | 1440 |

```
gtcgacaaga tggtgatctg gtgggaggag ggcaagatga cggccaaggt cgtggagtcc    1500
gccaaggcca ttctcggcgg cagcaaggtg cgcgtggacc aaaagtgcaa gtcgtccgcc    1560
cagatcgacc ccacccccgt gatcgtcacc tccaacacca acatgtgcgc cgtgattgac    1620
gggaacagca ccaccttcga gcaccagcag ccgttgcagg accggatgtt caaatttgaa    1680
ctcacccgcc gtctggagca cgactttggc aaggtgacga agcaggaagt caaagagttc    1740
ttccgctggg ccagtgatca cgtgaccgag gtggcgcatg agttctacgt cagaaagggc    1800
ggagccagca aaagacccgc ccccgatgac gcggatataa gcagcccaa gcgggcctgc    1860 ccctcagtcg cggatccatc gacgtcagac gcggaaggag ctccggtgga ctttgccgac    1920
aggtaccaaa acaaatgttc tcgtcacgcg ggcatgattc agatgctgtt ccctgcaaa    1980 acgtgcgaga gaatgaatca gaatttcaac atttgcttca cacacggggt cagagactgt    2040
ttagagtgtt tccccggcgt gtcagaatct caaccggtcg tcagaaaaaa gacgtatcgg    2100
aaactctgcg cgattcatca tctgctgggg cgggcgcccg agattgcttg ctcggcctgc    2160
gacctggtca acgtggacct ggacgactgc gtttctgagc aataaatgac ttaaaccagg    2220
tatggctgcc gatggttatc ttccagattg gctcgaggac aacctctctg agggcattcg    2280
cgagtggtgg gacctgaaac ctggagcccc gaaacccaaa gccaaccagc aaaagcagga    2340
caacggccgg ggtctggtgc ttcctggcta caagtacctc ggaccccttca acggactcga    2400 caaggggggag cccgtcaacg cggcggacgc agcggccctc gagcacgaca aggcctacga    2460
ccagcagctc aaagcgggtg acaatccgta cctgcggtat aaccacgccg acgccgagtt    2520
tcaggagcgt ctgcaagaag atacgtcatt tgggggcaac ctcgggcgag cagtcttcca    2580
ggccaagaag cggttctcg aacctctcgg tctggttgag gaaggcgcta agacggctcc    2640
tgcaaagaag agaccggtag agccgtcacc tcagcgttcc cccgactcct ccacgggcat    2700
cggcaagaaa ggccagcagc ccgccagaaa gagactcaat ttcggtcaga ctggcgactc    2760
agagtcagtc cccgaccctc aacctctcgg agaacctcca gcagcgccct ctagtgtggg    2820
atctggtaca gtggctgcag gcggtggcgc accaatggca gacaataacg aaggtgccga    2880
cggagtgggt aatgcctcag gaaattggca ttgcgattcc acatggctgg gcgacagagt    2940
cattaccacc agcacccgaa cctgggccct gcccacctac aacaaccacc tctacaagca    3000
aatctccagt gaaactgcag gtagtaccaa cgacaacacc tacttcggct acagcacccc    3060 ctggggtat tttgacttta acagattcca ctgccacttc tcaccacgtg actggcagcg    3120
actcatcaac aacaactggg gattccggcc caagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300
ccagggctgc ctgcctccgt tcccggcgga cgtcttcatg attcctcagt acggctacct    3360
gactctcaac aatggcagtc agtctgtggg acgttcctcc ttctactgcc tggagtactt    3420
cccctctcag atgctgagaa cgggcaacaa ctttgagttc agctacagct cgaggacgt    3480 gcctttccac agcagctacg cacacagcca gagcctggac cggctgatga atcccctcat    3540
cgaccagtac ttgtactacc tggccagaac acagagtaac ccaggaggca cagctggcaa    3600
tcgggaactg cagtttttacc agggcgggcc ttcaactatg gccgaacaag ccaagaattg    3660
gttacctgga ccttgcttcc ggcaacaaag agtctccaaa acgctggatc aaaacaacaa    3720
cagcaacttt gcttggactg gtgccaccaa atatcacctg aacggcagaa actcgttggt    3780
```

-continued

| | |
|---|---|
| taatcccggc gtcgccatgg caactcacaa ggacgacgag gaccgctttt tcccatccag | 3840 |
| cggagtcctg attttTggaa aaactggagc aactaacaaa actacattgg aaaatgtgtt | 3900 |
| aatgacaaat gaagaagaaa ttcgtcctac taatcctgta gccacggaag aatacgggat | 3960 |
| agtcagcagc aacttacaag cggctaatac tgcagcccag acacaagttg tcaacaacca | 4020 |
| gggagcctta cctggcatgg tctggcagaa ccgggacgtg tacctgcagg gtcccatctg | 4080 |
| ggccaagatt cctcacacgg atggcaactt tcacccgtct cctttgatgg gcggctttgg | 4140 |
| acttaaacat ccgcctcctc agatcctgat caagaacact cccgttcccg ctaatcctcc | 4200 |
| ggaggtgttt actcctgcca gtttgcttc gttcatcaca cagtacagca ccggacaagt | 4260 |
| cagcgtggaa atcgagtggg agctgcagaa ggaaaacagc aagcgctgga acccggagat | 4320 |
| tcagtacacc tccaactttg aaaagcagac tggtgtggac tttgccgttg acagccaggg | 4380 |
| tgtttactct gagcctcgcc ctattggcac tcgttacctc acccgtaatc tgtaattgca | 4440 |
| tgttaatcaa taaaccggtt gattcgtttc agttgaactt tggtctcctg tgcttcttat | 4500 |
| cttatcggtt tccatagcaa ctggttacac attaactgct tgggtgcgct tcacgataag | 4560 |
| aacactgacg tcaccgcggt accccctagtg atggagttgg ccactcccTc tatgcgcgct | 4620 |
| cgctcgctcg gtggggcctg cggaccaaag gtccgcagac ggcagagctc tgctctgccg | 4680 |
| gcccccaccga gcgagcgagc gcgcatagag ggagtggcca a | 4721 |

<210> SEQ ID NO 9
<211> LENGTH: 4393
<212> TYPE: DNA
<213> ORGANISM: Adeno-associated virus 8

<400> SEQUENCE: 9

| | |
|---|---|
| cagagaggga gtggccaact ccatcactag gggtagcgcg aagcgcctcc cacgctgccg | 60 |
| cgtcagcgct gacgtaaatt acgtcatagg ggagtggtcc tgtattagct gtcacgtgag | 120 |
| tgcttttgcg gcattttgcg acaccacgtg gccatttgag gtatatatgg ccagtgagc | 180 |
| gagcaggatc tccattttga ccgcgaaatt tgaacgagca gcagccatgc cgggcttcta | 240 |
| cgagatcgtg atcaaggtgc cgagcgacct ggacgagcac ctgccgggca tttctgactc | 300 |
| gtttgtgaac tgggtggccg agaaggaatg ggagctgccc ccggattctg acatggatcg | 360 |
| gaatctgatc gagcaggcac ccctgaccgt ggccgagaag ctgcagcgcg acttcctggt | 420 |
| ccaatggcgc cgcgtgagta aggcccccgga ggccctcttc tttgttcagt tcgagaaggg | 480 |
| cgagagctac tttcacctgc acgttctggt cgagaccacg ggggtcaagt ccatggtgct | 540 |
| aggccgcttc ctgagtcaga ttcgggaaaa gcttggtcca gaccatctac ccgcggggtc | 600 |
| gagccccacc ttgcccaact ggttcgcggt gaccaaagac gcggtaatgg cgccggcggg | 660 |
| ggggaacaag gtggtggacg agtgctacat ccccaactac ctcctgccca agactcagcc | 720 |
| cgagctgcag tgggcgtgga ctaacatgga ggagtatata agcgcgtgct gaacctggc | 780 |
| cgagcgcaaa cggctcgtgg cgcagcacct gacccacgtc agccagacgc aggagcagaa | 840 |
| caaggagaat ctgaacccca ttctgacgc gccgtgatc aggtcaaaaa cctccgcgcg | 900 |
| ctatatggag ctggtcgggt ggctggtgga ccggggcatc acctccgaga agcagtggat | 960 |
| ccaggaggac caggcctcgt acatctcctt caacgccgcc tccaactcgc ggtcccagat | 1020 |
| caaggccgcg ctggacaatg ccggcaagat catggcgctg accaaatccg cgcccgacta | 1080 |
| cctggtgggg cctctgctgc ccgcggacat tacccagaac cgcatctacc gcatcctcgc | 1140 |
| tctcaacggc tacgaccctg cctacgccgg ctccgtcttt ctcggctggg ctcagaaaaa | 1200 |

```
gttcgggaaa cgcaacacca tctggctgtt tggacccgcc accaccggca agaccaacat    1260
tgcggaagcc atcgcccacg ccgtgccctt ctacggctgc gtcaactgga ccaatgagaa    1320
ctttcccttc aatgattgcg tcgacaagat ggtgatctgg tgggaggagg gcaagatgac    1380
ggccaaggtc gtggagtccg ccaaggccat tctcggcggc agcaaggtgc gcgtggacca    1440
aaagtgcaag tcgtccgccc agatcgaccc caccccgtg atcgtcacct ccaacaccaa     1500
catgtgcgcc gtgattgacg ggaacagcac caccttcgag caccagcagc ctctccagga    1560
ccggatgttt aagttcgaac tcacccgccg tctggagcac gactttggca aggtgacaaa    1620
gcaggaagtc aaagagttct tccgctgggc cagtgatcac gtgaccgagg tggcgcatga    1680
gttttacgtc agaaagggcg gagccagcaa agacccgcc cccgatgacg cggataaaag     1740
cgagcccaag cgggcctgcc cctcagtcgc ggatccatcg acgtcagacg cggaaggagc    1800
tccggtggac tttgccgaca ggtaccaaaa caaatgttct cgtcacgcgg gcatgcttca    1860
gatgctgttt ccctgcaaaa cgtgcgagag aatgaatcag aatttcaaca tttgcttcac    1920
acacggggtc agagactgct cagagtgttt ccccggcgtg tcagaatctc aaccggtcgt    1980
cagaaagagg acgtatcgga aactctgtgc gattcatcat ctgctggggc gggctcccga    2040
gattgcttgc tcggcctgcg atctggtcaa cgtggacctg gatgactgtg tttctgagca    2100
ataaatgact taaaccaggt atggctgccg atggttatct tccagattgg ctcgaggaca    2160
acctctctga gggcattcgc gagtggtggg cgctgaaacc tggagcccg aagcccaaag     2220 ccaaccagca aaagcaggac gacggccggg gtctggtgct tcctggctac aagtacctcg    2280
gacccttcaa cggactcgac aaggggagc ccgtcaacgc ggcggacgca gcggccctcg     2340
agcacgacaa ggcctacgac cagcagctgc aggcgggtga caatccgtac ctgcggtata    2400
accacgccga cgccgagttt caggagcgtc tgcaagaaga tacgtctttt ggggcaacc     2460 tcgggcgagc agtcttccag gccaagaagc gggttctcga acctctcggt ctggttgagg    2520
aaggcgctaa dacggctcct ggaaagaaga daccggtaga gccatcaccc cagcgttctc    2580
cagactcctc tacgggcatc ggcaagaaag gccaacagcc cgccagaaaa agactcaatt    2640
ttggtcagac tggcgactca gagtcagttc cagaccctca acctctcgga gaacctccag    2700
cagcgccctc tggtgtggga cctaatacaa tggctgcagg cggtggcgca ccaatggcag    2760
acaataacga aggcgccgac ggagtgggta gttcctcggg aaattggcat tgcgattcca    2820
catggctggg cgacagagtc atcaccacca gcacccgaac ctgggccctg cccacctaca    2880
acaaccacct ctacaagcaa atctccaacg ggacatcggg aggagccacc aacgacaaca    2940
cctacttcgg ctacagcacc ccctgggggt attttgactt taacagattc cactgccact    3000
tttcaccacg tgactggcag cgactcatca acaacaactg gggattccgg cccaagagac    3060
tcagcttcaa gctcttcaac atccaggtca aggaggtcac gcagaatgaa ggcaccaaga    3120
ccatcgccaa taacctcacc agcaccatcc aggtgtttac ggactcggag taccagctgc    3180
cgtacgttct cggctctgcc caccagggct gcctgcctcc gttcccggcg acgtgttca     3240 tgattcccca gtacggctac ctaacactca acaacggtag tcaggccgtg ggacgctcct    3300
ccttctactg cctggaatac tttccttcgc agatgctgag aaccggcaac aacttccagt    3360
ttacttacac cttcgaggac gtgcctttcc acagcagcta cgcccacagc cagagcttgg    3420
accggctgat gaatcctctg attgaccagt acctgtacta cttgtctcgg actcaaacaa    3480
caggaggcac ggcaaatacg cagactctgg gcttcagcca aggtgggcct aatacaatgg    3540
```

```
ccaatcaggc aaagaactgg ctgccaggac cctgttaccg ccaacaacgc gtctcaacga   3600
caaccgggca aaacaacaat agcaactttg cctggactgc tgggaccaaa taccatctga   3660
atggaagaaa ttcattggct aatcctggca tcgctatggc aacacacaaa gacgacgagg   3720
agcgtttttt tcccagtaac gggatcctga ttttggcaa acaaaatgct gccagagaca   3780
atgcggatta cagcgatgtc atgctcacca gcgaggaaga aatcaaaacc actaaccctg   3840
tggctacaga ggaatacggt atcgtggcag ataacttgca gcagcaaaac acggctcctc   3900
aaattggaac tgtcaacagc cagggggcct acccggtat ggtctggcag aaccgggacg   3960
tgtacctgca gggtcccatc tgggccaaga ttcctcacac ggacggcaac ttccacccgt   4020
ctccgctgat gggcggcttt ggcctgaaac atcctccgcc tcagatcctg atcaagaaca   4080
cgcctgtacc tgcggatcct ccgaccacct caaccagtc aaagctgaac tctttcatca   4140
cgcaatacag caccggacag gtcagcgtgg aaattgaatg ggagctgcag aaggaaaaca   4200
gcaagcgctg gaaccccgag atccagtaca cctccaacta ctacaaatct acaagtgtgg   4260
actttgctgt taatacagaa ggcgtgtact ctgaaccccg ccccattggc acccgttacc   4320
tcacccgtaa tctgtaattg cctgttaatc aataaaccgg ttgattcgtt tcagttgaac   4380
tttggtctct gcg                                                      4393

<210> SEQ ID NO 10
<211> LENGTH: 4385
<212> TYPE: DNA
<213> ORGANISM: Adeno-associated virus 9

<400> SEQUENCE: 10
cagagaggga gtggccaact ccatcactag gggtaatcgc gaagcgcctc ccacgctgcc     60
gcgtcagcgc tgacgtagat tacgtcatag gggagtggtc ctgtattagc tgtcacgtga    120
gtgcttttgc gacatttgc gacaccacat ggccatttga ggtatatatg gccgagtgag    180
cgagcaggat ctccattttg accgcgaaat ttgaacgagc agcagccatg ccgggcttct    240
acgagattgt gatcaaggtg ccgagcgacc tggacgagca cctgccgggc atttctgact    300
cttttgtgaa ctgggtggcc gagaaggaat gggagctgcc cccggattct gacatggatc    360
ggaatctgat cgagcaggca cccctgaccg tggccgagaa gctgcagcgc gacttcctgg    420
tccaatggcg ccgcgtgagt aaggcccgg aggccctctt ctttgttcag ttcgagaagg    480
gcgagagcta ctttcacctg cacgttctgg tcgagaccac gggggtcaag tccatggtgc    540
taggccgctt cctgagtcag attcgggaga agctggtcca gaccatctac cgcgggatcg    600
agccgacccct gcccaactgg ttcgcggtga ccaagacgcg taatggcgcc ggcgggggga    660
acaaggtggt ggacgagtgc tacatcccca actacctcct gcccaagact cagcccgagc    720
tgcagtgggc gtggactaac atggaggagt atataagcgc gtgcttgaac ctggccgagc    780
gcaaacggct cgtggcgcag cacctgaccc acgtcagcca gacgcaggag cagaacaagg    840
agaatctgaa cccaattct gacgcgcccg tgatcaggtc aaaaacctcc gcgcgctaca    900
tggagctggt cgggtggctg gtggaccggg gcatcacctc cgagaagcag tggatccagg    960
aggaccaggc ctcgtacatc tccttcaacg ccgcctccaa ctcgcggtcc cagatcaagg   1020
ccgcgctgga caatgccggc aagatcatgg cgctgaccaa atccgcgccc gactacctgg   1080
taggcccttc acttccggtg acattacgc agaaccgcat ctaccgcatc ctgcagctca   1140
acggctacga ccctgcctac gccggctccg tctttctcgg ctgggcacaa aagaagttcg   1200
ggaaacgcaa caccatctgg ctgtttgggc cggccaccac gggaaagacc aacatcgcag   1260
```

```
aagccattgc ccacgccgtg cccttctacg gctgcgtcaa ctggaccaat gagaactttc    1320
ccttcaacga ttgcgtcgac aagatggtga tctggtggga ggagggcaag atgacggcca    1380
aggtcgtgga gtccgccaag gccattctcg gcggcagcaa ggtgcgcgtg gaccaaaagt    1440
gcaagtcgtc cgcccagatc gaccccactc ccgtgatcgt cacctccaac accaacatgt    1500
gcgccgtgat tgacgggaac agcaccacct tcgagcacca gcagcctctc caggaccgga    1560
tgtttaagtt cgaactcacc cgccgtctgg agcacgactt tggcaaggtg acaaagcagg    1620
aagtcaaaga gttcttccgc tgggccagtg atcacgtgac cgaggtggcg catgagtttt    1680
acgtcagaaa gggcggagcc agcaaaagac ccgcccccga tgacgcggat aaaagcgagc    1740
ccaagcgggc ctgcccctca gtcgcggatc catcgacgtc agacgcggaa ggagctccgg    1800
tggactttgc cgacaggtac caaaacaaat gttctcgtca cgcgggcatg cttcagatgc    1860
tgcttccctg caaaacgtgc gagagaatga atcagaattt caacatttgc ttcacacacg    1920
gggtcagaga ctgctcagag tgtttccccg gcgtgtcaga atctcaaccg gtcgtcagaa    1980
agaggacgta tcggaaactc tgtgcgattc atcatctgct ggggcgggct cccgagattg    2040
cttgctcggc ctgcgatctg gtcaacgtgg acctggatga ctgtgtttct gagcaataaa    2100
tgacttaaac caggtatggc tgccgatggt tatcttccag attggctcga ggacaacctc    2160
tctgagggca ttcgcgagtg gtgggcgctg aaacctggag ccccgaagcc caaagccaac    2220
cagcaaaagc aggacgacgg ccggggtctg gtgcttcctg gctacaagta cctcggaccc    2280
ttcaacggac tcgacaaggg ggagcccgtc aacgcggcgg acgcagcggc cctcgagcac    2340
ggcaaggcct acgaccagca gctgcaggcg ggtgacaatc cgtacctgcg gtataaccac    2400
gccgacgccg agtttcagga gcgtctgcaa gaagatacgt cttttggggg caacctcggg    2460
cgagcagtct tccaggccaa gaagcgggtt ctcgaacctc tcggtctggt tgaggaaggc    2520
gctaagacgg ctcctggaaa gaagagaccg gtagagccat caccccagcg ttctccagac    2580
tcctctacgg gcatcggcaa gaaaggccaa cagcccgcca gaaaaagact caattttggt    2640
cagactggcg actcagagtc agttccagac cctcaacctc tcggagaacc tccagcagcg    2700
ccctctggtg tgggacctaa tacaatggct gcaggcggtg gcgcaccaat ggcagacaat    2760
aacgaaggcg ccgacggagt gggtaattcc tcgggaaatt ggcattgcga ttccacatgg    2820
ctgggggaca gagtcatcac caccagcacc cgaacctggg cattgccccac ctacaacaac    2880 cacctctaca gcaaatctc caatggaaca tcgggaggaa gcaccaacga caacacctac    2940
tttggctaca gcaccccctg ggggtatttt gacttcaaca gattccactg ccacttctca    3000
ccacgtgact ggcagcgact catcaacaac aactgggat tccggccaaa gagactcaac    3060
ttcaagctgt tcaacatcca ggtcaaggag gttacgacga acgaaggcac caagaccatc    3120
gccaataacc ttaccagcac cgtccaggtc tttacggact cggagtacca gctaccgtac    3180
gtcctaggct ctgcccacca aggatgcctg ccaccgtttc ctgcagacgt cttcatggtt    3240
cctcagtacg gctacctgac gctcaacaat ggaagtcaag cgttaggacg ttcttctttc    3300
tactgtctgg aatacttccc ttctcagatg ctgagaaccg gcaacaactt tcagttcagc    3360
tacactttcg aggacgtgcc tttccacagc agctacgcac acagccagag tctagatcga    3420
ctgatgaacc ccctcatcga ccagtaccta tactacctgg tcagaacaca gacaactgga    3480
actgggggaa ctcaaacttt ggcattcagc caagcaggcc ctagctcaat ggccaatcag    3540 gctagaaaact gggtacccgg gccttgctac cgtcagcagc gcgtctccac aaccaccaac    3600
```

| | |
|---|---|
| caaaataaca acagcaactt tgcgtggacg ggagctgcta aattcaagct gaacgggaga | 3660 |
| gactcgctaa tgaatcctgg cgtggctatg catcgcaca aagacgacga ggaccgcttc | 3720 |
| tttccatcaa gtggcgttct catatttggc aagcaaggag ccgggaacga tggagtcgac | 3780 |
| tacagccagg tgctgattac agatgaggaa gaaattaaag ccaccaaccc tgtagccaca | 3840 |
| gaggaatacg gagcagtggc catcaacaac caggccgcta acacgcaggc gcaaactgga | 3900 |
| cttgtgcata accagggagt tattcctggt atggtctggc agaaccggga cgtgtacctg | 3960 |
| cagggcccta tttgggctaa aatacctcac acagatggca ctttcacccc gtctcctctg | 4020 |
| atgggtggat ttggactgaa acacccacct ccacagattc taattaaaaa tacaccagtg | 4080 |
| ccggcagatc ctcctcttac cttcaatcaa gccaagctga actctttcat cacgcagtac | 4140 |
| agcacgggac aagtcagcgt ggaaatcgag tgggagctgc agaaagaaaa cagcaagcgc | 4200 |
| tggaatccag agatccagta tacttcaaac tactacaaat ctacaaatgt ggactttgct | 4260 |
| gtcaatacca aaggtgttta ctctgagcct cgccccattg gtactcgtta cctcacccgt | 4320 |
| aatttgtaat tgcctgttaa tcaataaacc ggttaattcg tttcagttga actttggtct | 4380 |
| ctgcg | 4385 |

<210> SEQ ID NO 11
<211> LENGTH: 4087
<212> TYPE: DNA
<213> ORGANISM: Adeno-associated virus 11

<400> SEQUENCE: 11

| | |
|---|---|
| atgccgggct ctacgagat cgtgatcaag gtgccgagcg acctggacga gcacctgccg | 60 |
| ggcatttctg actcgtttgt gaactgggtg gccgagaagg aatgggagct gccccccggat | 120 |
| tctgacatgg atcggaatct gatcgagcag gcacccctga ccgtggccga gaagctgcag | 180 |
| cgcgacttcc tggtccactg gcgccgcgtg agtaaggccc cggaggccct cttctttgtt | 240 |
| cagttcgaga agggcgagtc ctacttccac ctccacgttc tcgtcgagac cacggggtc | 300 |
| aagtccatgg tcctgggccg cttcctgagt cagatcagag acaggctggt gcagaccatc | 360 |
| taccgcgggg tcgagcccac gctgcccaac tggttcgcgg tgaccaagac gcgaaatggc | 420 |
| gccggcgggg ggaacaaggt ggtggacgag tgctacatcc ccaactacct cctgcccaag | 480 |
| acccagcccg agctgcagtg ggcgtggact aacatggagg agtatataag cgcgtgtcta | 540 |
| aacctcgcgg agcgtaaacg gctcgtggcg cagcacctga cccacgtcag ccagacgcag | 600 |
| gagcagaaca aggagaatct gaacccgaat tctgacgcgc ccgtgatcag gtcaaaaacc | 660 |
| tccgcgcgct acatggagct ggtcgggtgg ctggtggacc ggggcatcac ctccgagaag | 720 |
| cagtggatcc aggaggacca ggcctcgtac atctccttca acgccgcctc caactcgcgg | 780 |
| tcccagatca aggccgcgct ggacaatgcc ggaaagatca tggcgctgac caaatccgcg | 840 |
| cccgactacc tggtaggccc gtccttaccc gcggacatta aggccaaccg catctaccgc | 900 |
| atcctggagc tcaacggcta cgaccccgcc tacgccggct ccgtcttcct gggctgggcg | 960 |
| cagaaaaagt tcggtaaacg caacaccatc tggctgtttg gcccgccac caccggcaag | 1020 |
| accaacatcg cggaagccat agcccacgcc gtgcccttct acggctgcgt gaactggacc | 1080 |
| aatgagaact ttcccttcaa cgattgcgtc gacaagatgg tgatctggtg ggaggagggc | 1140 |
| aagatgaccg ccaaggtcgt ggagtccgcc aaggccattc tgggcggaag caaggtcgcc | 1200 |
| gtggaccaaa agtgcaagtc ctcggcccag atcgaccca cgcccgtgat cgtcacctcc | 1260 |
| aacaccaaca tgtgcgccgt gatcgacggg aacagcacca ccttcgagca ccagcagccg | 1320 |

```
ctgcaggacc gcatgttcaa gttcgagctc acccgccgtc tggagcacga ctttggcaag   1380
gtgaccaagc aggaagtcaa agagttcttc cgctgggctc aggatcacgt gactgaggtg   1440
gcgcatgagt tctacgtcag aaagggcgga gccaccaaaa gacccgcccc cagtgacgcg   1500
gatataagcg agcccaagcg ggcctgcccc tcagttccgg agccatcgac gtcagacgcg   1560
gaagcaccgg tggactttgc ggacaggtac caaaacaaat gttctcgtca cgcgggcatg   1620
cttcagatgc tgtttccctg caagacatgc gagagaatga atcagaattt caacgtctgc   1680
ttcacgcacg gggtcagaga ctgctcagag tgcttccccg gcgcgtcaga atctcaaccc   1740
gtcgtcagaa aaaagacgta tcagaaactg tgcgcgattc atcatctgct ggggcgggca   1800
cccgagattg cgtgttcggc ctgcgatctc gtcaacgtgg acttggatga ctgtgtttct   1860
gagcaataaa tgacttaaac caggtatggc tgctgacggt tatcttccag attggctcga   1920
ggacaacctc tctgagggca ttcgcgagtg gtgggacctg aaacctggag ccccgaagcc   1980
caaggccaac cagcagaagc aggacgacgg ccggggtctg gtgcttcctg gctacaagta   2040
cctcggaccc ttcaacggac tcgacaaggg ggagcccgtc aacgcggcgg acgcagcggc   2100
cctcgagcac gacaaggcct acgaccagca gctcaaagcg ggtgacaatc cgtacctgcg   2160
gtataaccac gccgacgccg agtttcagga gcgtctgcaa gaagatacgt cttttggggg   2220
caacctcggg cgagcagtct tccaggccaa gaagagggta ctcgaacctc tgggcctggt   2280
tgaagaaggt gctaaaacgg ctcctggaaa gaagagaccg ttagagtcac cacaagagcc   2340
cgactcctcc tcgggcatcg gcaaaaaagg caaacaacca gccagaaaga ggctcaactt   2400
tgaagaggac actggagccg agacggacc ccctgaagga tcagatacca gcgccatgtc   2460
ttcagacatt gaaatgcgtg cagcaccggg cggaaatgct gtcgatgcgg acaaggttc   2520 cgatggagtg ggtaatgcct cgggtgattg gcattgcgat tccacctggt ctgagggcaa   2580
ggtcacaaca acctcgacca gaacctgggt cttgcccacc tacaacaacc acttgtacct   2640
gcgtctcgga acaacatcaa gcagcaacac ctacaacgga ttctccaccc cctggggata   2700
ttttgacttc aacagattcc actgtcactt ctcaccacgt gactggcaaa gactcatcaa   2760
caacaactgg ggactacgac caaaagccat gcgcgttaaa atcttcaata tccaagttaa   2820
ggaggtcaca acgtcgaacg gcgagactac ggtcgctaat aaccttacca gcacggttca   2880
gatatttgcg gactcgtcgt atgagctccc gtacgtgatg gacgctggac aagaggggag   2940
cctgcctcct ttccccaatg acgtgttcat ggtgcctcaa tatggctact gtggcatcgt   3000
gactggcgag aatcagaacc aaacggacag aaacgctttc tactgcctgg agtatttccc   3060
ttcgcaaatg ttgagaactg gcaacaactt tgaaatggct acaactttg agaaggtgcc   3120 gttccactca atgtatgctc acagccgagg cctggacaga ctgatgaatc ccctcctgga   3180
ccagtacctg tggcacttac agtcgactac ctctggagag actctgaatc aaggcaatgc   3240
agcaaccaca tttggaaaaa tcaggagtgg agactttgcc ttttacagaa gaactggct   3300 gcctgggcct tgtgttaaac agcagagatt ctcaaaaact gccagtcaaa attacaagat   3360
tcctgccagc gggggcaacg ctctgttaaa gtatgacacc cactatacct taaacaaccg   3420
ctggagcaac atcgcgcccg gacctccaat ggccacagcc ggaccttcgg atggggactt   3480
cagtaacgcc cagcttatat tccctggacc atctgttacc ggaaatacaa caacttcagc   3540
caacaatctt tgtttacat cagaagaaga aattgctgcc accaacccaa gagacacgga   3600
catgtttggc cagattgctg acaataatca gaatgctaca actgctccca taccggcaa   3660
```

```
cgtgactgct atgggagtgc tgcctggcat ggtgtggcaa acagagaca tttactacca    3720 agggccaatt tgggccaaga tcccacacgc ggacggacat tttcatcctt caccgctgat    3780
tggtgggttt ggactgaaac acccgcctcc ccagatattc atcaagaaca ctcccgtacc    3840
tgccaatcct gcgacaacct tcactgcagc cagagtggac tctttcatca cacaatacag    3900
caccggccag gtcgctgttc agattgaatg ggaaattgaa aaggaacgct ccaaacgctg    3960
gaatcctgaa gtgcagttta cttcaaacta tgggaaccag tcttctatgt tgtgggctcc    4020
tgatacaact gggaagtata cagagccgcg ggttattggc tctcgttatt tgactaatca    4080
tttgtaa                                                              4087

<210> SEQ ID NO 12
<211> LENGTH: 4180
<212> TYPE: DNA
<213> ORGANISM: Adeno-associated virus 13

<400> SEQUENCE: 12
ccgcgagtga gcgaaccagg agctccattt tgcccgcgaa ttttgaacga gcagcagcca      60
tgccgggatt ctacgagatt gtcctgaagg tgcccagcga cctggacgag cacctgcctg     120
gcatttctga ctcttttgta aactgggtgg cggagaagga atgggagctg ccgccggatt     180
ctgacatgga tctgaatctg attgagcagg caccctaac cgtggccgaa aagctgcaac     240
gcgaattcct ggtcgagtgg cgccgcgtga gtaaggcccc ggaggcctc ttctttgttc      300 agttcgagaa gggggacagc tacttccacc tacacattct ggtggagacc gtgggcgtga     360
aatccatggt ggtgggccgc tacgtgagcc agattaaaga gaagctggtg acccgcatct     420
accgcggggt cgagccgcag cttccgaact ggttcgcggt gaccaagacg cgtaatggcg     480
ccggaggcgg gaacaaggtg gtggacgact gctacatccc caactacctg ctccccaaga     540
cccagcccga gctccagtgg gcgtggacta atatggacca gtatttaagc gcctgtttga     600
atctcgcgga gcgtaaacgg ctggtggcgc agcatctgac gcacgtgtcg cagacgcagg     660
agcagaacaa agagaaccag aatcccaatt ctgacgcgcc ggtgatcaga tcaaaaacct     720
ccgcgaggta catggagctg gtcgggtggc tggtggaccg cggatcacg tcagaaaagc      780 aatggatcca ggaggaccag gcctcttaca tctccttcaa cgccgcctcc aactcgcggt     840
cacaaatcaa ggccgcactg gacaatgcct ccaaatttat gagcctgaca aaaacgctc     900 cggactacct ggtgggaaac aacccgccgg aggacattac cagcaaccgg atctacaaaa     960
tcctcgagat gaacgggtac gatccgcagt acgcggcctc cgtcttcctg ggctgggcgc    1020
aaaagaagtt cgggaagagg aacaccatct ggctctttgg gccggccacg acgggtaaaa    1080
ccaacatcgc tgaagctatc gcccacgccg tgccttttta cggctgcgtg aactggacca    1140
atgagaactt tccgttcaac gattgcgtcg acaagatggt gatctggtgg gaggagggca    1200
agatgacggc caaggtcgtg gagtccgcca aggccattct gggcggaagc aaggtgcgcg    1260
tggaccaaaa gtgcaagtca tcggcccaga tcgacccaac tcccgtcatc gtcacctcca    1320
acaccaacat gtgcgcggtc atcgacggaa attccaccac cttcgagcac caacaaccac    1380
tccaagaccg gatgttcaag ttcgagctca ccaagcgcct ggagcacgac tttggcaagg    1440
tcaccaagca ggaagtcaag gacttttttcc ggtgggcgtc agatcacgtg actgaggtgt    1500
ctcacgagtt ttacgtcaga aagggtggag ctagaaagag gccgccccc aatgacgcag      1560 atataagtga gcccaagcgg gcctgtccgt cagttgcgca gccatcgacg tcagacgcgg    1620
aagctccggt ggactacgcg gacaggtacc aaaacaaatg ttctcgtcac gtgggcatga    1680
```

-continued

```
atctgatgct ttttccctgc cggcaatgcg agagaatgaa tcagaatgtg gacatttgct   1740
tcacgcacgg ggtcatggac tgtgccgagt gcttccccgt gtcagaatct caacccgtgt   1800
ctgtcgtcag aaagcggaca tatcagaaac tgtgtccgat tcatcacatc atggggaggg   1860
cgcccgaggt ggcttgttcg gcctgcgatc tggccaatgt ggacttggat gactgtgaca   1920
tggagcaata aatgactcaa accagatatg actgacggtt accttccaga ttggctagag   1980
gacaacctct ctgaaggcgt tcgagagtgg tgggcgctgc aacctggagc ccctaaaccc   2040
aaggcaaatc aacaacatca ggacaacgct cggggtcttg tgcttccggg ttacaaatac   2100
ctcggacccg gcaacggact tgacaagggg gaacccgtca acgcagcgga cgcggcagcc   2160
ctcgaacacg acaaggccta cgaccagcag ctcaaggccg gtgacaaccc ctacctcaag   2220
tacaaccacg ccgacgccga gtttcaggag cgtcttcaag aagatacgtc ttttgggggc   2280
aacctcggac gagcagtctt ccaggccaaa aagaggatcc ttgagcctct gggtctggtt   2340
gaggaagcgg ctaagacggc tcctggaaaa aagagacctg tagagcaatc tccagcagaa   2400
ccggactcct cttcgggcat cggcaaatca ggccagcagc ccgctagaaa aagactgaat   2460
tttggtcaga ctggcgacac agagtcagtc ccagaccctc aaccactcgg acaacctccc   2520
gcagccccct ctggtgtggg atctactaca atggcttcag gcggtggcgc accaatggca   2580
gacaataacg agggtgccga tggagtgggt aattcctcag gaaattggca ttgcgattcc   2640
caatggctgg gcgacagagt catcaccacc agcacccgca cctgggccct gcccacctac   2700
aacaatcacc tctacaagca aatctccagc caatcaggag ccaccaacga caaccactac   2760
tttggctaca gcaccccctg ggggtatttt gacttcaaca gattccactg ccacttttca   2820 

ccacgtgact ggcaaagact catcaacaac aactggggat tccgacccaa gagactcaac   2880
ttcaagctct ttaacattca agtcaaagag gtcacgcaga atgacggtac gacgacgatt   2940
gccaataacc ttaccagcac ggttcaggtg tttactgact ccgagtacca gctcccgtac   3000
gtcctcggct cggcgcatca gggatgcctc ccgccgttcc cagcagacgt cttcatggtc   3060
ccacagtatg gatacctcac cctgaacaac gggagtcagg cggtaggacg ctcttccttt   3120
tactgcctgg agtactttcc ttctcagatg ctgcgtactg gaaacaactt tcagtttagc   3180
tacacttttg aagacgtgcc tttccacagc agctacgctc acagccaaag tctggaccgt   3240
ctcatgaatc ctctgatcga ccagtacctg tactatctga acaggacaca aacagccagt   3300
ggaactcagc agtctcggct actgtttagc caagctggac ccaccagtat gtctcttcaa   3360
gctaaaaact ggctgcctgg accttgctac agacagcagc gtctgtcaaa gcaggcaaac   3420
gacaacaaca acagcaactt tccctggact ggtgccacca aatatcatct gaatggccgg   3480
gactcattgg tgaacccggg ccctgctatg gccagtcaca aggatgacaa agaaaagttt   3540
ttccccatgc atggaaccct gatatttggt aaagaaggaa caaatgccaa caacgcggat   3600
ttggaaaatg tcatgattac agatgaagaa gaaatccgca ccaccaatcc cgtggctacg   3660
gagcagtacg ggactgtgtc aaataatttg caaaactcaa acgctggtcc aactactgga   3720
actgtcaatc accaaggagc gttacctggt atggtgtggc aggatcgaga cgtgtacctg   3780
cagggaccca tttgggccaa gattcctcac accgatggac actttcatcc ttctccactg   3840
atgggaggtt ttgggctcaa acacccgcct cctcagatca tgatcaaaaa cactcccgtt   3900
ccagccaatc ctcccacaaa ctttagtgcg gcaaagtttg cttccttcat cacacagtac   3960
tccacggggc aggtcagcgt ggagatcgag tgggagctgc agaaggagaa cagcaaacgc   4020
```

```
tggaatcccg aaattcagta cacttccaac tacaacaaat ctgttaatgt ggactttact     4080
gtggacacta atggtgtgta ttcagagcct cgccccattg caccagata cctgactcgt     4140 aatctgtaat tgcttgttaa tcaataaacc ggttaattcg                          4180

<210> SEQ ID NO 13
<211> LENGTH: 5594
<212> TYPE: DNA
<213> ORGANISM: Human parvovirus B19

<400> SEQUENCE: 13
ccaaatcaga tgccgccggt cgccgccggt aggcgggact tccggtacaa gatggcggac      60
aattacgtca tttcctgtga cgtcatttcc tgtgacgtca cttccggtgg gcgggacttc     120
cggaattagg gttggctctg gccagcttg cttggggttg ccttgacact aagacaagcg     180
gcgcgccgct tgtcttagtg gcacgtcaac cccaagcgct ggcccagagc caaccctaat     240
tccggaagtc ccgcccaccg gaagtgacgt cacaggaaat gacgtcacag gaaatgacgt     300
aattgtccgc catcttgtac cggaagtccc gcctaccggc ggcgaccggc ggcatctgat     360
ttggtgtctt cttttaaatt ttagcgggct ttttcccgc cttatgcaaa tgggcagcca     420
ttttaagtgt ttcactataa ttttattggt cagttttgta acggttaaaa tgggcggagc     480
gtaggcgggg actacagtat atatagcacg gcactgccgc agctcttcct ttctgggctg     540 cttttcctg gactttcttg ctgttttttg tgagctaact aacaggtatt tatactactt     600
gttaacatac taacatggag ctatttagag gggtgcttca agtttcttct aatgttctgg     660
actgtgctaa cgataactgg tggtgctctt tactggattt agacacttct gactgggaac     720
cactaactca tactaacaga ctaatggcaa tatacttaag cagtgtggct tctaagcttg     780
actttaccgg ggggccacta gcggggtgct tgtactttt tcaagtagaa tgtaacaaat     840
ttgaagaagg ctatcatatt catgtggtta ttggggggcc agggttaaac cccagaaacc     900
tcacagtgtg tgtagagggg ttatttaata atgtacttta tcaccttgta actgaaaatg     960
taaagctaaa attttttgcca ggaatgacta caaaaggcaa atactttaga gatggagagc    1020 agttttataga aaactatttta atgaaaaaaa tacctttaaa tgttgtatgg tgtgttacta    1080
atattgatgg atatatagat acctgtattt ctgctacttt tagaagggga gcttgccatg    1140
ccaagaaacc ccgcattacc acagccataa atgacactag tagtgatgct ggggagtcta    1200
gcggcacagg ggcagaggtt gtgccaatta atgggaaggg aactaaggct agcataaagt    1260
ttcaaactat ggtaaactgg ttgtgtgaaa acagagtgtt tacagaggat aagtggaaac    1320
tagttgactt taaccagtac actttactaa gcagtagtca cagtggaagt tttcaaattc    1380
aaagtgcact aaaactagca atttataaag caactaattt agtgcctaca agcacatttc    1440
tattgcatac agactttgag caggttatgt gtattaaaga caataaaatt gttaaattgt    1500
tactttgtca aaactatgac cccctattag tggggcagca tgtgttaaag tggattgata    1560
aaaaatgtgg caagaaaaat acactgtggt tttatgggcc gccaagtaca ggaaaaacaa    1620
acttggcaat ggccattgct aaaagtgttc cagtatatgg catggttaac tggaataatg    1680
aaaactttcc atttaatgat gtagcaggga aagcttggt ggtctgggat gaaggtatta    1740
ttaagtctac aattgtagaa gctgcaaaag ccatttttagg cgggcaaccc accagggtag    1800
atcaaaaaat gcgtggaagt gtagctgtgc ctgagtacc tgtggttata accagcaatg    1860
gtgacattac ttttgttgta agcgggaaca ctacaacaac tgtacatgct aaagccttaa    1920
aagagcgaat ggtaaagtta aactttactg taagatgcag ccctgacatg gggttactaa    1980
```

```
cagaggctga tgtacaacag tggcttacat ggtgtaatgc acaaagctgg gaccactatg    2040
aaaactgggc aataaactac acttttgatt tccctggaat taatgcagat gccctccacc    2100
cagacctcca aaccacccca attgtcacag acaccagtat cagcagcagt ggtggtgaaa    2160
gctctgaaga actcagtgaa agcagctttt ttaacctcat caccccaggc gcctggaaca    2220
ctgaaacccc gcgctctagt acgcccatcc ccgggaccag ttcaggagaa tcatttgtcg    2280
gaagctcagt ttcctccgaa gttgtagctg catcgtggga agaagccttc tacacacctt    2340
tggcagacca gtttcgtgaa ctgttagttg gggttgatta tgtgtgggac ggtgtaaggg    2400
gtttacctgt gtgttgtgtg caacatatta acaatagtgg gggaggcttg ggactttgtc    2460
cccattgcat taatgtaggg gcttggtata atggatggaa atttcgagaa tttaccccag    2520
atttggtgcg gtgtagctgc catgtgggag cttctaatcc cttttctgtg ctaacctgca    2580
aaaaatgtgc ttacctgtct ggattgcaaa gctttgtaga ttatgagtaa agaaagtggc    2640
aaatggtggg aaagtgatga taaatttgct aaagctgtgt atcagcaatt tgtggaattt    2700
tatgaaaagg ttactggaac agacttagag cttattcaaa tattaaaaga tcactataat    2760
atttctttag ataatcccct agaaaaccca tcctctctgt ttgacttagt tgctcgtatt    2820
aaaaataacc ttaaaaactc tccagactta tatagtcatc attttcaaag tcatggacag    2880
ttatctgacc accccatgc cttatcatcc agtagcagtc atgcagaacc tagaggagaa    2940
aatgcagtat tatctagtga agacttacac aagcctgggc aagttagcgt acaactaccc    3000
ggtactaact atgttgggcc tggcaatgag ctacaagctg gcccccgca aagtgctgtt    3060 gacagtgctg caaggattca tgactttagg tatagccaac tggctaagtt gggaataaat    3120
ccatatactc attggactgt agcagatgaa gagcttttaa aaatatataaa aaatgaaact    3180 gggtttcaag cacaagtagt aaaagactac tttactttaa aaggtgcagc tgcccctgtg    3240
gcccattttc aaggaagttt gccggaagtt cccgcttaca acgcctcaga aaaataccca    3300
agcatgactt cagttaattc tgcagaagcc agcactggtg caggaggggg tggcagtaat    3360
cctgtcaaaa gcatgtggag tgaggggcc acttttagtg ccaactctgt aacttgtaca    3420
ttttccagac agttttaat tccttatgac ccagagcacc attataaggt gttttctccc    3480
gcagcaagca gctgccacaa tgccagtgga aaggaggcaa aggtttgcac aattagtccc    3540
ataatgggat actcaacccc atggagatat ttagatttta atgctttaaa tttatttttt    3600
tcacctttag agtttcagca cttaattgaa aattatggaa gtatagctcc tgatgcttta    3660
actgtaacca tatcagaaat tgctgttaag gatgttacag acaaaactgg aggggggta    3720 caggttactg acagcactac agggcgccta tccatgttag tagaccatga atacaagtac    3780
ccatatgtgt taggacaagg tcaggatact ttagccccag aacttcctat ttgggtatac    3840
tttccccctc aatatgctta cttaacagta ggagatgtta acacacaagg aatctctgga    3900
gacagcaaaa aattagcaag tgaagaatca gcattttatg ttttggaaca cagttctttt    3960 cagctttag gtacaggagg tacagcaact atgtcttata gtttcctcc agtgccccca    4020 gaaaatttag agggctgcag tcaacacttt tatgaaatgt acaatcccct atacggatcc    4080
cgcttagggg ttcctgacac attaggaggt gacccaaaat ttagatcttt aacacatgaa    4140
gaccatgcaa ttcagcccca aaacttcatg ccagggccac tagtaaactc agtgtctaca    4200
aaggagggag acagctctaa tactggagct ggaaaagcct taacaggcct tagcacaggc    4260
acctctcaaa acactagaat atccttacgc cctgggccag tgtcacagcc ataccaccac    4320
```

| | |
|---|---:|
| tgggacacag ataaatatgt tccaggaata aatgccattt ctcatggtca gaccacttat | 4380 |
| ggtaacgctg aagacaaaga gtatcagcaa ggagtgggta gatttccaaa tgaaaaagaa | 4440 |
| cagctaaaac agttacaggg tttaaacatg cacacctatt tccccaataa aggaacccag | 4500 |
| caatatacag atcaaattga gcgccccta atggtgggtt ctgtatggaa cagaagagcc | 4560 |
| cttcactatg aaagccagct gtggagtaaa attccaaatt tagatgacag ttttaaaact | 4620 |
| cagtttgcag ccttaggagg atggggtttg catcagccac ctcctcaaat attttttaaaa | 4680 |
| atattaccac aaagtgggcc aattggaggt attaaatcaa tgggaattac taccttagtt | 4740 |
| cagtatgccg tgggaattat gacagtaact atgacattta aattggggcc ccgtaaagct | 4800 |
| acgggacggt ggaatcctca acctggagta tatccccgc acgcagcagg tcatttacca | 4860 |
| tatgtactat atgaccccac agctacagat gcaaaacaac accacaggca tggatacgaa | 4920 |
| aagcctgaag aattgtggac agccaaaagc cgtgtgcacc cattgtaaac actccccacc | 4980 |
| gtgccctcag ccaggatgcg taactaaacg cccaccagta ccaccagac tgtacctgcc | 5040 |
| ccctcctgta cctataagac agcctaacac aaaagatata gacaatgtag aatttaagta | 5100 |
| cttaaccaga tatgaacaac atgttattag aatgttaaga ttgtgtaata tgtatcaaaa | 5160 |
| tttagaaaaa taaacatttg ttgtggttaa aaaattatgt tgttgcgctt taaaaattta | 5220 |
| aaagaagaca ccaaatcaga tgccgccggt cgccgccggt aggcgggact tccggtacaa | 5280 |
| gatggcggac aattacgtca tttcctgtga cgtcatttcc tgtgacgtca cttccggtgg | 5340 |
| gcgggacttc cggaattagg gttggctctg gccagcgct tggggttgac gtgccactaa | 5400 |
| gacaagcggc gcgccgcttg tcttagtgtc aaggcaaccc caagcaagct ggcccagagc | 5460 |
| caaccctaat tccggaagtc ccgcccaccg gaagtgacgt cacaggaaat gacgtcacag | 5520 |
| gaaatgacgt aattgtccgc catcttgtac cggaagtccc gcctaccggc ggcgaccggc | 5580 |
| ggcatctgat ttgg | 5594 |

<210> SEQ ID NO 14
<211> LENGTH: 5149
<212> TYPE: DNA
<213> ORGANISM: Minute virus of mice

<400> SEQUENCE: 14

| | |
|---|---:|
| attttagaa ctgaccaacc atgttcacgt aagtgacgtg atgacgcgcg ctgcgcgcgc | 60 |
| gccttcggac gtcacacgtc acttacgttt cacatggttg gtcagttcta aaaatgataa | 120 |
| gcggttcagg gagtttaaac caaggcgcga aaaggaagtg ggcgtggttt aaagtatata | 180 |
| agcaactact gaagtcagtt acttatcttt tctttcattc tgtgagtcga gacgcacaga | 240 |
| aagagagtaa ccaactaacc atggctggaa atgcttactc tgatgaagtt ttgggagcaa | 300 |
| ccaactggtt aaaggaaaaa agtaaccagg aagtgttctc atttgttttt aaaaatgaaa | 360 |
| atgttcaact gaatggaaaa gatatcggat ggaatagtta caaaaaagag ctgcaggagg | 420 |
| acgagctgaa atctttacaa cgaggagcgg aaactacttg ggaccaaagc gaggacatgg | 480 |
| aatgggaaac cacagtggat gaaatgacca aaaagcaagt attcattttt gattctttgg | 540 |
| ttaaaaaatg tttatttgaa gtgcttaaca caaagaatat atttcctggt gatgttaatt | 600 |
| ggtttgtgca acatgaatgg ggaaaagacc aaggctggca ctgccatgta ctaattggag | 660 |
| gaaaggactt tagtcaagct caagggaaat ggtggagaag gcaactaaat gtttactgga | 720 |
| gcagatggtt ggtaacagcc tgtaatgtgc aactaacacc agctgaaaga attaaactaa | 780 |
| gagaaatagc agaagacaat gagtgggtta ctctacttac ttataagcat aagcaaacca | 840 |

```
aaaaagacta taccaagtgt gttcttttg gaaacatgat tgcttactat tttttaacta      900
aaaagaaaat aagcactagt ccaccaagag acggaggcta ttttcttagc agtgactctg      960
gctggaaaac taacttttta aaagaaggcg agcgccatct agtgagcaaa ctatacactg     1020
atgacatgcg gccagaaacg gttgaaacca cagtaaccac tgcgcaggaa actaagcgcg     1080
gcagaattca aactaaaaaa gaagtttcta ttaaaactac acttaaagag ctggtgcata     1140
aaagagtaac ctcaccagag gactggatga tgatgcagcc agacagttac attgaaatga     1200
tggctcaacc aggtggagaa aacctgctga aaatacgct agagatttgt acactaactc      1260
tagccagaac caaaacagca tttgacttaa ttttagaaaa agctgaaacc agcaaactaa     1320
ccaactttc actgcctgac acaagaacct gcagaatttt tgcttttcat ggctggaact      1380
atgttaaagt ttgccatgct atttgctgtg ttttaaacag acaaggaggc aaaagaaata     1440
ctgttttatt tcatggacca gccagcacag gcaaatctat tattgcacaa gccatagcac     1500
aagcagttgg caatgttggt tgctataatg cagccaatgt aaactttcca tttaatgact     1560
gtaccaacaa gaacttgatt tgggtagaag aagctggtaa ctttggacag caagtaaacc     1620
agtttaaagc catttgctct ggtcaaacta ttcgcattga tcaaaaagga aaaggcagca     1680
aacagattga accaacacca gtcatcatga ccacaaatga gaacattaca gtggtcagaa     1740
taggctgcga agaagaccca gaacacactc aaccaatcag agacagaatg cttaacattc     1800
atctaacaca taccttgcct ggtgactttg gtttggttga caaaaatgaa tggcccatga     1860
tttgtgcttg gttggtaaag aatggttacc aatctaccat ggcaagctac tgtgctaaat     1920
ggggcaaagt tcctgattgg tcagaaaact gggcggagcc aaaggtgcca actcctataa     1980
atttactagg ttcggcacgc tcaccattca cgacaccgaa aagtacgcct ctcagccaga     2040
actatgcact aactccactt gcatcggatc tcgaggacct ggctttagag ccttggagca     2100
caccaaatac tcctgttgcg ggcactgcag aaacccagaa cactgggaa gctggttcca      2160
aagcctgcca agatggtcaa ctgagcccaa cttggtcaga gatcgaggag gatttgagag     2220
cgtgcttcgg tgcggaaccg ttgaagaaag acttcagcga gccgctgaac ttggactaag     2280
gtacgatggc gcctccagct aaaagagcta aagaggtaa gggtttaagg gatggttggt      2340
tggtggggta ttaatgttta attacctgtt ttacaggcct gaaatcactt ggttttaggt     2400
tgggtgcctc ctggctacaa gtacctggga ccagggaaca gccttgacca aggagaacca     2460
accaatccat ctgacgccgc tgccaaagag cacgacgagg cctatgatca atacatcaaa     2520
tctggaaaaa atccttacct gtacttctct gctgctgatc aacgctttat tgaccaaacc     2580
aaggacgcca aagactgggg aggcaaggtt ggtcactact tttttagaac caagcgcgct     2640
tttgcaccta agcttgctac tgactctgaa cctggaactt ctggtgtaag cagagctggt     2700
aaacgcacta gaccacctgc ttacattttt attaaccaag ccagagctaa aaaaaactt      2760
acttcttctg ctgcacagca aagcagtcaa accatgagtg atggcaccag ccaacctgac     2820
agcggaaacg ctgtccactc agctgcaaga gttgaacgag cagctgacgg ccctggaggc     2880
tctgggggtg ggggctctgg cggggtggg gttggtgttt ctactgggtc ttatgataat      2940
caaacgcatt atagattctt gggtgacggc tgggtagaaa ttactgcact agcaactaga     3000
ctagtacatt taaacatgcc taaatcagaa aactattgca gaatcagagt tcacaataca     3060
acagacacat cagtcaaagg caacatggca aaagatgatg ctcatgagca aatttggaca     3120
ccatggagct tggtggatgc taatgcttgg ggagtttggc tccagccaag tgactggcaa     3180
```

```
tacatttgca acaccatgag ccagcttaac ttggtatcac ttgatcaaga aatattcaat    3240
gtagtgctga aaactgttac agagcaagac ttaggaggtc aagctataaa aatatacaac    3300 aatgaccttta cagcttgcat gatggttgca gtagactcaa acaacatttt gccatacaca    3360
cctgcagcaa actcaatgga aacacttggt ttctacccct ggaaaccaac catagcatca    3420
ccatacaggt actattttg cgttgacaga gatctttcag tgacctacga aaatcaagaa    3480
ggcacagttg aacataatgt gatgggaaca ccaaaaggaa tgaattctca attttttacc    3540
attgagaaca cacaacaaat cacattgctc agaacagggg acgaatttgc cacaggtact    3600
tactactttg acacaaattc agttaaactc acacacacgt ggcaaaccaa ccgtcaactt    3660
ggacagcctc cactgctgtc aacctttcct gaagctgaca ctgatgcagg tacacttact    3720
gctcaaggga gcagacatgg aacaacacaa atgggggtta actgggtgag tgaagcaatc    3780
agaaccagac ctgctcaagt aggattttgt caaccacaca atgactttga agccagcaga    3840
gctggaccat ttgctgcccc aaaagttcca gcagatatta ctcaaggagt agacaaagaa    3900
gccaatggca gtgttagata cagttatggc aaacagcatg tgaaaattg gcttcacat    3960 ggaccagcac cagagcgcta cacatgggat gaaacaagct ttggttcagg tagagacacc    4020
aaagatggtt ttattcaatc agcaccacta gttgttccac caccactaaa tggcattctt    4080
acaaatgcaa accctattgg gactaaaaat gacattcatt tttcaaatgt ttttaacagc    4140
tatggtccac taactgcatt ttcacaccca agtcctgtat accctcaagg acaaatatgg    4200
gacaaagaac tagatcttga acacaaacct agacttcaca taactgctcc atttgtttgt    4260
aaaaacaatg cacctggaca aatgttggtt agattaggac aaaacctaac tgaccaatat    4320
gatccaaacg gagccacact ttctagaatt gttacatacg gtacattttt ctggaaagga    4380
aaactaacca tgagagcaaa acttagagct aacaccactt ggaacccagt gtaccaagta    4440
agtgctgaag acaatggcaa ctcatacatg agtgtaacta aatggttacc aactgctact    4500
ggaaacatgc agtctgtgcc gcttataaca agacctgttg ctagaaatac ttactaacta    4560
accatgcttt ttctttctgt acttcatata ttattaagac taataaagat acaacataga    4620
aatataatat tacgtataga tttaagaaat agaataatat ggtacttagt aactgttaaa    4680
aataatagaa cctttggaat aacaagatag ttagttggtt aatgttagat agaataagaa    4740
gatcatgtat aatgaataaa agggtggaag ggtggttggt aggttaatgt tagatagaat    4800
aagaagatca tgtataatga ataaaagggt ggaagggtgg ttggtaggta ttcccttaga    4860
cttgatgtta aggaccaaaa aaataataaa acttttttaa aactcaacca agactactgt    4920
ctattcagtg aaccaactga accattagta ttactatgtt tttagggtgg gagggtggga    4980
gatacatgtg ttcgctatga gcgaactggt actggttggt tgctctgctc aaccaaccag    5040
accggcaaag ccggtctggt tggttgagcg caaccaacca gtaccagttc gctcatagcg    5100
aacacatgta tctcccaccc tcccacccta aaacatagt aatactaat    5149
```

<210> SEQ ID NO 15
<211> LENGTH: 5106
<212> TYPE: DNA
<213> ORGANISM: Goose parvovirus

<400> SEQUENCE: 15

```
ctcattggag ggttcgttcg ttcgaaccag ccaatcaggg gagggggaag tgacgcaagt      60
tccggtcaca tgcttccggt gacgcacatc cggtgacgta gttccggtca cgtgcttcct     120
gtcacgtgtt tccggtcacg tgacttccgg tcatgtgact tccggtgacg tgtttccggc     180
```

```
tgttaggttg accacgcgca tgccgcgcgg tcagcccaat agttaagccg gaaacacgtc    240
accggaagtc acatgaccgg aagtcacgtg accggaaaca cgtgacagga agcacgtgac    300
cggaactacg tcaccggatg tgcgtcaccg gaagcatgtg accggaactt gcgtcacttc    360
cccctcccct gattggctgg ttcgaacgaa cgaaccctcc aatgagactc aaggacaaga    420
ggatattttg cgcgccagga agtgacgtgc aatgccaccc tatataagcc aggaaacttc    480
cggtttagtt cattcgttac tctgctctca gagagaacgg acctcaggtc ggagagatgg    540
cactttctag gcctcttcag atttcttctg ataaattcta tgaagttatt attagattat    600
catcggatat tgatcaagat gtccccggtc tgtctcttaa ctttgtagaa tggctttcta    660
ccggagtttg ggagcccacg ggcatctgga acatggagca tgtgaatcta ccgatggtga    720
ccttggcaga aagatcaag aacatttca tacaaagatg gaatcagttc aaccaggacg    780
aaacggactt cttctttcaa ctggaagaag gcagtgagta cattcatctt cattgctgta    840
ttgcccaggg caatgtacgg tcttttgttc tcgggagata tatgtctcag ataaaagact    900
ctatcataag agatgtatat gaagggaaac aaatcaagat ccccgattgg tttgctatta    960
ctaaaaccaa gaggggagga cagaataaga ccgtgactgc agcatacata ctgcattacc   1020
ttattcctaa aaagcaacct gaactgcaat gggcctttac caatatgcct ttattcactg   1080
ctgctgctct ttgtctgcaa aagcggcaag aattgctgga tgcatttcaa gaaagtgatt   1140
tggctgcccc tttacctgat cctcaagcat caactgtggc accgcttatt ccaacagag   1200 cggcaaagaa ctatagcaac cttgttgatt ggctcattga atggggata acatctgaga   1260 agcaatggct cactgagaac cgagagagct acagaagctt tcaagcaact tcttcaaata   1320
atagacaagt gaaagctgca ctggaaaatg cccgtgctga atgttattg acaaagactg   1380 caactgatta cctgatagga aagaccctg tcctggatat aactaagaat agggtctatc   1440
aaattctgaa aatgaataac tacaaccctc aatacatagg aagtatcctg tgcggctggg   1500
tgaagagaga gttcaacaaa agaaacgcca tatggctcta cggacctgcc accaccggga   1560
agaccaacat tgcagaagct attgcccatg ctgtacccct ctatggctgt gttaactgga   1620
ctaatgagaa ctttccttt aatgattgtg ttgataaaat gctgatttgg tgggaggagg   1680
gaaaaatgac taataaggtt gttgaatctg caaaagcaat tttgggaggg tctgctgtcc   1740
gggtagacca gaaatgtaaa ggatctgttt gtattgaacc tactcctgta attattacta   1800
gtaatactga tatgtgtatg attgttgatg gcaactctac tacaatggaa catagaatac   1860
cattagagga gcgtatgttt caaattgtcc tatcacataa attggagcct tcttttggaa   1920
aaatttctaa aaaagaagtc agagaatttt tcaaatgggc caatgacaat ctagttcctg   1980
ttgtgtctga gttcaaagtc cgaactaatg aacaaaccaa cttgccagag cccgttcctg   2040
aacgagcgaa cgagccggag gagcctccta agatctgggc tcctcctact agggaggagt   2100
tagaagagct tttaagagcc agcccagaat tgttctcatc agtcgctcca attcctgtga   2160
ctcctcagaa ctcccctgag cctaagagaa gcaggaacaa ttaccaggta cgctgcgctt   2220
tgcatactta tgacaattct atggatgtat ttgaatgtat ggaatgtgag aaagcaaact   2280
ttcctgaatt tcaacctctg ggagaaaatt attgtgatga acatgggtgg tatgattgtg   2340
ctatatgtaa agagttgaaa aatgaacttg cagaaattga gcatgtgttt gagcttgatg   2400
atgctgaaaa tgaacaataa agatgactca aagcagatat gtctactttt ttagattctt   2460
ttgaagagtg gtatgagact gcagccgcct cgtggcggaa tctgaaagct ggagcccctc   2520
```

-continued

| | | | | |
|---|---|---|---|---|
| agccaaaacc | aaaccagcag | tctcagtctg | tgtctccaga | cagagaaccc gaacgaaaag | 2580 |
| ataataatcg | gggctttgta | cttcctggct | ataagtatct | tgggcctggt aacggcctgg | 2640 |
| ataaaggccc | acctgtcaat | aaggcggaca | gcgtcgcgct | tgaacacgac aaggcctatg | 2700 |
| accagcagct | taaagcggga | gacaacccat | atataaaatt | caatcacgct gaccaggact | 2760 |
| ttatagatag | cctccaagac | gaccagtcat | tcggaggtaa | tcttggaaag gctgtatttc | 2820 |
| aggccaaaaa | acgtatctta | gagccatttg | gcctagtaga | agatcctgtc aacacggcac | 2880 |
| ctgcaaaaaa | aaatacaggg | aagcttactg | accattaccc | ggtagttaag aagcctaaac | 2940 |
| ttaccgagga | agtcagtgcg | ggaggtggta | gcagtgccgt | acaagacgga ggagccaccg | 3000 |
| cggagggcac | cgaacctgtg | gcagcatctg | aaatggcaga | gggaggaggc ggagctatgg | 3060 |
| gcgactcttc | aggggggtgcc | gatggagtgg | gtaatgcctc | gggaaattgg cattgcgatt | 3120 |
| cccaatggat | gggaaacaca | gtcatcacaa | agaccaccag | aacctgggtc ctgccaagct | 3180 |
| acaacaacca | catctacaaa | gcaattacca | gcggaacctc | tcaagatgca aatgtccagt | 3240 |
| atgcaggata | cagtaccccc | tgggggtact | ttgatttcaa | ccgcttccac tgccacttct | 3300 |
| cccctagaga | ctggcagaga | cttatcaaca | accattgggg | aatcagaccc aagtctctta | 3360 |
| aattcaagat | cttcaatgtc | caagtcaaag | aagtcacaac | gcaggatcag acaaagacca | 3420 |
| ttgcaaacaa | tctcacctca | acaattcaag | tctttacgga | tgatgagcat caactcccgt | 3480 |
| atgtcctggg | ctcggctacg | gaaggcacca | tgccgccgtt | cccgtcggat gtctatgccc | 3540 |
| tgccgcagta | cgggtactgc | acaatgcaca | ccaaccagaa | tggagcacgg ttcaatgacc | 3600 |
| gtagtgcatt | ctactgctta | gagtacttcc | ctagtcagat | gctaagaaca ggcaacaact | 3660 |
| ttgagttcac | atttgacttt | gaagaagttc | ctttccatag | catgttcgct cattcacagg | 3720 |
| acttagacag | gctgatgaac | ccccctagtgg | atcaatacct | ctggaatttc aatgaggtag | 3780 |
| acagcagcag | aaatgctcaa | tttaaaaagg | ctgtgaaagg | ggcttatggc accatgggcc | 3840 |
| gcaattggct | gccaggacct | aaattcctgg | atcaaagagt | tagggcctac acaggaggaa | 3900 |
| cagacaacta | tgcaaactgg | aacatctgga | gtaatgggaa | caaggtgaat ttgaaagaca | 3960 |
| gacagtatct | cctacaaccc | ggacctgtgt | cagctactta | cacagaaggg gaggcttcca | 4020 |
| gccttccagc | tcaaaatatt | ttagggatag | ctaaagatcc | atacagatca ggcagcacta | 4080 |
| cagcaggaat | aagtgacatt | atggtcacgg | aagaacaaga | agtagcacct acaaatggag | 4140 |
| tagggtggaa | accatatggt | aggactgtaa | cgaatgaaca | aaacactact acagctccta | 4200 |
| caagttcaga | tctggatgtt | cttggagctt | taccaggaat | ggtttggcag aacagggata | 4260 |
| tatatctgca | gggacctatt | ggggcaaaaa | taccgaagac | tgatggtaaa ttccatcctt | 4320 |
| ctccgaatct | cggaggattt | ggcctgcaca | atccaccacc | gcaggtgttc atcaagaata | 4380 |
| caccagtgcc | tgcagaccct | ccagtagaat | acgtgcacca | gaagtggaat tcctacataa | 4440 |
| cccagtactc | tacgggccag | tgtacagtag | agatggtgtg | ggagctgaga aaagagaatt | 4500 |
| caaagagatg | gaacccagaa | atccagttca | ccagtaattt | cagtaacaga acaagcataa | 4560 |
| tgtttgcacc | taatgaaact | ggtggatatg | tagaagatag | attgattgga accagatatc | 4620 |
| taactcaaaa | tctgtaaatt | ctgtgtaaaa | attcaaataa | agcacttcct ggcgcgcaaa | 4680 |
| atatcctctt | gtccttgagt | ctcattggag | ggttcgttcg | ttcgaaccag ccaatcaggg | 4740 |
| gagggggaag | tgacgcaagt | tccggtcaca | tgcttccggt | gacgcacatc cggtgacgta | 4800 |
| gttccggtca | cgtgcttcct | gtcacgtgtt | tccggtcacg | tgacttccgg tcatgtgact | 4860 |
| tccggtgacg | tgtttccggc | ttaactattg | ggctgaccgc | gcgcatgcgc gtggtcaacc | 4920 |

-continued

| | |
|---|---|
| taacagccgg aaacacgtca ccggaagtca catgaccgga agtcacgtga ccggaaacac | 4980 |
| gtgacaggaa gcacgtgacc ggaactacgt caccggatgt gcgtcaccgg aagcatgtga | 5040 |
| ccggaacttg cgtcacttcc ccctcccctg attggctggt cgaacgaac gaaccctcca | 5100 |
| atgaga | 5106 |

<210> SEQ ID NO 16
<211> LENGTH: 4432
<212> TYPE: DNA
<213> ORGANISM: Snake parvovirus 1

<400> SEQUENCE: 16

| | |
|---|---|
| cgccccaccc ctagtgatcg cgcgcgctct ctcttggggc ctgacggccg aaggccgtca | 60 |
| gctgccgagc ttcgctcggc aggccccaag agagagcgcg cgcgatcact aggggtgggg | 120 |
| cgagtgccct gctcaacggg ttttttggtg ggcggagcaa tgacgtcagc ggacatgtct | 180 |
| ggacatgtct ttgagcaagt ccatataagg agttccgccg gatatgcaaa tgagcaatcg | 240 |
| cgcaaagcat tttgggtagt caccatgaat aaaaaggaca gcaagaaaga tgacgcccca | 300 |
| taattttaat aggaatttta accatggcgt tttacgaggt tgtgtttcgt ttgccaagag | 360 |
| acaataacaa cttgttggat gaagatagat atcagccaga gttgaaagaa gaagatgact | 420 |
| ggcctgagga atatttaacc agtgaagatg ccagctttat cggactagcg tatgctgtgc | 480 |
| taagtgaaat tcggagattc tttggaaagg aactacaatg gtttgcccag gttgaatggt | 540 |
| gtcctactgc tggttaccac atgcatgttt tgttgaacca tcctaagctg agtaaccaga | 600 |
| cttatggaag aaaggtcaat gaactggctt gccgtatagt cgatacctt ggcctaatta | 660 |
| atccagaaga agtcatcagt acccattatg ttaaaagcaa ctatggacat aaaaaggtga | 720 |
| gagtcattca cctagagtct tatttgaaga actactttt cagaaagact ttagctcctc | 780 |
| ccaattatac cgaggaagga gactataaaa gagaggaaga agtcgtgctg tgggcattta | 840 |
| cgaatatcgt cgcttggaag ccattcgtgc ggaatctcat caagagatcg gagctagcga | 900 |
| ctgttcctaa gcaaccagag aatccggcgg gagacggacc ggcacctcga gtgactgcag | 960 |
| gaacccgcca ttttatggaa accatcgact ggttggtgaa acatggaatt actacagaac | 1020 |
| gagaattctg ccacgccaac cgcccttgt acctgtctat gctggcttct acttcgggtg | 1080 |
| ctgggcagat taaagagcg ctggaccagg cgaaacacat gatgaccagc accatgtcag | 1140 |
| cagaggatta cctgacaaca gaagaggatg tgatcgaacc acctactgaa atagaatct | 1200 |
| acaagattat gaaactgaat cgctatgatc cagaactagc agctgctctc ttctacggct | 1260 |
| ggacctgcaa gaactttggc aagagaaaca ccatctggct gtatggtcca gctactaccg | 1320 |
| gcaaaaccat catcgctcaa gctattgcac atgctgttaa actgtttgct ggtgttaatt | 1380 |
| ggactaatga aaacttccc ttctgtaact gtccagggaa actgcttatc tggtgggagg | 1440 |
| agggcaagat gacaaacaaa atggtggaga cggctaaatg tatactgggg gatctgctg | 1500 |
| tacctgtaga catcaaaggc aaacccgctg aaatgtgtcc tcaaacaccc tgtattatta | 1560 |
| ctagcaatac taacatgtgt caagtatatg atggtaatag ttctagcttt gagcaccaag | 1620 |
| aaccccctaga ggaacgcatg tttatgttca gacttaatac taaactgcca tcgacctttg | 1680 |
| gcaagatcac agaagaggaa gtcaaacagt ttattacctg ggggaggagc ttaaaggttc | 1740 |
| aagttccaca tcagttcaga gtgcctacca caggagagta taaaaggcca gcccccgagg | 1800 |
| cgaaagctca ttcttcggat gagccgccaa aagagaaggt cgcgcgtatt gatgactctc | 1860 |

```
taaccaggta tgttaacaat attgatgagt cagctaccag tagagaaatg tttctagaga    1920
ttgctaatac taatcaatgt atgttgcatc attgcttttc ttgtaccgaa tgttatcctg    1980
aattgcttga tgacatggac aaggaacaat aaacttactg ataacagata tggattttct    2040
cgatgatttc tttgcagata aatataaaga gactgttaac gaactcggta aaccggtcaa    2100
tcctaaacct gtaaaacaca ttagcgaagc tcactcgcaa cctggcagca ggagggctt     2160
tgtggtgcct gggtatcggt atcttgggcc tggtaatagc ttggaccgtg aaagcccgt     2220
taacaaagca gacgaggctg ctaaaaagca cgatcaagaa tacgatcaac agcttaaagc    2280
gggagacaat ccctacataa aatataatca cgcggacgaa cagttccaga agacctaca     2340
aggtgatacc agtctagccg gcaacgcggc taacgctcta tttcaaggca aaaagactct    2400
actagcgccc cttggcctag tagagacccc tgtcggcaaa acgtctgaaa agcacaaatt    2460
agacgaatac tatcctaaag ctaaaaaggc caaacaaggc ttgcagatac cagctccacc    2520
taaaggcgga gaagaagaag ctacatcgtc acaatctgga gggagcccag caggttccga    2580
tactagcggc acatctgtca tggctacagg aggaggcggt ccgatggcag acgataacca    2640
gggcgccgag ggagtgggta attcctcagg tgattggcat tgcgatacca agtggatggg    2700
agaccacgtc attacaaagt caaccagaac ttgggtgctc cccacttacg ggaatcatct    2760
ctacgggcct atcaactttg acggcaccac aggttcgggt gctaatgcag cctatgcagg    2820
atacaagact ccctggggt  actttgactt caatcgattc cattgccact tctcccccg     2880
agactggcaa agactcatca caaccacac  aggcatcagg ccgaaaggac tcaaaatcaa    2940
agtctttaac gtccaagtca aagaagttac aacacaagat tcaacgaaaa caattgccaa    3000
caatctcacc agcaccgtac agatctttgc ggacgagaac tacgacttac catatgtatt    3060
aggcagtgct acacaaggca catttcctcc atttcccaat gatgtatttta tgttaccaca   3120
atatgcttat tgtacacttc aaggaaattc ggggaaattt gtagatagaa gtgccttta    3180
ttgtttagaa tattttcctt cacaaatgct gagaacagga acaattttg  agttccagtt    3240
taaatttgaa gaagttccct ttcattctgg atgggcacag agtcaaagcc tagacagatt    3300
gatgaatccg ttgcttgatc aatatctgat aggagactat ggaacagatg catcaggaaa    3360
ccttatttat cacagagctg gtccaaatga tttgaatgaa ttctacaaga attgggcacc    3420
tgcaccctat gaatgtatcc agaatattaa cagcagtgat aataccaaga atgctaattc    3480
tataaatggt tcaaattcta ccaacaaatg gggactacaa ggaagacaag catgggatgc    3540
tccaggattt gttcaagcta gtacctatga aggtgcagca gcaggacaat ctcttcttaa    3600
tggcgtactt actttcgata aaagttcagc tactacttca tctccagctg ctactgcagt    3660
aaacagaaca attgaagacg aaatacaggg taccaataat tttggtaatg ctagaaataa    3720
cattgttgct atcaatcaac aaacgaaagg aacaaatcca acaacaggta gtacatctca    3780
atttgagaca atgccaggta tggtgtggtc taatagagac atttacttac aggggcctat    3840
ttgggctaaa attccaaata cagatggaca ttttcatcct tctcccagaa tgggtggttt    3900
tggattaaaa catcctccgc ctatgattct gatcaaaaat acaccagttc ctgctgatcc    3960
tccaactacc ttcaatccaa tgccacagac tagtttcatt actgaataca gtacaggaca   4020
agtaactgtt gaaatgttgt gggaggtaca gaaagaatcc tccaaaagat ggaatccaga    4080
agtacagttt acttccaatt ttggaacttc agatccagct gttgatggaa taccgtttgg    4140
aattaataat ttgggtactt atgttgaatc tagacctatt ggaactcgtt atatttctaa    4200
acacttgtaa ataataaaaa ttgtcaaatt tgcactaaga attgttgtca cgtggttgtt    4260
```

```
tacatgcttg ctaaaacacg cccaccaaaa aacccgttga gcagggcact cgccccaccc    4320
ctagtgatcg cgcgcgctct ctcttgggc ctgccgagcg aagctcggca gctgacggcc     4380
ttcggccgtc aggccccaag agagagcgcg cgcgatcact aggggtgggg cg            4432
```

<210> SEQ ID NO 17
<211> LENGTH: 165
<212> TYPE: DNA
<213> ORGANISM: Artificial
<220> FEATURE:
<223> OTHER INFORMATION: Chimeric ITR sequence

<400> SEQUENCE: 17

```
aggaacccct agtgatggag ttggccactc cctctctgcg cgctcgctcg ctcactgagg    60
gcgggcgacc aaaggtcgcc cgagcccggc ccttgggcc gggcccctca gtgagcgagc     120
gagcgcgcag agaggagtg gccaactcca tcactagggg ttcct                     165
```

<210> SEQ ID NO 18
<211> LENGTH: 198
<212> TYPE: DNA
<213> ORGANISM: Artificial
<220> FEATURE:
<223> OTHER INFORMATION: Chimeric ITR sequence

<400> SEQUENCE: 18

```
tacaaaacct ccttgcttga gagtgtggca ctctccccc tgtcgcgttc gctcgctcgc     60
tggctcgttt ggggggcga cggcccaaag ggccgtcgtc tggcagctct ttgagctgcc     120 accccccaa acgagccagc gagcgagcga acgcgacagg ggggagagtg ccacactctc     180
aagcaaggag gttttgta                                                  198
```

<210> SEQ ID NO 19
<211> LENGTH: 189
<212> TYPE: DNA
<213> ORGANISM: Artificial
<220> FEATURE:
<223> OTHER INFORMATION: Chimeric ITR sequence

<400> SEQUENCE: 19

```
aggaacccct agtgatggag ttggccactc cctcccccct gtcgcgttcg cgcgctcgct    60
cgctcactga gggcgggcga ccaaaggtcg cccgagcccg gccctttggg ccgggccct     120 cagtgagcga gcgagcgcgc gaacgcgaca gggggaggg agtggccaac tccatcacta     180
ggggttcct                                                            189
```

<210> SEQ ID NO 20
<211> LENGTH: 190
<212> TYPE: DNA
<213> ORGANISM: Artificial
<220> FEATURE:
<223> OTHER INFORMATION: Chimeric ITR sequence

<400> SEQUENCE: 20

```
tacaaaacct ccttgcttga gagtgtggca ctctccccc tgtcgcgttc gcgcgctcgc     60
tcgctcactg agggcgggcg accaaaggtc gcccgagccc ggccctttgg gccgggcccc    120
tcagtgagcg agcgagcgcg cgaacgcgac agggggaga gtgccacact ctcaagcaag     180
gaggttttgt                                                           190
```

<210> SEQ ID NO 21

```
<211> LENGTH: 196
<212> TYPE: DNA
<213> ORGANISM: Artificial
<220> FEATURE:
<223> OTHER INFORMATION: Chimeric ITR sequence

<400> SEQUENCE: 21
aggaacccct agtgatggag ttggccactc cctcccccct gtcgcgttcg ctcgctcgct    60
ggctcgtttg ggggggcgac ggcccaaagg gccgtcgtct ggcagctctt tgagctgcca   120
cccccccaaa cgagccagcg agcgagcgaa cgcgacaggg ggagggagt ggccaactcc    180 atcactaggg gttcct                                                   196

<210> SEQ ID NO 22
<211> LENGTH: 170
<212> TYPE: DNA
<213> ORGANISM: Artificial
<220> FEATURE:
<223> OTHER INFORMATION: Chimeric ITR sequence

<400> SEQUENCE: 22
tacaaaacct ccttgcttga gagtgtggca ctctctctgc gcgctcgctc gctcactgag    60
ggcgggcgac caaaggtcgc ccgacgcccg gccctttggg ccgggcggcc ctcagtgagc   120
gagcgagcgc gcagagagag tgccacactc tcaagcaagg aggttttgta              170

<210> SEQ ID NO 23
<211> LENGTH: 164
<212> TYPE: DNA
<213> ORGANISM: Artificial
<220> FEATURE:
<223> OTHER INFORMATION: Chimeric ITR sequence

<400> SEQUENCE: 23
aggaacccct agtgatggag tggccctccc tctctgcgcg ctcgctcgct cactgagggc    60
gggcgaccaa aggtcgcccg acgcccggcc ctttgggccg gcggccctc agtgagcgag   120 cgagcgcgca gagggagg gccactccat cactagggt tcct                      164

<210> SEQ ID NO 24
<211> LENGTH: 202
<212> TYPE: DNA
<213> ORGANISM: Artificial
<220> FEATURE:
<223> OTHER INFORMATION: Chimeric ITR sequence

<400> SEQUENCE: 24
tacaaaacct ccttgcttga gagtgttgga cactctcccc cctgtcgcgt tcgctcgctc    60
gctggctcgt ttgggggggc gacggcccaa agggccgtcg tctggcagct ctttgagctg   120
ccaccccccc aaacgagcca gcgagcgagc gaacgcgaca ggggggagag tgtccaacac   180
tctcaagcaa ggaggttttg ta                                            202

<210> SEQ ID NO 25
<211> LENGTH: 161
<212> TYPE: DNA
<213> ORGANISM: Artificial
<220> FEATURE:
<223> OTHER INFORMATION: Chimeric ITR sequence

<400> SEQUENCE: 25
aggaacccct agtatggagt tggccactcc attctgcgcg ctcgctcgct cactgagggc    60
gggcgaccaa aggtcgcccg agcccggccc tttgggccgg gcccctcagt gagcgagcga   120
```
gcgcgcagaa tggagtggcc aactccatac tagggttcc t        161

<210> SEQ ID NO 26
<211> LENGTH: 202
<212> TYPE: DNA
<213> ORGANISM: Artificial
<220> FEATURE:
<223> OTHER INFORMATION: Chimeric ITR sequence

<400> SEQUENCE: 26
tacaaaacct ccttgcttgg agagtgtggc actctccccc cctgtcgcgt tcgctcgctc        60
gctggctcgt ttgggggggc gacggcccaa agggccgtcg tctggcagct ctttgagctg       120
ccaccccccc aaacgagcca gcgagcgagc gaacgcgaca ggggggggaga gtgccacact      180 ctccaagcaa ggaggttttg ta                                               202

<210> SEQ ID NO 27
<211> LENGTH: 155
<212> TYPE: DNA
<213> ORGANISM: Artificial
<220> FEATURE:
<223> OTHER INFORMATION: Chimeric ITR sequence

<400> SEQUENCE: 27
aggaacccct agtgctggag ttggccactc ccgcgcgctc gctcgctcac tgagggcggg        60
cgaccaaagg tcgcccgagc ccggcccttt gggccgggcc cctcagtgag cgagcgagcg      120
cgcgggagtg gccaactcca gcactagggg ttcct                                 155

<210> SEQ ID NO 28
<211> LENGTH: 153
<212> TYPE: DNA
<213> ORGANISM: Artificial
<220> FEATURE:
<223> OTHER INFORMATION: Chimeric ITR sequence

<400> SEQUENCE: 28
aggaacccct agtggagttg gccactcctc tgcgcgctcg ctcgctcact gagggcgggc        60
gaccaaaggt cgcccgagcc cggcccttg ggccgggccc ctcagtgagc gagcgagcgc       120
gcagaggagt ggccaactcc actagggggtt cct                                  153

<210> SEQ ID NO 29
<211> LENGTH: 182
<212> TYPE: DNA
<213> ORGANISM: Artificial
<220> FEATURE:
<223> OTHER INFORMATION: Chimeric ITR sequence

<400> SEQUENCE: 29
aggaacccct agtgatggag ttggccactc cctccacgcg ttctgcgcgc tcgctcgctc        60
actgagggcg gcgaccaaa ggtcgcccga cgcccggccc tttgggccgg gcggccctca       120
gtgagcgagc gagcgcgcag aacgcgtgga gggagtggcc aactccatca ctagggggttc    180 ct                                                                     182

<210> SEQ ID NO 30
<211> LENGTH: 161
<212> TYPE: DNA
<213> ORGANISM: Artificial
<220> FEATURE:
<223> OTHER INFORMATION: Chimeric ITR sequence

```
<400> SEQUENCE: 30
aggaacccct agtggatgga gttggccact ccctcctctg cgcgctcgct cgctcactga      60
gggcgggcga ccaaaggtcg cccgagcccg gccctttggg ccgggcccct cagtgagcga     120
gcgagcgcgc agaggagtgg ccaactccac tagggggttcc t                        161

<210> SEQ ID NO 31
<211> LENGTH: 182
<212> TYPE: DNA
<213> ORGANISM: Artificial
<220> FEATURE:
<223> OTHER INFORMATION: Chimeric ITR sequence

<400> SEQUENCE: 31
aggaacccct agtgatggag ttggccactc cctccacgcg ttctgcgcgc tcgctcgctc      60
actgagggcg gcgaccaaa ggtcgcccga cgccggccc tttgggccgg gcggccctca     120
gtgagcgagc gagcgcgcag aacgcgtgga gggagtggcc aactccatca ctagggggttc     180 ct                                                                   182

<210> SEQ ID NO 32
<211> LENGTH: 177
<212> TYPE: DNA
<213> ORGANISM: Artificial
<220> FEATURE:
<223> OTHER INFORMATION: Chimeric ITR sequence

<400> SEQUENCE: 32
aggaacccct agtcgtgatg gagttggcca ctccctcacg tctgcgcgct cgctcgctca      60
ctgagggcgg gcgaccaaag gtcgcccgag cccggccctt gggccgggc cctcagtga     120 gcgagcgagc gcgcagacgt gagggagtgg ccaactccat cacgactagg ggttcct        177

<210> SEQ ID NO 33
<211> LENGTH: 177
<212> TYPE: DNA
<213> ORGANISM: Artificial
<220> FEATURE:
<223> OTHER INFORMATION: Chimeric ITR sequence

<400> SEQUENCE: 33
aggaacccct agtgatggag ttggccactc cctcccccct gtcgcgttcg cgcgctcgct      60
cgctcactga gggcgggcga ccaaaggtcg cccgagcccg gccctttggg ccgggcccct     120
cagtgagcga gcgagcgcgc agagagggag tggccaactc catcactagg ggttcct        177

<210> SEQ ID NO 34
<211> LENGTH: 173
<212> TYPE: DNA
<213> ORGANISM: Artificial
<220> FEATURE:
<223> OTHER INFORMATION: Chimeric ITR sequence

<400> SEQUENCE: 34
tacaaaacct ccttgcttga gagtgtggca ctcttctgct cgctcgctgg ctcgtttggg      60
ggggcgacgg cccaaagggc cgtcgtctgg cagctctttg agctgccacc cccccaaacg     120
agccagcgag cgagcagaga gagtgccaca ctctcaagca aggaggtttt gta            173

<210> SEQ ID NO 35
<211> LENGTH: 194
<212> TYPE: DNA
<213> ORGANISM: Artificial
```

```
<220> FEATURE:
<223> OTHER INFORMATION: Chimeric ITR sequence

<400> SEQUENCE: 35
tacaaaacct ccttgcttag agtgtggcac tctcccctg tcgcgttcgc tcgctcgctg    60
gctcgtttgg gggggcgacg gcccaaaggg ccgtcgtctg gcagctcttt gagctgccac   120 cccccaaac gagccagcga gcgagcgaac gcgacagggg gagagtgcca cactctaagc    180
aaggaggttt tgta                                                     194

<210> SEQ ID NO 36
<211> LENGTH: 206
<212> TYPE: DNA
<213> ORGANISM: Artificial
<220> FEATURE:
<223> OTHER INFORMATION: Chimeric ITR sequence

<400> SEQUENCE: 36
tacaaaacct ccttgcttga gagagtgtgg cactctctcc ccctgtcgc gttcgctcgc    60 tcgctggctc gtttgggggg gcgacggccc aaagggccgt cgtctggcag ctctttgagc   120 tgccacccc ccaaacgagc cagcgagcga gcgaacgcga cagggggag agagtgccac    180 actctctcaa gcaaggaggt tttgta                                        206

<210> SEQ ID NO 37
<211> LENGTH: 210
<212> TYPE: DNA
<213> ORGANISM: Artificial
<220> FEATURE:
<223> OTHER INFORMATION: Chimeric ITR sequence

<400> SEQUENCE: 37
tacaaaacct ccttgcttga gagtgtggca ctctacgcgt cccccctgtc gcgttcgctc    60
gctcgctggc tcgtttgggg gggcgacggc caaagggcc gtcgtctggc agctctttga   120
gctgccaccc cccaaacga gccagcgagc gagcgaacgc gacagggggc gcgtggagag   180
tgccacactc tcaagcaagg aggttttgta                                   210

<210> SEQ ID NO 38
<211> LENGTH: 227
<212> TYPE: DNA
<213> ORGANISM: Artificial
<220> FEATURE:
<223> OTHER INFORMATION: Chimeric ITR sequence

<400> SEQUENCE: 38
tacaaaacct ccttgcttga gagtgtggca ctctcacgcg tagatctaga ccccctgtcg    60
cgttcgctcg ctcgctggct cgtttggggg ggcgacggcc caaagggccg tcgtctggca   120
gctctttgag ctgccacccc cccaaacgag ccagcgagcg agcgaacgcg acagggggtc   180
tagatctacg gtgagagtgc cacactctca gcaaggagg ttttgta                 227

<210> SEQ ID NO 39
<211> LENGTH: 198
<212> TYPE: DNA
<213> ORGANISM: Artificial
<220> FEATURE:
<223> OTHER INFORMATION: Chimeric ITR sequence

<400> SEQUENCE: 39
tacaaaacct ccttgcttga gagtgtggca ctctccccgc tcgctcgctc gctcgctcgc    60
```

-continued

```
tggctcgttt ggggggcga cggcccaaag gccgtcgtc tggcagctct ttgagctgcc    120 accccccaa acgagccagc gagcgagcga gcgagcgagc ggggagagtg ccacactctc    180
aagcaaggag gttttgta                                                 198
```

<210> SEQ ID NO 40
<211> LENGTH: 198
<212> TYPE: DNA
<213> ORGANISM: Artificial
<220> FEATURE:
<223> OTHER INFORMATION: Chimeric ITR sequence

<400> SEQUENCE: 40

```
tacaaaacct ccttgcttga gagtgtggca ctctccccag ctaagatgca gctcgctcgc    60
tggctcgttt ggggggcga cggcccaaag gccgtcgtc tggcagctct ttgagctgcc    120 accccccaa acgagccagc gagcgagctg catcttagct ggggagagtg ccacactctc    180
aagcaaggag gttttgta                                                 198
```

<210> SEQ ID NO 41
<211> LENGTH: 181
<212> TYPE: DNA
<213> ORGANISM: Artificial
<220> FEATURE:
<223> OTHER INFORMATION: Chimeric ITR sequence

<400> SEQUENCE: 41

```
aggaacccct agtgatggag ttggccactc cctctctgct cgctcgcgcg ctcgctcgct    60
cactgagggc gggcgaccaa aggtcgcccg agcccggccc tttgggccgg gcccctcagt    120
gagcgagcga gcgcgcgagc gagcagagag ggagtggcca actccatcac tagggggttcc    180 t                                                                   181
```

<210> SEQ ID NO 42
<211> LENGTH: 198
<212> TYPE: DNA
<213> ORGANISM: Artificial
<220> FEATURE:
<223> OTHER INFORMATION: Chimeric ITR sequence

<400> SEQUENCE: 42

```
tacaaaacct ccttgcttga gagtgtggca ctctccccc tgtcgcgttc gctcagctaa    60
gatgcagttt ggggggcga cggcccaaag gccgtcgtc tggcagctct ttgagctgcc    120 accccccaa actgcatctt agctgagcga acgcgacagg ggggagagtg ccacactctc    180
aagcaaggag gttttgta                                                 198
```

<210> SEQ ID NO 43
<211> LENGTH: 180
<212> TYPE: DNA
<213> ORGANISM: Artificial
<220> FEATURE:
<223> OTHER INFORMATION: Chimeric ITR sequence

<400> SEQUENCE: 43

```
aggaacccct agtgatggag ttggccactc cctctctgct cgctcgcgcg ctcaagatgc    60
actgagggcg ggcgaccaaa ggtcgcccga gcccggccct ttgggccggg cccctcagtt    120
gcatcttgag cgcgcgagcg agcagagagg gagtggccaa ctccatcact agggggttcct   180
```

<210> SEQ ID NO 44
<211> LENGTH: 197

```
<212> TYPE: DNA
<213> ORGANISM: Artificial
<220> FEATURE:
<223> OTHER INFORMATION: Chimeric ITR sequence

<400> SEQUENCE: 44
tacaaaacct ccttgcttga gagtgtggca ctctcccccc tgtcgcgttc gctcgctcgc      60
tggctcgttt ggggggcgg gcgaccaaag gtcgcccgag cccggcccct tgggccgggc     120
cccccccaaa cgagccagcg agcgagcgaa cgcgacaggg gggagagtgc cacactctca    180
agcaaggagg ttttgta                                                   197

<210> SEQ ID NO 45
<211> LENGTH: 135
<212> TYPE: DNA
<213> ORGANISM: Artificial
<220> FEATURE:
<223> OTHER INFORMATION: Chimeric ITR sequence

<400> SEQUENCE: 45
aggaacccct agtgatggag ttggccactc cctctctgcg cgctcgctcg ctcactgagg     60
cggccctttg ggccgcctca gtgagcgagc gagcgcgcag agagggagtg gccaactcca   120
tcactagggg ttcct                                                    135

<210> SEQ ID NO 46
<211> LENGTH: 153
<212> TYPE: DNA
<213> ORGANISM: Artificial
<220> FEATURE:
<223> OTHER INFORMATION: Chimeric ITR sequence

<400> SEQUENCE: 46
aggaacccct agtgatggag ttggggtctg cgcgcgctcg ctcgctcact gagggcgggc     60
gaccaaaggt cgcccgagcc cggccctttg ggccgggccc ctcagtgagc gagcgagcgc   120
gcgcagaccc caactccatc actagggggtt cct                               153

<210> SEQ ID NO 47
<211> LENGTH: 164
<212> TYPE: DNA
<213> ORGANISM: Artificial
<220> FEATURE:
<223> OTHER INFORMATION: Chimeric ITR sequence

<400> SEQUENCE: 47
aggaacccct agtgatggag ttgggactcc ctctctgcgc gctcgctcgc tcactgaggg     60
cgggcgacca aggtcgcccc gagcccggcc ctttgggccg ggcccctcag tgagcgagcg   120
agcgcgcaga gagggagtcc ccaactccat cactaggggt tcct                    164

<210> SEQ ID NO 48
<211> LENGTH: 159
<212> TYPE: DNA
<213> ORGANISM: Artificial
<220> FEATURE:
<223> OTHER INFORMATION: Chimeric ITR sequence

<400> SEQUENCE: 48
aggaacccct agtgatggag ttggggttaa ctctgcgcgc tcgctcgctc actgagggcg     60
ggcgaccaaa ggtcgcccga gcccggccct ttgggccggg cccctcagtg agcgagcgag   120
cgcgcagagt taaccccaac tccatcacta ggggttcct                          159
```

<210> SEQ ID NO 49
<211> LENGTH: 157
<212> TYPE: DNA
<213> ORGANISM: Artificial
<220> FEATURE:
<223> OTHER INFORMATION: Chimeric ITR sequence

<400> SEQUENCE: 49

```
aggaacccct agtgatggag ttggtccctc tctgcgcgct cgctcgctca ctgagggcgg    60
gcgaccaaag gtcgcccgag cccggccctt tgggccgggc ccctcagtga gcgagcgagc   120
gcgcagagag ggaccaactc catcactagg ggttcct                            157
```

<210> SEQ ID NO 50
<211> LENGTH: 165
<212> TYPE: DNA
<213> ORGANISM: Artificial
<220> FEATURE:
<223> OTHER INFORMATION: Chimeric ITR sequence

<400> SEQUENCE: 50

```
aggaacccct agtgatggag ttggggttaa cccctctgcg cgctcgctcg ctcactgagg    60
gcgggcgacc aaaggtcgcc cgagcccggc cctttgggcc gggcccctca gtgagcgagc   120
gagcgcgcag aggggttaac cccaactcca tcactagggg ttcct                   165
```

<210> SEQ ID NO 51
<211> LENGTH: 172
<212> TYPE: DNA
<213> ORGANISM: Artificial
<220> FEATURE:
<223> OTHER INFORMATION: Chimeric ITR sequence

<400> SEQUENCE: 51

```
aggaacccct agtgatggag ttggccactc cctcttcgct cgctcgctgg ctcgtttggg    60
ggggcgacgg cccaaagggc cgtcgtctgg cagctctttg agctgccacc cccccaaacg   120
agccagcgag cgagcgaaga gggagtggcc aactccatca ctaggggttc ct           172
```

<210> SEQ ID NO 52
<211> LENGTH: 181
<212> TYPE: DNA
<213> ORGANISM: Artificial
<220> FEATURE:
<223> OTHER INFORMATION: Chimeric ITR sequence

<400> SEQUENCE: 52

```
aggaacccct agtgatggag ttggggttaa ccccactccc tctctgcgcg ctcgctcgct    60
cactgagggc gggcgaccaa aggtcgcccg agcccggccc tttgggcggg cccctcagt   120 gagcgagcga gcgcgcagag agggagtggg gttaacccca actccatcac taggggttcc   180
t                                                                   181
```

<210> SEQ ID NO 53
<211> LENGTH: 621
<212> TYPE: PRT
<213> ORGANISM: Artificial
<220> FEATURE:
<223> OTHER INFORMATION: Chimeric Rep protein sequence

<400> SEQUENCE: 53

```
Met Ala Thr Phe Tyr Glu Val Ile Val Arg Val Pro Phe Asp Val Glu
1               5                   10                  15
```

-continued

```
Glu His Leu Pro Gly Ile Ser Asp Ser Phe Val Asp Trp Val Thr Gly
             20                  25                  30
Gln Ile Trp Glu Leu Pro Pro Glu Ser Asp Leu Asn Leu Thr Leu Val
         35                  40                  45
Glu Gln Pro Gln Leu Thr Val Ala Asp Arg Ile Arg Arg Val Phe Leu
 50                  55                  60
Tyr Glu Trp Asn Lys Phe Ser Lys Ala Pro Glu Ala Leu Phe Phe Val
 65                  70                  75                  80
Gln Phe Glu Lys Gly Glu Ser Tyr Phe His Met His Val Leu Val Glu
                 85                  90                  95
Thr Thr Gly Val Lys Ser Met Val Leu Gly Arg Phe Leu Ser Gln Ile
            100                 105                 110
Arg Glu Lys Leu Ile Gln Arg Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
        275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
```

```
                    435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                    485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                    565                 570                 575

Ser Gln Pro Val Ser Val Val Lys Lys Ala Tyr Gln Lys Leu Cys Tyr
                580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
610                 615                 620

<210> SEQ ID NO 54
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 54

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
50                  55                  60

Tyr Glu Trp Asn Lys Phe Ser Lys Gln Glu Ser Lys Phe Phe Val Gln
65                  70                  75                  80

Phe Glu Lys Gly Glu Ser Tyr Phe His Met His Val Leu Val Glu Thr
                85                  90                  95

Thr Gly Val Lys Ser Met Val Leu Gly Arg Phe Leu Ser Gln Ile Arg
                100                 105                 110

Glu Lys Leu Ile Gln Arg Ile Tyr Arg Gly Ile Glu Pro Thr Leu Pro
            115                 120                 125

Asn Trp Phe Ala Val Thr Lys Thr Arg Asn Gly Ala Gly Gly Gly Asn
130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
```

```
                180             185             190
Thr His Val Ser Gln Thr Gln Glu Gln Asn Lys Glu Asn Gln Asn Pro
            195             200             205
Asn Ser Asp Ala Pro Val Ile Arg Ser Lys Thr Ser Ala Arg Tyr Met
            210             215             220
Glu Leu Val Gly Trp Leu Val Asp Lys Gly Ile Thr Ser Glu Lys Gln
225             230             235             240
Trp Ile Gln Glu Asp Gln Ala Ser Tyr Ile Ser Phe Asn Ala Ala Ser
                245             250             255
Asn Ser Arg Ser Gln Ile Lys Ala Ala Leu Asp Asn Ala Gly Lys Ile
            260             265             270
Met Ser Leu Thr Lys Thr Ala Pro Asp Tyr Leu Val Gly Gln Gln Pro
            275             280             285
Val Glu Asp Ile Ser Ser Asn Arg Ile Tyr Lys Ile Leu Glu Leu Asn
            290             295             300
Gly Tyr Asp Pro Gln Tyr Ala Ala Ser Val Phe Leu Gly Trp Ala Thr
305             310             315             320
Lys Lys Phe Gly Lys Arg Asn Thr Ile Trp Leu Phe Gly Pro Ala Thr
                325             330             335
Thr Gly Lys Thr Asn Ile Ala Glu Ala Ile Ala His Thr Val Pro Phe
            340             345             350
Tyr Gly Cys Val Asn Trp Thr Asn Glu Asn Phe Pro Phe Asn Asp Cys
            355             360             365
Val Asp Lys Met Val Ile Trp Trp Glu Glu Gly Lys Met Thr Ala Lys
            370             375             380
Val Val Glu Ser Ala Lys Ala Ile Leu Gly Gly Ser Lys Val Arg Val
385             390             395             400
Asp Gln Lys Cys Lys Ser Ser Ala Gln Ile Asp Pro Thr Pro Val Ile
                405             410             415
Val Thr Ser Asn Thr Asn Met Cys Ala Val Ile Asp Gly Asn Ser Thr
            420             425             430
Thr Phe Glu His Gln Gln Pro Leu Gln Asp Arg Met Phe Lys Phe Glu
            435             440             445
Leu Thr Arg Arg Leu Asp His Asp Phe Gly Lys Val Thr Lys Gln Glu
            450             455             460
Val Lys Asp Phe Phe Arg Trp Ala Lys Asp His Val Val Glu Val Glu
465             470             475             480
His Glu Phe Tyr Val Lys Lys Gly Gly Ala Lys Lys Arg Pro Ala Pro
                485             490             495
Ser Asp Ala Asp Ile Ser Glu Pro Lys Arg Val Arg Glu Ser Val Ala
            500             505             510
Gln Pro Ser Thr Ser Asp Ala Glu Ala Ser Ile Asn Tyr Ala Asp Arg
            515             520             525
Tyr Gln Asn Lys Cys Ser Arg His Val Gly Met Asn Leu Met Leu Phe
            530             535             540
Pro Cys Arg Gln Cys Glu Arg Met Asn Gln Asn Ser Asn Ile Cys Phe
545             550             555             560
Thr His Gly Gln Lys Asp Cys Leu Glu Cys Phe Pro Val Ser Glu Ser
                565             570             575
Gln Pro Val Ser Val Val Lys Lys Ala Tyr Gln Lys Leu Cys Tyr Ile
            580             585             590
His His Ile Met Gly Lys Val Pro Asp Ala Cys Thr Ala Cys Asp Leu
            595             600             605
```

Val Asn Val Asp Leu Asp Asp Cys Ile Phe Glu Gln
610                 615                 620

<210> SEQ ID NO 55
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 55

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Gly Asn
130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
            180                 185                 190

Thr His Val Ser Gln Thr Gln Glu Gln Asn Lys Glu Asn Gln Asn Pro
        195                 200                 205

Asn Ser Asp Ala Pro Val Ile Arg Ser Lys Thr Ser Ala Arg Tyr Met
210                 215                 220

Glu Leu Val Gly Trp Leu Val Asp Lys Gly Ile Thr Ser Glu Lys Gln
225                 230                 235                 240

Trp Ile Gln Glu Asp Gln Ala Ser Tyr Ile Ser Phe Asn Ala Ala Ser
                245                 250                 255

Asn Ser Arg Ser Gln Ile Lys Ala Ala Leu Asp Asn Ala Gly Lys Ile
            260                 265                 270

Met Ser Leu Thr Lys Thr Ala Pro Asp Tyr Leu Val Gly Gln Gln Pro
        275                 280                 285

Val Glu Asp Ile Ser Ser Asn Arg Ile Tyr Lys Ile Leu Glu Leu Asn
290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
                325                 330                 335

Thr Gly Lys Thr Asn Ile Ala Glu Ala Ile Ala His Thr Val Pro Phe
            340                 345                 350

-continued

Tyr Gly Cys Val Asn Trp Thr Asn Glu Asn Phe Pro Phe Asn Asp Cys
          355                 360                 365

Val Asp Lys Met Val Ile Trp Trp Glu Glu Gly Lys Met Thr Ala Lys
    370                 375                 380

Val Val Glu Ser Ala Lys Ala Ile Leu Gly Gly Ser Lys Val Arg Val
385                 390                 395                 400

Asp Gln Lys Cys Lys Ser Ser Ala Gln Ile Asp Pro Thr Pro Val Ile
                405                 410                 415

Val Thr Ser Asn Thr Asn Met Cys Ala Val Ile Asp Gly Asn Ser Thr
            420                 425                 430

Thr Phe Glu His Gln Gln Pro Leu Gln Asp Arg Met Phe Lys Phe Glu
        435                 440                 445

Leu Thr Arg Arg Leu Asp His Asp Phe Gly Lys Val Thr Lys Gln Glu
    450                 455                 460

Val Lys Asp Phe Phe Arg Trp Ala Lys Asp His Val Val Glu Val Glu
465                 470                 475                 480

His Glu Phe Tyr Val Lys Lys Gly Gly Ala Lys Lys Arg Pro Ala Pro
                485                 490                 495

Ser Asp Ala Asp Ile Ser Glu Pro Lys Arg Val Arg Glu Ser Val Ala
            500                 505                 510

Gln Pro Ser Thr Ser Asp Ala Glu Ala Ser Ile Asn Tyr Ala Asp Arg
        515                 520                 525

Tyr Gln Asn Lys Cys Ser Arg His Val Gly Met Asn Leu Met Leu Phe
    530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
                565                 570                 575

Gln Pro Val Ser Val Val Lys Lys Ala Tyr Gln Lys Leu Cys Tyr Ile
            580                 585                 590

His His Ile Met Gly Lys Val Pro Asp Ala Cys Thr Ala Cys Asp Leu
        595                 600                 605

Val Asn Val Asp Leu Asp Asp Cys Ile Phe Glu Gln
    610                 615                 620

<210> SEQ ID NO 56
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 56

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

```
Ser Gly Ile Ser Ser Met Val Leu Gly Arg Tyr Val Ser Gln Ile Arg
        100                 105                 110
Ala Gln Leu Val Lys Val Val Phe Gln Gly Ile Glu Pro Thr Leu Pro
        115                 120                 125
Asn Trp Phe Ala Val Thr Lys Thr Arg Asn Gly Ala Gly Gly Gly Asn
        130                 135                 140
Lys Val Val Asp Glu Cys Tyr Ile Pro Asn Tyr Leu Leu Pro Lys Thr
145                 150                 155                 160
Gln Pro Glu Leu Gln Trp Ala Trp Thr Asn Met Glu Gln Tyr Leu Ser
                165                 170                 175
Ala Cys Leu Asn Leu Thr Glu Arg Lys Arg Leu Val Ala Gln His Leu
            180                 185                 190
Thr His Val Ser Gln Thr Gln Glu Gln Asn Lys Glu Asn Gln Asn Pro
        195                 200                 205
Asn Ser Asp Ala Pro Val Ile Arg Ser Lys Thr Ser Ala Arg Tyr Met
    210                 215                 220
Glu Leu Val Gly Trp Leu Val Asp Lys Gly Ile Thr Ser Glu Lys Gln
225                 230                 235                 240
Trp Ile Gln Glu Asp Gln Ala Ser Tyr Ile Ser Phe Asn Ala Ala Ser
                245                 250                 255
Asn Ser Arg Ser Gln Ile Lys Ala Ala Leu Asp Asn Ala Gly Lys Ile
            260                 265                 270
Met Ser Leu Thr Lys Thr Ala Pro Asp Tyr Leu Val Gly Gln Gln Pro
        275                 280                 285
Val Glu Asp Ile Ser Ser Asn Arg Ile Tyr Lys Ile Leu Glu Leu Asn
    290                 295                 300
Gly Tyr Asp Pro Gln Tyr Ala Ala Ser Val Phe Leu Gly Trp Ala Thr
305                 310                 315                 320
Lys Lys Phe Gly Lys Arg Asn Thr Ile Trp Leu Phe Gly Pro Ala Thr
                325                 330                 335
Thr Gly Lys Thr Asn Ile Ala Glu Ala Ile Ala His Thr Val Pro Phe
            340                 345                 350
Tyr Gly Cys Val Asn Trp Thr Asn Glu Asn Phe Pro Phe Asn Asp Cys
        355                 360                 365
Val Asp Lys Met Val Ile Trp Trp Glu Glu Gly Lys Met Thr Ala Lys
    370                 375                 380
Val Val Glu Ser Ala Lys Ala Ile Leu Gly Gly Ser Lys Val Arg Val
385                 390                 395                 400
Asp Gln Lys Cys Lys Ser Ser Ala Gln Ile Asp Pro Thr Pro Val Ile
                405                 410                 415
Val Thr Ser Asn Thr Asn Met Cys Ala Val Ile Asp Gly Asn Ser Thr
            420                 425                 430
Thr Phe Glu His Gln Gln Pro Leu Gln Asp Arg Met Phe Lys Phe Glu
        435                 440                 445
Leu Thr Arg Arg Leu Asp His Asp Phe Gly Lys Val Thr Lys Gln Glu
    450                 455                 460
Val Lys Asp Phe Phe Arg Trp Ala Lys Asp His Val Val Glu Val Glu
465                 470                 475                 480
His Glu Phe Tyr Val Lys Lys Gly Gly Ala Lys Lys Arg Pro Ala Pro
                485                 490                 495
Ser Asp Ala Asp Ile Ser Glu Pro Lys Arg Val Arg Glu Ser Val Ala
            500                 505                 510
```

-continued

```
Gln Pro Ser Thr Ser Asp Ala Glu Ala Ser Ile Asn Tyr Ala Asp Arg
    515                 520                 525

Tyr Gln Asn Lys Cys Ser Arg His Val Gly Met Asn Leu Met Leu Phe
530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
                565                 570                 575

Gln Pro Val Ser Val Lys Lys Ala Tyr Gln Lys Leu Cys Tyr Ile
                580                 585                 590

His His Ile Met Gly Lys Val Pro Asp Ala Cys Thr Ala Cys Asp Leu
            595                 600                 605

Val Asn Val Asp Leu Asp Asp Cys Ile Phe Glu Gln
    610                 615                 620

<210> SEQ ID NO 57
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 57

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
                100                 105                 110

Ala Gln Leu Val Lys Val Val Phe Gln Gly Ile Glu Pro Gln Ile Asn
            115                 120                 125

Asp Trp Val Ala Ile Thr Lys Val Lys Lys Gly Gly Asn Lys Val
        130                 135                 140

Val Asp Glu Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
                180                 185                 190

Val Ser Gln Thr Gln Glu Gln Asn Lys Glu Asn Gln Asn Pro Asn Ser
            195                 200                 205

Asp Ala Pro Val Ile Arg Ser Lys Thr Ser Ala Arg Tyr Met Glu Leu
        210                 215                 220

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
                245                 250                 255
```

Arg Ser Gln Ile Lys Ala Ala Leu Asp Asn Ala Gly Lys Ile Met Ser
              260                 265                 270

Leu Thr Lys Thr Ala Pro Asp Tyr Leu Val Gly Gln Gln Pro Val Glu
          275                 280                 285

Asp Ile Ser Ser Asn Arg Ile Tyr Lys Ile Leu Glu Leu Asn Gly Tyr
      290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Thr Gly
              325                 330                 335

Lys Thr Asn Ile Ala Glu Ala Ile Ala His Thr Val Pro Phe Tyr Gly
          340                 345                 350

Cys Val Asn Trp Thr Asn Glu Asn Phe Pro Phe Asn Asp Cys Val Asp
      355                 360                 365

Lys Met Val Ile Trp Trp Glu Glu Gly Lys Met Thr Ala Lys Val Val
370                 375                 380

Glu Ser Ala Lys Ala Ile Leu Gly Gly Ser Lys Val Arg Val Asp Gln
385                 390                 395                 400

Lys Cys Lys Ser Ser Ala Gln Ile Asp Pro Thr Pro Val Ile Val Thr
              405                 410                 415

Ser Asn Thr Asn Met Cys Ala Val Ile Asp Gly Asn Ser Thr Thr Phe
          420                 425                 430

Glu His Gln Gln Pro Leu Gln Asp Arg Met Phe Lys Phe Glu Leu Thr
      435                 440                 445

Arg Arg Leu Asp His Asp Phe Gly Lys Val Thr Lys Gln Glu Val Lys
450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
              485                 490                 495

Ala Asp Ile Ser Glu Pro Lys Arg Val Arg Glu Ser Val Ala Gln Pro
          500                 505                 510

Ser Thr Ser Asp Ala Glu Ala Ser Ile Asn Tyr Ala Asp Arg Tyr Gln
      515                 520                 525

Asn Lys Cys Ser Arg His Val Gly Met Asn Leu Met Leu Phe Pro Cys
530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
              565                 570                 575

Val Ser Val Val Lys Lys Ala Tyr Gln Lys Leu Cys Tyr Ile His His
          580                 585                 590

Ile Met Gly Lys Val Pro Asp Ala Cys Thr Ala Cys Asp Leu Val Asn
      595                 600                 605

Val Asp Leu Asp Asp Cys Ile Phe Glu Gln
    610                 615

<210> SEQ ID NO 58
<211> LENGTH: 617
<212> TYPE: PRT
<213> ORGANISM: Artificial
<220> FEATURE:
<223> OTHER INFORMATION: Chimeric Rep protein sequence

<400> SEQUENCE: 58

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205

Asp Ala Pro Val Ile Arg Ser Lys Thr Ala Arg Tyr Met Glu Leu Val
    210                 215                 220

Gly Trp Leu Val Asp Lys Gly Ile Thr Ser Glu Lys Gln Trp Ile Gln
225                 230                 235                 240

Glu Asp Gln Ala Ser Tyr Ile Ser Phe Asn Ala Ala Ser Asn Ser Arg
                245                 250                 255

Ser Gln Ile Lys Ala Ala Leu Asp Asn Ala Gly Lys Ile Met Ser Leu
            260                 265                 270

Thr Lys Thr Ala Pro Asp Tyr Leu Val Gly Gln Gln Pro Val Glu Asp
        275                 280                 285

Ile Ser Ser Asn Arg Ile Tyr Lys Ile Leu Glu Leu Asn Gly Tyr Asp
    290                 295                 300

Pro Gln Tyr Ala Ala Ser Val Phe Leu Gly Trp Ala Thr Lys Lys Phe
305                 310                 315                 320

Gly Lys Arg Asn Thr Ile Trp Leu Phe Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
        355                 360                 365

Met Val Ile Trp Trp Glu Glu Gly Lys Met Thr Ala Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Ala Gln Ile Asp Pro Thr Pro Val Ile Val Thr Ser
                405                 410                 415

Asn Thr Asn Met Cys Ala Val Ile Asp Gly Asn Ser Thr Thr Phe Glu
```

-continued

```
            420                 425                 430
    His Gln Gln Pro Leu Gln Asp Arg Met Phe Lys Phe Glu Leu Thr Arg
            435                 440                 445
    Arg Leu Asp His Asp Phe Gly Lys Val Thr Lys Gln Glu Val Lys Asp
            450                 455                 460
    Phe Phe Arg Trp Ala Lys Asp His Val Val Glu Val Glu His Glu Phe
    465                 470                 475                 480
    Tyr Val Lys Lys Gly Gly Ala Lys Lys Arg Pro Ala Pro Ser Asp Ala
                        485                 490                 495
    Asp Ile Ser Glu Pro Lys Arg Val Arg Glu Ser Val Ala Gln Pro Ser
                500                 505                 510
    Thr Ser Asp Ala Glu Ala Ser Ile Asn Tyr Ala Asp Arg Tyr Gln Asn
            515                 520                 525
    Lys Cys Ser Arg His Val Gly Met Asn Leu Met Leu Phe Pro Cys Arg
            530                 535                 540
    Gln Cys Glu Arg Met Asn Gln Asn Ser Asn Ile Cys Phe Thr His Gly
    545                 550                 555                 560
    Gln Lys Asp Cys Leu Glu Cys Phe Pro Val Ser Glu Ser Gln Pro Val
                        565                 570                 575
    Ser Val Val Lys Lys Ala Tyr Gln Lys Leu Cys Tyr Ile His His Ile
                580                 585                 590
    Met Gly Lys Val Pro Asp Ala Cys Thr Ala Cys Asp Leu Val Asn Val
            595                 600                 605
    Asp Leu Asp Asp Cys Ile Phe Glu Gln
            610                 615

<210> SEQ ID NO 59
<211> LENGTH: 616
<212> TYPE: PRT
<213> ORGANISM: Artificial
<220> FEATURE:
<223> OTHER INFORMATION: Chimeric Rep protein sequence

<400> SEQUENCE: 59

Met Ala Thr Phe Tyr Glu Val Ile Val Arg Val Pro Phe Asp Val Glu
    1               5                   10                  15
    Glu His Leu Pro Gly Ile Ser Asp Ser Phe Val Asp Trp Val Thr Gly
                20                  25                  30
    Gln Ile Trp Glu Leu Pro Pro Glu Ser Asp Leu Asn Leu Thr Leu Val
                35                  40                  45
    Glu Gln Pro Gln Leu Thr Val Ala Asp Arg Ile Arg Arg Val Phe Leu
            50                  55                  60
    Tyr Glu Trp Asn Lys Phe Ser Lys Gln Glu Ser Lys Phe Phe Val Gln
    65                  70                  75                  80
    Phe Glu Lys Gly Ser Glu Tyr Phe His Leu His Thr Leu Val Glu Thr
                        85                  90                  95
    Ser Gly Ile Ser Ser Met Val Leu Gly Arg Tyr Val Ser Gln Ile Arg
                100                 105                 110
    Ala Gln Leu Val Lys Val Val Phe Gln Gly Ile Glu Pro Gln Ile Asn
            115                 120                 125
    Asp Trp Val Ala Ile Thr Lys Val Lys Lys Gly Gly Ala Asn Lys Val
            130                 135                 140
    Val Asp Ser Gly Tyr Ile Pro Ala Tyr Leu Leu Pro Lys Val Gln Pro
    145                 150                 155                 160
    Glu Leu Gln Trp Ala Trp Thr Asn Leu Asp Glu Tyr Lys Leu Ala Cys
```

```
                165                 170                 175
Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Asp
            195                 200                 205

Ala Pro Val Ile Arg Ser Lys Thr Ala Arg Tyr Met Glu Leu Val Gly
            210                 215                 220

Trp Leu Val Asp Lys Gly Ile Thr Ser Glu Lys Gln Trp Ile Gln Glu
225                 230                 235                 240

Asp Gln Ala Ser Tyr Ile Ser Phe Asn Ala Ala Ser Asn Ser Arg Ser
                245                 250                 255

Gln Ile Lys Ala Ala Leu Asp Asn Ala Gly Lys Ile Met Ser Leu Thr
            260                 265                 270

Lys Thr Ala Pro Asp Tyr Leu Val Gly Gln Gln Pro Val Glu Asp Ile
            275                 280                 285

Ser Ser Asn Arg Ile Tyr Lys Ile Leu Glu Leu Asn Gly Tyr Asp Pro
    290                 295                 300

Gln Tyr Ala Ala Ser Val Phe Leu Gly Trp Ala Thr Lys Lys Phe Gly
305                 310                 315                 320

Lys Arg Asn Thr Ile Trp Leu Phe Gly Pro Ala Thr Thr Gly Lys Thr
                325                 330                 335

Asn Ile Ala Glu Ala Ile Ala His Thr Val Pro Phe Tyr Gly Cys Val
            340                 345                 350

Asn Trp Thr Asn Glu Asn Phe Pro Phe Asn Asp Cys Val Asp Lys Met
            355                 360                 365

Val Ile Trp Trp Glu Glu Gly Lys Met Thr Ala Lys Val Val Glu Ser
            370                 375                 380

Ala Lys Ala Ile Leu Gly Gly Ser Lys Val Arg Val Asp Gln Lys Cys
385                 390                 395                 400

Lys Ser Ser Ala Gln Ile Asp Pro Thr Pro Val Ile Val Thr Ser Asn
                405                 410                 415

Thr Asn Met Cys Ala Val Ile Asp Gly Asn Ser Thr Thr Phe Glu His
            420                 425                 430

Gln Gln Pro Leu Gln Asp Arg Met Phe Lys Phe Glu Leu Thr Arg Arg
            435                 440                 445

Leu Asp His Asp Phe Gly Lys Val Thr Lys Gln Glu Val Lys Asp Phe
            450                 455                 460

Phe Arg Trp Ala Lys Asp His Val Val Glu Val Glu His Glu Phe Tyr
465                 470                 475                 480

Val Lys Lys Gly Gly Ala Lys Lys Arg Pro Ala Pro Ser Asp Ala Asp
                485                 490                 495

Ile Ser Glu Pro Lys Arg Val Arg Glu Ser Val Ala Gln Pro Ser Thr
            500                 505                 510

Ser Asp Ala Glu Ala Ser Ile Asn Tyr Ala Asp Arg Tyr Gln Asn Lys
            515                 520                 525

Cys Ser Arg His Val Gly Met Asn Leu Met Leu Phe Pro Cys Arg Gln
            530                 535                 540

Cys Glu Arg Met Asn Gln Asn Ser Asn Ile Cys Phe Thr His Gly Gln
545                 550                 555                 560

Lys Asp Cys Leu Glu Cys Phe Pro Val Ser Glu Ser Gln Pro Val Ser
                565                 570                 575

Val Val Lys Lys Ala Tyr Gln Lys Leu Cys Tyr Ile His His Ile Met
            580                 585                 590
```

```
Gly Lys Val Pro Asp Ala Cys Thr Ala Cys Asp Leu Val Asn Val Asp
        595                 600                 605

Leu Asp Asp Cys Ile Phe Glu Gln
    610                 615

<210> SEQ ID NO 60
<211> LENGTH: 621
<212> TYPE: PRT
<213> ORGANISM: Artificial
<220> FEATURE:
<223> OTHER INFORMATION: Chimeric Rep protein sequence

<400> SEQUENCE: 60

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335
```

```
Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Glu Ser Ala Lys Ala Ile Leu Gly Gly Ser Lys Val Arg
385                 390                 395                 400

Val Asp Gln Lys Cys Lys Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
            485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
            565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
            610                 615                 620

<210> SEQ ID NO 61
<211> LENGTH: 617
<212> TYPE: PRT
<213> ORGANISM: Artificial
<220> FEATURE:
<223> OTHER INFORMATION: Chimeric Rep protein sequence

<400> SEQUENCE: 61

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80
```

```
Phe Glu Lys Gly Ser Glu Tyr Phe His Leu His Thr Leu Val Glu Thr
                    85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                    165                 170                 175

Leu Asn Leu Glu Glu Arg Lys Arg Leu Val Ala Gln Phe Leu Ala Glu
                180                 185                 190

Ser Ser Gln Arg Ser Glu Gln Asn Lys Glu Asn Gln Asn Pro Asn Ser
            195                 200                 205

Asp Ala Pro Val Ile Arg Ser Lys Ser Ala Arg Tyr Met Glu Leu Val
        210                 215                 220

Gly Trp Leu Val Asp Lys Gly Ile Thr Ser Glu Lys Gln Trp Ile Gln
225                 230                 235                 240

Glu Asp Gln Ala Ser Tyr Ile Ser Phe Asn Ala Ala Ser Asn Ser Arg
                    245                 250                 255

Ser Gln Ile Lys Ala Ala Leu Asp Asn Ala Gly Lys Ile Met Ser Leu
                260                 265                 270

Thr Lys Thr Ala Pro Asp Tyr Leu Val Gly Gln Gln Pro Val Glu Asp
            275                 280                 285

Ile Ser Ser Asn Arg Ile Tyr Lys Ile Leu Glu Leu Asn Gly Tyr Asp
        290                 295                 300

Pro Gln Tyr Ala Ala Ser Val Phe Leu Gly Trp Ala Thr Lys Lys Phe
305                 310                 315                 320

Gly Lys Arg Asn Thr Ile Trp Leu Phe Gly Pro Ala Thr Thr Gly Lys
                    325                 330                 335

Thr Asn Ile Ala Glu Ala Ile Ala His Thr Val Pro Phe Tyr Gly Cys
                340                 345                 350

Val Asn Trp Thr Asn Glu Asn Phe Pro Phe Asn Asp Cys Val Asp Lys
            355                 360                 365

Met Val Ile Trp Trp Glu Glu Gly Lys Met Thr Ala Lys Val Val Glu
        370                 375                 380

Ser Ala Lys Ala Ile Leu Gly Gly Ser Lys Val Arg Val Asp Gln Lys
385                 390                 395                 400

Cys Lys Ser Ser Ala Gln Ile Asp Pro Thr Pro Val Ile Val Thr Ser
                    405                 410                 415

Asn Thr Asn Met Cys Ala Val Ile Asp Gly Asn Ser Thr Thr Phe Glu
                420                 425                 430

His Gln Gln Pro Leu Gln Asp Arg Met Phe Lys Phe Glu Leu Thr Arg
            435                 440                 445

Arg Leu Asp His Asp Phe Gly Lys Val Thr Lys Gln Glu Val Lys Asp
        450                 455                 460

Phe Phe Arg Trp Ala Lys Asp His Val Val Glu Val Glu His Glu Phe
465                 470                 475                 480

Tyr Val Lys Lys Gly Gly Ala Lys Arg Pro Ala Pro Ser Asp Ala
                    485                 490                 495
```

-continued

```
Asp Ile Ser Glu Pro Lys Arg Val Arg Glu Ser Val Ala Gln Pro Ser
            500                 505                 510

Thr Ser Asp Ala Glu Ala Ser Ile Asn Tyr Ala Asp Arg Tyr Gln Asn
        515                 520                 525

Lys Cys Ser Arg His Val Gly Met Asn Leu Met Leu Phe Pro Cys Arg
    530                 535                 540

Gln Cys Glu Arg Met Asn Gln Asn Ser Asn Ile Cys Phe Thr His Gly
545                 550                 555                 560

Gln Lys Asp Cys Leu Glu Cys Phe Pro Val Ser Glu Ser Gln Pro Val
                565                 570                 575

Ser Val Val Lys Lys Ala Tyr Gln Lys Leu Cys Tyr Ile His His Ile
                580                 585                 590

Met Gly Lys Val Pro Asp Ala Cys Thr Ala Cys Asp Leu Val Asn Val
            595                 600                 605

Asp Leu Asp Asp Cys Ile Phe Glu Gln
        610                 615

<210> SEQ ID NO 62
<211> LENGTH: 610
<212> TYPE: PRT
<213> ORGANISM: Artificial
<220> FEATURE:
<223> OTHER INFORMATION: Chimeric Rep protein sequence

<400> SEQUENCE: 62

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205

Asp Pro Val Ile Lys Ser Lys Thr Ser Gln Lys Tyr Met Ala Leu Val
    210                 215                 220

Asn Trp Leu Val Glu His Gly Ile Thr Ser Glu Lys Gln Trp Ile Gln
225                 230                 235                 240
```

Glu Asn Gln Glu Ser Tyr Leu Ser Phe Asn Ser Thr Gly Asn Ser Arg
            245                 250                 255

Ser Gln Ile Lys Ala Ala Leu Asp Asn Ala Thr Lys Ile Met Ser Leu
        260                 265                 270

Thr Lys Ser Ala Val Asp Tyr Leu Val Gly Ser Ser Val Pro Glu Asp
    275                 280                 285

Ile Ser Lys Asn Arg Ile Trp Gln Ile Phe Glu Met Asn Gly Tyr Asp
290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
            325                 330                 335

Thr Asn Ile Ala Glu Ala Ile Ala His Thr Val Pro Phe Tyr Gly Cys
        340                 345                 350

Val Asn Trp Thr Asn Glu Asn Phe Pro Phe Asn Asp Cys Val Asp Lys
    355                 360                 365

Met Leu Ile Trp Trp Glu Gly Lys Met Thr Asn Lys Val Val Glu
370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
            405                 410                 415

Asn Thr Asn Met Cys Val Val Val Asp Gly Asn Ser Thr Thr Phe Glu
        420                 425                 430

His Gln Gln Pro Leu Glu Asp Arg Met Phe Lys Phe Glu Leu Thr Lys
    435                 440                 445

Arg Leu Pro Pro Asp Phe Gly Lys Ile Thr Lys Gln Glu Val Lys Asp
450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
            485                 490                 495

Lys Arg Pro Leu Gly Asp Val Thr Asn Thr Ser Tyr Lys Ser Leu Glu
        500                 505                 510

Lys Arg Ala Arg Leu Ser Phe Val Pro Glu Thr Pro Arg Ser Ser Asp
    515                 520                 525

Val Thr Val Asp Pro Ala Pro Leu Arg Pro Leu Asn Trp Asn Ser Arg
530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
            565                 570                 575

Cys His Asn Val Thr His Cys Gln Ile Cys His Gly Ile Pro Pro Trp
        580                 585                 590

Glu Lys Glu Asn Leu Ser Asp Phe Gly Asp Phe Asp Asp Ala Asn Lys
    595                 600                 605

Glu Gln
    610

<210> SEQ ID NO 63
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 63

```
Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Ser Glu Tyr Phe His Leu His Thr Leu Val Glu
                85                  90                  95

Thr Ser Gly Ile Ser Ser Met Val Leu Gly Arg Tyr Val Ser Gln Ile
            100                 105                 110

Arg Ala Gln Leu Val Lys Val Val Phe Gln Gly Ile Glu Pro Gln Ile
        115                 120                 125

Asn Asp Trp Val Ala Ile Thr Lys Val Lys Lys Gly Gly Ala Asn Lys
    130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
                165                 170                 175

Ala Leu Asn Leu Glu Glu Arg Lys Arg Leu Val Ala Gln Phe Leu Ala
            180                 185                 190

Glu Ser Ser Gln Arg Ser Gln Glu Ala Ala Ser Gln Arg Glu Phe Ser
        195                 200                 205

Ala Asp Pro Val Ile Lys Ser Lys Thr Ser Gln Lys Tyr Met Ala Leu
    210                 215                 220

Val Asn Trp Leu Val Glu His Gly Ile Thr Ser Glu Lys Gln Trp Ile
225                 230                 235                 240

Gln Glu Asn Gln Glu Ser Tyr Leu Ser Phe Asn Ser Thr Gly Asn Ser
                245                 250                 255

Arg Ser Gln Ile Lys Ala Ala Leu Asp Asn Ala Thr Lys Ile Met Ser
            260                 265                 270

Leu Thr Lys Ser Ala Val Asp Tyr Leu Val Gly Ser Ser Val Pro Glu
        275                 280                 285

Asp Ile Ser Lys Asn Arg Ile Trp Gln Ile Phe Glu Met Asn Gly Tyr
    290                 295                 300

Asp Pro Ala Tyr Ala Gly Ser Ile Leu Tyr Gly Trp Cys Gln Arg Ser
305                 310                 315                 320

Phe Asn Lys Arg Asn Thr Val Trp Leu Tyr Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Leu Ile Trp Trp Glu Glu Gly Lys Met Thr Asn Lys Val Val
    370                 375                 380

Glu Ser Ala Lys Ala Ile Leu Gly Gly Ser Lys Val Arg Val Asp Gln
385                 390                 395                 400

Lys Cys Lys Ser Ser Val Gln Ile Asp Ser Thr Pro Val Ile Val Thr
```

```
                405                 410                 415
Ser Asn Thr Asn Met Cys Val Val Asp Gly Asn Ser Thr Thr Phe
            420                 425                 430

Glu His Gln Gln Pro Leu Glu Asp Arg Met Phe Lys Phe Glu Leu Thr
            435                 440                 445

Lys Arg Leu Pro Pro Asp Phe Gly Lys Ile Thr Lys Gln Glu Val Lys
450                 455                 460

Asp Phe Phe Ala Trp Ala Lys Val Asn Gln Val Pro Val Thr His Glu
465                 470                 475                 480

Phe Lys Val Pro Arg Glu Leu Ala Gly Thr Lys Gly Ala Glu Lys Ser
                485                 490                 495

Leu Lys Arg Pro Leu Gly Asp Val Thr Asn Thr Ser Tyr Lys Ser Leu
            500                 505                 510

Glu Lys Arg Ala Arg Leu Ser Phe Val Pro Glu Thr Pro Arg Ser Ser
            515                 520                 525

Asp Val Thr Val Asp Pro Ala Pro Leu Arg Pro Leu Asn Trp Asn Ser
530                 535                 540

Arg Tyr Asp Cys Lys Cys Asp Tyr His Ala Gln Phe Asp Asn Ile Ser
545                 550                 555                 560

Asn Lys Cys Asp Glu Cys Tyr Leu Asn Arg Gly Lys Asn Gly Cys
                565                 570                 575

Ile Cys His Asn Val Thr His Cys Gln Ile Cys His Gly Ile Pro Pro
            580                 585                 590

Trp Glu Lys Glu Asn Leu Ser Asp Phe Gly Asp Phe Asp Ala Asn
            595                 600                 605

Lys Glu Gln
    610

<210> SEQ ID NO 64
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 64

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Ser Gly Ile Ser Ser Met Val Leu Gly Arg Tyr Val Ser Gln Ile
            100                 105                 110

Arg Ala Gln Leu Val Lys Val Phe Gln Gly Ile Glu Pro Gln Ile
        115                 120                 125

Asn Asp Trp Val Ala Ile Thr Lys Val Lys Gly Gly Ala Asn Lys
        130                 135                 140

Val Val Asp Ser Gly Tyr Ile Pro Ala Tyr Leu Leu Pro Lys Val Gln
```

-continued

```
145                 150                 155                 160
Pro Glu Leu Gln Trp Ala Trp Thr Asn Leu Asp Glu Tyr Lys Leu Ala
                165                 170                 175
Ala Leu Asn Leu Glu Glu Arg Lys Arg Leu Val Ala Gln Phe Leu Ala
                180                 185                 190
Glu Ser Ser Gln Arg Ser Gln Glu Ala Ala Ser Gln Arg Glu Phe Ser
                195                 200                 205
Ala Asp Pro Val Ile Lys Ser Lys Thr Ser Gln Lys Tyr Met Ala Leu
210                 215                 220
Val Asn Trp Leu Val Glu His Gly Ile Thr Ser Glu Lys Gln Trp Ile
225                 230                 235                 240
Gln Glu Asn Gln Glu Ser Tyr Leu Ser Phe Asn Ser Thr Gly Asn Ser
                245                 250                 255
Arg Ser Gln Ile Lys Ala Ala Leu Asp Asn Ala Thr Lys Ile Met Ser
                260                 265                 270
Leu Thr Lys Ser Ala Val Asp Tyr Leu Val Gly Ser Ser Val Pro Glu
                275                 280                 285
Asp Ile Ser Lys Asn Arg Ile Trp Gln Ile Phe Glu Met Asn Gly Tyr
                290                 295                 300
Asp Pro Ala Tyr Ala Gly Ser Ile Leu Tyr Gly Trp Cys Gln Arg Ser
305                 310                 315                 320
Phe Asn Lys Arg Asn Thr Val Trp Leu Tyr Gly Pro Ala Thr Thr Gly
                325                 330                 335
Lys Thr Asn Ile Ala Glu Ala Ile Ala His Thr Val Pro Phe Tyr Gly
                340                 345                 350
Cys Val Asn Trp Thr Asn Glu Asn Phe Pro Phe Asn Asp Cys Val Asp
                355                 360                 365
Lys Met Leu Ile Trp Trp Glu Glu Gly Lys Met Thr Asn Lys Val Val
                370                 375                 380
Glu Ser Ala Lys Ala Ile Leu Gly Gly Ser Lys Val Arg Val Asp Gln
385                 390                 395                 400
Lys Cys Lys Ser Ser Val Gln Ile Asp Ser Thr Pro Val Ile Val Thr
                405                 410                 415
Ser Asn Thr Asn Met Cys Val Val Asp Gly Asn Ser Thr Thr Phe
                420                 425                 430
Glu His Gln Gln Pro Leu Glu Asp Arg Met Phe Lys Phe Glu Leu Thr
                435                 440                 445
Lys Arg Leu Pro Pro Asp Phe Gly Lys Ile Thr Lys Gln Glu Val Lys
                450                 455                 460
Asp Phe Phe Ala Trp Ala Lys Val Asn Gln Val Pro Val Thr His Glu
465                 470                 475                 480
Phe Lys Val Pro Arg Glu Leu Ala Gly Thr Lys Gly Ala Glu Lys Ser
                485                 490                 495
Leu Lys Arg Pro Leu Gly Asp Val Thr Asn Thr Ser Tyr Lys Ser Leu
                500                 505                 510
Glu Lys Arg Ala Arg Leu Ser Phe Val Pro Glu Thr Pro Arg Ser Ser
                515                 520                 525
Asp Val Thr Val Asp Pro Ala Pro Leu Arg Pro Leu Asn Trp Asn Ser
530                 535                 540
Arg Tyr Asp Cys Lys Cys Asp Tyr His Ala Gln Phe Asp Asn Ile Ser
545                 550                 555                 560
Asn Lys Cys Asp Glu Cys Glu Tyr Leu Asn Arg Gly Lys Asn Gly Cys
                565                 570                 575
```

-continued

```
Ile Cys His Asn Val Thr His Cys Gln Ile Cys His Gly Ile Pro Pro
            580                 585                 590

Trp Glu Lys Glu Asn Leu Ser Asp Phe Gly Asp Phe Asp Ala Asn
        595                 600                 605

Lys Glu Gln
    610

<210> SEQ ID NO 65
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 65

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Lys Val Val Phe Gln Gly Ile Glu Pro Gln Ile
        115                 120                 125

Asn Asp Trp Val Ala Ile Thr Lys Val Lys Lys Gly Gly Ala Asn Lys
    130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
                165                 170                 175

Ala Leu Asn Leu Glu Glu Arg Lys Arg Leu Val Ala Gln Phe Leu Ala
            180                 185                 190

Glu Ser Ser Gln Arg Ser Gln Glu Ala Ala Ser Gln Arg Glu Phe Ser
        195                 200                 205

Ala Asp Pro Val Ile Lys Ser Lys Thr Ser Gln Lys Tyr Met Ala Leu
    210                 215                 220

Val Asn Trp Leu Val Glu His Gly Ile Thr Ser Glu Lys Gln Trp Ile
225                 230                 235                 240

Gln Glu Asn Gln Glu Ser Tyr Leu Ser Phe Asn Ser Thr Gly Asn Ser
                245                 250                 255

Arg Ser Gln Ile Lys Ala Ala Leu Asp Asn Ala Thr Lys Ile Met Ser
            260                 265                 270

Leu Thr Lys Ser Ala Val Asp Tyr Leu Val Gly Ser Ser Val Pro Glu
        275                 280                 285

Asp Ile Ser Lys Asn Arg Ile Trp Gln Ile Phe Glu Met Asn Gly Tyr
    290                 295                 300

Asp Pro Ala Tyr Ala Gly Ser Ile Leu Tyr Gly Trp Cys Gln Arg Ser
305                 310                 315                 320
```

```
Phe Asn Lys Arg Asn Thr Val Trp Leu Tyr Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Leu Ile Trp Trp Glu Glu Gly Lys Met Thr Asn Lys Val Val
    370                 375                 380

Glu Ser Ala Lys Ala Ile Leu Gly Gly Ser Lys Val Arg Val Asp Gln
385                 390                 395                 400

Lys Cys Lys Ser Ser Val Gln Ile Asp Ser Thr Pro Val Ile Val Thr
                405                 410                 415

Ser Asn Thr Asn Met Cys Val Val Val Asp Gly Asn Ser Thr Thr Phe
            420                 425                 430

Glu His Gln Gln Pro Leu Glu Asp Arg Met Phe Lys Phe Glu Leu Thr
        435                 440                 445

Lys Arg Leu Pro Pro Asp Phe Gly Lys Ile Thr Lys Gln Glu Val Lys
    450                 455                 460

Asp Phe Phe Ala Trp Ala Lys Val Asn Gln Val Pro Val Thr His Glu
465                 470                 475                 480

Phe Lys Val Pro Arg Glu Leu Ala Gly Thr Lys Gly Ala Glu Lys Ser
                485                 490                 495

Leu Lys Arg Pro Leu Gly Asp Val Thr Asn Thr Ser Tyr Lys Ser Leu
            500                 505                 510

Glu Lys Arg Ala Arg Leu Ser Phe Val Pro Glu Thr Pro Arg Ser Ser
        515                 520                 525

Asp Val Thr Val Asp Pro Ala Pro Leu Arg Pro Leu Asn Trp Asn Ser
    530                 535                 540

Arg Tyr Asp Cys Lys Cys Asp Tyr His Ala Gln Phe Asp Asn Ile Ser
545                 550                 555                 560

Asn Lys Cys Asp Glu Cys Gly Tyr Leu Asn Arg Gly Lys Asn Gly Cys
                565                 570                 575

Ile Cys His Asn Val Thr His Cys Gln Ile Cys His Gly Ile Pro Pro
            580                 585                 590

Trp Glu Lys Glu Asn Leu Ser Asp Phe Gly Asp Phe Asp Asp Ala Asn
        595                 600                 605

Lys Glu Gln
    610

<210> SEQ ID NO 66
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 66

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60
```

```
Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Gln Ile
        115                 120                 125

Asn Asp Trp Val Ala Ile Thr Lys Val Lys Lys Gly Ala Asn Lys
130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
                165                 170                 175

Ala Leu Asn Leu Glu Glu Arg Lys Arg Leu Val Ala Gln Phe Leu Ala
            180                 185                 190

Glu Ser Ser Gln Arg Ser Gln Glu Ala Ala Ser Gln Arg Glu Phe Ser
        195                 200                 205

Ala Asp Pro Val Ile Lys Ser Lys Thr Ser Gln Lys Tyr Met Ala Leu
210                 215                 220

Val Asn Trp Leu Val Glu His Gly Ile Thr Ser Glu Lys Gln Trp Ile
225                 230                 235                 240

Gln Glu Asn Gln Glu Ser Tyr Leu Ser Phe Asn Ser Thr Gly Asn Ser
                245                 250                 255

Arg Ser Gln Ile Lys Ala Ala Leu Asp Asn Ala Thr Lys Ile Met Ser
            260                 265                 270

Leu Thr Lys Ser Ala Val Asp Tyr Leu Val Gly Ser Ser Val Pro Glu
        275                 280                 285

Asp Ile Ser Lys Asn Arg Ile Trp Gln Ile Phe Glu Met Asn Gly Tyr
290                 295                 300

Asp Pro Ala Tyr Ala Gly Ser Ile Leu Tyr Gly Trp Cys Gln Arg Ser
305                 310                 315                 320

Phe Asn Lys Arg Asn Thr Val Trp Leu Tyr Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Leu Ile Trp Trp Glu Glu Gly Lys Met Thr Asn Lys Val Val
370                 375                 380

Glu Ser Ala Lys Ala Ile Leu Gly Gly Ser Lys Val Arg Val Asp Gln
385                 390                 395                 400

Lys Cys Lys Ser Ser Val Gln Ile Asp Ser Thr Pro Val Ile Val Thr
                405                 410                 415

Ser Asn Thr Asn Met Cys Val Val Asp Gly Asn Ser Thr Thr Phe
            420                 425                 430

Glu His Gln Gln Pro Leu Glu Asp Arg Met Phe Lys Phe Glu Leu Thr
        435                 440                 445

Lys Arg Leu Pro Pro Asp Phe Gly Lys Ile Thr Lys Gln Glu Val Lys
    450                 455                 460

Asp Phe Phe Ala Trp Ala Lys Val Asn Gln Val Pro Val Thr His Glu
465                 470                 475                 480
```

```
Phe Lys Val Pro Arg Glu Leu Ala Gly Thr Lys Gly Ala Glu Lys Ser
                485                 490                 495
Leu Lys Arg Pro Leu Gly Asp Val Thr Asn Thr Ser Tyr Lys Ser Leu
            500                 505                 510
Glu Lys Arg Ala Arg Leu Ser Phe Val Pro Glu Thr Pro Arg Ser Ser
        515                 520                 525
Asp Val Thr Val Asp Pro Ala Pro Leu Arg Pro Leu Asn Trp Asn Ser
    530                 535                 540
Arg Tyr Asp Cys Lys Cys Asp Tyr His Ala Gln Phe Asp Asn Ile Ser
545                 550                 555                 560
Asn Lys Cys Asp Glu Cys Glu Tyr Leu Asn Arg Gly Lys Asn Gly Cys
                565                 570                 575
Ile Cys His Asn Val Thr His Cys Gln Ile Cys His Gly Ile Pro Pro
            580                 585                 590
Trp Glu Lys Glu Asn Leu Ser Asp Phe Gly Asp Phe Asp Asp Ala Asn
        595                 600                 605
Lys Glu Gln
    610

<210> SEQ ID NO 67
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 67

Met Pro Gly Phe Tyr Glu Ile Val Ile Lys Val Pro Ser Asp Leu Asp
1               5                   10                  15
Gly His Leu Pro Gly Ile Ser Asp Ser Phe Val Asn Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Asp Phe Leu
    50                  55                  60
Thr Glu Trp Arg Arg Val Ser Lys Ala Pro Glu Ala Leu Phe Phe Val
65                  70                  75                  80
Gln Phe Glu Lys Gly Glu Ser Tyr Phe His Met His Val Leu Val Glu
                85                  90                  95
Thr Thr Gly Val Lys Ser Met Val Leu Gly Arg Phe Leu Ser Gln Ile
            100                 105                 110
Arg Glu Lys Leu Ile Gln Arg Ile Tyr Arg Gly Ile Glu Pro Thr Leu
        115                 120                 125
Pro Asn Trp Phe Ala Val Thr Lys Thr Arg Asn Gly Ala Gly Gly Ala
    130                 135                 140
Asn Lys Val Val Asp Ser Gly Tyr Ile Pro Ala Tyr Leu Leu Pro Lys
145                 150                 155                 160
Val Gln Pro Glu Leu Gln Trp Ala Trp Thr Asn Leu Asp Glu Tyr Lys
                165                 170                 175
Leu Ala Ala Leu Asn Leu Glu Glu Arg Lys Arg Leu Val Ala Gln Phe
            180                 185                 190
Leu Ala Glu Ser Ser Gln Arg Ser Gln Glu Ala Ala Ser Gln Arg Glu
        195                 200                 205
Phe Ser Ala Asp Pro Val Ile Lys Ser Lys Thr Ser Gln Lys Tyr Met
    210                 215                 220
```

-continued

```
Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
            245                 250                 255

Asn Ser Arg Ser Gln Ile Lys Ala Ala Leu Asp Asn Ala Thr Lys Ile
        260                 265                 270

Met Ser Leu Thr Lys Ser Ala Val Asp Tyr Leu Val Gly Ser Ser Val
    275                 280                 285

Pro Glu Asp Ile Ser Lys Asn Arg Ile Trp Gln Ile Phe Glu Met Asn
290                 295                 300

Gly Tyr Asp Pro Ala Tyr Ala Gly Ser Ile Leu Tyr Gly Trp Cys Gln
305                 310                 315                 320

Arg Ser Phe Asn Lys Arg Asn Thr Val Trp Leu Tyr Gly Pro Ala Thr
            325                 330                 335

Thr Gly Lys Thr Asn Ile Ala Glu Ala Ile Ala His Thr Val Pro Phe
        340                 345                 350

Tyr Gly Cys Val Asn Trp Thr Asn Glu Asn Phe Pro Phe Asn Asp Cys
    355                 360                 365

Val Asp Lys Met Leu Ile Trp Trp Glu Glu Gly Lys Met Thr Asn Lys
370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
            405                 410                 415

Val Thr Ser Asn Thr Asn Met Cys Val Val Asp Gly Asn Ser Thr
        420                 425                 430

Thr Phe Glu His Gln Gln Pro Leu Glu Asp Arg Met Phe Lys Phe Glu
    435                 440                 445

Leu Thr Lys Arg Leu Pro Pro Asp Phe Gly Lys Ile Thr Lys Gln Glu
450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
            485                 490                 495

Lys Ser Leu Lys Arg Pro Leu Gly Asp Val Thr Asn Thr Ser Tyr Lys
        500                 505                 510

Ser Leu Glu Lys Arg Ala Arg Leu Ser Phe Val Pro Glu Thr Pro Arg
    515                 520                 525

Ser Ser Asp Val Thr Val Asp Pro Ala Pro Leu Arg Pro Leu Asn Trp
530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
            565                 570                 575

Gly Cys Ile Cys His Asn Val Thr His Cys Gln Ile Cys His Gly Ile
        580                 585                 590

Pro Pro Trp Glu Lys Glu Asn Leu Ser Asp Phe Gly Asp Phe Asp Asp
    595                 600                 605

Ala Asn Lys Glu Gln
    610
```

<210> SEQ ID NO 68
<211> LENGTH: 613
<212> TYPE: PRT

<213> ORGANISM: Artificial
<220> FEATURE:
<223> OTHER INFORMATION: Chimeric Rep protein sequence

<400> SEQUENCE: 68

```
Met Pro Gly Phe Tyr Glu Ile Val Ile Lys Val Pro Ser Asp Leu Asp
1               5                   10                  15
Gly His Leu Pro Gly Ile Ser Asp Ser Phe Val Asn Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Asp Phe Leu
    50                  55                  60
Thr Glu Trp Arg Arg Val Ser Lys Ala Pro Glu Ala Leu Phe Phe Val
65                  70                  75                  80
Gln Phe Glu Lys Gly Glu Ser Tyr Phe His Met His Val Leu Val Glu
                85                  90                  95
Thr Thr Gly Val Lys Ser Met Val Leu Gly Arg Phe Leu Ser Gln Ile
            100                 105                 110
Arg Glu Lys Leu Ile Gln Arg Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Ser Gly Tyr Ile Pro Ala Tyr Leu Leu Pro Lys
145                 150                 155                 160
Val Gln Pro Glu Leu Gln Trp Ala Trp Thr Asn Leu Asp Glu Tyr Lys
                165                 170                 175
Leu Ala Ala Leu Asn Leu Glu Glu Arg Lys Arg Leu Val Ala Gln Phe
            180                 185                 190
Leu Ala Glu Ser Ser Gln Arg Ser Gln Glu Ala Ala Ser Gln Arg Glu
        195                 200                 205
Phe Ser Ala Asp Pro Val Ile Lys Ser Lys Thr Ser Gln Lys Tyr Met
    210                 215                 220
Ala Leu Val Asn Trp Leu Val Glu His Gly Ile Thr Ser Glu Lys Gln
225                 230                 235                 240
Trp Ile Gln Glu Asn Gln Glu Ser Tyr Leu Ser Phe Asn Ser Thr Gly
                245                 250                 255
Asn Ser Arg Ser Gln Ile Lys Ala Ala Leu Asp Asn Ala Thr Lys Ile
            260                 265                 270
Met Ser Leu Thr Lys Ser Ala Val Asp Tyr Leu Val Gly Ser Ser Val
        275                 280                 285
Pro Glu Asp Ile Ser Lys Asn Arg Ile Trp Gln Ile Phe Glu Met Asn
    290                 295                 300
Gly Tyr Asp Pro Ala Tyr Ala Gly Ser Ile Leu Tyr Gly Trp Cys Gln
305                 310                 315                 320
Arg Ser Phe Asn Lys Arg Asn Thr Val Trp Leu Tyr Gly Pro Ala Thr
                325                 330                 335
Thr Gly Lys Thr Asn Ile Ala Glu Ala Ile Ala His Thr Val Pro Phe
            340                 345                 350
Tyr Gly Cys Val Asn Trp Thr Asn Glu Asn Phe Pro Phe Asn Asp Cys
        355                 360                 365
Val Asp Lys Met Leu Ile Trp Trp Glu Glu Gly Lys Met Thr Asn Lys
    370                 375                 380
Val Val Glu Ser Ala Lys Ala Ile Leu Gly Gly Ser Lys Val Arg Val
```

```
                385                 390                 395                 400
Asp Gln Lys Cys Lys Ser Ser Val Gln Ile Asp Ser Thr Pro Val Ile
                    405                 410                 415

Val Thr Ser Asn Thr Asn Met Cys Val Val Asp Gly Asn Ser Thr
                420                 425                 430

Thr Phe Glu His Gln Gln Pro Leu Glu Asp Arg Met Phe Lys Phe Glu
                435                 440                 445

Leu Thr Lys Arg Leu Pro Pro Asp Phe Gly Lys Ile Thr Lys Gln Glu
            450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
                485                 490                 495

Lys Ser Leu Lys Arg Pro Leu Gly Asp Val Thr Asn Thr Ser Tyr Lys
                500                 505                 510

Ser Leu Glu Lys Arg Ala Arg Leu Ser Phe Val Pro Glu Thr Pro Arg
            515                 520                 525

Ser Ser Asp Val Thr Val Asp Pro Ala Pro Leu Arg Pro Leu Asn Trp
        530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
                565                 570                 575

Gly Cys Ile Cys His Asn Val Thr His Cys Gln Ile Cys His Gly Ile
                580                 585                 590

Pro Pro Trp Glu Lys Glu Asn Leu Ser Asp Phe Gly Asp Phe Asp Asp
            595                 600                 605

Ala Asn Lys Glu Gln
        610

<210> SEQ ID NO 69
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 69

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
```

```
            130                 135                 140
Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Leu Asp Glu Tyr Lys
                165                 170                 175

Leu Ala Ala Leu Asn Leu Glu Glu Arg Lys Arg Leu Val Ala Gln Phe
            180                 185                 190

Leu Ala Glu Ser Ser Gln Arg Ser Gln Glu Ala Ala Ser Gln Arg Glu
        195                 200                 205

Phe Ser Ala Asp Pro Val Ile Lys Ser Lys Thr Ser Gln Lys Tyr Met
    210                 215                 220

Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
                245                 250                 255

Asn Ser Arg Ser Gln Ile Lys Ala Ala Leu Asp Asn Ala Thr Lys Ile
            260                 265                 270

Met Ser Leu Thr Lys Ser Ala Val Asp Tyr Leu Val Gly Ser Ser Val
        275                 280                 285

Pro Glu Asp Ile Ser Lys Asn Arg Ile Trp Gln Ile Phe Glu Met Asn
    290                 295                 300

Gly Tyr Asp Pro Ala Tyr Ala Gly Ser Ile Leu Tyr Gly Trp Cys Gln
305                 310                 315                 320

Arg Ser Phe Asn Lys Arg Asn Thr Val Trp Leu Tyr Gly Pro Ala Thr
                325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
        355                 360                 365

Val Asp Lys Met Leu Ile Trp Trp Glu Gly Lys Met Thr Asn Lys
    370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
                405                 410                 415

Val Thr Ser Asn Thr Asn Met Cys Val Val Asp Gly Asn Ser Thr
            420                 425                 430

Thr Phe Glu His Gln Gln Pro Leu Glu Asp Arg Met Phe Lys Phe Glu
        435                 440                 445

Leu Thr Lys Arg Leu Pro Pro Asp Phe Gly Lys Ile Thr Lys Gln Glu
    450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
                485                 490                 495

Lys Ser Leu Lys Arg Pro Leu Gly Asp Val Thr Asn Thr Ser Tyr Lys
            500                 505                 510

Ser Leu Glu Lys Arg Ala Arg Leu Ser Phe Val Pro Glu Thr Pro Arg
        515                 520                 525

Ser Ser Asp Val Thr Val Asp Pro Ala Pro Leu Arg Pro Leu Asn Trp
    530                 535                 540

Asn Ser Arg Tyr Asp Cys Lys Cys Asp Tyr His Ala Gln Phe Asp Asn
545                 550                 555                 560
```

```
Ile Ser Asn Lys Cys Asp Glu Cys Glu Tyr Leu Asn Arg Gly Lys Asn
                565                 570                 575

Gly Cys Ile Cys His Asn Val Thr His Cys Gln Ile Cys His Gly Ile
            580                 585                 590

Pro Pro Trp Glu Lys Glu Asn Leu Ser Asp Phe Gly Asp Phe Asp Asp
        595                 600                 605

Ala Asn Lys Glu Gln
        610

<210> SEQ ID NO 70
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 70

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln Phe
            180                 185                 190

Leu Ala Glu Ser Ser Gln Arg Ser Gln Glu Ala Ala Ser Gln Arg Glu
        195                 200                 205

Phe Ser Ala Asp Pro Val Ile Lys Ser Lys Thr Ser Gln Lys Tyr Met
    210                 215                 220

Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
                245                 250                 255

Asn Ser Arg Ser Gln Ile Lys Ala Ala Leu Asp Asn Ala Thr Lys Ile
            260                 265                 270

Met Ser Leu Thr Lys Ser Ala Val Asp Tyr Leu Val Gly Ser Ser Val
        275                 280                 285

Pro Glu Asp Ile Ser Lys Asn Arg Ile Trp Gln Ile Phe Glu Met Asn
    290                 295                 300
```

-continued

```
Gly Tyr Asp Pro Ala Tyr Ala Gly Ser Ile Leu Tyr Gly Trp Cys Gln
305                 310                 315                 320

Arg Ser Phe Asn Lys Arg Asn Thr Val Trp Leu Tyr Gly Pro Ala Thr
                325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
        355                 360                 365

Val Asp Lys Met Leu Ile Trp Trp Glu Glu Gly Lys Met Thr Asn Lys
    370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
                405                 410                 415

Val Thr Ser Asn Thr Asn Met Cys Val Val Asp Gly Asn Ser Thr
            420                 425                 430

Thr Phe Glu His Gln Gln Pro Leu Glu Asp Arg Met Phe Lys Phe Glu
        435                 440                 445

Leu Thr Lys Arg Leu Pro Pro Asp Phe Gly Lys Ile Thr Lys Gln Glu
    450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
                485                 490                 495

Lys Ser Leu Lys Arg Pro Leu Gly Asp Val Thr Asn Thr Ser Tyr Lys
            500                 505                 510

Ser Leu Glu Lys Arg Ala Arg Leu Ser Phe Val Pro Glu Thr Pro Arg
        515                 520                 525

Ser Ser Asp Val Thr Val Asp Pro Ala Pro Leu Arg Pro Leu Asn Trp
    530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
                565                 570                 575

Gly Cys Ile Cys His Asn Val Thr His Cys Gln Ile Cys His Gly Ile
            580                 585                 590

Pro Pro Trp Glu Lys Glu Asn Leu Ser Asp Phe Gly Asp Phe Asp Asp
        595                 600                 605

Ala Asn Lys Glu Gln
    610
```

```
<210> SEQ ID NO 71
<211> LENGTH: 614
<212> TYPE: PRT
<213> ORGANISM: Artificial
<220> FEATURE:
<223> OTHER INFORMATION: Chimeric Rep protein sequence

<400> SEQUENCE: 71
```

```
Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45
```

```
Glu Gln Ala Pro Leu Thr Val Ala Glu Lys Leu Gln Arg Asp Phe Leu
        50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
                195                 200                 205

Pro Asn Ser Asp Ala Pro Val Ile Lys Ser Lys Thr Ser Gln Lys Tyr
    210                 215                 220

Met Ala Leu Val Asn Trp Leu Val Glu His Gly Ile Thr Ser Glu Lys
225                 230                 235                 240

Gln Trp Ile Gln Glu Asn Gln Glu Ser Tyr Leu Ser Phe Asn Ser Thr
                245                 250                 255

Gly Asn Ser Arg Ser Gln Ile Lys Ala Ala Leu Asp Asn Ala Thr Lys
                260                 265                 270

Ile Met Ser Leu Thr Lys Ser Ala Val Asp Tyr Leu Val Gly Ser Ser
                275                 280                 285

Val Pro Glu Asp Ile Ser Lys Asn Arg Ile Trp Gln Ile Phe Glu Met
    290                 295                 300

Asn Gly Tyr Asp Pro Ala Tyr Ala Gly Ser Ile Leu Tyr Gly Trp Cys
305                 310                 315                 320

Gln Arg Ser Phe Asn Lys Arg Asn Thr Val Trp Leu Tyr Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
            355                 360                 365

Cys Val Asp Lys Met Leu Ile Trp Trp Glu Gly Lys Met Thr Asn
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Val Gln Ile Asp Ser Thr Pro Val
            405                 410                 415

Ile Val Thr Ser Asn Thr Asn Met Cys Val Val Val Asp Gly Asn Ser
            420                 425                 430

Thr Thr Phe Glu His Gln Gln Pro Leu Glu Asp Arg Met Phe Lys Phe
            435                 440                 445

Glu Leu Thr Lys Arg Leu Pro Pro Asp Phe Gly Lys Ile Thr Lys Gln
    450                 455                 460
```

```
Glu Val Lys Asp Phe Phe Ala Trp Ala Lys Val Asn Gln Val Pro Val
465                 470                 475                 480

Thr His Glu Phe Lys Val Pro Arg Glu Leu Ala Gly Thr Lys Gly Ala
                485                 490                 495

Glu Lys Ser Leu Lys Arg Pro Leu Gly Asp Val Thr Asn Thr Ser Tyr
            500                 505                 510

Lys Ser Leu Glu Lys Arg Ala Arg Leu Ser Phe Val Pro Glu Thr Pro
        515                 520                 525

Arg Ser Ser Asp Val Thr Val Asp Pro Ala Pro Leu Arg Pro Leu Asn
    530                 535                 540

Trp Asn Ser Arg Tyr Asp Cys Lys Cys Asp Tyr His Ala Gln Phe Asp
545                 550                 555                 560

Asn Ile Ser Asn Lys Cys Asp Glu Cys Glu Tyr Leu Asn Arg Gly Lys
                565                 570                 575

Asn Gly Cys Ile Cys His Asn Val Thr His Cys Gln Ile Cys His Gly
            580                 585                 590

Ile Pro Pro Trp Glu Lys Glu Asn Leu Ser Asp Phe Gly Asp Phe Asp
        595                 600                 605

Asp Ala Asn Lys Glu Gln
    610

<210> SEQ ID NO 72
<211> LENGTH: 612
<212> TYPE: PRT
<213> ORGANISM: Artificial
<220> FEATURE:
<223> OTHER INFORMATION: Chimeric Rep protein sequence

<400> SEQUENCE: 72

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Val Phe Leu
50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Gly Asn
130                 135                 140

Lys Val Val Asp Ser Gly Tyr Ile Pro Ala Tyr Leu Leu Pro Lys Val
145                 150                 155                 160

Gln Pro Glu Leu Gln Trp Ala Trp Thr Asn Leu Asp Glu Tyr Lys Leu
                165                 170                 175

Ala Ala Leu Asn Leu Glu Glu Arg Lys Arg Leu Val Ala Gln Phe Leu
            180                 185                 190

Ala Glu Ser Ser Gln Arg Ser Gln Glu Ala Ala Ser Gln Arg Glu Phe
        195                 200                 205
```

-continued

```
Ser Ala Asp Pro Val Ile Lys Ser Lys Thr Ser Gln Lys Tyr Met Ala
    210                 215                 220
Leu Val Asn Trp Leu Val Glu His Gly Ile Thr Ser Glu Lys Gln Trp
225                 230                 235                 240
Ile Gln Glu Asn Gln Glu Ser Tyr Leu Ser Phe Asn Ser Thr Gly Asn
                245                 250                 255
Ser Arg Ser Gln Ile Lys Ala Ala Leu Asp Asn Ala Thr Lys Ile Met
        260                 265                 270
Ser Leu Thr Lys Ser Ala Val Asp Tyr Leu Val Gly Ser Ser Val Pro
            275                 280                 285
Glu Asp Ile Ser Lys Asn Arg Ile Trp Gln Ile Phe Glu Met Asn Gly
290                 295                 300
Tyr Asp Pro Ala Tyr Ala Gly Ser Ile Leu Tyr Gly Trp Cys Gln Arg
305                 310                 315                 320
Ser Phe Asn Lys Arg Asn Thr Val Trp Leu Tyr Gly Pro Ala Thr Thr
                325                 330                 335
Gly Lys Thr Asn Ile Ala Glu Ala Ile Ala His Thr Val Pro Phe Tyr
            340                 345                 350
Gly Cys Val Asn Trp Thr Asn Glu Asn Phe Pro Phe Asn Asp Cys Val
                355                 360                 365
Asp Lys Met Leu Ile Trp Trp Glu Glu Gly Lys Met Thr Asn Lys Val
        370                 375                 380
Val Glu Ser Ala Lys Ala Ile Leu Gly Gly Ser Lys Val Arg Val Asp
385                 390                 395                 400
Gln Lys Cys Lys Ser Ser Val Gln Ile Asp Ser Thr Pro Val Ile Val
                405                 410                 415
Thr Ser Asn Thr Asn Met Cys Val Val Val Asp Gly Asn Ser Thr Thr
            420                 425                 430
Phe Glu His Gln Gln Pro Leu Glu Asp Arg Met Phe Lys Phe Glu Leu
        435                 440                 445
Thr Lys Arg Leu Pro Pro Asp Phe Gly Lys Ile Thr Lys Gln Glu Val
    450                 455                 460
Lys Asp Phe Phe Ala Trp Ala Lys Val Asn Gln Val Pro Val Thr His
465                 470                 475                 480
Glu Phe Lys Val Pro Arg Glu Leu Ala Gly Thr Lys Gly Ala Glu Lys
                485                 490                 495
Ser Leu Lys Arg Pro Leu Gly Asp Val Thr Asn Thr Ser Tyr Lys Ser
            500                 505                 510
Leu Glu Lys Arg Ala Arg Leu Ser Phe Val Pro Glu Thr Pro Arg Ser
        515                 520                 525
Ser Asp Val Thr Val Asp Pro Ala Pro Leu Arg Pro Leu Asn Trp Asn
    530                 535                 540
Ser Arg Tyr Asp Cys Lys Cys Asp Tyr His Ala Gln Phe Asp Asn Ile
545                 550                 555                 560
Ser Asn Lys Cys Asp Glu Cys Gly Tyr Leu Asn Arg Gly Lys Asn Gly
                565                 570                 575
Cys Ile Cys His Asn Val Thr His Cys Gln Ile Cys His Gly Ile Pro
            580                 585                 590
Pro Trp Glu Lys Glu Asn Leu Ser Asp Phe Gly Asp Phe Asp Asp Ala
        595                 600                 605
Asn Lys Glu Gln
    610
```

```
<210> SEQ ID NO 73
<211> LENGTH: 610
<212> TYPE: PRT
<213> ORGANISM: Artificial
<220> FEATURE:
<223> OTHER INFORMATION: Chimeric Rep protein sequence

<400> SEQUENCE: 73

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Val Gln
65                  70                  75                  80

Phe Glu Lys Gly Ser Gly Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Phe Gln Gly Ile Glu Pro Gln Ile Asn
    115                 120                 125

Asp Trp Val Ala Ile Thr Lys Val Lys Lys Gly Ala Asn Lys Val
130                 135                 140

Val Asp Glu Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
    195                 200                 205

Asp Pro Val Ile Lys Ser Lys Thr Ser Gln Lys Tyr Met Ala Leu Val
210                 215                 220

Asn Trp Leu Val Glu His Gly Ile Thr Ser Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
    275                 280                 285

Ile Ser Lys Asn Arg Ile Trp Gln Ile Phe Glu Met Asn Gly Tyr Asp
290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
    355                 360                 365

Met Leu Ile Trp Trp Glu Glu Gly Lys Met Thr Asn Lys Val Val Glu
```

```
                    370                 375                 380
Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
                420                 425                 430

His Gln Gln Pro Leu Glu Asp Arg Met Phe Lys Phe Glu Leu Thr Lys
                435                 440                 445

Arg Leu Pro Pro Asp Phe Gly Lys Ile Thr Lys Gln Glu Val Lys Asp
            450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
            515                 520                 525

Val Thr Val Asp Pro Ala Pro Leu Arg Pro Leu Asn Trp Asn Ser Arg
            530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
                580                 585                 590

Glu Lys Glu Asn Leu Ser Asp Phe Gly Asp Phe Asp Ala Asn Lys
                595                 600                 605

Glu Gln
    610

<210> SEQ ID NO 74
<211> LENGTH: 612
<212> TYPE: PRT
<213> ORGANISM: Artificial
<220> FEATURE:
<223> OTHER INFORMATION: Chimeric Rep protein sequence

<400> SEQUENCE: 74

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Glu Lys Leu Ile Gln Arg Ile Tyr Arg Gly Ile Glu Pro Thr Leu Pro
```

-continued

```
            115                 120                 125
Asn Trp Phe Ala Val Thr Lys Thr Arg Asn Gly Ala Gly Gly Asn
        130                 135                 140
Lys Val Val Asp Glu Cys Tyr Ile Pro Asn Tyr Leu Leu Pro Lys Thr
145                 150                 155                 160
Gln Pro Glu Leu Gln Trp Ala Trp Thr Asn Met Glu Gln Tyr Leu Ser
                165                 170                 175
Ala Cys Leu Asn Leu Thr Glu Arg Lys Arg Leu Val Ala Gln Phe Leu
                180                 185                 190
Ala Glu Ser Ser Gln Arg Ser Gln Glu Ala Ala Ser Gln Arg Glu Phe
                195                 200                 205
Ser Ala Asp Pro Val Ile Lys Ser Lys Thr Ser Gln Lys Tyr Met Ala
210                 215                 220
Leu Val Asn Trp Leu Val Glu His Gly Ile Thr Ser Glu Lys Gln Trp
225                 230                 235                 240
Ile Gln Glu Asn Gln Glu Ser Tyr Leu Ser Phe Asn Ser Thr Gly Asn
                245                 250                 255
Ser Arg Ser Gln Ile Lys Ala Ala Leu Asp Asn Ala Thr Lys Ile Met
                260                 265                 270
Ser Leu Thr Lys Ser Ala Val Asp Tyr Leu Val Gly Ser Ser Val Pro
                275                 280                 285
Glu Asp Ile Ser Lys Asn Arg Ile Trp Gln Ile Phe Glu Met Asn Gly
                290                 295                 300
Tyr Asp Pro Ala Tyr Ala Gly Ser Ile Leu Tyr Gly Trp Cys Gln Arg
305                 310                 315                 320
Ser Phe Asn Lys Arg Asn Thr Val Trp Leu Tyr Gly Pro Ala Thr Thr
                325                 330                 335
Gly Lys Thr Asn Ile Ala Glu Ala Ile Ala His Thr Val Pro Phe Tyr
                340                 345                 350
Gly Cys Val Asn Trp Thr Asn Glu Asn Phe Pro Phe Asn Asp Cys Val
                355                 360                 365
Asp Lys Met Leu Ile Trp Trp Glu Glu Gly Lys Met Thr Asn Lys Val
        370                 375                 380
Val Glu Ser Ala Lys Ala Ile Leu Gly Gly Ser Lys Val Arg Val Asp
385                 390                 395                 400
Gln Lys Cys Lys Ser Ser Val Gln Ile Asp Ser Thr Pro Val Ile Val
                405                 410                 415
Thr Ser Asn Thr Asn Met Cys Val Val Asp Gly Asn Ser Thr Thr
                420                 425                 430
Phe Glu His Gln Gln Pro Leu Glu Asp Arg Met Phe Lys Phe Glu Leu
        435                 440                 445
Thr Lys Arg Leu Pro Pro Asp Phe Gly Lys Ile Thr Lys Gln Glu Val
        450                 455                 460
Lys Asp Phe Phe Ala Trp Ala Lys Val Asn Gln Val Pro Val Thr His
465                 470                 475                 480
Glu Phe Lys Val Pro Arg Glu Leu Ala Gly Thr Lys Gly Ala Glu Lys
                485                 490                 495
Ser Leu Lys Arg Pro Leu Gly Asp Val Thr Asn Thr Ser Tyr Lys Ser
                500                 505                 510
Leu Glu Lys Arg Ala Arg Leu Ser Phe Val Pro Glu Thr Pro Arg Ser
                515                 520                 525
Ser Asp Val Thr Val Asp Pro Ala Pro Leu Arg Pro Leu Asn Trp Asn
530                 535                 540
```

-continued

```
Ser Arg Tyr Asp Cys Lys Cys Asp Tyr His Ala Gln Phe Asp Asn Ile
545                 550                 555                 560

Ser Asn Lys Cys Asp Glu Cys Glu Tyr Leu Asn Arg Gly Lys Asn Gly
            565                 570                 575

Cys Ile Cys His Asn Val Thr His Cys Gln Ile Cys His Gly Ile Pro
            580                 585                 590

Pro Trp Glu Lys Glu Asn Leu Ser Asp Phe Gly Asp Phe Asp Asp Ala
        595                 600                 605

Asn Lys Glu Gln
        610

<210> SEQ ID NO 75
<211> LENGTH: 619
<212> TYPE: PRT
<213> ORGANISM: Artificial
<220> FEATURE:
<223> OTHER INFORMATION: Chimeric Rep protein sequence

<400> SEQUENCE: 75

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Ser Gly Ile Ser Ser Met Val Leu Gly Arg Tyr Val Ser Gln Ile
            100                 105                 110

Arg Ala Gln Leu Val Lys Val Val Phe Gln Gly Ile Glu Pro Gln Ile
        115                 120                 125

Asn Asp Trp Val Ala Ile Thr Lys Val Lys Lys Gly Gly Ala Asn Lys
    130                 135                 140

Val Val Asp Glu Cys Tyr Ile Pro Asn Tyr Leu Leu Pro Lys Thr Gln
145                 150                 155                 160

Pro Glu Leu Gln Trp Ala Trp Thr Asn Met Glu Gln Tyr Leu Ser Ala
                165                 170                 175

Cys Leu Asn Leu Thr Glu Arg Lys Arg Leu Val Ala Gln His Leu Thr
            180                 185                 190

His Val Ser Gln Thr Gln Glu Gln Asn Lys Glu Asn Gln Asn Pro Asn
        195                 200                 205

Ser Asp Ala Pro Val Ile Arg Ser Lys Thr Ser Ala Arg Tyr Met Glu
    210                 215                 220

Leu Val Gly Trp Leu Val Asp Lys Gly Ile Thr Ser Glu Lys Gln Trp
225                 230                 235                 240

Ile Gln Glu Asp Gln Ala Ser Tyr Ile Ser Phe Asn Ala Ala Ser Asn
                245                 250                 255

Ser Arg Ser Gln Ile Lys Ala Ala Leu Asp Asn Ala Gly Lys Ile Met
            260                 265                 270

Ser Leu Thr Lys Thr Ala Pro Asp Tyr Leu Val Gly Gln Gln Pro Val
        275                 280                 285
```

Glu Asp Ile Ser Ser Asn Arg Ile Tyr Lys Ile Leu Glu Leu Asn Gly
                290                 295                 300

Tyr Asp Pro Gln Tyr Ala Ala Ser Val Phe Leu Gly Trp Ala Thr Lys
305                 310                 315                 320

Lys Phe Gly Lys Arg Asn Thr Ile Trp Leu Phe Gly Pro Ala Thr Thr
                325                 330                 335

Gly Lys Thr Asn Ile Ala Glu Ala Ile Ala His Thr Val Pro Phe Tyr
                340                 345                 350

Gly Cys Val Asn Trp Thr Asn Glu Asn Phe Pro Phe Asn Asp Cys Val
                355                 360                 365

Asp Lys Met Val Ile Trp Trp Glu Glu Gly Lys Met Thr Ala Lys Val
                370                 375                 380

Val Glu Ser Ala Lys Ala Ile Leu Gly Gly Ser Lys Val Arg Val Asp
385                 390                 395                 400

Gln Lys Cys Lys Ser Ser Ala Gln Ile Asp Pro Thr Pro Val Ile Val
                405                 410                 415

Thr Ser Asn Thr Asn Met Cys Ala Val Ile Asp Gly Asn Ser Thr Thr
                420                 425                 430

Phe Glu His Gln Gln Pro Leu Gln Asp Arg Met Phe Lys Phe Glu Leu
                435                 440                 445

Thr Arg Arg Leu Asp His Asp Phe Gly Lys Val Thr Lys Gln Glu Val
450                 455                 460

Lys Asp Phe Phe Arg Trp Ala Lys Asp His Val Val Glu Val Glu His
465                 470                 475                 480

Glu Phe Tyr Val Lys Lys Gly Gly Ala Lys Lys Arg Pro Ala Pro Ser
                485                 490                 495

Asp Ala Asp Ile Ser Glu Pro Lys Arg Val Arg Glu Ser Val Ala Gln
                500                 505                 510

Pro Ser Thr Ser Asp Ala Glu Ala Ser Ile Asn Tyr Ala Asp Arg Tyr
                515                 520                 525

Gln Asn Lys Cys Ser Arg His Val Gly Met Asn Leu Met Leu Phe Pro
                530                 535                 540

Cys Arg Gln Cys Glu Arg Met Asn Gln Asn Ser Asn Ile Cys Phe Thr
545                 550                 555                 560

His Gly Gln Lys Asp Cys Leu Glu Cys Phe Pro Val Ser Glu Ser Gln
                565                 570                 575

Pro Val Ser Val Val Lys Lys Ala Tyr Gln Lys Leu Cys Tyr Ile His
                580                 585                 590

His Ile Met Gly Lys Val Pro Asp Ala Cys Thr Ala Cys Asp Leu Val
                595                 600                 605

Asn Val Asp Leu Asp Asp Cys Ile Phe Glu Gln
                610                 615

<210> SEQ ID NO 76
<211> LENGTH: 624
<212> TYPE: PRT
<213> ORGANISM: Artificial
<220> FEATURE:
<223> OTHER INFORMATION: Chimeric Rep protein sequence

<400> SEQUENCE: 76

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
                20                  25                  30

-continued

```
Lys Glu Trp Glu Leu Pro Pro Asp Ser Asp Met Asp Leu Asn Leu Ile
             35                  40                  45

Glu Gln Ala Pro Leu Thr Val Ala Glu Lys Leu Gln Arg Asp Phe Leu
 50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
        130                 135                 140

Asn Lys Val Val Asp Ser Gly Tyr Ile Pro Ala Tyr Leu Leu Pro Lys
145                 150                 155                 160

Val Gln Pro Glu Leu Gln Trp Ala Trp Thr Asn Leu Asp Glu Tyr Lys
                165                 170                 175

Leu Ala Ala Leu Asn Leu Glu Glu Arg Lys Arg Arg Lys Arg Leu Val
            180                 185                 190

Ala Gln His Leu Thr His Val Ser Gln Thr Gln Glu Gln Asn Lys Glu
        195                 200                 205

Asn Gln Asn Pro Asn Ser Asp Ala Pro Val Ile Arg Ser Lys Thr Ser
210                 215                 220

Ala Arg Tyr Met Glu Leu Val Gly Trp Leu Val Asp Lys Gly Ile Thr
225                 230                 235                 240

Ser Glu Lys Gln Trp Ile Gln Glu Asp Gln Ala Ser Tyr Ile Ser Phe
                245                 250                 255

Asn Ala Ala Ser Asn Ser Arg Ser Gln Ile Lys Ala Ala Leu Asp Asn
            260                 265                 270

Ala Gly Lys Ile Met Ser Leu Thr Lys Thr Ala Pro Asp Tyr Leu Val
        275                 280                 285

Gly Gln Gln Pro Val Glu Asp Ile Ser Ser Asn Arg Ile Tyr Lys Ile
290                 295                 300

Leu Glu Leu Asn Gly Tyr Asp Pro Gln Tyr Ala Ala Ser Val Phe Leu
305                 310                 315                 320

Gly Trp Ala Thr Lys Lys Phe Gly Lys Arg Asn Thr Ile Trp Leu Phe
                325                 330                 335

Gly Pro Ala Thr Thr Gly Lys Thr Asn Ile Ala Glu Ala Ile Ala His
            340                 345                 350

Thr Val Pro Phe Tyr Gly Cys Val Asn Trp Thr Asn Glu Asn Phe Pro
        355                 360                 365

Phe Asn Asp Cys Val Asp Lys Met Val Ile Trp Trp Glu Glu Gly Lys
370                 375                 380

Met Thr Ala Lys Val Val Glu Ser Ala Lys Ala Ile Leu Gly Gly Ser
385                 390                 395                 400

Lys Val Arg Val Asp Gln Lys Cys Lys Ser Ser Ala Gln Ile Asp Pro
                405                 410                 415

Thr Pro Val Ile Val Thr Ser Asn Thr Asn Met Cys Ala Val Ile Asp
            420                 425                 430

Gly Asn Ser Thr Thr Phe Glu His Gln Gln Pro Leu Gln Asp Arg Met
        435                 440                 445
```

```
Phe Lys Phe Glu Leu Thr Arg Arg Leu Asp His Asp Phe Gly Lys Val
    450                 455                 460

Thr Lys Gln Glu Val Lys Asp Phe Phe Arg Trp Ala Lys Asp His Val
465                 470                 475                 480

Val Glu Val Glu His Glu Phe Tyr Val Lys Lys Gly Gly Ala Lys Lys
                485                 490                 495

Arg Pro Ala Pro Ser Asp Ala Asp Ile Ser Glu Pro Lys Arg Val Arg
            500                 505                 510

Glu Ser Val Ala Gln Pro Ser Thr Ser Asp Ala Glu Ala Ser Ile Asn
        515                 520                 525

Tyr Ala Asp Arg Tyr Gln Asn Lys Cys Ser Arg His Val Gly Met Asn
    530                 535                 540

Leu Met Leu Phe Pro Cys Arg Gln Cys Glu Arg Met Asn Gln Asn Ser
545                 550                 555                 560

Asn Ile Cys Phe Thr His Gly Gln Lys Asp Cys Leu Glu Cys Phe Pro
                565                 570                 575

Val Ser Glu Ser Gln Pro Val Ser Val Lys Lys Ala Tyr Gln Lys
            580                 585                 590

Leu Cys Tyr Ile His His Ile Met Gly Lys Val Pro Asp Ala Cys Thr
    595                 600                 605

Ala Cys Asp Leu Val Asn Val Asp Leu Asp Cys Ile Phe Glu Gln
            610                 615                 620

<210> SEQ ID NO 77
<211> LENGTH: 622
<212> TYPE: PRT
<213> ORGANISM: Artificial
<220> FEATURE:
<223> OTHER INFORMATION: Chimeric Rep protein sequence

<400> SEQUENCE: 77

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Ser Gly Ile Ser Ser Met Val Leu Gly Arg Tyr Val Ser Gln Ile
            100                 105                 110

Arg Ala Gln Leu Val Lys Val Val Phe Gln Gly Ile Glu Pro Gln Ile
        115                 120                 125

Asn Asp Trp Val Ala Ile Thr Lys Val Lys Lys Gly Gly Ala Asn Lys
    130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
                165                 170                 175

Ala Leu Asn Leu Glu Glu Arg Lys Arg Arg Lys Arg Leu Val Ala Gln
            180                 185                 190
```

-continued

His Leu Thr His Val Ser Gln Thr Gln Glu Gln Asn Lys Glu Asn Gln
        195                 200                 205

Asn Pro Asn Ser Asp Ala Pro Val Ile Arg Ser Lys Thr Ser Ala Arg
    210                 215                 220

Tyr Met Glu Leu Val Gly Trp Leu Val Asp Lys Gly Ile Thr Ser Glu
225                 230                 235                 240

Lys Gln Trp Ile Gln Glu Asp Gln Ala Ser Tyr Ile Ser Phe Asn Ala
                245                 250                 255

Ala Ser Asn Ser Arg Ser Gln Ile Lys Ala Ala Leu Asp Asn Ala Gly
            260                 265                 270

Lys Ile Met Ser Leu Thr Lys Thr Ala Pro Asp Tyr Leu Val Gly Gln
        275                 280                 285

Gln Pro Val Glu Asp Ile Ser Ser Asn Arg Ile Tyr Lys Ile Leu Glu
    290                 295                 300

Leu Asn Gly Tyr Asp Pro Gln Tyr Ala Ala Ser Val Phe Leu Gly Trp
305                 310                 315                 320

Ala Thr Lys Lys Phe Gly Lys Arg Asn Thr Ile Trp Leu Phe Gly Pro
                325                 330                 335

Ala Thr Thr Gly Lys Thr Asn Ile Ala Glu Ala Ile Ala His Thr Val
            340                 345                 350

Pro Phe Tyr Gly Cys Val Asn Trp Thr Asn Glu Asn Phe Pro Phe Asn
        355                 360                 365

Asp Cys Val Asp Lys Met Val Ile Trp Trp Glu Glu Gly Lys Met Thr
    370                 375                 380

Ala Lys Val Val Glu Ser Ala Lys Ala Ile Leu Gly Gly Ser Lys Val
385                 390                 395                 400

Arg Val Asp Gln Lys Cys Lys Ser Ser Ala Gln Ile Asp Pro Thr Pro
                405                 410                 415

Val Ile Val Thr Ser Asn Thr Asn Met Cys Ala Val Ile Asp Gly Asn
            420                 425                 430

Ser Thr Thr Phe Glu His Gln Gln Pro Leu Gln Asp Arg Met Phe Lys
        435                 440                 445

Phe Glu Leu Thr Arg Arg Leu Asp His Asp Phe Gly Lys Val Thr Lys
    450                 455                 460

Gln Glu Val Lys Asp Phe Phe Arg Trp Ala Lys Asp His Val Val Glu
465                 470                 475                 480

Val Glu His Glu Phe Tyr Val Lys Lys Gly Gly Ala Lys Lys Arg Pro
                485                 490                 495

Ala Pro Ser Asp Ala Asp Ile Ser Glu Pro Lys Arg Val Arg Glu Ser
            500                 505                 510

Val Ala Gln Pro Ser Thr Ser Asp Ala Glu Ala Ser Ile Asn Tyr Ala
        515                 520                 525

Asp Arg Tyr Gln Asn Lys Cys Ser Arg His Val Gly Met Asn Leu Met
    530                 535                 540

Leu Phe Pro Cys Arg Gln Cys Glu Arg Met Asn Gln Asn Ser Asn Ile
545                 550                 555                 560

Cys Phe Thr His Gly Gln Lys Asp Cys Leu Glu Cys Phe Pro Val Ser
                565                 570                 575

Glu Ser Gln Pro Val Ser Val Lys Lys Ala Tyr Gln Lys Leu Cys
            580                 585                 590

Tyr Ile His His Ile Met Gly Lys Val Pro Asp Ala Cys Thr Ala Cys
        595                 600                 605

Asp Leu Val Asn Val Asp Leu Asp Asp Cys Ile Phe Glu Gln

<210> SEQ ID NO 78
<211> LENGTH: 1857
<212> TYPE: DNA
<213> ORGANISM: Artificial
<220> FEATURE:
<223> OTHER INFORMATION: Chimeric Rep protein coding sequence

<400> SEQUENCE: 78

```
atggctacct tctatgaagt cattgttcgc gtcccatttg acgtggagga acatctgcct      60
ggaatttctg acagctttgt ggactgggta actggtcaaa tttgggagct gcctccagag     120
tcagatttaa atttgactct ggttgaacag cctcagttga cggtggctga tagaattcgc     180
cgcgtgttcc tgtacgagtg aacaaattt tccaagcagg agtccaaatt ctttgtgcag     240
tttgaaaagg gatctgaata ttttcatctg cacacgcttg tggagacctc cggcatctct     300
tccatggtcc tcggccgcta cgtgagtcag attcgcgccc agctggtgaa agtggtcttc     360
cagggaattg aaccccagat caacgactgg gtcgccatca ccaaggtaaa gaagggcgga     420
gccaataagg tggtggatga gtgctacatc cccaattact tgctccccaa aacccagcct     480
gagctccagt gggcgtggac taatatgaaa cagtatttaa cgcctgtttt gaatctcacg     540
gagcgtaaac ggttggtggc gcagcatctg acgcacgtgt cgcagacgca ggagcagaac     600
aaagagaatc agaatcccaa ttctgatgcg ccggtgatca gatcaaaaac ttcagccagg     660
tacatggagc tggtcgggtg gctcgtggac aaggggatta cctcggagaa gcagtggatc     720
caggaggacc aggcctcata catctccttc aatgcggcct ccaactcgcg gtcccaaatc     780
aaggctgcct ggacaatgc gggaaagatt atgagcctga ctaaaaccgc cccgactac     840
ctggtgggcc agcagcccgt ggaggacatt ccagcaatcg gatttataaa attttggaa     900
ctaaacgggt acgatcccca atatgcggct ccgtctttc tgggatgggc acgaaaaag     960
ttcggcaaga ggaacaccat ctggctgttt gggcctgcaa ctaccgggaa gaccaacatc    1020
gcggaggcca tagcccacac tgtgcccttc tacgggtgcg taaactggac caatgagaac    1080
tttcccttca cgactgtgt cgacaagatg gtgatctggt gggaggaggg gaagatgacc    1140
gccaaggtcg tggagtcggc caaagccatt ctcggaggaa gcaaggtgcg cgtggaccag    1200
aaatgcaagt cctcggccca gatagacccg actcccgtga cgtcacctc caacaccaac    1260
atgtgcgccg tgattgacgg gaactcaacg accttcgaac accagcagcc gttgcaagac    1320
cggatgttca aatttgaact cacccgccgt ctggatcatg actttgggaa ggtcaccaag    1380
caggaagtca agactttttt ccggtgggca aaggatcacg tggttgaggt ggagcatgaa    1440
ttctacgtca aaaagggtgg agccaagaaa gacccgcccc cagtgacgc agatataagt    1500
gagcccaaac gggtgcgcga gtcagttgcg cagccatcga cgtcagacgc ggaagcttcg    1560
atcaactacg cagacaggta ccaaaacaaa tgttctcgtc acgtgggcat gaatctgatg    1620
ctgtttccct gcagacaatg cgagagaatg aatcagaatt caaatatctg cttcactcac    1680
ggacagaaag actgtttaga gtgctttccc gtgtcagaat ctcaacccgt ttctgtcgtc    1740
aaaaaggcgt atcagaaact gtgctacatt catcatatca tgggaaaggt gccagacgct    1800
tgcactgcct gcgatctggt caatgtggat ttggatgact gcatctttga acaataa      1857
```

<210> SEQ ID NO 79
<211> LENGTH: 618
<212> TYPE: PRT
<213> ORGANISM: Artificial

<220> FEATURE:
<223> OTHER INFORMATION: Chimeric Rep protein sequence

<400> SEQUENCE: 79

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Phe Gln Gly Ile Glu Pro Gln Ile Asn
        115                 120                 125

Asp Trp Val Ala Ile Thr Lys Val Lys Lys Gly Gly Ala Asn Lys Val
130                 135                 140

Val Asp Glu Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205

Asp Ala Pro Val Ile Arg Ser Lys Thr Ser Ala Arg Tyr Met Glu Leu
210                 215                 220

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
                245                 250                 255

Arg Ser Gln Ile Lys Ala Ala Leu Asp Asn Ala Gly Lys Ile Met Ser
            260                 265                 270

Leu Thr Lys Thr Ala Pro Asp Tyr Leu Val Gly Gln Gln Pro Val Glu
        275                 280                 285

Asp Ile Ser Ser Asn Arg Ile Tyr Lys Ile Leu Glu Leu Asn Gly Tyr
290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Val Ile Trp Trp Glu Glu Gly Lys Met Thr Ala Lys Val Val
370                 375                 380

Glu Ser Ala Lys Ala Ile Leu Gly Gly Ser Lys Val Arg Val Asp Gln
385                 390                 395                 400

```
Lys Cys Lys Ser Ser Ala Gln Ile Asp Pro Thr Pro Val Ile Val Thr
                405                 410                 415

Ser Asn Thr Asn Met Cys Ala Val Ile Asp Gly Asn Ser Thr Thr Phe
            420                 425                 430

Glu His Gln Gln Pro Leu Gln Asp Arg Met Phe Lys Phe Glu Leu Thr
        435                 440                 445

Arg Arg Leu Asp His Asp Phe Gly Lys Val Thr Lys Gln Glu Val Lys
    450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
                485                 490                 495

Ala Asp Ile Ser Glu Pro Lys Arg Val Arg Glu Ser Val Ala Gln Pro
            500                 505                 510

Ser Thr Ser Asp Ala Glu Ala Ser Ile Asn Tyr Ala Asp Arg Tyr Gln
        515                 520                 525

Asn Lys Cys Ser Arg His Val Gly Met Asn Leu Met Leu Phe Pro Cys
    530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
                565                 570                 575

Val Ser Val Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
        595                 600                 605

Val Asp Leu Asp Asp Cys Ile Phe Glu Gln
    610                 615

<210> SEQ ID NO 80
<211> LENGTH: 1857
<212> TYPE: DNA
<213> ORGANISM: Artificial
<220> FEATURE:
<223> OTHER INFORMATION: Chimeric Rep protein coding sequence

<400> SEQUENCE: 80
atggctacct tctatgaagt cattgttcgc gtcccatttg acgtggagga acatctgcct      60
ggaatttctg acagctttgt ggactgggta actggtcaaa tttgggagct gcctccagag     120
tcagatttaa atttgactct ggttgaacag cctcagttga cggtggctga tagaattcgc     180
cgcgtgttcc tgtacgagtg gaacaaattt ccaagcagga gtccaaatt ctttgtgcag      240 tttgaaaagg gatctgaata ttttcatctg cacacgcttg tggagacctc cggcatctct     300
tccatggtcc tcggccgcta cgtgagtcag attcgcgccc agctggtgaa agtggtcttc     360
cagggaattg aacccagat caacgactgg gtcgccatca ccaaggtaaa gaagggcgga     420
gccaataagg tggtggattc ttgctacatc cccaattact tgctccccaa acccagcct     480 gagctccagt gggcgtggac taatatggaa cagtatttaa gcgcctgttt gaatctcacg     540
gagcgtaaac ggttggtggc gcagcatctg acgcacgtgt cgcagacgca ggagcagaac     600
aaagagaatc agaatcccaa ttctgatgcg ccggtgatca gatcaaaaac ttcagccagg     660
tacatggagc tggtcgggtg gctcgtggac aagggggatta cctcggagaa gcagtggatc     720
caggaggacc aggcctcata catctccttc aatgcggcct ccaactcgcg gtcccaaatc     780
```

```
aaggctgcct tggacaatgc gggaaagatt atgagcctga ctaaaaccgc ccccgactac    840
ctggtgggcc agcagcccgt ggaggacatt ccagcaatc ggatttataa aattttggaa     900
ctaaacgggt acgatcccca atatgcggct ccgtctttc tgggatgggc cacgaaaaag     960
ttcggcaaga ggaacaccat ctggctgttt gggcctgcaa ctaccgggaa gaccaacatc   1020
gcggaggcca tagcccacac tgtgcccttc tacgggtgcg taaactggac caatgagaac   1080
tttcccttca cgactgtgt cgacaagatg gtgatctggt ggggaggagg gaagatgacc    1140
gccaaggtcg tggagtcggc caaagccatt ctcggaggaa gcaaggtgcg cgtggaccag   1200
aaatgcaagt cctcggccca gatagacccg actcccgtga tcgtcacctc caacaccaac   1260
atgtgcgccg tgattgacgg gaactcaacg accttcgaac accagcagcc gttgcaagac   1320
cggatgttca aatttgaact cacccgccgt ctggatcatg actttgggaa ggtcaccaag   1380
caggaagtca agacttttt ccggtgggca aggatcacg tggttgaggt ggagcatgaa     1440
ttctacgtca aaaagggtgg agccaagaaa agacccgccc ccagtgacgc agatataagt   1500
gagcccaaac gggtgcgcga gtcagttgcg cagccatcga cgtcagacgc ggaagcttcg   1560
atcaactacg cagacaggta ccaaaacaaa tgttctcgtc acgtgggcat gaatctgatg   1620
ctgtttccct gcagacaatg cgagagaatg aatcagaatt caaatatctg cttcactcac   1680
ggacagaaag actgtttaga gtgctttccc gtgtcagaat ctcaaccgt ttctgtcgtc    1740
aaaaaggcgt atcagaaact gtgctacatt catcatatca tggaaaaggt gccagacgct   1800
tgcactgcct gcgatctggt caatgtggat ttggatgact gcatctttga acaataa     1857
```

<210> SEQ ID NO 81
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 81

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175
```

-continued

```
Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205

Asp Ala Pro Val Ile Arg Ser Lys Thr Ser Ala Arg Tyr Met Glu Leu
    210                 215                 220

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
                245                 250                 255

Arg Ser Gln Ile Lys Ala Ala Leu Asp Asn Ala Gly Lys Ile Met Ser
            260                 265                 270

Leu Thr Lys Thr Ala Pro Asp Tyr Leu Val Gly Gln Gln Pro Val Glu
        275                 280                 285

Asp Ile Ser Ser Asn Arg Ile Tyr Lys Ile Leu Glu Leu Asn Gly Tyr
    290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Val Ile Trp Trp Glu Glu Gly Lys Met Thr Ala Lys Val Val
370                 375                 380

Glu Ser Ala Lys Ala Ile Leu Gly Gly Ser Lys Val Arg Val Asp Gln
385                 390                 395                 400

Lys Cys Lys Ser Ser Ala Gln Ile Asp Pro Thr Pro Val Ile Val Thr
                405                 410                 415

Ser Asn Thr Asn Met Cys Ala Val Ile Asp Gly Asn Ser Thr Thr Phe
            420                 425                 430

Glu His Gln Gln Pro Leu Gln Asp Arg Met Phe Lys Phe Glu Leu Thr
        435                 440                 445

Arg Arg Leu Asp His Asp Phe Gly Lys Val Thr Lys Gln Glu Val Lys
    450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
                485                 490                 495

Ala Asp Ile Ser Glu Pro Lys Arg Val Arg Glu Ser Val Ala Gln Pro
            500                 505                 510

Ser Thr Ser Asp Ala Glu Ala Ser Ile Asn Tyr Ala Asp Arg Tyr Gln
        515                 520                 525

Asn Lys Cys Ser Arg His Val Gly Met Asn Leu Met Leu Phe Pro Cys
    530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
                565                 570                 575

Val Ser Val Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
```

Val Asp Leu Asp Asp Cys Ile Phe Glu Gln
    610             615

<210> SEQ ID NO 82
<211> LENGTH: 1857
<212> TYPE: DNA
<213> ORGANISM: Artificial
<220> FEATURE:
<223> OTHER INFORMATION: Chimeric Rep protein coding sequence

<400> SEQUENCE: 82

| | | | | |
|---|---|---|---|---|
| atggctacct | tctatgaagt | cattgttcgc | gtcccatttg | acgtggagga | acatctgcct | 60 |
| ggaatttctg | acagctttgt | ggactgggta | actggtcaaa | tttgggagct | gcctccagag | 120 |
| tcagatttaa | atttgactct | ggttgaacag | cctcagttga | cggtggctga | tagaattcgc | 180 |
| cgcgtgttcc | tgtacgagtg | gaacaaattt | ccaagcagg | agtccaaatt | ctttgtgcag | 240 |
| tttgaaaagg | gatctgaata | ttttcatctg | cacacgcttg | tggagacctc | cggcatctct | 300 |
| tccatggtcc | tcggccgcta | cgtgagtcag | attcgcgccc | agctggtgaa | agtggtcttc | 360 |
| cagggaattg | aacccagat | caacgactgg | gtcgccatca | ccaaggtaaa | gaagggcgga | 420 |
| gccaataagg | tggtggattc | tgggtatatt | cccaattact | tgctccccaa | aacccagcct | 480 |
| gagctccagt | gggcgtggac | taatatggaa | cagtatttaa | gcgcctgttt | gaatctcacg | 540 |
| gagcgtaaac | ggttggtggc | gcagcatctg | acgcacgtgt | cgcagacgca | ggagcagaac | 600 |
| aaagagaatc | agaatcccaa | ttctgatgcg | ccggtgatca | gatcaaaaac | ttcagccagg | 660 |
| tacatggagc | tggtcgggtg | gctcgtggac | aaggggatta | cctcggagaa | gcagtggatc | 720 |
| caggaggacc | aggcctcata | catctccttc | aatgcggcct | ccaactcgcg | gtcccaaatc | 780 |
| aaggctgcct | tggacaatgc | ggggaaagatt | atgagcctga | ctaaaaccgc | cccgactac | 840 |
| ctggtgggcc | agcagcccgt | ggaggacatt | tccagcaatc | ggatttataa | aattttggaa | 900 |
| ctaaacgggt | acgatcccca | atatgcggct | tccgtctttc | tgggatgggc | cacgaaaaag | 960 |
| ttcggcaaga | gaacaccat | ctggctgttt | gggcctgcaa | ctaccgggaa | gaccaacatc | 1020 |
| gcggaggcca | tagcccacac | tgtgcccttc | tacgggtgcg | taaactggac | caatgagaac | 1080 |
| tttccccttca | acgactgtgt | cgacaagatg | gtgatctggt | gggaggaggg | gaagatgacc | 1140 |
| gccaaggtcg | tggagtcggc | caaagccatt | ctcggaggaa | gcaaggtgcg | cgtggaccag | 1200 |
| aaatgcaagt | cctcggccca | gatagacccg | actcccgtga | tcgtcacctc | caacaccaac | 1260 |
| atgtgcgccg | tgattgacgg | gaactcaacg | accttcgaac | accagcagcc | gttgcaagac | 1320 |
| cggatgttca | aatttgaact | cacccgccgt | ctggatcatg | actttgggaa | ggtcaccaag | 1380 |
| caggaagtca | agactttttt | ccggtgggca | aaggatcacg | tggttgaggt | ggagcatgaa | 1440 |
| ttctacgtca | aaaagggtgg | agccaagaaa | agacccgccc | ccagtgacgc | agatataagt | 1500 |
| gagcccaaac | gggtgcgcga | gtcagttgcg | cagccatcga | cgtcagacgc | ggaagcttcg | 1560 |
| atcaactacg | cagacaggta | ccaaaacaaa | tgttctcgtc | acgtgggcat | gaatctgatg | 1620 |
| ctgtttccct | gcagacaatg | cgagagaatg | aatcagaatt | caaatatctg | cttcactcac | 1680 |
| ggacagaaag | actgtttaga | gtgctttccc | gtgtcagaat | ctcaacccgt | ttctgtcgtc | 1740 |
| aaaaaggcgt | atcagaaact | gtgctacatt | catcatatca | tgggaaaggt | gccagacgct | 1800 |
| tgcactgcct | gcgatctggt | caatgtggat | ttggatgact | gcatctttga | acaataa | 1857 |

<210> SEQ ID NO 83

<211> LENGTH: 618
<212> TYPE: PRT
<213> ORGANISM: Artificial
<220> FEATURE:
<223> OTHER INFORMATION: Chimeric Rep protein sequence

<400> SEQUENCE: 83

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
130                 135                 140

Val Asp Ser Gly Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205

Asp Ala Pro Val Ile Arg Ser Lys Thr Ser Ala Arg Tyr Met Glu Leu
210                 215                 220

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
                245                 250                 255

Arg Ser Gln Ile Lys Ala Ala Leu Asp Asn Ala Gly Lys Ile Met Ser
            260                 265                 270

Leu Thr Lys Thr Ala Pro Asp Tyr Leu Val Gly Gln Gln Pro Val Glu
        275                 280                 285

Asp Ile Ser Ser Asn Arg Ile Tyr Lys Ile Leu Glu Leu Asn Gly Tyr
290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Thr Gly
                325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
        355                 360                 365

Lys Met Val Ile Trp Trp Glu Glu Gly Lys Met Thr Ala Lys Val Val
370                 375                 380
```

```
Glu Ser Ala Lys Ala Ile Leu Gly Gly Ser Lys Val Arg Val Asp Gln
385                 390                 395                 400

Lys Cys Lys Ser Ser Ala Gln Ile Asp Pro Thr Pro Val Ile Val Thr
            405                 410                 415

Ser Asn Thr Asn Met Cys Ala Val Ile Asp Gly Asn Ser Thr Thr Phe
        420                 425                 430

Glu His Gln Gln Pro Leu Gln Asp Arg Met Phe Lys Phe Glu Leu Thr
    435                 440                 445

Arg Arg Leu Asp His Asp Phe Gly Lys Val Thr Lys Gln Glu Val Lys
450                 455                 460

Asp Phe Phe Arg Trp Ala Lys Asp His Val Glu Val Glu His
465                 470                 475                 480

Phe Tyr Val Lys Lys Gly Gly Ala Lys Lys Arg Pro Ala Pro Ser Asp
                485                 490                 495

Ala Asp Ile Ser Glu Pro Lys Arg Val Arg Glu Ser Val Ala Gln Pro
            500                 505                 510

Ser Thr Ser Asp Ala Glu Ala Ser Ile Asn Tyr Ala Asp Arg Tyr Gln
        515                 520                 525

Asn Lys Cys Ser Arg His Val Gly Met Asn Leu Met Leu Phe Pro Cys
    530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
                565                 570                 575

Val Ser Val Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
        595                 600                 605

Val Asp Leu Asp Asp Cys Ile Phe Glu Gln
    610                 615

<210> SEQ ID NO 84
<211> LENGTH: 312
<212> TYPE: PRT
<213> ORGANISM: Adeno-associated virus 1

<400> SEQUENCE: 84

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
50                  55                  60

Pro Pro Ala Asp Ile Lys Thr Asn Arg Ile Tyr Arg Ile Leu Glu Leu
65                  70                  75                  80

Asn Gly Tyr Glu Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
```

```
              130                 135                 140
Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
                195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
            275                 280                 285

Ala Asp Pro Ser Thr Ser Asp Ala Glu Gly Ala Pro Val Asp Phe Ala
            290                 295                 300

Asp Leu Ala Arg Gly Gln Pro Leu
305                 310

<210> SEQ ID NO 85
<211> LENGTH: 312
<212> TYPE: PRT
<213> ORGANISM: Adeno-associated virus 2

<400> SEQUENCE: 85

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
                20                  25                  30

Ser Asn Ser Arg Ser Gln Ile Lys Ala Ala Leu Asp Asn Ala Gly Lys
            35                  40                  45

Ile Met Ser Leu Thr Lys Thr Ala Pro Asp Tyr Leu Val Gly Gln Gln
        50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190
```

```
Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Ala Lys Lys Arg Pro Ala
                260                 265                 270

Pro Ser Asp Ala Asp Ile Ser Glu Pro Lys Arg Val Arg Glu Ser Val
            275                 280                 285

Ala Gln Pro Ser Thr Ser Asp Ala Glu Ala Ser Ile Asn Tyr Ala Asp
290                 295                 300

Arg Leu Ala Arg Gly His Ser Leu
305                 310

<210> SEQ ID NO 86
<211> LENGTH: 311
<212> TYPE: PRT
<213> ORGANISM: Adeno-associated virus 3A

<400> SEQUENCE: 86

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
    50                  55                  60

Pro Pro Glu Asp Ile Thr Lys Asn Arg Ile Tyr Gln Ile Leu Glu Leu
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Glu Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255
```

Ala His Glu Phe Tyr Val Arg Lys Gly Gly Ala Lys Lys Arg Pro Ala
            260                 265                 270

Ser Asn Asp Ala Asp Val Ser Glu Pro Lys Arg Glu Cys Thr Ser Leu
        275                 280                 285

Ala Gln Pro Thr Thr Ser Asp Ala Glu Ala Pro Ala Asp Tyr Ala Asp
    290                 295                 300

Leu Ala Arg Gly Gln Pro Phe
305                 310

<210> SEQ ID NO 87
<211> LENGTH: 311
<212> TYPE: PRT
<213> ORGANISM: Adeno-associated virus 3B

<400> SEQUENCE: 87

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
    50                  55                  60

Pro Pro Glu Asp Ile Thr Lys Asn Arg Ile Tyr Gln Ile Leu Glu Leu
65                  70                  75                  80

Asn Gly Tyr Asp Pro Gln Tyr Ala Ala Ser Val Phe Leu Gly Trp Ala
            85                  90                  95

Gln Lys Lys Phe Gly Lys Arg Asn Thr Ile Trp Leu Phe Gly Pro Ala
        100                 105                 110

Thr Thr Gly Lys Thr Asn Ile Ala Glu Ala Ile Ala His Ala Val Pro
    115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
            165                 170                 175

Val Asp Gln Lys Cys Lys Ser Ser Ala Gln Ile Glu Pro Thr Pro Val
        180                 185                 190

Ile Val Thr Ser Asn Thr Asn Met Cys Ala Val Ile Asp Gly Asn Ser
    195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
            245                 250                 255

Ala His Glu Phe Tyr Val Arg Lys Gly Gly Ala Lys Lys Arg Pro Ala
        260                 265                 270

Ser Asn Asp Ala Asp Val Ser Glu Pro Lys Arg Gln Cys Thr Ser Leu
    275                 280                 285

Ala Gln Pro Thr Thr Ser Asp Ala Glu Ala Pro Ala Asp Tyr Ala Asp
    290                 295                 300

Leu Ala Arg Gly Gln Pro Phe
305                 310

<210> SEQ ID NO 88
<211> LENGTH: 311
<212> TYPE: PRT
<213> ORGANISM: Adeno-associated virus 4

<400> SEQUENCE: 88

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Gln Asn
    50                  55                  60

Pro Pro Glu Asp Ile Ser Ser Asn Arg Ile Tyr Arg Ile Leu Glu Met
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Lys Arg Leu Glu His Asp Phe Gly Lys Val Thr Lys Gln
225                 230                 235                 240

Glu Val Lys Asp Phe Phe Arg Trp Ala Ser Asp His Val Thr Glu Val
                245                 250                 255

Thr His Glu Phe Tyr Val Arg Lys Gly Gly Ala Arg Lys Arg Pro Ala
            260                 265                 270

Pro Asn Asp Ala Asp Ile Ser Glu Pro Lys Arg Ala Cys Pro Ser Val
        275                 280                 285

Ala Gln Pro Ser Thr Ser Asp Ala Glu Ala Pro Val Asp Tyr Ala Asp
    290                 295                 300

Leu Ala Arg Gly Gln Pro Leu
305                 310

<210> SEQ ID NO 89
<211> LENGTH: 329
<212> TYPE: PRT
<213> ORGANISM: Adeno-associated virus 5

<400> SEQUENCE: 89

Met Ala Leu Val Asn Trp Leu Val Glu His Gly Ile Thr Ser Glu Lys

```
  1               5                   10                  15
Gln Trp Ile Gln Glu Asn Gln Glu Ser Tyr Leu Ser Phe Asn Ser Thr
                20                  25                  30

Gly Asn Ser Arg Ser Gln Ile Lys Ala Ala Leu Asp Asn Ala Thr Lys
            35                  40                  45

Ile Met Ser Leu Thr Lys Ser Ala Val Asp Tyr Leu Val Gly Ser Ser
        50                  55                  60

Val Pro Glu Asp Ile Ser Lys Asn Arg Ile Trp Gln Ile Phe Glu Met
65                  70                  75                  80

Asn Gly Tyr Asp Pro Ala Tyr Ala Gly Ser Ile Leu Tyr Gly Trp Cys
                85                  90                  95

Gln Arg Ser Phe Asn Lys Arg Asn Thr Val Trp Leu Tyr Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
130                 135                 140

Cys Val Asp Lys Met Leu Ile Trp Trp Glu Glu Gly Lys Met Thr Asn
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Val Gln Ile Asp Ser Thr Pro Val
            180                 185                 190

Ile Val Thr Ser Asn Thr Asn Met Cys Val Val Asp Gly Asn Ser
        195                 200                 205

Thr Thr Phe Glu His Gln Gln Pro Leu Glu Asp Arg Met Phe Lys Phe
        210                 215                 220

Glu Leu Thr Lys Arg Leu Pro Pro Asp Phe Gly Lys Ile Thr Lys Gln
225                 230                 235                 240

Glu Val Lys Asp Phe Phe Ala Trp Ala Lys Val Asn Gln Val Pro Val
                245                 250                 255

Thr His Glu Phe Lys Val Pro Arg Glu Leu Ala Gly Thr Lys Gly Ala
            260                 265                 270

Glu Lys Ser Leu Lys Arg Pro Leu Gly Asp Val Thr Asn Thr Ser Tyr
        275                 280                 285

Lys Ser Leu Glu Lys Arg Ala Arg Leu Ser Phe Val Pro Glu Thr Pro
        290                 295                 300

Arg Ser Ser Asp Val Thr Val Asp Pro Ala Pro Leu Arg Pro Leu Asn
305                 310                 315                 320

Trp Asn Ser Leu Val Gly Pro Ser Trp
                325

<210> SEQ ID NO 90
<211> LENGTH: 312
<212> TYPE: PRT
<213> ORGANISM: Adeno-associated virus 6

<400> SEQUENCE: 90

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
                20                  25                  30

Ser Asn Ser Arg Ser Gln Ile Lys Ala Ala Leu Asp Asn Ala Gly Lys
            35                  40                  45
```

```
Ile Met Ala Leu Thr Lys Ser Ala Pro Asp Tyr Leu Val Gly Pro Ala
 50                  55                  60

Pro Pro Ala Asp Ile Lys Thr Asn Arg Ile Tyr Arg Ile Leu Glu Leu
 65                  70                  75                  80

Asn Gly Tyr Asp Pro Ala Tyr Ala Gly Ser Val Phe Leu Gly Trp Ala
                 85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
            115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
            275                 280                 285

Ala Asp Pro Ser Thr Ser Asp Ala Glu Gly Ala Pro Val Asp Phe Ala
            290                 295                 300

Asp Leu Ala Arg Gly Gln Pro Leu
305                 310

<210> SEQ ID NO 91
<211> LENGTH: 312
<212> TYPE: PRT
<213> ORGANISM: Adeno-associated virus 7

<400> SEQUENCE: 91

Met Glu Leu Val Gly Trp Leu Val Asp Arg Gly Ile Thr Ser Glu Lys
 1               5                  10                  15

Gln Trp Ile Gln Glu Asp Gln Ala Ser Tyr Ile Ser Phe Asn Ala Ala
             20                  25                  30

Ser Asn Ser Arg Ser Gln Ile Lys Ala Ala Leu Asp Asn Ala Gly Lys
            35                  40                  45

Ile Met Ala Leu Thr Lys Ser Ala Pro Asp Tyr Leu Val Gly Pro Ser
 50                  55                  60

Leu Pro Ala Asp Ile Lys Thr Asn Arg Ile Tyr Arg Ile Leu Glu Leu
 65                  70                  75                  80

Asn Gly Tyr Asp Pro Ala Tyr Ala Gly Ser Val Phe Leu Gly Trp Ala
                 85                  90                  95

Gln Lys Lys Phe Gly Lys Arg Asn Thr Ile Trp Leu Phe Gly Pro Ala
            100                 105                 110
```

```
Thr Thr Gly Lys Thr Asn Ile Ala Glu Ala Ile Ala His Ala Val Pro
            115                 120                 125

Phe Tyr Gly Cys Val Asn Trp Thr Asn Glu Asn Phe Pro Phe Asn Asp
        130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
        210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Ile Ser Glu Pro Lys Arg Ala Cys Pro Ser Val
        275                 280                 285

Ala Asp Pro Ser Thr Ser Asp Ala Glu Gly Ala Pro Val Asp Phe Ala
        290                 295                 300

Asp Leu Ala Arg Gly Gln Pro Leu
305                 310

<210> SEQ ID NO 92
<211> LENGTH: 312
<212> TYPE: PRT
<213> ORGANISM: Adeno-associated virus 8

<400> SEQUENCE: 92

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Thr Gln Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
            115                 120                 125

Phe Tyr Gly Cys Val Asn Trp Thr Asn Glu Asn Phe Pro Phe Asn Asp
        130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
```

```
                    165                 170                 175

Val Asp Gln Lys Cys Lys Ser Ser Ala Gln Ile Asp Pro Thr Pro Val
                180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
        210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Leu Ala Arg Gly Gln Pro Leu
305                 310

<210> SEQ ID NO 93
<211> LENGTH: 311
<212> TYPE: PRT
<213> ORGANISM: Artificial
<220> FEATURE:
<223> OTHER INFORMATION: AAV Rep40 consensus sequence
<220> FEATURE:
<221> NAME/KEY: MISC_FEATURE
<222> LOCATION: (63)..(63)
<223> OTHER INFORMATION: Xaa can be Gln, Pro or Ser
<220> FEATURE:
<221> NAME/KEY: MISC_FEATURE
<222> LOCATION: (290)..(290)
<223> OTHER INFORMATION: Xaa can be Asp, Gln or Thr

<400> SEQUENCE: 93

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Xaa Ser
    50                  55                  60

Pro Pro Glu Asp Ile Ser Thr Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175
```

```
Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
            210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Lys Lys Arg Pro Ala
            260                 265                 270

Pro Asp Asp Ala Asp Lys Ser Glu Pro Lys Arg Ala Cys Pro Ser Val
            275                 280                 285

Ala Xaa Pro Ser Thr Ser Asp Ala Glu Ala Pro Val Asp Phe Ala Asp
            290                 295                 300

Leu Ala Arg Gly Gln Pro Leu
305                 310

<210> SEQ ID NO 94
<211> LENGTH: 399
<212> TYPE: PRT
<213> ORGANISM: Adeno-associated virus 1

<400> SEQUENCE: 94

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
    50                  55                  60

Pro Pro Ala Asp Ile Lys Thr Asn Arg Ile Tyr Arg Ile Leu Glu Leu
65                  70                  75                  80

Asn Gly Tyr Glu Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
            210                 215                 220

Glu Leu Thr Arg Arg Leu Glu His Asp Phe Gly Lys Val Thr Lys Gln
```

```
                225                 230                 235                 240
        Glu Val Lys Glu Phe Phe Arg Trp Ala Gln Asp His Val Thr Glu Val
                        245                 250                 255

Ala His Glu Phe Tyr Val Arg Lys Gly Gly Ala Asn Lys Arg Pro Ala
                        260                 265                 270

Pro Asp Ala Asp Lys Ser Glu Pro Lys Arg Ala Cys Pro Ser Val
                    275                 280                 285

Ala Asp Pro Ser Thr Ser Asp Ala Glu Gly Ala Pro Val Asp Phe Ala
                    290                 295                 300

Asp Arg Tyr Gln Asn Lys Cys Ser Arg His Ala Gly Met Leu Gln Met
        305                 310                 315                 320

Leu Phe Pro Cys Lys Thr Cys Glu Arg Met Asn Gln Asn Phe Asn Ile
                        325                 330                 335

Cys Phe Thr His Gly Thr Arg Asp Cys Ser Cys Pro Gly Val
                    340                 345                 350

Ser Glu Ser Gln Pro Val Val Arg Lys Arg Thr Tyr Arg Lys Leu Cys
                    355                 360                 365

Ala Ile His His Leu Leu Gly Arg Ala Pro Glu Ile Ala Cys Ser Ala
                    370                 375                 380

Cys Asp Leu Val Asn Val Asp Leu Asp Asp Cys Val Ser Glu Gln
        385                 390                 395

<210> SEQ ID NO 95
<211> LENGTH: 397
<212> TYPE: PRT
<213> ORGANISM: Adeno-associated virus 2

<400> SEQUENCE: 95

Met Glu Leu Val Gly Trp Leu Val Asp Lys Gly Ile Thr Ser Glu Lys
        1               5                   10                  15

Gln Trp Ile Gln Glu Asp Gln Ala Ser Tyr Ile Ser Phe Asn Ala Ala
                        20                  25                  30

Ser Asn Ser Arg Ser Gln Ile Lys Ala Ala Leu Asp Asn Ala Gly Lys
                    35                  40                  45

Ile Met Ser Leu Thr Lys Thr Ala Pro Asp Tyr Leu Val Gly Gln Gln
        50                  55                  60

Pro Val Glu Asp Ile Ser Ser Asn Arg Ile Tyr Lys Ile Leu Glu Leu
        65                  70                  75                  80

Asn Gly Tyr Asp Pro Gln Tyr Ala Ala Ser Val Phe Leu Gly Trp Ala
                        85                  90                  95

Thr Lys Lys Phe Gly Lys Arg Asn Thr Ile Trp Leu Phe Gly Pro Ala
                        100                 105                 110

Thr Thr Gly Lys Thr Asn Ile Ala Glu Ala Ile Ala His Thr Val Pro
                    115                 120                 125

Phe Tyr Gly Cys Val Asn Trp Thr Asn Glu Asn Phe Pro Phe Asn Asp
        130                 135                 140

Cys Val Asp Lys Met Val Ile Trp Trp Glu Glu Gly Lys Met Thr Ala
        145                 150                 155                 160

Lys Val Val Glu Ser Ala Lys Ala Ile Leu Gly Gly Ser Lys Val Arg
                        165                 170                 175

Val Asp Gln Lys Cys Lys Ser Ser Ala Gln Ile Asp Pro Thr Pro Val
                    180                 185                 190

Ile Val Thr Ser Asn Thr Asn Met Cys Ala Val Ile Asp Gly Asn Ser
                    195                 200                 205
```

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
                260                 265                 270

Pro Ser Asp Ala Asp Ile Ser Glu Pro Lys Arg Val Arg Glu Ser Val
            275                 280                 285

Ala Gln Pro Ser Thr Ser Asp Ala Glu Ala Ser Ile Asn Tyr Ala Asp
290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
            355                 360                 365

Ile His His Ile Met Gly Lys Val Pro Asp Ala Cys Thr Ala Cys Asp
370                 375                 380

Leu Val Asn Val Asp Leu Asp Asp Cys Ile Phe Glu Gln
385                 390                 395

<210> SEQ ID NO 96
<211> LENGTH: 400
<212> TYPE: PRT
<213> ORGANISM: Adeno-associated virus 3A

<400> SEQUENCE: 96

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
50                  55                  60

Pro Pro Glu Asp Ile Thr Lys Asn Arg Ile Tyr Gln Ile Leu Glu Leu
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Glu Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Gly Ala Lys Lys Arg Pro Ala
                260                 265                 270

Ser Asn Asp Ala Asp Val Ser Glu Pro Lys Arg Glu Cys Thr Ser Leu
            275                 280                 285

Ala Gln Pro Thr Thr Ser Asp Ala Glu Ala Pro Ala Asp Tyr Ala Asp
        290                 295                 300

Arg Tyr Gln Asn Lys Cys Ser Arg His Val Gly Met Asn Leu Met Leu
305                 310                 315                 320

Phe Pro Cys Lys Thr Cys Glu Arg Met Asn Gln Ile Ser Asn Val Cys
                325                 330                 335

Phe Thr His Gly Gln Arg Asp Cys Gly Glu Cys Phe Pro Gly Met Ser
                340                 345                 350

Glu Ser Gln Pro Val Ser Val Val Lys Lys Lys Thr Tyr Gln Lys Leu
            355                 360                 365

Cys Pro Ile His His Ile Leu Gly Arg Ala Pro Glu Ile Ala Cys Ser
        370                 375                 380

Ala Cys Asp Leu Ala Asn Val Asp Leu Asp Asp Cys Val Ser Glu Gln
385                 390                 395                 400

<210> SEQ ID NO 97
<211> LENGTH: 400
<212> TYPE: PRT
<213> ORGANISM: Adeno-associated virus 3B

<400> SEQUENCE: 97

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
    50                  55                  60

Pro Pro Glu Asp Ile Thr Lys Asn Arg Ile Tyr Gln Ile Leu Glu Leu
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg

```
                    165                 170                 175
Val Asp Gln Lys Cys Lys Ser Ser Ala Gln Ile Glu Pro Thr Pro Val
                180                 185                 190

Ile Val Thr Ser Asn Thr Asn Met Cys Ala Val Ile Asp Gly Asn Ser
                195                 200                 205

Thr Thr Phe Glu His Gln Gln Pro Leu Gln Asp Arg Met Phe Lys Phe
            210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Gly Ala Lys Lys Arg Pro Ala
            260                 265                 270

Ser Asn Asp Ala Asp Val Ser Glu Pro Lys Arg Gln Cys Thr Ser Leu
            275                 280                 285

Ala Gln Pro Thr Thr Ser Asp Ala Glu Ala Pro Ala Asp Tyr Ala Asp
            290                 295                 300

Arg Tyr Gln Asn Lys Cys Ser Arg His Val Gly Met Asn Leu Met Leu
305                 310                 315                 320

Phe Pro Cys Lys Thr Cys Glu Arg Met Asn Gln Ile Ser Asn Val Cys
                325                 330                 335

Phe Thr His Gly Gln Arg Asp Cys Gly Glu Cys Phe Pro Gly Met Ser
            340                 345                 350

Glu Ser Gln Pro Val Ser Val Val Lys Lys Thr Tyr Gln Lys Leu
            355                 360                 365

Cys Pro Ile His His Ile Leu Gly Arg Ala Pro Glu Ile Ala Cys Ser
            370                 375                 380

Ala Cys Asp Leu Ala Asn Val Asp Leu Asp Asp Cys Val Ser Glu Gln
385                 390                 395                 400

<210> SEQ ID NO 98
<211> LENGTH: 399
<212> TYPE: PRT
<213> ORGANISM: Adeno-associated virus 4

<400> SEQUENCE: 98

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Gln Asn
    50                  55                  60

Pro Pro Glu Asp Ile Ser Ser Asn Arg Ile Tyr Arg Ile Leu Glu Met
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140
```

-continued

Cys Val Asp Lys Met Val Ile Trp Trp Glu Gly Lys Met Thr Ala
145                 150                 155                 160

Lys Val Val Glu Ser Ala Lys Ala Ile Leu Gly Gly Ser Lys Val Arg
            165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
            210                 215                 220

Glu Leu Thr Lys Arg Leu Glu His Asp Phe Gly Lys Val Thr Lys Gln
225                 230                 235                 240

Glu Val Lys Asp Phe Phe Arg Trp Ala Ser Asp His Val Thr Glu Val
            245                 250                 255

Thr His Glu Phe Tyr Val Arg Lys Gly Gly Ala Arg Lys Arg Pro Ala
            260                 265                 270

Pro Asn Asp Ala Asp Ile Ser Glu Pro Lys Arg Ala Cys Pro Ser Val
            275                 280                 285

Ala Gln Pro Ser Thr Ser Asp Ala Glu Ala Pro Val Asp Tyr Ala Asp
            290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Val Asp Ile Cys
            325                 330                 335

Phe Thr His Gly Val Met Asp Cys Ala Glu Cys Phe Pro Val Ser Glu
            340                 345                 350

Ser Gln Pro Val Ser Val Val Arg Lys Arg Thr Tyr Gln Lys Leu Cys
            355                 360                 365

Pro Ile His His Ile Met Gly Arg Ala Pro Glu Val Ala Cys Ser Ala
            370                 375                 380

Cys Glu Leu Ala Asn Val Asp Leu Asp Asp Cys Asp Met Glu Gln
385                 390                 395

<210> SEQ ID NO 99
<211> LENGTH: 390
<212> TYPE: PRT
<213> ORGANISM: Adeno-associated virus 5

<400> SEQUENCE: 99

Met Ala Leu Val Asn Trp Leu Val Glu His Gly Ile Thr Ser Glu Lys
1               5                   10                  15

Gln Trp Ile Gln Glu Asn Gln Glu Ser Tyr Leu Ser Phe Asn Ser Thr
            20                  25                  30

Gly Asn Ser Arg Ser Gln Ile Lys Ala Ala Leu Asp Asn Ala Thr Lys
        35                  40                  45

Ile Met Ser Leu Thr Lys Ser Ala Val Asp Tyr Leu Val Gly Ser Ser
    50                  55                  60

Val Pro Glu Asp Ile Ser Lys Asn Arg Ile Trp Gln Ile Phe Glu Met
65                  70                  75                  80

Asn Gly Tyr Asp Pro Ala Tyr Ala Gly Ser Ile Leu Tyr Gly Trp Cys
            85                  90                  95

Gln Arg Ser Phe Asn Lys Arg Asn Thr Val Trp Leu Tyr Gly Pro Ala
            100                 105                 110

Thr Thr Gly Lys Thr Asn Ile Ala Glu Ala Ile Ala His Thr Val Pro
            115                 120                 125

Phe Tyr Gly Cys Val Asn Trp Thr Asn Glu Asn Phe Pro Phe Asn Asp
        130                 135                 140

Cys Val Asp Lys Met Leu Ile Trp Trp Glu Glu Gly Lys Met Thr Asn
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Val Gln Ile Asp Ser Thr Pro Val
                180                 185                 190

Ile Val Thr Ser Asn Thr Asn Met Cys Val Val Asp Gly Asn Ser
        195                 200                 205

Thr Thr Phe Glu His Gln Gln Pro Leu Glu Asp Arg Met Phe Lys Phe
        210                 215                 220

Glu Leu Thr Lys Arg Leu Pro Pro Asp Phe Gly Lys Ile Thr Lys Gln
225                 230                 235                 240

Glu Val Lys Asp Phe Phe Ala Trp Ala Lys Val Asn Gln Val Pro Val
                245                 250                 255

Thr His Glu Phe Lys Val Pro Arg Glu Leu Ala Gly Thr Lys Gly Ala
        260                 265                 270

Glu Lys Ser Leu Lys Arg Pro Leu Gly Asp Val Thr Asn Thr Ser Tyr
        275                 280                 285

Lys Ser Leu Glu Lys Arg Ala Arg Leu Ser Phe Val Pro Glu Thr Pro
290                 295                 300

Arg Ser Ser Asp Val Thr Val Asp Pro Ala Pro Leu Arg Pro Leu Asn
305                 310                 315                 320

Trp Asn Ser Arg Tyr Asp Cys Lys Cys Asp Tyr His Ala Gln Phe Asp
                325                 330                 335

Asn Ile Ser Asn Lys Cys Asp Glu Cys Glu Tyr Leu Asn Arg Gly Lys
        340                 345                 350

Asn Gly Cys Ile Cys His Asn Val Thr His Cys Gln Ile Cys His Gly
        355                 360                 365

Ile Pro Pro Trp Glu Lys Glu Asn Leu Ser Asp Phe Gly Asp Phe Asp
        370                 375                 380

Asp Ala Asn Lys Glu Gln
385                 390

<210> SEQ ID NO 100
<211> LENGTH: 399
<212> TYPE: PRT
<213> ORGANISM: Adeno-associated virus 6

<400> SEQUENCE: 100

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
                20                  25                  30

Ser Asn Ser Arg Ser Gln Ile Lys Ala Ala Leu Asp Asn Ala Gly Lys
            35                  40                  45

Ile Met Ala Leu Thr Lys Ser Ala Pro Asp Tyr Leu Val Gly Pro Ala
        50                  55                  60

Pro Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala 100                 105                 110
Thr Thr Gly Lys Thr Asn Ile Ala Glu Ala Ile Ala His Ala Val Pro
            115                 120                 125
Phe Tyr Gly Cys Val Asn Trp Thr Asn Glu Asn Phe Pro Phe Asn Asp
        130                 135                 140
Cys Val Asp Lys Met Val Ile Trp Trp Glu Gly Lys Met Thr Ala
145                 150                 155                 160
Lys Val Val Glu Ser Ala Lys Ala Ile Leu Gly Gly Ser Lys Val Arg
            165                 170                 175
Val Asp Gln Lys Cys Lys Ser Ser Ala Gln Ile Asp Pro Thr Pro Val
        180                 185                 190
Ile Val Thr Ser Asn Thr Asn Met Cys Ala Val Ile Asp Gly Asn Ser
        195                 200                 205
Thr Thr Phe Glu His Gln Gln Pro Leu Gln Asp Arg Met Phe Lys Phe
            210                 215                 220
Glu Leu Thr Arg Arg Leu Glu His Asp Phe Gly Lys Val Thr Lys Gln
225                 230                 235                 240
Glu Val Lys Glu Phe Phe Arg Trp Ala Gln Asp His Val Thr Glu Val
            245                 250                 255
Ala His Glu Phe Tyr Val Arg Lys Gly Gly Ala Asn Lys Arg Pro Ala
            260                 265                 270
Pro Asp Asp Ala Asp Lys Ser Glu Pro Lys Arg Ala Cys Pro Ser Val
        275                 280                 285
Ala Asp Pro Ser Thr Ser Asp Ala Glu Gly Ala Pro Val Asp Phe Ala
        290                 295                 300
Asp Arg Tyr Gln Asn Lys Cys Ser Arg His Ala Gly Met Leu Gln Met
305                 310                 315                 320
Leu Phe Pro Cys Lys Thr Cys Glu Arg Met Asn Gln Asn Phe Asn Ile
            325                 330                 335
Cys Phe Thr His Gly Thr Arg Asp Cys Ser Glu Cys Phe Pro Gly Val
            340                 345                 350
Ser Glu Ser Gln Pro Val Val Arg Lys Arg Thr Tyr Arg Lys Leu Cys
            355                 360                 365
Ala Ile His His Leu Leu Gly Arg Ala Pro Glu Ile Ala Cys Ser Ala
        370                 375                 380
Cys Asp Leu Val Asn Val Asp Leu Asp Asp Cys Val Ser Glu Gln
385                 390                 395

<210> SEQ ID NO 101
<211> LENGTH: 399
<212> TYPE: PRT
<213> ORGANISM: Adeno-associated virus 7

<400> SEQUENCE: 101

Met Glu Leu Val Gly Trp Leu Val Asp Arg Gly Ile Thr Ser Glu Lys
1               5                   10                  15
Gln Trp Ile Gln Glu Asp Gln Ala Ser Tyr Ile Ser Phe Asn Ala Ala
            20                  25                  30
Ser Asn Ser Arg Ser Gln Ile Lys Ala Ala Leu Asp Asn Ala Gly Lys
        35                  40                  45
Ile Met Ala Leu Thr Lys Ser Ala Pro Asp Tyr Leu Val Gly Pro Ser
    50                  55                  60
Leu Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Ile Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Arg Tyr Gln Asn Lys Cys Ser Arg His Ala Gly Met Ile Gln Met
305                 310                 315                 320

Leu Phe Pro Cys Lys Thr Cys Glu Arg Met Asn Gln Asn Phe Asn Ile
                325                 330                 335

Cys Phe Thr His Gly Val Arg Asp Cys Leu Glu Cys Phe Pro Gly Val
            340                 345                 350

Ser Glu Ser Gln Pro Val Val Arg Lys Lys Thr Tyr Arg Lys Leu Cys
        355                 360                 365

Ala Ile His His Leu Leu Gly Arg Ala Pro Glu Ile Ala Cys Ser Ala
    370                 375                 380

Cys Asp Leu Val Asn Val Asp Leu Asp Asp Cys Val Ser Glu Gln
385                 390                 395

<210> SEQ ID NO 102
<211> LENGTH: 399
<212> TYPE: PRT
<213> ORGANISM: Adeno-associated virus 8

<400> SEQUENCE: 102

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

```
Leu Pro Ala Asp Ile Thr Gln Asn Arg Ile Tyr Arg Ile Leu Ala Leu
 65                  70                  75                  80

Asn Gly Tyr Asp Pro Ala Tyr Ala Gly Ser Val Phe Leu Gly Trp Ala
                 85                  90                  95

Gln Lys Lys Phe Gly Lys Arg Asn Thr Ile Trp Leu Phe Gly Pro Ala
                100                 105                 110

Thr Thr Gly Lys Thr Asn Ile Ala Glu Ala Ile Ala His Ala Val Pro
                115                 120                 125

Phe Tyr Gly Cys Val Asn Trp Thr Asn Glu Asn Phe Pro Phe Asn Asp
                130                 135                 140

Cys Val Asp Lys Met Val Ile Trp Trp Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
                180                 185                 190

Ile Val Thr Ser Asn Thr Asn Met Cys Ala Val Ile Asp Gly Asn Ser
                195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
                260                 265                 270

Pro Asp Asp Ala Asp Lys Ser Glu Pro Lys Arg Ala Cys Pro Ser Val
                275                 280                 285

Ala Asp Pro Ser Thr Ser Asp Ala Gly Ala Pro Val Asp Phe Ala
290                 295                 300

Asp Arg Tyr Gln Asn Lys Cys Ser Arg His Ala Gly Met Leu Gln Met
305                 310                 315                 320

Leu Phe Pro Cys Lys Thr Cys Glu Arg Met Asn Gln Asn Phe Asn Ile
                325                 330                 335

Cys Phe Thr His Gly Val Arg Asp Cys Ser Glu Cys Phe Pro Gly Val
                340                 345                 350

Ser Glu Ser Gln Pro Val Val Arg Lys Arg Thr Tyr Arg Lys Leu Cys
                355                 360                 365

Ala Ile His His Leu Leu Gly Arg Ala Pro Glu Ile Ala Cys Ser Ala
                370                 375                 380

Cys Asp Leu Val Asn Val Asp Leu Asp Asp Cys Val Ser Glu Gln
385                 390                 395

<210> SEQ ID NO 103
<211> LENGTH: 398
<212> TYPE: PRT
<213> ORGANISM: Artificial
<220> FEATURE:
<223> OTHER INFORMATION: AAV Rep52 consensus sequence
<220> FEATURE:
<221> NAME/KEY: MISC_FEATURE
<222> LOCATION: (63)..(63)
<223> OTHER INFORMATION: Xaa can be Gln, Pro or Ser
<220> FEATURE:
<221> NAME/KEY: MISC_FEATURE
<222> LOCATION: (317)..(317)
<223> OTHER INFORMATION: Xaa can be Asn, Asp, Ile or Leu
```

```
<220> FEATURE:
<221> NAME/KEY: MISC_FEATURE
<222> LOCATION: (333)..(333)
<223> OTHER INFORMATION: Xaa can be Lys, Phe, Ser or Val
<220> FEATURE:
<221> NAME/KEY: MISC_FEATURE
<222> LOCATION: (341)..(341)
<223> OTHER INFORMATION: Xaa can be Gln, Thr or Val
<220> FEATURE:
<221> NAME/KEY: MISC_FEATURE
<222> LOCATION: (345)..(345)
<223> OTHER INFORMATION: Xaa can be Ala, Gln, Gly, Leu or Ser
<220> FEATURE:
<221> NAME/KEY: MISC_FEATURE
<222> LOCATION: (356)..(356)
<223> OTHER INFORMATION: Xaa can be Pro or Ser
<220> FEATURE:
<221> NAME/KEY: MISC_FEATURE
<222> LOCATION: (364)..(364)
<223> OTHER INFORMATION: Xaa can be Gln or Arg
<220> FEATURE:
<221> NAME/KEY: MISC_FEATURE
<222> LOCATION: (368)..(368)
<223> OTHER INFORMATION: Xaa can be Ala, Pro or Tyr

<400> SEQUENCE: 103
```

| Met | Glu | Leu | Val | Gly | Trp | Leu | Val | Asp | Arg | Gly | Ile | Thr | Ser | Glu | Lys |
|---|---|---|---|---|---|---|---|---|---|---|---|---|---|---|---|
| 1 | | | | 5 | | | | | 10 | | | | | 15 | |

| Gln | Trp | Ile | Gln | Glu | Asp | Gln | Ala | Ser | Tyr | Ile | Ser | Phe | Asn | Ala | Ala |
| | | | 20 | | | | | 25 | | | | | 30 | | |

| Ser | Asn | Ser | Arg | Ser | Gln | Ile | Lys | Ala | Ala | Leu | Asp | Asn | Ala | Gly | Lys |
| | | 35 | | | | | 40 | | | | | 45 | | | |

| Ile | Met | Ala | Leu | Thr | Lys | Ser | Ala | Pro | Asp | Tyr | Leu | Val | Gly | Xaa | Ser |
| 50 | | | | | 55 | | | | | 60 | | | | | |

| Pro | Pro | Glu | Asp | Ile | Ser | Thr | Asn | Arg | Ile | Tyr | Arg | Ile | Leu | Ala | Leu |
| 65 | | | | | 70 | | | | | 75 | | | | | 80 |

| Asn | Gly | Tyr | Asp | Pro | Ala | Tyr | Ala | Gly | Ser | Val | Phe | Leu | Gly | Trp | Ala |
| | | | | 85 | | | | | 90 | | | | | 95 | |

| Gln | Lys | Lys | Phe | Gly | Lys | Arg | Asn | Thr | Ile | Trp | Leu | Phe | Gly | Pro | Ala |
| | | | 100 | | | | | 105 | | | | | 110 | | |

| Thr | Thr | Gly | Lys | Thr | Asn | Ile | Ala | Glu | Ala | Ile | Ala | His | Ala | Val | Pro |
| | | 115 | | | | | 120 | | | | | 125 | | | |

| Phe | Tyr | Gly | Cys | Val | Asn | Trp | Thr | Asn | Glu | Asn | Phe | Pro | Phe | Asn | Asp |
| 130 | | | | | 135 | | | | | 140 | | | | | |

| Cys | Val | Asp | Lys | Met | Val | Ile | Trp | Trp | Glu | Glu | Gly | Lys | Met | Thr | Ala |
| 145 | | | | | 150 | | | | | 155 | | | | | 160 |

| Lys | Val | Val | Glu | Ser | Ala | Lys | Ala | Ile | Leu | Gly | Gly | Ser | Lys | Val | Arg |
| | | | | 165 | | | | | 170 | | | | | 175 | |

| Val | Asp | Gln | Lys | Cys | Lys | Ser | Ser | Ala | Gln | Ile | Asp | Pro | Thr | Pro | Val |
| | | | 180 | | | | | 185 | | | | | 190 | | |

| Ile | Val | Thr | Ser | Asn | Thr | Asn | Met | Cys | Ala | Val | Ile | Asp | Gly | Asn | Ser |
| | | 195 | | | | | 200 | | | | | 205 | | | |

| Thr | Thr | Phe | Glu | His | Gln | Gln | Pro | Leu | Gln | Asp | Arg | Met | Phe | Lys | Phe |
| 210 | | | | | 215 | | | | | 220 | | | | | |

| Glu | Leu | Thr | Arg | Arg | Leu | Glu | His | Asp | Phe | Gly | Lys | Val | Thr | Lys | Gln |
| 225 | | | | | 230 | | | | | 235 | | | | | 240 |

| Glu | Val | Lys | Glu | Phe | Phe | Arg | Trp | Ala | Ser | Asp | His | Val | Thr | Glu | Val |
| | | | | 245 | | | | | 250 | | | | | 255 | |

| Ala | His | Glu | Phe | Tyr | Val | Arg | Lys | Gly | Gly | Ala | Lys | Lys | Arg | Pro | Ala |
| | | | 260 | | | | | 265 | | | | | 270 | | |

| Pro | Asp | Asp | Ala | Asp | Lys | Ser | Glu | Pro | Lys | Arg | Ala | Cys | Pro | Ser | Val |

```
                    275                 280                 285
Ala Asp Pro Ser Thr Ser Asp Ala Glu Ala Pro Val Asp Phe Ala Asp
290                 295                 300

Arg Tyr Gln Asn Lys Cys Ser Arg His Ala Gly Met Xaa Gln Met Leu
305                 310                 315                 320

Phe Pro Cys Lys Thr Cys Glu Arg Met Asn Gln Asn Xaa Asn Ile Cys
                325                 330                 335

Phe Thr His Gly Xaa Arg Asp Cys Xaa Glu Cys Phe Pro Gly Val Ser
            340                 345                 350

Glu Ser Gln Xaa Val Val Arg Lys Arg Thr Tyr Xaa Lys Leu Cys Xaa
        355                 360                 365

Ile His His Leu Leu Gly Arg Ala Pro Glu Ile Ala Cys Ser Ala Cys
370                 375                 380

Asp Leu Val Asn Val Asp Leu Asp Asp Cys Val Ser Glu Gln
385                 390                 395

<210> SEQ ID NO 104
<211> LENGTH: 536
<212> TYPE: PRT
<213> ORGANISM: Adeno-associated virus 1

<400> SEQUENCE: 104

Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255
```

-continued

```
Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
    290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Leu Ala Arg Gly Gln Pro Leu
    530                 535

<210> SEQ ID NO 105
<211> LENGTH: 536
<212> TYPE: PRT
<213> ORGANISM: Adeno-associated virus 2

<400> SEQUENCE: 105

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95
```

```
Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
        130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
                195                 200                 205

Pro Asn Ser Asp Ala Pro Val Ile Arg Ser Lys Thr Ser Ala Arg Tyr
        210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ser Leu Thr Lys Thr Ala Pro Asp Tyr Leu Val Gly Gln Gln
                275                 280                 285

Pro Val Glu Asp Ile Ser Ser Asn Arg Ile Tyr Lys Ile Leu Glu Leu
        290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
        500                 505                 510
```

Ala Gln Pro Ser Thr Ser Asp Ala Glu Ala Ser Ile Asn Tyr Ala Asp
            515                 520                 525

Arg Leu Ala Arg Gly His Ser Leu
    530                 535

<210> SEQ ID NO 106
<211> LENGTH: 535
<212> TYPE: PRT
<213> ORGANISM: Adeno-associated virus 3A

<400> SEQUENCE: 106

Met Pro Gly Phe Tyr Glu Ile Val Leu Lys Val Pro Ser Asp Leu Asp
1               5                   10                  15

Glu Arg Leu Pro Gly Ile Ser Asn Ser Phe Val Asn Trp Val Ala Glu
            20                  25                  30

Lys Glu Trp Asp Val Pro Pro Asp Ser Asp Met Asp Pro Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Ser Asn
        275                 280                 285

Pro Pro Glu Asp Ile Thr Lys Asn Arg Ile Tyr Gln Ile Leu Glu Leu
    290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

```
Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Glu Phe
            435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Glu Cys Thr Ser Leu
            500                 505                 510

Ala Gln Pro Thr Thr Ser Asp Ala Glu Ala Pro Ala Asp Tyr Ala Asp
    515                 520                 525

Leu Ala Arg Gly Gln Pro Phe
530                 535

<210> SEQ ID NO 107
<211> LENGTH: 535
<212> TYPE: PRT
<213> ORGANISM: Adeno-associated virus 3B

<400> SEQUENCE: 107

Met Pro Gly Phe Tyr Glu Ile Val Leu Lys Val Pro Ser Asp Leu Asp
1               5                   10                  15

Glu His Leu Pro Gly Ile Ser Asn Ser Phe Val Asn Trp Val Ala Glu
            20                  25                  30

Lys Glu Trp Glu Leu Pro Pro Asp Ser Asp Met Asp Pro Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
```

180                 185                 190
Leu Thr His Val Ser Gln Thr Gln Glu Gln Asn Lys Glu Asn Gln Asn
                195                 200                 205

Pro Asn Ser Asp Ala Pro Val Ile Arg Ser Lys Thr Ser Ala Arg Tyr
            210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Ser Asn
        275                 280                 285

Pro Pro Glu Asp Ile Thr Lys Asn Arg Ile Tyr Gln Ile Leu Glu Leu
        290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Gln Cys Thr Ser Leu
            500                 505                 510

Ala Gln Pro Thr Thr Ser Asp Ala Glu Ala Pro Ala Asp Tyr Ala Asp
        515                 520                 525

Leu Ala Arg Gly Gln Pro Phe
        530                 535

<210> SEQ ID NO 108
<211> LENGTH: 535
<212> TYPE: PRT
<213> ORGANISM: Adeno-associated virus 4

<400> SEQUENCE: 108

Met Pro Gly Phe Tyr Glu Ile Val Leu Lys Val Pro Ser Asp Leu Asp
1               5                   10                  15

-continued

Glu His Leu Pro Gly Ile Ser Asp Ser Phe Val Ser Trp Ala Glu
            20                  25                  30

Lys Glu Trp Glu Leu Pro Pro Asp Ser Asp Met Asp Leu Asn Leu Ile
                35                  40                  45

Glu Gln Ala Pro Leu Thr Val Ala Glu Lys Leu Gln Arg Glu Phe Leu
 50                  55                  60

Val Glu Trp Arg Arg Val Ser Lys Ala Pro Glu Ala Leu Phe Phe Val
 65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
                115                 120                 125

Pro Asn Trp Phe Ala Val Thr Lys Thr Arg Asn Gly Ala Gly Gly Gly
            130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Gln Asn
                195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Val Gly Gln Asn
                275                 280                 285

Pro Pro Glu Asp Ile Ser Ser Asn Arg Ile Tyr Arg Ile Leu Glu Met
            290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe

-continued

```
                435                 440                 445
Glu Leu Thr Lys Arg Leu Glu His Asp Phe Gly Lys Val Thr Lys Gln
450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
                    485                 490                 495

Pro Asn Asp Ala Asp Ile Ser Glu Pro Lys Arg Ala Cys Pro Ser Val
                500                 505                 510

Ala Gln Pro Ser Thr Ser Asp Ala Glu Ala Pro Val Asp Tyr Ala Asp
                515                 520                 525

Leu Ala Arg Gly Gln Pro Leu
530                 535

<210> SEQ ID NO 109
<211> LENGTH: 549
<212> TYPE: PRT
<213> ORGANISM: Adeno-associated virus 5

<400> SEQUENCE: 109

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
                100                 105                 110

Ala Gln Leu Val Lys Val Phe Gln Gly Ile Glu Pro Gln Ile Asn
            115                 120                 125

Asp Trp Val Ala Ile Thr Lys Val Lys Lys Gly Gly Ala Asn Lys Val
130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
                180                 185                 190

Ser Ser Gln Arg Ser Gln Glu Ala Ala Ser Gln Arg Glu Phe Ser Ala
            195                 200                 205

Asp Pro Val Ile Lys Ser Lys Thr Ser Gln Lys Tyr Met Ala Leu Val
210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
                260                 265                 270
```

Thr Lys Ser Ala Val Asp Tyr Leu Val Gly Ser Ser Val Pro Glu Asp
            275                 280                 285

Ile Ser Lys Asn Arg Ile Trp Gln Ile Phe Glu Met Asn Gly Tyr Asp
        290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
        355                 360                 365

Met Leu Ile Trp Trp Glu Glu Gly Lys Met Thr Asn Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Val Asp Gly Asn Ser Thr Thr Phe Glu
            420                 425                 430

His Gln Gln Pro Leu Glu Asp Arg Met Phe Lys Phe Glu Leu Thr Lys
        435                 440                 445

Arg Leu Pro Pro Asp Phe Gly Lys Ile Thr Lys Gln Glu Val Lys Asp
    450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
        515                 520                 525

Val Thr Val Asp Pro Ala Pro Leu Arg Pro Leu Asn Trp Asn Ser Leu
    530                 535                 540

Val Gly Pro Ser Trp
545

<210> SEQ ID NO 110
<211> LENGTH: 536
<212> TYPE: PRT
<213> ORGANISM: Adeno-associated virus 6

<400> SEQUENCE: 110

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

```
Thr Thr Gly Val Lys Ser Met Val Leu Gly Arg Phe Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
        130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
                180                 185                 190

Leu Thr His Val Ser Gln Thr Gln Glu Gln Asn Lys Glu Asn Leu Asn
                195                 200                 205

Pro Asn Ser Asp Ala Pro Val Ile Arg Ser Lys Thr Ser Ala Arg Tyr
            210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ala Leu Thr Lys Ser Ala Pro Asp Tyr Leu Val Gly Pro Ala
            275                 280                 285

Pro Pro Ala Asp Ile Lys Thr Asn Arg Ile Tyr Arg Ile Leu Glu Leu
        290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
        450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510
```

Ala Asp Pro Ser Thr Ser Asp Ala Glu Gly Ala Pro Val Asp Phe Ala
    515                 520                 525

Asp Leu Ala Arg Gly Gln Pro Leu
    530                 535

<210> SEQ ID NO 111
<211> LENGTH: 536
<212> TYPE: PRT
<213> ORGANISM: Adeno-associated virus 7

<400> SEQUENCE: 111

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

```
Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
        450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
            515                 520                 525

Asp Leu Ala Arg Gly Gln Pro Leu
            530                 535

<210> SEQ ID NO 112
<211> LENGTH: 538
<212> TYPE: PRT
<213> ORGANISM: Adeno-associated virus 8

<400> SEQUENCE: 112

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Gly Pro Asp His Leu Pro Ala Gly Ser Ser Pro Thr
        115                 120                 125

Leu Pro Asn Trp Phe Ala Val Thr Lys Asp Ala Val Met Ala Pro Ala
    130                 135                 140

Gly Gly Asn Lys Val Val Asp Glu Cys Tyr Ile Pro Asn Tyr Leu Leu
145                 150                 155                 160

Pro Lys Thr Gln Pro Glu Leu Gln Trp Ala Trp Thr Asn Met Glu Glu
                165                 170                 175

Tyr Ile Ser Ala Cys Leu Asn Leu Ala Glu Arg Lys Arg Leu Val Ala
```

```
                180                 185                 190
Gln His Leu Thr His Val Ser Gln Thr Gln Glu Gln Asn Lys Glu Asn
            195                 200                 205

Leu Asn Pro Asn Ser Asp Ala Pro Val Ile Arg Ser Lys Thr Ser Ala
210                 215                 220

Arg Tyr Met Glu Leu Val Gly Trp Leu Val Asp Arg Gly Ile Thr Ser
225                 230                 235                 240

Glu Lys Gln Trp Ile Gln Glu Asp Gln Ala Ser Tyr Ile Ser Phe Asn
            245                 250                 255

Ala Ala Ser Asn Ser Arg Ser Gln Ile Lys Ala Ala Leu Asp Asn Ala
            260                 265                 270

Gly Lys Ile Met Ala Leu Thr Lys Ser Ala Pro Asp Tyr Leu Val Gly
            275                 280                 285

Pro Ser Leu Pro Ala Asp Ile Thr Gln Asn Arg Ile Tyr Arg Ile Leu
290                 295                 300

Ala Leu Asn Gly Tyr Asp Pro Ala Tyr Ala Gly Ser Val Phe Leu Gly
305                 310                 315                 320

Trp Ala Gln Lys Lys Phe Gly Lys Arg Asn Thr Ile Trp Leu Phe Gly
            325                 330                 335

Pro Ala Thr Thr Gly Lys Thr Asn Ile Ala Glu Ala Ile Ala His Ala
            340                 345                 350

Val Pro Phe Tyr Gly Cys Val Asn Trp Thr Asn Glu Asn Phe Pro Phe
            355                 360                 365

Asn Asp Cys Val Asp Lys Met Val Ile Trp Trp Glu Glu Gly Lys Met
            370                 375                 380

Thr Ala Lys Val Val Glu Ser Ala Lys Ala Ile Leu Gly Gly Ser Lys
385                 390                 395                 400

Val Arg Val Asp Gln Lys Cys Lys Ser Ser Ala Gln Ile Asp Pro Thr
            405                 410                 415

Pro Val Ile Val Thr Ser Asn Thr Asn Met Cys Ala Val Ile Asp Gly
            420                 425                 430

Asn Ser Thr Thr Phe Glu His Gln Gln Pro Leu Gln Asp Arg Met Phe
            435                 440                 445

Lys Phe Glu Leu Thr Arg Arg Leu Glu His Asp Phe Gly Lys Val Thr
450                 455                 460

Lys Gln Glu Val Lys Glu Phe Phe Arg Trp Ala Ser Asp His Val Thr
465                 470                 475                 480

Glu Val Ala His Glu Phe Tyr Val Arg Lys Gly Gly Ala Ser Lys Arg
            485                 490                 495

Pro Ala Pro Asp Asp Ala Asp Lys Ser Glu Pro Lys Arg Ala Cys Pro
            500                 505                 510

Ser Val Ala Asp Pro Ser Thr Ser Asp Ala Glu Gly Ala Pro Val Asp
            515                 520                 525

Phe Ala Asp Leu Ala Arg Gly Gln Pro Leu
530                 535

<210> SEQ ID NO 113
<211> LENGTH: 623
<212> TYPE: PRT
<213> ORGANISM: Adeno-associated virus 1

<400> SEQUENCE: 113

Met Pro Gly Phe Tyr Glu Ile Val Ile Lys Val Pro Ser Asp Leu Asp
1               5                   10                  15
```

Glu His Leu Pro Gly Ile Ser Asp Ser Phe Val Ser Trp Ala Glu
             20                  25                  30

Lys Glu Trp Glu Leu Pro Pro Asp Ser Asp Met Asp Leu Asn Leu Ile
         35                  40                  45

Glu Gln Ala Pro Leu Thr Val Ala Glu Lys Leu Gln Arg Asp Phe Leu
     50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                 85                  90                  95

Thr Thr Gly Val Lys Ser Met Val Leu Gly Arg Phe Leu Ser Gln Ile
             100                 105                 110

Arg Asp Lys Leu Val Gln Thr Ile Tyr Arg Gly Ile Glu Pro Thr Leu
         115                 120                 125

Pro Asn Trp Phe Ala Val Thr Lys Thr Arg Asn Gly Ala Gly Gly Gly
     130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                 165                 170                 175

Ser Ala Cys Leu Asn Leu Ala Glu Arg Lys Arg Leu Val Ala Gln His
             180                 185                 190

Leu Thr His Val Ser Gln Thr Gln Glu Gln Asn Lys Glu Asn Leu Asn
         195                 200                 205

Pro Asn Ser Asp Ala Pro Val Ile Arg Ser Lys Thr Ser Ala Arg Tyr
     210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                 245                 250                 255

Ser Asn Ser Arg Ser Gln Ile Lys Ala Ala Leu Asp Asn Ala Gly Lys
             260                 265                 270

Ile Met Ala Leu Thr Lys Ser Ala Pro Asp Tyr Leu Val Gly Pro Ala
         275                 280                 285

Pro Pro Ala Asp Ile Lys Thr Asn Arg Ile Tyr Arg Ile Leu Glu Leu
     290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                 325                 330                 335

Thr Thr Gly Lys Thr Asn Ile Ala Glu Ala Ile Ala His Ala Val Pro
             340                 345                 350

Phe Tyr Gly Cys Val Asn Trp Thr Asn Glu Asn Phe Pro Phe Asn Asp
         355                 360                 365

Cys Val Asp Lys Met Val Ile Trp Trp Glu Glu Gly Lys Met Thr Ala
     370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                 405                 410                 415

Ile Val Thr Ser Asn Thr Asn Met Cys Ala Val Ile Asp Gly Asn Ser
             420                 425                 430

Thr Thr Phe Glu His Gln Gln Pro Leu Gln Asp Arg Met Phe Lys Phe

```
                435                 440                 445
Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                    485                 490                 495

Pro Asp Asp Ala Asp Lys Ser Glu Pro Lys Arg Ala Cys Pro Ser Val
                500                 505                 510

Ala Asp Pro Ser Thr Ser Asp Ala Glu Gly Ala Pro Val Asp Phe Ala
                515                 520                 525

Asp Arg Tyr Gln Asn Lys Cys Ser Arg His Ala Gly Met Leu Gln Met
                530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                    565                 570                 575

Ser Glu Ser Gln Pro Val Val Arg Lys Arg Thr Tyr Arg Lys Leu Cys
                580                 585                 590

Ala Ile His His Leu Leu Gly Arg Ala Pro Glu Ile Ala Cys Ser Ala
                595                 600                 605

Cys Asp Leu Val Asn Val Asp Leu Asp Asp Cys Val Ser Glu Gln
                610                 615                 620

<210> SEQ ID NO 114
<211> LENGTH: 621
<212> TYPE: PRT
<213> ORGANISM: Adeno-associated virus 2

<400> SEQUENCE: 114

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
        130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190
```

```
Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
            485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
            565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
```

<210> SEQ ID NO 115
<211> LENGTH: 624
<212> TYPE: PRT
<213> ORGANISM: Adeno-associated virus 3A

<400> SEQUENCE: 115

| | | | | | | | | | | | | | | |
|---|---|---|---|---|---|---|---|---|---|---|---|---|---|---|
| Met | Pro | Gly | Phe | Tyr | Glu | Ile | Val | Leu | Lys | Val | Pro | Ser | Asp | Leu | Asp |
| 1 | | | | 5 | | | | | 10 | | | | | 15 | |
| Glu | Arg | Leu | Pro | Gly | Ile | Ser | Asn | Ser | Phe | Val | Asn | Trp | Val | Ala | Glu |
| | | | 20 | | | | | 25 | | | | | 30 | | |
| Lys | Glu | Trp | Asp | Val | Pro | Pro | Asp | Ser | Asp | Met | Asp | Pro | Asn | Leu | Ile |
| | | 35 | | | | | 40 | | | | | 45 | | | |
| Glu | Gln | Ala | Pro | Leu | Thr | Val | Ala | Glu | Lys | Leu | Gln | Arg | Glu | Phe | Leu |
| | 50 | | | | | 55 | | | | | 60 | | | | |
| Val | Glu | Trp | Arg | Arg | Val | Ser | Lys | Ala | Pro | Glu | Ala | Leu | Phe | Phe | Val |
| 65 | | | | | 70 | | | | | 75 | | | | | 80 |
| Gln | Phe | Glu | Lys | Gly | Glu | Thr | Tyr | Phe | His | Leu | His | Val | Leu | Ile | Glu |
| | | | | 85 | | | | | 90 | | | | | 95 | |
| Thr | Ile | Gly | Val | Lys | Ser | Met | Val | Val | Gly | Arg | Tyr | Val | Ser | Gln | Ile |
| | | | 100 | | | | | 105 | | | | | 110 | | |
| Lys | Glu | Lys | Leu | Val | Thr | Arg | Ile | Tyr | Arg | Gly | Val | Glu | Pro | Gln | Leu |
| | | 115 | | | | | 120 | | | | | 125 | | | |
| Pro | Asn | Trp | Phe | Ala | Val | Thr | Lys | Thr | Arg | Asn | Gly | Ala | Gly | Gly | Gly |
| 130 | | | | | 135 | | | | | 140 | | | | | |
| Asn | Lys | Val | Val | Asp | Asp | Cys | Tyr | Ile | Pro | Asn | Tyr | Leu | Leu | Pro | Lys |
| 145 | | | | | 150 | | | | | 155 | | | | | 160 |
| Thr | Gln | Pro | Glu | Leu | Gln | Trp | Ala | Trp | Thr | Asn | Met | Asp | Gln | Tyr | Leu |
| | | | | 165 | | | | | 170 | | | | | 175 | |
| Ser | Ala | Cys | Leu | Asn | Leu | Ala | Glu | Arg | Lys | Arg | Leu | Val | Ala | Gln | His |
| | | | 180 | | | | | 185 | | | | | 190 | | |
| Leu | Thr | His | Val | Ser | Gln | Thr | Gln | Glu | Gln | Asn | Lys | Glu | Asn | Gln | Asn |
| | | 195 | | | | | 200 | | | | | 205 | | | |
| Pro | Asn | Ser | Asp | Ala | Pro | Val | Ile | Arg | Ser | Lys | Thr | Ser | Ala | Arg | Tyr |
| 210 | | | | | 215 | | | | | 220 | | | | | |
| Met | Glu | Leu | Val | Gly | Trp | Leu | Val | Asp | Arg | Gly | Ile | Thr | Ser | Glu | Lys |
| 225 | | | | | 230 | | | | | 235 | | | | | 240 |
| Gln | Trp | Ile | Gln | Glu | Asp | Gln | Ala | Ser | Tyr | Ile | Ser | Phe | Asn | Ala | Ala |
| | | | | 245 | | | | | 250 | | | | | 255 | |
| Ser | Asn | Ser | Arg | Ser | Gln | Ile | Lys | Ala | Ala | Leu | Asp | Asn | Ala | Ser | Lys |
| | | | 260 | | | | | 265 | | | | | 270 | | |
| Ile | Met | Ser | Leu | Thr | Lys | Thr | Ala | Pro | Asp | Tyr | Leu | Val | Gly | Ser | Asn |
| | | 275 | | | | | 280 | | | | | 285 | | | |
| Pro | Pro | Glu | Asp | Ile | Thr | Lys | Asn | Arg | Ile | Tyr | Gln | Ile | Leu | Glu | Leu |
| 290 | | | | | 295 | | | | | 300 | | | | | |
| Asn | Gly | Tyr | Asp | Pro | Gln | Tyr | Ala | Ala | Ser | Val | Phe | Leu | Gly | Trp | Ala |
| 305 | | | | | 310 | | | | | 315 | | | | | 320 |
| Gln | Lys | Lys | Phe | Gly | Lys | Arg | Asn | Thr | Ile | Trp | Leu | Phe | Gly | Pro | Ala |
| | | | | 325 | | | | | 330 | | | | | 335 | |
| Thr | Thr | Gly | Lys | Thr | Asn | Ile | Ala | Glu | Ala | Ile | Ala | His | Ala | Val | Pro |
| | | | 340 | | | | | 345 | | | | | 350 | | |
| Phe | Tyr | Gly | Cys | Val | Asn | Trp | Thr | Asn | Glu | Asn | Phe | Pro | Phe | Asn | Asp |
| | | 355 | | | | | 360 | | | | | 365 | | | |

```
Cys Val Asp Lys Met Val Ile Trp Trp Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Glu Phe
            435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Glu Cys Thr Ser Leu
                500                 505                 510

Ala Gln Pro Thr Thr Ser Asp Ala Glu Ala Pro Ala Asp Tyr Ala Asp
            515                 520                 525

Arg Tyr Gln Asn Lys Cys Ser Arg His Val Gly Met Asn Leu Met Leu
    530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
                565                 570                 575

Glu Ser Gln Pro Val Ser Val Val Lys Lys Lys Thr Tyr Gln Lys Leu
                580                 585                 590

Cys Pro Ile His His Ile Leu Gly Arg Ala Pro Glu Ile Ala Cys Ser
            595                 600                 605

Ala Cys Asp Leu Ala Asn Val Asp Leu Asp Asp Cys Val Ser Glu Gln
    610                 615                 620

<210> SEQ ID NO 116
<211> LENGTH: 624
<212> TYPE: PRT
<213> ORGANISM: Adeno-associated virus 3B

<400> SEQUENCE: 116

Met Pro Gly Phe Tyr Glu Ile Val Leu Lys Val Pro Ser Asp Leu Asp
1               5                   10                  15

Glu His Leu Pro Gly Ile Ser Asn Ser Phe Val Asn Trp Val Ala Glu
                20                  25                  30

Lys Glu Trp Glu Leu Pro Pro Asp Ser Asp Met Asp Pro Asn Leu Ile
            35                  40                  45

Glu Gln Ala Pro Leu Thr Val Ala Glu Lys Leu Gln Arg Glu Phe Leu
        50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125
```

```
Pro Asn Trp Phe Ala Val Thr Lys Thr Arg Asn Gly Ala Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Ser Asn
        275                 280                 285

Pro Pro Glu Asp Ile Thr Lys Asn Arg Ile Tyr Gln Ile Leu Glu Leu
    290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Gln Cys Thr Ser Leu
            500                 505                 510

Ala Gln Pro Thr Thr Ser Asp Ala Glu Ala Pro Ala Asp Tyr Ala Asp
        515                 520                 525

Arg Tyr Gln Asn Lys Cys Ser Arg His Val Gly Met Asn Leu Met Leu
    530                 535                 540
```

```
Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
            565                 570                 575

Glu Ser Gln Pro Val Ser Val Val Lys Lys Thr Tyr Gln Lys Leu
            580                 585                 590

Cys Pro Ile His His Ile Leu Gly Arg Ala Pro Glu Ile Ala Cys Ser
            595                 600                 605

Ala Cys Asp Leu Ala Asn Val Asp Leu Asp Asp Cys Val Ser Glu Gln
610                 615                 620
```

<210> SEQ ID NO 117
<211> LENGTH: 623
<212> TYPE: PRT
<213> ORGANISM: Adeno-associated virus 4

<400> SEQUENCE: 117

```
Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Val Gly Gln Asn
            275                 280                 285

Pro Pro Glu Asp Ile Ser Ser Asn Arg Ile Tyr Arg Ile Leu Glu Met
    290                 295                 300
```

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
        340                 345                 350

Phe Tyr Gly Cys Val Asn Trp Thr Asn Glu Asn Phe Pro Phe Asn Asp
    355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
        420                 425                 430

Thr Thr Phe Glu His Gln Gln Pro Leu Gln Asp Arg Met Phe Lys Phe
    435                 440                 445

Glu Leu Thr Lys Arg Leu Glu His Asp Phe Gly Lys Val Thr Lys Gln
450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
            485                 490                 495

Pro Asn Asp Ala Asp Ile Ser Glu Pro Lys Arg Ala Cys Pro Ser Val
        500                 505                 510

Ala Gln Pro Ser Thr Ser Asp Ala Glu Ala Pro Val Asp Tyr Ala Asp
    515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Val Asp Ile Cys
545                 550                 555                 560

Phe Thr His Gly Val Met Asp Cys Ala Glu Cys Phe Pro Val Ser Glu
            565                 570                 575

Ser Gln Pro Val Ser Val Val Arg Lys Arg Thr Tyr Gln Lys Leu Cys
        580                 585                 590

Pro Ile His His Ile Met Gly Arg Ala Pro Glu Val Ala Cys Ser Ala
    595                 600                 605

Cys Glu Leu Ala Asn Val Asp Leu Asp Asp Cys Asp Met Glu Gln
610                 615                 620

<210> SEQ ID NO 118
<211> LENGTH: 610
<212> TYPE: PRT
<213> ORGANISM: Adeno-associated virus 5

<400> SEQUENCE: 118

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu

```
                50                  55                  60
Tyr Glu Trp Asn Lys Phe Ser Lys Gln Glu Ser Lys Phe Phe Val Gln
 65                  70                  75                  80

Phe Glu Lys Gly Ser Glu Tyr Phe His Leu His Thr Leu Val Glu Thr
                 85                  90                  95

Ser Gly Ile Ser Ser Met Val Leu Gly Arg Tyr Val Ser Gln Ile Arg
                100                 105                 110

Ala Gln Leu Val Lys Val Val Phe Gln Gly Ile Glu Pro Gln Ile Asn
                115                 120                 125

Asp Trp Val Ala Ile Thr Lys Val Lys Lys Gly Gly Ala Asn Lys Val
            130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
                180                 185                 190

Ser Ser Gln Arg Ser Gln Glu Ala Ala Ser Gln Arg Glu Phe Ser Ala
            195                 200                 205

Asp Pro Val Ile Lys Ser Lys Thr Ser Gln Lys Tyr Met Ala Leu Val
210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
            275                 280                 285

Ile Ser Lys Asn Arg Ile Trp Gln Ile Phe Glu Met Asn Gly Tyr Asp
            290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
            355                 360                 365

Met Leu Ile Trp Trp Glu Glu Gly Lys Met Thr Asn Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
            420                 425                 430

His Gln Gln Pro Leu Glu Asp Arg Met Phe Lys Phe Glu Leu Thr Lys
            435                 440                 445

Arg Leu Pro Pro Asp Phe Gly Lys Ile Thr Lys Gln Glu Val Lys Asp
    450                 455                 460

Phe Phe Ala Trp Ala Lys Val Asn Gln Val Pro Val Thr His Glu Phe
465                 470                 475                 480
```

-continued

```
Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
        515                 520                 525

Val Thr Val Asp Pro Ala Pro Leu Arg Pro Leu Asn Trp Asn Ser Arg
    530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
        595                 600                 605

Glu Gln
    610

<210> SEQ ID NO 119
<211> LENGTH: 623
<212> TYPE: PRT
<213> ORGANISM: Adeno-associated virus 6

<400> SEQUENCE: 119

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
```

```
            225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
                260                 265                 270
Ile Met Ala Leu Thr Lys Ser Ala Pro Asp Tyr Leu Val Gly Pro Ala
            275                 280                 285
Pro Pro Ala Asp Ile Lys Thr Asn Arg Ile Tyr Arg Ile Leu Glu Leu
        290                 295                 300
Asn Gly Tyr Asp Pro Ala Tyr Ala Gly Ser Val Phe Leu Gly Trp Ala
305                 310                 315                 320
Gln Lys Arg Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
                340                 345                 350
Phe Tyr Gly Cys Val Asn Trp Thr Asn Glu Asn Phe Pro Phe Asn Asp
            355                 360                 365
Cys Val Asp Lys Met Val Ile Trp Trp Glu Glu Gly Lys Met Thr Ala
        370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
                420                 425                 430
Thr Thr Phe Glu His Gln Gln Pro Leu Gln Asp Arg Met Phe Lys Phe
            435                 440                 445
Glu Leu Thr Arg Arg Leu Glu His Asp Phe Gly Lys Val Thr Lys Gln
        450                 455                 460
Glu Val Lys Glu Phe Phe Arg Trp Ala Gln Asp His Val Thr Glu Val
465                 470                 475                 480
Ala His Glu Phe Tyr Val Arg Lys Gly Gly Ala Asn Lys Arg Pro Ala
                485                 490                 495
Pro Asp Asp Ala Asp Lys Ser Glu Pro Lys Arg Ala Cys Pro Ser Val
                500                 505                 510
Ala Asp Pro Ser Thr Ser Asp Ala Glu Gly Ala Pro Val Asp Phe Ala
            515                 520                 525
Asp Arg Tyr Gln Asn Lys Cys Ser Arg His Ala Gly Met Leu Gln Met
        530                 535                 540
Leu Phe Pro Cys Lys Thr Cys Glu Arg Met Asn Gln Asn Phe Asn Ile
545                 550                 555                 560
Cys Phe Thr His Gly Thr Arg Asp Cys Ser Glu Cys Phe Pro Gly Val
                565                 570                 575
Ser Glu Ser Gln Pro Val Val Arg Lys Arg Thr Tyr Arg Lys Leu Cys
                580                 585                 590
Ala Ile His His Leu Leu Gly Arg Ala Pro Glu Ile Ala Cys Ser Ala
            595                 600                 605
Cys Asp Leu Val Asn Val Asp Leu Asp Asp Cys Val Ser Glu Gln
        610                 615                 620

<210> SEQ ID NO 120
<211> LENGTH: 623
<212> TYPE: PRT
<213> ORGANISM: Adeno-associated virus 7
```

<400> SEQUENCE: 120

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
                100                 105                 110

Arg Glu Lys Leu Val Gln Thr Ile Tyr Arg Gly Val Glu Pro Thr Leu
            115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ala Leu Thr Lys Ser Ala Pro Asp Tyr Leu Val Gly Pro Ser
            275                 280                 285

Leu Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val

```
                    405                 410                 415
Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
        450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Ile Gln Met
    530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
                565                 570                 575

Ser Glu Ser Gln Pro Val Val Arg Lys Lys Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
    610                 615                 620

<210> SEQ ID NO 121
<211> LENGTH: 625
<212> TYPE: PRT
<213> ORGANISM: Adeno-associated virus 8

<400> SEQUENCE: 121

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Gly Pro Asp His Leu Pro Ala Gly Ser Ser Pro Thr
        115                 120                 125

Leu Pro Asn Trp Phe Ala Val Thr Lys Asp Ala Val Met Ala Pro Ala
    130                 135                 140

Gly Gly Asn Lys Val Val Asp Glu Cys Tyr Ile Pro Asn Tyr Leu Leu
145                 150                 155                 160
```

```
Pro Lys Thr Gln Pro Glu Leu Gln Trp Ala Trp Thr Asn Met Glu Glu
            165                 170                 175
Tyr Ile Ser Ala Cys Leu Asn Leu Ala Glu Arg Lys Arg Leu Val Ala
            180                 185                 190
Gln His Leu Thr His Val Ser Gln Thr Gln Glu Gln Asn Lys Glu Asn
            195                 200                 205
Leu Asn Pro Asn Ser Asp Ala Pro Val Ile Arg Ser Lys Thr Ser Ala
210                 215                 220
Arg Tyr Met Glu Leu Val Gly Trp Leu Val Asp Arg Gly Ile Thr Ser
225                 230                 235                 240
Glu Lys Gln Trp Ile Gln Glu Asp Gln Ala Ser Tyr Ile Ser Phe Asn
            245                 250                 255
Ala Ala Ser Asn Ser Arg Ser Gln Ile Lys Ala Ala Leu Asp Asn Ala
            260                 265                 270
Gly Lys Ile Met Ala Leu Thr Lys Ser Ala Pro Asp Tyr Leu Val Gly
            275                 280                 285
Pro Ser Leu Pro Ala Asp Ile Thr Gln Asn Arg Ile Tyr Arg Ile Leu
            290                 295                 300
Ala Leu Asn Gly Tyr Asp Pro Ala Tyr Ala Gly Ser Val Phe Leu Gly
305                 310                 315                 320
Trp Ala Gln Lys Lys Phe Gly Lys Arg Asn Thr Ile Trp Leu Phe Gly
            325                 330                 335
Pro Ala Thr Thr Gly Lys Thr Asn Ile Ala Glu Ala Ile Ala His Ala
            340                 345                 350
Val Pro Phe Tyr Gly Cys Val Asn Trp Thr Asn Glu Asn Phe Pro Phe
            355                 360                 365
Asn Asp Cys Val Asp Lys Met Val Ile Trp Trp Glu Glu Gly Lys Met
370                 375                 380
Thr Ala Lys Val Val Glu Ser Ala Lys Ala Ile Leu Gly Gly Ser Lys
385                 390                 395                 400
Val Arg Val Asp Gln Lys Cys Lys Ser Ser Ala Gln Ile Asp Pro Thr
            405                 410                 415
Pro Val Ile Val Thr Ser Asn Thr Asn Met Cys Ala Val Ile Asp Gly
            420                 425                 430
Asn Ser Thr Thr Phe Glu His Gln Gln Pro Leu Gln Asp Arg Met Phe
            435                 440                 445
Lys Phe Glu Leu Thr Arg Arg Leu Glu His Asp Phe Gly Lys Val Thr
            450                 455                 460
Lys Gln Glu Val Lys Glu Phe Phe Arg Trp Ala Ser Asp His Val Thr
465                 470                 475                 480
Glu Val Ala His Glu Phe Tyr Val Arg Lys Gly Gly Ala Ser Lys Arg
            485                 490                 495
Pro Ala Pro Asp Asp Ala Asp Lys Ser Glu Pro Lys Arg Ala Cys Pro
            500                 505                 510
Ser Val Ala Asp Pro Ser Thr Ser Asp Ala Glu Gly Ala Pro Val Asp
            515                 520                 525
Phe Ala Asp Arg Tyr Gln Asn Lys Cys Ser Arg His Ala Gly Met Leu
            530                 535                 540
Gln Met Leu Phe Pro Cys Lys Thr Cys Glu Arg Met Asn Gln Asn Phe
545                 550                 555                 560
Asn Ile Cys Phe Thr His Gly Val Arg Asp Cys Ser Glu Cys Phe Pro
            565                 570                 575
Gly Val Ser Glu Ser Gln Pro Val Val Arg Lys Arg Thr Tyr Arg Lys
```

```
                    580               585               590
Leu Cys Ala Ile His His Leu Leu Gly Arg Ala Pro Glu Ile Ala Cys
        595               600               605

Ser Ala Cys Asp Leu Val Asn Val Asp Leu Asp Asp Cys Val Ser Glu
        610               615               620

Gln
625

<210> SEQ ID NO 122
<211> LENGTH: 622
<212> TYPE: PRT
<213> ORGANISM: Artificial
<220> FEATURE:
<223> OTHER INFORMATION: AAV Rep78 consensus sequence
<220> FEATURE:
<221> NAME/KEY: MISC_FEATURE
<222> LOCATION: (118)..(118)
<223> OTHER INFORMATION: Xaa can be Gln, Lys, Pro or Thr
<220> FEATURE:
<221> NAME/KEY: MISC_FEATURE
<222> LOCATION: (119)..(119)
<223> OTHER INFORMATION: Xaa can be Arg, Asp, Thr or Val
<220> FEATURE:
<221> NAME/KEY: MISC_FEATURE
<222> LOCATION: (287)..(287)
<223> OTHER INFORMATION: Xaa can be Gln, Pro or Ser
<220> FEATURE:
<221> NAME/KEY: MISC_FEATURE
<222> LOCATION: (541)..(541)
<223> OTHER INFORMATION: Xaa can be Asn, Asp, Ile and Leu
<220> FEATURE:
<221> NAME/KEY: MISC_FEATURE
<222> LOCATION: (557)..(557)
<223> OTHER INFORMATION: Xaa can be Lys, Phe, Ser or Val
<220> FEATURE:
<221> NAME/KEY: MISC_FEATURE
<222> LOCATION: (565)..(565)
<223> OTHER INFORMATION: Xaa can be Gln, Thr or Val
<220> FEATURE:
<221> NAME/KEY: MISC_FEATURE
<222> LOCATION: (569)..(569)
<223> OTHER INFORMATION: Xaa can be Ala, Gln, Gly, Leu or Ser
<220> FEATURE:
<221> NAME/KEY: MISC_FEATURE
<222> LOCATION: (580)..(580)
<223> OTHER INFORMATION: Xaa can be Pro or Ser
<220> FEATURE:
<221> NAME/KEY: MISC_FEATURE
<222> LOCATION: (588)..(588)
<223> OTHER INFORMATION: Xaa can be Arg or Gln
<220> FEATURE:
<221> NAME/KEY: MISC_FEATURE
<222> LOCATION: (592)..(592)
<223> OTHER INFORMATION: Xaa can be Ala, Pro or Tyr

<400> SEQUENCE: 122

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95
```

```
Thr Thr Gly Val Lys Ser Met Val Leu Gly Arg Phe Leu Ser Gln Ile
            100                 105                 110

Arg Glu Lys Leu Val Xaa Xaa Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Xaa Ser
        275                 280                 285

Pro Pro Glu Asp Ile Ser Thr Asn Arg Ile Tyr Arg Ile Leu Ala Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Lys Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Ala Pro Val Asp Phe Ala Asp
```

```
              515                 520                 525
Arg Tyr Gln Asn Lys Cys Ser Arg His Ala Gly Met Xaa Gln Met Leu
        530                 535                 540

Phe Pro Cys Lys Thr Cys Glu Arg Met Asn Gln Asn Xaa Asn Ile Cys
545                 550                 555                 560

Phe Thr His Gly Xaa Arg Asp Cys Xaa Glu Cys Phe Pro Gly Val Ser
                565                 570                 575

Glu Ser Gln Xaa Val Val Arg Lys Arg Thr Tyr Xaa Lys Leu Cys Xaa
            580                 585                 590

Ile His His Leu Leu Gly Arg Ala Pro Glu Ile Ala Cys Ser Ala Cys
                595                 600                 605

Asp Leu Val Asn Val Asp Leu Asp Asp Cys Val Ser Glu Gln
            610                 615                 620

<210> SEQ ID NO 123
<211> LENGTH: 122
<212> TYPE: DNA
<213> ORGANISM: Snake parvovirus

<400> SEQUENCE: 123
cgccccaccc ctagtgatcg cgcgcgctct ctcttggggc ctgacggccg aaggccgtca     60
gctgccgagc ttcgctcggc aggccccaag agagagcgcg cgcgatcact aggggtgggg    120
cg                                                                   122

<210> SEQ ID NO 124
<211> LENGTH: 6107
<212> TYPE: DNA
<213> ORGANISM: Artificial
<220> FEATURE:
<223> OTHER INFORMATION: Snake ITR eGFP vector sequence

<400> SEQUENCE: 124
gtggcacttt tcggggaaat gtgcgcggaa cccctatttg tttatttttc taaatacatt     60
caaatatgta tccgctcatg agacaataac cctgataaat gcttcaataa tattgaaaaa    120
ggaagagtat gagtattcaa catttccgtg tcgcccttat tccttttttt gcggcatttt    180
gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca acatggggga tcatgtaa     600 ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
```

```
atctcatgac caaaatccct taacgtgagt tttcgttcca ctgagcgtca gaccccgtag    1140
aaaagatcaa aggatcttct tgagatcctt tttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtgcg ataagtcgtg tcttaccggg ttggactcaa     1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatggaaaaa cgccagcaac gcggcctttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct gggtaccggg ccccccctcg    2220
aggtcgacgg tatcgataag cttgatcgcc ccacccctag tgatcgcgcg cgctctctct    2280
tggggcctga cggccgaagg ccgtcagctg ccgagcttcg ctcggcaggc cccaagagag    2340
agcgcgcgcg atcactaggg gtggggcgag tgccctgctc aacgggtttt ttggtgggcg    2400
gagcaatgac gtcagcggac atgtctggac atgtctttga gcaagtccat ataaggagtt    2460
ccgccggata tgcaaatgag caatcgcgca aagcattttg ggtagtcacc atgaataaaa    2520
aggacagcaa gaaagatgac gccccataat tttaatagga atttttaacca tgttctttcc    2580 tgcgttatcc cctgattctg tggataaccg tattaccgcc tttgagtgag ctgataccgc    2640
tcgccgcagc cgaacgaccg agcgcagcga gtcagtgagc gaggaagcgg aagagcgccc    2700
aatacgcaaa ccgcctctcc ccgcgcgttg gccgattcat taatgcagct ggcacgacag    2760
gtttcccgac tggaaagcgg gcagtgagcg caacgcaatt aatgtgagtt agctcactca    2820
ttaggcaccc caggctttac actttatgct tccggctcgt atgttgtgtg gaattgtgag    2880
cggataacaa tttcacacag gaaacagcta tgaccatgat tacgaattgt tgttgttaac    2940
ttgtttattg cagcttataa tggttacaaa taaagcaata gcatcacaaa tttcacaaat    3000
aaagcatttt tttcactgca ttctagttgt ggtttgtcca aactcatcaa tgtatcttat    3060
catgtctgga tccccgcggc cgctttactt gtacagctcg tccatgccga gagtgatccc    3120
ggcggcggtc acgaactcca gcaggaccat gtgatcgcgc ttctcgttgg ggtcttttgct   3180 cagggcggac tgggtgctca ggtagtggtt gtcgggcagc agcacgggc cgtcgccgat     3240 gggggtgttc tgctggtagt ggtcggcgag ctgcacgctg ccgtcctcga tgttgtggcg    3300
gatcttgaag ttcaccttga tgccgttctt ctgcttgtcg gccatgatat agacgttgtg    3360
gctgttgtag ttgtactcca gcttgtgccc caggatgttg ccgtcctcct tgaagtcgat    3420
```

```
gcccttcagc tcgatgcggt tcaccagggt gtcgccctcg aacttcacct cggcgcgggt    3480
cttgtagttg ccgtcgtcct tgaagaagat ggtgcgctcc tggacgtagc cttcgggcat    3540
ggcggacttg aagaagtcgt gctgcttcat gtggtcgggg tagcggctga agcactgcac    3600
gccgtaggtc agggtggtca cgagggtggg ccagggcacg ggcagcttgc cggtggtgca    3660
gatgaacttc agggtcagct tgccgtaggt ggcatcgccc tcgccctcgc cggacacgct    3720
gaacttgtgg ccgtttacgt cgccgtccag ctcgaccagg atgggcacca ccccggtgaa    3780
cagctcctcg cccttgctca ccatggtggc gaccggtgga tcccgggccg cgggtacaat    3840
tccgcagctt ttagagcaga agtaacactt ccgtacaggc ctagaagtaa aggcaacatc    3900
cactgaggag cagttctttg atttgcacca ccaccggatc cgggacctga aataaaagac    3960
aaaaagacta aacttaccag ttaactttct ggttttcag ttcctcgagt accggatcct    4020
ctagagtccg gaggctggat cggtcccggt gtcttctatg gaggtcaaaa cagcgtggat    4080
ggcgtctcca ggcgatctga cggttcacta acgagctct gcttatatag acctcccacc    4140
gtacacgcct accgcccatt tgcgtcaatg gggcggagtt gttacgacat tttggaaagt    4200
cccgttgatt ttggtgccaa aacaaactcc cattgacgtc aatggggtgg agacttggaa    4260
atccccgtga gtcaaaccgc tatccacgcc cattgatgta ctgccaaaac cgcatcacca    4320
tggtaatagc gatgactaat acgtagatgt actgccaagt aggaaagtcc cataaggtca    4380
tgtactgggc ataatgccag gcgggccatt taccgtcatt gacgtcaata ggggcgtac    4440
ttggcatatg atacacttga tgtactgcca agtgggcagt ttaccgtaaa tactccaccc    4500
attgacgtca atggaaagtc cctattggcg ttactattga cgtcaatggg cggggtcgt    4560
tgggcggtca gccaggcggg ccatttaccg taagttatgt aacgggtacc cggggatcct    4620
ctagagtcga cctgcagtaa acagaacaat tgaagacgaa atacagggta ccaataattt    4680
tggtaatgct agaaataaca ttgttgctat caatcaacaa acgaaaggaa caaatccaac    4740
aacaggtagt acatctcaat ttgagacaat gccaggtatg gtgtggtcta atagagacat    4800
ttacttacag gggcctattt gggctaaaat tccaaataca gatggacatt ttcatccttc    4860
tcccagaatg ggtggttttg gattaaaaca tcctccgcct atgattctga tcaaaaatac    4920
accagttcct gctgatcctc caactacctt caatccaatg ccacagacta gtttcattac    4980
tgaatacagt acaggacaag taactgttga aatgttgtgg gaggtacaga agaatcctc     5040
caaaagatgg aatccagaag tacagtttac ttccaatttt ggaacttcag atccagctgt    5100
tgatggaata ccgtttggaa ttaataattt gggtacttat gttgaatcta gacctattgg    5160
aactcgttat atttctaaac acttgtaaat aataaaaatt gtcaaatttg cactaagaat    5220
tgttgtcacg tggttgttta catgcttgct aaaacacgcc caccaaaaaa cccgttgagc    5280
agggcactcg ccccacccct agtgatcgcg cgcgctctct cttggggcct gccgagcgaa    5340
gctcggcagc tgacgccctt cggccgtcag gccccaagag agagcgcgcg cgatcactag    5400
gggtggggcg gggggatcca ctagttctag agcggccgcc accgcggtgg agctccaatt    5460
cgccctatag tgagtcgtat tacgcgcgct cactggccgt cgttttacaa cgtcgtgact    5520
gggaaaaccc tggcgttacc caacttaatc gccttgcagc acatccccct ttcgccagct    5580
ggcgtaatag cgaagaggcc cgcaccgatc gcccttccca acagttgcgc agcctgaatg    5640
gcgaatggga cgcgccctgt agcggcgcat taagcgcggc gggtgtggtg gttacgcgca    5700
gcgtgaccgc tacacttgcc agcgccctag cgcccgctcc tttcgctttc ttcccttcct    5760
ttctcgccac gttcgccggc tttccccgtc aagctctaaa tcggggggctc cctttagggt    5820
```

-continued

```
tccgatttag tgctttacgg cacctcgacc ccaaaaaact tgattagggt gatggttcac    5880
gtagtgggcc atcgccctga tagacggttt ttcgcccttt gacgttggag tccacgttct    5940
ttaatagtgg actcttgttc caaactggaa caacactcaa ccctatctcg gtctattctt    6000
ttgatttata agggattttg ccgatttcgg cctattggtt aaaaaatgag ctgatttaac    6060
aaaaatttaa cgcgaatttt aacaaaatat taacgcttac aatttag                  6107
```

<210> SEQ ID NO 125
<211> LENGTH: 7302
<212> TYPE: DNA
<213> ORGANISM: Artificial
<220> FEATURE:
<223> OTHER INFORMATION: pSnRepCap2 plasmid sequence

<400> SEQUENCE: 125

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctggc ttaactatg cggcatcaga gcagattgta ctgagagtgc     180
accatatgcg gtgtgaaata ccgcacagat gcgtaaggag aaaataccgc atcaggaaat     240
tgtaaacgtt aatattttgt taaaattcgc gttaaatttt tgttaaatca gctcattttt     300
taaccaatag gccgaaatcg gcaaaatccc ttataaatca aaagaataga ccgagatagg     360
gttgagtgtt gttccagttt ggaacaagag tccactatta agaacgtgg actccaacgt     420 caaagggcga aaaccgtctc atcagggcga tggcccacta cgtgaaccat cacctaatc      480 aagttttttg gggtcgaggt gccgtaaagc actaaatcgg aaccctaaag ggagccccg      540 atttagagct tgacggggaa agccggcgaa cgtggcgagg aaggaaggga agaaagcgaa     600
aggagcgggc gctagggcgc tggcaagtgt agcggtcacg ctgcgcgtaa ccaccacacc     660
cgccgcgctt aatgcgccgc tacagggcgc gtcgcgccat tcgccattca ggctgcgcaa     720
ctgttgggaa gggcgatcgg tgcgggcctc ttcgctatta cgccagctgg cgaaaggggg     780
atgtgctgca aggcgattaa gttgggtaac gccagggttt tcccagtcac gacgttgtaa     840
aacgacggcc agtgaattgt aatacgactc actatagggc gaattcgagc tcgcagcgga     900
catgtctgga catgtctttg agcaagtcca tataaggagt tccgccggat atgcaaatga     960
gcaatcgcgc aaagcatttt gggtagtcac catgaataaa aaggacagca agaaagatga    1020
cgccccataa ttttaatagg aattttaacc atggcgtttt acgaggttgt gtttcgtttg    1080
ccaagagaca ataacaactt gttggatgaa gatagatatc agccagagtt gaagaagaa     1140 gatgactggc ctgaggaata tttaaccagt gaagatgcca gctttatcgg actagcgtat    1200
gctgtgctaa gtgaaattcg gagattcttt ggaaaggaac tacaatggtt tgcccaggtt    1260
gaatggtgtc ctactgctgg ttaccacatg catgtttgt tgaaccatcc taagctgagt    1320
aaccagactt atgaagaaa ggtcaatgaa ctggcttgcc gtatagtcga tacctttggc    1380
ctaattaatc cagaagaagt catcagtacc cattatgtta aaagcaacta tggacataaa    1440
aaggtgagag tcattcacct agagtcttat ttgaagaact acttttttcag aaagactta    1500 gctcctccca attataccga ggaaggagac tataaaagag aggaagaagt cgtgctgtgg    1560
gcatttacga atatcgtcgc ttggaagcca ttcgtgcgga atctcatcaa gagatcggag    1620
ctagcgactg ttcctaagca accagagaat ccggcgggag acggaccggc acctcgagtg    1680
actgcaggaa cccgccattt tatggaaacc atcgactggt tggtgaaaca tggaattact    1740
```

-continued

```
acagaacgag aattctgcca cgccaaccgc cctttgtacc tgtctatgct ggcttctact    1800
tcgggtgctg ggcagattaa aagagcgctg gaccaggcga acacatgat gaccagcacc    1860
atgtcagcag aggattacct gacaacagaa gaggatgtga tcgaaccacc tactgaaaat    1920
agaatctaca agattatgaa actgaatcgc tatgatccag aactagcagc tgctctcttc    1980
tacggctgga cctgcaagaa ctttggcaag agaaacacca tctggctgta tggtccagct    2040
actaccggca aaaccatcat cgctcaagct attgcacatg ctgttaaact gtttgctggt    2100
gttaattgga ctaatgaaaa ctttcccttc tgtaactgtc agggaaact gcttatctgg    2160
tgggaggagg gcaagatgac aaacaaaatg gtgggagacgg ctaaatgtat actgggggga    2220
tctgctgtac ctgtagacat caaaggcaaa cccgctgaaa tgtgtcctca acaccctgt    2280
attattacta gcaatactaa catgtgtcaa gtatatgatg gtaatagttc tagctttgag    2340
caccaagaac ccctagagga acgcatgttt atgttcagac ttaatactaa actgccatcg    2400
acctttggca agatcacaga agaggaagtc aaacagttta ttacctgggg gaggagctta    2460
aaggttcaag ttccacatca gttcagagtg cctaccacag gagagtataa aaggccagcc    2520
cccgaggcga aagctcattc ttcggatgag ccgccaaaag agaaggtcgc gcgtattgat    2580
gactctctaa ccaggtatgt taacaatatt gatgagtcag ctaccagtag agaaatgttt    2640
ctagagattg ctaatactaa tcaatgtatg ttgcatcatt gcttttcttg taccgaatgt    2700
tatcctgaat tgcttgatga catggacaag gaacaataaa cttactgata acagatatgg    2760
ctgccgatgg ttatcttcca gattggctcg aggacactct ctctgaagga ataagacagt    2820
ggtggaagct caaacctggc ccaccaccac caaagcccgc agagcggcat aaggacgaca    2880
gcagggtgtct tgtgcttcct gggtacaagt acctcggacc cttcaacgga ctcgacaagg    2940
gagagccggt caacgaggca gacgccgcg ccctcgagca cgacaaagcc tacgaccggc    3000
agctcgacag cggagacaac ccgtacctca gtacaaccac cgccgacgcg gagtttcagg    3060
agcgccttaa agaagatacg tcttttgggg gcaacctcgg acgagcagtc ttccaggcga    3120
aaaagagggt tcttgaacct ctgggcctgg ttgaggaacc tgttaagacg gctccgggaa    3180
aaaagaggcc ggtagagcac tctcctgtgg agccagactc ctcctcggga accggaaagg    3240
cgggccagca gcctgcaaga aaaagattga attttggtca gactggagac gcagactcag    3300
tacctgaccc ccagcctctc ggacagccac cagcagcccc ctctggtctg ggaactaata    3360
cgatggctac aggcagtggc gcaccaatgg cagacaataa cgagggcgcc gacggagtgg    3420
gtaattcctc gggaaattgg cattgcgatt ccacatggat gggcgacaga gtcatcacca    3480
ccagcacccg aacctgggcc ctgcccacct acaacaacca cctctacaaa caaatttcca    3540
gccaatcagg agcctcgaac gacaatcact actttggcta cagcacccct tgggggtatt    3600
ttgacttcaa cagattccac tgccactttt caccacgtga ctggcaaaga ctcatcaaca    3660
acaactgggg attccgaccc aagagactca acttcaagct cttttaacatt caagtcaaag    3720
aggtcacgca gaatgacggt acgacgacga ttgccaataa ccttaccagc acggttcagg    3780
tgtttactga ctcggagtac cagctcccgt acgtcctcgg ctcggcgcat caaggatgcc    3840
tcccgccgtt cccagcagac gtcttcatgg tgccacagta tggatacctc accctgaaca    3900
acgggagtca ggcagtagga cgctcttcat tttactgcct ggagtacttt ccttctcaga    3960
tgctgcgtac cggaaacaac tttaccttca gctacacttt tgaggacgtt cctttccaca    4020
gcagctacgc tcacagccag agtctggacc gtctcatgaa tcctctcatc gaccagtacc    4080
tgtattactt gagcagaaca aacactccaa gtggaaccac cacgcagtca aggcttcagt    4140
```

```
tttctcaggc cggagcgagt gacattcggg accagtctag gaactggctt cctggaccct    4200
gttaccgcca gcagcgagta tcaaagacat ctgcggataa caacaacagt gaatactcgt    4260
ggactggagc taccaagtac cacctcaatg gcagagactc tctggtgaat ccgggcccgg    4320
ccatggcaag ccacaaggac gatgaagaaa agttttttcc tcagagcggg gttctcatct    4380
ttgggaagca aggctcagag aaaacaaatg tggacattga aaaggtcatg attacagacg    4440
aagaggaaat caggacaacc aatcccgtgg ctacggagca gtatggttct gtatctacca    4500
acctccagag aggcaacaga caagcagcta ccgcagatgt caacacacaa ggcgttcttc    4560
caggcatggt ctggcaggac agagatgtgt accttcaggg gcccatctgg gcaaagattc    4620
cacacacgga cggacatttt cacccctctc ccctcatggg tggattcgga cttaaacacc    4680
ctcctccaca gattctcatc aagaacaccc cggtacctgc gaatccttcg accaccttca    4740
gtgcggcaaa gtttgcttcc ttcatcacac agtactccac gggacaggtc agcgtggaga    4800
tcgagtggga gctgcagaag gaaaacagca acgctggaa tcccgaaatt cagtacactt    4860
ccaactacaa caagtctgtt aatgtggact ttactgtgga cactaatggc gtgtattcag    4920
agcctcgccc cattggcacc agatacctga ctcgtaatct gtaattgctt gttaatcaat    4980
aaaccgttta attcgtttca gttgaacttt ggtgtcgcgg ccgctcgata gcttttgtt    5040
ccctttagtg agggttaatt ccgagcttgg cgtaatcatg gtcatagctg tttcctgtgt    5100
gaaattgtta tccgctcaca attccacaca acatacgagc cggaagcata agtgtaaag    5160
cctggggtgc ctaatgagtg agctaactca cattaattgc gttgcgctca ctgcccgctt    5220
tccagtcggg aaacctgtcg tgccagctgc attaatgaat cggccaacgc gcggggagag    5280
gcggtttgcg tattgggcgc tcttccgctt cctcgctcac tgactcgctg cgctcggtcg    5340
ttcggctgcg gcgagcggta tcagctcact caaaggcggt aatacggtta tccacagaat    5400
caggggataa cgcaggaaag aacatgtgag caaaaggcca gcaaaaggcc aggaaccgta    5460
aaaaggccgc gttgctggcg ttttccata ggctccgccc ccctgacgag catcacaaaa    5520
atcgacgctc aagtcagagg tggcgaaacc cgacaggact ataaagatac caggcgtttc    5580
cccctggaag ctccctcgtg cgctctcctg ttccgaccct gccgcttacc ggatacctgt    5640
ccgcctttct cccttcggga agcgtggcgc tttctcatag ctcacgctgt aggtatctca    5700
gttcggtgta ggtcgttcgc tccaagctgg gctgtgtgca cgaaccccc gttcagcccg    5760
accgctgcgc cttatccggt aactatcgtc ttgagtccaa cccggtaaga cacgacttat    5820
cgccactggc agcagccact ggtaacagga ttagcagagc gaggtatgta ggcggtgcta    5880
cagagttctt gaagtggtgg cctaactacg gctacactag aaggacagta tttggtatct    5940
gcgctctgct gaagccagtt accttcggaa aaagagttgg tagctcttga tccggcaaac    6000
aaaccaccgc tggtagcggt ggttttttg tttgcaagca gcagattacg cgcagaaaaa    6060
aaggatctca agaagatcct ttgatctttt ctacggggtc tgacgctcag tggaacgaaa    6120
actcacgtta agggattttg gtcatgagat tatcaaaaag gatcttcacc tagatccttt    6180
taaattaaaa atgaagtttt aaatcaatct aaagtatata tgagtaaact tggtctgaca    6240
gttaccaatg cttaatcagt gaggcaccta tctcagcgat ctgtctattt cgttcatcca    6300
tagttgcctg actccccgtc gtgtagataa ctacgatacg ggagggctta ccatctggcc    6360
ccagtgctgc aatgataccg cgagacccac gctcaccggc tccagattta tcagcaataa    6420
accagccagc cggaagggcc gagcgcagaa gtggtcctgc aactttatcc gcctccatcc    6480
```

```
agtctattaa ttgttgccgg gaagctagag taagtagttc gccagttaat agtttgcgca      6540
acgttgttgc cattgctaca ggcatcgtgg tgtcacgctc gtcgtttggt atggcttcat      6600
tcagctccgg ttcccaacga tcaaggcgag ttacatgatc ccccatgttg tgcaaaaaag      6660
cggttagctc cttcggtcct ccgatcgttg tcagaagtaa gttggccgca gtgttatcac      6720
tcatggttat ggcagcactg cataattctc ttactgtcat gccatccgta agatgctttt      6780
ctgtgactgg tgagtactca accaagtcat tctgagaata gtgtatgcgg cgaccgagtt      6840
gctcttgccc ggcgtcaata cgggataata ccgcgccaca tagcagaact ttaaaagtgc      6900
tcatcattgg aaaacgttct cgggggcgaa aactctcaag gatcttaccg ctgttgagat      6960
ccagttcgat gtaacccact cgtgcaccca actgatcttc agcatctttt actttcacca      7020
gcgtttctgg gtgagcaaaa acaggaaggc aaaatgccgc aaaaaaggga taagggcga      7080 cacggaaatg ttgaatactc atactcttcc tttttcaata ttattgaagc atttatcagg      7140
gttattgtct catgagcgga tacatatttg aatgtattta gaaaaataaa caaatagggg      7200
ttccgcgcac atttccccga aaagtgccac ctgacgtcta agaaaccatt attatcatga      7260
cattaaccta taaaaatagg cgtatcacga ggccctttcg tc                        7302

<210> SEQ ID NO 126
<211> LENGTH: 30
<212> TYPE: DNA
<213> ORGANISM: Artificial
<220> FEATURE:
<223> OTHER INFORMATION: PCR primer

<400> SEQUENCE: 126
cgaaaagtgc cacctgacgt ctaagaaacc                                        30

<210> SEQ ID NO 127
<211> LENGTH: 35
<212> TYPE: DNA
<213> ORGANISM: Artificial
<220> FEATURE:
<223> OTHER INFORMATION: PCR primer

<400> SEQUENCE: 127
tcgaattcga cggccagtga attgtaatac gactc                                  35

<210> SEQ ID NO 128
<211> LENGTH: 37
<212> TYPE: DNA
<213> ORGANISM: Artificial
<220> FEATURE:
<223> OTHER INFORMATION: PCR primer

<400> SEQUENCE: 128
ccatgattac gccaagctcg gaattaaccg catgcga                                37

<210> SEQ ID NO 129
<211> LENGTH: 23
<212> TYPE: DNA
<213> ORGANISM: Artificial
<220> FEATURE:
<223> OTHER INFORMATION: PCR primer

<400> SEQUENCE: 129
ccatggccgg gcccggattc acc                                               23

<210> SEQ ID NO 130
<211> LENGTH: 69
```

```
<212> TYPE: DNA
<213> ORGANISM: Artificial
<220> FEATURE:
<223> OTHER INFORMATION: PCR primer

<400> SEQUENCE: 130
ttcaccccgg tggtttccac gagcacgtgc atgtggaagt agctctctcc cttttcaaac    60
tgcacaaag                                                            69

<210> SEQ ID NO 131
<211> LENGTH: 45
<212> TYPE: DNA
<213> ORGANISM: Artificial
<220> FEATURE:
<223> OTHER INFORMATION: PCR primer

<400> SEQUENCE: 131
cctcggccgc tacgtgagtc agattcgcga aaaactgatt cagag                    45

<210> SEQ ID NO 132
<211> LENGTH: 48
<212> TYPE: DNA
<213> ORGANISM: Artificial
<220> FEATURE:
<223> OTHER INFORMATION: PCR primer

<400> SEQUENCE: 132
gtggtcttcc agggaattga acccactttg ccaaactggt tcgcggtc                 48

<210> SEQ ID NO 133
<211> LENGTH: 55
<212> TYPE: DNA
<213> ORGANISM: Artificial
<220> FEATURE:
<223> OTHER INFORMATION: PCR primer

<400> SEQUENCE: 133
ctgggtcgcc atcaccaagg taaagaaggg aggcgggaac aaggtggtgg atgag         55

<210> SEQ ID NO 134
<211> LENGTH: 50
<212> TYPE: DNA
<213> ORGANISM: Artificial
<220> FEATURE:
<223> OTHER INFORMATION: PCR primer

<400> SEQUENCE: 134
gcggagccaa taaggtggtg gatgagtgct acatccccaa ttacttgctc               50

<210> SEQ ID NO 135
<211> LENGTH: 35
<212> TYPE: DNA
<213> ORGANISM: Artificial
<220> FEATURE:
<223> OTHER INFORMATION: PCR primer

<400> SEQUENCE: 135
actggagctc aggttggacc ttcggcagca ggtag                               35

<210> SEQ ID NO 136
<211> LENGTH: 57
<212> TYPE: DNA
<213> ORGANISM: Artificial
<220> FEATURE:
<223> OTHER INFORMATION: PCR primer
```

<400> SEQUENCE: 136
cgtggacaaa cctggacgag tataaattgg cctgtttgaa tctcacggag cgtaaac            57

<210> SEQ ID NO 137
<211> LENGTH: 48
<212> TYPE: DNA
<213> ORGANISM: Artificial
<220> FEATURE:
<223> OTHER INFORMATION: PCR primer

<400> SEQUENCE: 137
ctgaatctgg aggagcgcaa acggttggtg gcgcagcatc tgacgcac                      48

<210> SEQ ID NO 138
<211> LENGTH: 36
<212> TYPE: DNA
<213> ORGANISM: Artificial
<220> FEATURE:
<223> OTHER INFORMATION: PCR primer

<400> SEQUENCE: 138
gatcaccggc gcatccgaga actcacgctg cgaagc                                   36

<210> SEQ ID NO 139
<211> LENGTH: 47
<212> TYPE: DNA
<213> ORGANISM: Artificial
<220> FEATURE:
<223> OTHER INFORMATION: PCR primer

<400> SEQUENCE: 139
taaggccccg gaggcccttt tctttgtgca gtttgaaaag ggatctg                       47

<210> SEQ ID NO 140
<211> LENGTH: 50
<212> TYPE: DNA
<213> ORGANISM: Artificial
<220> FEATURE:
<223> OTHER INFORMATION: PCR primer

<400> SEQUENCE: 140
ccacatgcac gtgctcgtgg aaacctccgg catctcttcc atggtcctcg                    50

<210> SEQ ID NO 141
<211> LENGTH: 38
<212> TYPE: DNA
<213> ORGANISM: Artificial
<220> FEATURE:
<223> OTHER INFORMATION: PCR primer

<400> SEQUENCE: 141
tcagattcgc gaaaaactgg tgaaagtggt cttccagg                                 38

<210> SEQ ID NO 142
<211> LENGTH: 47
<212> TYPE: DNA
<213> ORGANISM: Artificial
<220> FEATURE:
<223> OTHER INFORMATION: PCR primer

<400> SEQUENCE: 142
gaatttaccg cgggatcgag ccgcagatca acgactgggt cgccatc                       47

<210> SEQ ID NO 143
<211> LENGTH: 54

```
<212> TYPE: DNA
<213> ORGANISM: Artificial
<220> FEATURE:
<223> OTHER INFORMATION: PCR primer

<400> SEQUENCE: 143
ggtcacaaag accagaaatg gcgccggcgg agccaataag gtggtggatt ctgg        54

<210> SEQ ID NO 144
<211> LENGTH: 48
<212> TYPE: DNA
<213> ORGANISM: Artificial
<220> FEATURE:
<223> OTHER INFORMATION: PCR primer

<400> SEQUENCE: 144
gaggcgggaa caaggtggtg gattctgggt atattcccgc ctacctgc               48

<210> SEQ ID NO 145
<211> LENGTH: 34
<212> TYPE: DNA
<213> ORGANISM: Artificial
<220> FEATURE:
<223> OTHER INFORMATION: PCR primer

<400> SEQUENCE: 145
ccagcctgag ctccagtggg cgtggacaaa cctg                              34

<210> SEQ ID NO 146
<211> LENGTH: 48
<212> TYPE: DNA
<213> ORGANISM: Artificial
<220> FEATURE:
<223> OTHER INFORMATION: PCR primer

<400> SEQUENCE: 146
gtttgaatct cacggagcgt aaacggctcg tcgcgcagtt tctggcag               48

<210> SEQ ID NO 147
<211> LENGTH: 42
<212> TYPE: DNA
<213> ORGANISM: Artificial
<220> FEATURE:
<223> OTHER INFORMATION: PCR primer

<400> SEQUENCE: 147
atgcgccggt gatcaaaagc aagacttccc agaaatacat gg                     42

<210> SEQ ID NO 148
<211> LENGTH: 29
<212> TYPE: DNA
<213> ORGANISM: Artificial
<220> FEATURE:
<223> OTHER INFORMATION: PCR primer

<400> SEQUENCE: 148
attataggta ccaggaaccc ctagtgatg                                    29

<210> SEQ ID NO 149
<211> LENGTH: 22
<212> TYPE: DNA
<213> ORGANISM: Artificial
<220> FEATURE:
<223> OTHER INFORMATION: PCR primer

<400> SEQUENCE: 149
```
taatagggcc caaagggccg gg                                    22

<210> SEQ ID NO 150
<211> LENGTH: 22
<212> TYPE: DNA
<213> ORGANISM: Artificial
<220> FEATURE:
<223> OTHER INFORMATION: PCR primer

<400> SEQUENCE: 150
ttaataggcc ctttgggccg gg                                    22

<210> SEQ ID NO 151
<211> LENGTH: 32
<212> TYPE: DNA
<213> ORGANISM: Artificial
<220> FEATURE:
<223> OTHER INFORMATION: PCR primer

<400> SEQUENCE: 151
tataataagc ttaggaaccc ctagtgatgg ag                         32

<210> SEQ ID NO 152
<211> LENGTH: 33
<212> TYPE: DNA
<213> ORGANISM: Artificial
<220> FEATURE:
<223> OTHER INFORMATION: PCR primer

<400> SEQUENCE: 152
attataggta cctacaaaac ctccttgctt gag                        33

<210> SEQ ID NO 153
<211> LENGTH: 24
<212> TYPE: DNA
<213> ORGANISM: Artificial
<220> FEATURE:
<223> OTHER INFORMATION: PCR primer

<400> SEQUENCE: 153
ttaataggcc ctttgggccg tcgc                                  24

<210> SEQ ID NO 154
<211> LENGTH: 25
<212> TYPE: DNA
<213> ORGANISM: Artificial
<220> FEATURE:
<223> OTHER INFORMATION: PCR primer

<400> SEQUENCE: 154
ttaataggcc caaagggccg tcgtc                                 25

<210> SEQ ID NO 155
<211> LENGTH: 35
<212> TYPE: DNA
<213> ORGANISM: Artificial
<220> FEATURE:
<223> OTHER INFORMATION: PCR primer

<400> SEQUENCE: 155
tataataagc tttacaaaac ctccttgctt gagag                      35